United States Patent
Allen et al.

(10) Patent No.: US 10,351,575 B2
(45) Date of Patent: Jul. 16, 2019

(54) BICYCLIC UREA, THIOUREA, GUANIDINE AND CYANOGUANIDINE COMPOUNDS USEFUL FOR THE TREATMENT OF PAIN

(71) Applicant: Array BioPharma Inc., Boulder, CO (US)

(72) Inventors: Shelley Allen, Boulder, CO (US); Steven Wade Andrews, Boulder, CO (US); James F. Blake, Boulder, CO (US); Barbara J. Brandhuber, Boulder, CO (US); Julia Haas, Boulder, CO (US); Yutong Jiang, Boulder, CO (US); Timothy Kercher, San Diego, CA (US); Gabrielle R. Kolakowski, Boulder, CO (US); Allen A. Thomas, Kearney, NE (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 345 days.

(21) Appl. No.: 14/442,609

(22) PCT Filed: Nov. 13, 2013

(86) PCT No.: PCT/US2013/069951
§ 371 (c)(1),
(2) Date: May 13, 2015

(87) PCT Pub. No.: WO2014/078454
PCT Pub. Date: May 22, 2014

(65) Prior Publication Data
US 2016/0355521 A1   Dec. 8, 2016

Related U.S. Application Data

(60) Provisional application No. 61/725,925, filed on Nov. 13, 2012.

(51) Int. Cl.

| | |
|---|---|
| *C07D 401/14* | (2006.01) |
| *C07D 491/048* | (2006.01) |
| *C07D 405/14* | (2006.01) |
| *C07D 231/40* | (2006.01) |
| *C07D 231/54* | (2006.01) |
| *C07D 401/12* | (2006.01) |
| *C07D 403/02* | (2006.01) |
| *C07D 403/04* | (2006.01) |
| *C07D 403/14* | (2006.01) |
| *C07D 405/12* | (2006.01) |
| *C07D 413/12* | (2006.01) |

(Continued)

(52) U.S. Cl.
CPC ....... *C07D 491/048* (2013.01); *C07D 231/40* (2013.01); *C07D 231/52* (2013.01); *C07D 231/54* (2013.01); *C07D 231/56* (2013.01); *C07D 401/04* (2013.01); *C07D 401/12* (2013.01); *C07D 401/14* (2013.01); *C07D 403/02* (2013.01); *C07D 403/04* (2013.01); *C07D 403/14* (2013.01); *C07D 405/12* (2013.01); *C07D 405/14* (2013.01); *C07D 409/14* (2013.01); *C07D 413/12* (2013.01); *C07D 453/02* (2013.01); *C07D 471/08* (2013.01)

(58) Field of Classification Search
CPC .......................... C07D 491/048; C07D 401/04
See application file for complete search history.

(56) References Cited

U.S. PATENT DOCUMENTS

| | | |
|---|---|---|
| 5,849,779 A | 12/1998 | Hirota et al. |
| 5,998,424 A | 12/1999 | Galemmo, Jr. et al. |

(Continued)

FOREIGN PATENT DOCUMENTS

| | | |
|---|---|---|
| EP | 0761658 A1 | 12/1997 |
| EP | 1043995 B1 | 11/2006 |

(Continued)

OTHER PUBLICATIONS

Cancer and Metastasis Reviews (1998), 17(1), 91-106.*

(Continued)

*Primary Examiner* — Shawquia Jackson
(74) *Attorney, Agent, or Firm* — Viksnins Harris Padys Malen LLP; Sarah S. Mastous

(57) ABSTRACT

Compounds of Formula I: or stereoisomers, tautomers, or pharmaceutically acceptable salts, solvates or prodrugs thereof, wherein Ring A, Ring C and X are as defined herein, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

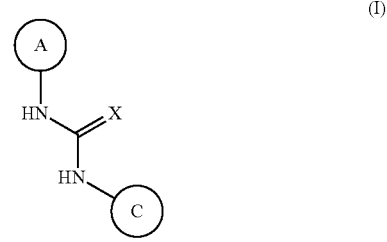

(I)

48 Claims, No Drawings

(51) Int. Cl.
C07D 453/02 (2006.01)
C07D 231/52 (2006.01)
C07D 231/56 (2006.01)
C07D 401/04 (2006.01)
C07D 409/14 (2006.01)
C07D 471/08 (2006.01)

(56) References Cited

U.S. PATENT DOCUMENTS

| | | |
|---|---|---|
| 6,197,798 B1 | 3/2001 | Fink et al. |
| 6,410,533 B1 | 6/2002 | Hirth et al. |
| 7,223,782 B2 | 5/2007 | Atkinson et al. |
| 7,625,915 B2 | 12/2009 | Dumas et al. |
| 8,592,454 B2 | 11/2013 | Shirai et al. |
| 2012/0157442 A1 | 6/2012 | Bui et al. |
| 2012/0264755 A1 | 10/2012 | Christensen et al. |

FOREIGN PATENT DOCUMENTS

| | | |
|---|---|---|
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |
| WO | 9923091 A1 | 5/1999 |
| WO | 9932110 A1 | 7/1999 |
| WO | 99032111 | 7/1999 |
| WO | 0039116 A1 | 7/2000 |
| WO | 0043384 A1 | 7/2000 |
| WO | 200112188 A1 | 2/2001 |
| WO | 200202525 A2 | 1/2002 |
| WO | 2002088101 A2 | 11/2002 |
| WO | 2002090326 A1 | 11/2002 |
| WO | 2003037274 A2 | 5/2003 |
| WO | 2003045920 A1 | 6/2003 |
| WO | 2003051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A2 | 11/2012 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078378 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Vippagunta, et al. Advanced Drug Delivery Reviews 48 (2001) 3-26.*
Tsuzuki, Y., et al., Tetrahedron Asymmetry 12 (2001), 2989-2997.
Wadhwa, S., et al., Journal of Biosciences, 2003, 28(2), 181-188.
Wang, T., et al., Expert Opinion in Therapeutic Patents (2009) 19(3):305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Patent Cooperation Treaty, International Searching Authority, Search Report and Written Opinion for PCT/US2013/069951, dated Feb. 3, 2014, 9 pages.
Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.

(56) References Cited

OTHER PUBLICATIONS

Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K., et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.
McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et al., Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.
Montalban, A.G., et al.,European J. Pharmacology 2010, 632:93-102.
Opposition letter from P/Asociacion De La Industria Farmaceutica Nacional (ASIFN) dated Oct. 8, 2015 received in corresponding Costa Rican patent application No. 2015-0264; 10 pages.

* cited by examiner

BICYCLIC UREA, THIOUREA, GUANIDINE AND CYANOGUANIDINE COMPOUNDS USEFUL FOR THE TREATMENT OF PAIN

RELATED APPLICATIONS

This application is a 371 filing of PCT Application No. PCT/US2013/069951, filed Nov. 13, 2013, which claims priority to U.S. Provisional Application Ser. No. 61/725,925, filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to bicyclic urea, thiourea, guanidine and cyanoguanidine compounds which exhibit TrkA kinase inhibition and which are useful in the treatment of pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C.J. et al. (1994) *Neuroscience* 62, 327-331; Zahn, P.K. et al. (2004) *J. Pain* 5, 157-163; McMahon, S.B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) BJU International, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A.L., et al., (2009) Scandinavian Journal of Rheumatology, 38(1), pp. 50-57), endometriosis (Barcena De Arellano, M.L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H.C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108(2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Representative compounds of the invention (See Table B below), were found to be highly selective for TrkA over a panel of about 230 other kinases at 10 µM concentration. In addition, compounds of the invention such as those shown in Table A below, were found to be at least 1000 fold more selective for TrkA versus p38α.

More specifically, provided herein are compounds of Formula I:

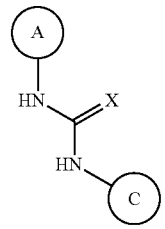

I or stereoisomers, tautomers, or pharmaceutically acceptable salts, solvates or prodrugs thereof, wherein Ring A, Ring C and X are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are potentially useful in the treatment of diseases, conditions and/or disorders modulated by TrkA.

Representative compounds of the invention (See Table B below), were found to be highly selective for TrkA over a panel of about 230 other kinases at 10 µM concentration. In addition, compounds of the invention such as those shown in Table A below, were found to be at least 1000 fold more selective for TrkA versus p38α.

One embodiment provides a compound of Formula I:

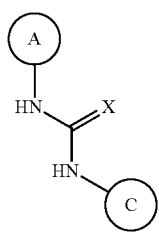

I or stereoisomers, tautomers, or pharmaceutically acceptable salts, solvates or prodrugs thereof, wherein:
X is O, S, NH or N—CN;
Ring A is formula A-1 or A-2

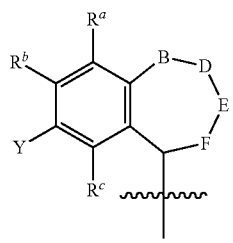

A-1

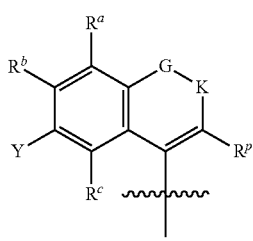

A-2

Y is H, halogen, (1-3C alkoxy)(1-6C)alkyl, (1-6C)alkyl [optionally substituted with 1-5 fluoros], cyano(1-6C)alkyl, hydroxy(1-6C)alkyl, dihydroxy(2-6C)alkyl, aminocarbonyl (1-6C)alkyl, (1-6C)alkoxy [optionally substituted with 1-5 fluoros], CN, aminocarbonyl or (1-4C alkoxy)carbonyl;

$R^a$, $R^b$ and $R^c$ are independently selected from H, halogen, (1-3C)alkyl, (1-3C)alkoxy and CN;
B is $NR^1$, O, a bond, $CR^dR^e$, S or $SO_2$;
D is $NR^1$, O, a bond, $CR^fR^g$, S or $SO_2$;
E is $NR^1$, O, a bond, $CR^hR^i$, S or $SO_2$;
F is $CR^jR^k$;
provided that the ring formed by B, D, E, and F together with the atoms to which they are attached contains at least five atoms and zero or one of B, D or E is $NR^1$ or O;
G is $CR^mR^n$;
K is $NR^1$;
$R^1$ is (1-6C)alkyl [optionally substituted with one to five fluoros], (1-6C)cycloalkyl [optionally substituted with one to five fluoros], (1-3C alkoxy)(2-6C)alkyl [optionally substituted with one to five fluoros], (1-6C)alkylC(=O)— or (1-6C alkoxy)C=O—;
$R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros],
or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring,
or one of a pair of $R^d$ and $R^e$, or $R^f$ and $R^g$, or $R^h$ and $R^i$, or $R^j$ and $R^k$ form an oxo group,
and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;
$R^m$ is H, (1-3C)alkyl [optionally substituted with 1-5 fluoros], cyclopropyl or cyclobutyl, and
$R^n$ is H or (1-3C)alkyl [optionally substituted with 1-5 fluoros], or
$R^m$ and $R^n$ together form an oxo group;
$R^p$ is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C) cyanoalkyl;
Ring C is formula C-1 or C-2

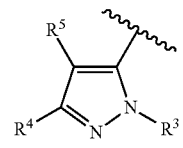

C-1

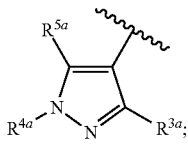

C-2

R³ is (1-6C)alkyl, hydroxy(1-6C)alkyl, Ar², hetCyc¹, (3-7C)cycloalkyl, or hetAr²;

Ar² is phenyl optionally substituted with one or more groups independently selected from halogen and (1-6C) alkyl;

hetCyc¹ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with one or more groups independently selected from (1-6C)alkyl and halogen;

R⁴ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C) alkoxy, trifluoro(1-6C)alkoxy, tetrafluoro(2-6C)alkoxy, pentafluoro(2-6C)alkoxy, cyano(1-6C)alkoxy, hydroxy(1-6C) alkoxy, dihydroxy(2-6C)alkoxy, amino(2-6C)alkoxy, hydroxyl-carbonyl(1-6C)alkoxy, hetCyc²(1-6C)alkoxy, hetAr³ (1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkyl sulfonamido(1-6C)alkoxy, (1-3C) alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl) oxadiazolonyl, hetAr⁵ or hetCyc⁴-O—;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C) alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl) CH₂— (3-6C cycloalkyl)C(=O)—, (1-3C alkoxy)(1-6C) alkyl, (1-6C)alkoxy, (1-6C)alkylsulfonyl, NH₂, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

hetAr⁵ is a group selected from the structures:

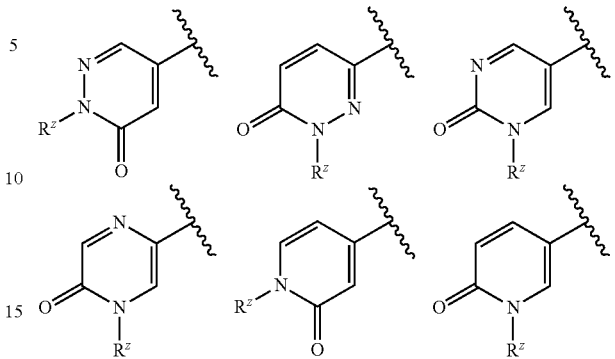

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

hetCyc⁴ is a 7-8 membered bridged heterocycle having a ring nitrogen atom and optionally substituted with one or more groups independently selected from (1-6C)alkyl and halogen;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl) OC(=O)—;

R⁵ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R^{3a} is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R^{4a} is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl) SO₂—, HOC(=O)— and (1-3C alkoxy)(1-3C alkyl)OC (=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C) alkoxy, (1-6C)alkylsulfonyl, NH$_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment compounds of Formula I include Formula I-1:

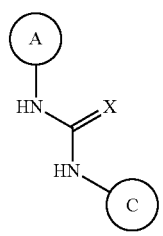

I-1 or stereoisomers, tautomers, or pharmaceutically acceptable salts, or solvates or prodrugs thereof, wherein:

X is O, S, NH or N—CN;
Ring A is formula A-1 or A-2

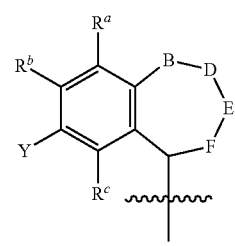

A-1

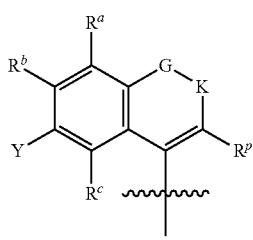

A-2

Y is H, halogen, (1-3C alkoxy)(1-6C)alkyl, (1-6C)alkyl [optionally substituted with 1-5 fluoros], cyano(1-6C)alkyl, hydroxy(1-6C)alkyl, dihydroxy(2-6C)alkyl, aminocarbonyl (1-6C)alkyl, (1-6C)alkoxy [optionally substituted with 1-5 fluoros], or CN;

$R^a$, $R^b$ and $R^c$ are independently selected from H, halogen, (1-3C)alkyl, (1-3C)alkoxy and CN;

B is NR$^1$, O, a bond, or CR$^d$R$^e$;
D is NR$^1$, O, a bond, or CR$^f$R$^g$;
E is NR$^1$, O, a bond, or CR$^h$R$^i$;
F is CR$^j$R$^k$;

provided that the ring formed by B, D, E, and F together with the atoms to which they are attached contains at least five atoms and zero or one of B, D or E is NR$^1$ or O;

G is CR$^m$R$^n$;
K is NR$^1$;

$R^1$ is (1-6C)alkyl [optionally substituted with one to five fluoros], (1-6C)cycloalkyl [optionally substituted with one to five fluoros], (1-3C alkoxy)(2-6C)alkyl [optionally substituted with one to five fluoros], (1-6C)alkylC(=O)— or (1-6C alkoxy)C=O—;

$R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl, or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

$R^m$ is H, (1-3C)alkyl [optionally substituted with 1-5 fluoros], cyclopropyl or cyclobutyl, and $R^n$ is H or (1-3C)alkyl [optionally substituted with 1-5 fluoros], or $R^m$ and $R^n$ together form an oxo group;

$R^p$ is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C) cyanoalkyl;

Ring C is formula C-1 or C-2

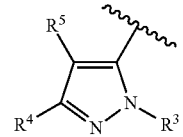

C-1

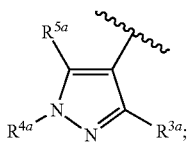

C-2

$R^3$ is (1-6C)alkyl, hydroxy(1-6C)alkyl, Ar$^2$, hetCyc$^1$, (3-7C)cycloalkyl, or hetAr$^2$;

Ar$^2$ is phenyl optionally substituted with one or more groups independently selected from halogen and (1-6C)alkyl;

hetCyc$^1$ is a 5-6-membered saturated or partially unsaturated heterocyclic ring having 1-2 ring heteroatoms independently selected from N and O;

hetAr$^2$ is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc$^2$(1-6C)alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C)alkoxy, or (1-3C alkoxy)(1-6C)alkyl], hetAr$^4$, hetAr$^4$—O—, Ar$^4$, hetCyc$^2$(O)CH$_2$—, (1-4C alkoxycarbonyl)(1-6C)alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc$^2$C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc$^3$, halogen, CN, trifluoromethylsulfonyl, N-(1-3C alkyl)oxadiazolonyl, or hetAr$^5$;

hetCyc$^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc$^3$ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr$^3$ is a 5-membered heteroaryl ring having 1-3 ring atoms independently selected from N, O and S and optionally substituted with (1-6C)alkyl;

Ar$^3$ is phenyl optionally substituted with (1-4C)alkoxy;

hetAr$^4$ is a 5-6 membered heteroaryl ring having 1-3 heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH$_2$— (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr$^5$ is a group selected from the structures:

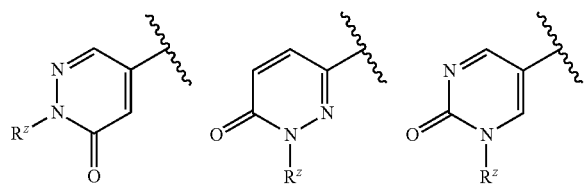

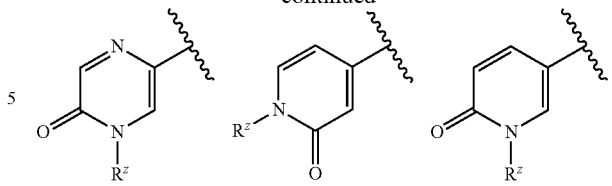

where $R^z$ is (3-4C)cycloalkyl or (1-3C)alkyl (optionally substituted with 1-3 fluoros), wherein each of said hetAr$^5$ groups is optionally further substituted with one or more groups independently selected from F and (1-3C)alkyl optionally substituted with 1-3 fluoros;

Ar$^4$ is phenyl optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy; or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO$_2$;

$R^{3a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is hydrogen, (1-6C)alkyl, trifluoro(1-6C)alkyl, phenyl [optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH$_2$— (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment compounds of Formula I include Formula I-2:

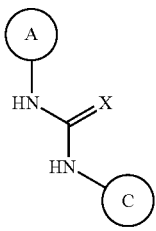

or stereoisomers, tautomers, or pharmaceutically acceptable salts, solvates or prodrugs thereof, wherein:

X is O, S, NH or N—CN;
Ring A is formula A-1 or A-2

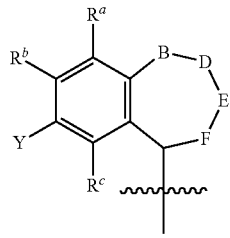

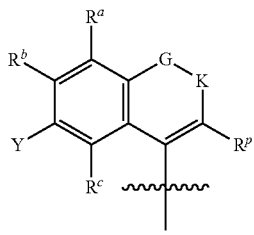

Y is H, halogen, (1-3C alkoxy)(1-6C)alkyl, (1-6C)alkyl [optionally substituted with 1-5 fluoros], cyano(1-6C)alkyl, hydroxy(1-6C)alkyl, dihydroxy(2-6C)alkyl, aminocarbonyl(1-6C)alkyl, (1-6C)alkoxy [optionally substituted with 1-5 fluoros], CN, aminocarbonyl or (1-4C alkoxy)carbonyl;

$R^a$, $R^b$ and $R^c$ are independently selected from H, halogen, (1-3C)alkyl, (1-3C)alkoxy and CN;

B is $NR^1$, O, a bond, $CR^dR^e$, S or $SO_2$;
D is $NR^1$, O, a bond, $CR^fR^g$, S or $SO_2$;
E is $NR^1$, O, a bond, or $CR^hR^i$, S or $SO_2$;
F is $CR^jR^k$;

provided that the ring formed by B, D, E, and F together with the atoms to which they are attached contains at least five atoms and zero or one of B, D or E is $NR^1$ or O;

G is $CR^mR^n$;
K is $NR^1$;
$R^1$ is (1-6C)alkyl [optionally substituted with one to five fluoros], (1-6C)cycloalkyl [optionally substituted with one to five fluoros], (1-3C alkoxy)(1-6C)alkyl [optionally substituted with one to five fluoros], (1-6C)alkylC(=O)— or (1-6C alkoxy)C=O—;

$R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(1-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

$R^m$ is H, (1-3C)alkyl [optionally substituted with 1-5 fluoros], cyclopropyl or cyclobutyl, and $R^n$ is H or (1-3C)alkyl [optionally substituted with 1-5 fluoros], or $R^m$ and $R^n$ together form an oxo group;

$R^p$ is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl;

Ring C is formula C-1 or C-2

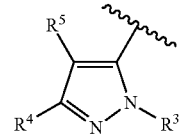

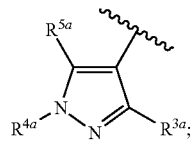

$R^3$ is (1-6C)alkyl, hydroxy(1-6C)alkyl, $Ar^2$, hetCyc$^1$, (3-7C)cycloalkyl, or hetAr$^2$;

$Ar^2$ is phenyl optionally substituted with one or more groups independently selected from halogen and (1-6C) alkyl;

hetCyc$^1$ is a 5-6-membered saturated or partially unsaturated heterocyclic ring having 1-2 ring heteroatoms independently selected from N and O;

hetAr$^2$ is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³ (1-6C)alkyl, Ar³ (1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³ (1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkyl carboxyl)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, hetAr⁵ or hetCyc⁴-O—;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C) alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

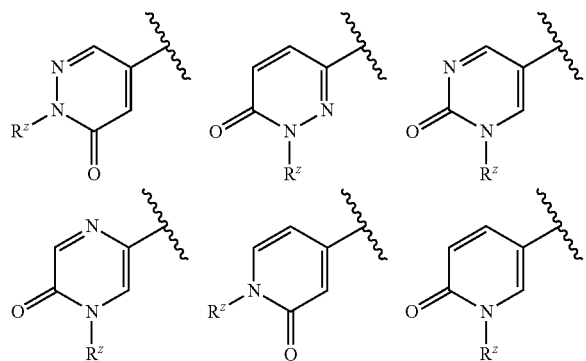

where R$^z$ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

hetCyc⁴ is a 7-8 membered bridged heterocycle having a ring nitrogen atom and optionally substituted with one or more groups independently selected from (1-6C)alkyl and halogen;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R$^{3a}$ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R$^{4a}$ is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R$^{5a}$ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C)alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where R is (1-4C)alkyl, (1-3C)alkyl, (1-6C)alkyl, or (2-6C)alkyl, respectively, as defined above. Examples include methoxy, ethoxy, and the like.

"(1-6)Acyl" means a RC(=O)— radical where R is a linear monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C)alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" and "(1-4C)alkoxycarbonyl" mean a (1-6C)—O—C(=O)— and (1-4C)—O—C(=O)— group, respectively.

"(1-4C Alkoxycarbonyl)(1-6C alkoxy)" means a (1-6C) alkoxy group as defined herein wherein one of the carbon atoms is substituted with one (1-4C alkoxy)carbonyl group, i.e., an alkyl-O—C(=O)— group.

"(1-3C Alkoxy)hydroxycarbonylalkyl" means a hydroxycarbonylalkyl group as defined herein wherein one of the carbon atoms is substituted with one (1-3C alkoxy) group.

"Amino" means a —NRR' group where R and R' are independently selected from hydrogen or (1-3C)alkyl as defined herein. Examples include H₂N—, CH₃NH—, (CH₃)₂N, and the like. "Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen or (1-3C)alkyl as defined herein.

"Aminocarbonyl" means a RR'NCO— radical where R and R' are independently hydrogen or (1-6C)alkyl as defined herein. Examples include H₂NCO—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"(1-3C)Alkylamido(1-6C)alkoxy" means a (1-6C)alkoxy as defined herein, wherein one of the carbon atoms is substituted with one alkylamido group, i.e., substituted with a (1-3C)C(=O)NH— group.

"(1-4C alkyl)carboxy" means a R'—C(=O)O— group where R' is (1-4C)alkyl.

"(1-4C alkylsiloxy)(1-6C)alkoxy" means a (1-6C)alkoxy group as defined herein wherein one of the carbon atoms is substituted with one (1-4C alkyl)siloxy group, e.g., a (1-4C alkyl)Si—O— group such as a tert-butylsiloxy group.

"(1-3C)Alkylsulfonamido" means a (1-3C)alkylSO₂NH— radical where (1-3C)alkyl is as defined herein.

"(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"Hydroxycarbonyl" means HOC(=O)—.

"(1-4C alkyl)carboxy(1-6C)alkyl" means a (1-6C)alkyl group as defined herein wherein one of the carbon atoms is substituted with a (1-4C alkyl)carboxy group as defined herein.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring-system having one or more ring heteroatoms as recited for the specific heteroaryl group, wherein the heteroaryl is optionally substituted with substituents as defined for that particular heteroaryl group.

"hetCyc²C(=O)(1-6C)alkoxy" means a (1-6C)alkoxy as defined herein, wherein one of the carbon atoms is substituted with a hetCyc²C(=O) group, wherein hetCyc² is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C) alkyl group as defined herein, wherein one of the carbon atoms is substituted with a hydroxy group.

"Hydroxytrifluoro(1-6C)alkoxy" means a trifluoro(1-6C) alkoxy group as defined herein, wherein one of the carbon atoms is substituted with a hydroxy group.

"Hydroxycarbonylalkyl" means a linear saturated hydrocarbon radical of one to six carbon atoms or a branched saturated monovalent hydrocarbon radical of three to six carbons substituted with one —COOH group. Examples include 2-hydroxycarbonylethyl, 1-, 2-, or 3-hydroxycarbonylpropyl, and the like.

"Isoindoline-1,3-dionyl(1-6C)alkoxy" means a (1-6C) alkoxy group as defined herein, wherein one of the carbon atoms is substituted with an isoindoline-1,3-dionyl group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"Trifluro(1-3C alkyl)amido" means a (1-3C alkyl)C(=O) NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido (H₂NSO₂NH—) group.

It should be noted that compounds of the invention may contain groups that may exist in tautomeric forms, such as heteroatom substituted heteroaryl or heterocyclic groups and the like, which are illustrated in the following general and specific examples:

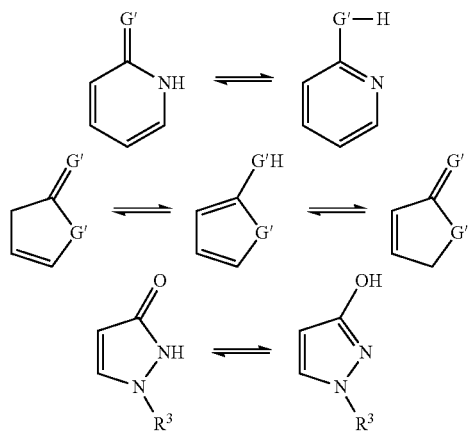

where G'=O, S, or NR, and though one form is named, described, displayed and/or claimed herein, all the tautomeric forms are intended to be inherently included in such name, description, display and/or claim.

In one embodiment of Formula I, X is O.
In one embodiment of Formula I, X is S.
In one embodiment of Formula I, X is NH.
In one embodiment of Formula I, X is N—CN.
In one embodiment of Formula I, Y is H.
In one embodiment of Formula I, Y is halogen. In one embodiment, Y is F, Cl or Br.

In one embodiment of Formula I, Y is (1-3C alkoxy)(1-6C)alkyl. In one embodiment, Y is CH₃OCH₂—.

In one embodiment of Formula I, Y is (1-6C)alkyl optionally substituted with 1-5 fluoros. In one embodiment, Y is methyl, ethyl, propyl, isopropyl or trifluoromethyl.

In one embodiment of Formula I, Y is cyano(1-6C)alkyl. In one embodiment, Y is CNCH₂—.

In one embodiment of Formula I, Y is hydroxy(1-6C) alkyl. In one embodiment, Y is HOCH₂.

In one embodiment of Formula I, Y is dihydroxy(2-6C) alkyl. In one embodiment, Y is HOCH₂CH(OH).

In one embodiment of Formula I, Y is aminocarbonyl(1-6C)alkyl. In one embodiment, Y is H₂NC(=O)CH₂CH₂—, CH₃NHC(=O)CH₂CH₂—, or (CH₃)₂NC(=O)CH₂CH₂—.

In one embodiment of Formula I, Y is (1-6C)alkoxy optionally substituted with 1-5 fluoros. In one embodiment, Y is CH₃O—, CH₃CH₂O—, CF₃O— or CF₃CH₂O—.

In one embodiment of Formula I, Y is CN.

In one embodiment of Formula I, Y is aminocarbonyl. In one embodiment, Y is H₂NC(=O)—.

In one embodiment of Formula I, Y is (1-4C alkoxy) carbonyl. In one embodiment, Y is CH₃OC(=O)—.

In one embodiment of Formula I, Y is H, halogen or (1-3C alkoxy)(1-6C)alkyl.

In one embodiment of Formula I, R$^a$, R$^b$ and R$^c$ are hydrogen.

In one embodiment of Formula I, R$^a$, R$^b$ and R$^c$ are independently selected from halogen, (1-3C)alkyl, (1-3C) alkoxy and CN.

In one embodiment of Formula I, one of R$^a$, R$^b$ and R$^c$ is selected from halogen, (1-3C)alkyl, (1-3C)alkoxy and CN and the other two are hydrogen.

In one embodiment of Formula I, one of R$^a$, R$^b$ and R$^c$ is selected from halogen and (1-3C)alkoxy and the other two are hydrogen.

In one embodiment of Formula I, zero to four of R$^d$, R$^e$, R$^f$, R$^g$, R$^h$, R$^i$, R$^j$ and R$^k$ are independently H, OH, (1-6C)

alkyl [optionally substituted with one to five fluoros], (3-6C) cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C) cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C) cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, zero to four of $R^d$, $R^e$, $R^f$, $R^g$, $R^h$, $R^i$, $R^j$ and $R^k$ are independently OH, methyl, methoxy, cyclopropyl, or 2-methoxyethoxy, or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, zero to two of $R^d$, $R^e$, $R^f$, $R^g$, $R^h$, $R^i$, $R^j$ and $R^k$ are independently OH, (1-6C)alkyl [optionally substituted with one to five fluoros], (3-6C) cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, zero to two of $R^d$, $R^e$, $R^f$, $R^g$, $R^h$, $R^i$, $R^j$ and $R^k$ are independently OH, (1-6C)alkyl [optionally substituted with one to five fluoros], (3-6C) cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C) cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, zero to two of $R^d$, $R^e$, $R^f$, $R^g$, $R^h$, $R^i$, $R^j$ and $R^k$ are independently OH, methyl, methoxy, cyclopropyl, or 2-methoxyethoxy, or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

In one embodiment of Formula I, one of $R^d$, $R^e$, $R^f$, $R^g$, $R^h$, $R^i$, $R^j$ and $R^k$ is halogen or (1-3C)alkoxy, and the remainder are hydrogen.

In one embodiment of Formula I, $R^d$, $R^e$, $R^f$, $R^g$, $R^h$, $R^i$, $R^j$ and $R^k$ are hydrogen.

As used herein, the phrase "one of a pair of $R^d$ and $R^e$, or $R^f$ and $R^g$, or $R^h$ and $R^i$, or $R^j$ and $R^k$, together with the carbon atom to which they are attached form a (3-6C) cycloalkyl, oxetanyl or azetidinyl ring" refers a spirocyclic (3-6C)cycloalkyl, oxetanyl or azetidinyl ring formed from a pair of said R groups, wherein each R group of said pair is attached to the same carbon atom. Examples of such structures include, but are not limited to the following:

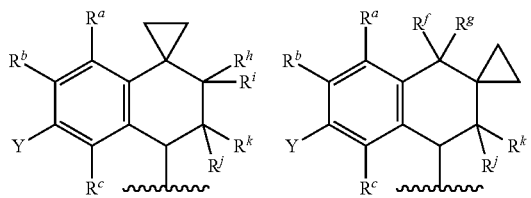

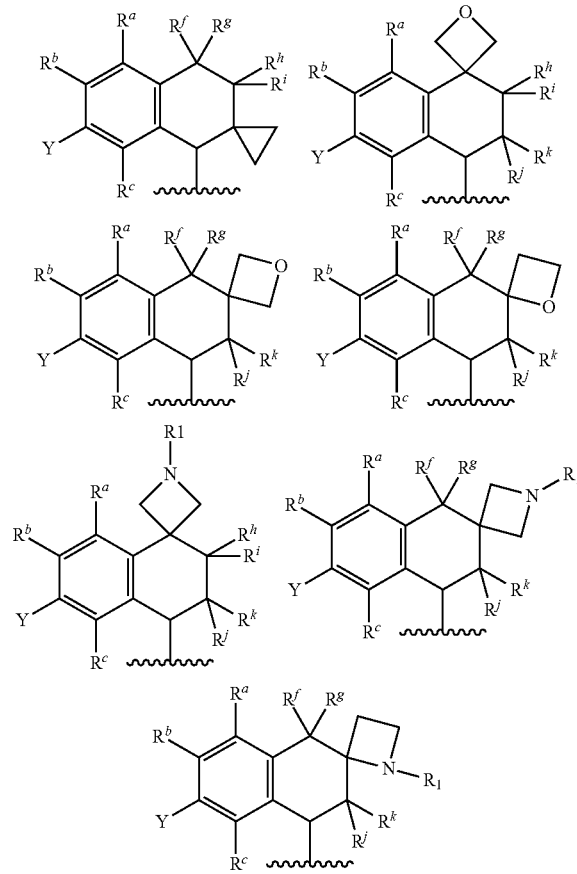

and the like, wherein the remaining $R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl and $R^1$ is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl.

As used herein, the phrase "one of a pair of $R^d$ and $R^e$, or $R^f$ and $R^g$, or $R^h$ and $R^i$, or $R^j$ and $R^k$, together with the carbon atom to which they are attached form an oxo group" refers to an oxo group formed from a pair of said R groups, wherein each R group of said pair is attached to the same carbon atom. Examples of such structures include, but are not limited to the following:

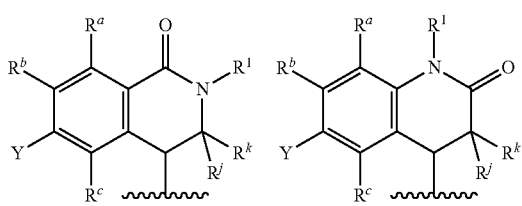

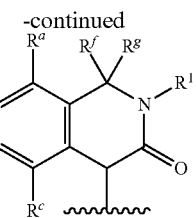

and the like, wherein the remaining $R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl.

The phrase "$R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C)cyanoalkyl, or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group" refers to a compound having a spirocyclic group which is formed from a first pair of said R groups, wherein each R group of said first pair is attached to a first carbon atom, and further contains an oxo group formed from a second pair of said R groups, wherein each R group of said second pair is attached to a second carbon atom. Examples of such structures include, but are not limited to the following:

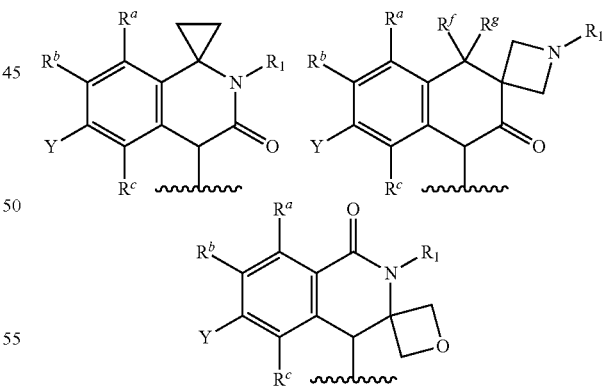

and the like, wherein the remaining groups such as $R^f$, $R^g$, $R^h$, $R^i$, $R^j$ and $R^k$ are independently selected from H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], and (2-6C)cyanoalkyl and R1 is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C) cyanoalkyl.

In one embodiment of Formula I, Ring A is formula A-1.

In one embodiment of Formula I, Ring A is formula A-1, where B is a bond or $CR^dR^e$, D is a bond or $CR^fR^g$, E is a bond or $CR^hR^i$, and F is $CR^jR^k$, provided that the ring formed by B, D, E, and F together with the atoms to which they are attached contains at least five atoms, where $R^d$, $R^e$, $R^f$, $R^g$, $R^h$, $R^i$, $R^j$ and $R^k$ are as defined for Formula I.

Examples of such ring systems include the structures:

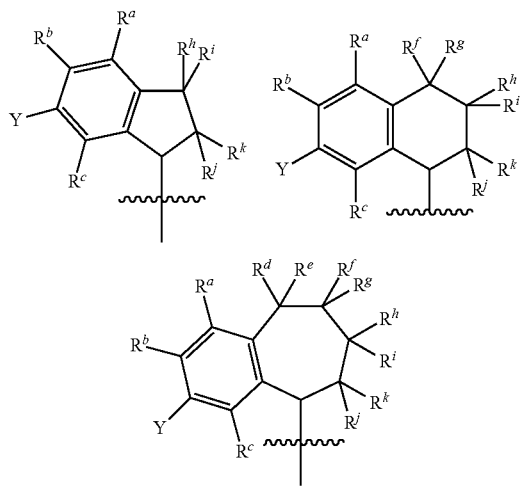

where $R^a$, $R^b$, $R^c$, $R^d$, $R^e$, $R^f$, $R^g$, $R^h$, $R^i$, $R^j$, $R^k$ and Y are as defined for Formula I. In one embodiment of Formula I, Ring A is formula A-1, where B is a bond or $CR^dR^e$, D is a bond or $CR^fR^g$, E is a bond or $CR^hR^i$, and F is $CR^jR^k$, provided that the ring formed by B, D, E, and F together with the atoms to which they are attached contains 5-6 atoms.

In one embodiment of Formula I, Ring A when represented by formula A-1 includes, but is not limited to, the following structures:

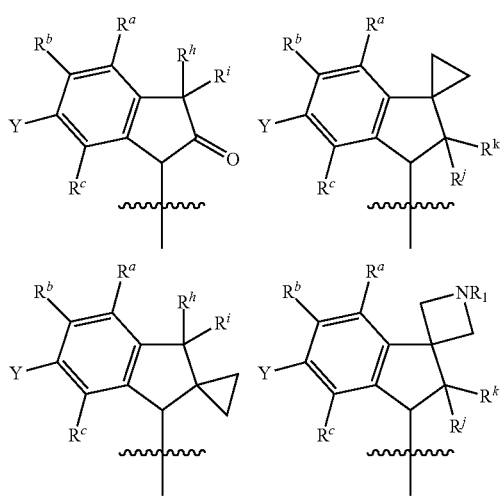

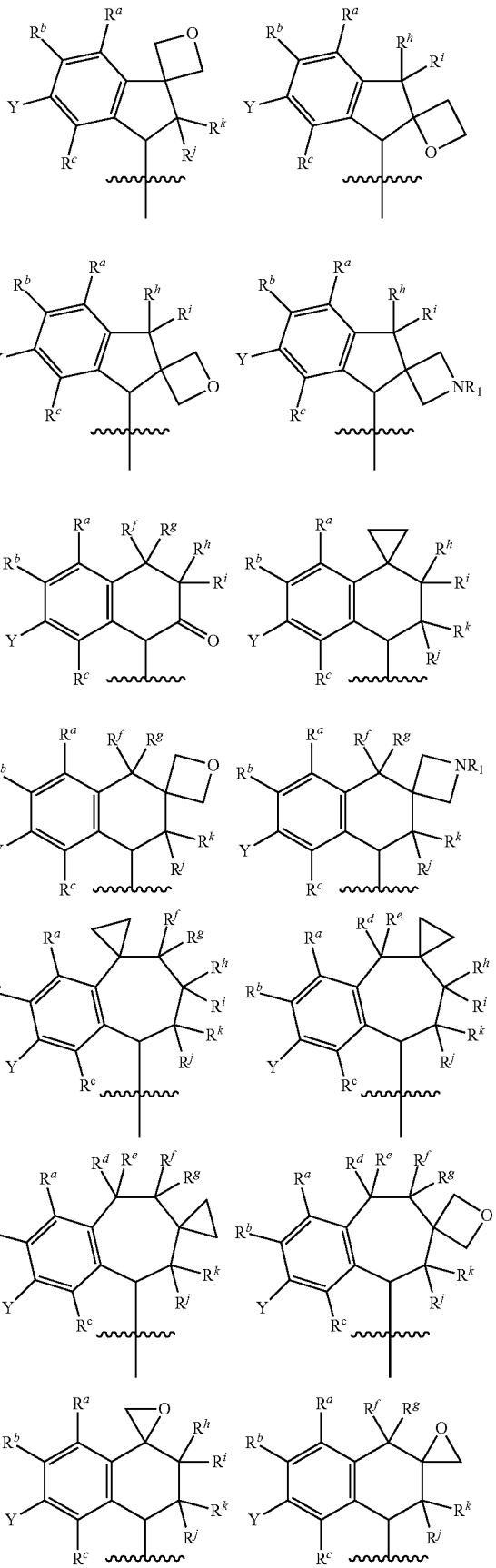

-continued

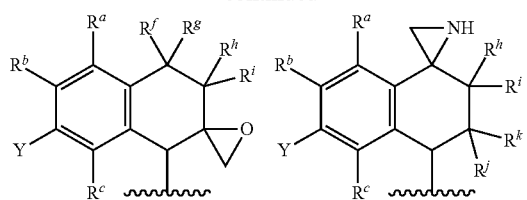

where $R^a$, $R^b$, $R^c$, $R^d$, $R^e$, $R^f$, $R^g$, $R^h$, $R^i$, $R^j$, $R^k$ and Y are as defined for Formula I. In one embodiment of the above structures, $R^a$, $R^b$, $R^c$, $R^d$, $R^e$, $R^f$, $R^g$, $R^h$, $R^i$, $R^j$, $R^k$ and Y are as defined for Formula I-2. In one embodiment of the above structures, and $R^a$, $R^b$, $R^c$, $R^d$, $R^e$, $R^f$, $R^g$, $R^h$, $R^i$, $R^j$, $R^k$ and Y are as defined for Formula I-2.

In one embodiment of Formula I, Ring A when represented by formula A-1 is selected from the structures:

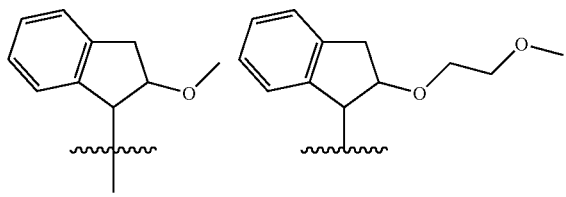

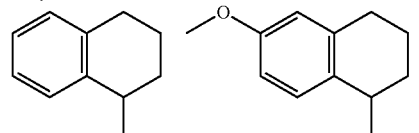

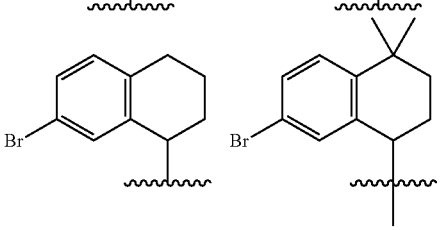

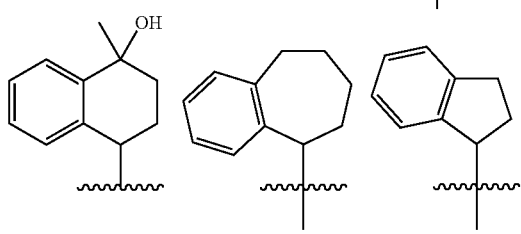

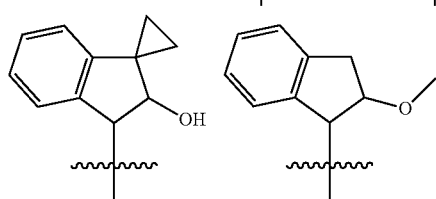

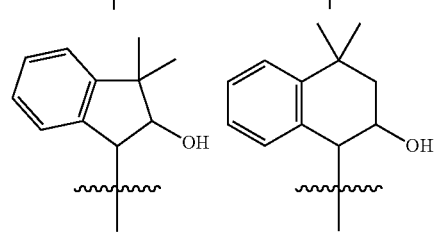

-continued

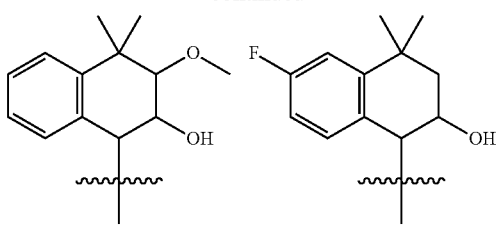

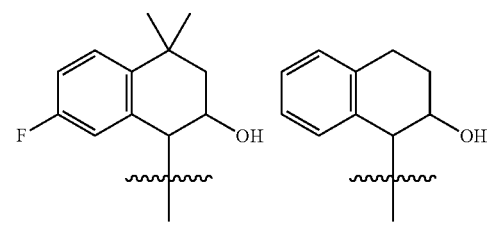

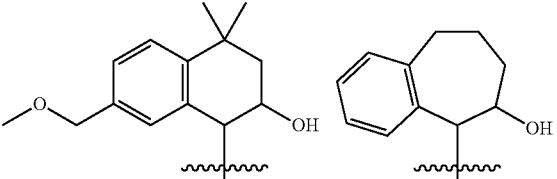

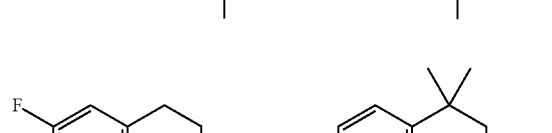

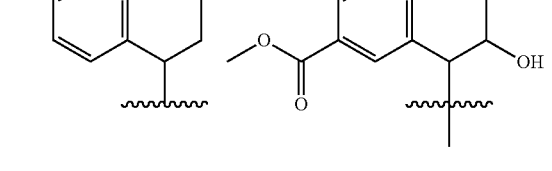

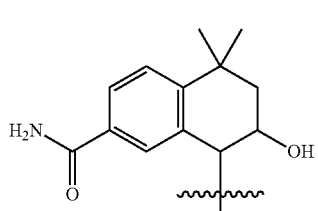

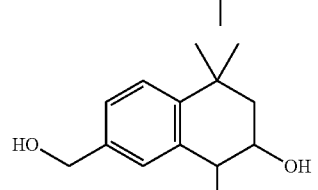

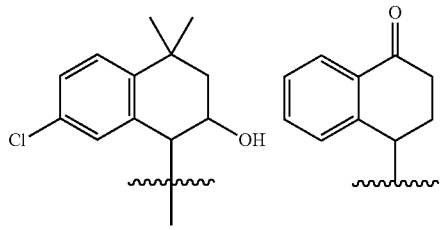

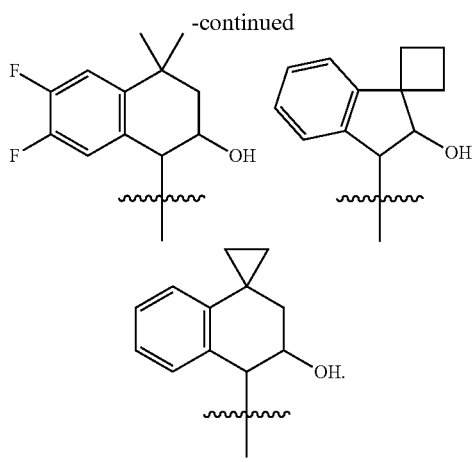

In one embodiment of Formula I, Ring A is A-1, wherein B is O, a bond or $CR^dR^e$; D is O, a bond or $CR^fR^g$; E is O, a bond or $CR^hR^i$; and F is $CR^jR^k$, provided that the ring formed by B, D, E, and F together with the atoms to which they are attached contains at least five atoms and contains one oxygen atom, where $R^d$, $R^e$, $R^f$, $R^g$, $R^h$, $R^i$, $R^j$, and $R^k$ are as defined for Formula I. Examples of such ring systems include, but are not limited to, the following structures:

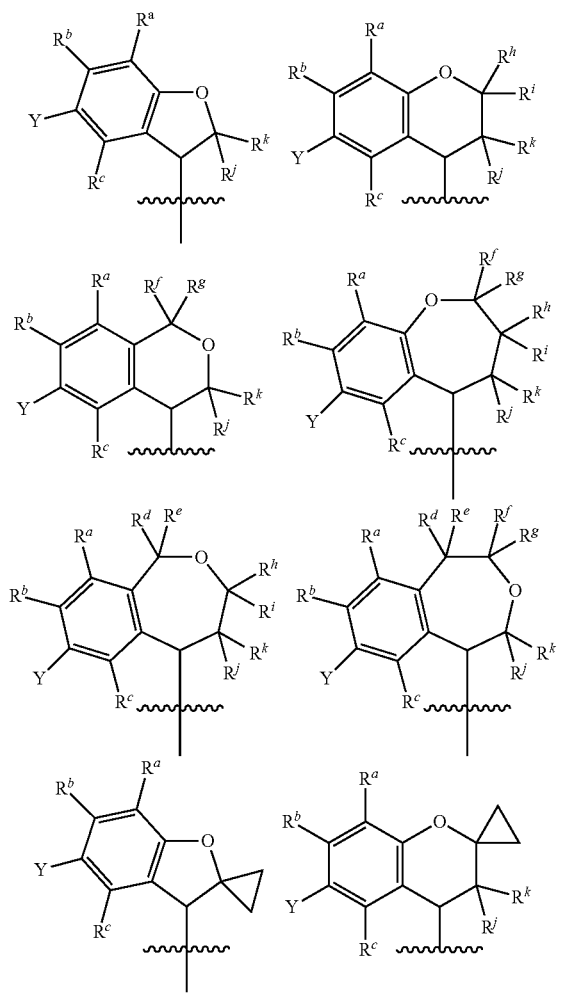

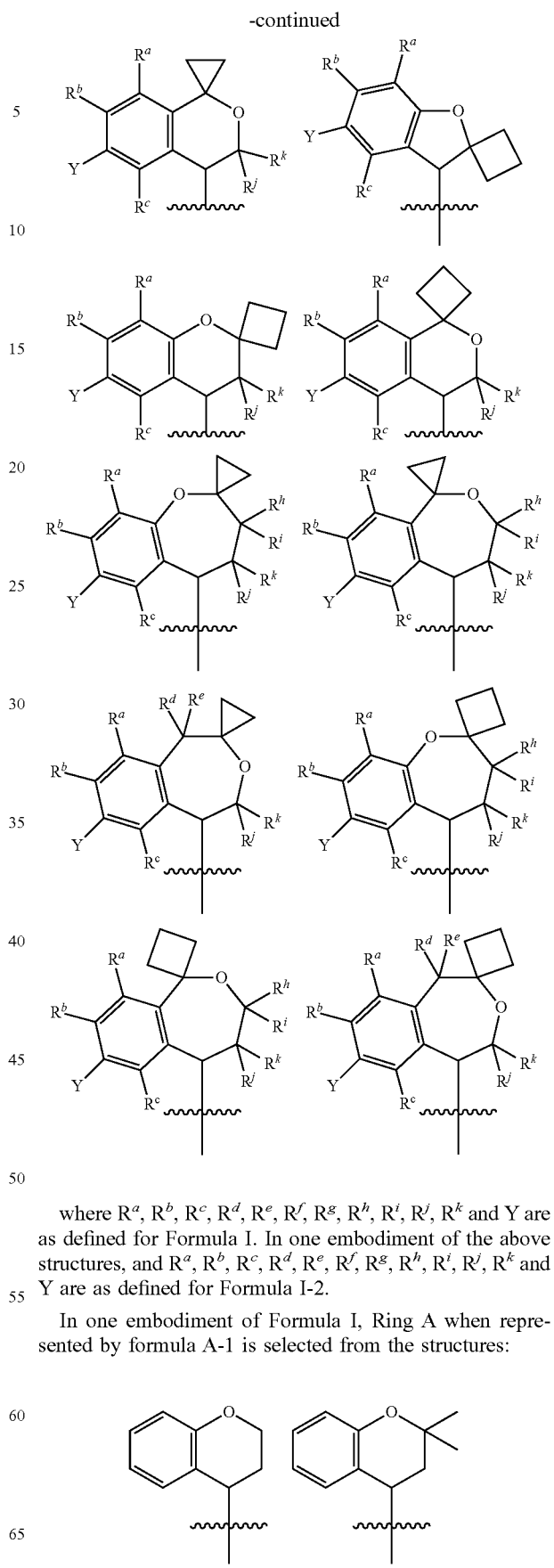

where $R^a$, $R^b$, $R^c$, $R^d$, $R^e$, $R^f$, $R^g$, $R^h$, $R^i$, $R^j$, $R^k$ and Y are as defined for Formula I. In one embodiment of the above structures, and $R^a$, $R^b$, $R^c$, $R^d$, $R^e$, $R^f$, $R^g$, $R^h$, $R^i$, $R^j$, $R^k$ and Y are as defined for Formula I-2.

In one embodiment of Formula I, Ring A when represented by formula A-1 is selected from the structures:

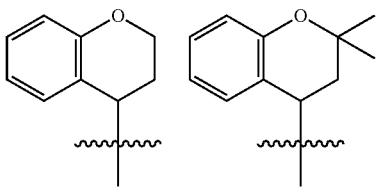

-continued

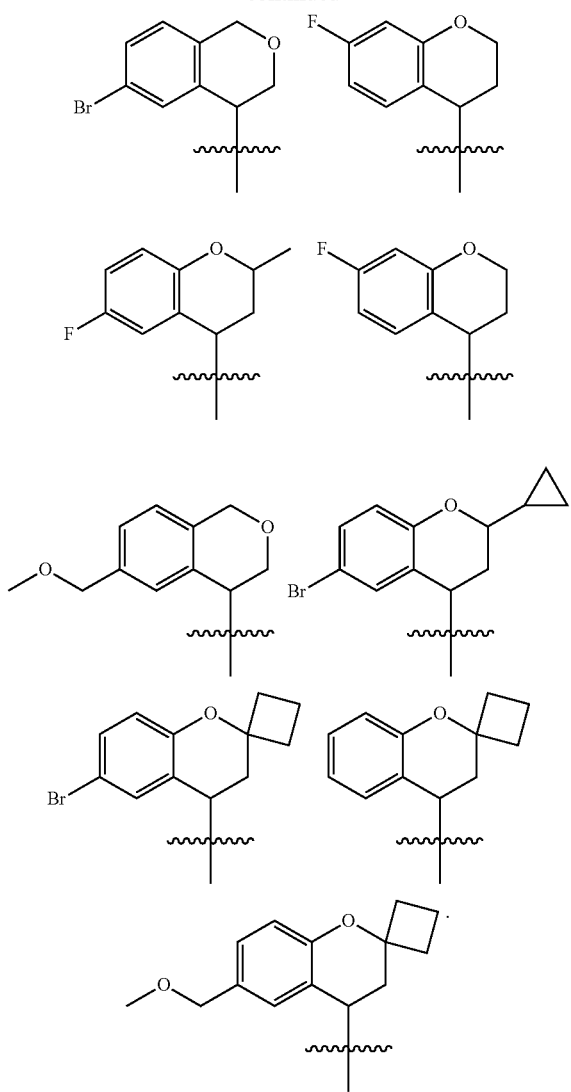

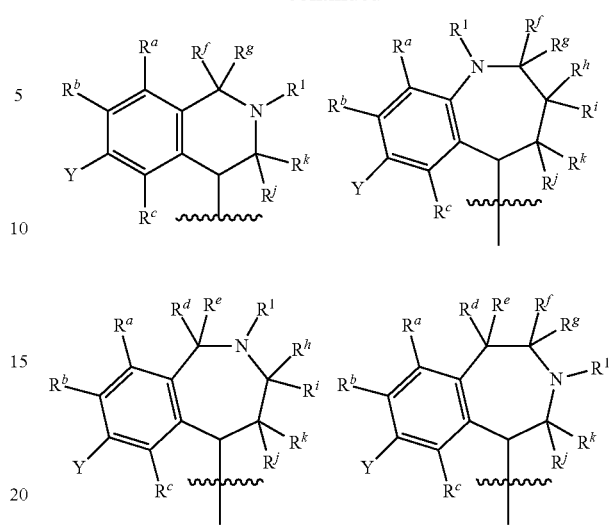

and the like, where $R^1$, $R^a$, $R^b$, $R^c$, $R^d$, $R^e$, $R^f$, $R^g$, $R^h$, $R^i$, $R^j$, $R^k$ and Y are as defined for Formula I. In one embodiment of the above structures, and $R^a$, $R^b$, $R^c$, $R^d$, $R^e$, $R^f$, $R^g$, $R^h$, $R^i$, $R^j$, $R^k$ and Y are as defined for Formula I-2.

In one embodiment of Formula I, Ring A when represented by formula A-1 is selected from the structures:

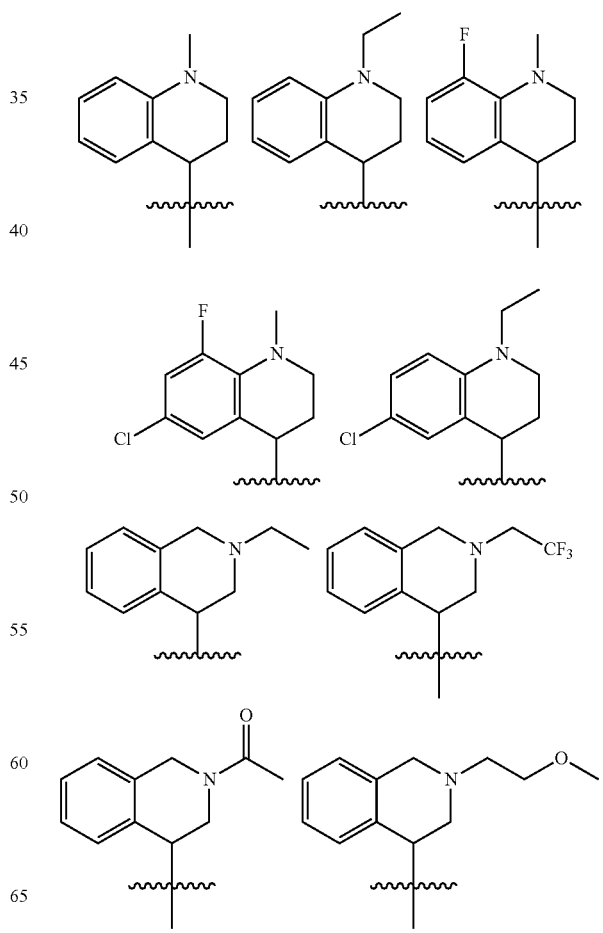

In one embodiment of Formula I, Ring A is formula A-1, wherein B is $NR^1$, a bond or $CR^dR^e$; D is $NR^1$, a bond or $CR^fR^g$; E is $NR^1$, a bond or $CR^hR^i$; and F is $CR^jR^k$, provided that the ring formed by B, D, E, and F together with the atoms to which they are attached contains at least five atoms and contains one nitrogen atom, where $R^d$, $R^e$, $R^f$, $R^g$, $R^h$, $R^i$, $R^j$, and $R^k$ are as defined for Formula I.

In one embodiment of Formula I, Ring A when represented by formula A-1 includes, but is not limited to, the following structures:

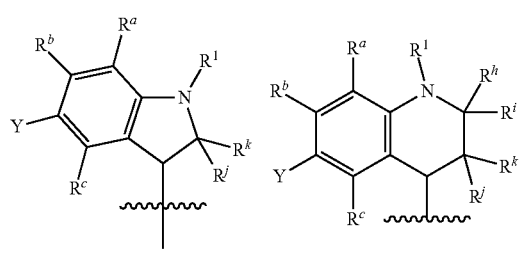

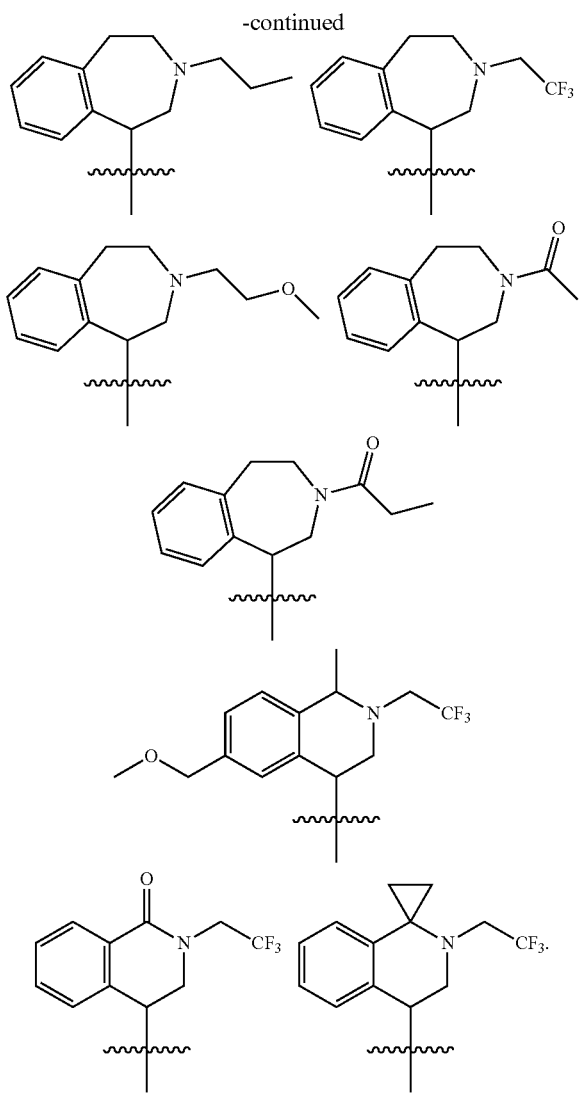

In one embodiment of Formula I, Ring A when represented by formula A-1 includes, but is not limited to, the following structures:

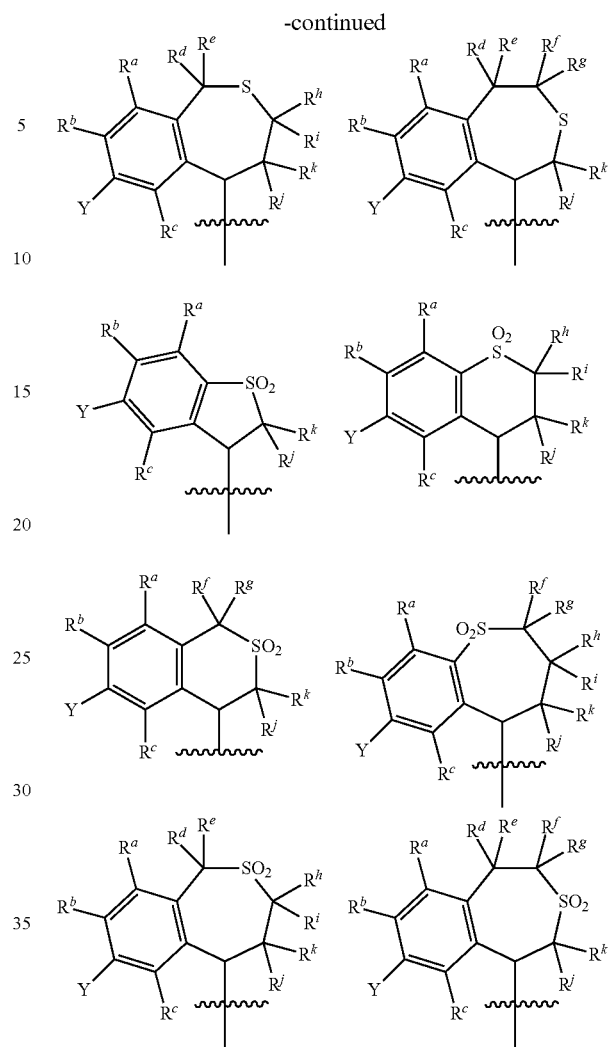

and the like, where $R^1$, $R^a$, $R^b$, $R^c$, $R^d$, $R^e$, $R^f$, $R^g$, $R^h$, $R^i$, $R^j$, $R^k$ and Y are as defined for Formula I. In one embodiment of the above structures, and $R^a$, $R^b$, $R^c$, $R^d$, $R^e$, $R^f$, $R^g$, $R^h$, $R^i$, $R^j$, $R^k$ and Y are as defined for Formula I-2.

In one embodiment of Formula I, Ring A when represented by formula A-1 is selected from the structures:

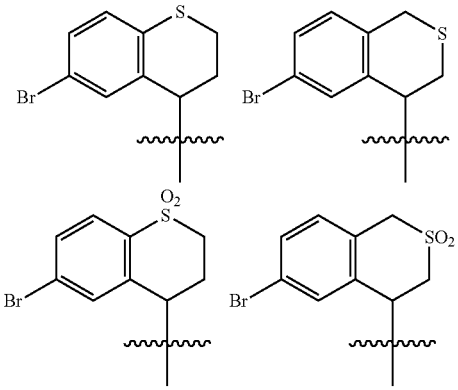

In one embodiment of Formula I, Ring A is formula A-1, wherein B is $NR^1$ or O; D is a bond or $CR^fR^g$; E is a bond or CR$^h$R$^i$; and F is CR$^j$R$^k$, provided that the ring formed by B, D, E, and F together with the atoms to which they are attached contains at least five atoms, where R$^e$, R$^f$, R$^g$, R$^h$, R$^i$, R$^j$ and R$^k$ are as defined for Formula I.

In one embodiment of Formula I, Ring A is formula A-1, wherein B is a bond or CR$^d$R$^e$; D is NR$^1$ or O; E is a bond or CR$^h$R$^i$; and F is CR$^j$R$^k$, provided that the ring formed by B, D, E, and F together with the atoms to which they are attached contains at least five atoms, where R$^d$, R$^e$, R$^h$, R$^i$, R$^j$, and R$^k$ are as defined for Formula I.

In one embodiment of Formula I, Ring A is formula A-2, where G is CR$^m$R$^n$ and K is NR$^1$, and R$^m$, R$^n$, R$^p$ and R$^1$ are as defined for Formula I.

In one embodiment of Formula I, Ring A is formula A-2, where G is CR$^m$R$^n$ and K is NR$^1$; R$^m$ is H, (1-3C)alkyl [optionally substituted with 1-5 fluoros], cyclopropyl or cyclobutyl; R$^n$ is H or (1-3C)alkyl [optionally substituted with 1-5 fluoros]; and R$^1$ and R$^p$ are as defined for Formula I.

In one embodiment of Formula I, Ring A is formula A-2, where G is CR$^m$R$^n$ and K is NR$^1$; R$^m$ and R$^n$ together form an oxo group; and R$^1$ and R$^p$ are as defined for Formula I.

In one embodiment of Formula I, Ring A when represented by formula A-2 is selected from the structures:

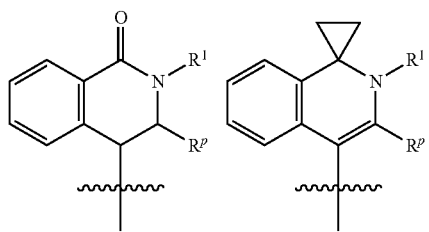

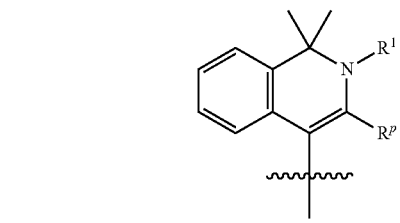

and the like, where R$^1$ and R$^p$ are as defined for Formula I.

In one embodiment of Formula I, Ring A when represented by formula A-2

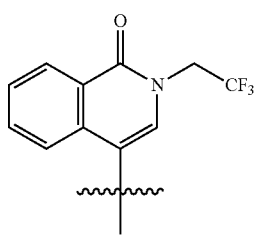

Reference will now be made to Ring C.
In one embodiment, Ring C is formula C-1:

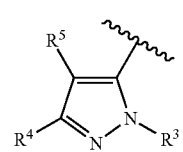

C-1 where R$^3$, R$^4$ and R$^5$ are as defined for Formula I.

In one embodiment, R$^3$ is (1-6C)alkyl. In one embodiment, R$^3$ is methyl or ethyl.

In one embodiment, R$^3$ is hydroxy(1-6C)alkyl. An example of R$^3$ is 2-hydroxyethyl.

In one embodiment, R$^3$ is Ar$^2$, where Ar$^2$ is phenyl optionally substituted with one or more groups independently selected from halogen and (1-6C)alkyl.

In one embodiment, R$^3$ when represented by Ar$^2$ is phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, R$^3$ when represented by Ar$^2$ is phenyl, 2-fluorophenyl, 3-fluorophenyl, 4-fluorophenyl, 2-methylphenyl, 3-methylphenyl or 4-methylphenyl. In one embodiment, R$^3$ is phenyl.

In one embodiment, R$^3$ is hetCyc$^1$, where hetCyc$^1$ is a 5-6-membered saturated or partially unsaturated heterocyclic ring having 1-2 ring heteroatoms independently selected from N and O. In one embodiment, R$^3$ is a pyrrolidinyl, tetrahydrofuranyl, imidazolidinyl, piperidinyl, piperazinyl, tetrahydropyranyl, or morpholinyl ring. In one embodiment, R$^3$ is tetrahydro-2H-pyran-4-yl.

In one embodiment, R$^3$ is (3-7C)cycloalkyl. In one embodiment R$^3$ is cyclohexyl.

In one embodiment, R$^3$ is hetAr$^2$, where hetAr$^2$ is 5-6 membered heteroaryl ring having 1-3 ring heteroatoms independently selected from N, O and S and optionally substituted with one or more substituents independently selected from (1-6C)alkyl and halogen. In one embodiment, R$^3$ is thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, R$^3$ is pyrazolyl, pyridyl or pyridazinyl optionally substituted with one or more groups independently selected from (1-6C)alkyl and halogen. In one embodiment, R$^3$ is pyrazolyl, pyridyl or pyridazinyl optionally substituted with (1-6C)alkyl or halogen. In one embodiment, R$^3$ when represented by hetAr$^2$ is 1-methyl-1H-pyrazol-4-yl, pyrid-2-yl, pyrid-3-yl, pyrid-4-yl, pyridazinyl or 3-chloropyrid-5-yl.

In one embodiment, R$^3$ is selected from Ar$^2$ and hetAr$^2$.
In one embodiment, R$^3$ is Ar$^2$. In one embodiment, R$^3$ is phenyl.

In one embodiment, R$^4$ is OH. An examples of a C-1 ring when R$^4$ is OH includes the following tautomeric structures:

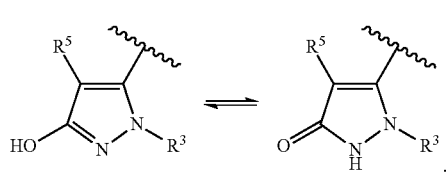

In one embodiment, R$^4$ is (1-6C)alkyl. In one embodiment, R$^4$ is methyl, ethyl, isopropyl or tert-butyl.

In one embodiment, R⁴ is monofluoro(1-6C)alkyl, difluoro(1-6C)alkyl, trifluoro(1-6C)alkyl, tetrafluoro(2-6C)alkyl or pentafluoro(2-6C)alkyl. In one embodiment, R⁴ is fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl or 2,2,3,3,3-pentafluoropropyl.

In one embodiment, R⁴ is trifluoro(1-6C)alkyl. In one embodiment, R⁴ is CF₃.

In one embodiment, R⁴ is cyano(1-6C)alkyl. In one embodiment, R⁴ is cyanomethyl or 2-cyanopropan-2-yl.

In one embodiment, R⁴ is hydroxy(1-6C)alkyl. In one embodiment, R⁴ is hydroxymethyl, 2-hydroxyethyl, 2-hydroxypropyl, 2-hydroxy-2-methylpropyl or 1-hydroxy-2-methylpropan-2-yl.

In one embodiment, R⁴ is dihydroxy(2-6C)alkyl. In one embodiment, R⁴ is 2,3-dihydroxypropyl.

In one embodiment, R⁴ is (1-3C alkoxy)(1-6C)alkyl. In one embodiment, R⁴ is methoxymethyl, 2-methoxyethyl or 3-methoxypropyl.

In one embodiment, R⁴ is amino(1-6C)alkyl. In one embodiment, R⁴ is aminomethyl, 2-aminoethyl or 3-aminopropyl.

In one embodiment, R⁴ is aminocarbonyl(1-6C)alkyl. In one embodiment, R⁴ is aminocarbonylmethyl and 2-(aminocarbonyl)ethyl.

In one embodiment, R⁴ is (1-3C)alkylsulfonamido(1-6C) alkyl. In one embodiment, R⁴ is CH₃SO₂NHCH₂— or CH₃SO₂NHCH₂CH₂—.

In one embodiment, R⁴ is hydroxycarbonyl(1-6C)alkyl. In one embodiment, R⁴ is HOC(=O)CH₂— and HOC(=O)CH₂CH₂—.

In one embodiment, R⁴ is hetAr³(1-6C)alkyl, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, R⁴ when represented by hetAr³(1-6C)alkyl is (1-methyl-1H-1,2,4-triazol-3-yl)methyl or (5-methyl-1,3,4-oxadiazol-2-yl)methyl.

In one embodiment, R⁴ is Ar³(1-6C)alkyl, where phenyl optionally substituted with (1-4C)alkoxy or hydroxy(1-4C) alkyl. In one embodiment, Ar³(1-6C)alkyl is benzyl.

In one embodiment, R⁴ is (1-6C)alkoxy. Examples include methoxy and ethoxy.

In one embodiment, R⁴ is monofluoro(1-6C)alkoxy, difluoro(1-6C)alkoxy trifluoro(1-6C)alkoxy, tetrafluoro(2-6C) alkoxy or pentafluoro(2-6C)alkoxy. In one embodiment, R⁴ is fluoromethoxy, 2-fluoroethoxy, 2,2-difluoromethoxy, trifluoromethoxy, 2,2,2-trifluoroethoxy or 2,2-difluoroethoxy. In one embodiment, R⁴ is 2-fluoroethoxy.

In one embodiment, R⁴ is cyano(1-6C)alkoxy. In one embodiment, R⁴ is cyanomethoxy or 2-cyanoethoxy.

In one embodiment, R⁴ is hydroxy(1-6C)alkoxy. In one embodiment, R⁴ is 2-hydroxy-2-methylpropoxy, 2-hydroxyethoxy, 2-hydroxypropoxy, 2-hydroxy-2-methylpropoxy or 2-hydroxybutoxy.

In one embodiment, R⁴ is dihydroxy(2-6C)alkoxy. In one embodiment, R⁴ is 2,3-dihydroxypropoxy or 3-hydroxy-2-(hydroxymethyl)propoxy.

In one embodiment, R⁴ is amino(2-6C)alkoxy. In one embodiment, R⁴ is H₂NCH₂CH₂O— or (CH₃)₃NCH₂CH₂O—.

In one embodiment, R⁴ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, R⁴ when represented by hetCyc²(1-6C)alkoxy is oxetan-2-ylmethoxy, 2-(oxetan-2-yl)propoxy, (2,2-dimethyl-1,3-dioxolan-4-yl)methoxy, (1,3-dioxolan-4-yl)methoxy, 2-morpholinoethoxy, 2-morpholinomethoxy, piperazinylethyoxy, piperidinylethoxy or piperidinylmethoxy optionally substituted with 1-2 groups independently selected from (1-6C)alkyl, (1-4C alkoxy) carbonyl and (1-6C)acyl. In one embodiment, R⁴ is represented by the structures:

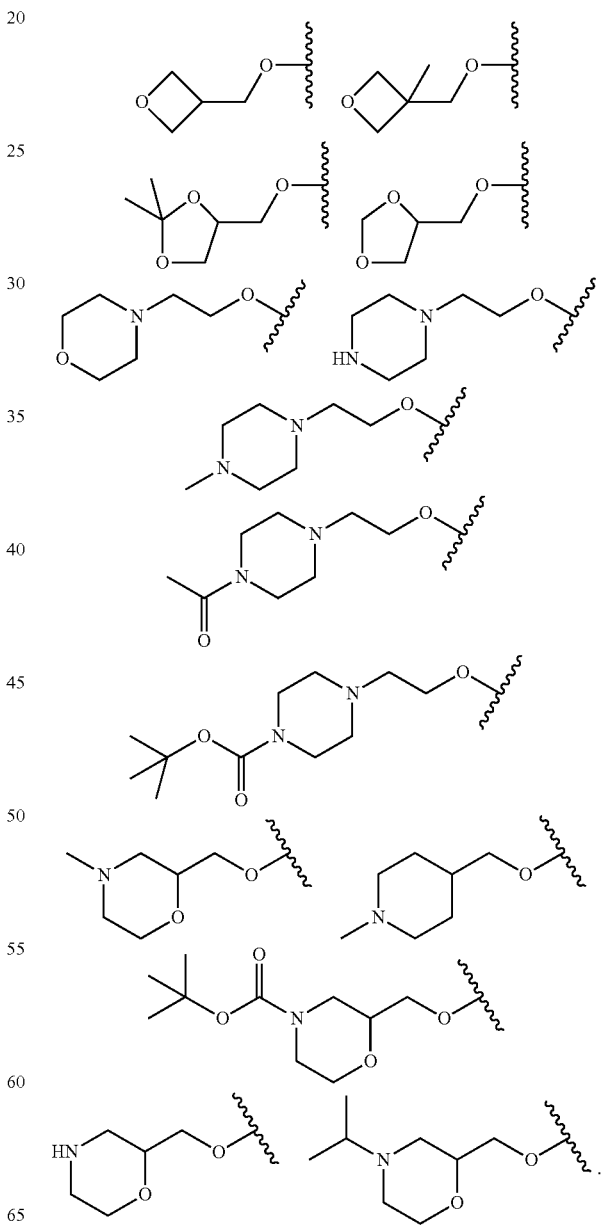

In one embodiment, R⁴ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. In one embodiment, R⁴ when represented by hetAr³(1-6C)alkoxy is (1-methyl-1H-1,2,4-triazol-3-yl) methoxy or (5-methyl-1,3,4-oxadiazol-2-yl)methoxy, which can be represented by the structures:

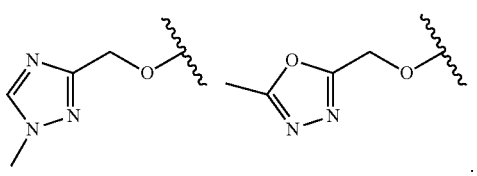

In one embodiment, R⁴ is Ar³(1-6C)alkoxy, where Ar³ is phenyl optionally substituted with (1-4C)alkoxy. In one embodiment, R⁴ is phenylmethoxy or (4-methoxyphenyl) methoxy having the structures:

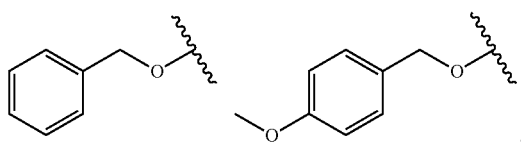

In one embodiment, R⁴ is (1-4C alkoxy)(1-6C)alkoxy. In one embodiment, R⁴ is (2-methoxy)ethoxy having the structure:

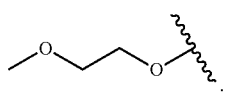 [SMILES: *OCCOC]

In one embodiment, R⁴ is (1-3Calkylsulfonyl)(1-6C) alkoxy. In one embodiment, R⁴ is (2-methylsulfonyl)ethoxy having the structure:

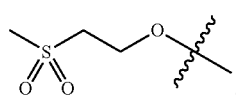

In one embodiment, R⁴ is (3-6C)cycloalkyl optionally substituted with F, OH, (1-6C alkyl), (1-6C)alkoxy or (1-3C alkoxy)(1-6C)alkyl. Examples include cyclopropyl, cyclobutyl, cyclopentyl, cyclohexyl, 2-hydroxycyclobutyl. In one embodiment, R⁴ is cyclopropyl or 2-hydroxycyclobutyl. In one embodiment, R⁴ is cyclopropyl.

In one embodiment, R⁴ is hetAr⁴, where hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C) alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C) alkoxy, (1-6C)alkylsulfonyl, NH₂, (1-6C alkyl)amino, di(1-6C alkyl)amino, (1-3C trifluoroalkoxy), fluoro(1-6C alkyl) amino, difluoro(1-6C alkyl)amino, trifluoro(1-6C alkyl) amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C) alkyl, halogen, CN, hydroxy(1-6C)alkyl, trifluoro(1-6C) alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C) alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy)(1-3C)tri fluoroalkyl and cyclopropylNH—.

In one embodiment, R⁴ is hetAr⁴, where hetAr⁴ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ is hetAr⁴, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—.

In one embodiment, R⁴ when represented by hetAr⁴ is selected from the structures:

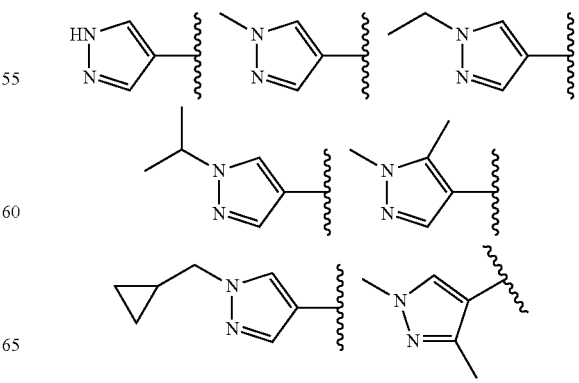

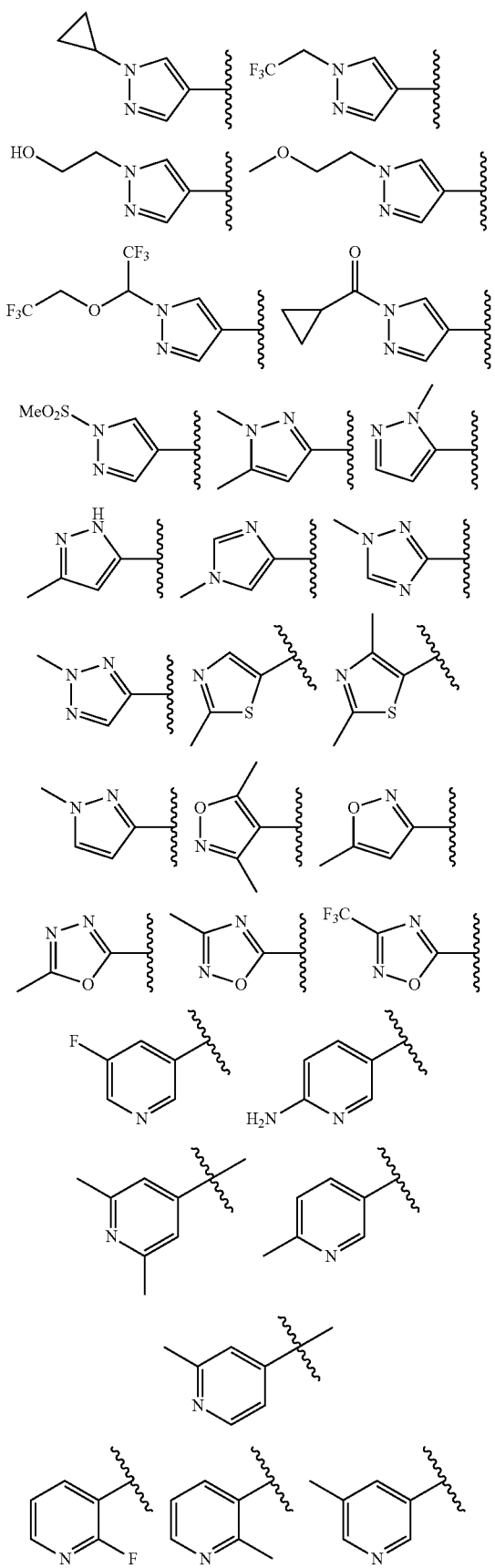
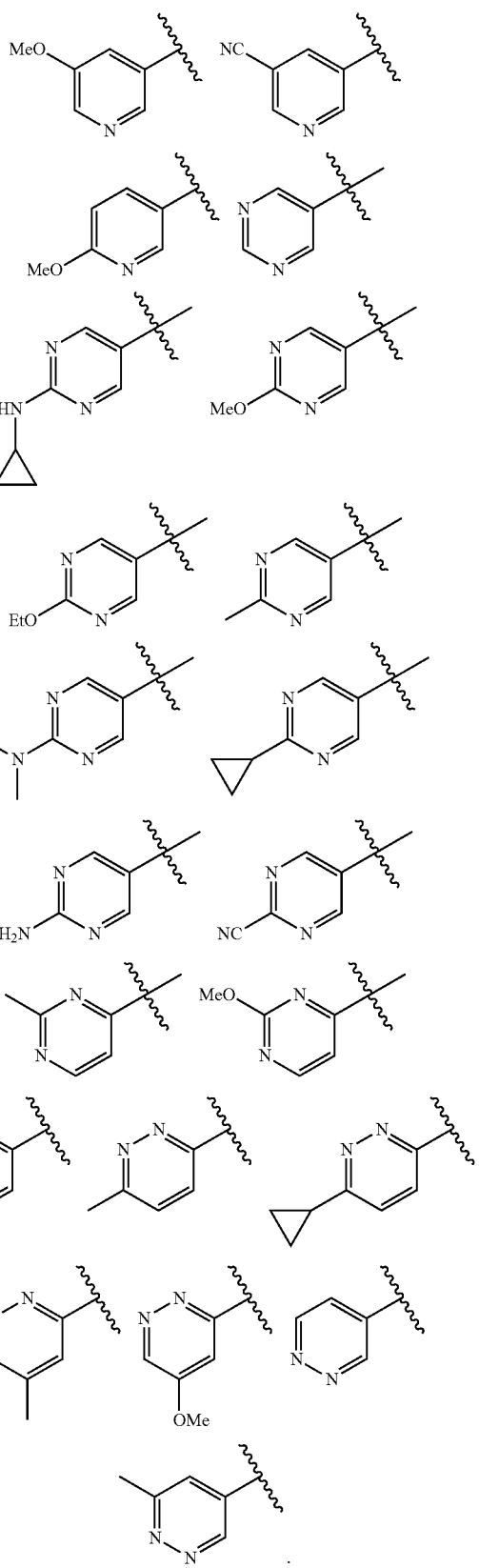
In one embodiment, $R^4$ is hetAr$^4$—O—. In one embodiment, $R^4$ is the structure:

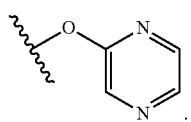 [SMILES: *Oc1cnccn1]

In one embodiment, R⁴ is Ar⁴, where Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—. In one embodiment, Ar⁴ is phenyl optionally substituted with one or more groups independently selected from methyl, F, Cl, CN, methoxy, CH₃OC(=O)—, aminocarbonyl, methylaminocarbonyl, dimethylaminocarbonyl, methylthio, CH₃SO₂—, HOC(=O)— and CH₃OCH₂CH₂OC(=O)—. In one embodiment, Ar⁴ is phenyl optionally substituted with one or two of said substituents. In one embodiment, Ar⁴ is selected from the structures:

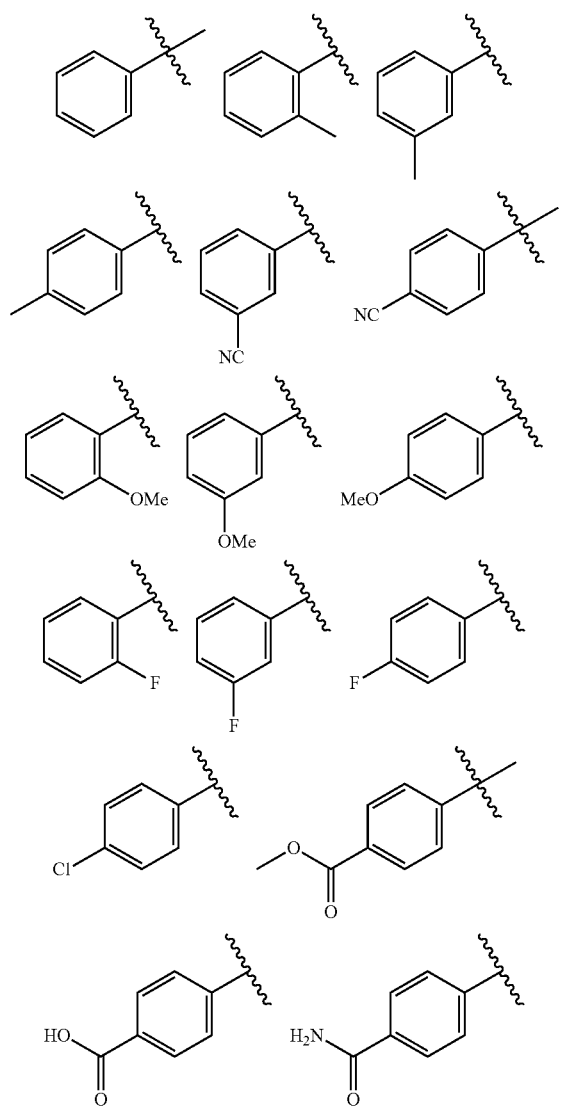

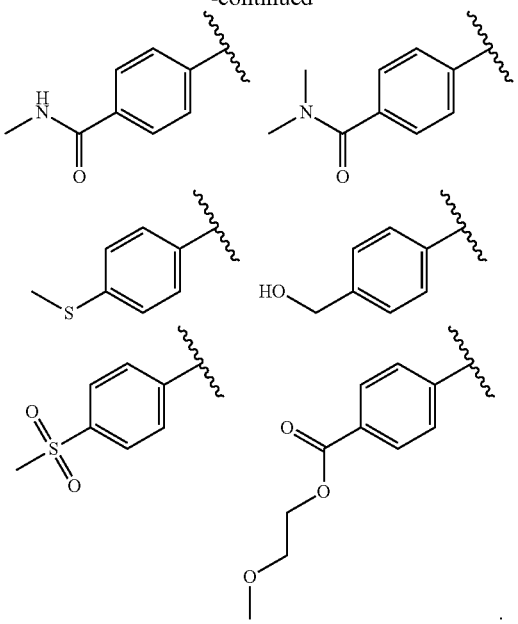

In one embodiment, R⁴ is hetCyc²(O)CH₂, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, R⁴ when represented by hetCyc²(O)CH₂, is selected from the structures:

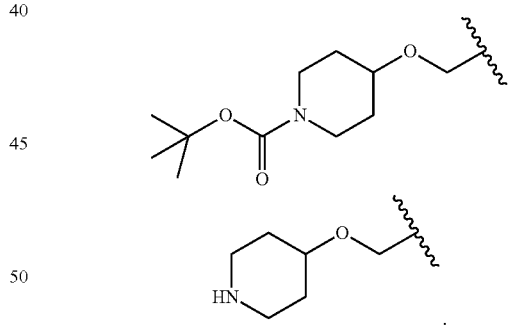

In one embodiment, R⁴ is (1-4C alkoxycarbonyl)(1-6C)alkoxy. In one embodiment, R⁴ is methoxycarbonyl(1-6C)alkoxy or ethylcarbonyl(1-6C)alkoxy. A particular example is ethoxycarbonylmethoxy.

In one embodiment, R⁴ is hydroxycarbonyl(1-6C)alkoxy. In one embodiment, R⁴ is hydroxycarbonylmethoxy.

In one embodiment, R⁴ is aminocarbonyl(1-6C)alkoxy. In one embodiment, R⁴ is H₂NC(=O)(1-6C)alkoxy, (1-6C alkyONHC(=O)(1-6C)alkoxy, or di(1-6Calkyl)NC(=O)(1-6C)alkoxy. In one embodiment, R⁴ is H₂NC(=O)CH₂O—, H₂NC(=O)CH₂CH₂O, or CH₃CH₂NC(=O)CH₂O—.

In one embodiment, R⁴ is hetCyc²C(=O)(1-6C)alkoxy, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O)(1-6C)alkoxy is the structure:

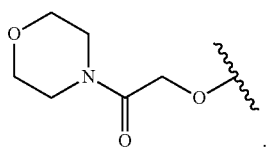 [SMILES: *OCC(=O)N1CCOCC1]

In one embodiment, R⁴ is hydroxy(1-3C alkoxy)(1-6C)alkoxy. In one embodiment, R⁴ is 2-hydroxy-3-methoxypropoxy, having the structure:

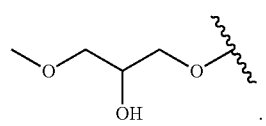 [SMILES: *OCC(O)COC]

In one embodiment, R⁴ is hydroxytrifluoro(1-6C)alkoxy. In one embodiment, R⁴ is 3,3,3-difluoro-2-hydroxypropoxy having the structure:

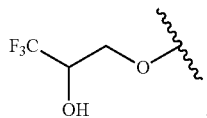

In one embodiment, R⁴ is (1-3C)alkylsulfonamido(1-6C)alkoxy. In one embodiment, R⁴ is methanesulfonamido(1-6C)alkoxy. In one embodiment, R⁴ is 2-methanesulfonamidoethoxy having the structure:

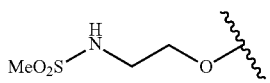

In one embodiment, R⁴ is (1-3C)alkylamido(1-6C)alkoxy. In one embodiment, R⁴ is 2-(methylamido)ethoxy having the structure:

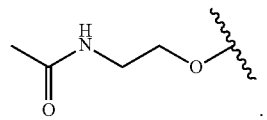 [SMILES: *OCCNC(C)=O]

In one embodiment, R⁴ is di(1-3C alkyl)aminocarboxy. In one embodiment, R⁴ is dimethylaminocarboxy having the structure:

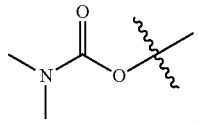

In one embodiment, R⁴ is hetCyc²C(=O)O—, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O)O— is the structure:

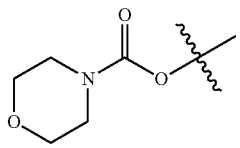

In one embodiment, R⁴ is hydroxydifluoro(1-6C)alkyl. In one embodiment, R⁴ is 2,2-difluro-2-hydroxyethyl.

In one embodiment, R⁴ is (1-4C alkylcarboxy)(1-6C)alkyl. In one embodiment, R⁴ is methylcarboxy(1-6C)alkyl. In one embodiment, R⁴ is 2-(methylcarboxy)ethyl.

In one embodiment, R⁴ is (1-6C)alkoxycarbonyl. In one embodiment, R⁴ is methoxycarbonyl or ethoxycarbonyl.

In one embodiment, R⁴ is hydroxycarbonyl.

In one embodiment, R⁴ is aminocarbonyl, that is, a RR'NCO— radical where R and R' are independently hydrogen or (1-6C)alkyl as defined herein. In one embodiment, R⁴ is aminocarbonyl, methylaminocarbonyl, dimethylaminocarbonyl, ethylcarbonyl or isopropylaminocarbonyl.

In one embodiment, R⁴ is (1-3C alkoxy)aminocarbonyl. In one embodiment, R⁴ is methoxyaminocarbonyl.

In one embodiment, R⁴ is hetCyc³, where is a 4-7 membered heterocycle having 1-2 ring heteroatoms independently selected from N and O and optionally substituted with one or more substituents independently selected from F, CN, CF₃, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is tetrahydropyranyl, piperidinyl, pyrrolidinyl or azetidinyl optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is optionally substituted with one or two of said substituents. In one embodiment, hetCyc³ is tetrahydropyranyl, piperidinyl, pyrrolidinyl or azetidinyl optionally substituted with CN, Me, CH₃C(=O)—, MeSO₂—, or CF₃SO₂—. In one embodiment, R⁴ when represented by hetCyc³ is selected from the structures:

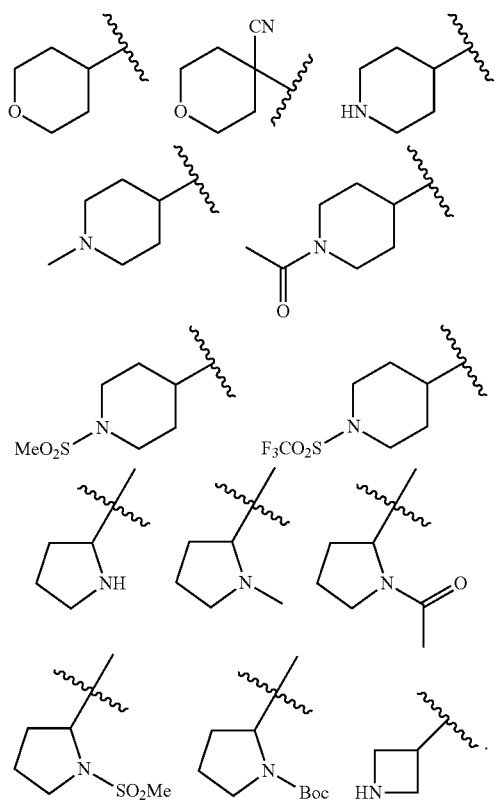

In one embodiment, R⁴ is halogen. In one embodiment, R⁴ is Br.

In one embodiment, R⁴ is CN.

In one embodiment, R⁴ is trifluoromethylsulfonyl.

In one embodiment, R⁴ is hetAr⁵, where hetAr⁵ is a group selected from the structures:

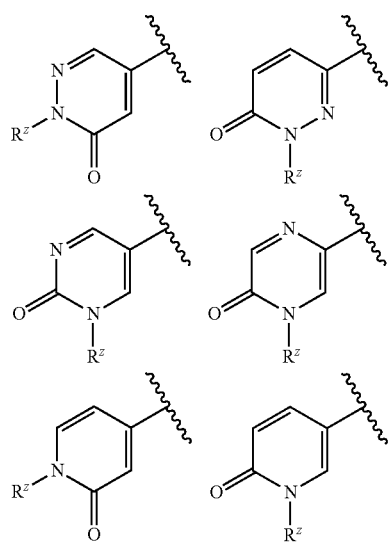

where R$^z$ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros.

In one embodiment, R⁴ when represented by hetAr⁵ is selected from the structures:

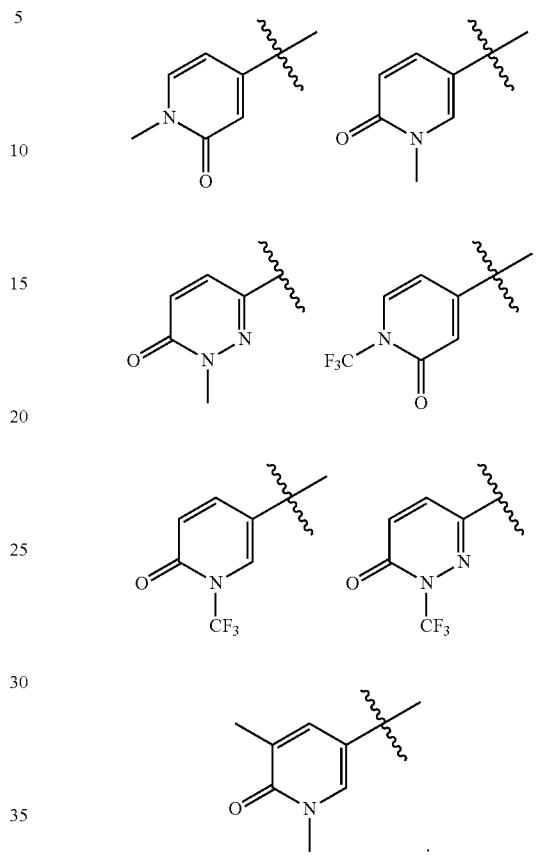

In one embodiment, R⁴ is N-(1-3C alkyl)oxadiazolonyl.
In one embodiment, R⁴ is represented by the structures:

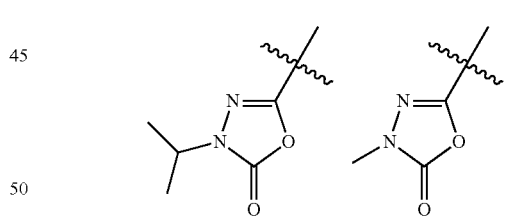

In one embodiment, R⁴ is selected from H, (1-6C)alkyl, trifluoro(1-6C)alkyl, hydroxy(1-6C)alkyl, cyano(1-6C)alkyl, (1-3C alkoxy)(1-6C)alkyl, (1-6C)alkoxy, monofluoro(1-6C)alkoxy, cyano(1-6C)alkoxy, hydroxy(1-6C)alkoxy, dihydroxy(2-6C)alkoxy, hetCyc²(1-6C)alkoxy, Ar³ (1-6C)alkoxy, (1-4C alkoxy)(1-6C)alkoxy, (1-3C alkylsulfonyl)(1-6C)alkoxy, (3-6C)cycloalkyl, hetAr⁴, hetAr⁴—O—, Ar⁴, and hetAr⁵.

In one embodiment, R⁴ is hetAr⁴, Ar⁴, or hetAr⁵.

In one embodiment, R⁴ is hetAr⁴ or hetAr⁵.

In one embodiment, R⁴ is pyrazolyl optionally substituted with one or more groups independently selected from (1-6C)alkyl, or a hetAr⁵ group having the structure:

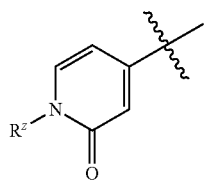

where $R^z$ is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros.

In one embodiment, $R^5$ is (1-6C)alkyl. In one embodiment, $R^5$ is methyl, ethyl, propyl, isopropyl or butyl.

In one embodiment, $R^5$ is monofluoro(1-6C)alkyl, difluoro(1-6C)alkyl, trifluoro(1-6C)alkyl, tetrafluoro(2-6C)alkyl or pentafluro(2-6C)alkyl. In one embodiment, $R^5$ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane or 2,2,3,3,3-pentafluoropropyl.

In one embodiment, $R^5$ is halogen. In one embodiment, $R^5$ is F. In one embodiment, $R^5$ is Cl. In one embodiment, $R^5$ is Br.

In one embodiment, $R^5$ is CN.

In one embodiment, $R^5$ is (1-4C)alkoxy. In one embodiment, $R^5$ is methoxy or ethoxy.

In one embodiment, $R^5$ is hydroxy(1-4C)alkyl. In one embodiment, $R^5$ is hydroxymethyl or 3-hydroxypropyl.

In one embodiment, $R^5$ is (1-4C alkyl)OC(=O)—. In one embodiment, $R^5$ is $CH_3CH_2OC(=O)$—.

In one embodiment, $R^5$ is (1-6C)alkylthio. In one embodiment, $R^5$ is methylthio (MeS—).

In one embodiment, $R^5$ is phenyl optionally substituted with one or more groups independently selected from halogen, (1-6C)alkyl and (1-6C)alkoxy. In one embodiment, $R^5$ is phenyl optionally substituted with one or more groups independently selected from F, Cl, methyl, ethyl, methoxy and ethoxy. In one embodiment, $R^5$ is phenyl.

In one embodiment, $R^5$ is (3-4C)cycloalkyl. In one embodiment, $R^5$ is cyclopropyl. In one embodiment, $R^5$ is cyclobutyl.

In one embodiment, $R^5$ is amino. In one embodiment, $R^5$ is $NH_2$.

In one embodiment, $R^5$ is aminocarbonyl. In one embodiment, $R^5$ is $H_2NC(=O)$—.

In one embodiment, $R^5$ is trifluoro(1-3C alkyl)amido. In one embodiment, $R^5$ is $CF_3C(=O)NH$—.

In one embodiment, $R^5$ is halogen, CN, (1-6C)alkyl, (1-4C)alkoxy, hydroxy(1-4C)alkyl, or phenyl optionally substituted with one or more groups independently selected from halogen, (1-6C)alkyl and (1-6C)alkoxy.

In one embodiment, $R^5$ is selected from halogen, and (1-6C)alkyl.

In one embodiment, $R^5$ is selected from methyl, Cl and Br.

In one embodiment of Formula I, $R^4$ is selected from H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C) cycloalkyl, hetAr⁴, Ar⁴, and hetAr⁵; and $R^5$ is selected from halogen, CN, (1-6C)alkyl, (1-4C)alkoxy, hydroxy(1-4C) alkyl, (1-6C)alkylthio, and phenyl optionally substituted with one or more groups independently selected from halogen, (1-6C)alkyl and (1-6C)alkoxy.

In one embodiment of Formula I, $R^4$ is selected from hetAr⁴, Ar⁴, and hetAr⁵; and $R^5$ is selected from (1-6C)alkyl.

In one embodiment of Formula I, $R^4$ is selected from hetAr⁴ and hetAr⁵; and $R^5$ is selected from (1-6C)alkyl.

In one embodiment of Formula I, $R^4$ is hetAr⁴ and $R^5$ is selected from (1-6C)alkyl.

In one embodiment of Formula I, $R^4$ is pyrazolyl optionally substituted with one or more substituents independently selected from (1-6C)alkyl; and $R^5$ is selected from (1-6C) alkyl.

In one embodiment of Formula I, $R^4$ is hetAr⁵; and $R^5$ is selected from (1-6C)alkyl.

In one embodiment of Formula I, $R^4$ is a hetAr⁵ group having the structure:

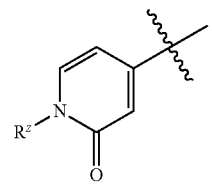

where $R^z$ is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros; and $R^5$ is selected from (1-6C) alkyl.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl; or $R^4$ and $R^5$ together with the atoms to which they are attached form a 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl. In one embodiment, Ring C when $R^4$ and $R^5$ together with the atoms to which they are attached form a 5-6 membered saturated or unsaturated carbocyclic ring is selected from the structures:

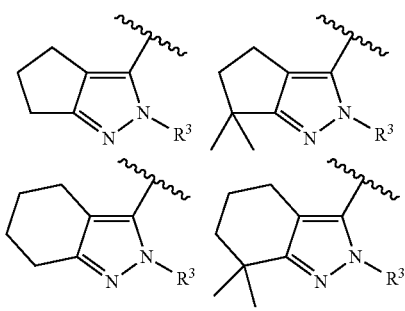

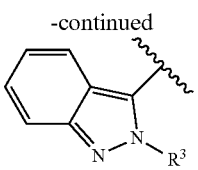

where R³ is as defined for Formula I. In one embodiment of said structures, R³ is phenyl.

In one embodiment, R⁴ and R⁵ together with the atoms to which they are attached form a 5-6 membered saturated carbocyclic ring optionally substituted with one or more substituents independently selected from (1-6C)alkyl, or R⁴ and R⁵ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6C)acyl, and said sulfur ring atom is optionally oxidized to S(=O) or SO₂.

In one embodiment, R⁴ and R⁵ together with the atoms to which they are attached form a 5-6 membered saturated carbocyclic ring optionally substituted with one or more substituents independently selected from (1-6C)alkyl. In one embodiment, Ring C when R⁴ and R⁵ together with the atoms to which they are attached form a 5-6 membered saturated carbocyclic ring is selected from the structures:

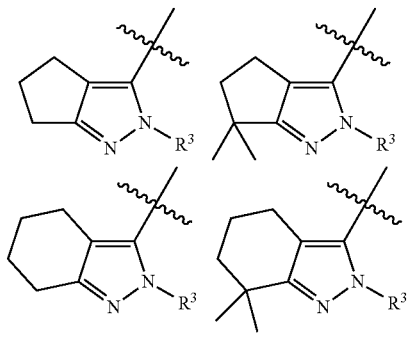

where R³ is as defined for Formula I. In one embodiment of said structures, R³ is phenyl.

In one embodiment, R⁴ and R⁵ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O)O—, (1-6C alkyl)C(=O)—, (1-6C)alkyl or oxo, and said S ring atom is optionally oxidized to S(=O) or SO₂. In one embodiment, Ring C when R⁴ and R⁵ together with the atoms to which they are attached form a 5-6 membered saturated heterocyclic ring is selected from the structures:

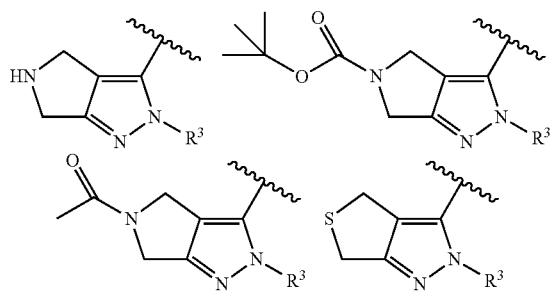

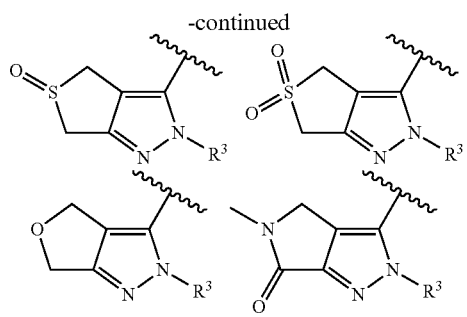

where R³ is as defined for Formula I. In one embodiment of said structures, R³ is phenyl.

In one embodiment, R⁴ and R⁵ together with the atoms to which they are attached form a 5-6 membered saturated heterocyclic ring having a ring heteroatom selected from N, O or S, wherein said ring N atom is optionally substituted with (1-6C alkyl)C(=O)O— or (1-6C alkyl)C(=O)—, and said S ring atom is optionally oxidized to S(=O) or SO₂. In one embodiment, Ring C when R⁴ and R⁵ together with the atoms to which they are attached form a 5-6 membered saturated heterocyclic ring is selected from the structures:

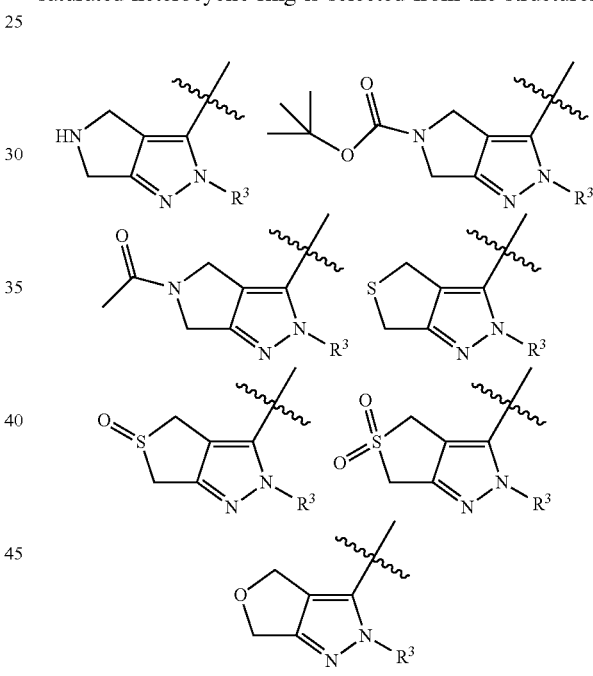

where R³ is as defined for Formula I. In one embodiment of said structures, R³ is phenyl.

In one embodiment, Ring C is formula C-2

C-2

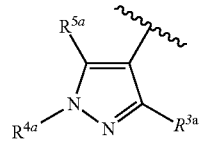

where R³ᵃ, R⁴ᵃ and R⁵ᵃ are as defined for Formula I. In one embodiment, R³ᵃ, R⁴ᵃ and R⁵ᵃ are as defined for Formula I, with the exception that R³ᵃ and R⁵ᵃ are not hydrogen.

In one embodiment, $R^{3a}$ is hydrogen.

In one embodiment, $R^{3a}$ is halogen.

In one embodiment, $R^{3a}$ is (1-6C)alkyl. In one embodiment, $R^{3a}$ is methyl.

In one embodiment, $R^{3a}$ is trifluoro(1-6C)alkyl. In one embodiment, $R^{3a}$ is $CF_3$.

In one embodiment, $R^{3a}$ is (3-6C)cycloalkyl. In one embodiment, $R^{3a}$ is cyclopropyl.

In one embodiment, $R^{3a}$ is phenyl optionally substituted with one or more substituents independently selected from halogen and (1-6C)alkyl. In one embodiment, $R^{3a}$ is phenyl, fluorophenyl or methylphenyl, for example include phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, $R^{3a}$ is phenyl.

In one embodiment, $R^{3a}$ is a 5-6 membered heteroaryl ring having 1-3 ring heteroatoms independently selected from N, O and S and optionally substituted with one or more groups independently selected from (1-6C)alkyl and halogen. In one embodiment, $R^{3a}$ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C) alkyl or halogen. In one embodiment, $R^{3a}$ is pyrazolyl, pyridyl or pyridazinyl optionally substituted with one or more groups independently selected from (1-6C)alkyl and halogen. In one embodiment, $R^{3a}$ is pyrazolyl, pyridyl or pyridazinyl optionally substituted with (1-6C)alkyl or halogen.

In one embodiment, $R^{4a}$ is hydrogen.

In one embodiment, $R^{4a}$ is (1-6C)alkyl. In one embodiment, $R^{4a}$ is methyl, ethyl or isopropyl.

In one embodiment, $R^{4a}$ is trifluoro(1-6C)alkyl. In one embodiment, $R^{4a}$ is 2,2,2-trifluoroethyl.

In one embodiment, $R^{4a}$ is phenyl optionally substituted with one or more groups independently selected from (1-6C) alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—. In one embodiment, $R^{4a}$ is phenyl optionally substituted with one or more groups independently selected from methyl, F, Cl, CN, methoxy, $CH_3OC(=O)$—, aminocarbonyl, methylaminocarbonyl, dimethylaminocarbonyl, methylthio, $CH_3SO_2$—, HOC(=O)— or $CH_3OCH_2CH_2OC(=O)$—. In certain embodiments, $R^{4a}$ is phenyl optionally substituted with one or two of said substituents. In one embodiment, $R^{4a}$ is phenyl.

In one embodiment, $R^{4a}$ is a 5-6 membered heteroaryl ring having 1-3 ring heteroatoms independently selected from N, S and O and optionally substituted with 1-2 substituents independently selected from (1-6C)alkyl, hydroxy (1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, and (1-3C trifluoroalkoxy)(1-3C)trifluoroalkyl. In one embodiment, $R^{4a}$ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl optionally substituted with 1-2 substituents independently selected from (1-6C)alkyl, hydroxy(1-6C) alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, and (1-3C trifluoroalkoxy)(1-3C)trifluoroalkyl. In one embodiment, $R^{4a}$ is pyrazinyl.

In one embodiment, $R^{5a}$ is as defined for Formula I.

In one embodiment, $R^{5a}$ is selected from hydrogen, halogen, (1-6C)alkyl and phenyl.

In one embodiment, $R^{5a}$ is hydrogen.

In one embodiment, $R^{5a}$ is halogen.

In one embodiment, $R^{5a}$ is (1-6C)alkyl. In one embodiment, $R^{5a}$ is methyl.

In one embodiment, $R^{5a}$ is phenyl.

In one embodiment, Ring C is formula C-2, in which $R^{3a}$ is (1-6C)alkyl, trifluoro(1-6C)alkyl or phenyl; $R^{4a}$ is (1-6C) alkyl, trifluoro(1-6C)alkyl, phenyl or pyrazinyl; and $R^{5a}$ is hydrogen, (1-6C)alkyl or phenyl.

In another embodiment of the present invention there is provided a compound according to Formula I, which is designated as Formula I-a, wherein:

X is O;

Ring C is C-1

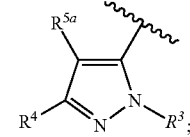

C-1

$R^3$ is (1-6C)alkyl, hydroxy(1-6C)alkyl, $Ar^2$, hetCyc$^1$, (3-7C)cycloalkyl, or hetAr$^2$;

$R^4$ is H, OH, (1-6C)alkyl, monofluoro(1-6C)alkyl, difluoro(1-6C)alkyl, trifluoro(1-6C)alkyl, tetrafluro(2-6C) alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C) alkoxy trifluoro(1-6C)alkoxy, tetrafluoro(2-6C)alkoxy, pentafluoro(2-6C)alkoxy cyano(1-6C)alkoxy, hydroxy(1-6C) alkoxy, dihydroxy(2-6C)alkoxy, amino(2-6C)alkoxy, hydroxyl-carbonyl(1-6C)alkoxy, hetCyc$^2$(1-6C)alkoxy, hetAr$^3$(1-6C)alkoxy, Ar$^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr$^4$, hetAr$^4$—O—, Ar$^4$, hetCyc$^2$(O)$CH_2$—, (1-4C alkoxycarbonyl)(1-6C) alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, hetCyc$^2$C(=O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, hetCyc$^3$, halogen, CN, trifluoromethylsulfonyl, N-(1-3C alkyl)oxadiazolonyl, or hetAr$^5$;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (=O)—, or phenyl optionally substituted with one or more groups independently selected from halogen, (1-6C)alkyl and (1-6C)alkoxy; or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$;

and

Ring A, Y, $R^a$, $R^b$, $R^{b'}$, B, D, E, F, G, K, $R^1$, $R^e$, $R^f$, $R^g$, $R^h$, $R^i$, $R^j$, $R^k$, $R^m$, $R^n$, $R^p$, $Ar^2$, $hetCyc^1$, $hetCyc^2$, $hetCyc^3$, $hetAr^3$, $Ar^3$, $hetAr^4$ $hetAr^5$, and $Ar^4$ are as defined for Formula I.

In one embodiment of Formula I-a, $R^4$ is (1-6C)alkoxy, $hetAr^4$, $Ar^4$ or $hetAr^5$; and Ring A, Y, $R^a$, $R^b$, $R^{b'}$, B, D, E, F, G, K, $R^p$, $R^3$, $R^5$, $Ar^2$, $hetAr^4$, $Ar^4$, and $hetAr^5$ are as defined for Formula I.

In one embodiment of Formula I-a, Ring A is formula A-1; B is a bond or $CR^dR^e$, D is a bond or $CR^fR^g$, E is a bond or $CR^hR^i$, and F is $CR^jR^k$, wherein the ring formed by B, D, E, and F together with the atoms to which they are attached contains 5-6 atoms, and Y, $R^a$, $R^b$, $R^{b'}$, $R^p$, $R^3$, $R^4$, $R^5$, $Ar^2$, $hetAr^4$, $Ar^4$, and $hetAr^5$ are as defined for Formula I.

In one embodiment of Formula I-a, $R^3$ is $Ar^2$; $R^4$ is (1-6C)alkoxy, $hetAr^4$, $Ar^4$ or $hetAr^5$; $R^5$ is (1-6C)alkyl; and Ring A, Y, $R^a$, $R^b$, $R^{b'}$, B, D, E, F, G, K, $R^1$, $R^e$, $R^f$, $R^g$, $R^h$, $R^i$, $R^j$, $R^k$, $R^m$, $R^n$, $R^p$, $Ar^2$, $hetAr^4$, $Ar^4$, and $hetAr^5$ are as defined for Formula I. In one embodiment, $R^3$ is phenyl.

In one embodiment of Formula I-a, $R^3$ is $Ar^2$; $R^4$ is (1-6C)alkoxy, $hetAr^4$ or $hetAr^5$; $R^5$ is (1-6C)alkyl; and Ring A, Y, $R^a$, $R^b$, $R^{b'}$, B, D, E, F, G, K, $R^1$, $R^e$, $R^f$, $R^g$, $R^h$, $R^i$, $R^j$, $R^k$, $R^m$, $R^n$, $R^p$, $Ar^2$, $hetAr^4$, and $hetAr^5$ are as defined for Formula I. In one embodiment, $R^3$ is phenyl.

In one embodiment of Formula I-a, $R^3$ is $Ar^2$; $R^4$ is (1-6C)alkoxy or $hetAr^5$; $R^5$ is (1-6C)alkyl; and Ring A, Y, $R^a$, $R^b$, $R^{b'}$, B, D, E, F, G, K, $R^1$, $R^e$, $R^f$, $R^g$, $R^h$, $R^i$, $R^j$, $R^k$, $R^m$, $R^n$, $R^p$, $Ar^2$, $hetAr^5$ and $Ar^4$ are as defined for Formula I. In one embodiment, $R^3$ is phenyl.

In one embodiment of Formula I-a, $R^3$ is $Ar^2$; $R^4$ is (1-6C)alkoxy or $hetAr^4$; $R^5$ is (1-6C)alkyl; Ring A is formula A-1; and Y, $R^a$, $R^b$, $R^{b'}$, B, D, E, F, $R^1$, $R^e$, $R^f$, $R^g$, $R^h$, $R^i$, $R^j$, $R^k$, $Ar^2$, $hetAr^4$ and $Ar^4$ are as defined for Formula I. In one embodiment, $R^3$ is phenyl.

In one embodiment of Formula I-a, $R^3$ is $Ar^2$; $R^4$ is (1-6C)alkoxy or $hetAr^4$; $R^5$ is (1-6C)alkyl; Y is H; Ring A is formula A-1; B is a bond or $CR^dR^e$, D is a bond or $CR^fR^g$, E is a bond or $CR^hR^i$, and F is $CR^jR^k$, wherein the ring formed by B, D, E, and F together with the atoms to which they are attached contains 5-6 atoms, and $R^a$, $R^b$, $R^{b'}$, $R^1$, $R^e$, $R^f$, $R^g$, $R^h$, $R^i$, $R^j$, $R^k$, $Ar^2$, $hetAr^4$ and $Ar^4$ are as defined for Formula I. In one embodiment, $R^3$ is phenyl.

In one embodiment of Formula I-a, $R^3$ is $Ar^2$; $R^4$ is (1-6C)alkoxy, $hetAr^4$ or $hetAr^5$; $R^5$ is halogen or (1-6C)alkyl; Ring A is formula A-2; and Y, $R^a$, $R^b$, $R^{b'}$, G, K, $R^1$, $R^m$, $R^n$, $R^p$, $Ar^2$, $hetAr^4$, and $hetAr^5$ are as defined for Formula I. In one embodiment, $R^3$ is phenyl.

In another embodiment of the present invention there is provided a compound according to Formula I, which is designated as Formula I-b, wherein:

X is O;

Ring A is formula A-1:

B is a bond or $CR^dR^e$,

D is a bond or $CR^fR^g$,

E is a bond or $CR^hR^i$, and

F is $CR^jR^k$, provided that the ring formed by B, D, E, and F together with the atoms to which they are attached contains at least five atoms;

zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

and $R^a$, $R^b$, Y and Ring C are as defined for Formula I. In a further embodiment of Formula I-b, Ring C is C-1. In a further embodiment of Formula I-b, $R^4$ is (1-6C)alkoxy, $hetAr^4$ or $hetAr^5$. In a further embodiment of Formula I-b, $R^3$ is $Ar^2$. In a further embodiment of Formula I-b, $R^5$ is halogen or (1-6C)alkyl. In a further embodiment of Formula I-b, Y is H, halogen, or (1-3C alkoxy)(1-6C)alkyl. In a further embodiment of Formula I-b, $R^3$ is phenyl.

In another embodiment of the present invention there is provided a compound according to Formula I, which is designated as Formula I-c, wherein:

X is O;

B is O, a bond or $CR^dR^e$,

D is O, a bond or $CR^fR^g$,

E is O, a bond or $CR^hR^i$, and

F is $CR^jR^k$, provided that the ring formed by B, D, E, and F together with the atoms to which they are attached contains at least five atoms and contains one oxygen atom;

zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

and $R^a$, $R^b$, $R^c$, Y and Ring C are as defined for Formula I. In one embodiment, B is O, D is a bond or $CR^fR^g$, and E is a bond or $CR^hR^i$. In one embodiment, B is a bond or $CR^dR^e$, D is O, and E is a bond or $CR^hR^i$. In one embodiment, B is a bond or $CR^dR^e$, D is a bond or $CR^fR^g$, and E is O. In a further embodiment of Formula I-c, $R^4$ is (1-6C)alkoxy, $hetAr^4$ or $hetAr^5$. In a further embodiment of Formula I-c, $R^3$ is $Ar^2$. In a further embodiment of Formula I-c, $R^5$ is halogen or (1-6C)alkyl. In a further embodiment of Formula I-c, Y is H, halogen or (1-3C alkoxy)(1-6C)alkyl. In a further embodiment of Formula I-c, $R^3$ is phenyl.

In another embodiment of the present invention there is provided a compound according to Formula I, which is designated as Formula I-d, wherein:
X is O;
B is $NR^1$, a bond or $CR^dR^e$,
D is $NR^1$, a bond or $CR^fR^g$,
E is $NR^1$, a bond or $CR^hR^i$,
F is $CR^jR^k$,
provided that the ring formed by B, D, E, and F together with the atoms to which they are attached contains at least five atoms and contains one nitrogen atom;
zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros],
or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen,
and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;
and $R^1$, $R^a$, $R^b$, $R^c$, Y and Ring C are as defined for Formula I. In one embodiment, B is $NR^1$, D is a bond or $CR^fR^g$, and E is a bond or $CR^hR^i$. In one embodiment, B is a bond or $CR^dR^e$, D is $NR^1$, and E is a bond or $CR^hR^i$. In one embodiment, B is a bond or $CR^dR^e$, D is a bond or $CR^fR^g$, and E is $NR^1$. In a further embodiment of Formula I-d, $R^4$ is (1-6C)alkoxy, $hetAr^4$ or $hetAr^5$. In a further embodiment of Formula I-d, $R^3$ is $Ar^2$. In a further embodiment of Formula I-d, $R^5$ is halogen or (1-6C)alkyl. In a further embodiment of Formula I-d, Y is H, halogen or (1-3C alkoxy)(1-6C)alkyl. In a further embodiment of Formula I-d, $R^3$ is phenyl.

In another embodiment of the present invention there is provided a compound according to Formula I, which is designated as Formula wherein:
X is O;
Ring A is formula A-2;
and G, K, Y, $R^1$, $R^m$, $R^n$, $R^p$, and Ring C are as defined for Formula I. In a further embodiment of Formula I-e, Ring C is C-1. In a further embodiment of Formula I-e, $R^4$ is (1-6C)alkoxy, $hetAr^4$ or $hetAr^5$, and $R^3$ and $R^5$ are as defined for Formula I. In a further embodiment of Formula I-e, $R^3$ is $Ar^2$, and $R^5$ is as defined for Formula I. In a further embodiment of Formula I-e, $R^5$ is (1-6C)alkyl. In a further embodiment of Formula I-e, $R^p$ is H. In a further embodiment of Formula I-e, Y is H, halogen or (1-3C alkoxy)(1-6C)alkyl. In a further embodiment of Formula I-e, $R^3$ is phenyl.

In another embodiment of the present invention there is provided a compound according to Formula I, which is designated as Formula I-f, wherein:
X is O;
Ring A is formula A-2;
B is $NR^1$ or O, D is a bond or $CR^fR^g$, E is a bond or $CR^hR^i$, and F is $CR^jR^k$, provided that the ring formed by B, D, E, and F together with the atoms to which they are attached contains at least five atoms;
zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros],
or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen,
and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;
and $R^1$, $R^a$, $R^b$, $R^c$, Y and Ring C are as defined for Formula I. In a further embodiment of Formula I-f, $R^4$ is (1-6C)alkoxy, $hetAr^4$ or $hetAr^5$. In a further embodiment of Formula I-f, $R^3$ is $Ar^2$. In a further embodiment of Formula I-f, $R^5$ is halogen or (1-6C)alkyl. In a further embodiment of Formula I-f, Y is H, halogen or (1-3C alkoxy)(1-6C)alkyl. In a further embodiment of Formula I-f, $R^3$ is phenyl.

In another embodiment of the present invention there is provided a compound according to Formula I, which is designated as Formula I-g, wherein:
X is O;
Ring A is formula A-2;
B is a bond or $CR^dR^e$; D is $NR^1$ or O, E is a bond or $CR^hR^i$, and F is $CR^jR^k$, provided that the ring formed by B, D, E, and F together with the atoms to which they are attached contains at least five atoms;
zero to four of $R^d$, $R^e$, $R^f$, $R^g$, $R^h$, $R^i$, $R^j$ and $R^k$ are independently OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], (1-6C)alkoxy [optionally substituted with one to five fluoros], or (1-3C alkoxy)(2-6C)alkoxy [optionally substituted with one to five fluoros],
or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen,
and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

and $R^1$, $R^a$, $R^b$, $R^c$, Y and Ring C are as defined for Formula I. In a further embodiment of Formula I-g, $R^4$ is (1-6C)alkoxy, hetAr$^4$ or hetAr$^5$. In a further embodiment of Formula I-g, $R^3$ is Ar$^2$. In a further embodiment of Formula I-g, $R^5$ is halogen or (1-6C)alkyl. In a further embodiment of Formula I-g, Y is H, halogen or (1-3C alkoxy)(1-6C)alkyl. In a further embodiment of Formula I-g, $R^3$ is phenyl.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts or trifluoroacetate salts.

In one embodiment, the compounds of Formula I include the free base form of compounds of Examples 1-160, or pharmaceutically acceptable salts thereof.

In one embodiment, the compounds of Formula I include the hydrochloride salts of compounds of Examples 1-160.

In one embodiment, the compounds of Formula I include the trifluoroacetate salts of compounds of Examples 1-160.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

II with a corresponding compound having the formula III

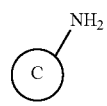

III in the presence carbonyldiimidazole or triphosgene and a base; or (b) for a compound of Formula I where X is S, coupling a corresponding compound having the formula II

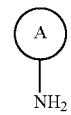

II with a corresponding compound having the formula III

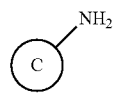

III in the presence di(1H-imidazol-2-yl)methanethione and a base; or (c) for a compound of Formula I where X is O, coupling a corresponding compound having the formula II

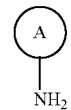

II with a corresponding compound having the formula IV

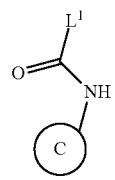

IV where $L^1$ is a leaving group, in the presence of a base; or (d) for a compound of Formula I where X is O, coupling a corresponding compound having the formula V

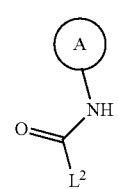

V where $L^2$ is a leaving group, with a corresponding compound having the formula III

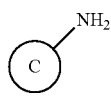

in the presence of a base; or (e) for a compound of Formula I where X is O, activating a corresponding compound having the formula VI

with diphenylphosphoryl azide followed by coupling the activated intermediate with a corresponding compound having the formula III

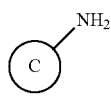

in the presence of a base; or (f) for a compound of Formula I where X is O, coupling a corresponding compound having the formula II

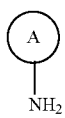

with a corresponding compound having the formula VII

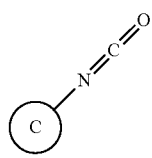

in the presence of a base; or (g) for a compound of Formula I where X is O, coupling a corresponding compound having the formula VIII

with a corresponding compound having the formula III

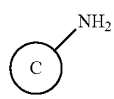

in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), benzyloxycarbonyl (Cbz), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include acetyl, benzyl, trityl, silyl ethers, and the like.

The compounds of the formulas II, III, IV, V, VI, VII and VIII are also provided as further aspects of the invention. In one embodiment, the compounds of the formulas II, III, IV, V, VI, VII and VIII are useful as intermediates for the preparation of compounds of Formula I.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:
LMNA=Prelamin-A/C;
TFG=TRK-fused gene protein;
TPM3=Tropomysin alpha-3;
CD74=HLA class II histocompatibility antigen gamma chain;

NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180 Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314 Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal.

In another embodiment, the present invention provides a compound of Formula I or a pharmaceutically acceptable salt thereof, for use in the treatment of prostatitis in a mammal.

In another embodiment, the present invention provides a compound of Formula I or a pharmaceutically acceptable salt thereof, for use in the treatment of pelvic pain syndrome in a mammal.

In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. THF, DCM, toluene, DMF and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value<100 nM; B represents an averaged $IC_{50}$ value from 100 to 1,000 nM, and C represents an averaged $IC_{50}$ value between >1,000 nM and 3,000 nM.

TABLE A

| Ex. # | TrkA Enzyme $IC_{50}$ (nM) |
|---|---|
| 1 | A |
| 2 | A |
| 3 | A |
| 4 | B |
| 5 | B |
| 6 | A |
| 7 | B |
| 8 | B |
| 9 | B |
| 10 | A |
| 11 | A |
| 12 | A |
| 13 | B |
| 14 | B |
| 15 | A |
| 16 | A |
| 17 | B |
| 18 | B |
| 19 | B |
| 20 | B |
| 21 | B |
| 22 | B |
| 23 | B |
| 24 | B |
| 25 | A |
| 26 | A |
| 27 | A |
| 28 | A |
| 29 | A |
| 30 | A |
| 31 | A |
| 32 | A |
| 33 | A |
| 34 | A |
| 35A | A |
| 35B | B |
| 36 | B |
| 37 | B |
| 38 | B |
| 39 | A |
| 40 | B |
| 41 | A |
| 42 | A |
| 43 | B |
| 44 | A |
| 45 | A |
| 46 | A |
| 47 | B |
| 48 | B |
| 49 | B |
| 50 | B |
| 51 | B |
| 52 | B |
| 53 | B |
| 54 | B |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | C |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | B |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | B |
| 127 | B |

TABLE A-continued

| Ex. # | TrkA Enzyme IC$_{50}$ (nM) |
|---|---|
| 128 | B |
| 129 | A |
| 130 | A |
| 131 | A |
| 132 | A |
| 133 | A |
| 134 | A |
| 135 | C |
| 136 | A |
| 137 | A |
| 138 | B |
| 139 | A |
| 140 | A |
| 141 | A |
| 142 | A |
| 143 | A |
| 144 | A |
| 145 | B |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A | p38α Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [Na$^+$] HEPES pH 7.3, 10 mM MgCl$_2$, 100 μM NaVO$_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The IC$_{50}$ values were determined by fitting a four parameter model to the percent of control data. The compounds of Examples 1-160 were tested in this assay, and all compounds were found to be about 1000 fold more potent against TrkA than p38α.

Example B

Off-Target Kinase Profiling

Representative compounds (Examples 12, 32, 26 and 2) of the invention were tested for off-target kinase activity at a concentration of 10 μM by Millipore, Inc. in their KinaseProfiler™ service against all the kinases available in their full kinase panel. Compounds were run in duplicate at a concentration of ATP near the Km for each individual kinase according to Millipore's specifications. The results are shown in Table B. Data are reported as percent of control (POC) and are the average of the two replicates.

In the KinaseProfiler™ the representative compounds showed remarkable and unexpected selectivity for inhibiting TrkA and TrkB versus other kinases in the panel. In fact, the compounds were largely inactive against off-target kinases at a concentration of 10 μM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 12 Avg. POC | Example 32 Avg. POC | Example 26 Avg. POC | Example 2 Avg. POC |
|---|---|---|---|---|
| Abl2 | 118 | 121.5 | 105 | 112.5 |
| Abl-P | 135.5 | 124.5 | 131 | 146.5 |
| AKT1 | 105.5 | 92 | 100 | 130.5 |
| AKT2 | 127 | 121 | 130 | 132 |
| AKT3 | 94 | 77.5 | 96 | 116.5 |
| ALK | 103 | 127 | 117 | 111 |
| ALK4 | 101 | 100.5 | 102.5 | 98.5 |
| AMPK(A1/B1/G1) | 117 | 138.5 | 122.5 | 152.5 |
| ARK5 | 99.5 | 118.5 | 100.5 | 109.5 |
| AURKA | 111 | 112.5 | 107.5 | 126 |
| Axl | 106 | 119.5 | 107 | 113.5 |
| BLK_m | 112 | 111 | 103.5 | 126 |
| Bmx | 115.5 | 106.5 | 109.5 | 113 |
| BrSK1 | 111.5 | 114.5 | 105.5 | 119 |
| BrSK2 | 147 | 128.5 | 118 | 139.5 |
| BTK | 127 | 119 | 139 | 111.5 |
| CAMK1 | 102 | 100 | 106 | 109.5 |
| CAMK1d | 137 | 114 | 97 | 127 |
| CAMK2b | 106 | 102.5 | 107 | 106.5 |
| CAMK2d | 110.5 | 108.5 | 99.5 | 119 |
| CAMK2g | 107.5 | 105 | 101 | 107.5 |
| CAMK4 | 113.5 | 102 | 121 | 137.5 |
| CDK1/cyclinB | 107.5 | 104 | 103 | 122.5 |
| CDK2/cyclinA | 112 | 118 | 114.5 | 127 |
| CDK2/cyclinE | 96.5 | 106 | 97.5 | 116.5 |
| CDK3/cyclinE | 98.5 | 102.5 | 101.5 | 105.5 |
| CDK5/p25 | 104 | 106 | 109 | 107.5 |
| CDK5/p35 | 106.5 | 112 | 110.5 | 124 |
| CDK6/cyclinD3 | 103 | 108 | 104.5 | 100 |
| CDK7/cyclinH/MAT1 | 101 | 122.5 | 113.5 | 111 |
| CDK9/cyclinT1 | 106 | 106.5 | 112.5 | 127 |
| CHK1 | 99.5 | 103 | 70.5 | 106.5 |
| CHK2 | 92 | 112 | 109 | 119 |
| CK1_y | 101 | 107.5 | 104.5 | 100.5 |
| CK1delta | 109.5 | 135.5 | 121.5 | 117.5 |
| CK1gamma1 | 98.5 | 111.5 | 106.5 | 116.5 |
| CK1gamma2 | 114.5 | 101.5 | 112.5 | 142.5 |
| CK1gamma3 | 104.5 | 102 | 102.5 | 118 |
| CK2 | 98 | 97 | 110.5 | 107 |
| CK2alpha2 | 107.5 | 104 | 114 | 125 |
| CLK2 | 100 | 105.5 | 108.5 | 115.5 |
| CLK3 | 100 | 109 | 106 | 108 |
| c-RAF | 96 | 101.5 | 106.5 | 103.5 |
| CSK | 131.5 | 123 | 118.5 | 124 |
| DAPK1 | 136 | 131 | 135 | 108.5 |
| DAPK2 | 102.5 | 103 | 108.5 | 123.5 |
| DAPK3 | 103 | 111 | 103 | 125.5 |
| DCAMKL2 | 169 | 146 | 135 | 157.5 |
| DDR2 | 107 | 116 | 111 | 113 |
| DMPK | 104 | 98.5 | 106 | 105 |
| DRAK1 | 114 | 105.5 | 125 | 108.5 |
| DYRK2 | 97.5 | 97.5 | 103 | 98 |
| eEF-2K | 140 | 115 | 127.5 | 138 |
| EGFR | 109.5 | 102 | 108 | 114 |
| EphA1 | 100 | 114 | 101 | 85 |
| EphA2 | 113 | 118 | 102 | 129 |
| EphA3 | 114.5 | 122 | 128 | 123.5 |
| EphA4 | 114.5 | 103 | 110 | 111.5 |

TABLE B-continued

| Kinase | Example 12 Avg. POC | Example 32 Avg. POC | Example 26 Avg. POC | Example 2 Avg. POC |
|---|---|---|---|---|
| EphA5 | 118.5 | 104.5 | 106.5 | 119 |
| EphA7 | 96.5 | 100.5 | 108 | 116 |
| EphA8 | 122.5 | 109 | 118.5 | 128.5 |
| EphB1 | 114 | 145.5 | 116.5 | 108.5 |
| EphB2 | 112 | 96.5 | 109.5 | 125 |
| EphB3 | 89 | 87.5 | 97 | 110 |
| EphB4 | 121 | 106 | 115 | 118.5 |
| ErbB4 | 122 | 108.5 | 115.5 | 148 |
| ERK1 | 105 | 107 | 109.5 | 120.5 |
| ERK2 | 106.5 | 128.5 | 107.5 | 112.5 |
| FAK | 104 | 116.5 | 105 | 116.5 |
| FAK2 | 111 | 101.5 | 104.5 | 120 |
| Fer | 100.5 | 85 | 98 | 110.5 |
| Fes | 110 | 112.5 | 100.5 | 129.5 |
| FGFR1 | 90 | 104.5 | 104.5 | 114 |
| FGFR2 | 114 | 110.5 | 112 | 112.5 |
| FGFR3 | 109 | 107 | 101 | 113.5 |
| FGFR4 | 119 | 139.5 | 123 | 124 |
| Fgr | 114.5 | 109.5 | 114.5 | 131 |
| Flt1 | 93 | 103 | 104 | 105.5 |
| Flt3 | 90 | 115 | 97.5 | 96.5 |
| Flt4 | 83.5 | 98 | 106 | 99 |
| Fms | 91 | 102 | 96 | 82 |
| Fyn | 92.5 | 111 | 115.5 | 123.5 |
| GRK5 | 83.5 | 90 | 86 | 106.5 |
| GRK6 | 103 | 101 | 100.5 | 103.5 |
| GRK7 | 117 | 117.5 | 118 | 108.5 |
| GSK3alpha | 119.5 | 112.5 | 115.5 | 123.5 |
| GSK3beta | 109.5 | 84.5 | 124.5 | 126 |
| Haspin | 97 | 94 | 92 | 92.5 |
| Hck | 103.5 | 98 | 91.5 | 85.5 |
| HIPK1 | 102.5 | 115 | 111 | 97 |
| HIPK2 | 91.5 | 99.5 | 103 | 97 |
| HIPK3 | 102.5 | 107 | 111 | 119.5 |
| IGF-1R | 80 | 84.5 | 60.5 | 18 |
| IGF-1R Activated | 102.5 | 112.5 | 98 | 95 |
| IKKalpha | 119.5 | 102 | 112.5 | 141.5 |
| IKKbeta | 102 | 105.5 | 103.5 | 116 |
| IR | 92 | 109 | 82.5 | 44 |
| IR Activated | 109 | 111.5 | 106 | 103 |
| IRAK1 | 102.5 | 113.5 | 110.5 | 107 |
| IRAK4 | 95.5 | 99 | 102 | 125.5 |
| IRR | 91 | 109.5 | 89 | 2.5 |
| ITK | 114.5 | 124 | 122 | 117.5 |
| JAK2 | 122.5 | 122.5 | 134.5 | 233 |
| JAK3 | 112 | 109.5 | 112 | 142.5 |
| JNK1alpha1 | 109.5 | 118 | 112 | 94 |
| JNK2alpha2 | 96 | 102.5 | 104 | 103.5 |
| JNK3 | 107.5 | 104 | 116 | 117.5 |
| KDR | 119.5 | 129 | 144.5 | 123.5 |
| KIT | 102.5 | 94.5 | 94 | 104 |
| Lck | 92 | 104.5 | 96.5 | 97.5 |
| LIMK1 | 97.5 | 95 | 102 | 105 |
| LKB1 | 91 | 100 | 95 | 103.5 |
| LOK | 116 | 103.5 | 109 | 109.5 |
| Lyn | 104.5 | 106.5 | 110.5 | 115 |
| MAP3K5 | 111 | 116 | 116.5 | 105 |
| MAP4K2 | 107.5 | 119.5 | 121 | 110 |
| MAPKAP-K2 | 122.5 | 117.5 | 120 | 137.5 |
| MAPKAP-K3 | 112 | 105 | 108.5 | 128 |
| MAPKAP-K5 | 96 | 108 | 101.5 | 113.5 |
| MARK1 | 104 | 98.5 | 98.5 | 103 |
| MARK2 | 105.5 | 107.5 | 102.5 | 109 |
| MEK1 | 106.5 | 102 | 97 | 100.5 |
| MELK | 67 | 98 | 86 | 142 |
| Mer | 98 | 104 | 98 | 109.5 |
| Met | 109 | 118.5 | 81 | 148.5 |
| MINK | 102 | 124 | 126.5 | 110.5 |
| MKK4_m | 144.5 | 133 | 99.5 | 102.5 |
| MKK6 | 123 | 134.5 | 121.5 | 130 |
| MKK7beta | 122.5 | 138.5 | 144.5 | 129.5 |
| MKNK2 | 103.5 | 99.5 | 99.5 | 106.5 |
| MLK1 | 103.5 | 104.5 | 105.5 | 75 |
| MRCKalpha | 139 | 131 | 124.5 | 127.5 |
| MRCKbeta | 103.5 | 103 | 110 | 129.5 |
| MSK1 | 127.5 | 118 | 114 | 113.5 |
| MSK2 | 127 | 99.5 | 107.5 | 112 |
| MSSK1 | 112.5 | 105.5 | 120.5 | 116 |
| MST1 | 92 | 105.5 | 102 | 111.5 |
| MST2 | 106.5 | 111.5 | 111 | 110.5 |
| MST3 | 131.5 | 130.5 | 108.5 | 120 |
| mTOR | 104.5 | 94.5 | 102.5 | 116 |
| mTOR/FKBP12 | 105.5 | 113.5 | 107.5 | 105 |
| MuSK | 98.5 | 104.5 | 99.5 | 103.5 |
| MYLK | 99 | 97.5 | 101 | 100 |
| NEK11 | 84.5 | 108 | 113.5 | 108.5 |
| NEK2 | 91.5 | 108 | 100.5 | 104 |
| NEK3 | 102 | 113 | 105 | 105 |
| NEK6 | 121 | 123 | 123.5 | 125.5 |
| NEK7 | 133.5 | 122.5 | 126 | 94.5 |
| NLK | 115.5 | 125.5 | 100.5 | 111 |
| p38alpha | 110 | 96.5 | 104.5 | 102.5 |
| p38beta | 115.5 | 119 | 115.5 | 113 |
| p38delta | 99.5 | 113.5 | 102 | 96.5 |
| p38gamma | 111 | 116.5 | 118 | 115 |
| p70S6K | 124.5 | 110.5 | 116 | 172 |
| PAK2 | 97 | 108.5 | 99.5 | 104 |
| PAK4 | 103 | 98 | 100.5 | 95 |
| PAK5 | 143 | 111 | 121.5 | 109.5 |
| PAK6 | 139 | 116.5 | 116.5 | 119.5 |
| PASK | 125.5 | 137 | 124.5 | 143 |
| PDGFRalpha | 104.5 | 112.5 | 104.5 | 123 |
| PDGFRbeta | 125.5 | 131.5 | 122.5 | 149 |
| PDK1 | 105.5 | 101.5 | 115 | 120.5 |
| PhKgamma2 | 110 | 102.5 | 108.5 | 113 |
| Pim-1 | 106 | 109 | 97.5 | 173 |
| Pim-2 | 118.5 | 116.5 | 120.5 | 148 |
| Pim-3 | 100.5 | 112 | 98 | 98 |
| PKAC-alpha | 120.5 | 90 | 116 | 138.5 |
| PKCalpha | 104 | 110 | 107.5 | 96 |
| PKCbetaI | 93.5 | 80 | 89 | 99 |
| PKCbetaII | 100 | 100.5 | 99 | 95.5 |
| PKCdelta | 97.5 | 99 | 105 | 95 |
| PKCepsilon | 97.5 | 97.5 | 106.5 | 101.5 |
| PKCeta | 100 | 111.5 | 98 | 107 |
| PKCgamma | 104.5 | 104 | 99 | 102 |
| PKCiota | 69.5 | 71 | 85.5 | 95.5 |
| PKCtheta | 117.5 | 117 | 109 | 101 |
| PKCzeta | 99.5 | 115 | 108.5 | 122.5 |
| PKD1 | 115 | 98.5 | 113.5 | 110.5 |
| PKD2 | 94 | 110.5 | 102 | 102 |
| Plk1 | 98.5 | 108 | 108 | 95 |
| Plk2 | 103.5 | 103 | 101.5 | 102 |
| Plk3 | 115 | 103.5 | 119 | 103 |
| PRK2 | 97.5 | 99.5 | 110.5 | 128 |
| PRKG1alpha | 89.5 | 84 | 98 | 127.5 |
| PRKG1beta | 95.5 | 80.5 | 111.5 | 122 |
| PrKX | 118.5 | 110 | 109 | 152 |
| PTK5 | 100 | 104 | 110 | 122 |
| PTK6 | 125.5 | 100 | 121 | 129 |
| Ret | 85 | 100.5 | 106.5 | 118.5 |
| RIPK2 | 99 | 99.5 | 98 | 108 |
| ROCK-I | 116.5 | 103 | 112 | 116.5 |
| ROCK-II | 99 | 106 | 110 | 108 |
| Ron | 116.5 | 107 | 101 | 106.5 |
| Ros | 97.5 | 97.5 | 106.5 | 106.5 |
| Rse | 106 | 105 | 109.5 | 109 |
| Rsk1 | 107.5 | 111.5 | 121 | 117 |
| Rsk2 | 103 | 92.5 | 105.5 | 137 |
| Rsk3 | 90 | 92 | 76.5 | 106 |
| Rsk4 | 101 | 95 | 99.5 | 140 |
| SGK1 | 129 | 119 | 97.5 | 150 |
| SGK2 | 148 | 123.5 | 123.5 | 166.5 |
| SGK3 | 143.5 | 134 | 104 | 137.5 |
| SIK | 133.5 | 97 | 121.5 | 121.5 |
| SRC | 97 | 108.5 | 104.5 | 99.5 |
| SRPK1 | 97.5 | 99.5 | 102.5 | 122 |
| SRPK2 | 101.5 | 106.5 | 106 | 106 |
| STK33 | 106.5 | 115 | 111 | 110.5 |
| Syk | 108.5 | 115 | 93.5 | 115 |
| TAK1 | 97 | 99.5 | 108.5 | 106 |
| TAO1 | 104 | 100 | 105.5 | 110.5 |

TABLE B-continued

| Kinase | Example 12 Avg. POC | Example 32 Avg. POC | Example 26 Avg. POC | Example 2 Avg. POC |
|---|---|---|---|---|
| TAO2 | 121 | 104 | 111 | 110 |
| TAO3 | 99 | 105 | 109 | 111 |
| TBK1 | 103 | 108.5 | 113 | 116 |
| TEC Activated | 122.5 | 108.5 | 113.5 | 153 |
| Tie2 | 104.5 | 121 | 106.5 | 126 |
| TLK2 | 98 | 92 | 97 | 100 |
| TNK2 | 117.5 | 132 | 123 | 100.5 |
| TrkA | −0.5 | 0 | 0.5 | 1.5 |
| TrkB | 1 | −0.5 | 1.5 | −2 |
| TSSK1 | 79 | 88.5 | 71.5 | 106 |
| TSSK2 | 139 | 120.5 | 128 | 118.5 |
| Txk | 139 | 127 | 119 | 125 |
| ULK2 | 99 | 103 | 102 | 99 |
| ULK3 | 89.5 | 92 | 92.5 | 105 |
| VRK2 | 95 | 100.5 | 98 | 109 |
| WNK2 | 106.5 | 108.5 | 108 | 99 |
| WNK3 | 112.5 | 103.5 | 103.5 | 109.5 |
| Yes | 119.5 | 114.5 | 117.5 | 132.5 |
| ZAP-70 | 140 | 124 | 120.5 | 124 |

PREPARATION OF SYNTHETIC INTERMEDIATES

Intermediate 1

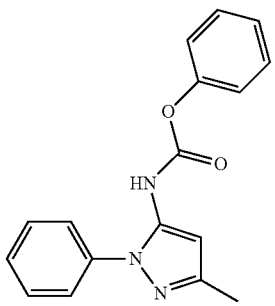 [SMILES: Cc1cc(NC(=O)Oc2ccccc2)n(-c2ccccc2)n1]

Preparation of phenyl (3-methyl-1-phenyl-1H-pyrazol-5-yl)carbamate

To a solution of 3-methyl-1-phenyl-1H-pyrazol-5-amine (500 mg, 2.887 mmol) in EtOAc (25 mL) was added aqueous sodium hydroxide (2 M) (4.33 mL, 8.660 mmol) followed by phenyl carbonochloridate (0.54 mL, 4.33 mmol). The reaction was stirred at ambient temperature overnight, diluted with EtOAc (10 mL) and the phases were separated. The organic phase was washed with H$_2$O (10 mL), brine (10 mL), dried (MgSO$_4$), filtered and concentrated to a pale yellow solid. The crude product was triturated with hexanes (20 mL) and filtered, yielding pure product as off-white solid. MS (apci) m/z=294.1 (M+H).

Intermediate 2

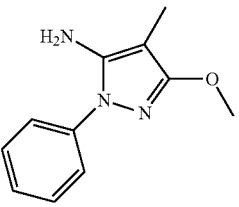

3-methoxy-4-methyl-1-phenyl-1H-pyrazol-5-amine

Step A: Preparation of 5-amino-4-methyl-1-phenyl-1H-pyrazol-3(2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The mixture was cooled to ambient temperature and concentrated. The residual solid was triturated with cold EtOH and suspended in Et$_2$O. The solid was filtered, washed with Et$_2$O and dried under vacuum to give the product as a white solid (3.4 g, 39% yield). MS (apci) m/z=190.0 (M−H).

Step B: Preparation of 3-methoxy-4-methyl-1-phenyl-1H-pyrazol-5-amine: To a fine suspension of 5-amino-4-methyl-1-phenyl-1H-pyrazol-3(2H)-one (300 mg, 1.59 mmol) in 1:1 CH$_2$Cl$_2$-MeOH (6.0 mL) was added 2M TMSCHN$_2$ in hexanes (951 μL, 1.90 mmol). The mixture was stirred at ambient temperature for 2 hours and additional 2M TMSCHN$_2$ in hexanes (1.0 mL) was added. The mixture was stirred for 2 hours and concentrated. The residual syrup was partitioned into H$_2$O and 50% EtOAc-hexanes and stirred for 15 minutes. The organic layer was removed and the aqueous layer was extracted with 50% EtOAc-hexanes (2×). The combined organic fractions were washed with saturated NaCl and dried over MgSO$_4$/activated carbon. The dried solution was eluted through a SiO$_2$ plug eluting with 50% EtOAc-hexanes. The eluent was concentrated to a colorless syrup that was dried under vacuum to afford the title compound as a white solid (153 mg, 47% yield). $^1$H NMR (CDCl$_3$) δ 7.52 (d, J=7.7 Hz, 2H), 7.42 (t, J=7.6 Hz, 2H), 7.24 (t, J=7.3 Hz, 1H), 3.94 (s, 3H), 3.59 (br s, 2H), 1.83 (s, 3H) ppm.

Intermediate 3

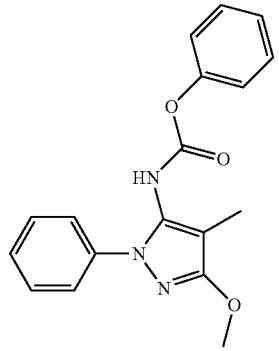 [SMILES: COc1nn(-c2ccccc2)c(NC(=O)Oc2ccccc2)c1C]

phenyl (3-methoxy-4-methyl-1-phenyl-1H-pyrazol-5-yl)carbamate

A solution of 3-methoxy-4-methyl-1-phenyl-1H-pyrazol-5-amine (140 mg, 0.689 mmol) in EtOAc (3.0 mL) was cooled to 0° C. and 2M NaOH (689 µL, 1.38 mmol) and phenylchloroformate (129 µL, 1.03 mmol) were added sequentially. The mixture was stirred for 5 minutes, allowed to reach ambient temperature and stirred for 3 hours. The reaction mixture was diluted with hexanes (3 mL) and washed with H₂O (2×), 1M HCl, H₂O and saturated NaCl. The organic fraction was dried over MgSO₄/activated carbon and filtered through a SiO₂ plug eluting with 50% EtOAc-hexanes. The eluent was concentrated, and the residual colorless syrup was dissolved in dry Et₂O and concentrated to a white foam. The foam was sonicated under hexanes until a fine granular suspension formed. The solvent was decanted, the residual solid was washed with hexanes and dried under vacuum to afford the title compound as a white solid (185 mg, 83% yield). ¹H NMR (CDCl₃) δ 7.50-7.10 (m, 9H), 6.75 (br unresolved, 1H), 6.47 (s, 1H), 3.97 (s, 3H), 1.96 (s, 3H) ppm.

Intermediate 4

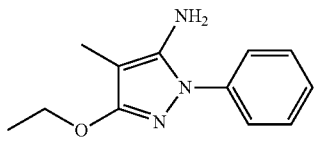 [SMILES: CCOc1nn(-c2ccccc2)c(N)c1C]

3-ethoxy-4-methyl-1-phenyl-1H-pyrazol-5-amine

Step A: Preparation of 5-amino-4-methyl-1-phenyl-1H-pyrazol-3(2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and Et₂O. The resultant solid was filtered, washed with Et₂O, and dried under vacuum to give the product as a white solid (3.4 g, 39% yield). MS (apci) m/z=190.0 (M–H).

Step B: Preparation of 3-ethoxy-4-methyl-1-phenyl-1H-pyrazol-5-amine: To a suspension of 5-amino-4-methyl-1-phenyl-1H-pyrazol-3(2H)-one (10.0 g, 52.9 mmol) in DMF (100 mL) was added K₂CO₃ (14.6 g, 106 mmol) and bromoethane (4.34 mL, 58.1) at ambient temperature. After stirring for 17 hours, the reaction mixture was treated with EtOAc and washed with water (3×) and brine, dried (MgSO₄), filtered, and concentrated to give the product (5.35 g, 47% yield). MS (apci) m/z=218.1 (M+H).

Intermediate 5

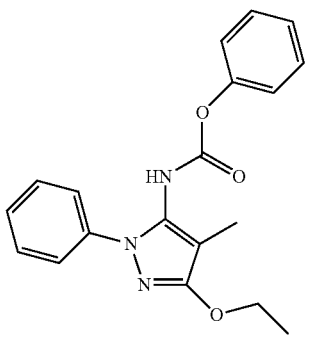 [SMILES: CCOc1nn(-c2ccccc2)c(NC(=O)Oc2ccccc2)c1C]

phenyl 3-ethoxy-4-methyl-1-phenyl-1H-pyrazol-5-carbamate

Prepared by the method as described for Intermediate 1 using 3-ethoxy-4-methyl-1-phenyl-1H-pyrazol-5-amine instead of 3-methyl-1-phenyl-1H-pyrazol-5-amine. The material (4.43 g, 13.13 mmol, 99.8% yield) was used without purification. MS (apci) m/z=338.1 (M+H).

Intermediate 6

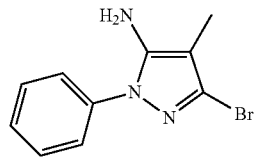

3-bromo-4-methyl-1-phenyl-1H-pyrazol-5-amine

To a stirred solution of 5-amino-4-methyl-1-phenyl-1H-pyrazol-3(2H)-one (1.00 g, 5.29 mmol) in MeCN (20 mL) was added POBr₃ (2.27 g, 7.93 mmol). The reaction mixture was heated at reflux for 3 hours. The reaction was concentrated under vacuum. The residue was taken up in DCM. Saturated aqueous NaHCO₃ solution was carefully added. The aqueous layer was extracted with DCM. The combined organic extracts were washed with brine, dried and concentrated. The residue was purified by flash chromatography on silica gel (1:2 hexane/EtOAc to give the title compound (0.23 g, 17% yield). MS (apci) m/z=252.0; 254.0 (M+H).

Intermediate 7

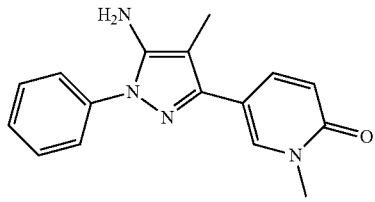 [SMILES: Cc1c(-c2ccc(=O)n(C)c2)nn(-c2ccccc2)c1N]

5-(5-amino-4-methyl-1-phenyl-1H-pyrazol-3-yl)-1-methylpyridin-2(1H)-one 3-bromo-4-methyl-1-phenyl-1H-pyrazol-5-amine (763 mg, 3.03 mmol), 1-methyl-5-(4,4,5,5-tetramethyl-1,3,2-dioxaborolan-2-yl)pyridin-2(1H)-one (1.42 g, 6.05 mmol), K₂CO₃ (1.67 g, 12.1 mmol) and Pd(PPh₃)₄ (350 mg, 0.30 mmol) were combined in toluene (10 mL), water (5 mL) and EtOH (2.5 mL) and warmed to 95° C. in a sealed tube for 16 hours. The cooled mixture was filtered and the filtrate partitioned between water (30 mL) and EtOAc (30 mL). The aqueous layer was extracted with EtOAc (2×20 mL) and the combined organic extracts were washed with brine (20 mL), dried over Na₂SO₄, filtered and concentrated under vacuum. The residue was purified by silica column chromatography eluting with 2% MeOH/DCM to afford the title compound (504 mg, 59% yield) as a yellow foam. MS (apci) m/z=281.2 (M+H).

Intermediate 8

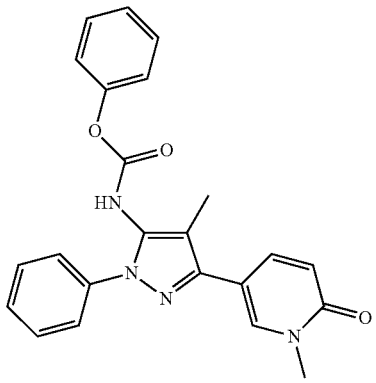 [SMILES: Cc1c(-c2ccc(=O)n(C)c2)nn(-c2ccccc2)c1NC(=O)Oc1ccccc1]

phenyl (4-methyl-3-(1-methyl-6-oxo-1,6-dihydropyridin-3-yl)-1-phenyl-1H-pyrazol-5-yl)carbamate To a suspension of 5-(5-amino-4-methyl-1-phenyl-1H-pyrazol-3-yl)-1-methylpyridin-2(1H)-one (2.80 g, 9.99 mmol) in EtOAc (120 mL) was added 2N NaOH (14.98 mL, 29.97 mmol) followed by phenyl chloroformate (2.5 mL, 19.98 mmol). The mixture was stirred at ambient temperature for 16 hours then partitioned between water (100 mL) and EtOAc (100 mL) and the aqueous layer extracted with EtOAc (2×50 mL). The combined organic extracts were washed with saturated NaHCO$_3$ (50 mL) and brine (50 mL) then dried over Na$_2$SO$_4$, filtered and concentrated to afford the title compound as a pale yellow syrup which was used directly without purification, assuming 100% yield. MS (apci) m/z=401.2 (M+H).

Intermediate 9

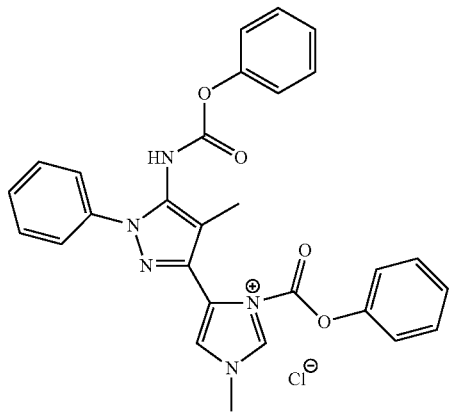 [SMILES: Cc1c(-c2cn(C)c[n+]2C(=O)Oc2ccccc2)nn(-c2ccccc2)c1NC(=O)Oc1ccccc1 ; [Cl-]]

Preparation of 1-methyl-4-(4-methyl-5-(phenoxycarbonylamino)-1-phenyl-1H-pyrazol-3-yl)-3-(phenoxycarbonyl)-1H-imidazol-3-ium chloride Step A: Preparation of 2-methyl-3-(1-methyl-1H-imidazol-4-yl)-3-oxopropanenitrile. Propiononitrile (0.893 g, 16.2 mmol) was added dropwise to a 1M solution of LHMDS (13.0 mL, 13.0 mmol) in THF at −78° C. The mixture was stirred for 30 minutes and a solution of ethyl 1-methyl-1H-imidazole-4-carboxylate (1.00 g, 6.49 mmol) in THF (20 mL, heated to dissolve the starting material) was added dropwise. The reaction was allowed to warm to ambient temperature, stirred overnight, poured into ice water (50 mL) and extracted with EtOAc (100 mL) The pH was adjusted to 6.5 using 2N HCl and the mixture was extracted with EtOAc (100 mL). The pH was then adjusted to 6 using 2N HCl and the mixture was extracted with EtOAc (2×100 mL). The combined extracts from the pH 6.5 and pH 6 extractions were dried (MgSO$_4$), filtered and concentrated to provide the title compound (1.02 g, 6.25 mmol, 96.4% yield). MS (apci) m/z=164.2 (M+H).

Step B: Preparation of 4-methyl-3-(1-methyl-1H-imidazol-4-yl)-1-phenyl-1H-pyrazol-5-amine hydrochloride. A pressure vessel was charged with 2-methyl-3-(1-methyl-1H-imidazol-4-yl)-3-oxopropanenitrile (1.00 g, 6.13 mmol), absolute EtOH (12.3 mL, 6.13 mmol) and phenylhydrazine hydrochloride (0.975 g, 6.74 mmol). The reaction was sealed, heated at 80° C. overnight and concentrated to afford the title compound (1.70 g, 5.87 mmol, 95.7% yield). MS (apci) m/z=254.1 (M+H).

Step C: Preparation of 1-methyl-4-(4-methyl-5-(phenoxycarbonylamino)-1-phenyl-1H-pyrazol-3-yl)-3-(phenoxycarbonyl)-1H-imidazol-3-ium chloride. 4-methyl-3-(1-methyl-1H-imidazol-4-yl)-1-phenyl-1H-pyrazol-5-amine hydrochloride (2 g, 6.90 mmol) was dissolved in 100 mL of CHCl$_3$ and pyridine (6.386 mL, 78.96 mmol) was added followed by phenylchloroformate (2.972 mL, 23.69 mmol). The reaction was stirred at ambient for 2 hours and quenched with 1N NaOH (100 mL) The layers were separated and the aqueous layer was washed with DCM. The combined organic extracts were dried (MgSO$_4$) and concentrated. The crude material was purified by silica gel column chromatography, eluting with 25-100% acetone/hexanes, to afford the title compound (2.35 g, 4.752 mmol, 68.8% yield). MS (apci) m/z=494.1 (M+H). This intermediate needs to be reacted with two equivalents of an amine to afford the desired urea products.

Intermediate 10

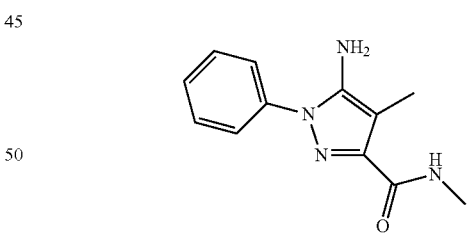

5-amino-N,4-dimethyl-1-phenyl-1H-pyrazole-3-carboxamide

Step A: Preparation of ethyl 3-cyano-2-oxobutanoate: To a solution of lithium bis(trimethylsilyl)amide (1M in THF, 46.4 mL, 46.39 mmol) in THF (100 mL) under N$_2$ at −78° C. was added propiononitrile (3.08 mL, 53.01 mmol) dropwise over 2 min. The mixture was stirred at −78° C. for 1 hour, then diethyl oxalate (6.0 mL, 44.18 mmol) was added dropwise over 5 minutes. The reaction mixture was stirred at −78° C. for 45 minutes, then at 0° C. for 4 hours, then was diluted with H$_2$O (100 mL) and extracted with Et$_2$O (100 mL). The aqueous phase was neutralized with 6M HCl (7 mL), then extracted with Et$_2$O (3×100 mL), and the combined organic extracts were washed with brine (100 mL), dried (MgSO$_4$), filtered, and concentrated to afford the product as a yellow syrup (6.6 g, 96% yield). $^1$H NMR (CDCl$_3$) δ 4.46 (q, 2H), 4.38 (dq, 1H), 1.44 (t, 3H), 1.38 (dt, 3H) ppm.

Step B: Preparation of ethyl 5-amino-4-methyl-1-phenyl-1H-pyrazole-3-carboxylate: To a suspension of phenylhydrazine hydrochloride (6.15 g, 42.54 mmol) in EtOH (150 mL) was added ethyl 3-cyano-2-oxobutanoate (6.6 g, 42.54 mmol). The reaction mixture was heated to reflux for 16 hours, then cooled to ambient temperature. The reaction mixture was diluted with saturated aqueous NaHCO$_3$ (50 mL), extracted with DCM (3×100 mL), and the combined organic phases were dried (MgSO$_4$), filtered and concentrated under vacuum. The crude product was purified by silica column chromatography, eluting with 0-60% acetone in hexanes to afford the product as a yellow solid (7.1 g, 68% yield). MS (apci) m/z=246.1 (M+H).

Step C: Preparation of 5-amino-4-methyl-1-phenyl-1H-pyrazole-3-carboxylic acid: To a solution of ethyl 5-amino-4-methyl-1-phenyl-1H-pyrazole-3-carboxylate (1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO$_4$), filtered and concentrated to give the title compound as a yellow solid (1.3 g, 96% yield). MS (apci) m/z=218.1 (M+H).

Step D: Preparation of 5-amino-N,4-dimethyl-1-phenyl-1H-pyrazole-3-carboxamide: To a solution of 5-amino-4-methyl-1-phenyl-1H-pyrazole-3-carboxylic acid (223 mg, 1.02 mmol) in acetonitrile (10 mL) were added DIEA (0.71 mL, 4.10 mmol), methanamine hydrochloride (138 mg, 2.05 mmol), DMF (2 mL), followed by addition of HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

Intermediate 11

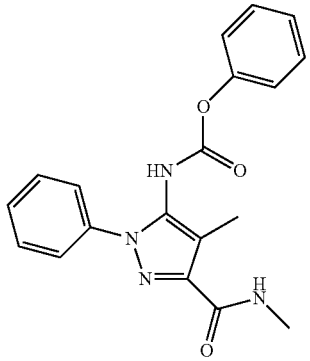 [SMILES: CNC(=O)c1nn(-c2ccccc2)c(NC(=O)Oc2ccccc2)c1C]

Phenyl 4-methyl-3-(methyl carbamoyl)-1-phenyl-1H-pyrazol-5-ylcarbamate

Prepared by the method as described for Intermediate 1 using 5-amino-N,4-dimethyl-1-phenyl-1H-pyrazole-3-carboxamide instead of 3-methyl-1-phenyl-1H-pyrazol-5-amine. The crude material (75.6 mg, 0.2158 mmol, 99.4% yield) was used without purification. MS (apci) m/z=351.1 (M+H).

Intermediate 12

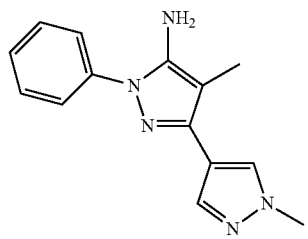 [SMILES: Cc1c(-c2cnn(C)c2)nn(-c2ccccc2)c1N]

1',4-dimethyl-1-phenyl-1H,1'H-[3,4'-bipyrazol]-5-amine

Step A: ethyl 1-methyl-1H-pyrazole-4-carboxylate: To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield the title compound as a tan orange oil (106 g, 99.1% yield).

Step B: 2-methyl-3-(1-methyl-1H-pyrazol-4-yl)-3-oxopropanenitrile: To a four-necked 5-liter round bottomed flask fitted with an overhead stirrer and addition funnel was charged LHMDS (1444 mL, 1444 mmol) (1.0M in THF). The solution was cooled in an acetone/dry ice bath (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the orange glass was dissolved in warm water. The aqueous mixture was washed with ether (3×1000 mL) The aqueous phase was then pH-adjusted to 5 (pH paper) using concentrated HCl and saturated bicarbarbonate solution The aqueous layer was extracted with DCM (3×1000 mL) The combined organic extracts were dried over MgSO$_4$, filtered and concentrated to yield 2-methyl-3-(1-methyl-1H- pyrazol-4-yl)-3-oxopropanenitrile as an amber oil (92 g, 82% yield). MS (apci) m/z=162.1 (M–H).

Step C: 1',4-dimethyl-1-phenyl-1H,1'H-[3,4'-bipyrazol]-5-amine: A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H,1'H-3,4'-bipyrazol-5-amine (93 g, 100% yield).

Step D: phenyl 1',4-dimethyl-1-phenyl-1H,1'H-3,4'-bipyrazol-5-ylcarbamate: In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated under vacuum. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4% yield).

Intermediate 13

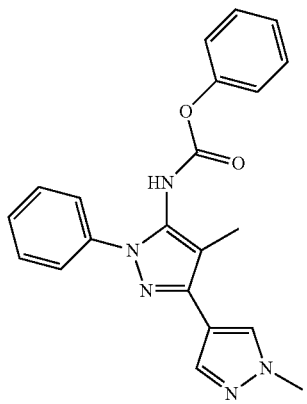 [SMILES: Cc1c(-c2cnn(C)c2)nn(-c2ccccc2)c1NC(=O)Oc1ccccc1]

phenyl (1',4-dimethyl-1-phenyl-1H,1'H-[3,4'-bipyrazol]-5-yl)carbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added aqueous NaOH (2M; 500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated under vacuum. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4% yield).

Intermediate 14

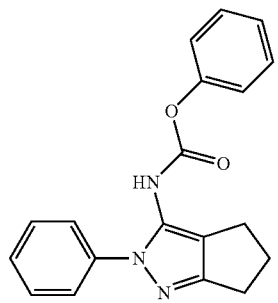 [SMILES: O=C(Nc1c2c(nn1-c1ccccc1)CCC2)Oc1ccccc1]

phenyl (2-phenyl-2,4,5,6-tetrahydrocyclopenta[c]pyrazol-3-yl)carbamate

A suspension of 2-phenyl-2,4,5,6-tetrahydrocyclopenta[c]pyrazol-3-amine (6.0 g, 30.11 mmol) in EtOAc (250 mL) was first cooled in ice bath, followed by addition of NaOH (2N aq, 30.11 mL, 60.23 mmol) in one portion and then PhOCOCl (6.800 mL, 54.20 mmol) drop-wise. The reaction was warmed up to ambient temperature and stirred for 18 hours. The reaction mixture was diluted with EtOAc (100 mL) and phase-separated. The organic layer was washed with water (2×150 mL) and brine (150 mL), dried (MgSO$_4$), filtered and concentrated. The crude was taken up in DCM and concentrated to dryness. The crude solid was triturated with ether/hexanes (2:1, 2×100 mL), filtered and dried, to provide the product as an off-white solid (7.4 g, 77% yield). MS (apci) m/z=320.1 (M+H).

Intermediate 15

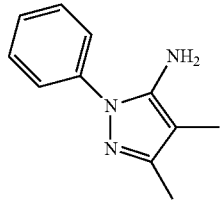

3,4-dimethyl-1-phenyl-1H-pyrazol-5-amine

To a solution of 2-methyl-3-oxobutanenitrile (295 mg, 3.038 mmol) in EtOH (40 mL) were added HCl (5-6M in iPrOH, 0.6 mL) and phenylhydrazine (0.299 mL, 3.038 mmol). The reaction mixture was heated at reflux for 17 hours, then cooled to ambient temperature. The reaction mixture was diluted with saturated aqueous NaHCO$_3$ (20 mL), extracted with DCM (2×25 mL), and the combined organic phases were dried (MgSO$_4$), filtered and concentrated. The crude product was purified by silica column chromatography, eluting with 0-3% MeOH/DCM to yield the product as a tan solid (555 mg, 97% yield). MS (apci) m/z=188.2 (M+H).

Intermediate 16

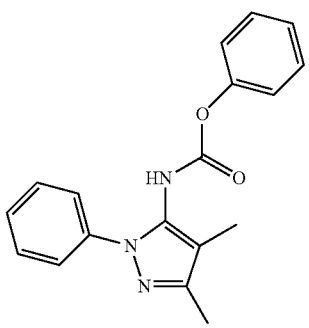 [SMILES: Cc1nn(-c2ccccc2)c(NC(=O)Oc2ccccc2)c1C]

phenyl 3,4-dimethyl-1-phenyl-1H-pyrazol-5-ylcarbamate

Prepared by the method as described for Intermediate 1, using 3,4-dimethyl-1-phenyl-1H-pyrazol-5-amine instead of 3-methyl-1-phenyl-1H-pyrazol-5-amine. The crude product (0.933 g, 3.036 mmol, quantitative yield) was used without purification. MS (apci) m/z=308.1 (M+H).

SYNTHETIC EXAMPLES

Table 1 provides a list of commercially available compounds that were used in the synthesis of intermediates and examples.

TABLE 1

| Structure | Vendor/Catalog # | CAS # |
|---|---|---|
| H$_2$N-pyrazole-cyclopentane, N-phenyl | Ryan Scientific, Inc., EN300-14400 | 89399-92-8 |
| H$_2$N-pyrazole with CN, methyl, N-phenyl | Combi-Blocks, Inc., HI-1327 | 5346-56-5 |
| tetrahydronaphthalen-1-amine | Aldrich/24, 782-0 | 2217-40-5 |

TABLE 1-continued

| Structure | Vendor/Catalog # | CAS # |
|---|---|---|
| (R)-tetrahydronaphthalen-1-amine | Lancaster Synthesis Inc./17022 | 23357-52-0 |
| (S)-tetrahydronaphthalen-1-amine | Aldrich/668,818 | 21966-60-9 |
| 6-methoxy-tetrahydronaphthalen-1-amine | ChemBridge/4102674 | 52373-02-1 |
| chroman-4-amine | J & W PharmLab, LLC/20-1070 | 53981-38-7 |
| 2,2-dimethylchroman-4-amine | Matrix Scientific/021506 | N/A |
| isochroman-4-amine | Activate Scientific/D4046 | 147663-00-1 |
| 6-bromo-isochroman-4-amine | Activate Scientific/AS2094G1 | N/A |
| 1,2,3,4-tetrahydroisoquinolin-4-amine | AstaTech, Inc./52240 | 486453-50-3 |
| 6,7,8,9-tetrahydro-5H-benzo[7]annulen-5-amine | Ryan Scientific, Inc./EN400-13090 | N/A |

TABLE 1-continued

| Structure | Vendor/Catalog # | CAS # |
|---|---|---|
| 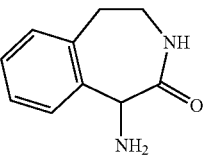 | APAC Pharmaceutical/552625 | 253185-43-2 |
| 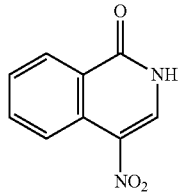 | Ubichem plc/cat# UB-10298 | N/A |
| 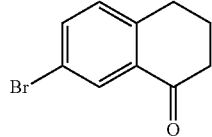 [SMILES: O=C1CCCc2ccc(Br)cc21] | Maybridge/MO 01275 | 32281-97-3 |
| 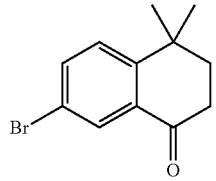 | CiVenti Chem/CV-1709 | 166978-46-7 |
| 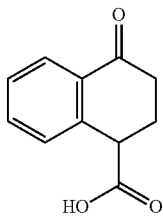 [SMILES: O=C1CCC(C(=O)O)c2ccccc21] | Key Organics Ltd./SS-3938 | N/A |

TABLE 1-continued

| Structure | Vendor/Catalog # | CAS # |
|---|---|---|
| 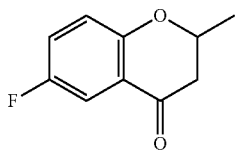 | Oakwood Products, Inc./008563 | 88754-96-5 |
| 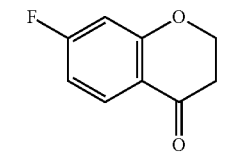 [SMILES: O=C1CCOc2cc(F)ccc21] | Chemgenx, LLC/CX-01571 | 113209-68-0 |
| 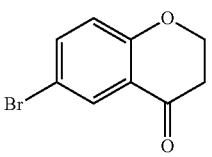 | Carbocore/CH-0014 | 49660-57-3 |
| 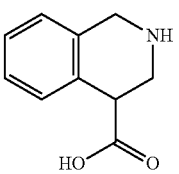 [SMILES: O=C(O)C1CNCc2ccccc21] | Enamine/EN300-31791 | 116140-19-3 |
| 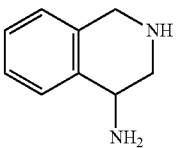 [SMILES: NC1CNCc2ccccc21] | AstaTech, Inc./52240 | 486453-50-3 |

N/A = Not available

Table 1 provides a list of commercially available pyrazole intermediates can be used in the synthesis of compounds described in the Examples.

TABLE 1

| Pyrazole | Vendor/Catalog# | CAS# |
|---|---|---|
| 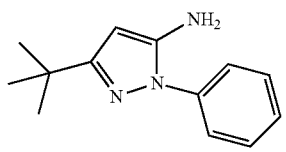 [SMILES: CC(C)(C)c1cc(N)n(-c2ccccc2)n1] | Oakwood, 021512 | 126208-61-5 |
| 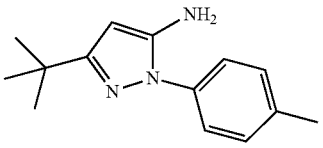 [SMILES: Cc1ccc(-n2nc(C(C)(C)C)cc2N)cc1] | Array BioPharma, A1075-0 | N/A |
| 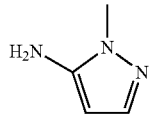 | Maybridge, GK03066 | 1192-21-8 |

TABLE 1-continued
| Pyrazole | Vendor/Catalog# | CAS# |
|---|---|---|
| 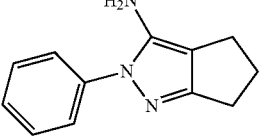 | Ryan Scientific, EN300-14400 | 89399-92-8 |
| 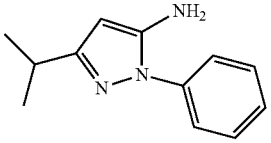 | Oakwood, 021516 | N/A |
| 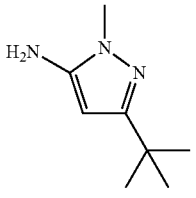 | Alfa Aesar, AAB20095-06 | 118430-73-2 |
| 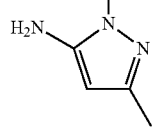 | Aldrich, 532223 | 3524-32-1 |
| 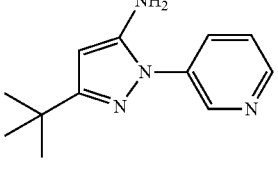 | Accela ChemBio Chem Co, SY003755 | 876299-97-7 |
| 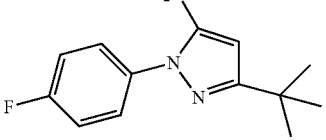 | ChemImpex, 18122 | 778611-16-8 |
| 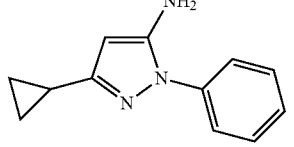 | Oakwood, 017105 | 175137-45-8 |
| 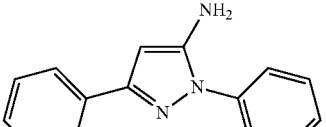 | Alfa Aesar, AAB20464-06 | 5356-71-8 |
| 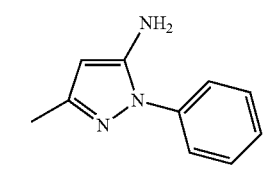 | Aldrich, 541001 | 1131-18-6 |

TABLE 1-continued

| Pyrazole | Vendor/Catalog# | CAS# |
|---|---|---|
| 5-amino-1-methyl-3-phenylpyrazole | Alfa Aesar, AAA15754-06 | 10199-50-5 |
| 5-amino-1-phenylpyrazole | TCI America, A0174 | 826-85-7 |
| 5-amino-3-tert-butyl-1-(2-fluorophenyl)pyrazole | Oakwood, 023890 | N/A |
| 5-amino-3-tert-butyl-1-(3-fluorophenyl)pyrazole | J & W Pharmalab, 68-0035S | 1187931-80-1 |
| 5-amino-3-cyclopentyl-1-phenylpyrazole | VWR, EN300-09508 | N/A |
| 3-amino-2-methyl-2,4,5,6-tetrahydrocyclopenta[c]pyrazole | ChemBridge, 4019184 | 885529-68-0 |
| 5-amino-1-methyl-3-methyl-4-phenylpyrazole | ChemBridge, 4001950 | N/A |
| 5-amino-3-tert-butyl-1-(2-methylphenyl)pyrazole | ChemImpex, 19156 | 337533-96-7 |
| 5-amino-3-tert-butyl-1-(3-methylphenyl)pyrazole | ChemImpex, 19155 | 898537-77-4 |

TABLE 1-continued

| Pyrazole | Vendor/Catalog# | CAS# |
| --- | --- | --- |
| (5-amino-1-methyl-4-phenyl-1H-pyrazole) | ChemBridge, 4006072 | N/A |
| (5-amino-3-methyl-1-phenyl-1H-pyrazole-4-carbonitrile) | Oakwood, 005982 | 5346-56-5 |
| (5-amino-1-phenyl-3-(trifluoromethyl)-1H-pyrazole) | ChemImpex, 18771 | 182923-55-3 |
| (5-amino-3-cyclopropyl-1-methyl-1H-pyrazole) | Maybridge, KM00278 | 118430-74-3 |
| (5-amino-1-methyl-3-(thiophen-2-yl)-1H-pyrazole) | Maybridge, KM00835 | 118430-78-7 |
| (5-amino-1-methyl-3-(pyridin-2-yl)-1H-pyrazole) | ChemBridge, 4015288 | N/A |
| (5-amino-1-methyl-3-(pyridin-3-yl)-1H-pyrazole) | ChemBridge, 4015289 | N/A |
| (5-amino-3-(4-fluorophenyl)-1-methyl-1H-pyrazole) | Matrix, 020274 | N/A |
| (5-amino-3-(4-methoxyphenyl)-1-methyl-1H-pyrazole) | Matrix, 019183 | N/A |
| (5-amino-3-(4-chlorophenyl)-1-methyl-1H-pyrazole) | Maybridge, KM 04038 | 126417-82-1 |
| (4-amino-1,3-dimethyl-5-phenyl-1H-pyrazole) | ChemBridge, 4001950 | N/A |

TABLE 1-continued

| Pyrazole | Vendor/Catalog# | CAS# |
|---|---|---|
|  | Lancaster, AAA17470-06 | 7152-40-1 |
|  | ChemBridge, 4010196 | 91642-97-6 |
|  | VWR, AAA13296-14 | 16078-71-0 |

N/A = Not available

Intermediate P1

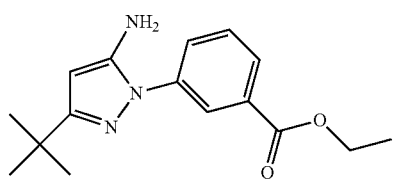 [SMILES: CCOC(=O)c1cccc(-n2nc(C(C)(C)C)cc2N)c1]

Ethyl 3-(5-amino-3-tert-butyl-1H-pyrazol-1-yl)benzoate

To a suspension of ethyl 3-hydrazinylbenzoate hydrochloride (500 mg, 2.31 mmol) in EtOH (20 mL) was added 4,4-dimethyl-3-oxopentanenitrile (318 mg, 2.54 mmol). The reaction mixture was heated to reflux for 18 hours, then cooled to ambient temperature and concentrated in vacuo. The crude product was purified by silica column chromatography, eluting with 0-5% MeOH/DCM to yield the product as a yellow oil (154 mg, 23% yield). MS (apci) m/z=288.2 (M+H).

The compounds in Table 2 were prepared by the method as described for Intermediate P1, substituting 4,4-dimethyl-3-oxopentanenitrile with the appropriate cyanoketone and ethyl 3-hydrazinylbenzoate hydrochloride with the appropriate hydrazine.

TABLE 2

| Intermediate # | Structure | Data |
|---|---|---|
| P2 | 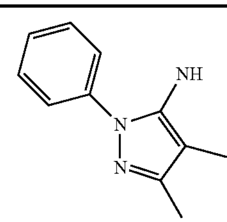 | MS (apci) m/z = 188.2 (M + H) |
| P3 | 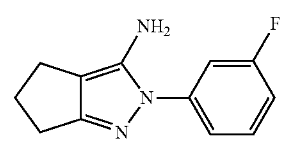 [SMILES: Nc1c2c(nn1-c1cccc(F)c1)CCC2] | MS (apci) m/z = 218.1 (M + H) |
| P4 | 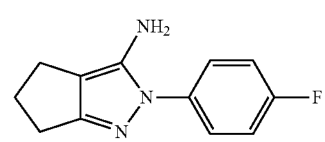 [SMILES: Nc1c2c(nn1-c1ccc(F)cc1)CCC2] | MS (apci) m/z = 218.2 (M + H) |
| P5 | 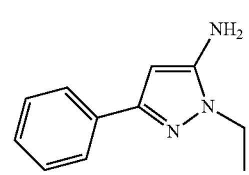 | MS (apci) m/z = 188.2 (M + H) |
| P6 | 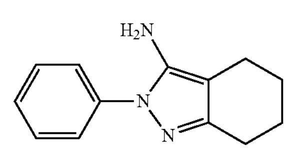 [SMILES: Nc1c2c(nn1-c1ccccc1)CCCC2] | MS (apci) m/z = 214.2 (M + H) |

TABLE 2-continued

| Intermediate # | Structure | Data |
|---|---|---|
| P7 | 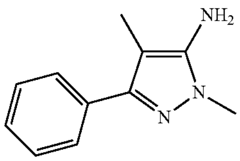 | MS (apci) m/z = 188.2 (M + H) |
| P8 | 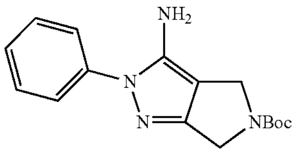 [SMILES: CC(C)(C)OC(=O)N1Cc2nn(-c3ccccc3)c(N)c2C1] | MS (apci) m/z = 301.0 (M + H) |
| P9 | 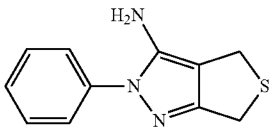 [SMILES: Nc1c2c(nn1-c1ccccc1)CSC2] | MS (apci) m/z = 218.1 (M + H) |
| P10 | 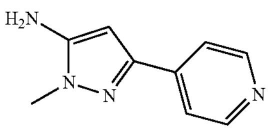 | MS (apci) m/z = 175.2 (M + H) |
| P11 | 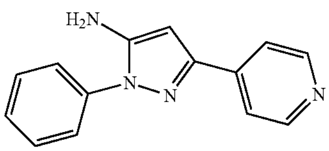 [SMILES: Nc1cc(-c2ccncc2)nn1-c1ccccc1] | MS (apci) m/z = 237.3 (M + H) |
| P12 | 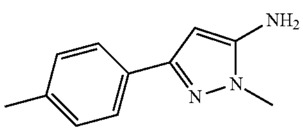 | MS (apci) m/z = 188.2 (M + H) |
| P13 | 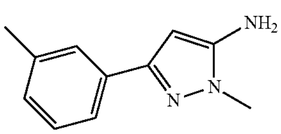 | MS (apci) m/z = 188.2 (M + H) |
| P14 | 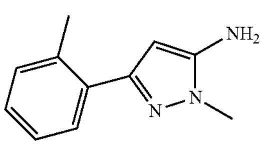 | MS (apci) m/z = 188.2 (M + H) |
| P15 | 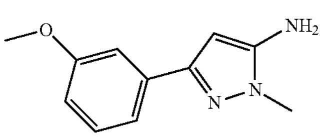 | MS (apci) m/z = 204.2 (M + H) |
| P16 | 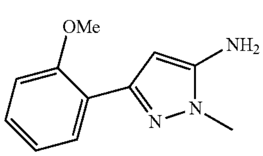 | MS (apci) m/z = 204.2 (M + H) |
| P17 | | MS (apci) m/z = 199.0 (M + H) |
| P18 | | MS (apci) m/z = 199.1 (M + H) |
| P19 | | MS (apci) m/z = 192.2 (M + H) |
| P20 | | MS (apci) m/z = 192.2 (M + H) |
| P21 | | MS (apci) m/z = 232.2 (M + H) |
| P22 | | MS (apci) m/z = 204.2 (M + H) |
| P23 | | MS (apci) m/z = 206.1 (M + H) |

Intermediate P101

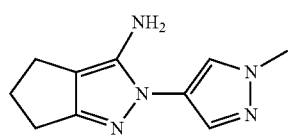

2-(1-methyl-1H-pyrazol-4-yl)-2,4,5,6-tetrahydrocyclopenta-[c]pyrazol-3-amine

Step A: Preparation of di-tert-butyl 1-(1-methyl-1H-pyrazol-4-yl)hydrazine-1,2-dicarboxylate: To a solution of 4-bromo-1-methyl-1H-pyrazole (1.93 mL, 18.6 mmol) in ether (37.3 mL) cooled to −78° C. was added nBuLi (23.3 mL, 37.3 mmol). After stirring at −78° C. for 30 minutes, a solution of di-t-butyl azodicarboxylate (4.29 g, 18.6 mmol) in Et₂O (37.3 mL, 18.6 mmol) was added dropwise. After 1 hour, the reaction mixture was warmed up to −20° C. and quenched with ice. After warming to ambient temperature, the mixture was filtered and rinsed with Et₂O. The resulting solid was taken up in a mixture of DCM and water, and the mixture was phase separated. The organic layer was dried with MgSO₄, filtered and concentrated in vacuo to afford the first batch of product as a white solid (1.64 g, 28% yield). A second batch of product was recovered from the filtrate by silica column chromatography, eluting with 40-60% hexanes/EtOAc (0.51 g, 8.8% yield). MS (apci) m/z=313.0 (M+H).

Step B: Preparation of 2-(1-methyl-1H-pyrazol-4-yl)-2,4,5,6-tetrahydrocyclopenta-[c]pyrazol-3-amine: To a solution of di-tert-butyl 1-(1-methyl-1H-pyrazol-4-yl)hydrazine-1,2-dicarboxylate (103 mg, 0.330 mmol) in EtOH (1.65 mL, 0.330 mmol) was added concentrated HCl (137 µL, 1.65 mmol). The mixture was stirred at ambient temperature for 5 minutes, then cooled in an ice bath followed by addition of 2-oxocyclopentanecarbonitrile (36.0 mg, 0.330 mmol). After stirring for 5 minutes, the reaction mixture was warmed to ambient temperature overnight. The reaction mixture was concentrated and partitioned in water and DCM. After phase-separation, the aqueous layer was basified (pH 10) and then extracted with DCM (3×10 mL). The combined organic extracts were dried with MgSO₄, filtered and concentrated in vacuo. The crude material was purified by reverse-phase column chromatography, eluting with 0-100% acetonitrile/water to afford the product as a yellow solid (4.5 mg, 6.7% yield). MS (apci) m/z=204.1 (M+H).

Intermediate P102

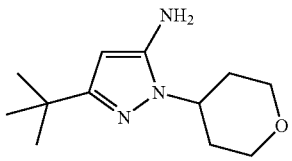 [SMILES: CC(C)(C)c1cc(N)n(C2CCOCC2)n1]

3-tert-butyl-1-(tetrahydro-2H-pyran-4-yl)-1H-pyrazol-5-amine

Step A: Preparation of (tetrahydro-2H-pyran-4-yl)hydrazine hydrochloride: A suspension of dihydro-2H-pyran-4(3H)-one (2.00 g, 20.0 mmol) and tert-butyl hydrazinecarboxylate (2.64 g, 20.0 mmol) in hexanes (20.0 mL) was refluxed for 2 hours. After cooling, BH₃-THF complex (20.0 mL, 20.0 mmol) was added and the reaction mixture was stirred for 1 hour. The mixture was then treated with 4 N HCl in dioxane (20.0 mL, 79.9 mmol), followed by 3 drops of water. After stirring at ambient temperature for 1 hour, the reaction mixture was filtered and rinsed with EtOAc to afford the product as a solid (2.39 g, 78.4% yield). MS (apci) m/z=117.0 (M+H).

Step B: Preparation of 3-tert-butyl-1-(tetrahydro-2H-pyran-4-yl)-1H-pyrazol-5-amine: Prepared by the method as described in for the preparation of Intermediate P1, substituting (tetrahydro-2H-pyran-4-yl)hydrazine dihydrochloride for ethyl 3-hydrazinylbenzoate hydrochloride to yield the product as a yellow oil (0.472 g, 99.9% yield). MS (apci) m/z=224.1 (M+H).

Intermediate P103

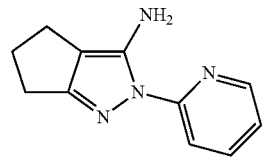 [SMILES: Nc1c2c(nn1-c1ccccn1)CCC2]

2-(pyridin-2-yl)-2,4,5,6-tetrahydrocyclopenta[c]pyrazol-3-amine

Step A: Preparation of 2-(2-(pyridin-2-yl)hydrazono)cyclopentane-carbonitrile: A solution of 2-hydrazinylpyridine (0.200 g, 1.83 mmol) and 2-oxocyclopentanecarbonitrile (0.200 g, 1.83 mmol) in MeOH (9.16 mL) was treated with concentrated HCl (0.764 mL, 9.16 mmol) and refluxed for 16 hours. The reaction mixture was concentrated in vacuo, and then partitioned in water and DCM. After phase-separation, the aqueous layer was washed with DCM, basified (saturated NaHCO₃, pH 10), and extracted with DCM. The combined organic layers were dried with MgSO₄, filtered and concentrated. The crude material was purified by silica column chromatography, eluting with 100% EtOAc to afford the product (0.289 g, 78.6% yield). MS (apci) m/z=201.2 (M+H).

Step B: Preparation of 2-(pyridin-2-yl)-2,4,5,6-tetrahydrocyclopenta[c]pyrazol-3-amine: A solution of 2-(2-(pyridin-2-yl)hydrazono)cyclopentanecarbonitrile (0.243 g, 1.21 mmol) in EtOH (6.06 mL, 1.21 mmol) was treated with 6 M HCl (0.202 mL, 1.21 mmol) and refluxed for 3 days. After removal of the solvent, the crude residue was diluted in water, basified (saturated NaHCO₃, pH 10) and extracted with DCM. The combined organic layers were dried with MgSO₄, filtered and concentrated. The crude material was purified by silica column chromatography, eluting with 50% EtOAc/hexanes to afford the product (0.198 g, 81.6% yield). MS (apci) m/z=201.2 (M+H).

Intermediate P104

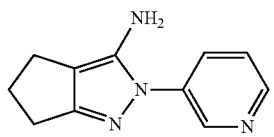 [SMILES: Nc1c2c(nn1-c1cccnc1)CCC2]

2-(pyridin-3-yl)-2,4,5,6-tetrahydrocyclopenta[c]pyrazol-3-amine

Prepared by the method described above for Intermediate P103, substituting 3-hydrazinylpyridine for 2-hydrazinylpyridine to afford the title product. MS (apci) m/z=201.1 (M+H).

Intermediate P105

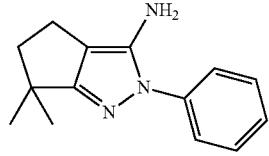 [SMILES: CC1(C)CCc2c1nn(-c1ccccc1)c2N]

6,6-dimethyl-2-phenyl-2,4,5,6-tetrahydrocyclopenta[c]pyrazol-3-amine

Step A: Preparation of 5-chloro-2,2-dimethylpentanenitrile: Isobutyronitrile (1.38 g, 20.0 mmol) and 1-bromo-3-chloropropane (3.46 g, 22.0 mmol) were sequentially added to a 1 M solution of lithium bis(trimethylsilyl)amide (20.0 mL, 20.0 mmol) while stirring. After stirring at 70° C. for 16 hours, the reaction mixture was quenched with water then extracted with DCM. The combined organic layers were dried with MgSO$_4$, filtered and concentrated in vacuo to afford 5-chloro-2,2-dimethylpentanenitrile (2.91 g, 100% yield). $^1$H NMR (CDCl$_3$) δ 3.57-3.61 (m, 2H), 1.94-2.02 (m, 2H), 1.67-1.72 (m, 2H), 1.37 (s, 6H).

Step B: Preparation of 2,2-dimethylhexanedinitrile: A suspension of 5-chloro-2,2-dimethylpentanenitrile (2.91 g, 20.0 mmol) and NaCN (1.57 g, 32.0 mmol) in DMF (20.0 mL) and water (1 mL) was heated at 100° C. for 16 hours. After cooling, the reaction mixture was diluted with water and refluxed for 30 minutes, then cooled, poured into water and stirred for 3 hours. The solution was then extracted with Et$_2$O. The combined Et$_2$O extracts were washed with H$_2$O, dried with MgSO$_4$, filtered and concentrated in vacuo to afford the product (2.20 g, 80.7% yield). $^1$H NMR (CDCl$_3$) δ 2.42-2.47 (m, 2H), 1.83-1.92 (m, 2H), 1.67-1.72 (m, 2H), 1.39 (s, 6H).

Step C: Preparation of 3,3-dimethyl-2-oxocyclopentanecarbonitrile: A suspension of KOtBu (0.511 g, 4.55 mmol) in toluene (18.4 mL) was treated a toluene (2.0 mL) solution of 2,2-dimethylhexanedinitrile (1.00 g, 7.34 mmol) and heated at 80° C. for 2 hours. The reaction mixture was then cooled to ambient temperature and quenched with water. The mixture was separated and the organic layer was stirred in 2 N HCl (20 mL) for 16 hours. The mixture was separated and the organic layer dried with MgSO$_4$, filtered and concentrated in vacuo to a yellow-white solid. The crude solid was purified by silica column chromatography, eluting with 10-40% EtOAc/hexanes, to afford the product (0.250 g, 24.8% yield). $^1$H NMR (CDCl$_3$) δ 3.20-3.26 (m, 1H), 2.38-2.47 (m, 1H), 2.14-2.25 (m, 1H), 1.97-2.05 (m, 1H), 1.74-1.83 (m, 1H), 1.14 (s, 6H).

Step D: Preparation of 6,6-dimethyl-2-phenyl-2,4,5,6-tetrahydrocyclopenta[c] pyrazol-3-amine: Prepared by the method as described for Intermediate P1, substituting phenylhydrazine for ethyl 3-hydrazinylbenzoate hydrochloride and 3,3-dimethyl-2-oxocyclopentanecarbonitrile for 4,4-dimethyl-3-oxopentanenitrile to afford the product (0.192 g, 46.2% yield) as a yellow solid. MS (apci) m/z=228.2 (M+H).

Intermediate P106

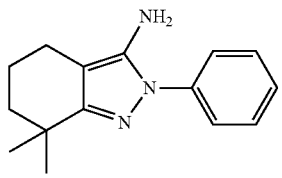 [SMILES: CC1(C)CCCc2c1nn(-c1ccccc1)c2N]

7,7-dimethyl-2-phenyl-4,5,6,7-tetrahydro-2H-indazol-3-amine

Step A: Preparation of 2,2-dimethylheptanedinitrile: Prepared as described for Intermediate P105, Steps A and B, substituting 1-bromo-4-chlorobutane for 1-bromo-3-chloropropane to yield the product (2.21 g, 73.7% yield). $^1$H NMR (CDCl$_3$) δ 2.37-2.42 (m, 2H), 1.53-1.77 (m, 6H), 1.36 (s, 6H).

Step B: Preparation of 3,3-dimethyl-2-oxocyclohexanecarbonitrile: A suspension of KOtBu (0.463 g, 4.13 mmol) in toluene (16.6 mL) was treated with a solution of 2,2-dimethylheptanedinitrile (1.00 g, 6.66 mmol) in toluene (2.0 mL) and heated at 80° C. for 48 hours. After cooling to ambient temperature, the reaction mixture was quenched with water and phase-separated, and the organic layer was stirred with 2 N HCl (20 mL) for 16 hours. After phase-separation, the organic layer was dried with MgSO$_4$, filtered and concentrated in vacuo. The crude material was purified by silica column chromatography, eluting with 10-20% EtOAc/hexanes to afford the product (0.374 g, 37.2% yield). $^1$H NMR (CDCl$_3$) δ 3.72-3.78 (m, 1H), 2.42-2.50 (m. 1H), 1.78-2.04 (m, 4H), 1.60-1.70 (m, 1H), 1.21 (s, 3H), 1.16 (s, 3H).

Step C: Preparation of 7,7-dimethyl-2-phenyl-4,5,6,7-tetrahydro-2H-indazol-3-amine: Prepared by the method as described for Intermediate P1, substituting phenylhydrazine for ethyl 3-hydrazinylbenzoate hydrochloride and 3,3-dimethyl-2-oxocyclohexanecarbonitrile for 4,4-dimethyl-3-oxopentanenitrile to yield the product as an off-white solid (0.490 g, 54.2% yield, 66% purity). MS (apci) m/z=242.2 (M+H).

Intermediate P107

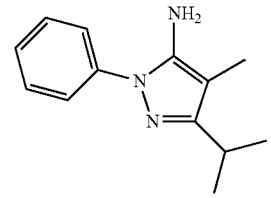 [SMILES: Cc1c(C(C)C)nn(-c2ccccc2)c1N]

3-isopropyl-4-methyl-1-phenyl-1H-pyrazol-5-amine

Step A: Preparation of 2,4-dimethyl-3-oxopentanenitrile: To a solution of propiononitrile (518 mg, 9.40 mmol) in THF (50 mL, 7.83 mmol) at −78° C. under N$_2$ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with H$_2$O (50 mL) to dissolve the solids. The mixture was extracted with Et$_2$O (25 mL), and the basic aqueous phase was acidified with 2M HCl (5 mL) and extracted with Et$_2$O (2×50 mL). The combined organic phases were washed with brine (50 mL), dried with MgSO$_4$, filtered, and concentrated to afford the product (421 mg, 42.9% yield)

Step B: Preparation of 3-isopropyl-4-methyl-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

Intermediate P108

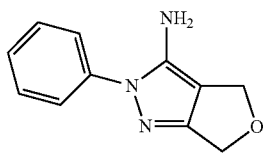 [SMILES: Nc1c2c(nn1-c1ccccc1)COC2]

2-phenyl-4,6-dihydro-2H-furo[3,4-c]pyrazol-3-amine

Step A: Preparation of 4-oxotetrahydrofuran-3-carbonitrile: To a suspension of KOtBu (996.6 mg, 8.881 mmol) in THF (640.4 mg, 8.881 mmol) cooled to 0° C. was added dropwise methyl 2-hydroxyacetate (675.7 µL, 8.881 mmol) and stirred for 10 minutes. The acrylonitrile (589.1 µL, 8.881 mmol) was then added and the reaction stirred at ambient temperature. After 3 hours, the reaction was diluted with H$_2$O (50 mL), then extracted with Et$_2$O (25 mL) to remove any starting ester. The basic aqueous phase was acidified with 2M HCl (5 mL), then extracted with Et$_2$O (2×50 mL). The combined organic phases were dried with MgSO$_4$, filtered, and concentrated to afford a light brown oil (446 mg, 45.2% yield). $^1$H NMR (CDCl$_3$) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine: Prepared by the method as described for Intermediate P1, substituting phenyl hydrazine for ethyl 3-hydrazinylbenzoate hydrochloride and 4,4-dimethyl-3-oxopentanenitrile with 4-oxotetrahydrofuran-3-carbonitrile to yield the product as a reddish-brown syrup (182 mg, 22.5% yield). MS (apci) m/z=202.1 (M+H).

Intermediate P109

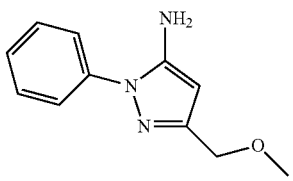

3-(methoxymethyl)-1-phenyl-1H-pyrazol-5-amine

Step A: Preparation of 4-methoxy-3-oxobutanenitrile: To a solution of methyl 2-methoxyacetate (0.4753 mL, 4.803 mmol) in THF (20 mL, 4.803 mmol) at −78° C. under N$_2$ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with H$_2$O (25 mL), washed with Et$_2$O (25 mL), then neutralized with 2 M HCl (1.5 mL). This was extracted with Et$_2$O (2×25 mL) and the combined organic phases were washed with brine (25 mL), dried with MgSO$_4$, filtered, and concentrated to afford the product (169 mg, 31.1% yield). $^1$H NMR (CDCl$_3$) δ 4.09 (s, 2H), 3.66 (s, 2H), 3.46 (s, 3H)

Step B: Preparation of 3-(methoxymethyl)-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

Intermediate P110

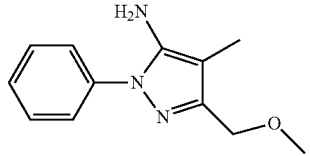 [SMILES: COCc1nn(-c2ccccc2)c(N)c1C]

3-(methoxymethyl)-4-methyl-1-phenyl-1H-pyrazol-5-amine

Prepared according to the method as described for Intermediate P109, replacing acetonitrile with propionitrile to afford the product as an orange residue. MS (apci) m/z=218.0 (M+H).

Intermediate P111

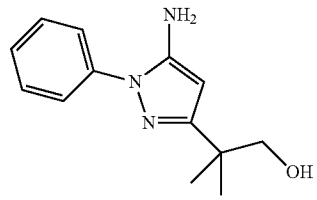 [SMILES: CC(C)(CO)c1cc(N)n(-c2ccccc2)n1]

2-(5-amino-1-phenyl-1H-pyrazol-3-yl)-2-methylpropan-1-ol

Step A: Preparation of methyl 3-(tert-butyldimethylsilyloxy)-2,2-dimethylpropanoate: Methyl 3-hydroxy-2,2-dimethylpropanoate (1.000 g, 7.567 mmol), TBDMS-Cl (1.140 g, 7.567 mmol) and imidazole (0.5666 g, 8.323 mmol) were dissolved in DMF (5 mL, 7.567 mmol) and stirred at ambient temperature overnight. The reaction mixture was diluted with H$_2$O (25 mL) and extracted with EtOAc (2×25 mL). The combined organic phases were washed with brine (25 mL), dried with MgSO$_4$, filtered and concentrated to afford the product (1.92 g, 103% yield). $^1$H NMR (CDCl$_3$) δ 3.66 (s, 3H), 3.57 (s, 2H), 1.15 (s, 6H), 0.87 (s, 9H), 0.02 (s, 6H).

Step B: Preparation of 5-(tert-butyldimethylsilyloxy)-4,4-dimethyl-3-oxopentanenitrile: Prepared according to the method described for Intermediate P109, replacing methyl 2-methoxyacetate with methyl 3-(tert-butyldimethylsilyloxy)-2,2-dimethylpropanoate to afford the product as a pale yellow residue. $^1$H NMR (CDCl$_3$) δ 3.70 (s, 2H), 3.55 (s, 2H), 1.15 (s, 6H), 0.89 (s, 9H), 0.06 (s, 6H).

Step C: Preparation of 2-(5-amino-1-phenyl-1H-pyrazol-3-yl)-2-methylpropan-1-ol: Prepared by the method as described for Intermediate P1, substituting phenyl hydrazine for ethyl 3-hydrazinylbenzoate hydrochloride and 4,4-dimethyl-3-oxopentanenitrile with methyl 3-(tert-butyldimethylsilyloxy)-2,2-dimethylpropanoate to yield the product as yellow syrup (74 mg, 66% yield). MS (apci) m/z=232.2 (M+H).

Intermediate P112

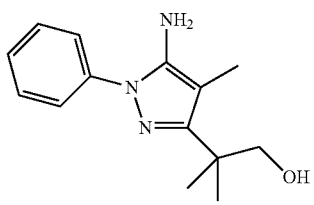 [SMILES: Cc1c(C(C)(C)CO)nn(-c2ccccc2)c1N]

2-(5-amino-4-methyl-1-phenyl-1H-pyrazol-3-yl)-2-methylpropan-1-ol

Prepared according to the method described for Intermediate P111, replacing acetonitrile with propionitrile to afford the product as a yellow residue. MS (apci) m/z=246.2 (M+H).

Intermediate P113

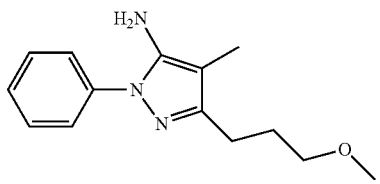 [SMILES: COCCCc1nn(-c2ccccc2)c(N)c1C]

3-(3-methoxypropyl)-4-methyl-1-phenyl-1H-pyrazol-5-amine

Prepared according to the method described for Intermediate P109, replacing methyl 2-methoxyacetate with methyl 4-methoxybutanoate and replacing acetonitrile with propionitrile in Step A to afford the product as an orange-brown syrup. MS (apci) m/z=246.1 (M+H).

Intermediate P114

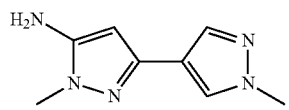

1,1'-dimethyl-1H,1'H-3,4'-bipyrazol-5-amine

Step A: Preparation of 3-(1-methyl-1H-pyrazol-4-yl)-3-oxopropanenitrile: A solution of ethyl 1-methyl-1H-pyrazole-4-carboxylate (500 mg, 3.24 mmol), toluene (7.50 mL, 70.4 mmol), and acetonitrile (346 µL, 6.49 mmol) was treated in one portion with KOtBu (1092 mg, 9.73 mmol) to give a hazy solution. The reaction was allowed to stir at ambient temperature for one hour, and was determined to be complete by HPLC analysis. The mixture was treated with water (7.5 mL) and stirred for 1 minute, then acidified with 3M HCl (3027 µL, 9.08 mmol) to pH 5.5-6. The aqueous layer was extracted with ethyl acetate (3×5 mL) and the combined organic extracts were concentrated in vacuo to give a yellow viscous oil, which completely solidified upon placing under high vacuum to afford the product (102 mg, 21.1% yield). $^1$H NMR (CDCl$_3$) δ 8.02 (s, 1H), 7.94 (s, 1H), 3.98 (s, 3H), 3.82 (s, 2H)

Step B: Preparation of 1,1'-dimethyl-1H,1'H-3,4'-bipyrazol-5-amine: Prepared by the method as described for Intermediate P1, substituting methyl hydrazine for ethyl 3-hydrazinylbenzoate hydrochloride and replacing 4,4-dimethyl-3-oxopentanenitrile with 3-(1-methyl-1H-pyrazol-4-yl)-3-oxopropanenitrile to yield the product as an ivory white solid (45 mg, 44.6% yield). MS (apci) m/z=178.1 (M+H).

Intermediate P115

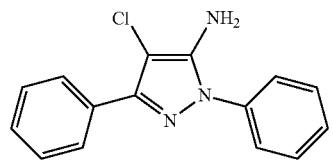 [SMILES: Nc1c(Cl)c(-c2ccccc2)nn1-c1ccccc1]

4-chloro-1,3-diphenyl-1H-pyrazol-5-amine

To a solution of 1,3-diphenyl-1H-pyrazol-5-amine (Table 1; 0.100 g, 0.425 mmol) in acetonitrile (2 mL) was added N-chlorosuccinimide (0.0568 g, 0.425 mmol). The pale yellow solution was stirred at ambient temperature for 3 hours, then concentrated in vacuo and purified by silica column chromatography eluting with 20% EtOAc/Hexanes to afford the product as a light brown oil (0.10 g, 87% yield). MS (apci) m/z=270.0 (M+H).

Intermediate P116

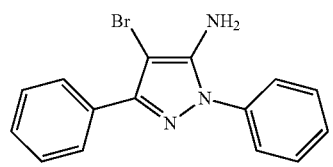 [SMILES: Nc1c(Br)c(-c2ccccc2)nn1-c1ccccc1]

4-bromo-1,3-diphenyl-1H-pyrazol-5-amine

Prepared according to the procedure described for Intermediate P115, substituting N-chloro succinimide with N-bromo-succinimide. MS (apci) m/z=313.9 (M+H).

Intermediate P117

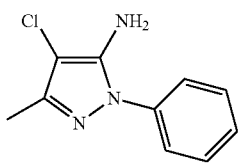

4-chloro-3-methyl-1-phenyl-1H-pyrazol-5-amine

Prepared according to the procedure described for Intermediate P115, substituting 1,3-diphenyl-1H-pyrazol-5-amine with 3-methyl-1-phenyl-1H-pyrazol-5-amine. MS (apci) m/z=207.9 (M+H).

Intermediate P118

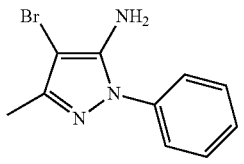

4-bromo-3-methyl-1-phenyl-1H-pyrazol-5-amine

Prepared according to the procedure described for Intermediate P117, substituting N-chloro succinimide with N-bromo-succinimide. MS (apci) m/z=251.9 (M+H).

Intermediate P119

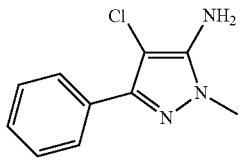

4-chloro-1-methyl-3-phenyl-1H-pyrazol-5-amine

Prepared according to the procedure described for Intermediate P115, substituting 1,3-diphenyl-1H-pyrazol-5-amine with 1-methyl-3-phenyl-1H-pyrazol-5-amine (Table 1). MS (apci) m/z=208.0 (M+H).

Intermediate P120

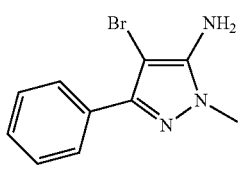

4-bromo-1-methyl-3-phenyl-1H-pyrazol-5-amine

Prepared according to the procedure described for Intermediate P119, substituting N-chloro succinimide with N-bromo-succinimide. MS (apci) m/z=251.9 (M+H).

Intermediate P121

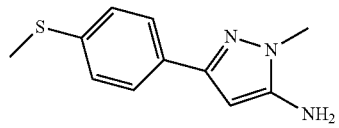

1-methyl-3-(4-(methylthio)phenyl)-1H-pyrazol-5-amine

Step A: Preparation of 3-(4-(methylthio)phenyl)-3-oxo-propanenitrile: To a suspension of NaH (60% in mineral oil) (154 mg, 3.84 mmol) in dioxane (25.0 mL, 2.74 mmol) was added acetonitrile (0.217 mL, 4.12 mmol). The reaction mixture was stirred at ambient temperature for 30 minutes, then treated with methyl 4-(methylthio)benzoate (500 mg, 2.74 mmol) and heated to reflux for 15 hours. The suspension was cooled, then diluted with water (25 mL) and washed with Et$_2$O (25 mL). The aqueous layer was neutralized with 2M HCl (1.8 mL) and extracted with Et$_2$O (2×25 mL). The combined organic phases were washed with brine (25 mL), dried with MgSO$_4$, filtered and concentrated in vacuo. The resultant residue was purified by silica column chromatography eluting with 0-5% MeOH/DCM to afford the product (317 mg, 60.4% yield). $^1$H NMR (CDCl$_3$) δ 7.82 (d, 2H), 7.30 (d, 2H), 4.02 (s, 2H), 2.54 (s, 3H).

Step B: Preparation of 1-methyl-3-(4-(methylthio)phenyl)-1H-pyrazol-5-amine: Prepared by the method as described in Intermediate P1, substituting methylhydrazine for ethyl 3-hydrazinylbenzoate hydrochloride and substituting 3-(4-(methylthio)phenyl)-3-oxopropanenitrile for 4,4-dimethyl-3-oxopentanenitrile to yield the product as a yellow solid (0.307 g, 96.7% yield). MS (apci) m/z=220.0 (M+H).

Intermediate P122

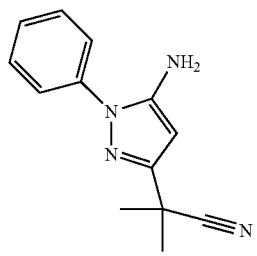 [SMILES: CC(C)(C#N)c1cc(N)n(-c2ccccc2)n1]

2-(5-amino-1-phenyl-1H-pyrazol-3-yl)-2-methylpropanenitrile

Prepared according to the procedure for Intermediate P121, substituting methyl 4-(methylthio)benzoate with ethyl 2-cyano-2-methylpropanoate in Step A and phenyl hydrazine hydrochloride for methyl hydrazine in Step B. MS (apci) m/z=227.1 (M+H).

Intermediate P123

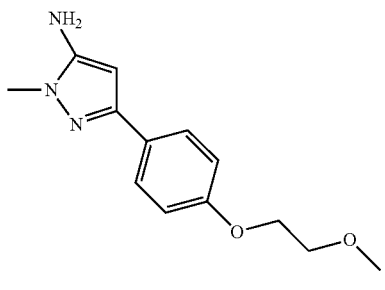

3-(4-(2-methoxyethoxy)phenyl)-1-methyl-1H-pyrazol-5-amine

Step A: Preparation of 3-(4-(benzyloxy)phenyl)-3-oxopropanenitrile: Prepared according to the procedure described for Intermediate P121, substituting methyl 4-(methylthio)benzoate with methyl 4-(benzyloxy)benzoate in Step A. $^1$H NMR (CDCl$_3$) δ 7.90 (d, 2H), 7.42 (m, 4H), 7.37 (m, 1H), 7.05 (d, 2H), 5.16 (s, 2H), 4.00 (s, 2H).

Step B: Preparation of 3-(4-(benzyloxy)phenyl)-1-methyl-1H-pyrazol-5-amine: Prepared by the method as described for Intermediate P1, substituting methylhydrazine for ethyl 3-hydrazinylbenzoate hydrochloride and 3-(4-(benzyloxy)phenyl)-3-oxopropanenitrile for 4,4-dimethyl-3-oxopentanenitrile to yield the product as a yellow solid. MS (apci) m/z=280.1 (M+H).

Step C: Preparation of 4-(5-amino-1-methyl-1H-pyrazol-3-yl)phenol: To a solution of 3-(4-(benzyloxy)phenyl)-1-methyl-1H-pyrazol-5-amine (47 mg, 0.17 mmol) in EtOH (5.0 mL) was added 5% Pd/C (9.0 mg, 0.0084 mmol) and stirred under a H$_2$ balloon for 17 hours. The reaction mixture was filtered through Celite®, rinsed with EtOH and concentrated in vacuo to afford the product (28 mg, 88% yield). MS (apci) m/z=190.1 (M+H).

Step D: Preparation of 3-(4-(2-methoxyethoxy)phenyl)-1-methyl-1H-pyrazol-5-amine: To a solution of 4-(5-amino-1-methyl-1H-pyrazol-3-yl)phenol (14 mg, 0.074 mmol) in DMSO (0.50 mL, 7.0 mmol) was added Cs$_2$CO$_3$ (48 mg, 0.15 mmol) and 1-bromo-2-methoxyethane (9.7 μL, 0.10 mmol). The reaction mixture was stirred for 16 hours, then diluted with water (10 mL) and extracted with DCM (3×10 mL). The combined organic extracts were washed with brine (10 mL), dried with MgSO$_4$, filtered and concentrated to afford the crude product (22 mg, 120% yield). The crude product was used without purification in subsequent steps. MS (apci) m/z=248.0 (M+H).

Intermediate P124

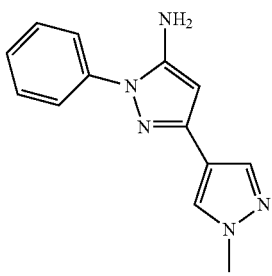 [SMILES: Cn1cc(-c2cc(N)n(-c3ccccc3)n2)cn1]

1'-methyl-1-phenyl-1H,1'H-3,4'-bipyrazol-5-amine

Prepared according to the procedure described for Intermediate P114, substituting methylhydrazine with phenylhydrazine in Step B. MS (apci) m/z=240.0 (M+H).

Intermediate P125

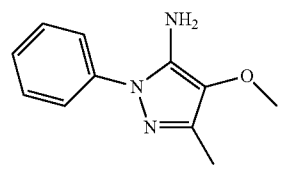

4-methoxy-3-methyl-1-phenyl-1H-pyrazol-5-amine

Prepared according to the procedure for Intermediate P121, substituting methyl 4-(methylthio)benzoate with ethyl acetate and substituting acetonitrile with 2-methoxyacetonitrile in Step A and phenyl hydrazine hydrochloride for methyl hydrazine in Step B. MS (apci) m/z=204.0 (M+H).

Intermediate P126

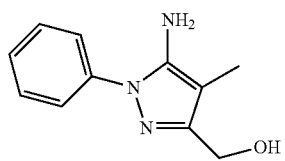

(5-amino-4-methyl-1-phenyl-1H-pyrazol-3-yl)methanol

Prepared according to the procedure for Intermediate P112, substituting methyl 3-hydroxy-2,2-dimethylpropanoate with ethyl 2-hydroxyacetate in Step A. MS (apci) m/z=204.1 (M+H).

Intermediate P127

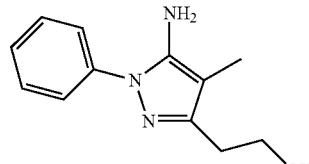

2-(5-amino-4-methyl-1-phenyl-1H-pyrazol-3-yl)ethanol

Prepared according to the procedure for Intermediate P112, substituting methyl 3-hydroxy-2,2-dimethylpropanoate with methyl 3-hydroxypropanoate in Step A. MS (apci) m/z=218.0 (M+H).

Intermediate P128

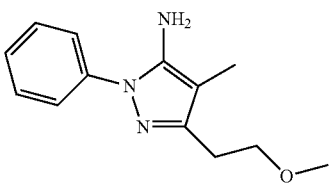 [SMILES: COCCc1nn(-c2ccccc2)c(N)c1C]

3-(2-methoxyethyl)-4-methyl-1-phenyl-1H-pyrazol-5-amine

Step A: Preparation of 5-methoxy-2-methyl-3-oxopentanenitrile: To a suspension of NaNH$_2$ (50 wt % suspension in toluene) (330 mg, 4.23 mmol) in THF (25 mL, 4.23 mmol) under N$_2$ at −78° C. was added propiononitrile (0.448 mL, 6.35 mmol), and the reaction mixture was stirred for 30 minutes. Methyl 3-methoxypropanoate (0.495 mL, 4.23 mmol) was added and the reaction mixture was stirred at −78° C. for 1 hour, then at 0° C. for 2.5 hours. The reaction mixture was diluted with H$_2$O (25 mL) and washed with Et$_2$O (25 mL). The basic aqueous phase was neutralized with 2M HCl (1.6 mL), then extracted with Et$_2$O (3×25 mL). The combined organic phases were washed with brine (25 mL), dried with MgSO$_4$, filtered, and concentrated to afford the crude product as a pale greenish oil (171 mg). The crude mixture was taken directly to the next step.

Step B: Preparation of 3-(2-methoxyethyl)-4-methyl-1-phenyl-1H-pyrazol-5-amine: Prepared by the method as described for Intermediate P1, substituting 5-methoxy-2-methyl-3-oxopentanenitrile for 4,4-dimethyl-3-oxopentanenitrile and substituting phenylhydrazine hydrochloride for ethyl 3-hydrazinylbenzoate hydrochloride to yield the product as a yellow solid (56 mg, 20% yield). MS (apci) m/z=232.0 (M+H).

Intermediate P129

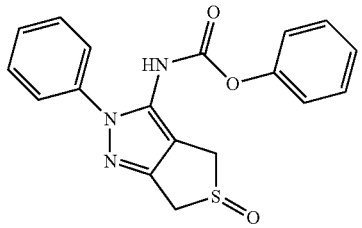 [SMILES: O=C(Nc1c2c(nn1-c1ccccc1)CS(=O)C2)Oc1ccccc1]

Phenyl (5-oxido-2-phenyl-4,6-dihydro-2H-thieno[3,4-c]pyrazol-3-yl)carbamate

A THF (4 mL) solution of phenyl 2-phenyl-4,6-dihydro-2H-thieno[3,4-c]pyrazol-3-ylcarbamate (Intermediate P130, Step B; 50 mg, 0.15 mmol) was cooled to −50° C. with an external dry-ice/MeCN bath and treated with a THF (2 mL) solution of 3-chlorobenzoperoxoic acid (33 mg, 0.13 mmol). After stirring for 1 hour, the mixture was quenched with Na$_2$S$_2$O$_3$ and water, extracted with EtOAc, washed with NaHCO$_3$ and brine, dried with MgSO$_4$, filtered, and concentrated to give the product which was directly used in next step without further purification. MS (apci) m/z=354.1 (M+H).

Intermediate P130

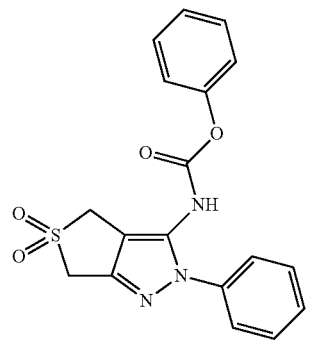 [SMILES: O=C(Nc1c2c(nn1-c1ccccc1)CS(=O)(=O)C2)Oc1ccccc1]

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine: A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL) The solid was collected by filtration, washed with 0.1 N NaOH, water, and hexanes (approx. 10 mL each) then dried on high vacuum to yield the product as white solid (1.6 g, 95% yield). MS (apci pos) m/z=218.1 (M+H).

Step B: Preparation of phenyl 2-phenyl-4,6-dihydro-2H-thieno[3,4-c]pyrazol-3-ylcarbamate. To a suspension of 2-phenyl-4,6-dihydro-2H-thieno[3,4-c]pyrazol-3-amine (500 mg, 2.30 mmol) in EtOAc (10 mL) was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with H$_2$O, brine (25 mL each), then dried with Na$_2$SO$_4$, filtered and concentrated. The crude material was purified by reverse-phase column chromatography, eluting with 5-70% acetonitrile/water to yield the product as white solid (0.5 g, 64% yield). MS (apci pos) m/z=338.1 (M+H).

Step C: Preparation of phenyl (5,5-dioxido-2-phenyl-4,6-dihydro-2H-thieno[3,4-c]pyrazol-3-yl)carbamate. To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 min. The mixture was then diluted with DCM (3 mL) and washed with saturated aqueous NaHCO$_3$ (3×2 mL) and saturated aqueous Na$_2$S$_2$O$_3$ (3×2 mL). The organic layer was dried with MgSO$_4$, filtered and concentrated under reduced pressure to yield the title product as light yellowish foamy solid (31 mg, 57% yield, 95% pure). MS (apci pos) m/z=371.0 (M+H).

Intermediate P132

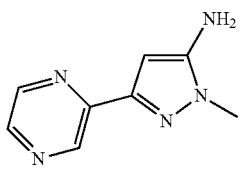

1-methyl-3-(pyrazin-2-yl)-1H-pyrazol-5-amine

Step A: Preparation of 3-oxo-3-(pyrazin-2-yl)propanenitrile: To a suspension of NaH (60% in mineral oil, 81.1 mg, 2.03 mmol) in dioxane (15 mL) was added acetonitrile (0.114 mL, 2.17 mmol), followed by methyl pyrazine-2-carboxylate (200 mg, 1.45 mmol) and the reaction heated to reflux for 2.5 hours. The reaction mixture was cooled to ambient temperature and diluted with $H_2O$ (25 mL) and extracted with $Et_2O$ (25 mL). The aqueous phase was neutralized with 2M aqueous HCl (0.7 mL), then extracted with 10% MeOH/DCM (3×25 mL). The combined organic phases were washed with brine (25 mL), dried with $MgSO_4$, filtered, and concentrated to yield the crude product as an orange syrup (134 mg, 62.9% yield). $^1$H NMR (CDCl$_3$) δ 9.32 (d, 1H), 8.87 (d, 1H), 8.68 (dd, 1H), 4.34 (s, 2H).

Step B: Preparation of 1-methyl-3-(pyrazin-2-yl)-1H-pyrazol-5-amine: To a suspension of 3-oxo-3-(pyrazin-2-yl)propanenitrile (67.0 mg, 0.455 mmol) in EtOH (5 mL) was added methylhydrazine (0.024 mL, 0.455 mmol). The reaction mixture was refluxed for 15 hours, then concentrated in vacuo. The crude product was purified by silica column chromatography, eluting with 0-5% MeOH/DCM to yield the product as a brown residue (33 mg, 41% yield). MS (apci) m/z=176.2 (M+H).

Intermediate P133

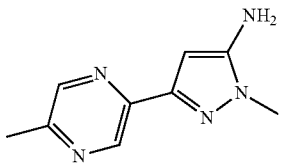

1-methyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate and propionitrile with acetonitrile to afford 3-(5-methylpyrazin-2-yl)-3-oxopropanenitrile. In Step B, phenylhydrazine was replaced by methylhydrazine to afford the title pyrazole. MS (apci) m/z=190.2 (M+H).

Intermediate P134

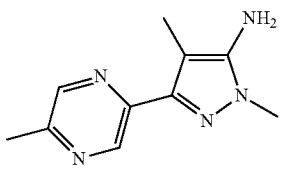

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate P135

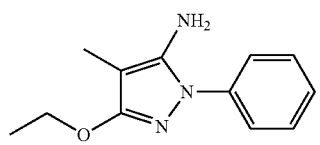 [SMILES: CCOc1nn(-c2ccccc2)c(N)c1C]

3-ethoxy-4-methyl-1-phenyl-1H-pyrazol-5-amine

Step A: Preparation of 5-amino-4-methyl-1-phenyl-1H-pyrazol-3(2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and $Et_2O$. The resultant solid was filtered, washed with $Et_2O$, and dried under vacuum to give the product as a white solid (3.4 g, 39% yield). MS (apci) m/z=190.0 (M–H).

Step B: Preparation of 3-ethoxy-4-methyl-1-phenyl-1H-pyrazol-5-amine: To a suspension of 5-amino-4-methyl-1-phenyl-1H-pyrazol-3(2H)-one (10.0 g, 52.9 mmol) in DMF (100 mL) was added $K_2CO_3$ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with $MgSO_4$, filtered, and concentrated to give the product (5.35 g, 47% yield). MS (apci) m/z=218.1 (M+H).

The compounds in Table 3 were prepared by the method as described for Intermediate P135, substituting bromoethane with the appropriate alkyl halide or alkyl methanesulfonate.

TABLE 3

| Intermediate # | Structure | Data |
|---|---|---|
| P200 | ![structure] | MS (apci) m/z = 248.1 (M + H) |
| P201 | ![structure] | MS (apci) m/z = 204.1 (M + H) |

TABLE 3-continued

| Intermediate # | Structure | Data |
|---|---|---|
| P202 | 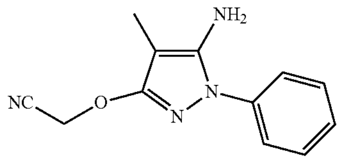 [SMILES: Cc1c(OCC#N)nn(-c2ccccc2)c1N] | MS (apci) m/z = 229.0 (M + H) |
| P203 | 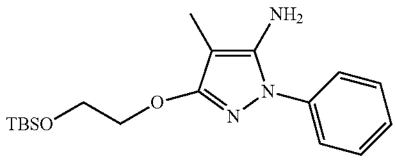 [SMILES: Cc1c(OCCO[Si](C)(C)C(C)(C)C)nn(-c2ccccc2)c1N] | MS (apci) m/z = 348.1 (M + H) |
| P204 | 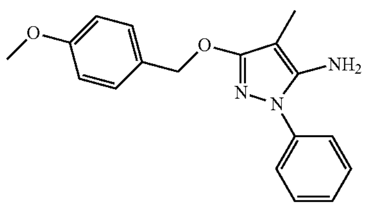 [SMILES: COc1ccc(COc2nn(-c3ccccc3)c(N)c2C)cc1] | MS (apci) m/z = 310.0 (M + H) |
| P205 | 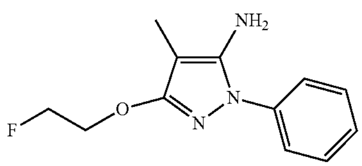 [SMILES: Cc1c(OCCF)nn(-c2ccccc2)c1N] | MS (apci) m/z = 236.1 (M + H) |
| P206 | 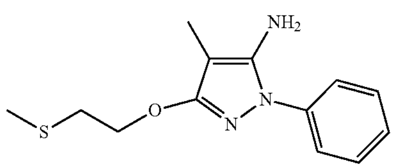 [SMILES: CSCCOc1nn(-c2ccccc2)c(N)c1C] | MS (apci) m/z = 264.0 (M + H) |
| P207 | 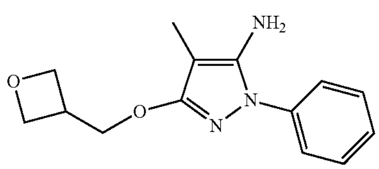 [SMILES: Cc1c(OCC2COC2)nn(-c2ccccc2)c1N] | MS (apci) m/z = 260.1 (M + H) |
| P208 | 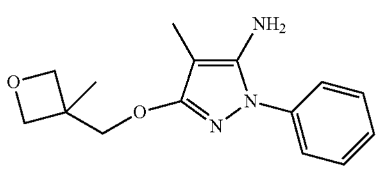 [SMILES: Cc1c(OCC2(C)COC2)nn(-c2ccccc2)c1N] | MS (apci) m/z = 274.1 (M + H) |
| P209 | 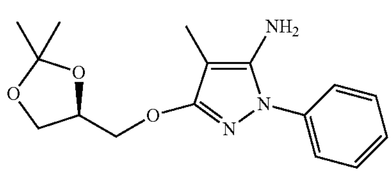 [SMILES: Cc1c(OC[C@H]2COC(C)(C)O2)nn(-c2ccccc2)c1N] | MS (apci) m/z = 304.1 (M + H) |
| P210 | 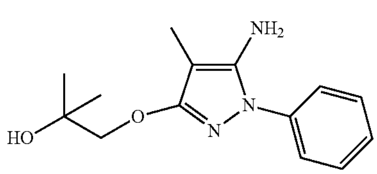 [SMILES: Cc1c(OCC(C)(C)O)nn(-c2ccccc2)c1N] | MS (apci) m/z = 262.1 (M + H) |
| P211 | | MS (apci) m/z = 362.0 (M + H) |
| P212 | | MS (apci) m/z = 304.1 (M + H) |

Intermediate P136

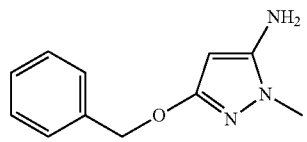

3-(benzyloxy)-1-methyl-1H-pyrazol-5-amine

Step A: Preparation of 5-amino-1-methyl-4-phenyl-1H-pyrazol-3(2H)-one: To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 15 hours. The reaction mixture was cooled to 0° C. and filtered. The resultant solid was washed with cold EtOH (20 mL) and Et$_2$O (20 mL) to give the desired product (2.10 g, 83.7% yield). MS (apci) m/z=190.2 (M+H)

Step B: Preparation of 3-(benzyloxy)-1-methyl-1H-pyrazol-5-amine: A suspension of 5-amino-1-methyl-1H-pyrazol-3(2H)-one (0.35 g, 3.1 mmol), Benzyl chloride (0.43 g, 3.4 mmol), and K$_2$CO$_3$ (1.3 g, 9.3 mmol) in DMF (4 mL) was heated at 70° C. for 17 hours. After cooling, the reaction mixture was treated with EtOAc, washed with water and brine, dried with MgSO$_4$, and concentrated in vacuo. The crude product was purified by silica column chromatography eluting with 2-6% MeOH/DCM to afford the title compound (0.16 g, 25% yield). MS (apci) m/z=204.0 (M+H).

Intermediate P137

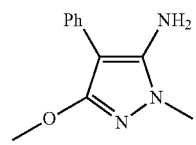

3-methoxy-1-methyl-4-phenyl-1H-pyrazol-5-amine

To a suspension of 5-amino-1-methyl-4-phenyl-1H-pyrazol-3(2H)-one (Step A of the preparation of Intermediate P136; 208 mg, 1.10 mmol) and K$_2$CO$_3$ (456 mg, 3.30 mmol) in DMF (5 mL) was added dropwise iodomethane (172 mg, 1.21 mmol). The reaction mixture was stirred for 15 hours. The solvent was removed under reduced pressure and the residue was purified by silica column chromatography eluting with 33% EtOAc/Hexanes to give the title pyrazole (66.0 mg, 30.4% yield). MS (apci) m/z=204.1 (M+H).

Intermediate P138

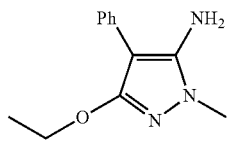

3-ethoxy-1-methyl-4-phenyl-1H-pyrazol-5-amine

Prepared as described in Intermediate P137, replacing iodomethane with iodoethane in Step B to afford the title compound. MS (apci) m/z=218.2 (M+H).

Intermediate P139

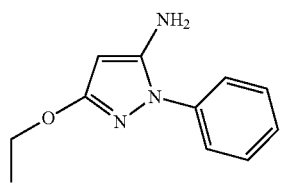

3-ethoxy-1-phenyl-1H-pyrazol-5-amine

Prepared according to the procedure described for Intermediate 135, substituting ethyl-2-cyanopropanoate with ethyl-2-cyanoacetate in Step A. MS (apci) m/z=204.0 (M+H).

The compounds in the following Table were prepared by the method as described for Intermediate P135, substituting bromoethane with the appropriate alkyl halide, alkyl methanesulfonate or epoxide.

| Intermediate # | Structure | MS (apci) m/z |
|---|---|---|
| P140 | 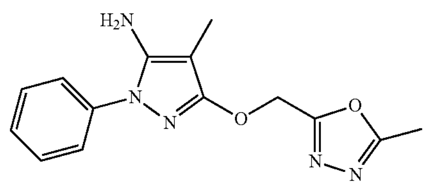 [SMILES: Cc1nnc(COc2nn(-c3ccccc3)c(N)c2C)o1] | 286.1 (M + H) |
| P141 | 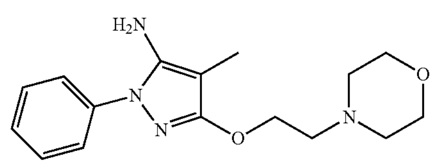 [SMILES: Cc1c(OCCN2CCOCC2)nn(-c2ccccc2)c1N] | 303.1 (M + H) |
| P142 | 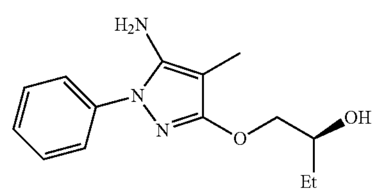 [SMILES: CC[C@H](O)COc1nn(-c2ccccc2)c(N)c1C] | 262.1 (M + H) |
| P143 | 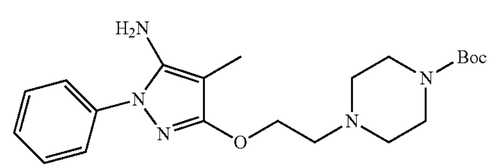 [SMILES: Cc1c(OCCN2CCN(C(=O)OC(C)(C)C)CC2)nn(-c2ccccc2)c1N] | 402.2 (M + H) |
| P144 | 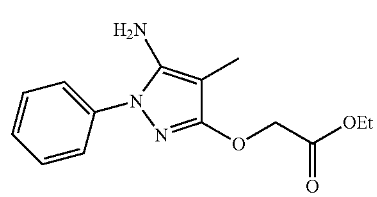 [SMILES: CCOC(=O)COc1nn(-c2ccccc2)c(N)c1C] | 276.1 (M + H) |

| Intermediate # | Structure | MS (apci) m/z |
|---|---|---|
| P145 | 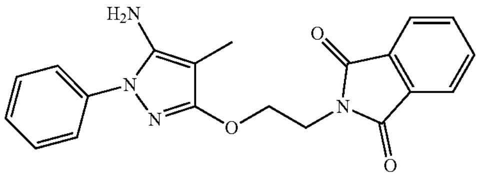 [SMILES: Cc1c(OCCN2C(=O)c3ccccc3C2=O)nn(-c2ccccc2)c1N] | 363.1 (M + H) |
| P146 | 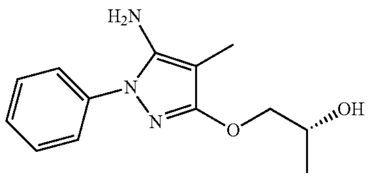 [SMILES: Cc1c(OC[C@@H](C)O)nn(-c2ccccc2)c1N] | 248.1 (M + H) |
| P147 | 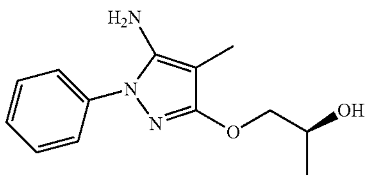 [SMILES: Cc1c(OC[C@H](C)O)nn(-c2ccccc2)c1N] | 248.1 (M + H) |
| P148 | 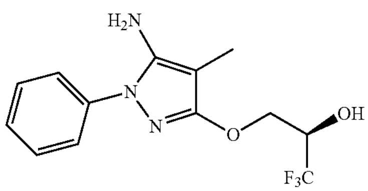 [SMILES: Cc1c(OC[C@@H](O)C(F)(F)F)nn(-c2ccccc2)c1N] | 302.1 (M + H) |
| P149 | 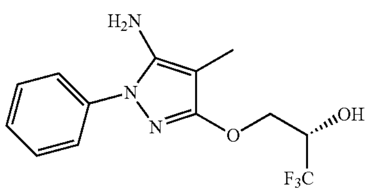 [SMILES: Cc1c(OC[C@H](O)C(F)(F)F)nn(-c2ccccc2)c1N] | 302.1 (M + H) |
| P150 | 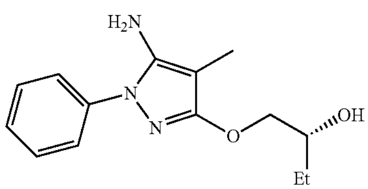 [SMILES: CC[C@@H](O)COc1nn(-c2ccccc2)c(N)c1C] | 262.1 (M + H) |

Intermediate 151

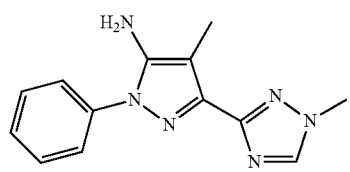 [SMILES: Cc1c(-c2ncn(C)n2)nn(-c2ccccc2)c1N]

1'-(2-methoxyethyl)-1-phenyl-1H,1'H-[3,4'-bipyrazol]-5-amine

Step A: Preparation of methyl 1-methyl-1H-1,2,4-triazole-3-carboxylate: To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H, 1'H-[3,4'-bipyrazol]-5-amine: Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

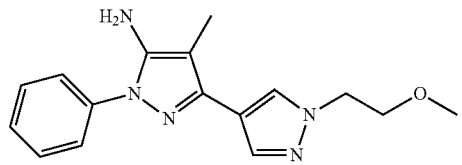 [SMILES: COCCn1cc(-c2nn(-c3ccccc3)c(N)c2C)cn1]

1'-(2-methoxyethyl)-4-methyl-1-phenyl-1H,1'H-[3,4'-bipyrazol]-5-amine

Prepared according to the method described for Intermediate P109, using ethyl 1-(2-methoxyethyl)-1H-pyrazole-4-carboxylate as a replacement for methyl 2-methoxyacetate, and substituting propionitrile for acetonitrile in Step A.

Intermediate 153

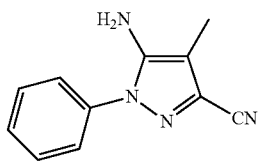

5-amino-4-methyl-1-phenyl-1H-pyrazole-3-carbonitrile

To a stirred solution of aniline (2.02 g, 21.7 mmol) in 6 N HCl (22 mL) was added dropwise a solution of NaNO₂ (1.50 g, 21.7 mmol) in water (20 mL) at 0-5° C. The reaction mixture was stirred at 0° C. for 15 minutes. Acetic acid (10 mL) was added. This solution was added dropwise to a stirred solution of ethyl 2,3-dicyanobutanoate (Prepared according to the procedure described in *Bioorganic & Medicinal Chemistry*, 2004, 12, 3345-3356, 3.60 g, 21.7 mmol) in acetic acid (12 mL) and water (18 mL) at 0° C. After stirring for 1 hour, concentrated ammonium hydroxide (50 mL) was added dropwise followed by THF (50 mL). The reaction was stirred at ambient temperature overnight. The organic layer was separated. The aqueous layer was extracted with EtOAc. The combined organic layers were washed with brine, dried and concentrated. The residue was purified by flash chromatography on silica gel (3:1 hexanes/EtOAc) to give the title compound (2.95 g, 69% yield). MS (apci) m/z=198.9 (M+H).

Intermediate 155

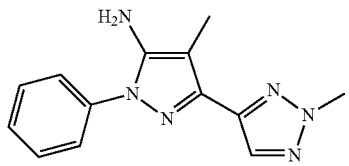 [SMILES: Cc1c(-c2cnn(C)n2)nn(-c2ccccc2)c1N]

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate: A mixture of ethyl 2H-1,2,3-triazole-4-carboxylate (2.00 g, 14.2 mmol), K₂CO₃ (3.53 g, 25.5 mmol) and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl-1H-pyrazol-5-amine: Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

Intermediate 156

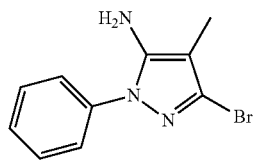

3-bromo-4-methyl-1-phenyl-1H-pyrazol-5-amine

To a stirred solution of 5-amino-4-methyl-1-phenyl-1H-pyrazol-3(2H)-one (Intermediate P135, Step A, 1.00 g, 5.29 mmol) in MeCN (20 mL) was added POBr₃ (2.27 g, 7.93 mmol). The reaction mixture was heated at reflux for 3 hours. The reaction was concentrate in vacuo. The residue was taken up in DCM. Saturated aqueous NaHCO₃ solution was carefully added. The aqueous layer was extracted with DCM. The combined organic layers were washed with brine, dried and concentrated. The residue was purified by flash chromatography on silica gel (1:2 hexane/EtOAc to give the title compound (0.23 g, 17% yield). MS (apci) m/z=251.8 (M+H).

Intermediate 157

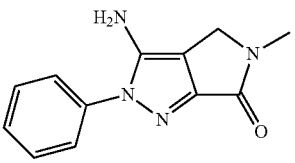 [SMILES: CN1Cc2c(nn(-c3ccccc3)c2N)C1=O]

3-amino-5-methyl-2-phenyl-4,5-dihydropyrrolo[3,4-c]pyrazol-6(2H)-one

Step A: Preparation of ethyl 5-amino-4-((methylamino)methyl)-1-phenyl-1H-pyrazole-3-carboxylate: To a stirred solution of ethyl 5-amino-4-formyl-1-phenyl-1H-pyrazole- 3-carboxylate (Prepared according to the procedure described in *J. Heterocyclic Chemistry*, 2010, 47, p. 287-291, 142 mg, 0.548 mmol) in DCM (3 mL) was added 2.0 M MeNH$_2$ in THF (0.822 mL, 1.64 mmol). Two drops of acetic acid was added. The reaction mixture was stirred at ambient temperature overnight. MeOH (0.4 mL) was added followed by NaBH$_4$ (31 mg, 0.82 mmol) portionwise. The reaction was quenched by the slow addition of water. The mixture was extracted with DCM. The combined organic layers were washed with brine, dried and concentrated. The crude was used in the next step without further purification. MS (apci) m/z=275.0 (M+H).

Step B: Preparation of 3-amino-5-methyl-2-phenyl-4,5-dihydropyrrolo[3,4-c]pyrazol-6(2H)-one: To a stirred solution of ethyl 5-amino-4-((methylamino)methyl)-1-phenyl-1H-pyrazole-3-carboxylate (crude, 65 mg, 0.24 mmol) in MeOH (0.5 mL) and THF (0.5 mL) was added 2 N NaOH (0.24 mL, 0.47 mmol). The reaction mixture was stirred at ambient temperature for 4 hours and then concentrated in vacuo. To the residue was added water. The pH was adjusted to 4-5 using 1 N HCl. Water was evaporated under reduced pressure. The crude acid (58 mg) was dissolved in DMF (3 mL). Et$_3$N (66 µL, 0.47 mmol) was added followed by EDCI (90 mg, 0.47 mmol) and HOBt (32 mg, 0.24 mmol). The reaction mixture was stirred at ambient temperature overnight and then partitioned between EtOAc and water. The aqueous layer was extracted with EtOAc. The combined organic layers were washed with water and brine, dried and concentrated. The residue was purified by flash chromatography on silica gel (2% MeOH in DCM) to give the title compound (15 mg, 28%) as a white solid. MS (apci) m/z=228.9 (M+H).

Intermediate 158

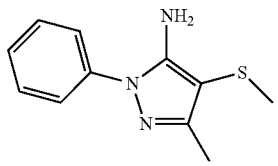

3-methyl-4-(methylthio)-1-phenyl-1H-pyrazol-5-amine

Prepared according to the method described for Intermediate P109, replacing methyl 2-methoxyacetate with ethyl acetate and replacing acetonitrile with 2-(methylthio)acetonitrile in Step A to afford the product as a brown oil. MS (apci) m/z=220.1 (M+H).

Intermediate 159

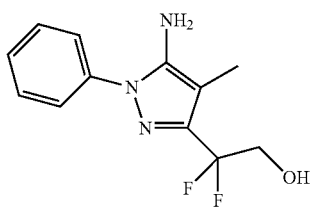 [SMILES: Cc1c(C(F)(F)CO)nn(-c2ccccc2)c1N]

2-(5-amino-4-methyl-1-phenyl-1H-pyrazol-3-yl)-2,2-difluoroethanol

Prepared according to the method described for Intermediate P111, replacing acetonitrile with propionitrile and replacing methyl 3-hydroxy-2,2-dimethylpropanoate with ethyl 2,2-difluoro-3-hydroxypropanoate to afford the product as a pale yellow solid. MS (apci) m/z=254.1 (M+H).

Intermediate 160

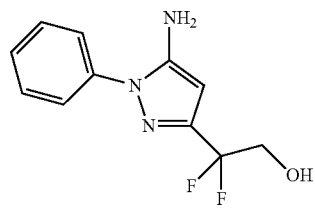 [SMILES: Nc1cc(C(F)(F)CO)nn1-c1ccccc1]

2-(5-amino-1-phenyl-1H-pyrazol-3-yl)-2,2-difluoroethanol

Prepared according to the method described for Intermediate P111, replacing methyl 3-hydroxy-2,2-dimethylpropanoate with ethyl 2,2-difluoro-3-hydroxypropanoate to afford the product as a pale yellow solid. MS (apci) m/z=240.0 (M+H).

Intermediate 161

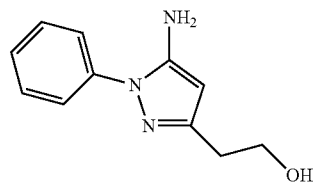 [SMILES: Nc1cc(CCO)nn1-c1ccccc1]

2-(5-amino-1-phenyl-1H-pyrazol-3-yl)ethanol

Prepared according to the method described in Intermediate P111, replacing methyl 3-hydroxy-2,2-dimethylpropanoate with methyl 3-hydroxypropanoate in Step A. MS (apci) m/z=204.1 (M+H).

Intermediate 162

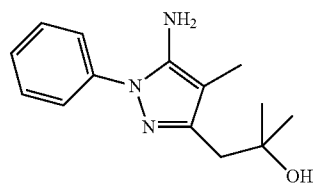 [SMILES: Cc1c(CC(C)(C)O)nn(-c2ccccc2)c1N]

1-(5-amino-4-methyl-1-phenyl-1H-pyrazol-3-yl)-2-methylpropan-2-ol

Step A: Preparation of ethyl 3-hydroxy-3-methylbutanoate: To a solution of lithium bis(trimethylsilyl)amide (1M in THF) (100 mL, 100 mmol) in THF (100 mL) under $N_2$ and cooled to −78° C. was added ethyl acetate (9.74 mL, 100 mmol). The reaction mixture was stirred for 30 minutes, and then acetone (8.81 mL, 120 mmol) was added. The reaction mixture was stirred for 10 minutes, and then quenched with HCl (2M aqueous, 70 mL, 140 mmol) and allowed to warm to ambient temperature. The reaction mixture was extracted with EtOAc (2×150 mL). The organic phases were combined and washed with saturated aqueous $NaHCO_3$ (2×50 mL), dried ($MgSO_4$), filtered and concentrated to afford the product as a yellow oil (12.8 g, 88% yield). $^1$H NMR ($CDCl_3$) δ 4.18 (q, 3H), 2.49 (s, 2H), 1.29 (m, 9H).

Step B: Preparation of 5-hydroxy-5-methyl-3-oxohexanenitrile: To a solution of propionitrile (1.77 mL, 30.5 mmol) in THF (100 mL) under $N_2$ at −78° C. was added lithium bis(trimethylsilyl)amide (1M in THF) (27.9 mL, 27.9 mmol). Stirred 1 hour, then ethyl 3-hydroxy-3-methylbutanoate (1.86 g, 12.7 mmol) was added. The reaction mixture was stirred at −78° C. for 1 hour, then stirred at 0° C. for 1.5 hours, then diluted with $H_2O$ (100 mL) and extracted with $Et_2O$ (50 mL). The phases were separated and the basic aqueous phase was neutralized with HCl (6M aqueous, 4.5 mL), then extracted with $Et_2O$ (3×75 mL). The combined organic phases were washed with brine (75 mL), dried ($MgSO_4$), filtered, and concentrated to afford the product as a pale yellow oil (1.24 g, 63% yield). $^1$H NMR ($CDCl_3$) δ 3.54 (m, 1H), 2.89 (s, 2H), 1.50 (d, 3H), 1.32 (s, 3H), 1.31 (s, 3H).

Step C: Preparation of 1-(5-amino-4-methyl-1-phenyl-1H-pyrazol-3-yl)-2-methylpropan-2-ol: To a suspension of phenylhydrazine (0.793 mL, 7.99 mmol) and HCl (5-6M in iPrOH, 1.60 mL, 7.99 mmol) in EtOH (25 mL) was added a solution of 5-hydroxy-2,5-dimethyl-3-oxohexanenitrile (1.24 g, 7.99 mmol) in EtOH (25 mL) The reaction mixture was refluxed for 17 hours, then cooled to ambient temperature, diluted with saturated aqueous $NaHCO_3$ (10 mL), extracted 10:90 MeOH/DCM (3×25 mL), and the combined organic phases were dried ($MgSO_4$), filtered and concentrated. Purified by silica column chromatography eluting with 0-75% acetone/hexanes to afford the title compound as an orange oil (1.13 g, 58% yield). MS (apci) m/z=246.1 (M+H).

The following pyrazole intermediates were prepared according to the method used for the preparation of Intermediate 162, Steps B and C, using the appropriate starting material. For the preparation of Intermediates 168 and 169, the starting material (purchased from Oakwood) was a mixture of cis and trans diastereomers.

| Intermediate # | Structure | Name | MS (apci) m/z |
|---|---|---|---|
| 163 | 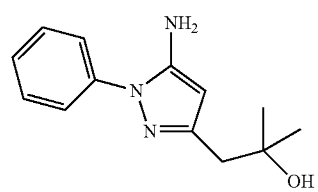 [SMILES: CC(C)(O)Cc1cc(N)n(-c2ccccc2)n1] | 1-(5-amino-1-phenyl-1H-pyrazol-3-yl)-2-methylpropan-2-ol | 232.1 (M + H) |
| 164 | 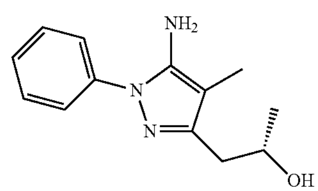 [SMILES: Cc1c(C[C@H](C)O)nn(-c2ccccc2)c1N] | (S)-1-(5-amino-4-methyl-1-phenyl-1H-pyrazol-3-yl)propan-2-ol | 232.1 (M + H) |
| 165 | 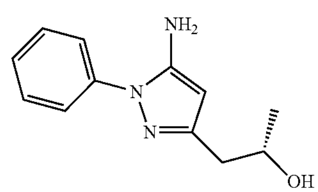 [SMILES: C[C@H](O)Cc1cc(N)n(-c2ccccc2)n1] | (S)-1-(5-amino-1-phenyl-1H-pyrazol-3-yl)propan-2-ol | 218.1 (M + H) |
| 166 | 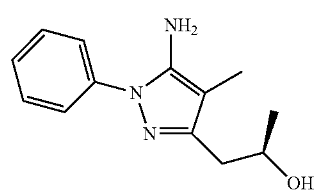 [SMILES: Cc1c(C[C@@H](C)O)nn(-c2ccccc2)c1N] | (R)-1-(5-amino-4-methyl-1-phenyl-1H-pyrazol-3-yl)propan-2-ol | 232.1 (M + H) |

-continued

| Intermediate # | Structure | Name | MS (apci) m/z |
|---|---|---|---|
| 167 | 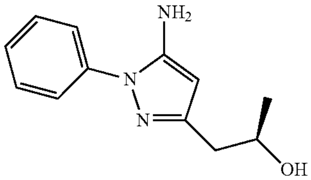 [SMILES: C[C@@H](O)Cc1cc(N)n(-c2ccccc2)n1] | (R)-1-(5-amino-1-phenyl-1H-pyrazol-3-yl)propan-2-ol | 218.1 (M + H) |
| 168 | 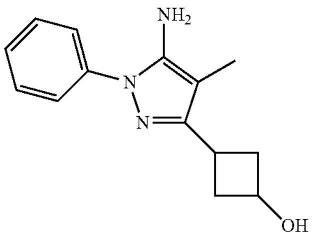 [SMILES: Cc1c(C2CC(O)C2)nn(-c2ccccc2)c1N] | 3-(5-amino-4-methyl-1-phenyl-1H-pyrazol-3-yl)cyclobutanol | 244.1 (M + H) |
| 169 | 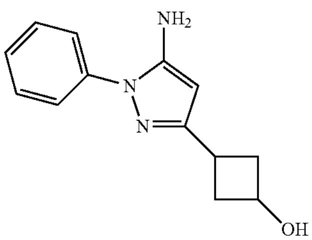 [SMILES: Nc1cc(C2CC(O)C2)nn1-c1ccccc1] | 3-(5-amino-1-phenyl-1H-pyrazol-3-yl)cyclobutanol | 230.1 (M + H) |

Intermediate 170

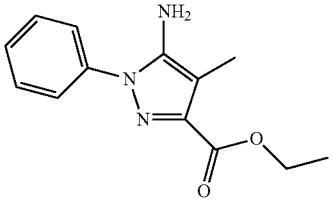 [SMILES: CCOC(=O)c1nn(-c2ccccc2)c(N)c1C]

ethyl 5-amino-4-methyl-1-phenyl-1H-pyrazole-3-carboxylate

Prepared according to the method described for Intermediate P109, replacing methyl 2-methoxyacetate with diethyl oxalate and replacing acetonitrile with propionitrile in Step A to afford the product as a yellow solid. MS (apci) m/z=246.1 (M+H).

Intermediate 171

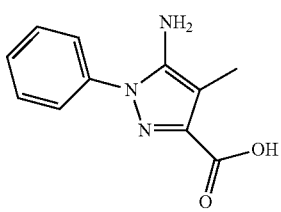 [SMILES: Cc1c(C(=O)O)nn(-c2ccccc2)c1N]

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO$_4$), filtered and concentrated to give the title compound as a yellow solid (1.3 g, 96% yield) MS (apci) m/z=218.1 (M+H).

Intermediate 172

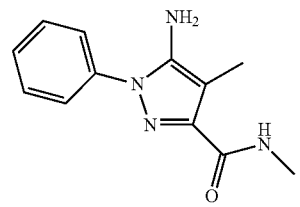 [SMILES: CNC(=O)c1nn(-c2ccccc2)c(N)c1C]

5-amino-N,4-dimethyl-1-phenyl-1H-pyrazole-3-carboxamide

To a solution of 5-amino-4-methyl-1-phenyl-1H-pyrazole-3-carboxylic acid (Intermediate 171, 223 mg, 1.02 mmol) in acetonitrile (10 mL) were added DIEA (0.71 mL, 4.10 mmol), methanamine hydrochloride (138 mg, 2.05 mmol), DMF (2 mL), and then HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

Intermediate 173

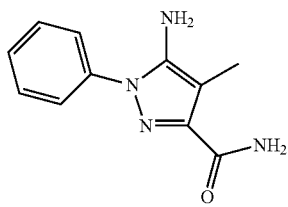 [SMILES: Cc1c(C(N)=O)nn(-c2ccccc2)c1N]

5-amino-4-methyl-1-phenyl-1H-pyrazole-3-carboxamide

A solution of 5-amino-4-methyl-1-phenyl-1H-pyrazole-3-carbonitrile (150 mg, 0.757 mmol) in concentrated H₂SO₄ (0.5 mL) was stirred at ambient temperature for 17 hours. The reaction mixture was cooled and neutralized by the addition of aqueous NaOH (2M, 11 mL), then extracted 10% MeOH/DCM (5×10 mL), and the combined organic extracts were washed with brine, dried (MgSO₄), filtered and concentrated under reduced pressure to afford the title compound as a white solid (151 mg, 95% yield). MS (apci) m/z=239.1 (M+Na).

Intermediate 174

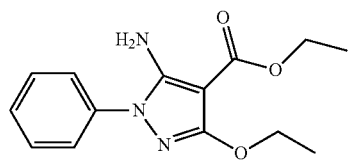 [SMILES: CCOC(=O)c1c(OCC)nn(-c2ccccc2)c1N]

ethyl 5-amino-3-ethoxy-1-phenyl-1H-pyrazole-4-carboxylate

Step A: Preparation of diethyl 2-cyanomalonate: To a suspension of NaH (60 wt % in mineral oil, 499 mg, 12.49 mmol) in THF (100 mL) under N₂ at 0° C. was added diethyl malonate (1.90 mL, 12.49 mmol). The ice bath was removed and the reaction mixture was stirred at ambient temperature for 30 minutes, then cooled to 0° C. and cyanic bromide (5M in MeCN, 2.5 mL, 12.49 mmol) was added. The reaction mixture was stirred at ambient temperature for 19 hours, then diluted with H₂O (50 mL), extracted with Et₂O (50 mL). The aqueous phase was neutralized with HCl (2M aq, 3 mL) then extracted with DCM (2×50 mL). The combined DCM extracts were dried (MgSO₄), filtered, and concentrated to afford the product as a yellow oil (837 mg, 36% yield). 1H NMR (CDCl₃) δ 4.46 (s, 1H), 4.35 (q, 4H), 1.35 (t, 6H).

Step B: Preparation of ethyl 5-amino-3-ethoxy-1-phenyl-1H-pyrazole-4-carboxylate: Prepared according to the method described for Intermediate P135, replacing ethyl 2-cyanopropanoate with diethyl 2-cyanomalonate in Step A to afford the product as a brown syrup (400 mg, 32% yield). MS (apci) m/z=276.1 (M+H).

Intermediate 175

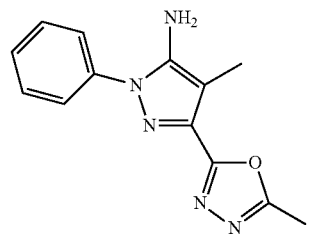 [SMILES: Cc1nnc(-c2nn(-c3ccccc3)c(N)c2C)o1]

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide: To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H₂O (10 mL), extracted DCM (2×10 mL), dried (MgSO₄), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine: A mixture of N'-acetyl-5-amino-4-methyl-1-phenyl-1H-pyrazole-3-carbohydrazide (117 mg, 0.428 mmol) and POCl₃ (0.5 mL) was heated in a pressure tube to 90° C. for 1 hour. The reaction mixture was transferred to a separatory funnel with EtOAc (5 mL), then diluted with saturated aqueous NaHCO₃ (20 mL), extracted with EtOAc (2×15 mL), dried (MgSO₄), filtered and concentrated. The residue was purified by silica column chromatography eluting with 0-75% acetone/hexanes to afford the title compound as a yellow solid (19.6 mg, 18% yield). MS (apci) m/z=256.1 (M+H).

Intermediate 176

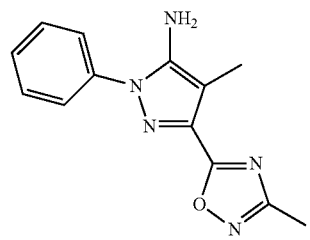 [SMILES: Cc1noc(-c2nn(-c3ccccc3)c(N)c2C)n1]

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N₂ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H₂O (10 mL), extracted DCM (2×15 mL), and the combined organic extracts were dried (MgSO₄), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

Intermediate 177

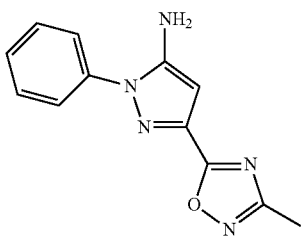 [SMILES: Cc1noc(-c2cc(N)n(-c3ccccc3)n2)n1]

3-(3-methyl-1,2,4-oxadiazol-5-yl)-1-phenyl-1H-pyrazol-5-amine

Prepared according to the method described in Intermediate 176, replacing ethyl 5-amino-4-methyl-1-phenyl-1H-pyrazole-3-carboxylate with ethyl 5-amino-1-phenyl-1H-pyrazole-3-carboxylate (Nanjing Chemlin Chemical Co.) to afford the product as a tan solid (83 mg, 53% yield). MS (apci) m/z=242.1 (M+H).

Intermediate 178

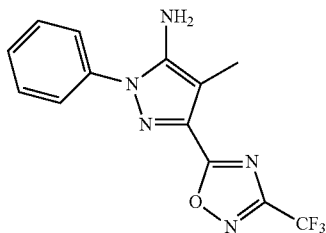 [SMILES: Cc1c(-c2nc(C(F)(F)F)no2)nn(-c2ccccc2)c1N]

4-methyl-1-phenyl-3-(3-(trifluoromethyl)-1,2,4-oxadiazol-5-yl)-1H-pyrazol-5-amine Step A: Preparation of 2,2,2-trifluoro-N'-hydroxyacetimidamide: To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). ¹H NMR (CD₃CN) δ 8.32 (s, 1H), 5.25 (br s, 2H). ¹⁹F NMR (CD₃CN) δ −71.8 (s).

Step B: Preparation of 4-methyl-1-phenyl-3-(3-(trifluoromethyl)-1,2,4-oxadiazol-5-yl)-1H-pyrazol-5-amine: To a suspension of NaH (60% in mineral oil, 356 mg, 0.897 mmol) in THF (5 mL, 0.815 mmol) under N₂ was added 2,2,2-trifluoro-N'-hydroxyacetimidamide (115 mg, 0.897 mmol). The reaction mixture was heated to reflux for 1 hour, then cooled to ambient temperature and powdered 4 A molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H₂O (15 mL), extracted DCM (2×25 mL), and the combined organic extracts were washed with brine (25 mL), dried (MgSO₄), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

Intermediate 179

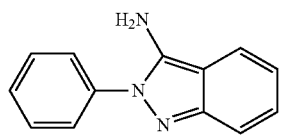 [SMILES: Nc1c2ccccc2nn1-c1ccccc1]

2-phenyl-2H-indazol-3-amine

Step A: Preparation of 1-(2-iodophenyl)-2-phenyldiazene: To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO₃ until basic. The mixture was extracted with EtOAc (3×) and the combined extracts were washed with water, saturated NaCl and dried over MgSO₄. The solution was filtered, concentrated and the residue purified by reverse phase chromatography to provide the title compound as a red solid (0.880 g, 63% yield). ¹H NMR (CDCl₃) δ 7.23-7.39 (m, 3H), 7.64 (d, 1H), 7.56-7.51 (m, 3H), 7.45 (t, 1H), 7.1 (t, 1H).

Step B: 2-(phenyldiazenyl)benzonitrile: To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with CH₂Cl₂. The combined filtrate and washes were concentrated to provide the title compound as red-orange solid that was dried in vacuum (0.280 g, 95% yield). ¹H NMR (CDCl₃) δ 8.03-8.06 (m, 2H), 7.88 (dd, 2H), 7.71 (t, 1H), 7.54-7.58 (m, 4H).

Step C: 2-phenyl-2H-indazol-3-amine: A mixture of 2-(phenyldiazenyl)benzonitrile (0.28 g, 1.35 mmol) and SnCl₂ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO₃ and extracted with CH₂Cl₂ (2×). The combined organic layers were dried over MgSO₄, filtered and concentrated to provide the title compound as a light purple solid that was dried in vacuum (0.241 g, 85% yield). ¹H NMR (CDCl₃) δ 7.69 (d, 2H), 7.52-7.58 (m, 3H), 7.47 (d, 2H), 7.26 (t, 1H), 6.90 (t, 1H), 4.28 (br s, 2H).

Intermediate 180

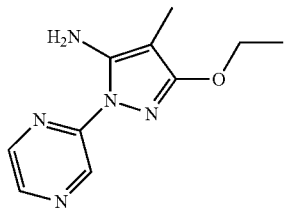 [SMILES: CCOc1nn(-c2cnccn2)c(N)c1C]

3-ethoxy-4-methyl-1-(pyrazin-2-yl)-1H-pyrazol-5-amine

Step A: 5-amino-4-methyl-1-(pyrazin-2-yl)-1H-pyrazol-3(2H)-one: To a mixture of 2-hydrazinylpyrazine (0.551 g, 5.00 mmol) and ethyl 2-cyanopropanoate (0.669 g, 5.00 mmol) in abs. EtOH (10 mL) was added 3M NaOEt in EtOH (0.167 mL, 0.501 mmol) and the mixture was heated at reflux for 64 hours. The mixture was concentrated and the residual yellow-brown solid was treated with EtOAc (30 mL) and sonicated. The resulting tan suspension was stirred vigorously for 8 hours. The solid was collected via vacuum filtration, washed with EtOAc and dried in vacuum to afford the title compound as a light tan powder (682 mg, 71%). ¹H NMR (DMSO d₆) δ 10.3 (br s, 1H), 8.82 (s, 1H), 8.30 (d, 2H), 6.55 (s, 2H), 1.71 (s, 3H).

Step B: 3-ethoxy-4-methyl-1-(pyrazin-2-yl)-1H-pyrazol-5-amine: A mixture of 5-amino-4-methyl-1-(pyrazin-2-yl)-1H-pyrazol-3(2H)-one (382 mg, 2.00 mmol) and powdered K₂CO₃ (552 mg, 4.00 mmol) in dry DMF (3.0 mL) was stirred at ambient temperature for 10 minutes. The mixture was cooled to 0° C. and bromoethane (229 mg, 2.10 mmol) was added. The mixture was allowed to reach ambient temperature and was stirred 24 hours. The reaction mixture poured into cold H₂O (12 mL), allowed to reach ambient temperature and was extracted with EtOAc (3×). The combined extracts were washed with saturated NaCl (2×), dried over MgSO₄ and activated carbon. The dried solution was diluted with and equal volume of hexanes and filtered through a SiO₂ plug capped with a MgSO₄ layer eluting with 50% EtOAc-hexanes. The filtrate was concentrated and the residual yellow solid was washed with hexanes (3×) and dried in vacuum to afford the title compound as a light yellow crystalline solid (195 mg, 45%). ¹H NMR (CDCl₃) δ 9.10 (s, 1H), 8.23 (s, 1H), 8.14 (s, 1H), 5.50 (br s, 2H), 4.33 (q, 2H), 1.80 (s, 3H), 1.42 (t, 3H).

Intermediate 181

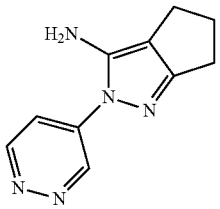 [SMILES: Nc1c2c(nn1-c1ccnnc1)CCC2]

2-(pyridazin-4-yl)-2,4,5,6-tetrahydrocyclopenta[c]pyrazol-3-amine

A suspension of 4-hydrazinylpyridazine hydrobromide (0.368 g, 1.93 mmol) in absolute EtOH (5 mL) was treated with 2-oxocyclopentanecarbonitrile (0.191 g, 1.75 mmol) and the mixture was heated at reflux for 22 hours. The mixture was cooled to ambient temperature and was concentrated to an orange solid. The solid was suspended in 1M NaOH and stirred for 10 minutes. The solid was collected, washed thoroughly with H₂O and Et₂O and dried in vacuum to furnish title compound as a tan powder (0.323 g, 92%). MS (apci) m/z=202.1 (M+H).

Intermediate 182

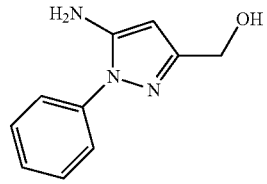 [SMILES: Nc1cc(CO)nn1-c1ccccc1]

(5-amino-1-phenyl-1H-pyrazol-3-yl)methanol

Step A: Ethyl 2-(tert-butyldimethylsilyloxy)acetate: A mixture of ethyl 2-hydroxyacetate (3.00 g, 28.8 mmol), TBDMS-Cl (5.21 g, 34.6 mmol) and imidazole (2.55 g, 37.5 mmol) was stirred at ambient temperature for 60 hours. The mixture was concentrated and the residue was purified by SiO₂ chromatography eluting with 10% EtOAc-hexanes to provide the title compound as a colorless oil (4.12 g, 65%). ¹H NMR (CDCl₃) δ 4.12 (s, 2H), 4.09 (q, 2H), 1.17 (t, 3H), 0.18 (s, 9H), 0.00 (s, 6H).

Step B: (5-amino-1-phenyl-1H-pyrazol-3-yl)methanol: A solution of acetonitrile (0.526 mL, 10.1 mmol) in dry THF (20.4 mL, 9.16 mmol) was cooled to −78° C. and 2.5M nBuLi in hexanes (4.21 mL, 10.5 mmol) was added dropwise. The reaction mixture was stirred for 15 minutes and ethyl 2-(tert-butyldimethylsilyloxy)acetate (2.00 g, 9.16 mmol) was added. The reaction mixture was allowed to warm to ambient temperature and was stirred for 2 hours. The reaction mixture was diluted with ice water and was concentrated. The residual aqueous mixture was acidified to pH=5 and extracted with EtOAc (3×). The combined organics were washed with brine, dried over MgSO₄, filtered and concentrated. The residual brown oil was dissolved in MeOH (23 mL) and phenyl hydrazine (0.907 mL, 9.14 mmol) was added. The mixture was treated with concentrated HCl (3.81 mL, 45.7 mmol) and heated at reflux for 18 hours. Upon cooling, the mixture was concentrated and the residue was partitioned into in H₂O and CH₂Cl₂. The mixture was filtered and the organic layer was removed from the filtrate. The aqueous portion was washed with CH₂Cl₂ and was treated with saturated NaHCO₃ until basic. The aqueous mixture was extracted with CH₂Cl₂ (3×) and the combined organic fractions were dried over MgSO₄, filtered and concentrated. The residue was purified by silica column chromatography using 70-100% EtOAc/hexanes gradient elution followed by 0-5% MeOH/EtOAc. The product pools were combined and concentrated to give the title compound as a yellow foam (0.760 g, 44% yield). MS (apci) m/z=190.1 (M+H).

Intermediate 183

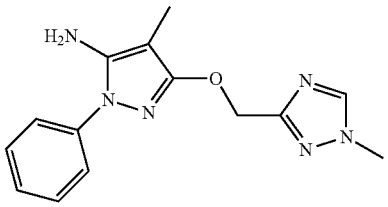 [SMILES: Cc1c(OCc2ncn(C)n2)nn(-c2ccccc2)c1N]

4-methyl-3-((1-methyl-1H-1,2,4-triazol-3-yl)methoxy)-1-phenyl-1H-pyrazol-5-amine The title compound was prepared by the method as described for Intermediate P135, substituting bromoethane with 3-(chloromethyl)-1-methyl-1H-1,2,4-triazole hydrochloride. The product was isolated as a gold syrup (110 mg, 27%). MS (apci) m/z=285.1 (M+H).

Intermediate 184

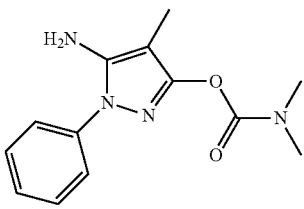 [SMILES: Cc1c(OC(=O)N(C)C)nn(-c2ccccc2)c1N]

5-amino-4-methyl-1-phenyl-1H-pyrazol-3-yl dimethylcarbamate

A mixture of 5-amino-4-methyl-1-phenyl-1H-pyrazol-3(2H)-one (Intermediate P135 Step A, 0.378 g, 2.00 mmol) and powdered K₂CO₃ (0.553 g, 4.00 mmol) in dry DMF (4 mL) was stirred at ambient temperature for 5 minutes. Dimethylcarbamoyl chloride (0.206 mL, 2.20 mmol) was added and the mixture was stirred for 6 hours. The mixture was poured into chilled H₂O (40 mL) and was extracted with EtOAc (3×). The combined extracts were washed with saturated NaCl (2×), dried over MgSO₄ and filtered through a SiO₂ plug capped with a MgSO₄ layer (EtOAc elution). The filtrate was concentrated and the residue dried in vacuum to give the title compound as a light gold syrup (0.507 g, 97%). MS (apci) m/z=261.1 (M+H).

Intermediate 185

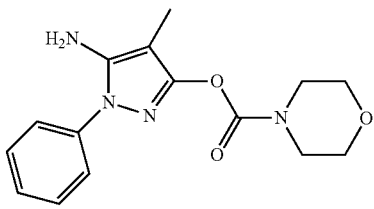 [SMILES: Cc1c(OC(=O)N2CCOCC2)nn(-c2ccccc2)c1N]

5-amino-4-methyl-1-phenyl-1H-pyrazol-3-yl morpholine-4-carboxylate

The title compound was prepared using morpholine-4-carbonyl chloride in the procedure outlined for 5-amino-4-methyl-1-phenyl-1H-pyrazol-3-yl dimethylcarbamate (Intermediate 184). The compound was isolated as a light yellow wax (0.285 g, 47%). ¹H NMR (CDCl₃) δ 7.54 (d, 2H), 7.43 (t, 2H), 7.31 (t, 1H), 3.66-3.78 (m, 8H), 3.57 (br s, 2H), 1.85 (s, 3H).

Intermediate 186

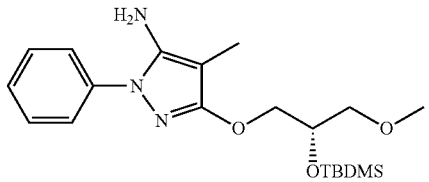 [SMILES: COC[C@@H](COc1nn(-c2ccccc2)c(N)c1C)O[Si](C)(C)C(C)(C)C]

(S)-3-(2-((tert-butyldimethylsilyl)oxy)-3-methoxypropoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol: A mixture of 5-amino-4-methyl-1-phenyl-1H-pyrazol-3(2H)-one (P135 Step A, 1.21 g, 6.40 mmol) and powdered K₂CO₃ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled H₂O (25 mL) and extracted with EtOAc (3×). The combined extracts were washed with saturated NaCl (2×), dried over MgSO₄ and filtered through a SiO₂ plug capped with a layer of MgSO₄ eluting with EtOAc. The filtrate was concentrated to give the title compound as a colorless, viscous oil (701 mg, 40%). MS (apci) m/z=278.1 (M+H).

Step B: (S)-3-(2-((tert-butyldimethylsilyl)oxy)-3-methoxypropoxy)-4-methyl-1-phenyl-1H-pyrazol-5-amine: To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to H₂O (70 mL), mixed for 5 minutes and extracted with Et$_2$O (3x). The combined extracts were washed with saturated NaCl (2x) and dried over MgSO$_4$. The dried solution was filtered through a SiO$_2$ plug capped with a layer of MgSO$_4$ (Et$_2$O elution). The filtrate was concentrated to give the title compound as a colorless oil that was dried in vacuum (940 mg, 105%). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 187

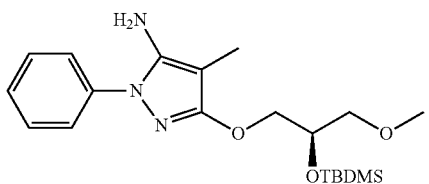 [SMILES: COC[C@H](COc1nn(-c2ccccc2)c(N)c1C)O[Si](C)(C)C(C)(C)C]

(R)-3-(2-((tert-butyldimethylsilyl)oxy)-3-methoxypropoxy)-4-methyl-1-phenyl-1H-pyrazol-5-amine The title compound was prepared using the procedure described for (S)-3-(2-((tert-butyldimethylsilyl)oxy)-3-methoxypropoxy)-4-methyl-1-phenyl-1H-pyrazol-5-amine (Intermediate 186) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 188

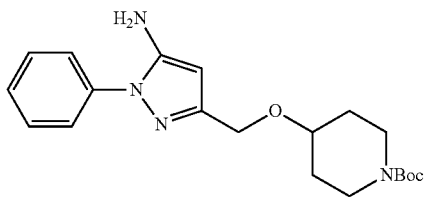 [SMILES: CC(C)(C)OC(=O)N1CCC(OCc2cc(N)n(-c3ccccc3)n2)CC1]

tert-butyl 4-((5-amino-1-phenyl-1H-pyrazol-3-yl)methoxy)piperidine-1-carboxylate Step A: tert-butyl 4-(2-ethoxy-2-oxoethoxy)piperidine-1-carboxylate: A solution of tert-butyl 4-hydroxypiperidine-1-carboxylate (2.00 g, 9.94 mmol) in dry THF (25 mL) was cooled to 0° C. and KOtBu (1.12 g, 9.94 mmol) was added. The mixture was allowed to reach ambient temperature and was stirred for 10 minutes. The mixture was cooled to 0° C. and ethyl 2-bromoacetate (1.65 mL, 14.9 mmol) was added dropwise. The reaction was allowed to reach ambient temperature and was stirred for 17 hours. The mixture was partitioned into in H$_2$O and EtOAc, mixed and the organic layer was removed. The organic layer was dried over MgSO$_4$, filtered and concentrated. The residual thick yellow oil was purified by silica chromatography using a 10-25% EtOAc/hexanes gradient elution to afford the title compound as a colorless oil (0.967 g, 34% yield). $^1$H NMR (CDCl$_3$) δ 4.22 (q, 2H), 4.12 (s, 2H), 3.67-3.84 (m, 2H), 3.52-3.63 (m, 1H), 3.05-3.11 (m, 2H), 1.81-1.90 (m, 2H), 1.53-1.62 (m, 2H), 1.45 (s, 9H), 1.29 (t, 3H).

Step B: tert-butyl 4-((5-amino-1-phenyl-1H-pyrazol-3-yl)methoxy)piperidine-1-carboxylate: A solution of diisopropylamine (1.08 mL, 7.74 mmol) in dry THF (5 mL) was cooled to 0° C. and 2.5M nBuLi in hexanes (2.96 mL, 7.41 mmol) was slowly added. The mixture was stirred at 0° C. for 10 minutes and was cooled to −78° C. Acetonitrile (0.404 mL, 7.74 mmol) was added and the mixture was stirred for 15 minutes. A solution of tert-butyl 4-(2-ethoxy-2-oxoethoxy)piperidine-1-carboxylate (0.967 g, 3.37 mmol) in THF (2.5 mL) was added and the mixture was stirred at −78° C. for 1 hour. The mixture was allowed to reach ambient temperature, was quenched with ice water and concentrated. The residual aqueous mixture was neutralized with 2M HCl and was extracted with CH$_2$Cl$_2$ (3x). The combined organic fractions were dried over MgSO$_4$, filtered and concentrated to provide the crude cyano-ketone as a yellow oil that was used immediately in the next step.

Step C: tert-butyl 4-((5-amino-1-phenyl-1H-pyrazol-3-yl)methoxy)piperidine-1-carboxylate: The crude oil obtained in Step B was dissolved in EtOH (17 mL) and phenylhydrazine (0.396 mL, 3.99 mmol) was added. The mixture was heated at 60° C. for 60 hours, was cooled to ambient temperature and was concentrated. The residue was partitioned into EtOAc and water, mixed and the organic layer removed. The aqueous layer was extracted with EtOAc (2x) and the combined EtOAc portions were dried over MgSO$_4$, filtered and concentrated. The residual orange oil was purified by silica chromatography using a 10-100% EtOAc/hexanes gradient elution. The pooled product fractions were concentrated and the residual yellow-orange oil was re-purified by reverse phase HPLC using a 0-100% acetonitrile/water gradient to provide the title compound as an orange foam (0.264 g, 21% yield). MS (apci) m/z=373.2 (M+H).

Intermediate 189

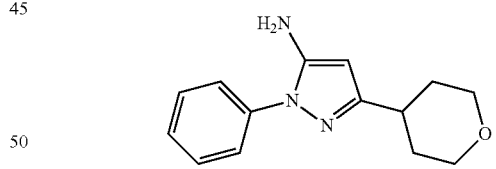

1-phenyl-3-(tetrahydro-2H-pyran-4-yl)-1H-pyrazol-5-amine

Step A: 3-oxo-3-(tetrahydro-2H-pyran-4-yl)propanenitrile: A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled H$_2$O (250 mL) and was extracted with Et$_2$O (3x). The aqueous portion was cooled to 0° C. and 6M HCl was added dropwise to pH=3 (starting pH=12). The mixture was extracted with EtOAc (3×) and the combined extracts were dried over MgSO₄. The solution eluted through a SiO₂ plug eluting with EtOAc. The filtrate was concentrated to give the title compound as a colorless oil (2.52 g, 66%). $^1$H NMR (CDCl$_3$) δ 3.99-4.06 (m, 2H), 3.54 (s, 2H), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine: To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in H₂O (75 mL) and EtOAc (40 mL). 2M NaOH was added to pH=5 with vigorous mixing, the organic layer was removed and the aqueous was extracted with EtOAc (2×). The combined EtOAc fractions were washed with H₂O and saturated NaCl. The solution was diluted with an equal volume of hexanes, dried over MgSO₄/activated carbon and eluted through a SiO₂ plug eluting with 50% EtOAc-hexanes. The filtrate was concentrated to give a gold syrup. The syrup was treated with Et₂O and stirred until a fine, granular suspension formed. The solid was collected, washed with Et₂O and dried in vacuum to furnish the title compound as a white solid (2.01 g, 65%). $^1$H NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compounds were prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
|---|---|---|
| 190 | | MS (apci) m/z = 343.1 (M + H) |
| 191 | | MS (apci) m/z = 258.0 (M + H) |
| 192 | | $^1$H NMR (CDCl$_3$) δ 7.62 (d, 2H), 7.50 (t, 2H), 7.37 (t, 1H), 5.72 (s, 1H), 3.91 (br s, 2H), 2.58 (s, 3H), 2.44 (s, 3H). |
| 193 | | $^1$H NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |
| 194 | 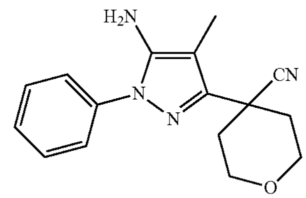 [SMILES: Cc1c(C2(C#N)CCOCC2)nn(-c2ccccc2)c1N] | $^1$H NMR (CDCl$_3$) δ 7.45-7.56 (m, 4H), 7.35 (t, 1H), 4.00-4.06 (m, 2H), 3.88 (dt, 2H), 3.62 (br s, 2H), 2.18-2.34 (m, 4H), 2.11 (s, 3H). |
| 195 | 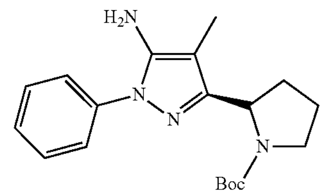 | MS (apci) m/z = 343.2 (M + H) |
| 196 | 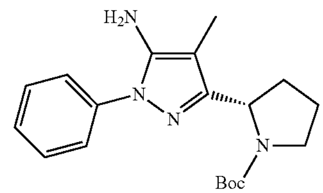 [SMILES: Cc1c([C@@H]2CCCN2C(=O)OC(C)(C)C)nn(-c2ccccc2)c1N] | MS (apci) m/z = 343.2 (M + H) |
| 197 | 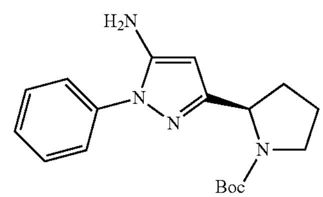 [SMILES: CC(C)(C)OC(=O)N1CCC[C@@H]1c1cc(N)n(-c2ccccc2)n1] | MS (apci) m/z = 329.2 (M + H) |
| 198 | 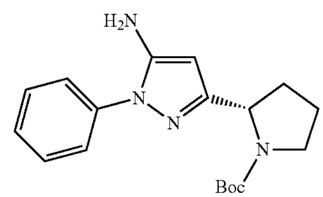 [SMILES: CC(C)(C)OC(=O)N1CCC[C@H]1c1cc(N)n(-c2ccccc2)n1] | MS (apci) m/z = 329.2 (M + H) |

Intermediate 199

Phenyl 1',4-dimethyl-1-phenyl-1H,1'H-3,4'-bipyrazol-5-ylcarbamate

Step A: ethyl 1-methyl-1H-pyrazole-4-carboxylate: To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile: To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of –79° C.) under nitrogen, followed by slow addition of propiononitrile (103 mL, 1444 mmol) via dropping funnel. The mixture was stirred at –80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below –76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbonate solution The aqueous layer was extracted with DCM (3×1000 mL). The combined organic extracts were dried over MgSO$_4$ filtered and concentrated to yield the 2-methyl-3-(1-methyl-1H-pyrazol-4-yl)-3-oxopropanenitrile as an amber oil (92 g, 82%). MS (apci) m/z=162.1 (M–H).

Step C: 1',4-dimethyl-1-phenyl-1H,1'H-3,4'-bipyrazol-5-amine: A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL) The solid was collected filtration, washed with hexanes and air dried under vacuum to provide 1',4-dimethyl-1-phenyl-1H,1'H-3,4'-bipyrazol-5-amine (93 g, 100%).

Step D: phenyl 1',4-dimethyl-1-phenyl-1H,1'H-3,4'-bipyrazol-5-ylcarbamate: In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

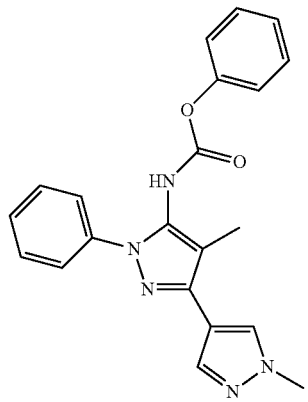 [SMILES: Cc1c(-c2cnn(C)c2)nn(-c2ccccc2)c1NC(=O)Oc1ccccc1]

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 201

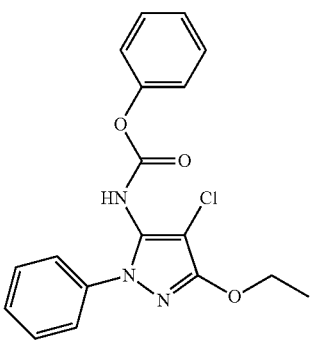 [SMILES: CCOc1nn(-c2ccccc2)c(NC(=O)Oc2ccccc2)c1Cl]

phenyl (4-chloro-3-ethoxy-1-phenyl-1H-pyrazol-5-yl)carbamate

Step A: Preparation of phenyl (3-ethoxy-1-phenyl-1H-pyrazol-5-yl)carbamate: To a suspension of 3-ethoxy-1- phenyl-1H-pyrazol-5-amine (Intermediate P139, 169 mg, 0.832 mmol) in EtOAc (5 mL) at 0° C. was added 2.0 M aqueous NaOH solution (1.25 mL, 2.50 mmol), followed by dropwise addition of phenyl carbonochloridate (0.178 mL, 1.41 mmol). The reaction was stirred at ambient temperature for 15 hours. The reaction mixture was diluted with EtOAc and phase-separated. The organic layer was washed with water and brine, dried over MgSO$_4$, and concentrated. The residue was purified by flash chromatography on silica gel (6:1 hexanes:EtOAc) to give the title compound (219 mg, 81% yield). MS (apci) m/z=324.1 (M+H).

Step B: Preparation of phenyl (4-chloro-3-ethoxy-1-phenyl-1H-pyrazol-5-yl)carbamate: To a solution of phenyl 3-ethoxy-1-phenyl-1H-pyrazol-5-ylcarbamate (92 mg, 0.28 mmol) and pyridinium 4-methylbenzenesulfonate (7.2 mg, 0.028 mmol) in DCM (2 mL) was added N-chlorosuccinimide (42 mg, 0.31 mmol) at ambient temperature. The mixture was stirred at ambient temperature for 2 days and then concentrated under reduced pressure. The residue was purified by flash chromatography on silica gel (9:1, hexanes/EtOAc) to give the title compound (76 mg, 75% yield). MS (apci) m/z=358.1 (M+H).

Intermediate 203

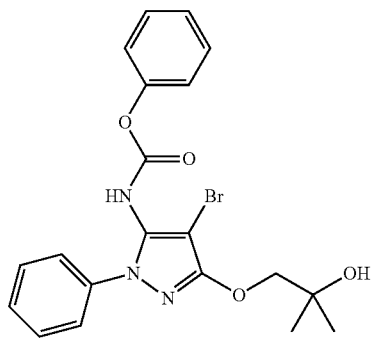 [SMILES: CC(C)(O)COc1nn(-c2ccccc2)c(NC(=O)Oc2ccccc2)c1Br]

Phenyl (4-bromo-3-(2-hydroxy-2-methylpropoxy)-1-phenyl-1H-pyrazol-5-yl)carbamate Step A: Preparation of 5-amino-1-phenyl-1H-pyrazol-3 (2H)-one: Prepared according to the method described for Intermediate P1, replacing 4,4-dimethyl-3-oxopentanenitrile with ethyl 2-cyanoacetate, and substituting phenylhydrazine for ethyl 3-hydrazinylbenzoate hydrochloride. MS (apci) m/z=176.0 (M+H).

Step B: Preparation of 1-((5-amino-1-phenyl-1H-pyrazol-3-yl)oxy)-2-methylpropan-2-ol: A mixture of 5-amino-1-phenyl-1H-pyrazol-3 (2M-one (0.330 g, 1.88 mmol), 2,2-dimethyloxirane (0.143 g, 1.98 mmol) and K$_2$CO$_3$ (0.521 g, 3.77 mmol) in DMA (5 mL) was heated at 80° C. for 3 days. After cooling, the reaction mixture was diluted with EtOAc, washed with water and brine and dried over MgSO$_4$. The mixture was filtered through a pad of SiO$_2$ eluting with EtOAc to yield the title compound. MS (apci) m/z=248.1 (M+H).

Step C: Preparation of phenyl (3-(2-hydroxy-2-methylpropoxy)-1-phenyl-1H-pyrazol-5-yl)carbamate: Prepared according to the method described for Intermediate 201. Step A using 1-((5-amino-1-phenyl-1H-pyrazol-3-yl)oxy)-2-methylpropan-2-ol as a replacement for 3-ethoxy-1-phenyl-1H-pyrazol-5-amine. MS (apci) m/z=368.1 (M+H).

Step D: Preparation of phenyl (4-bromo-3-(2-hydroxy-2-methylpropoxy)-1-phenyl-1H-pyrazol-5-yl)carbamate: Prepared according to the method described for Intermediate 201, Step B using N-bromosuccinimide as a replacement for N-chlorosuccinimide, and substituting phenyl (3-(2-hydroxy-2-methylpropoxy)-1-phenyl-1H-pyrazol-5-yl)carbamate for phenyl 3-ethoxy-1-phenyl-1H-pyrazol-5-ylcarbamate. MS (apci) m/z=446.1 (M+H).

The following compounds prepared according to the method describe for the preparation of Intermediate 200, using the appropriate amino pyrazole intermediate:

| Intermediate # | Structure | Name | Data |
|---|---|---|---|
| 204 | ![structure] | phenyl 3-(3-methoxypropyl)-4-methyl-1-phenyl-1H-pyrazol-5-ylcarbamate | MS (apci) m/z = 366.1 (M + H). |
| 205 | ![structure] | phenyl 3-(1,1-difluoro-2-hydroxyethyl)-4-methyl-1-phenyl-1H-pyrazol-5-ylcarbamate | MS (apci) m/z = 374.1 (M + H). |

-continued

| Intermediate # | Structure | Name | Data |
|---|---|---|---|
| 206 | 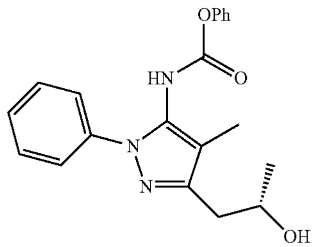 [SMILES: Cc1c(C[C@H](C)O)nn(-c2ccccc2)c1NC(=O)Oc1ccccc1] | (S)-phenyl 3-(2-hydroxypropyl)-4-methyl-1-phenyl-1H-pyrazol-5-ylcarbamate | MS (apci) m/z = 352.1 (M + H). |
| 207 | 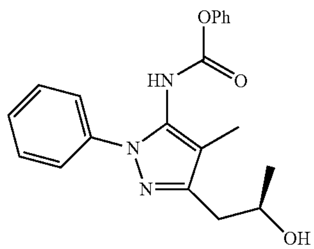 [SMILES: Cc1c(C[C@@H](C)O)nn(-c2ccccc2)c1NC(=O)Oc1ccccc1] | (R)-phenyl 3-(2-hydroxypropyl)-4-methyl-1-phenyl-1H-pyrazol-5-ylcarbamate | MS (apci) m/z = 352.1 (M + H). |
| 208 | 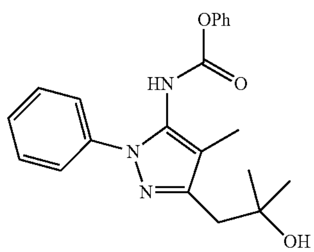 [SMILES: Cc1c(CC(C)(C)O)nn(-c2ccccc2)c1NC(=O)Oc1ccccc1] | phenyl 3-(2-hydroxy-2-methylpropyl)-4-methyl-1-phenyl-1H-pyrazol-5-ylcarbamate | MS (apci) m/z = 366.2 (M + H). |
| 209 | 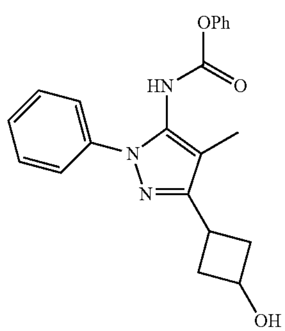 [SMILES: Cc1c(C2CC(O)C2)nn(-c2ccccc2)c1NC(=O)Oc1ccccc1] | phenyl 3-(3-hydroxycyclobutyl)-4-methyl-1-phenyl-1H-pyrazol-5-ylcarbamate | MS (apci) m/z = 364.2 (M + H). |
| 210 | 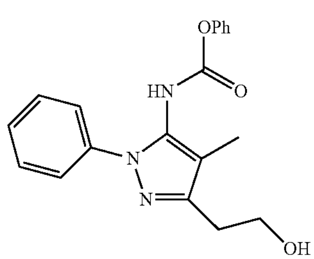 [SMILES: Cc1c(CCO)nn(-c2ccccc2)c1NC(=O)Oc1ccccc1] | phenyl 3-(2-hydroxyethyl)-4-methyl-1-phenyl-1H-pyrazol-5-ylcarbamate | MS (apci) m/z = 338.1 (M + H). |

-continued

| Intermediate # | Structure | Name | Data |
|---|---|---|---|
| 211 | 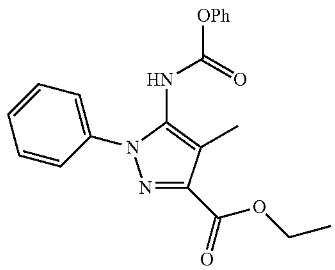 [SMILES: CCOC(=O)c1nn(-c2ccccc2)c(NC(=O)Oc2ccccc2)c1C] | ethyl 4-methyl-5-(phenoxycarbonylamino)-1-phenyl-1H-pyrazole-3-carboxylate | MS (apci) m/z = 366.1 (M + H). |
| 212 | 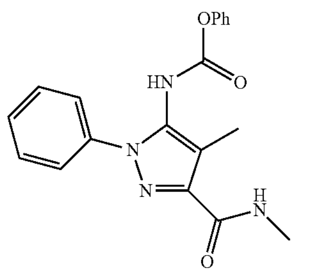 [SMILES: CNC(=O)c1nn(-c2ccccc2)c(NC(=O)Oc2ccccc2)c1C] | phenyl 4-methyl-3-(methylcarbamoyl)-1-phenyl-1H-pyrazol-5-ylcarbamate | MS (apci) m/z = 351.1 (M + H). |
| 213 | 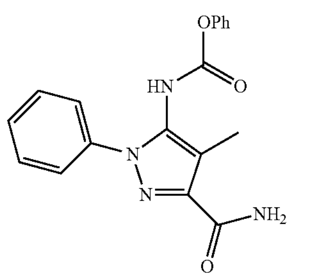 [SMILES: Cc1c(C(N)=O)nn(-c2ccccc2)c1NC(=O)Oc1ccccc1] | phenyl 3-carbamoyl-4-methyl-1-phenyl-1H-pyrazol-5-ylcarbamate | MS (apci) m/z = 337.1 (M + H). |
| 214 | 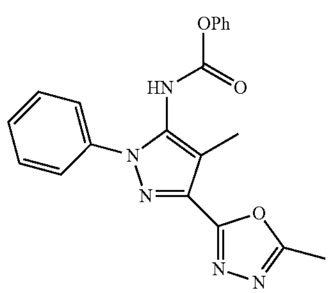 [SMILES: Cc1nnc(-c2nn(-c3ccccc3)c(NC(=O)Oc3ccccc3)c2C)o1] | phenyl (4-methyl-3-(5-methyl-1,3,4-oxadiazol-2-yl)-1-phenyl-1H-pyrazol-5-yl)carbamate | MS (apci) m/z = 376.1 (M + H). |
| 215 | 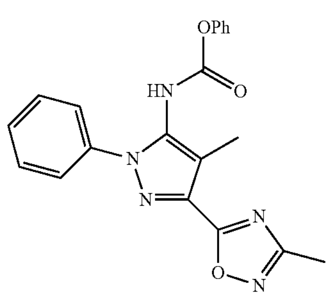 [SMILES: Cc1noc(-c2nn(-c3ccccc3)c(NC(=O)Oc3ccccc3)c2C)n1] | phenyl 4-methyl-3-(3-methyl-1,2,4-oxadiazol-5-yl)-1-phenyl-1H-pyrazol-5-ylcarbamate | MS (apci) m/z = 376.1 (M + H). |

-continued

| Intermediate # | Structure | Name | Data |
|---|---|---|---|
| 216 | 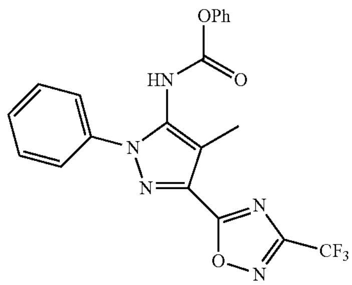 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |
| 217 | 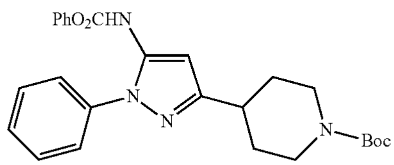 | tert-butyl 4-(5-((phenoxycarbonyl)amino)-1-phenyl-1H-pyrazol-3-yl)piperidine-1-carboxylate | MS (apci) m/z = 463.3 (M + H) |
| 218 | 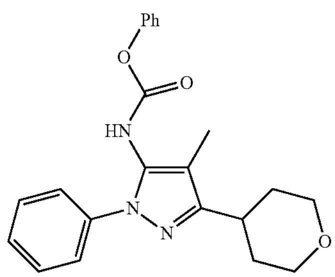 [SMILES: Cc1c(C2CCOCC2)nn(-c2ccccc2)c1NC(=O)Oc1ccccc1] | phenyl (4-methyl-1-phenyl-3-(tetrahydro-2H-pyran-4-yl)-1H-pyrazol-5-yl)carbamate | MS (apci) m/z = 378.2 (M + H) |
| 219 | 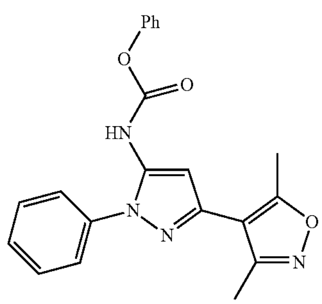 [SMILES: Cc1noc(C)c1-c1cc(NC(=O)Oc2ccccc2)n(-c2ccccc2)n1] | phenyl (3-(3,5-dimethylisoxazol-4-yl)-1-phenyl-1H-pyrazol-5-yl)carbamate | $^1$H NMR (CDCl$_3$) δ 7.56-7.64 (m, 4H), 7.48-7.52 (m, 1H), 7.40 (t, 2H), 7.26 (t, 2H), 7.16 (br s, 2H), 6.71 (br s, 1H), 2.60 (s, 3H) 2.46 (s, 3H) |
| 220 | 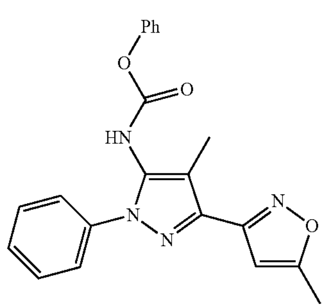 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$H NMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |

| Intermediate # | Structure | Name | Data |
|---|---|---|---|
| 221 | 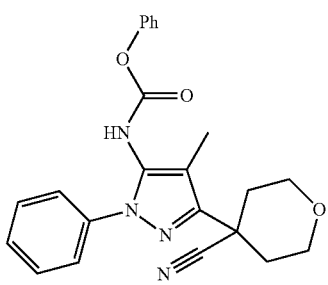 [SMILES: Cc1c(C2(C#N)CCOCC2)nn(-c2ccccc2)c1NC(=O)Oc1ccccc1] | phenyl (3-(4-cyanotetrahydro-2H-pyran-4-yl)-4-methyl-1-phenyl-1H-pyrazol-5-yl)carbamate | $^1$H NMR (CDCl$_3$) δ 7.06-7.56 (m, 9H), 6.75 (br s, 1H), 6.51 (s, 1H), 4.04 (d, 2H) 3.89 (t, 2H), 2.20-2.39 (m, 4H), 2.28 (s, 3H) |
| 222 | 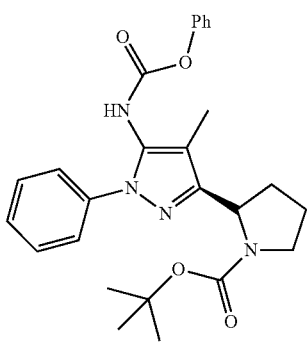 | (R)-tert-butyl 2-(4-methyl-5-((phenoxy-carbonyl)amino)-1-phenyl-1H-pyrazol-3-yl)pyrrolidine-1-carboxylate | MS (apci) m/z = 463.2 (M + H) |
| 223 | 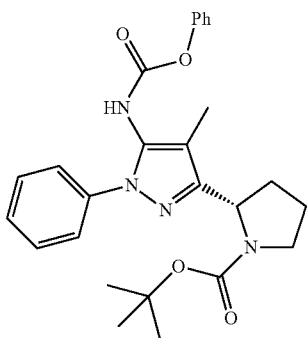 [SMILES: Cc1c([C@@H]2CCCN2C(=O)OC(C)(C)C)nn(-c2ccccc2)c1NC(=O)Oc1ccccc1] | (S)-tert-butyl 2-(4-methyl-5-((phenoxy-carbonyl)amino)-1-phenyl-1H-pyrazol-3-yl)pyrrolidine-1-carboxylate | MS (apci) m/z = 463.2 (M + H) |
| 224 | 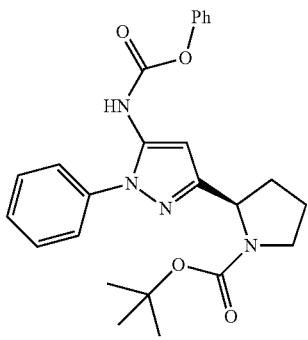 [SMILES: CC(C)(C)OC(=O)N1CCC[C@@H]1c1cc(NC(=O)Oc2ccccc2)n(-c2ccccc2)n1] | (R)-tert-butyl 2-(5-((phenoxycarbonyl)amino)-1-phenyl-1H-pyrazol-3-yl)pyrrolidine-1-carboxylate | MS (apci) m/z = 449.2 (M + H) |

| Intermediate # | Structure | Name | Data |
|---|---|---|---|
| 225 | 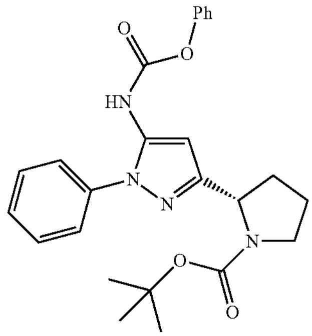 [SMILES: CC(C)(C)OC(=O)N1CCC[C@H]1c1cc(NC(=O)Oc2ccccc2)n(-c2ccccc2)n1] | (S)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 226 | 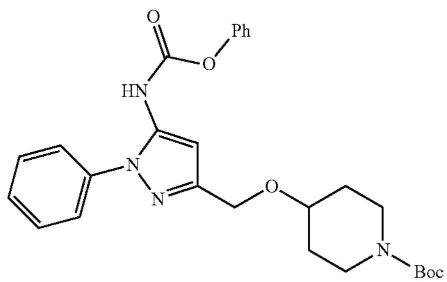 [SMILES: CC(C)(C)OC(=O)N1CCC(OCc2cc(NC(=O)Oc3ccccc3)n(-c3ccccc3)n2)CC1] | tert-butyl 4-((5-((phenoxycarbonyl)amino)-1-phenyl-1H-pyrazol-3-yl)methoxy)piperidine-1-carboxylate | MS (apci) m/z = 493.2 (M + H) |
| 227 | 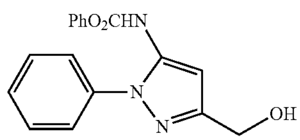 | phenyl (3-(hydroxymethyl)-1-phenyl-1H-pyrazol-5-yl)carbamate | MS (apci) m/z = 310.1 (M + H) |

Intermediate 228

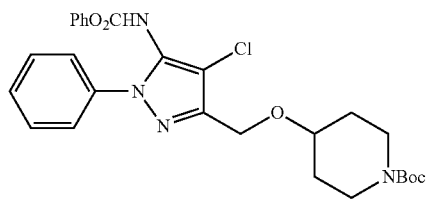

tert-butyl 4-((4-chloro-5-((phenoxycarbonyl)amino)-1-phenyl-1H-pyrazol-3-yl)methoxy)piperidine-1-carboxylate To a suspension of tert-butyl 4-((5-(phenoxycarbonylamino)-1-phenyl-1H-pyrazol-3-yl)methoxy)piperidine-1-carboxylate (Intermediate 226), 98.5 mg, 0.200 mmol) in DCM (2.0 mL) was added pyridinium 4-methylbenzenesulfonate (PPTS) (5.03 mg, 0.020 mmol) and N-chlorosuccinimide (40.1 mg, 0.300 mmol). The resulting solution was stirred at ambient temperature for 8 days. The mixture was diluted with water and CH$_2$Cl$_2$, the organic layer was separated and the aqueous was extracted with CH$_2$Cl$_2$ (2×). The combined organic fractions were dried over MgSO$_4$, filtered and concentrated. The residue was purified by silica chromatography using 30-40% EtOAc/hexanes gradient elution to afford the title compound as an orange oil (73.5 mg, 70% yield). MS (apci) m/z=527.2 (M+H).

Intermediate 229

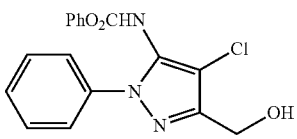

Phenyl (4-chloro-3-(hydroxymethyl)-1-phenyl-1H-pyrazol-5-yl)carbamate

Prepared from phenyl 3-(hydroxymethyl)-1-phenyl-1H-pyrazol-5-ylcarbamate (Intermediate 227) using the procedure outlined for the preparation of tert-butyl 4-((4-chloro-5-((phenoxycarbonyl)amino)-1-phenyl-1H-pyrazol-3-yl)methoxy)piperidine-1-carboxylate (Intermediate 228). In this instance, the compound was isolated a white solid (108 mg, 28%). MS (apci) m/z=344.0 (M+H).

Intermediate 230

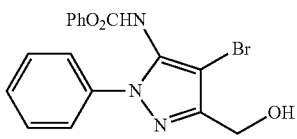

Phenyl (4-bromo-3-(hydroxymethyl)-1-phenyl-1H-pyrazol-5-yl)carbamate

To a suspension of phenyl 3-(hydroxymethyl)-1-phenyl-1H-pyrazol-5-ylcarbamate (Intermediate 227, 100 mg, 0.323 mmol) in CH$_2$Cl$_2$ (1.6 mL) was added pyridinium 4-methylbenzenesulfonate (PPTS) (8.12 mg, 0.0323 mmol) and N-bromosuccinimide (86.3 mg, 0.485 mmol). The reaction mixture was stirred for 16 hours at ambient temperature. The resulting suspension was filtered and the collected solid washed briefly with CH$_2$Cl$_2$ and dried in vacuum to afford the title compound a white solid (48.5 mg, 39%). MS (apci) m/z=388.0 (M+H).

The following pyrazole intermediates were made according to the methods described for the preparation of Intermediate 228, 229 or 230.

| Intermediate | Structure | Name | MS (apci) m/z |
|---|---|---|---|
| 231 | 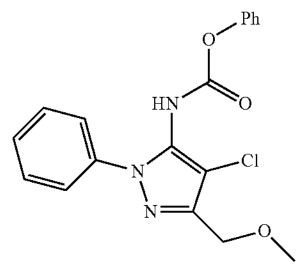 [SMILES: COCc1nn(-c2ccccc2)c(NC(=O)Oc2ccccc2)c1Cl] | phenyl (4-chloro-3-(methoxymethyl)-1-phenyl-1H-pyrazol-5-yl)carbamate | 358.1 (M + H) |
| 232 | 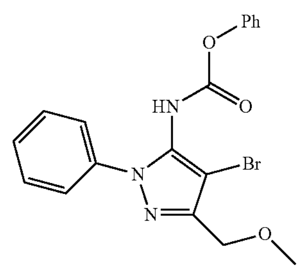 [SMILES: COCc1nn(-c2ccccc2)c(NC(=O)Oc2ccccc2)c1Br] | phenyl (4-bromo-3-(methoxymethyl)-1-phenyl-1H-pyrazol-5-yl)carbamate | 402.2 (M + H) |
| 233 | 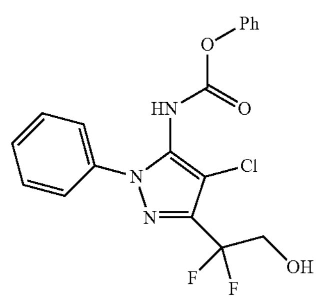 [SMILES: O=C(Nc1c(Cl)c(C(F)(F)CO)nn1-c1ccccc1)Oc1ccccc1] | phenyl (4-chloro-3-(1,1-difluoro-2-hydroxyethyl)-1-phenyl-1H-pyrazol-5-yl)carbamate | 394.1 (M + H) |
| 234 | 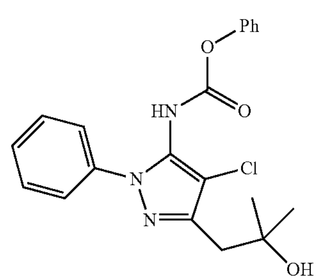 [SMILES: CC(C)(O)Cc1nn(-c2ccccc2)c(NC(=O)Oc2ccccc2)c1Cl] | phenyl (4-chloro-3-(2-hydroxy-2-methylpropyl)-1-phenyl-1H-pyrazol-5-yl)carbamate | 386.1 (M + H) |

-continued

| Intermediate | Structure | Name | MS (apci) m/z |
|---|---|---|---|
| 235 | 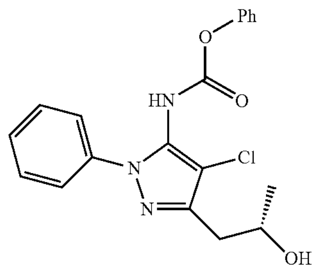 [SMILES: C[C@H](O)Cc1nn(-c2ccccc2)c(NC(=O)Oc2ccccc2)c1Cl] | (S)-phenyl (4-chloro-3-(2-hydroxypropyl)-1-phenyl-1H-pyrazol-5-yl)carbamate | 372.1 (M + H) |
| 236 | 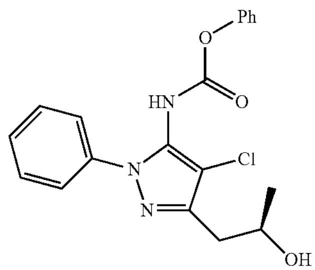 [SMILES: C[C@@H](O)Cc1nn(-c2ccccc2)c(NC(=O)Oc2ccccc2)c1Cl] | (R)-phenyl (4-chloro-3-(2-hydroxypropyl)-1-phenyl-1H-pyrazol-5-yl)carbamate | 372.1 (M + H) |
| 237 | 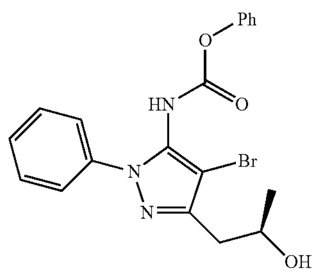 [SMILES: C[C@@H](O)Cc1nn(-c2ccccc2)c(NC(=O)Oc2ccccc2)c1Br] | (R)-phenyl (4-bromo-3-(2-hydroxypropyl)-1-phenyl-1H-pyrazol-5-yl)carbamate | 416.0 (M + H) |
| 238 | 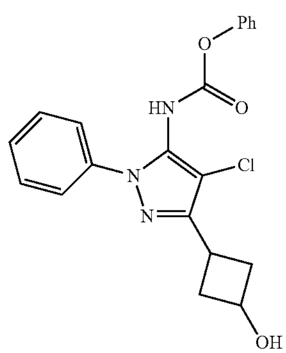 [SMILES: O=C(Nc1c(Cl)c(C2CC(O)C2)nn1-c1ccccc1)Oc1ccccc1] | phenyl (4-chloro-3-(3-hydroxycyclobutyl)-1-phenyl-1H-pyrazol-5-yl)carbamate | 384.1 (M + H) |
| 239 | 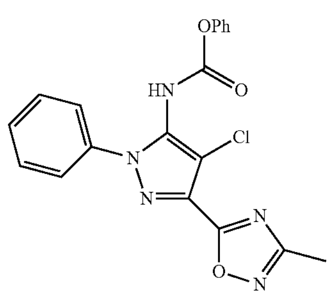 [SMILES: Cc1noc(-c2nn(-c3ccccc3)c(NC(=O)Oc3ccccc3)c2Cl)n1] | phenyl 4-chloro-3-(3-methyl-1,2,4-oxadiazol-5-yl)-1-phenyl-1H-pyrazol-5-ylcarbamate | 396.0 (M + H) |

-continued

| Intermediate | Structure | Name | MS (apci) m/z |
|---|---|---|---|
| 240 | 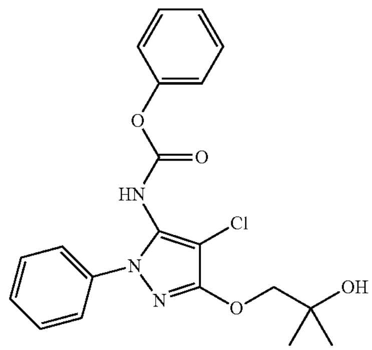 | phenyl (4-chloro-3-(2-hydroxy-2-methylpropoxy)-1-phenyl-1H-pyrazol-5-yl)carbamate | 446.1 (M + H) |
| 241 | 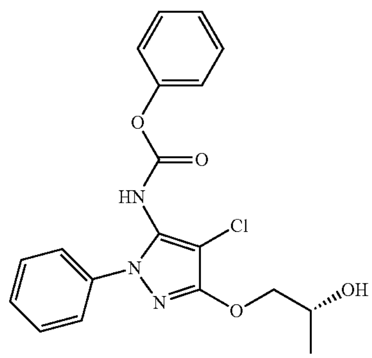 [SMILES: C[C@@H](O)COc1nn(-c2ccccc2)c(NC(=O)Oc2ccccc2)c1Cl] | phenyl (4-chloro-3-(2-hydroxy-2-methylpropoxy)-1-phenyl-1H-pyrazol-5-yl)carbamate | 388.1 (M + H) |
| 242 | 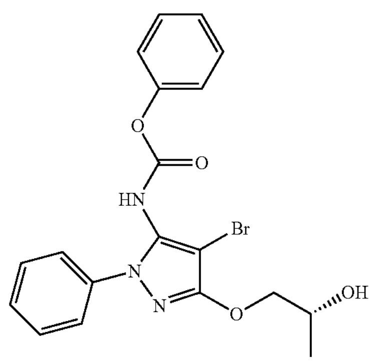 [SMILES: C[C@@H](O)COc1nn(-c2ccccc2)c(NC(=O)Oc2ccccc2)c1Br] | phenyl (4-bromo-3-(2-hydroxy-2-methylpropoxy)-1-phenyl-1H-pyrazol-5-yl)carbamate | 433.0 (M + H) |
| 243 | 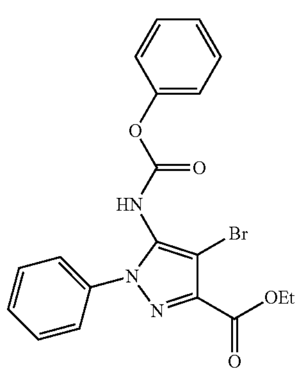 [SMILES: CCOC(=O)c1nn(-c2ccccc2)c(NC(=O)Oc2ccccc2)c1Br] | ethyl 4-bromo-5-((phenoxycarbonyl)amino)-1-phenyl-1H-pyrazole-3-carboxylate | 430.0 (M + H) |

Intermediate 245

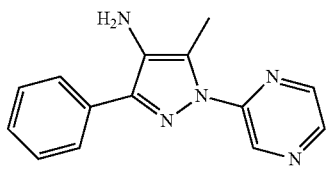 [SMILES: Cc1c(N)c(-c2ccccc2)nn1-c1cnccn1]

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine. To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with H$_2$O (30 mL). The green suspension was stirred for 1 hour and the solid was collected via vacuum filtration. The collected solid was washed with H$_2$O and dried in vacuum. The solid was suspended in EtOH (25 mL) and concentrated HCl (500 µL) was added. The mixture was heated at reflux for 20 hours, cooled to ambient temperature and diluted with chilled H$_2$O (75 mL). The mixture was treated with 1M NaOH to pH=7 and was extracted with Et$_2$O (3×). The combined extracts were washed with saturated NaCl and dried over MgSO$_4$. The dried solution was filtered through packed Celite® and concentrated. The residual green-yellow solid was purified on a SiO$_2$ column using step gradient elution (25% CH$_2$Cl$_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine. To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 µL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with H$_2$O and mixed. The resulting orange suspension treated with 2M HCl to pH=1 and the mixture was extracted with Et$_2$O (3×). The aqueous portion was treated with 2M NaOH to pH=8 and extracted with EtOAc (3×). The combined EtOAc extracts were washed with saturated NaCl and dried over MgSO$_4$/activated carbon. The solution was eluted through a SiO$_2$ plug eluting with EtOAc. The eluent was concentrated to give the title compound as a light yellow wax (33 mg, 13%). MS (esi) m/z=252.2 (M+H).

Intermediate 246

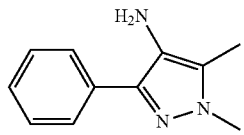

1,5-dimethyl-3-phenyl-1H-pyrazol-4-amine

Step A: 1,5-dimethyl-4-nitroso-3-phenyl-1H-pyrazole: To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. Et$_2$O (50 mL) and H$_2$O (10 mL) were added to the mixture followed by slow addition of saturated Na$_2$CO$_3$ until pH=8 was obtained. The organic layer was removed and the aqueous layer was extracted with Et$_2$O (2×). The combined organic fractions were dried over Na$_2$SO$_4$, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine: To a solution of 1,5-dimethyl-4-nitroso-3-phenyl-1H-pyrazole (1.32 g, 6.60 mmol) in MeOH (50 mL) was added Pd(OH)$_2$ on carbon (200 mg, 20 wt %, 0.286 mmol) and the reaction mixture was shaken under 50 psi of H$_2$ for 3 hours at ambient temperature. The reaction mixture was evacuated, purged with N$_2$ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate 247

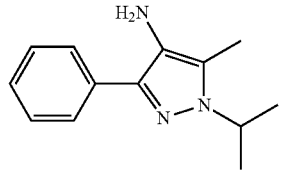 [SMILES: Cc1c(N)c(-c2ccccc2)nn1C(C)C]

1-isopropyl-5-methyl-3-phenyl-1H-pyrazol-4-amine

The title compound was prepared according to the method described for Intermediate 246, using isopropylhydrazine hydrochloride in place of methylhydrazine in Step A to provide 620 mg (57%) of the title compound over 2 steps. MS (apci) m/z=216.1 (M+H).

Intermediate 248

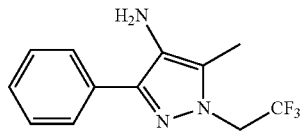

5-methyl-3-phenyl-1-(2,2,2-trifluoroethyl)-1H-pyrazol-4-amine

Step A: 5-methyl-4-nitroso-3-phenyl-1-(2,2,2-trifluoroethyl)-1H-pyrazole: The title compound was prepared using (2,2,2-trifluoroethyl)hydrazine in place of methylhydrazine in Step A of the procedure described for the preparation of 1,5-dimethyl-3-phenyl-1H-pyrazol-4-amine (Intermediate 246). The compound was isolated as a green solid (999 mg, 71%). ¹H NMR (CDCl₃) δ 7.60-7.73 (m, 5H), 4.70 (q, 2H), 2.27 (t, 3H).

Step B: 5-methyl-3-phenyl-1-(2,2,2-trifluoroethyl)-1H-pyrazol-4-amine: To a mixture of 5-methyl-4-nitroso-3-phenyl-1-(2,2,2-trifluoroethyl)-1H-pyrazole (50 mg, 0.186 mmol) and Zn dust (60.7 mg, 0.929 mmol) in EtOH (0.4 mL) was added concentrated HCl (17.0 pt, 0.204 mmol) and the mixture was heated at reflux for 3 hours. The mixture was cooled to ambient temperature and was diluted with MeOH and filtered. The filtrate was concentrated and the residue was diluted in water. The aqueous mixture was treated with saturated NaHCO₃ until pH=10 was achieved. The mixture was extracted with DCM (3×) and the combined extracts were dried over Na₂SO₄, filtered and concentrated afford the title compound as a yellow oil (47.1 mg, 99.4% yield). MS (apci) m/z=256.1 (M+H).

Intermediate 249

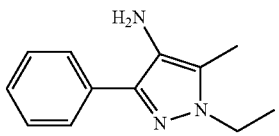

1-ethyl-5-methyl-3-phenyl-1H-pyrazol-4-amine

Step A: 1-ethyl-5-methyl-4-nitroso-3-phenyl-1H pyrazole: The title compound was prepared according to the procedure described for the preparation of Intermediate 246, using ethylhydrazine oxalate in place of methylhydrazine in Step A. 1-Ethyl-5-methyl-4-nitroso-3-phenyl-1H-pyrazole was isolated as a green oil (288 mg, 26%). ¹H NMR (CDCl₃) δ 8.19 (d, 2H), 7.46-7.50 (m, 3H), 4.15 (q, 2H), 2.43 (s, 3H), 1.50 (t, 3H). The minor regioisomer, 1-ethyl-3-methyl-4-nitroso-5-phenyl-1H-pyrazole, was also obtained as a blue-green solid (165 mg, 15%). ¹H NMR (CDCl₃) δ 7.71 (dd, 2H), 7.59 (m, 3H), 4.17 (q, 2H), 2.28 (s, 3H), 1.51 (t, 3H).

Step B: 1-ethyl-5-methyl-3-phenyl-1H-pyrazol-4-amine: Prepared according to the procedure described for the preparation of Intermediate 248, using 1-ethyl-5-methyl-4-nitroso-3-phenyl-1H-pyrazole in Step B. the title compound was isolated as a light purple solid (281 mg, 104%). MS (apci) m/z=202.1 (M+H).

Intermediate 250

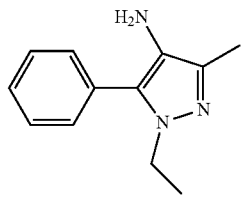

1-ethyl-3-methyl-5-phenyl-1H-pyrazol-4-amine

Prepared according to the procedure described for the preparation of Intermediate 249, using 1-ethyl-3-methyl-4-nitroso-5-phenyl-1H-pyrazole in Step A. The title compound was prepared according to Step B. The compound was isolated as a colorless oil (82.4 mg, 52.5%) after purification by reverse-phase chromatography. MS (apci) m/z=202.1 (M+H).

Intermediate 251

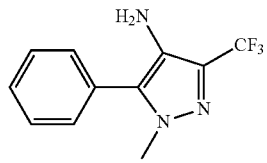 [SMILES: Cn1nc(C(F)(F)F)c(N)c1-c1ccccc1]

1-methyl-5-phenyl-3-(trifluoromethyl)-1H-pyrazol-4-amine

Step A: 4,4,4-trifluoro-2-(hydroxyimino)-1-phenylbutane-1,3-dione: A solution of 4,4,4-trifluoro-1-phenylbutane-1,3-dione (5.00 g, 23.1 mmol) in HOAc (46.3 mL) was chilled to 10° C. and sodium nitrite (1.84 g, 26.6 mmol) in water (6.0 mL) was added. The mixture was stirred at ambient temperature for 90 minutes and was diluted with H₂O (150 mL). The mixture was extracted with Et₂O (3×) and the combined organic fractions were carefully washed with saturated NaHCO₃ until pH=9. The Et₂O solution was washed with H₂O and saturated NaCl and was dried over MgSO₄. The dried solution was filtered and concentrated to afford the title compound as a yellow foam (4.21 g, 74.2% yield). MS (apci) m/z=244.1 (M−H).

Step B: 4-nitroso-3-phenyl-5-(trifluoromethyl)-1H-pyrazole: A solution of hydrazine monohydrate (0.204 g, 4.08 mmol) in EtOH (5 mL) was cooled to 0° C. and 4,4,4-trifluoro-2-(hydroxyimino)-1-phenylbutane-1,3-dione (1.00 g, 4.08 mmol) in EtOH (15 mL) was added. The reaction mixture was stirred at ambient temperature for 3 hours, excess powdered MgSO₄ was added and the mixture was heated at 60° C. for 16 hours. The mixture was cooled to ambient temperature, filtered and concentrated to afford the crude title compound as a green solid (78.7 mg, 8.0%) that was taken directly to the next step. MS (apci) m/z=240.0 (M−H).

Step C: 1-methyl-5-phenyl-3-(trifluoromethyl)-1H-pyrazol-4-amine: To a solution of 4-nitroso-3-phenyl-5-(trifluoromethyl)-1H-pyrazole (78.7 mg, 0.326 mmol) in DMF (1.6 mL) was added NaH (14.4 mg, 0.359 mmol) and the mixture was stirred at ambient temperature for 30 minutes. The mixture was treated with methyl iodide (40.6 μL, 0.653 mmol) and stirred for 17 hours. The reaction mixture was directly purified by reverse phase HPLC using 20-100% acetonitrile/water gradient elution to provide a light blue solid (40.2 mg). The solid was dissolved in EtOH (0.35 mL) and was subjected to the reduction procedure described in Step B of the preparation of 5-methyl-3-phenyl-1-(2,2,2-trifluoroethyl)-1H-pyrazol-4-amine (Intermediate 248). The title compound was obtained as white solid (25.1 mg, 66.1%).

Intermediate 252

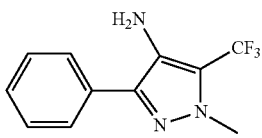 [SMILES: Cn1nc(-c2ccccc2)c(N)c1C(F)(F)F]

1-methyl-3-phenyl-5-(trifluoromethyl)-1H-pyrazol-4-amine

Step A: 1-methyl-4-nitroso-3-phenyl-5-(trifluoromethyl)-1H-pyrazole. To a solution of methylhydrazine (0.214 mL, 4.08 mmol) in EtOH (20 mL) was added 4,4,4-trifluoro-2-(hydroxyimino)-1-phenylbutane-1,3-dione (Intermediate 251, Step A; 1.00 g, 4.079 mmol). The reaction mixture was stirred at ambient temperature for 1 hour and excess MgSO$_4$ was added. The mixture was stirred at 60° C. for 48 hours and was cooled to ambient temperature. The mixture was filtered and the filtrate concentrated to a green residue. The residue was purified by silica gel chromatography using a 10-30% EtOAc/hexanes gradient for elution to provide the title compound as a green solid (482 mg, 46%). $^1$H NMR (CDCl$_3$) δ 7.89 (d, 2H), 7.45-7.52 (m, 3H), 4.15 (s, 3H).

Step B: 1-methyl-3-phenyl-5-(trifluoromethyl)-1H-pyrazol-4-amine. Prepared from 1-methyl-4-nitroso-3-phenyl-5-(trifluoromethyl)-1H-pyrazole according to the method described for the preparation of Intermediate 248, Step B. The title compound was obtained as white solid (309 mg, 68%). $^1$H NMR (CDCl$_3$) δ 7.65 (d, 2H), 7.45 (t, 2H), 7.35 (t, 1H), 3.93 (s, 3H), 3.52 (br s, 2H).

Intermediate X1

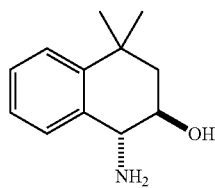

trans-1-amino-4,4-dimethyl-1,2,3,4-tetrahydronaphthalen-2-ol

Step A: Preparation of 4,4-dimethyl-1,2,3,4-tetrahydronaphthalen-1 To a suspension of sodium borohydride (3.12 g, 82.5 mmol) in 4:1 THF:MeOH (250 mL) was added 4,4-dimethyl-3,4-dihydronaphthalen-1(2H)-one (13.1 g, 75.0 mmol) dropwise over 15 minutes. The mixture was stirred at ambient temperature for 15 minutes and was quenched with 1M NaOH (50 mL). After stirring for 15 minutes, the mixture was concentrated and the aqueous residue was diluted with 1M NaOH (50 mL) and H$_2$O (50 mL). The mixture was extracted with hexanes (3×) and the combined extracts washed with H$_2$O and saturated NaCl. The organic portion was dried over MgSO$_4$/activated charcoal, filtered through packed Celite® and concentrated to provide the crude product as a faint yellow syrup after drying in vacuum (11.8 g, 89%). $^1$H NMR (CDCl$_3$) δ 7.41 (dd, J=7.6, 1.6 Hz, 1H), 7.33 (dd, J=7.9, 1.5 Hz, 1H), 7.25 (dt, J=7.3, 1.6 Hz, 1H), 7.18 (dd, J=7.5, 1.5 Hz, 1H), 4.72 (dd, J=5.5, 5.1 Hz, 1H), 2.11-2.03 (m, 1H), 1.93-1.83 (m, 2H), 1.73 (br s, 1H), 1.63-1.57 (m, 1H), 1.33 (s, 3H), 1.24 (s, 3H) ppm.

Step B: Preparation of 1,1-dimethyl-1,2-dihydronaphthalene: To a solution of crude 4,4-dimethyl-1,2,3,4-tetrahydronaphthalen-1-ol (11.3 g, 64.1 mmol) in dry benzene (150 mL) was added MP-TsOH (0.788 g, 3.21 mmol, 4.07 mmol/g) and the mixture was stirred for 18 hours. Molecular sieves (4 angstrom, 10 g) and a second charge of MP-TsOH (0.80 g) were added and the mixture was stirred 6 hours. The mixture was filtered through a SiO$_2$ plug capped with a MgSO$_4$ layer (benzene elution) and concentrated. The residue was purified on a SiO$_2$ column (hexanes elution) to give the product as a colorless oil (4.54 g, 45%). $^1$H NMR (CDCl$_3$) δ 7.29 (d, J=7.1 Hz, 1H), 7.20-7.12 (m, 2H), 7.04 (dd, J=7.2, 1.6 Hz, 1H), 6.45 (d, J=9.6 Hz, 1H), 5.93 (app. dt, J=9.6, 4.4 Hz, 2H), 2.24 (dd, J=4.4, 1.8 Hz, 2H), 1.24 (s, 6H) ppm.

Step C: Preparation of 3,3-dimethyl-1a,2,3,7b-tetrahydronaphtho[1,2-b]oxirene: To a solution of 1,1-dimethyl-1,2-dihydronaphthalene (2.64 g, 14.5 mmol) in toluene (60 mL) was added mCPBA (4.29 g, 17.4 mmol) and the reaction mixture was stirred at ambient temperature for 4.5 hours. The mixture was eluted through a SiO$_2$ plug capped with a layer of MgSO$_4$ (toluene for elution) and concentrated to provide the title compound as a colorless oil after drying in vacuum (1.62 g, 64%). $^1$H NMR (CDCl$_3$) δ 7.44-7.13 (m, 4H), 3.84 (d, J=4.2, 1H), 3.72 (ddd, J=4.2, 2.1, 2.1, 1H), 2.21 (dd, J=15, 2.6 Hz, 1H), 1.83 (d, J=15 Hz, 1H), 1.35 (s, 3H), 1.31 (s, 3H) ppm.

Step D: Preparation of trans-1-amino-4,4-dimethyl-1,2,3,4-tetrahydronaphthalen-2-ol: A sealed pressure vessel was charged with 3,3-dimethyl-1a,2,3,7b-tetrahydronaphtho[1,2-b]oxirene (1.60 g, 8.26 mmol), 7M NH$_3$ in MeOH (30 mL) and concentrated NH$_4$OH (30 mL). The reaction vessel was sealed and the reaction mixture heated at 70° C. for 16 hours. The reaction was cooled to ambient temperature and concentrated to an aqueous mixture. The mixture was diluted with H$_2$O (50 mL) and extracted with EtOAc (3×). The extracts were combined and washed with H$_2$O (2×) and saturated NaCl. The solution was dried over MgSO$_4$/activated charcoal, filtered and concentrated. The residual solid was washed with hexanes and dried in vacuum to provide the title compound as a white solid (1.17 g, 74%). $^1$H NMR (CDCl$_3$) δ 7.46 (dd, 6.4, 4.7 Hz, 1H), 7.28 (m, 1H), 7.22 (m, 2H), 3.63 (m, 2H), 2.20 (br s, 3H), 1.99 (dd, J=13, 2.8 Hz, 1H), 1.75 (dd, J=12, 12 Hz, 1H), 1.35 (s, 3H), 1.31 (s, 3H) ppm.

Intermediate X2

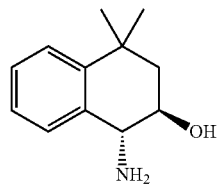

(1R,2R)-1-amino-4,4-dimethyl-1,2,3,4-tetrahydronaphthalen-2-ol

The title compound was isolated as a white solid from separation of racemic trans-1-amino-4,4-dimethyl-1,2,3,4- tetrahydronaphthalen-2-ol (Intermediate X1) using preparative chiral HPLC (Chiral Tech OD-H®, 5% EtOH/hexane, Peak 1).

Intermediate X3

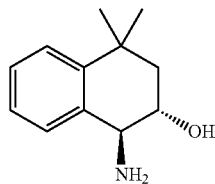

(1S,2S)-1-amino-4,4-dimethyl-1,2,3,4-tetrahydronaphthalen-2-ol

The title compound was isolated as a white solid from separation of racemic trans-1-amino-4,4-dimethyl-1,2,3,4-tetrahydronaphthalen-2-ol (Intermediate X1) using preparative chiral HPLC (Chiral Tech OD-H®, 5% EtOH/hexane, Peak 2).

Intermediate X4

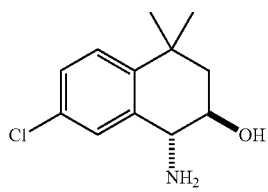

trans-1-amino-7-chloro-4,4-dimethyl-1,2,3,4-tetrahydronaphthalen-2-ol

Step A: Preparation of 7-bromo-4,4-dimethyl-1,2,3,4-tetrahydronaphthalen-1-ol: 7-bromo-4,4-dimethyl-3,4-dihydronaphthalen-1(2H)-one (1.60 g, 6.32 mmol) was dissolved in MeOH (100 mL) and NaBH$_4$ (0.287 g, 7.58 mmol) was added in small portions. The reaction was stirred at ambient temperature for 1 hour and partially concentrated in vacuo. 2N NaOH (50 mL) was added and the mixture was extracted with EtOAc (2×100 mL), filtered through phase separator paper and concentrated to afford 7-bromo-4,4-dimethyl-1,2,3,4-tetrahydronaphthalen-1-ol (1.60 g, 6.27 mmol, 99.2% yield). MS (apci) m/z=255.1; 257.1 (M+H).

Step B: Preparation of 6-bromo-1,1-dimethyl-1,2-dihydronaphthalene: 7-bromo-4,4-dimethyl-1,2,3,4-tetrahydronaphthalen-1-ol (1.60 g, 6.27 mmol) and MP-TsOH (1.17 g, 6.27 mmol) were combined in 50 mL of toluene and left to stand overnight. The reaction was filtered, concentrated and purified by silica gel column using 100% hexanes as the eluent to afford 6-bromo-1,1-dimethyl-1,2-dihydronaphthalene (520 mg, 2.19 mmol, 35.0% yield). $^1$H NMR (CDCl$_3$) δ 7.25-7.30 (m, 1H), 7.12-7.17 (m, 2H), 6.35-6.39 (m, 1H), 5.95-6.01 (m, 1H), 2.22-2.25 (m, 2H), 1.24 (s, 6H) ppm.

Step C: Preparation of 6-chloro-1,1-dimethyl-1,2-dihydronaphthalene: 6-bromo-1,1-dimethyl-1,2-dihydronaphthalene (200 mg, 0.843 mmol) was dissolved in THF (10 mL) and cooled to −78° C. A solution of tert-BuLi in pentane (1637 μL, 2.78 mmol) was added dropwise and the reaction was stirred at −78° C. for 20 minutes. 1,1,1,2,2,2-hexachloroethane (477 μL, 4.22 mmol) was added and the reaction was allowed to warm to ambient temperature overnight, quenched with brine (10 ml) and extracted with EtOAc (2×25 mL). The combined organic extracts were filtered through phase separator paper and concentrated. The crude product was purified by silica gel column (100% hexanes) to afford 6-chloro-1,1-dimethyl-1,2-dihydronaphthalene (17 mg, 0.09 mmol, 10.5% yield). $^1$H NMR (CDCl$_3$) δ 7.18-7.22 (m, 1H), 7.11-7.14 (m, 1H), 6.99-7.01 (m, 1H), 6.35-6.40 (m, 1H), 5.95-6.01 (m, 1H), 2.22-2.26 (m, 2H), 1.24 (s, 6H) ppm.

Step D: Preparation of trans-1-amino-7-chloro-4,4-dimethyl-1,2,3,4-tetrahydronaphthalen-2-ol: 6-chloro-1,1-dimethyl-1,2-dihydronaphthalene (15 mg, 0.08 mmol) was dissolved in DCM (5 mL) and NaHCO$_3$ (saturated aqueous, 5 ml) and stirred at 0° C. mCPBA (20 mg, 0.08 mmol) was added and the reaction was allowed to warm to ambient temperature and stirred for 3 days. The mixture was extracted with several portions of DCM in a phase separator frit, concentrated, and taken up in concentrated ammonium hydroxide (906 μL, 8.1 mmol). The reaction was stirred at ambient temperature overnight and then in a 100° C. sand bath for 3 h. The reaction was cooled and concentrated to afford trans-1-amino-7-chloro-4,4-dimethyl-1,2,3,4-tetrahydronaphthalen-2-ol (21 mg). This material contained some mCPBA-derived impurities but was used in subsequent reactions without purification. MS (apci) m/z=226.1 (M+H).

Intermediate X5

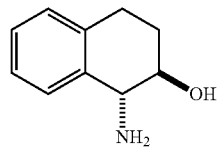

trans-1-amino-1,2,3,4-tetrahydronaphthalen-2-ol

Step A: Preparation of 1a,2,3,7b-tetrahydronaphtho[1,2-b]oxirene: 1,2-dihydronaphthalene (2.00 g, 15.4 mmol) was dissolved in DCM (75 mL) and saturated aqueous NaHCO$_3$ (75 mL) and cooled to 0° C. mCPBA (4.17 g, 16.9 mmol) was added and the reaction was allowed to warm to ambient temperature overnight. The layers were separated and the aqueous layer was extracted with EtOAc (100 mL). The combined organic extracts were filtered through phase separator paper and concentrated to afford 1a,2,3,7b-tetrahydronaphtho[1,2-b]oxirene (2.20 g, 15.0 mmol, 98.0% yield). MS (apci) m/z=147.1 (M+H).

Step B: Preparation of trans-1-amino-1,2,3,4-tetrahydronaphthalen-2-ol: 1a,2,3,7b-tetrahydronaphtho[1,2-b]oxirene (1.00 g, 6.8 mmol) and NH$_4$OH (4.8 g, 136 mmol) were combined in a sealed tube and heated at 60° C. for 3 hours. The precipitate that formed was collected and washed with water and ether to afford trans-1-amino-1,2,3,4-tetrahydronaphthalen-2-ol (122 mg, 0.7475 mmol, 10.93% yield). MS (apci) m/z=147.1 (M-NH$_3$).

Intermediate X6

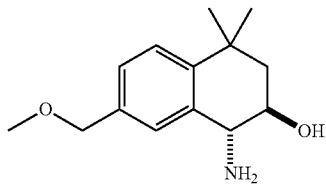 [SMILES: COCc1ccc2c(c1)[C@@H](N)[C@H](O)CC2(C)C]

trans-1-amino-7-(methoxymethyl)-4,4-dimethyl-1,2,3,4-tetrahydronaphthalen-2-ol

Step A: Preparation of 7-(methoxymethyl)-4,4-dimethyl-3,4-dihydronaphthalen-1(2H)-one: Potassium methoxymethyltrifluoroborate (1.20 g, 7.90 mmol), 7-bromo-4,4-dimethyl-3,4-dihydronaphthalen-1(2H)-one (1.00 g, 3.95 mmol), Dichloro[1,1'-bis(diphenylphosphino)ferrocene]palladium (II) dichloromethane adduct (0.645 g, 0.790 mmol) and $Cs_2CO_3$ (6.44 g, 19.8 mmol) were combined in dioxane (2 mL) and water (0.5 mL) and degassed by bubbling $N_2$ through the solution for 10 minutes, The reaction was then sealed in a glass tube and heated in a 100° C. sand bath for 6 hours and then in a 120° C. sand bath for 15 hours. The reaction was cooled, poured into brine (50 mL) and extracted with EtOAc (2×100 mL). The combined organic extracts were concentrated and purified by silica gel column (0-10% EtOAc/hexanes) to afford 7-(methoxymethyl)-4,4-dimethyl-3,4-dihydronaphthalen-1(2H)-one (162 mg, 0.742 mmol, 18.8% yield). MS (apci) m/z=219.1 (M+H).

Step B: Preparation of 7-(methoxymethyl)-4,4-dimethyl-1,2,3,4-tetrahydronaphthalen-1-ol: 7-(methoxymethyl)-4,4-dimethyl-3,4-dihydronaphthalen-1(2H)-one (210 mg, 0.962 mmol) was dissolved in MeOH (20 mL) and $NaBH_4$ (54.6 mg, 1.44 mmol) was added in small portions. The reaction was stirred at ambient temperature for 1 hour and partially concentrated. 2N NaOH (20 mL) was added and the mixture was extracted with EtOAc (2×50 mL), filtered through phase separator paper and concentrated to afford 7-(methoxymethyl)-4,4-dimethyl-1,2,3,4-tetrahydronaphthalen-1-ol (203 mg, 0.921 mmol, 95.8% yield). $^1$H NMR ($CDCl_3$) δ 7.38-7.40 (m, 1H), 7.30-7.34 (m, 1H), 7.20-7.25 (m, 1H), 4.71-4.75 (m, 1H), 4.42 (s, 2H), 3.39 (s, 3H), 2.02-2.12 (m, 1H), 1.82-1.93 (m, 2H), 1.56-1.64 (m, 1H), 1.32 (s, 3H), 1.24 (s, 3H) ppm.

Step C: Preparation of 6-(methoxymethyl)-1,1-dimethyl-1,2-dihydronaphthalene: 7-(methoxymethyl)-4,4-dimethyl-1,2,3,4-tetrahydronaphthalen-1-ol (130 mg, 0.590 mmol) was dissolved in 10 ml of dry ether and Martin Sulfurane (516 mg, 0.767 mmol) added. The reaction was stirred at ambient temperature overnight, 5 mL of 2M saturated aqueous $Na_2CO_3$ added and the reaction was stirred for 1 hour and filtered through Celite®. Brine was added to the filtrate and the mixture was extracted with several portions of EtOAc. The combined organic extracts were filtered through phase separator paper, concentrated and purified by silica gel column (0-10% EtOAc/hexanes) to afford 6-(methoxymethyl)-1,1-dimethyl-1,2-dihydronaphthalene (100 mg, 0.49 mmol, 83.8% yield). MS (apci) m/z=203.1 (M+H).

Step D: Preparation of trans-1-amino-7-(methoxymethyl)-4,4-dimethyl-1,2,3,4-tetrahydronaphthalen-2-ol: 6-(methoxymethyl)-1,1-dimethyl-1,2-dihydronaphthalene (100 mg, 0.494 mmol) was dissolved in DCM (10 mL) and saturated aqueous $NaHCO_3$ (10 ml) and stirred at 0° C. mCPBA (183 mg, 0.742 mmol) was added and the reaction was allowed to warm to ambient temperature overnight. The mixture was extracted with several portions of DCM in a phase separator frit, concentrated, and taken up in concentrated ammonium hydroxide (2623.2 µL, 45.810 mmol). The reaction was stirred in a 60° C. sand bath for 2 hours, cooled and concentrated to afford trans-1-amino-7-(methoxymethyl)-4,4-dimethyl-1,2,3,4-tetrahydronaphthalen-2-ol (100 mg, 0.42 mmol, 88% yield for two steps). This material contained some impurities but was used in subsequent reactions without purification. MS (apci) m/z=219.1 (M-$NH_3$).

Intermediate X7

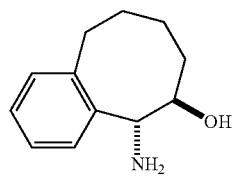 [SMILES: N[C@@H]1c2ccccc2CCCC[C@H]1O]

trans-5-amino-6,7,8,9-tetrahydro-5H-benzo[7]annulen-6-ol trans-5-amino-6,7,8,9-tetrahydro-5H-benzo[7]annulen-6-ol was synthesized from 1-Benzosuberone in 23.9% overall yield using the method as described for Intermediate X1, Steps A-D. The obtained trans-5-amino-6,7,8,9-tetrahydro-5H-benzo[7]annulen-6-ol contained some impurities but was used in subsequent reactions without purification MS (apci) m/z=178.1 (M+H).

Intermediate X8

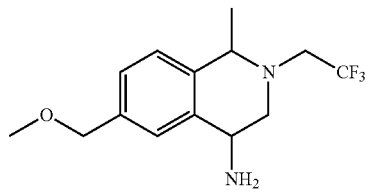 [SMILES: COCc1ccc2c(c1)C(N)CN(CC(F)(F)F)C2C]

6-(methoxymethyl)-1-methyl-2-(2,2,2-trifluoroethyl)-1,2,3,4-tetrahydroisoquinolin-4-amine Step A: Preparation of 2,2-dimethoxy-N-(1-(4-(methoxymethyl)phenyl)ethyl)ethanamine: 1-(4-(methoxymethyl)phenyl)ethanone (500 mg, 3.05 mmol) and 2,2-dimethoxyethanamine (480 mg, 4.57 mmol) were combined in 3 mL of $CHCl_3$ and stirred for 15 minutes. $Na(OAc)_3$ BH (839 mg, 3.96 mmol) was added and the reaction was stirred for 2 hours. AcOH (1 drop) was added and the reaction was stirred at ambient temperature overnight, quenched with water (3 mL) and extracted with DCM (3×10 mL) in a Phase Separator frit. The combined organic extracts were concentrated to afford 2,2-dimethoxy-N-(1-(4-(methoxymethyl)phenyl)ethyl)ethanamine (610 mg, 2.41 mmol, 79.1% yield). MS (apci) m/z=254.2 (M+H).

Step B: Preparation of N-(2,2-dimethoxyethyl)-2,2,2-trifluoro-N-(1-(4-(methoxymethyl)phenyl)ethyl)ethanamine: 2,2-dimethoxy-N-(1-(4-(methoxymethyl)phenyl)ethyl) ethanamine (250 mg, 0.987 mmol), NEt₃ (413 μl, 2.96 mmol) and 2,2,2-trifluoroethyl trifluoromethanesulfonate (275 mg, 1.18 mmol) were combined and stirred at ambient temperature overnight, at 60° C. for 24 hours and then at 100° C. for 24 hours. The reaction was loaded onto a samplet and purified by reverse phase column (0-80% Acetonitrile/ H₂O) to afford N-(2,2-dimethoxyethyl)-2,2,2-trifluoro-N-(1-(4-(methoxymethyl)phenyl)ethyl)ethanamine (278 mg, 0.829 mmol, 84.0% yield). MS (apci) m/z=254.2 (M-MeOH).

Step C: Preparation of 6-(methoxymethyl)-1-methyl-2-(2, 2,2-trifluoroethyl)-1,2,3,4-tetrahydroisoquinolin-4-ol: N-(2, 2-dimethoxyethyl)-2,2,2-trifluoro-N-(1-(4-(methoxymethyl)phenyl)ethyl)ethanamine (330 mg, 0.984 mmol) and perchloric acid (70% in water, 2 mL) were combined and stirred at ambient temperature for 4 hours. The reaction was poured into a mixture of ice and 2N NaOH (50 mL) and extracted with several portions of EtOAc, filtered through PS paper and concentrated. The mixture was purified by reverse phase column using 0-70% acetonitrile/H₂O as the eluent to afford 6-(methoxymethyl)-1-methyl-2-(2,2,2-trifluoroethyl)-1,2,3,4-tetrahydroisoquinolin-4-ol (143 mg, 0.494 mmol, 50.2% yield) as a ~1:2 mixture of diastereomers. MS (apci) m/z=290.1 (M+H)

Step D: Preparation of 4-azido-6-(methoxymethyl)-1-methyl-2-(2,2,2-trifluoroethyl)-1,2,3,4-tetrahydroisoquinoline: 6-(methoxymethyl)-1-methyl-2-(2,2,2-trifluoroethyl)-1,2,3,4-tetrahydroisoquinolin-4-ol (25 mg, 0.086 mmol) was dissolved in DCM (2 mL) and thionyl chloride (13 μL, 0.17 mmol) was added. The reaction was stirred at ambient temperature for 2 h and then at 50° C. for 20 minutes, concentrated, and DMF and NaN₃ (52.8 mg, 0.812 mmol) were added. The reaction was stirred ambient temperature for 1 hour and then at 100° C. for 30 minutes. The mixture was loaded onto a samplet and purified by reverse phase column chromatography using 0-70% acetonitrile/H₂O as the eluent to afford 4-azido-6-(methoxymethyl)-1-methyl-2-(2,2,2-trifluoroethyl)-1,2,3,4-tetrahydroisoquinoline (20 mg, 0.0636 mmol, 78.3% yield). MS (apci) m/z=287.1 (M-N₂).

Step E: Preparation of 6-(methoxymethyl)-1-methyl-2-(2, 2,2-trifluoroethyl)-1,2,3,4-tetrahydroisoquinolin-4-amine: 4-azido-6-(methoxymethyl)-1-methyl-2-(2,2,2-trifluoroethyl)-1,2,3,4-tetrahydroisoquinoline (20 mg, 0.064 mmol) and 10% Pd/C (6.8 mg, 0.0064 mmol) were mixed in 1 mL of MeOH and stirred under a balloon of H₂ for 3 hours. The reaction was filtered and concentrated to afford 6-(methoxymethyl)-1-methyl-2-(2,2,2-trifluoroethyl)-1,2,3, 4-tetrahydroisoquinolin-4-amine (18 mg, 0.062 mmol, 98% yield) which was used without purification. MS (apci) m/z=272.1 (M-NH₃).

Intermediate X9

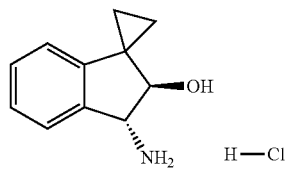 [SMILES: N[C@@H]1c2ccccc2C2(CC2)[C@H]1O ; Cl]

(2'R,3'R)-3'-amino-2',3'-dihydrospiro[cyclopropane-1,1'-inden]-2'-ol hydrochloride Step A: Preparation of tert-butyl (trans-2'-hydroxy-2',3'-dihydrospiro[cyclopropane-1,1'-inden]-3'-yl)carbamate: To a solution of trans-3'-amino-2',3'-dihydrospiro[cyclopropane-1,1'-inden]-2'-ol (Example 55, Step C, 425 mg, 2.425 mmol) in DCM (15 mL) were added DIEA (845 μL, 4.851 mmol) and Boc₂O (582 mg, 2.668 mmol). The reaction mixture was stirred at ambient temperature for 22 hours, then diluted with H₂O (25 mL), extracted with DCM (2×25 mL), and the combined organic phases were washed with brine (40 mL), dried (MgSO₄), filtered, and concentrated to afford the product as a beige solid (636 mg, 95% yield).

Step B: Preparation of trans-3'-((tert-butoxycarbonyl) amino)-2',3'-dihydrospiro[cyclopropane-1,1'-inden]-2'-yl acetate: To a solution of tert-butyl (trans-2'-hydroxy-2',3'-dihydrospiro[cyclopropane-1,1'-inden]-3'-yl)carbamate (455 mg, 1.65 mmol) in pyridine (4.13 mL, 1.65 mmol) were added DMAP (20.2 mg, 0.165 mmol) then Ac₂O (468 μl, 4.96 mmol). The reaction mixture was stirred at ambient temperature for 17 hours, then was diluted with aqueous HCl (1 M, 60 mL), then extracted with DCM (2×50 mL). The combined organic phases were washed with H₂O (50 mL), dried (MgSO₄), filtered, concentrated, and dried under high vacuum to afford the product as a brown solid (477 mg, 91% yield).

Step C: Preparation of (2'R,3'R)-3'-((tert-butoxycarbonyl) amino)-2',3'-dihydrospiro[cyclopropane-1,1'-inden]-2'-yl acetate: Racemic trans-3'-((tert-butoxycarbonyl)amino)-2', 3'-dihydrospiro[cyclopropane-1,1'-inden]-2'-yl acetate (477 mg, 1.503 mmol) was separated by chiral HPLC (Chiral Tech OJ-H, 22 mm×250 mm, 5μ particle size, 7.5% ethanol: 92.5% hexanes, 22 mL/min, 220 nm). The first peak to elute was collected and concentrated to afford the product as a white solid (168 mg, 35% yield). ¹H NMR (CDCl₃) δ 7.33 (d, 1H), 7.28-7.19 (m, 2H), 6.71 (d, 1H), 5.28 (d, 1H), 5.20 (br m, 1H), 4.82 (br m, 1H), 2.07 (s, 3H), 1.48 (s, 9H), 1.25 (m, 1H), 1.16 (m, 1H), 1.00 (m, 1H), 0.88 (m, 1H).

Step D: Preparation of tert-butyl ((2'R,3'R)-2'-hydroxy-2',3'-dihydrospiro[cyclopropane-1,1'-inden]-3'-yl)carbamate: To a solution of (2'R,3'R)-3'-((tert-butoxycarbonyl) amino)-2',3'-dihydrospiro[cyclopropane-1,1'-inden]-2'-yl acetate (168 mg, 0.529 mmol) in MeOH (2 mL) was added K₂CO₃ (109.7 mg, 0.794 mmol). The reaction mixture was stirred at ambient temperature for 2 hours, then diluted with 20% iPrOH/80% DCM (10 mL), filtered through a plug of silica, rinsing with 20% iPrOH/80% DCM (2×20 mL). The eluent was concentrated to afford the product as an off-white solid (145 mg, 99% yield). ¹H NMR (CDCl₃) δ 7.15-7.25 (m, 3H), 6.73 (d, 1H), 5.03 (br s, 1H), 4.93 (t, 1H), 4.25 (d, 1H), 1.52 (m, 1H), 1.48 (s, 9H), 1.10 (m, 1H), 0.96 (m, 1H), 0.60 (m, 1H).

Step E: Preparation of (2'R,3'R)-3'-amino-2',3'-dihydrospiro[cyclopropane-1,1'-inden]-2'-ol hydrochloride: To a solution of tert-butyl ((2'R,3'R)-2'-hydroxy-2',3'-dihydrospiro[cyclopropane-1,1'-inden]-3'-yl)carbamate (145 mg, 0.527 mmol) in iPrOH (2.5 mL) was added HCl (5-6M in iPrOH, 1.05 mL). The reaction mixture was stirred at ambient temperature for 17 hours and then concentrated. The solid was diluted with Et₂O (1 mL) and concentrated (3×), then dried under high vacuum to afford the HCl salt of the product as a pale yellow solid (110 mg, 99% yield). ¹H NMR (CD₃OD) δ 7.43 (dd, 1H), 7.34 (tt, 1H), 7.26 (dt, 1H), 6.87 (br d, 1H), 4.51 (d, 1H), 4.25 (d, 1H), 1.41 (m, 1H), 1.16 (m, 1H), 1.02 (m, 1H), 0.75 (m, 1H).

Intermediate X10

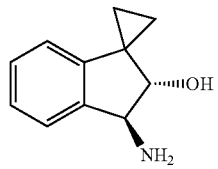 [SMILES: N[C@H]1c2ccccc2C2(CC2)[C@@H]1O]

(2'S,3'S)-3'-amino-2',3'-dihydrospiro[cyclopropane-1,1'-inden]-2'-ol

Step A: Preparation of (2'S,3'S)-3'-((tert-butoxycarbonyl)amino)-2',3'-dihydrospiro[cyclopropane-1,1'-inden]-2'-yl acetate: Racemic trans-3'-((tert-butoxycarbonyl)amino)-2',3'-dihydrospiro[cyclopropane-1,1'-inden]-2'-yl acetate (Intermediate X9, Step B, 176 mg, 0.555 mmol) was separated by chiral HPLC (Chiral Tech OJ-H, 22 mm×250 mm, 5μ particle size, 7.5% ethanol: 92.5% hexanes, 22 mL/min, 220 nm). The second peak to elute was collected and concentrated to afford the product as a beige solid (63.4 mg, 36% yield). $^1$H NMR (CDCl$_3$) δ 7.32 (d, 1H), 7.21 (m, 2H), 6.70 (d, 1H), 5.26 (d, 1H), 5.19 (br s, 1H), 4.80 (br s, 1H), 2.05 (s, 3H), 1.46 (s, 9H), 1.24 (m, 1H), 1.13 (m, 1H), 1.00 (m, 1H), 0.86 (m, 1H).

Step B: Preparation of tert-butyl ((2'S,3'S)-2'-hydroxy-2',3'-dihydrospiro[cyclopropane-1,1'-inden]-3'-yl)carbamate: To a solution of (2'S,3'S)-3'-((tert-butoxycarbonyl)amino)-2',3'-dihydrospiro[cyclopropane-1,1'-inden]-2'-yl acetate (55.4 mg, 0.200 mmol) in MeOH (2 mL) was added K$_2$CO$_3$ (41.4 mg, 0.300 mmol). The reaction mixture was stirred at ambient temperature for 2 hours, then diluted with 20% iPrOH/80% DCM (10 mL), filtered through a plug of silica, rinsing with 20% iPrOH/80% DCM (2×20 mL). The eluent was concentrated to afford the product as a pale orange solid (55.4 mg, 100% yield).

Step C: Preparation of (2'S,3'S)-3'-amino-2',3'-dihydrospiro[cyclopropane-1,1'-inden]-2'-ol: To a solution of tert-butyl ((2'S,3'S)-2'-hydroxy-2',3'-dihydrospiro[cyclopropane-1,1'-inden]-3'-yl)carbamate (55.4 mg, 0.201 mmol) in iPrOH (1.3 mL) was added HCl (5-6M in iPrOH, 0.2 mL). The reaction mixture was stirred at ambient temperature for 1 hour, and additional HCl (5-6M in iPrOH, 0.2 mL) was added. The reaction mixture was stirred at ambient temperature for 19 hours, and additional HCl (5-6M in iPrOH, 0.2 mL) was added. The reaction mixture was stirred at ambient temperature for 2 hours, then diluted with saturated aqueous NaHCO$_3$ (25 mL), extracted with 10% MeOH/90% DCM (3×25 mL), and the combined organic phases were dried (MgSO$_4$), filtered, and concentrated to afford the product as a pale blue solid (18.4 mg, 52% yield). $^1$H NMR (CD$_3$OD) δ 7.31 (m, 1H), 7.22 (m, 2H), 6.75 (m, 1H), 4.17 (d, 1H), 3.98 (d, 1H), 1.36 (m, 1H), 1.12 (m, 1H), 0.96 (m, 1H), 0.68 (m, 1H).

Intermediate X11

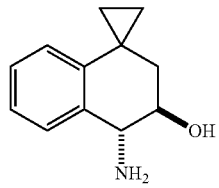

trans-4'-amino-3',4'-dihydro-2'H-spiro[cyclopropane-1,1'-naphthalen]-3'-ol

Step A: Preparation of 1-methylene-1,2,3,4-tetrahydronaphthalene: To a suspension of methyltriphenylphosphonium bromide (8.797 g, 24.626 mmol) in Et$_2$O (90 mL) under N$_2$ was added KOtBu (2.763 g, 24.626 mmol) in several portions over 5 minutes. The reaction mixture was stirred at ambient temperature for 2 hours, then was cooled to 0° C. and a solution of 3,4-dihydronaphthalen-1(2H)-one (2.737 mL, 20.522 mmol) in Et$_2$O (10 mL) was added. The reaction mixture was allowed to warm to ambient temperature and stirred for 2 hours. The reaction mixture was filtered through Celite® and rinsed with Et$_2$O (4×100 mL), and concentrated. The crude oil was purified by silica column chromatography, eluting with hexanes, to afford the product as a colorless oil (3.02 g, 102% yield). $^1$H NMR (CDCl$_3$) δ 7.64 (m, 1H), 7.16 (m, 2H), 7.09 (m, 1H), 5.47 (dd, 1H), 4.95 (dd, 1H), 2.85 (dd, 2H), 2.55 (m, 2H), 1.88 (m, 2H).

Step B: Preparation of 3',4'-dihydro-2'H-spiro[cyclopropane-1,1'-naphthalene]: To a solution of diethyl zinc (1M in hexanes, 31.2 mL, 31.2 mmol) and DCM (80 mL), under N$_2$ flow and cooled to 0° C., was added a solution of TFA (2.40 mL, 31.204 mmol) in DCM (10 mL) dropwise over 25 minutes. At the end of the addition, DCM (10 mL) was added, and the reaction mixture was stirred at 0° C. for 30 minutes. Diiodomethane (2.51 mL, 31.204 mmol) was added dropwise over 5 minutes, and the reaction mixture was stirred at 0° C. for 1 hour. A solution of 1-methylene-1,2,3,4-tetrahydronaphthalene (3.0 g, 20.803 mmol) in DCM (10 mL) was added dropwise over 5 minutes, then the reaction mixture was stirred at 0° C. for 2 hours. The reaction mixture was diluted with H$_2$O (50 mL), stirred for 30 minutes, then filtered through Celite®, rinsing with DCM (3×50 mL). The phases were separated and the aqueous phase extracted with DCM (50 mL). The combined organic phases were dried (MgSO$_4$), filtered, and partially concentrated afford the product as a yellow oil (12.88 g, 389% yield). The product contained both DCM and CH$_2$I$_2$ by $^1$H NMR analysis and was used in the next step without further purification. $^1$H NMR (CDCl$_3$) δ 7.04 (m, 3H), 6.66 (d, 1H), 5.30 (s, 5H, CH$_2$Cl$_2$), 3.87 (s, 10H, CH$_2$I$_2$), 2.88 (dd, 2H), 1.90 (m, 2H), 1.67 (m, 2H), 0.96 (m, 2H), 0.78 (m, 2H).

Step C: Preparation of 2'H-spiro[cyclopropane-1,1'-naphthalen]-4'(3'H)-one: To a solution of 3',4'-dihydro-2'H-spiro[cyclopropane-1,1'-naphthalene] (3.29 g, 20.791 mmol) in DCM (100 mL) cooled to 0° C. were added CrO$_3$ (0.416 g, 4.158 mmol), then tert-butyl hydroperoxide (43.1 mL, 311.9 mmol). The reaction mixture was allowed to warm to ambient temperature slowly and stirred for 24 hours, then the reaction mixture was diluted with MeOH (50 mL) and water (200 mL), then extracted with Et$_2$O (3×150 mL). The combined organic phases were washed with saturated aqueous NaHCO$_3$ (100 mL) and brine (100 mL), dried (MgSO$_4$), filtered and concentrated. The crude oil was purified by silica column chromatography, eluting with 0-30% acetone/hexanes, to afford the product as an orange oil (1.68 g, 47% yield). $^1$H NMR (CDCl$_3$) δ 8.04 (dd, 1H), 7.45 (ddd, 1H), 7.25 (m, 1H), 6.83 (dd, 1H), 2.78 (dd, 2H), 1.99 (dd, 2H), 1.10 (m, 2H), 0.99 (m, 2H).

Step D: Preparation of 3',4'-dihydro-2'H-spiro[cyclopropane-1,1'-naphthalen]-4'-ol: To a solution of 2'H-spiro[cyclopropane-1,1'-naphthalen]-4'(3'H)-one (1.68 g, 9.755 mmol) in MeOH (32 mL) cooled to 0° C. was added NaBH$_4$ (0.443 g, 11.706 mmol) in several portions over 10 min. The reaction mixture was allowed to warm to ambient temperature slowly and stirred for 17 hours. The reaction mixture was diluted with H$_2$O (100 mL) and extracted with DCM (3×100 mL). The combined organic extracts were washed with brine (50 mL), dried (MgSO$_4$), filtered, and concentrated to afford the product as a peachy-orange syrup (927 mg, 55% yield).

Step E: Preparation of 2'H-spiro[cyclopropane-1,1'-naphthalene]: To a solution of 3',4'-dihydro-2'H-spiro[cyclopropane-1,1'-naphthalen]-4'-ol (927 mg, 5.320 mmol) in toluene (17 mL) was added TsOH—H$_2$O (50.6 mg, 0.266 mmol). The reaction mixture was heated to 110° C. for 90 minutes, then cooled to ambient temperature. The reaction mixture was diluted with H$_2$O (50 mL) and extracted with DCM (3×50 mL). The combined organic extracts were dried (MgSO$_4$), filtered, and concentrated. The crude oil was purified by silica column chromatography, eluting with hexanes, to afford the product as a solution in hexanes and toluene (3.13 g, 377% yield). The product contained both hexanes and toluene by $^1$H NMR analysis and was used in the next step without further purification.

Step F: Preparation of trans-3'-bromo-3',4'-dihydro-2'H-spiro[cyclopropane-1,1'-naphthalen]-4'-ol: To a solution of 2'H-spiro[cyclopropane-1,1'-naphthalene] (100 mg, 0.640 mmol) in DMSO (1.3 mL) were added H$_2$O (115 µL, 6.401 mmol) then NBS (125 mg, 0.704 mmol). The reaction mixture was stirred at ambient temperature for 21 hours, then was diluted with water (20 mL) and extracted with Et$_2$O (3×20 mL). The combined organic phases were washed with brine (25 mL), dried (MgSO$_4$), filtered and concentrated. The crude oil was purified by silica column chromatography, eluting with 0-50% acetone/hexanes, to afford the product as a pale yellow residue (13 mg, 8% yield). $^1$H NMR (CDCl$_3$) δ 7.56 (m, 1H), 7.21 (m, 2H), 6.63 (m, 1H), 4.99 (d, 1H), 4.49 (ddd, 1H), 2.62 (br s, 1H), 2.53 (dd, 1H), 2.05 (dd, 1H), 1.22 (m, 1H), 0.94 (m, 2H), 0.86 (m, 1H).

Step G: Preparation of 2',7b'-dihydro-1a'H-spiro[cyclopropane-1,3'-naphtho[1,2-b]oxirene]: To a solution of trans-3'-bromo-3',4'-dihydro-2'H-spiro[cyclopropane-1,1'-naphthalen]-4'-ol (13 mg, 0.0514 mmol) in Et$_2$O (2.5 mL) was added KOH (140 mg, 2.495 mmol). The reaction mixture was stirred at ambient temperature for 23 hours, then additional KOH (140 mg, 2.495 mmol) was added. The reaction mixture was stirred at ambient temperature for 3 hours, then was filtered, rinsed with Et$_2$O, and concentrated to afford the product as a colorless oil (18 mg, 204% yield). The product contained Et$_2$O by NMR analysis, and was used in the next step without further purification.

Step H: Preparation of trans-4'-amino-3',4'-dihydro-2'H-spiro[cyclopropane-1,1'-naphthalen]-3'-ol: To a solution of 2',7b'-dihydro-1a'H-spiro[cyclopropane-1,3'-naphtho[1,2-b]oxirene] (8 mg, 0.047 mmol) NH$_3$ (7N in MeOH, 0.5 mL) was added NH$_4$OH (0.5 mL) The reaction mixture was heated to 70° C. for 2.5 hours, then cooled to ambient temperature. The reaction mixture was diluted with H$_2$O (10 mL), acidified with HCl (1 M aqueous, 4 mL), then extracted with Et$_2$O (10 mL), which was discarded. The aqueous phase was then made basic by addition of aqueous NaOH (4 M aqueous, 0.5 mL), then extracted with 10% MeOH/90% DCM (3×10 mL). The combined organic phases were dried (MgSO$_4$), filtered, concentrated, and dried under high vacuum to afford the product as a beige solid (5.6 mg, 64% yield). $^1$H NMR (CDCl$_3$) δ 7.45 (m, 1H), 7.17 (m, 2H), 6.62 (m, 1H), 3.75 (m, 2H), 2.16 (m, 1H), 1.99 (br s, 3H), 1.64 (m, 1H), 1.18 (m, 1H), 0.90 (m, 2H), 0.81 (m, 1H).

Intermediate X12

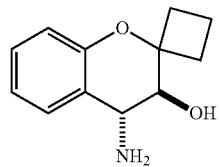

trans-4-aminospiro[chroman-2,1'-cyclobutan]-3-ol

Step A: spiro[chroman-2,1'-cyclobutan]-4-one: To a suspension of 1-(2-hydroxyphenyl)ethanone (3.0 g, 22.035 mmol) in MeOH (37 mL) was added pyrrolidine (3.679 mL, 44.070 mmol). The reaction mixture was stirred at ambient temperature for 15 minutes, and then cyclobutanone (1.65 mL, 22.035 mmol) was added. The reaction mixture was heated to 50° C. for 19 hours, then additional cyclobutanone (1.0 mL) was added and the reaction mixture was heated to 65° C. for 5 days. The reaction mixture was diluted with H$_2$O (100 mL), extracted DCM (3×100 mL), and the combined organic phases were washed with aqueous HCl (1 M, 200 mL), then H$_2$O (200 mL), then brine (200 mL), dried (MgSO$_4$), filtered, and concentrated. The crude oil was purified by silica column chromatography, eluting with 0-30% acetone/hexanes, to afford the product as an orange oil (2.92 mg, 70% yield). $^1$H NMR (CDCl$_3$) δ 7.85 (dd, 1H), 7.47 (ddd, 1H), 6.99 (m, 2H), 2.90 (s, 2H), 2.33 (m, 2H), 2.17 (m, 2H), 1.93 (m, 1H), 1.72 (m, 1H).

Step B: spiro[chroman-2,1'-cyclobutan]-4-ol: To a solution of spiro[chroman-2,1'-cyclobutan]-4-one (1.00 g, 5.313 mmol) in MeOH (17 mL) cooled to 0° C. was added NaBH$_4$ (0.241 g, 6.375 mmol) in several portions over 10 minutes. The reaction mixture was allowed to warm to ambient temperature slowly and stirred for 19 hours. The reaction mixture was diluted with H$_2$O (100 mL) and extracted with DCM (3×100 mL) The combined organic extracts were washed with brine (50 mL), dried (MgSO$_4$), filtered, and concentrated to afford the product as a thick yellow syrup (715 mg, 71% yield). $^1$H NMR (CDCl$_3$) δ 7.38 (dd, 1H), 7.17 (ddd, 1H), 6.91 (ddd, 1H), 6.82 (dd, 1H), 4.84 (dd, 1H), 2.35-2.23 (m, 4H), 2.13-2.03 (m, 2H), 1.95-1.85 (m, 1H), 1.78-1.66 (m, 1H).

Step C: spiro[chromene-2,1'-cyclobutane]: To a solution of spiro[chroman-2,1'-cyclobutan]-4-ol (715 mg, 3.758 mmol) in DCM (7.5 mL) were added molecular sieves (350 mg, 4 A, powdered, activated, oven-dried) and MP-TsOH (46 mg, 0.188 mmol). The reaction mixture was stirred at ambient temperature for 4 days, then additional molecular sieves (300 mg, 4 A, powdered, activated, oven-dried) and MP-TsOH (46 mg, 0.188 mmol) were added, and the reaction mixture was stirred at ambient temperature for 17 hours.

The reaction mixture was filtered, rinsed with DCM, and concentrated. The crude oil was purified by silica column chromatography, eluting with 0-25% acetone/hexanes, to afford the product as a pale yellow oil (135 mg, 21% yield). The product was impure by $^1$H NMR analysis and was used in the next step without further purification.

Step D: trans-3-bromospiro[chroman-2,1'-cyclobutan]-4-ol: To a solution of spiro[chromene-2,1'-cyclobutane] (135 mg, 0.784 mmol) in DMSO (1.5 mL) were added H$_2$O (141 μL, 7.839 mmol) then NBS (153 mg, 0.862 mmol). The reaction mixture was stirred at ambient temperature for 17 hours, then was diluted with water (20 mL) and extracted with Et$_2$O (3×20 mL). The combined organic phases were washed with brine (25 mL), dried (MgSO$_4$), filtered and concentrated. The crude oil was purified by silica column chromatography, eluting with 0-25% acetone/hexanes, to afford the product as a thick colorless syrup (115 mg, 55% yield). $^1$H NMR (CDCl$_3$) δ 7.37 (dd, 1H), 7.26 (dt, 1H), 7.00 (dd, 1H), 6.94 (dt, 1H), 4.98 (d, 1H), 4.45 (d, 1H), 2.74 (m, 1H), 2.43 (m, 1H), 2.35 (m, 1H), 2.26 (m, 1H), 2.09 (m, 1H), 1.86 (m, 1H).

Step E: 1a',7b'-dihydrospiro[cyclobutane-1,2'-oxireno[2,3-c]chromene]: To a solution of trans-3-bromospiro[chroman-2,1'-cyclobutan]-4-ol (115 mg, 0.427 mmol) in Et$_2$O (21 mL) was added KOH (1.2 g, 21.4 mmol). The reaction mixture was stirred at ambient temperature for 19 hours, then was filtered, rinsed with Et$_2$O, and concentrated to afford the product as a colorless oil (79.8 mg, 99% yield). $^1$H NMR (CDCl$_3$) δ 7.31 (m, 1H), 7.21 (m, 1H), 6.91 (m, 1H), 6.83 (m, 1H), 3.90 (m, 2H), 2.55 (m, 2H), 2.19 (m, 2H), 1.99 (m, 1H), 1.79 (m, 1H).

Step F: trans-4-aminospiro[chroman-2,1'-cyclobutan]-3-ol: To a hazy solution of 1a',7b'-dihydrospiro[cyclobutane-1,2'-oxireno[2,3-c]chromene] (80 mg, 0.425 mmol) in NH$_3$ (7N in MeOH, 0.5 mL) was added NH$_4$OH (1 mL). The reaction mixture was heated to 70° C. for 2 hours, then cooled to ambient temperature. The reaction mixture was diluted with H$_2$O (10 mL), then extracted with 10% MeOH/90% DCM (2×15 mL). The combined organic phases were dried (MgSO$_4$), filtered, concentrated, and dried under high vacuum to afford the product as a white solid (76 mg, 87% yield). $^1$H NMR (CDCl$_3$) δ 7.35 (m, 1H), 7.16 (m, 1H), 6.94 (m, 1H), 6.84 (m, 1H), 3.79 (d, 1H), 3.54 d, 1H), 2.62 (m, 1H), 2.52 (br s, 2H), 2.31 (m, 2H), 2.02 (m, 2H), 1.83 (m, 1H).

Intermediate Y1

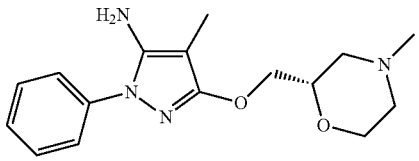 [SMILES: Cc1c(OC[C@@H]2CN(C)CCO2)nn(-c2ccccc2)c1N]

(S)-4-methyl-3-((4-methylmorpholin-2-yl)methoxy)-1-phenyl-1H-pyrazol-5-amine

Step A: Preparation of (S)-tert-butyl 2-(((5-amino-4-methyl-1-phenyl-1H-pyrazol-3-yl)oxy)methyl)morpholine-4-carboxylate: A mixture of 5-amino-4-methyl-1-phenyl-1H-pyrazol-3(2H)-one (Intermediate 2, Step A, 335 mg, 1.77 mmol), (S)-tert-butyl 2-(bromomethyl)morpholine-4-carboxylate (496 mg, 1.77 mmol) and potassium carbonate (612 mg, 4.43 mmol) in dry DMF (15 mL) was heated at 70° C. for 45 hours. The reaction mixture was cooled to ambient temperature and was added to ice-H$_2$O (10 mL) with dissolving of all of the K$_2$CO$_3$. The mixture was extracted with 50% EtOAc/hexanes (3×) and the combined extracts were washed with H$_2$O (2×) and saturated NaCl. The organic portion was dried over MgSO$_4$/activated charcoal, eluted through a thin SiO$_2$ plug (50% EtOAc/hexanes) and concentrated to give the product as a white foam that was dried in vacuum (418 mg, 61%). MS (apci) m/z=389.3 (M+H).

Step B: Preparation of (S)-4-methyl-3-(morpholin-2-ylmethoxy)-1-phenyl-1H-pyrazol-5-amine: (S)-tert-butyl 2-(((5-amino-4-methyl-1-phenyl-1H-pyrazol-3-yl)oxy)methyl)morpholine-4-carboxylate (332 mg, 0.855 mmol) was dissolved in chilled 5M HCl in iPrOH (10 mL) and the solution was stirred at ambient temperature for 2 hours. The mixture was concentrated and the residual white solid was washed with Et$_2$O (2×) and dried. The solid was dissolved in H$_2$O (5 mL) and 2M NaOH was added to pH=13. The solution was saturated with NaCl(s) and EtOAc (5 mL) was added. The biphasic mixture was stirred for 1 hour, the organic layer removed and the aqueous portion extracted with EtOAc (2×). The combined EtOAc fractions were dried over MgSO$_4$, filtered and concentrated. The resulting colorless syrup was dried in vacuum to provide the title compound as a white foam (220 mg, 89%). MS (apci) m/z=289.2 (M+H).

Step C: (S)-4-methyl-3-((4-methylmorpholin-2-yl)methoxy)-1-phenyl-1H-pyrazol-5-amine: A mixture of (S)-4-methyl-3-(morpholin-2-ylmethoxy)-1-phenyl-1H-pyrazol-5-amine (218 mg, 0.756 mmol) and NaBH(OAc)$_3$ (506 mg, 2.27 mmol) in 1,2-DCE (4 mL) was cooled to 0° C. and 37% aqueous formaldehyde (62.5 μL, 0.832 mmol) was added. The mixture was stirred for 15 hours during which time the temperature gradually reached ambient. The mixture was treated with chilled 1.0M NaOH (8 mL) and mixed at ambient temperature for 30 minutes. NaCl (s) was added to saturation and the organic layer was removed. The aqueous portion was extracted with CH$_2$Cl$_2$ (2×) and the combined organic fractions dried over Na$_2$SO$_4$/activated charcoal. The solution was filtered through a SiO$_2$ plug capped with a layer of MgSO$_4$ using CH$_2$Cl$_2$, EtOAc then 5% (9:1 MeOH/NH$_4$OH)/EtOAc for elution. The product pool was concentrated to give the title compound as a colorless waxy solid that was dried in vacuum (155 mg, 68%). MS (apci) m/z=303.2 (M+H).

Intermediate Y2

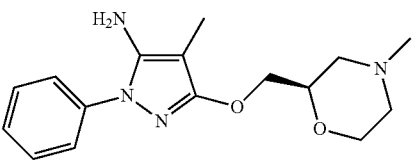 [SMILES: Cc1c(OC[C@H]2CN(C)CCO2)nn(-c2ccccc2)c1N]

(R)-4-methyl-3-((4-methylmorpholin-2-yl)methoxy)-1-phenyl-1H-pyrazol-5-amine

Using (R)-tert-butyl 2-(bromomethyl)morpholine-4-carboxylate in the procedure described for Intermediate Y1, the title compound was prepared as a white foam (44% over 3 steps). MS (apci) m/z=303.2 (M+H).

Intermediate Y3

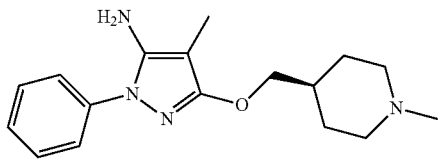

4-methyl-3-((1-methylpiperidin-4-yl)methoxy)-1-phenyl-1H-pyrazol-5-amine

Using tert-butyl 4-(bromomethyl)piperidine-1-carboxylate in the procedure described for Intermediate Y1, the title compound was prepared as a white solid (25% over 3 steps). MS (apci) m/z=301.2 (M+H).

Intermediate Y4

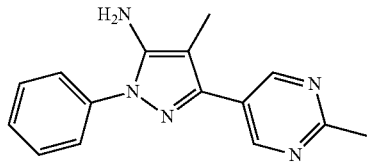 [SMILES: Cc1ncc(-c2nn(-c3ccccc3)c(N)c2C)cn1]

4-methyl-3-(2-methylpyrimidin-5-yl)-1-phenyl-1H-pyrazol-5-amine

Step A: Preparation of 5-amino-4-methyl-1-phenyl-1H-pyrazol-3(2H)-one: A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume then cooled in ice and triturated with cold Et₂O. The resulting solids were filtered, washed extensively with Et2O and dried in vacuo to afford 5-amino-4-methyl-1-phenyl-1H-pyrazol-3(2H)-one (34.69 g, 46% yield) as a fluffy white powder. MS (apci) m/z=190.1 (M+H).

Step B: Preparation of 5-amino-4-methyl-1-phenyl-1H-pyrazol-3-yl trifluoromethane sulfonate: A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture stirred at ambient temperature for 16 hours. The mixture was partitioned between saturated NaHCO3 (400 mL) and EtOAc (200 mL) and the aqueous layer was extracted with EtOAc (2×200 mL). The combined organic phases were washed with water (5×50 mL) and brine (50 mL) then dried over Na₂SO₄, filtered and concentrated in vacuo. The residue was purified by silica column chromatography eluting with 4:1 hexanes/EtOAc, to afford 5-amino-4-methyl-1-phenyl-1H-pyrazol-3-yl trifluoromethane sulfonate (23.1 g, 99% yield) as a pale yellow solid. MS (apci) m/z=322.0 (M+H).

Step C: Preparation of 4-methyl-3-(2-methylpyrimidin-5-yl)-1-phenyl-1H-pyrazol-5-amine: 5-Amino-4-methyl-1-phenyl-1H-pyrazol-3-yl trifluoromethane sulfonate (900 mg, 2.8 mmol), 2-methyl-5-(4,4,5,5-tetramethyl-1,3,2-dioxaborolan-2-yl)pyrimidine (925 mg, 4.2 mmol), K₂CO₃ (1.55 g, 11.2 mmol) and Pd(PPh₃)₄ (324 mg, 0.28 mmol) were combined in toluene (10 mL), water (5 mL) and EtOH (2.5 mL) and warmed to 95° C. in a sealed tube for 16 hours. The cooled mixture was filtered and the filtrate partitioned between water (50 mL) and EtOAc (50 mL). The aqueous layer was extracted with EtOAc (2×30 mL) and the combined organic phases were washed with brine (30 mL), dried over Na₂SO₄, filtered and concentrated in vacuo. The residue was purified by silica column chromatography eluting with 2% MeOH/DCM to afford the title compound (533 mg, 72% yield) as a pink solid. MS (apci) m/z=266.1 (M+H).

Intermediate Y5

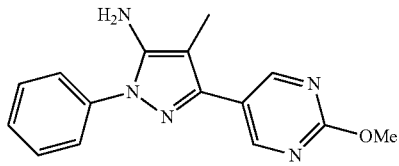 [SMILES: COc1ncc(-c2nn(-c3ccccc3)c(N)c2C)cn1]

3-(2-methoxypyrimidin-5-yl)-4-methyl-1-phenyl-1H-pyrazol-5-amine

Prepared according to the procedure for Intermediate Y4, substituting 2-methyl-5-(4,4,5,5-tetramethyl-1,3,2-dioxaborolan-2-yl)pyrimidine for 2-methoxypyrimidin-5-ylboronic acid in Step C, to afford the title compound (138 mg, 78% yield) as a cream foam. MS (apci) m/z=282.1 (M+H).

Intermediate Y6

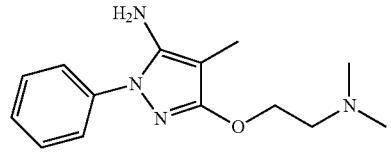 [SMILES: Cc1c(OCCN(C)C)nn(-c2ccccc2)c1N]

3-(2-(dimethylamino)ethoxy)-4-methyl-1-phenyl-1H-pyrazol-5-amine

To a thick-walled pressure reaction tube filled with a mixture of 5-amino-4-methyl-1-phenyl-1H-pyrazol-3(2H)-one (Intermediate 2, Step A, 171 mg, 0.903 mmol), 2-chloro-N,N-dimethylethanamine hydrochloride (130 mg, 0.903 mmol) and Cs2CO3 (882 mg, 2.71 mmol) was added DMA (1.8 mL) The white suspension was stirred at ambient temperature for 30 minutes and then at 100° C. overnight. The reaction mixture was partitioned between water and DCM (20 mL each). The phases were separated, and the aqueous phase was extracted with DCM (2×10 mL). The combined organic phases were washed with brine (3×20 mL), dried (Na₂SO₄), filtered, and concentrated to a dark brownish oil. The crude was purified by silica chromatography (10-20% MeOH/DCM) to yield the product as beige solid (0.13 g, 51% yield). MS (apci) m/z=261.2 (M+H).

Intermediate Y6

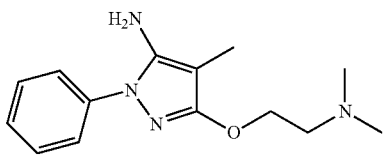 [SMILES: Cc1c(OCCN(C)C)nn(-c2ccccc2)c1N]

3-(2-(dimethylamino)ethoxy)-4-methyl-1-phenyl-1H-pyrazol-5-amine

To a thick-walled pressure reaction tube filled with a mixture of 5-amino-4-methyl-1-phenyl-1H-pyrazol-3(2H)-one (Intermediate 2, Step A, 171 mg, 0.903 mmol), 2-chloro-N,N-dimethylethanamine hydrochloride (130 mg, 0.903 mmol) and Cs2CO3 (882 mg, 2.71 mmol) was added DMA (1.8 mL). The white suspension was stirred at ambient temperature for 30 minutes and then at 100° C. overnight. The reaction mixture was partitioned between water and DCM (20 mL each). The phases were separated, and the aqueous phase was extracted with DCM (2×10 mL). The combined organic phases were washed with brine (3×20 mL), dried (Na$_2$SO$_4$), filtered, and concentrated to a dark brownish oil. The crude was purified by silica chromatography (10-20% MeOH/DCM) to yield the product as beige solid (0.13 g, 51% yield). MS (apci) m/z=261.2 (M+H).

Intermediate Y7

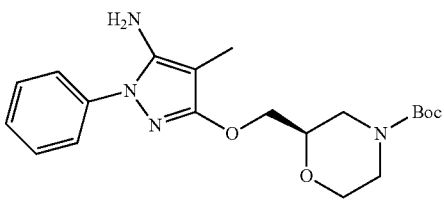 [SMILES: Cc1c(OC[C@H]2CN(C(=O)OC(C)(C)C)CCO2)nn(-c2ccccc2)c1N]

(R)-tert-butyl 2-(((5-amino-4-methyl-1-phenyl-1H-pyrazol-3-yl)oxy)methyl)morpholine-4-carboxylate Step A: Preparation of (R)-tert-butyl 2-(((methylsulfonyl)oxy)methyl)morpholine-4-carboxylate: To a solution of (R)-tert-butyl 2-(hydroxymethyl)morpholine-4-carboxylate (2.0 g, 9.205 mmol) and DIEA (2.084 mL, 11.97 mmol) in DCM (46 mL), cooled to 0° C., was added MsCl (0.819 mL, 10.59 mmol). The reaction mixture was allowed to warm slowly to ambient temperature over 2 hours, then was diluted with H$_2$O (50 mL), phases separated, and the aqueous phase extracted with DCM (2×25 mL). The combined organic phases were washed with brine (50 mL), dried (MgSO$_4$), filtered, and concentrated to give the product as a pale yellow oil (3.11 g, 114% yield). $^1$H NMR (CDCl3) δ 4.24 (d, 2H), 3.99-3.80 (m, 3H), 3.70 (m, 1H), 3.55 (m, 1H), 3.07 (s, 3H), 2.95 (m, 1H), 2.77 (m, 1H), 1.47 (s, 9H).

Step B: Preparation of (R)-tert-butyl 2-(((5-amino-4-methyl-1-phenyl-1H-pyrazol-3-yl)oxy)methyl)morpholine-4-carboxylate: To 5-amino-4-methyl-1-phenyl-1H-pyrazol-3(2H)-one (Intermediate 2, Step A, 640 mg, 3.386 mmol) were added DMA (7 mL), Cs$_2$CO$_3$ (2.21 g, 6.772 mmol), and (R)-tert-butyl 2-(((methylsulfonyl)oxy)methyl)morpholine-4-carboxylate (1.00 g, 3.386 mmol). The mixture was heated in a sealed pressure tube at 110° C. for 17 hours, then cooled to ambient temperature. The reaction mixture was partitioned between water (40 mL) and DCM (40 mL). The phases were separated, and the aqueous phase was extracted with DCM (2×25 mL) The combined organic phases were washed with brine (3×50 mL), dried (MgSO$_4$), filtered, and concentrated. The crude oil was purified by silica column chromatography, eluting with 0-50% acetone/hexanes, to afford the product as a thick amber syrup (871 mg, 66% yield). MS (apci) m/z=389.2 (M+H).

Intermediate Y8

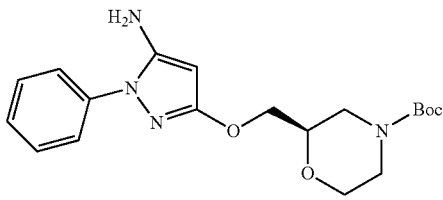 [SMILES: CC(C)(C)OC(=O)N1CCO[C@@H](COc2cc(N)n(-c3ccccc3)n2)C1]

(R)-tert-butyl 2-(((5-amino-1-phenyl-1H-pyrazol-3-yl)oxy)methyl)morpholine-4-carboxylate Prepared according to the procedure of Intermediate Y7, replacing 5-amino-4-methyl-1-phenyl-1H-pyrazol-3(2H)-one in Step B with 5-amino-1-phenyl-1H-pyrazol-3(2H)-one (Intermediate 203, Step A), to afford the product as a thick amber syrup (489 mg, 39% yield). MS (apci) m/z=375.2 (M+H).

Intermediate Y9

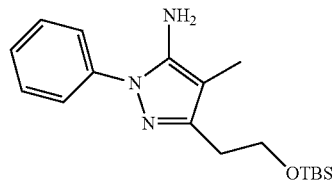 [SMILES: Cc1c(CCO[Si](C)(C)C(C)(C)C)nn(-c2ccccc2)c1N]

3-(2-(tert-butyldimethylsilyloxy)ethyl)-4-methyl-1-phenyl-1H-pyrazol-5-amine

To a solution of 2-(5-amino-4-methyl-1-phenyl-1H-pyrazol-3-yl)ethanol (Intermediate P127, 172 mg, 0.792 mmol) in DMF (1 mL) were added TBDMS-Cl (263 mg, 1.74 mmol), then imidazole (135 mg, 1.98 mmol). The reaction mixture was stirred at ambient temperature for 17 hours, then was diluted with H$_2$O (20 mL) and extracted with DCM (3×20 mL). The combined organic phases were washed with brine (20 mL), dried (MgSO$_4$), filtered and concentrated to afford the product as a pale brown syrup (249 mg, 95% yield). MS (apci) m/z=332.2 (M+H).

The table below provides a list of commercially available compounds that were used in the synthesis of intermediates and examples.

| Structure | Vendor/Catalog# | CAS# |
|---|---|---|
| 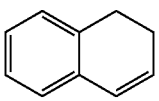 | Alfa Aesar/AAAL11430-06 | 447-53-0 |
| 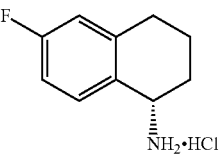 | J & W/20-0827S | Not available |
| 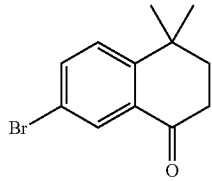 | CiVenti Chem/CV-1709 | 166978-46-7 |
| 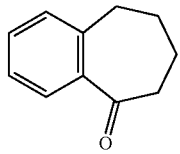 [SMILES: O=C1CCCCc2ccccc21] | Aldrich/B10587 | 826-73-3 |
| 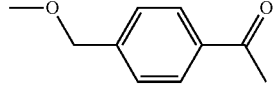 | NOVEL Chemical Solutions/AC0320 | Not available |
| 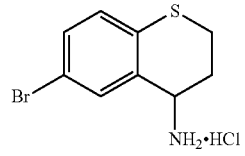 | Combi-Blocks, Inc./SS-0260 | 1170470-60-6 |
| 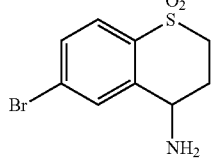 | Activate Scientific/AS2100M500 | Not available |
| 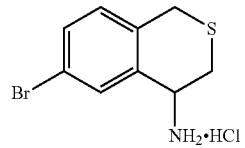 | Combi-Blocks, Inc./SS-0277 | Not available |
| 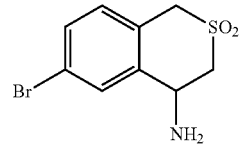 | Activate Scientific/AS2096M500 | Not available |

PREPARATION OF SYNTHETIC EXAMPLES

Example 1

1-(1',4-dimethyl-1-phenyl-1H,1'H-3,4'-bipyrazol-5-yl)-3-(1,2,3,4-tetrahydronaphthalen-1-yl)urea

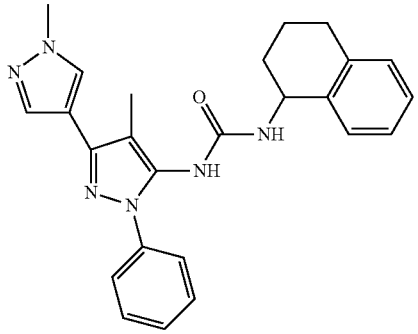 [SMILES: Cc1c(-c2cnn(C)c2)nn(-c2ccccc2)c1NC(=O)NC1CCCc2ccccc21]

1,2,3,4-tetrahydronaphthalen-1-amine (59.1 mg, 0.402 mmol), phenyl 1',4-dimethyl-1-phenyl-1H,1'H-3,4'-bipyrazol-5-ylcarbamate (Intermediate 13; 100 mg, 0.268 mmol) and DIEA (233 μL, 1.34 mmol) were combined in 0.2 mL of DMF and stirred at ambient temperature for 1 hour. The mixture was loaded onto a samplet and purified by reverse-phase column chromatography, eluting with 10-80% acetonitrile/water, to afford the title compound (71 mg, 0.166 mmol, 62.2% yield). (MS (apci) m/z=427.2 (M+H).

The compounds in Table 2 were prepared by reacting the appropriate amine from Table 1 with the appropriate intermediate phenylcarbamate using the method described for Example 1.

TABLE 2

| Example # | Structure | Name | MS (apci) m/z |
|---|---|---|---|
| 2 | 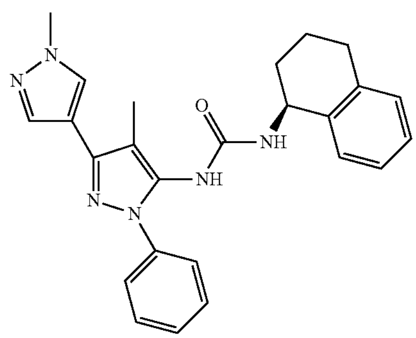 [SMILES: Cc1c(-c2cnn(C)c2)nn(-c2ccccc2)c1NC(=O)N[C@H]1CCCc2ccccc21] | (S)-1-(1',4-dimethyl-1-phenyl-1H,1'H-3,4'-bipyrazol-5-yl)-3-(1,2,3,4-tetrahydronaphthalen-1-yl)urea | 427.2 (M + H) |
| 3 | 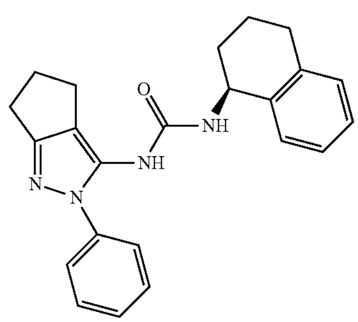 [SMILES: O=C(Nc1c2c(nn1-c1ccccc1)CCC2)N[C@H]1CCCc2ccccc21] | (S)-1-(2-phenyl-2,4,5,6-tetrahydrocyclopenta[c]pyrazol-3-yl)-3-(1,2,3,4-tetrahydronaphthalen-1-yl)urea | 373.2 (M + H) |
| 4 | 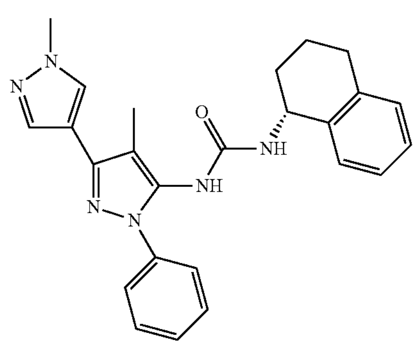 [SMILES: Cc1c(-c2cnn(C)c2)nn(-c2ccccc2)c1NC(=O)N[C@@H]1CCCc2ccccc21] | (R)-1-(1',4-dimethyl-1-phenyl-1H,1'H-3,4'-bipyrazol-5-yl)-3-(1,2,3,4-tetrahydronaphthalen-1-yl)urea | 427.2 (M + H) |

TABLE 2-continued

| Example # | Structure | Name | MS (apci) m/z |
|---|---|---|---|
| 5 | 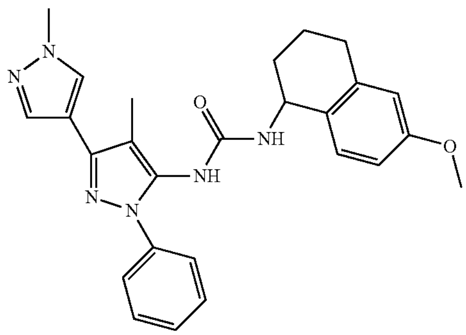 [SMILES: COc1ccc2c(c1)CCCC2NC(=O)Nc1c(C)c(-c2cnn(C)c2)nn1-c1ccccc1] | 1-(1',4-dimethyl-1-phenyl-1H,1'H-3,4'-bipyrazol-5-yl)-3-(6-methoxy-1,2,3,4-tetrahydronaphthalen-1-yl)urea | 457.2 (M + H) |
| 6 | 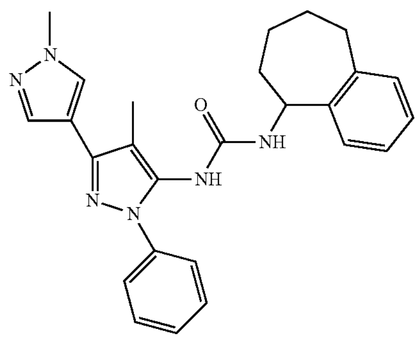 [SMILES: Cc1c(-c2cnn(C)c2)nn(-c2ccccc2)c1NC(=O)NC1CCCCc2ccccc21] | 1-(1',4-dimethyl-1-phenyl-1H,1'H-3,4'-bipyrazol-5-yl)-3-(6,7,8,9-tetrahydro-5H-benzo[7]annulen-5-yl)urea | 441.2 (M + H) |
| 7 | 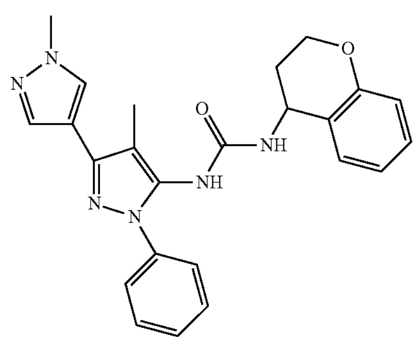 [SMILES: Cc1c(-c2cnn(C)c2)nn(-c2ccccc2)c1NC(=O)NC1CCOc2ccccc21] | 1-(chroman-4-yl)-3-(1',4-dimethyl-1-phenyl-1H,1'H-3,4'-bipyrazol-5-yl)urea | 429.2 (M + H) |
| 8 | 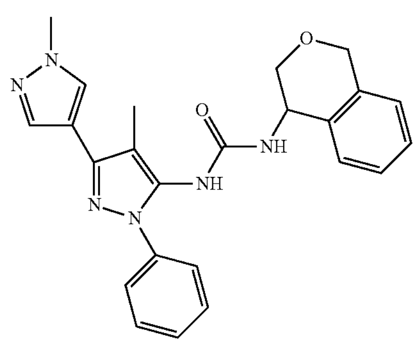 | 1-(1',4-dimethyl-1-phenyl-1H,1'H-3,4'-bipyrazol-5-yl)-3-(isochroman-4-yl)urea | 429.2 (M + H) |

TABLE 2-continued

| Example # | Structure | Name | MS (apci) m/z |
|---|---|---|---|
| 9 | 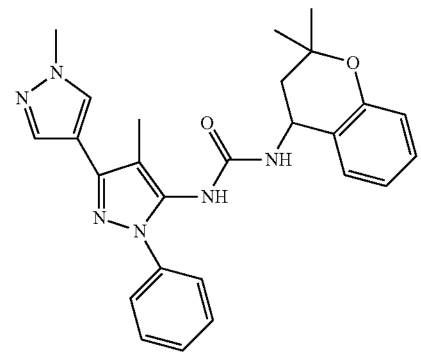 [SMILES: Cc1c(-c2cnn(C)c2)nn(-c2ccccc2)c1NC(=O)NC1CC(C)(C)Oc2ccccc21] | 1-(1',4-dimethyl-1-phenyl-1H,1'H-3,4'-bipyrazol-5-yl)-3-(2,2-dimethylchroman-4-yl)urea | 457.2 (M + H) |
| 10 | 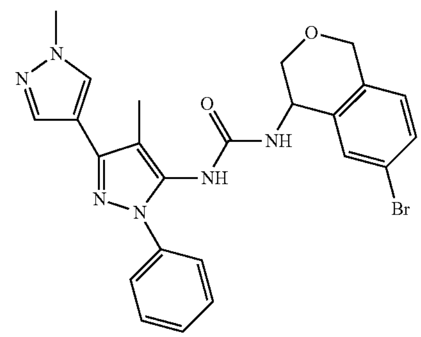 [SMILES: Cc1c(-c2cnn(C)c2)nn(-c2ccccc2)c1NC(=O)NC1COCc2ccc(Br)cc21] | 1-(6-bromoisochroman-4-yl)-3-(1',4-dimethyl-1-phenyl-1H,1'H-[3,4'-bipyrazol]-5-yl)urea | 507.1; 509.1 (M + H) |

Example 11

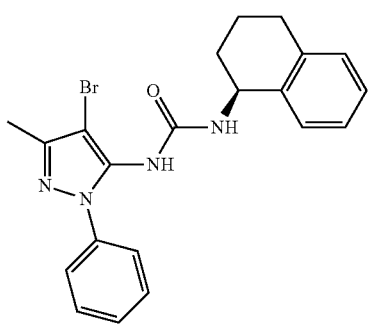 [SMILES: Cc1nn(-c2ccccc2)c(NC(=O)N[C@H]2CCCc3ccccc32)c1Br]

(S)-1-(4-bromo-3-methyl-1-phenyl-1H-pyrazol-5-yl)-3-(1,2,3,4-tetrahydronaphthalen-1-yl)urea Phenyl (3-methyl-1-phenyl-1H-pyrazol-5-yl)carbamate (Intermediate 1; 40 mg, 0.136 mmol) was dissolved in 1 mL of DCM and N-Bromosuccinimide (29.1 mg, 0.164 mmol) was added. (S)-1,2,3,4-tetrahydronaphthalen-1-amine (30.1 mg, 0.205 mmol) was added followed by DIEA (119 µL, 0.682 mmol). The reaction was stirred for 2 hours, concentrated and purified by reverse-phase column chromatography, eluting with 0-90% acetonitrile/water, to afford the title compound (56 mg, 0.132 mmol, 96.5% yield). (MS (apci) m/z=425.0; 427.0 (M+H).

Example 12

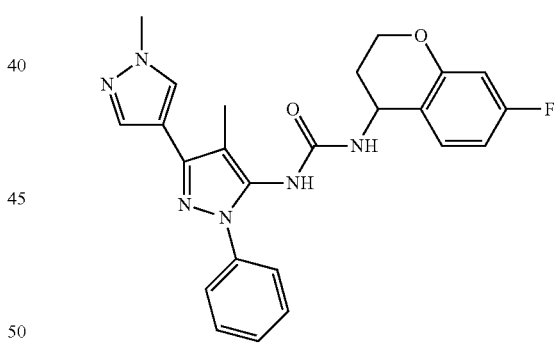

1-(1',4-dimethyl-1-phenyl-1H,1'H-[3,4'-bipyrazol]-5-yl)-3-(7-fluorochroman-4-yl)urea Step A: Preparation of 7-fluorochroman-4-one oxime. 7-fluorochroman-4-one (1.00 g, 6.02 mmol), hydroxylamine hydrochloride (0.627 g, 9.03 mmol) and NaOAc (0.741 g, 9.03 mmol) were combined in EtOH (40 mL) and heated at 100° C. in a sealed vessel overnight. The reaction was filtered through Celite® to afford the title compound as a 0.15M solution in EtOH (40 mL, 6.02 mmol). MS (apci) m/z=182.1 (M+H).

Step B: Preparation of 7-fluorochroman-4-amine. Zn dust (1970 mg, 30.1 mmol) was added to 7-fluorochroman-4-one oxime (solution in EtOH, 20056 µL, 3.01 mmol) and the reaction was stirred at ambient temperature for 4 hours. The reaction was filtered through Celite® and concentrated. The crude product was taken up in 1N HCl (20 ml) and washed with EtOAc (40 mL). The aqueous layer was adjusted to pH>10 with 2N NaOH and extracted with DCM (2×50 mL). The combined DCM extracts were dried (MgSO$_4$), filtered and concentrated to provide the title compound (488 mg, 2.92 mmol, 97.0% yield). MS (apci) m/z=151.1 (M+H—NH$_3$).

Step C: Preparation of 1-(1',4-dimethyl-1-phenyl-1H,1'H-[3,4'-bipyrazol]-5-yl)-3-(7-fluorochroman-4-yl)urea. Phenyl (1',4-dimethyl-1-phenyl-1H,1'H-[3,4'-bipyrazol]-5-yl)carbamate (25 mg, 0.0670 mmol), 7-fluorochroman-4-amine (16.8 mg, 0.100 mmol) and DIEA (117 μL, 0.670 mmol) were combined in 0.2 mL of DMF and stirred ambient temperature for 1 hour. The mixture was loaded onto a samplet and purified by reverse-phase column chromatography, eluting with 0-70% acetonitrile/water, to afford the title compound (19.5 mg, 0.0437 mmol, 65.2% yield). MS (apci) m/z=447.1 (M+H).

The compounds in Table 3 were prepared using the appropriate ketone from Table 1 according to the method as described for Example 12 and using the appropriate intermediate phenylcarbamate in Step C.

TABLE 3

| Example # | Structure | Name | MS (apci) m/z |
|---|---|---|---|
| 13 | 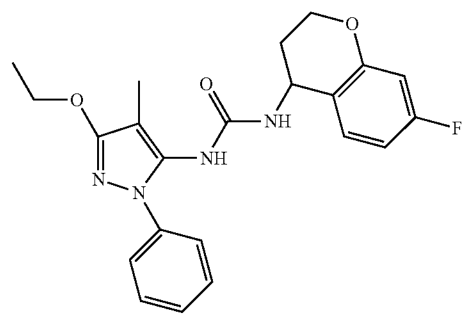 [SMILES: CCOc1nn(-c2ccccc2)c(NC(=O)NC2CCOc3cc(F)ccc32)c1C] | 1-(3-ethoxy-4-methyl-1-phenyl-1H-pyrazol-5-yl)-3-(7-fluorochroman-4-yl)urea | 411.2 (M + H) |
| 14 | 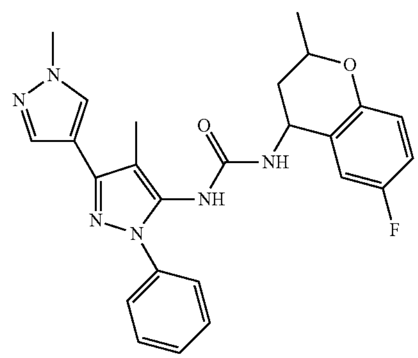 [SMILES: Cc1c(-c2cnn(C)c2)nn(-c2ccccc2)c1NC(=O)NC1CC(C)Oc2ccc(F)cc21] | 1-(1',4-dimethyl-1-phenyl-1H,1'H-[3,4'-bipyrazol]-5-yl)-3-(6-fluoro-2-methylchroman-4-yl)urea | 461.2 (M + H) |
| 15 | 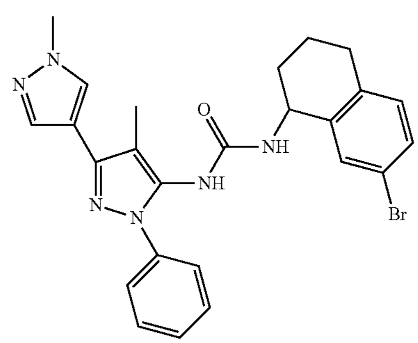 [SMILES: Cc1c(-c2cnn(C)c2)nn(-c2ccccc2)c1NC(=O)NC1CCCc2ccc(Br)cc21] | 1-(7-bromo-1,2,3,4-tetrahydronaphthalen-1-yl)-3-(1',4-dimethyl-1-phenyl-1H,1'H-[3,4'-bipyrazol]-5-yl)urea | 503.1; 505.0 (M − H) |

TABLE 3-continued

| Example # | Structure | Name | MS (apci) m/z |
|---|---|---|---|
| 16 | 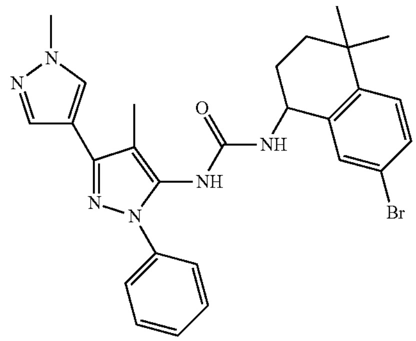 [SMILES: Cc1c(-c2cnn(C)c2)nn(-c2ccccc2)c1NC(=O)NC1CCC(C)(C)c2ccc(Br)cc21] | 1-(7-bromo-4,4-dimethyl-1,2,3,4-tetrahydronaphthalen-1-yl)-3-(1',4-dimethyl-1-phenyl-1H,1'H-[3,4'-bipyrazol]-5-yl)urea | 533.1; 535.1 (M + H) |

Example 17

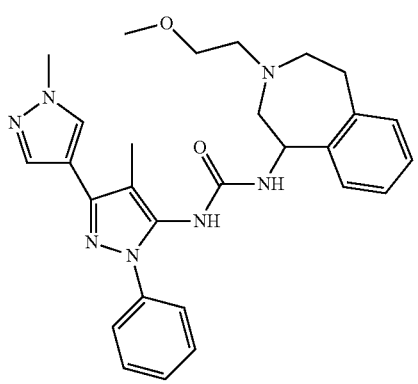 [SMILES: COCCN1CCc2ccccc2C(NC(=O)Nc2c(C)c(-c3cnn(C)c3)nn2-c2ccccc2)C1]

1-(1',4-dimethyl-1-phenyl-1H,1'H-3,4'-bipyrazol-5-yl)-3-(3-(2-methoxyethyl)-2,3,4,5-tetrahydro-1H-benzo[d]azepin-1-yl)urea Step A: Preparation of 1-(1',4-dimethyl-1-phenyl-1H,1H-3,4'-bipyrazol-5-yl)-3-(2-oxo-2,3,4,5-tetrahydro-1H-benzo[d]azepin-1-yl)urea. 1-Amino-4,5-dihydro-1H-benzo[d]azepin-2(3H)-one (260 mg, 1.47 mmol), phenyl 1',4-dimethyl-1-phenyl-1H,1'H-3,4'-bipyrazol-5-ylcarbamate (Intermediate 13; 500 mg, 1.34 mmol) and DIEA (1166 µL, 6.70 mmol) were combined in 0.2 mL of DMF and stirred ambient temperature for 2 hours. A thick white slurry formed. Water (2 mL) was added and the white solid was collected, washed with water (1 mL) and DCM (2×1 mL) and air-dried to afford the title compound (517 mg, 1.13 mmol, 84.8% yield). MS (apci) m/z=456.2 (M+H).

Step B: Preparation of 1-(1',4-dimethyl-1-phenyl-1H,1'H-3,4'-bipyrazol-5-yl)-3-(2,3,4,5-tetrahydro-1H-benzo[d]azepin-1-yl)urea. 1-(1',4-dimethyl-1-phenyl-1H,1'H-3,4'-bipyrazol-5-yl)-3-(2-oxo-2,3,4,5-tetrahydro-1H-benzo[d]azepin-1-yl)urea (100 mg, 0.2195 mmol) was dissolved in 5 mL of THF and a solution of LAH in THF (548.8 µL, 0.5488 mmol) was added dropwise. The reaction was stirred at ambient temperature overnight. Additional LAH (548.8 µL, 0.5488 mmol) was added and the reaction was stirred at ambient temperature for 24 hours. $Na_2SO_4 \cdot (10H_2O)$ (3537 mg, 10.98 mmol) was added and the reaction was stirred for 2 hours, filtered and concentrated. The crude product was by reverse-phase column chromatography, eluting with 0-70% acetonitrile/water, to afford the title compound (40 mg, 0.09059 mmol, 41.27% yield). MS (apci) m/z=442.2 (M+H).

Step C: Preparation of 1-(1',4-dimethyl-1-phenyl-1H,1'H-3,4'-bipyrazol-5-yl)-3-(3-(2-methoxyethyl)-2,3,4,5-tetrahydro-1H-benzo[d]azepin-1-yl)urea. 1-(1',4-dimethyl-1-phenyl-1H,1'H-3,4'-bipyrazol-5-yl)-3-(2,3,4,5-tetrahydro-1H-benzo[d]azepin-1-yl)urea (20.00 mg, 0.04530 mmol), 1-bromo-2-methoxyethane (18.89 mg, 0.1359 mmol) and DIEA (39.45 µl, 0.2265 mmol) were combined in 0.2 mL of DMF and stirred at ambient temperature overnight. The mixture was loaded onto a samplet and purified by reverse-phase column chromatography, eluting with 0-70% acetonitrile/water, to afford the title compound (6.3 mg, 0.01261 mmol, 27.84% yield). MS (apci) m/z=500.3 (M+H).

The compounds in Table 4 were prepared using the method as described for Example 17, Step C using the electrophile specified instead of 1-bromo-2-methoxyethane.

TABLE 4

| Ex. # | Electrophile | Structure | Name | MS (apci) m/z |
|---|---|---|---|---|
| 18 | F₃C⌒OTf | 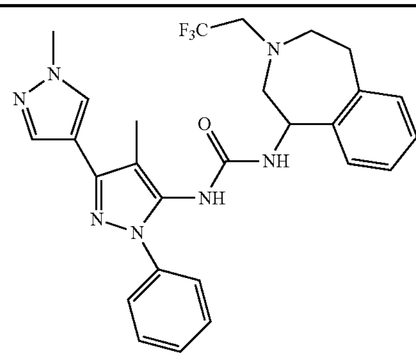 | 1-(1',4-dimethyl-1-phenyl-1H,1'H-3,4'-bipyrazol-5-yl)-3-(3-(2,2,2-trifluoroethyl)-2,3,4,5-tetrahydro-1H-benzo[d]azepin-1-yl)urea | 522.2 (M − H) |
| 19 | acetyl bromide | 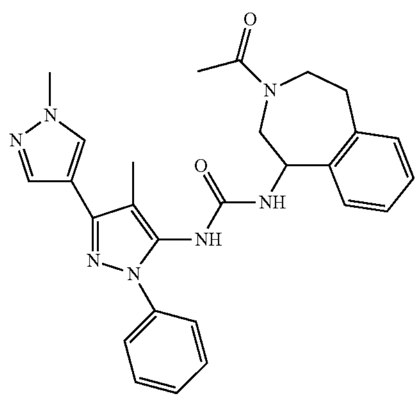 [SMILES: CC(=O)N1CCc2ccccc2C(NC(=O)Nc2c(C)c(-c3cnn(C)c3)nn2-c2ccccc2)C1] | 1-(3-acetyl-2,3,4,5-tetrahydro-1H-benzo[d]azepin-1-yl)-3-(1',4-dimethyl-1-phenyl-1H,1'H-3,4'-bipyrazol-5-yl)urea | 482.2 (M − H) |
| 20 | propionic anhydride | 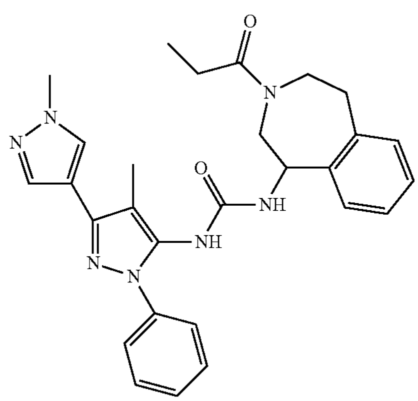 [SMILES: CCC(=O)N1CCc2ccccc2C(NC(=O)Nc2c(C)c(-c3cnn(C)c3)nn2-c2ccccc2)C1] | 1-(1',4-dimethyl-1-phenyl-1H,1'H-3,4'-bipyrazol-5-yl)-3-(3-propionyl-2,3,4,5-tetrahydro-1H-benzo[d]azepin-1-yl)urea | 498.2 (M + H) |

Example 21

(1-(1',4-dimethyl-1-phenyl-1H,1'H-3,4'-bipyrazol-5-yl)-3-(3-propyl-2,3,4,5-tetrahydro-1H-benzo[d]azepin-1-yl)urea 1-(1',4-dimethyl-1-phenyl-1H,1'H-3,4'-bipyrazol-5-yl)-3-(2,3,4,5-tetrahydro-1H-benzo[d]azepin-1-yl)urea (15.00 mg, 0.03397 mmol), propionaldehyde (9.866 mg, 0.1699 mmol) and NaBH(OAc)₃ (14.40 mg, 0.06795 mmol) were combined in 1 mL of DCM and stirred at ambient temperature for 3 days. Additional NaBH(OAc)₃ (14.40 mg, 0.06795 mmol) and 1 mL of THF were added and the reaction was stirred at ambient temperature overnight. NaOH (1N, 1 mL) and DCM (3 mL) were added and the reaction was agitated and filtered through a Phase Separator frit. The organic extract was concentrated and purified by reverse-phase column chromatography, eluting with 0-80% acetonitrile/ water, to afford the title compound (1.0 mg, 0.0021 mmol, 6.09% yield). (MS (apci) m/z=484.3 (M+H).

Example 22

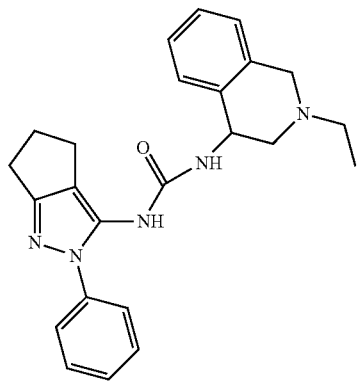 [SMILES: CCN1Cc2ccccc2C(NC(=O)Nc2c3c(nn2-c2ccccc2)CCC3)C1]

1-(2-ethyl-1,2,3,4-tetrahydroisoquinolin-4-yl)-3-(2-phenyl-2,4,5,6-tetrahydrocyclopenta[c]pyrazol-3-yl)urea Step A: Preparation of 2-(tert-butoxycarbonyl)-1,2,3,4-tetrahydroisoquinoline-4-carboxylic acid. 1,2,3,4-tetrahydroisoquinoline-4-carboxylic acid (530 mg, 2.99 mmol), Boc₂O (685 mg, 3.14 mmol) and NEt₃ (1251 µl, 8.97 mmol) were combined in DCM (20 mL) and stirred at ambient temperature overnight. The reaction was poured into 1N HCl (20 mL), the layers were separated and the aqueous layer was extracted with EtOAc (2×25 mL) The combined organic extracts were dried (MgSO₄) and concentrated to provide the title compound (830 mg, 2.99 mmol, 100% yield). MS (apci) m/z=178.1 (M+H-Boc).

Step B: Preparation of tert-butyl 4-(3-(2-phenyl-2,4,5,6-tetrahydrocyclopenta[c]pyrazol-3-yl)ureido)-3,4-dihydroisoquinoline-2(1H)-carboxylate. 2-(tert-butoxycarbonyl)-1,2,3,4-tetrahydroisoquinoline-4-carboxylic acid (325 mg, 1.17 mmol), NEt₃ (490 µL, 3.52 mmol), and diphenylphosphoryl azide (379 µL, 1.76 mmol) were combined in 2 mL of Toluene in a pressure tube and stirred at 80° C. for 30 minutes. The reaction was cooled and 2-phenyl-2,4,5,6-tetrahydrocyclopenta[c]pyrazol-3-amine (304 mg, 1.52 mmol) added. The reaction was stirred at 80° C. overnight, cooled, concentrated and purified by reverse-phase column chromatography, eluting with 0-70% acetonitrile/water, to afford the title compound (320 mg, 0.676 mmol, 57.7% yield). MS (apci) m/z=474.2 (M+H).

Step C: Preparation of 1-(2-phenyl-2,4,5,6-tetrahydrocyclopenta[c]pyrazol-3-yl)-3-(1,2,3,4-tetrahydroisoquinolin-4-yl)urea hydrochloride. Tert-butyl 4-(3-(2-phenyl-2,4,5,6-tetrahydrocyclopenta[c]pyrazol-3-yl)ureido)-3,4-dihydroisoquinoline-2(1H)-carboxylate (400 mg, 0.845 mmol) and HCl in IPA (507 µL, 2.53 mmol) were combined in 2 mL of DCM and stirred ambient temperature for 3 days. The mixture was concentrated to afford the title compound (320 mg, 0.781 mmol, 92.4% yield). MS (apci) m/z=374.2 (M+H).

Step D: Preparation of 1-(2-ethyl-1,2,3,4-tetrahydroisoquinolin-4-yl)-3-(2-phenyl-2,4,5,6-tetrahydrocyclopenta[c]pyrazol-3-yl)urea. 1-(2-phenyl-2,4,5,6-tetrahydrocyclopenta[c]pyrazol-3-yl)-3-(1,2,3,4-tetrahydroisoquinolin-4-yl)urea hydrochloride (15 mg, 0.037 mmol), iodoethane (17 mg, 0.11 mmol) and DIEA (32 µL, 0.18 mmol) were combined in 0.2 mL of DMF and stirred ambient temperature overnight. The mixture was loaded onto a samplet and purified by reverse-phase column chromatography, eluting with 0-70% acetonitrile/water, to afford the title compound (4.0 mg, 0.0100 mmol, 27% yield. MS (apci) m/z=402.2 (M+H).

Example 23

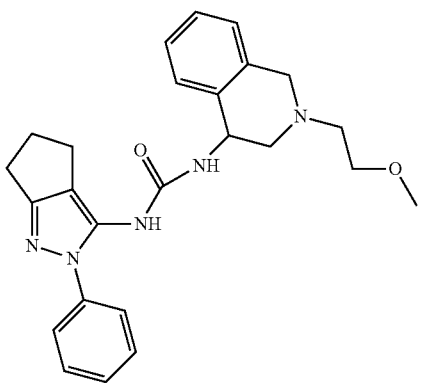 [SMILES: COCCN1Cc2ccccc2C(NC(=O)Nc2c3c(nn2-c2ccccc2)CCC3)C1]

1-(2-(2-methoxyethyl)-1,2,3,4-tetrahydroisoquinolin-4-yl)-3-(2-phenyl-2,4,5,6-tetrahydrocyclopenta[c]pyrazol-3-yl)urea Prepared by the method as described in Example 28, step D using 1-bromo-2-methoxyethane instead of iodoethane. The material was purified by reverse-phase column chromatography using 0-60% acetonitrile/H₂O as the eluent to provide the title compound (10.1 mg, 0.0234 mmol, 64.0% yield). MS (apci) m/z=432.2 (M+H).

Example 24

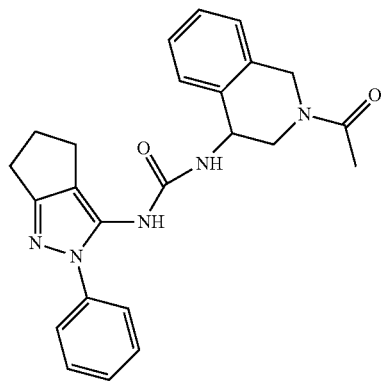 [SMILES: CC(=O)N1Cc2ccccc2C(NC(=O)Nc2c3c(nn2-c2ccccc2)CCC3)C1]

1-(2-acetyl-1,2,3,4-tetrahydroisoquinolin-4-yl)-3-(2-phenyl-2,4,5,6-tetrahydrocyclopenta[c]pyrazol-3-yl)urea 1-(2-phenyl-2,4,5,6-tetrahydrocyclopenta[c]pyrazol-3-yl)-3-(1,2,3,4-tetrahydroisoquinolin-4-yl)urea hydrochloride (20 mg, 0.049 mmol), Ac₂O (7.58 µL, 0.0803 mmol) and NEt₃ (7.46 µL, 0.0536 mmol) were combined in 2 mL of DCM and stirred ambient temperature for 1 hour. NaOH (1N, 3 mL) was added and the reaction was extracted with several portions of DCM in a phase separator frit and concentrated to provide the title compound (18.6 mg, 0.0448 mmol, 91.8% yield). MS (apci) m/z=416.2 (M+H).

Example 25

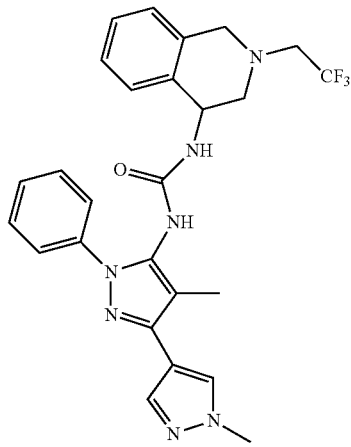 [SMILES: Cc1c(-c2cnn(C)c2)nn(-c2ccccc2)c1NC(=O)NC1CN(CC(F)(F)F)Cc2ccccc21]

1-(1',4-dimethyl-1-phenyl-1H,1'H-3,4'-bipyrazol-5-yl)-3-(2-(2,2,2-trifluoroethyl)-1,2,3,4-tetrahydroisoquinolin-4-yl)urea Step A: Preparation of 2-(2,2,2-trifluoroethyl)-1,2,3,4-tetrahydroisoquinolin-4-amine. 1,2,3,4-tetrahydroisoquinolin-4-amine dihydrochloride (660 mg, 2.98 mmol) was suspended in DMF (5 mL) and NEt₃ (437 μL, 3.13 mmol) added. The mixture was stirred for 4 hours and 2,2,2-trifluoroethyl trifluoromethanesulfonate (693 mg, 2.98 mmol) added. The mixture was stirred for 4 days, quenched with aqueous NaOH (4477 μL, 8.95 mmol) and extracted with several portions of EtOAc. The combined organic extracts were filtered through phase separator paper, concentrated and purified by reverse-phase column chromatography, eluting with 0-60% acetonitrile/water, to afford the title compound (2-(2,2,2-trifluoroethyl)-1,2,3,4-tetrahydroisoquinolin-4-amine (195 mg, 0.847 mmol, 28.4% yield). 1H NMR (CDCl₃) 7.32-7.39 (m, 1H), 7.15-7.26 (m, 2H), 7.00-7.06 (m, 1H), 3.91-4.04 (m, 2H), 3.78 (d, J=15 Hz, 1H), 3.14-3.25 (m, 2H), 2.91-3.09 (m, 2H), 1.71 (bs, 2H) ppm.

Step B: Preparation of 1-(1',4-dimethyl-1-phenyl-1H,1'H-3,4'-bipyrazol-5-yl)-3-(2-(2,2,2-trifluoroethyl)-1,2,3,4-tetrahydroisoquinolin-4-yl)urea. 2-(2,2,2-trifluoroethyl)-1,2,3,4-tetrahydroisoquinolin-4-amine (19 mg, 0.0825 mmol), phenyl 1',4-dimethyl-1-phenyl-1H,1'H-3,4'-bipyrazol-5-ylcarbamate (Intermediate 13; 28.0 mg, 0.0750 mmol) and NEt₃ (31.4 μL, 0.225 mmol) were combined in 0.2 mL of DMF and stirred ambient temperature for 2 hours. The mixture was loaded onto a samplet and purified by reverse-phase column chromatography, eluting with 10-80% acetonitrile/water, to afford the title compound (27.7 mg, 0.0544 mmol, 72.5% yield). MS (apci) m/z=510.2 (M+H).

The compounds in Table 5 were prepared using the method described for Example 25, Step C, using the appropriate intermediate phenylcarbamate instead of phenyl 1',4-dimethyl-1-phenyl-1H,1'H-3,4'-bipyrazol-5-ylcarbamate.

TABLE 5

| Ex. # | Structure | Name | MS (apci) m/z |
|---|---|---|---|
| 26 | 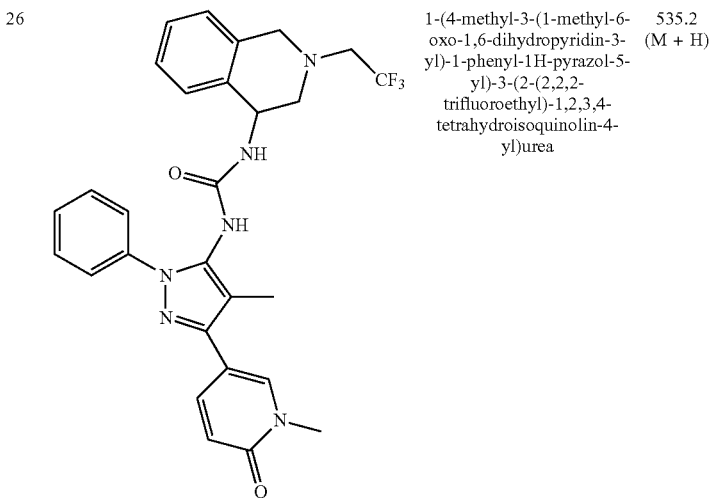 | 1-(4-methyl-3-(1-methyl-6-oxo-1,6-dihydropyridin-3-yl)-1-phenyl-1H-pyrazol-5-yl)-3-(2-(2,2,2-trifluoroethyl)-1,2,3,4-tetrahydroisoquinolin-4-yl)urea | 535.2 (M + H) |

TABLE 5-continued

| Ex. # | Structure | Name | MS (apci) m/z |
|---|---|---|---|
| 27 | 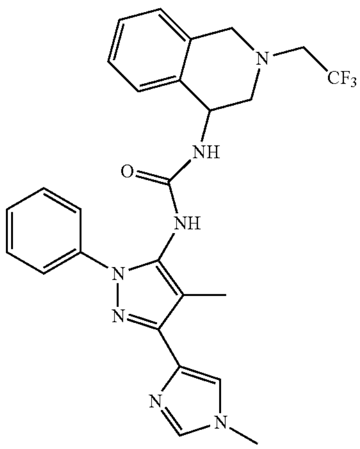 [SMILES: Cc1c(-c2cn(C)cn2)nn(-c2ccccc2)c1NC(=O)NC1CN(CC(F)(F)F)Cc2ccccc21] | 1-(4-methyl-3-(1-methyl-1H-imidazol-4-yl)-1-phenyl-1H-pyrazol-5-yl)-3-(2-(2,2,2-trifluoroethyl)-1,2,3,4-tetrahydroisoquinolin-4-yl)urea | 510.2 (M + H) |
| 28 | 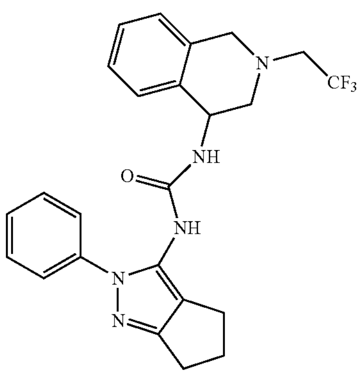 [SMILES: O=C(Nc1c2c(nn1-c1ccccc1)CCC2)NC1CN(CC(F)(F)F)Cc2ccccc21] | 1-(2-phenyl-2,4,5,6-tetrahydrocyclopenta[c]pyrazol-3-yl)-3-(2-(2,2,2-trifluoroethyl)-1,2,3,4-tetrahydroisoquinolin-4-yl)urea | 456.2 (M + H) |
| 29 | 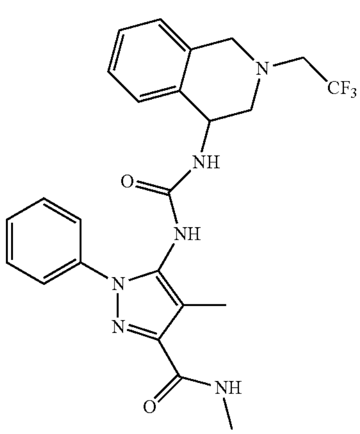 [SMILES: CNC(=O)c1nn(-c2ccccc2)c(NC(=O)NC2CN(CC(F)(F)F)Cc3ccccc32)c1C] | N,4-dimethyl-1-phenyl-5-(3-(2-(2,2,2-trifluoroethyl)-1,2,3,4-tetrahydroisoquinolin-4-yl)ureido)-1H-pyrazole-3-carboxamide | 485.2 (M − H) |

Example 30

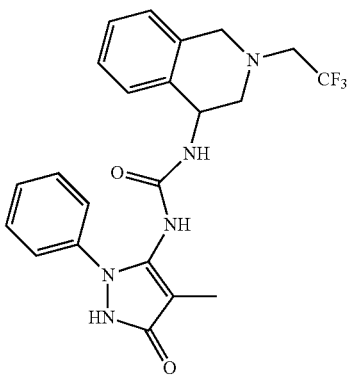 [SMILES: Cc1c(NC(=O)NC2CN(CC(F)(F)F)Cc3ccccc32)n(-c2ccccc2)[nH]c1=O]

1-(4-methyl-5-oxo-2-phenyl-2,5-dihydro-1H-pyrazol-3-yl)-3-(2-(2,2,2-trifluoroethyl)-1,2,3,4-tetrahydroisoquinolin-4-yl)urea CDI (360 mg, 2.22 mmol), 5-amino-4-methyl-1-phenyl-1H-pyrazol-3(2H)-one (350 mg, 1.85 mmol) and DIEA (805 μL, 4.62 mmol) were combined in 3 mL of DMF and stirred at ambient temperature overnight. Additional CDI (360 mg, 2.22 mmol) was added and the reaction stirred for 24 hours. A portion of the reaction mixture (365 μL; 0.182 mmol) was combined with NEt₃ (63.6 μL, 0.456 mmol) and 2-(2,2,2-trifluoroethyl)-1,2,3,4-tetrahydroisoquinolin-4-amine (35 mg, 0.152 mmol) in 0.1 mL of DMF, and the mixture was stirred ambient temperature for 2 hours. The mixture was loaded onto a samplet and purified by reverse-phase column chromatography using 0-60% acetonitrile/H₂O as the eluent to provide the title compound (59 mg, 0.132 mmol, 87.1% yield). MS (apci) m/z=446.2 (M+H).

Example 31

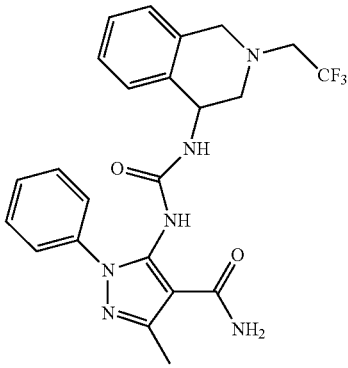 [SMILES: Cc1nn(-c2ccccc2)c(NC(=O)NC2CN(CC(F)(F)F)Cc3ccccc32)c1C(N)=O]

3-methyl-1-phenyl-5-(3-(2-(2,2,2-trifluoroethyl)-1,2,3,4-tetrahydroisoquinolin-4-yl)ureido)-1H-pyrazole-4-carboxamide Step A: Preparation of 1-(4-cyano-3-methyl-1-phenyl-1H-pyrazol-5-yl)-3-(2-(2,2,2-trifluoroethyl)-1,2,3,4-tetrahydroisoquinolin-4-yl)urea. 5-amino-3-methyl-1-phenyl-1H-pyrazole-4-carbonitrile (23.7 mg, 0.119 mmol), CDI (22.9 mg, 0.141 mmol) and NEt₃ (45.4 μL, 0.326 mmol) were combined in 0.2 mL of DMF and stirred ambient temperature overnight. 2-(2,2,2-trifluoroethyl)-1,2,3,4-tetrahydroisoquinolin-4-amine (25 mg, 0.109 mmol) was added and the reaction was stirred at ambient temperature for 2 hours. The mixture was loaded onto a samplet and purified by reverse-phase column chromatography using 0-80% acetonitrile/H₂O as the eluent to afford the title compound (38 mg, 0.084 mmol, 77.0% yield), which was used immediately in the next step. MS (apci) m/z=453.2 (M−H).

Step B: Preparation of 3-methyl-1-phenyl-5-(3-(2-(2,2,2-trifluoroethyl)-1,2,3,4-tetrahydroisoquinolin-4-yl)ureido)-1H-pyrazole-4-carboxamide. 1-(4-cyano-3-methyl-1-phenyl-1H-pyrazol-5-yl)-3-(2-(2,2,2-trifluoroethyl)-1,2,3,4-tetrahydroisoquinolin-4-yl)urea (35 mg, 0.07702 mmol), and aqueous concentrated HCl (390.01 mg, 3.8508 mmol) were combined and stirred at ambient temperature for 5 days. The reaction was poured into NaOH (aqueous, 3850.8 μL, 7.702 mmol) and ice (2 g) and extracted with several portions of 10% IPA/DCM in a phase separator frit. The combined organic extracts were concentrated and purified by reverse-phase column chromatography using 0-80% acetonitrile/H₂O as the eluent to provide the title compound (5.3 mg, 0.0112 mmol, 14.6% yield). MS (apci) m/z=471.2 (M−H).

Example 32

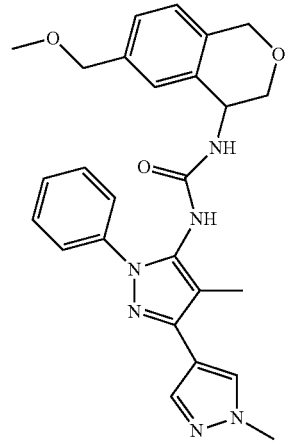 [SMILES: COCc1ccc2c(c1)C(NC(=O)Nc1c(C)c(-c3cnn(C)c3)nn1-c1ccccc1)COC2]

1-(1',4-dimethyl-1-phenyl-1H,1'H-[3,4'-bipyrazol]-5-yl)-3-(6-(methoxymethyl)isochroman-4-yl)urea Potassium methoxymethyltrifluoroborate (12 mg, 0.079 mmol), 1-(6-bromoisochroman-4-yl)-3-(1',4-dimethyl-1-phenyl-1H,1'H-[3,4'-bipyrazol]-5-yl)urea (20 mg, 0.039 mmol), Dichloro[1,1'-bis(diphenylphosphino)ferrocene]palladium (II) dichloromethane adduct (6.4 mg, 0.0079 mmol) and Cs₂CO₃ (64 mg, 0.20 mmol) were combined in dioxane (2 mL) and water (0.5 mL) in a pressure tube and degassed by bubbling N₂ through the mixture for 10 minutes, The reaction was sealed and heated at 100° C. for 16 hours, cooled, poured into brine (10 mL), and extracted with EtOAc (2×10 mL). The combined organic extracts were concentrated and purified by reverse-phase column chromatography using 0-70% acetonitrile/H₂O as the eluent to provide the title compound (9.8 mg, 0.021 mmol, 53% yield). MS (apci) m/z=473.2 (M+H).

Example 33

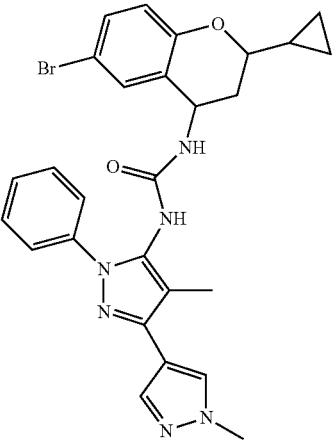 [SMILES: Cc1c(-c2cnn(C)c2)nn(-c2ccccc2)c1NC(=O)NC1CC(C2CC2)Oc2ccc(Br)cc21]

1-(6-bromo-2-cyclopropylchroman-4-yl)-3-(1',4-dimethyl-1-phenyl-1H,1'H-[3,4'-bipyrazo]-5-yl)urea Step A: Preparation of 6-bromo-2-cyclopropylchroman-4-one. 1-(5-bromo-2-hydroxyphenyl)ethanone (2.0 g, 9.3 mmol), cyclopropanecarbaldehyde (0.78 g, 11 mmol), and pyrrolidine (0.78 mL, 9.3 mmol) were combined in CH₃CN (20 mL), and stirred at ambient temperature for 18 hours. The mixture was concentrated and diluted with diethyl ether (50 mL) and aqueous 1N HCl (20 mL). The phases were separated and the organic phase was washed with aqueous 1N NaOH (20 mL), then brine (200 mL), dried (MgSO₄), filtered, and concentrated. The crude product was purified by silica gel column chromatography using 5-20% EtOAc/hexanes as the eluent to afford the title compound (1.7 g, 6.4 mmol, 68% yield). MS (apci) m/z=264.9; 266.9 (M−H).

Step B: Preparation of 1-(6-bromo-2-cyclopropylchroman-4-yl)-3-(1',4-dimethyl-1-phenyl-1H,1'H-[3,4'-bipyrazol]-5-yl)urea. Prepared using 6-bromo-2-cyclopropylchroman-4-one according to the procedure described in Example 12, Steps A-C. The final compound was purified by reverse-phase column chromatography using 0-80% acetonitrile/H₂O as the eluent to provide the title compound as a mixture of diastereomers (85 mg, 0.1553 mmol, 23.8% yield for three steps). MS (apci) m/z=545.1; 547.2 (M−H).

Example 34

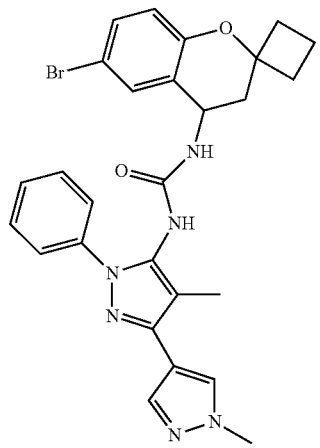 [SMILES: Cc1c(-c2cnn(C)c2)nn(-c2ccccc2)c1NC(=O)NC1CC2(CCC2)Oc2ccc(Br)cc21]

1-(6-bromospiro[chroman-2,1'-cyclobutan]-4-yl)-3-(1',4-dimethyl-1-phenyl-1H,1'H-[3,4'-bipyrazol]-5-yl)urea Step A: Preparation of 6-bromospiro[chroman-2,1'-cyclobutan]-4-one. A solution of 1-(5-bromo-2-hydroxyphenyl)ethanone (20 g, 93.00 mmol), cyclobutanone (27.80 mL, 372.0 mmol) and pyrrolidine (8.540 mL, 102.3 mmol) in toluene (150 mL, 93.00 mmol) was heated at reflux overnight. The reaction was partitioned between EtOAc and 2 N HCl, the aqueous layer was washed with EtOAc, and the combined organic extracts were washed with brine, dried (Na₂SO₄) and concentrated. The crude product was purified by silica gel column chromatography using 1-15% EtOAc/hexanes as the eluent to afford the title compound (14.04 g, 52.56 mmol, 56.5% yield) as a yellow solid. MS (apci) m/z=266.0; 268.0 (M+).

Step B: Preparation 1-(6-bromospiro[chroman-2,1'-cyclobutan]-4-yl)-3-(1',4-dimethyl-1-phenyl-1H,1'H-[3,4'-bipyrazol]-5-yl)urea. Prepared from 6-bromo-2-cyclopropylchroman-4-one according to the procedure described in Example 12, Steps A-C. The final compound was purified by reverse-phase column chromatography using 0-80% acetonitrile/H₂O as the eluent to provide the title compound (99 mg, 0.1808 mmol, 20.0% yield for three steps). MS (apci) m/z=545.2; 547.2 (M−H).

Example 35A and 35B

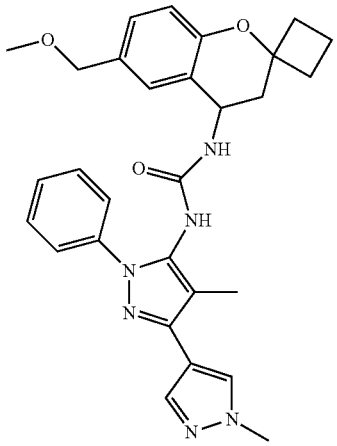

211

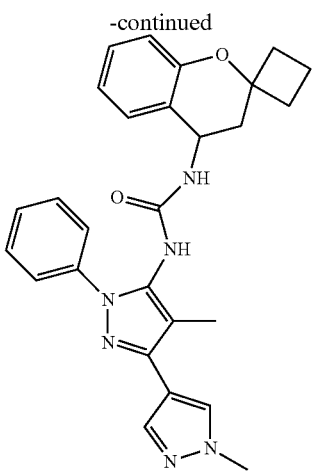

1-(1',4-dimethyl-1-phenyl-1H,1'H-[3,4'-bipyrazol]-5-yl)-3-(6-(methoxymethyl)spiro[chroman-2,1'-cyclobutan]-4-yl)urea and 1-(1',4-dimethyl-1-phenyl-1H,1'H-[3,4'-bipyrazol]-5-yl)-3-(spiro[chroman-2,1'-cyclobutan]-4-yl)urea Potassium methoxymethyltrifluoroborate (18 mg, 0.12 mmol), 1-(6-bromospiro[chroman-2,1'-cyclobutan]-4-yl)-3-(1',4-dimethyl-1-phenyl-1H,1'H-[3,4'-bipyrazol]-5-yl)urea (Example 34; 33 mg, 0.060 mmol), dichloro[1,1'-bis(diphenylphosphino)-ferrocene]palladium (II) dichloromethane adduct (9.8 mg, 0.012 mmol) and $Cs_2CO_3$ (98 mg, 0.30 mmol) were combined in dioxane (2 mL) and water (0.5 mL) and degassed by bubbling N2 through the mixture for 10 minutes, The reaction was then sealed in a glass tube and heated at 100° C. for 3 hours. The reaction was cooled, poured into brine (10 mL) and extracted with EtOAc (2×10 mL). The combined organic extracts were concentrated and purified by reverse-phase column chromatography using 0-70% acetonitrile/$H_2O$ as the eluent to provide the title compounds: 1-(1',4-dimethyl-1-phenyl-1H,1'H-[3,4'-bipyrazol]-5-yl)-3-(6-(methoxymethyl)spiro[chroman-2,1'-cyclobutan]-4-yl)urea [second peak, 2.8 mg, 0.0055 mmol, 9.1% yield, MS (apci) m/z=513.3 (M+H)] and 1-(1',4-dimethyl-1-phenyl-1H,1'H-[3,4'-bipyrazol]-5-yl)-3-(spiro[chroman-2,1'-cyclobutan]-4-yl)urea [first peak, 2.50 mg, 0.0053 mmol, 8.8% yield, MS (apci) m/z=469.2 (M+H)].

Example 36

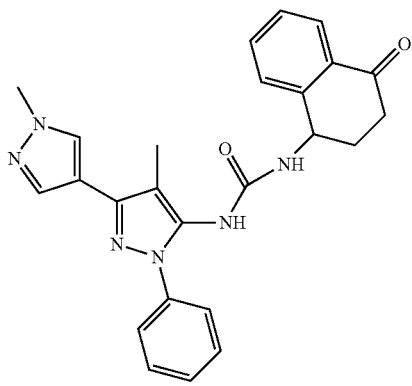 [SMILES: Cc1c(-c2cnn(C)c2)nn(-c2ccccc2)c1NC(=O)NC1CCC(=O)c2ccccc21]

212

1-(1',4-dimethyl-1-phenyl-1H,1'H-[3,4'-bipyrazol]-5-yl)-3-(4-oxo-1,2,3,4-tetrahydronaphthalen-1-yl)urea 4-Oxo-1,2,3,4-tetrahydronaphthalene-1-carboxylic acid (50 mg, 0.263 mmol), 1',4-dimethyl-1-phenyl-1H,1'H-[3,4'-bipyrazol]-5-amine (Intermediate 12; 66.6 mg, 0.263 mmol), $NEt_3$ (110 µL, 0.789 mmol) and diphenylphosphoryl azide (85.0 µL, 0.394 mmol) were combined in 2 mL of toluene in a sealed pressure tube and stirred at 80° C. overnight. The reaction was cooled, concentrated and purified by reverse-phase column chromatography using 0-60% acetonitrile/$H_2O$ as the eluent to provide the title compound (68 mg, 0.154 mmol, 58.7% yield). MS (apci) m/z=441.2 (M+H).

Example 37

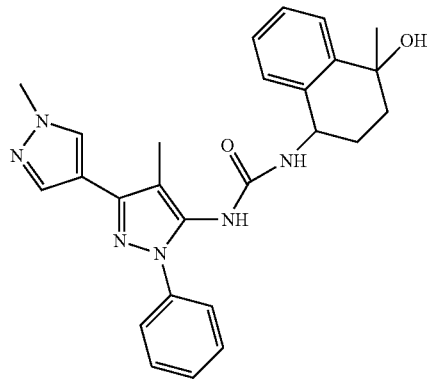 [SMILES: Cc1c(-c2cnn(C)c2)nn(-c2ccccc2)c1NC(=O)NC1CCC(C)(O)c2ccccc21]

1-(1',4-dimethyl-1-phenyl-1H,1'H-[3,4'-bipyrazol]-5-yl)-3-(4-hydroxy-4-methyl-1,2,3,4-tetrahydronaphthalen-1-yl)urea 1-(1',4-dimethyl-1-phenyl-1H,1'H-[3,4'-bipyrazol]-5-yl)-3-(4-oxo-1,2,3,4-tetrahydronaphthalen-1-yl)urea (20 mg, 0.0454 mmol) was dissolved in 5 mL of THF and the solution cooled to 0° C. MeMgBr in THF (81.1 µL, 0.114 mmol) was added and the reaction was allowed to warm to ambient temperature over 2 hours. Additional MeMgBr in THF (81.1 µL, 0.114 mmol) was added and the reaction stirred at ambient temperature for 1 hours. The reaction was quenched with water and extracted with several portions of EtOAc. The combined organic extracts were filtered through phase separator paper, concentrated and purified by silica gel column chromatography using 5-100% acetone/hexanes as the eluent to afford the title compound (4.4 mg, 0.00964 mmol, 21.2% yield). MS (apci) m/z=457.2 (M+H).

Example 38

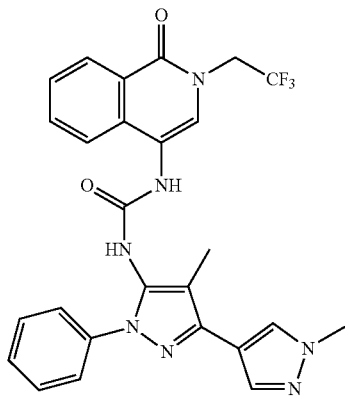 [SMILES: Cc1c(-c2cnn(C)c2)nn(-c2ccccc2)c1NC(=O)Nc1cn(CC(F)(F)F)c(=O)c2ccccc12]

1-(1',4-dimethyl-1-phenyl-1H,1'H-[3,4'-bipyrazol]-5-yl)-3-(1-oxo-2-(2,2,2-trifluoroethyl)-1,2-dihydroisoquinolin-4-yl)urea Step A: Preparation of 4-nitro-2-(2,2,2-trifluoroethyl)isoquinolin-1(2H)-one. 4-Nitroisoquinolin-1(2H)-one (50 mg, 0.26 mmol), 2,2,2-trifluoroethyl trifluoromethanesulfonate (79 mg, 0.34 mmol) and $K_2CO_3$ (182 mg, 1.3 mmol) were combined in 0.2 mL of DMF and stirred at ambient temperature for 2 hours. The mixture was filtered, loaded onto a samplet, and purified by reverse-phase column chromatography eluting with 0-80% acetonitrile/water to afford the title compound (63 mg, 0.23 mmol, 88% yield) as a white solid. $^1$H NMR (CDCl$_3$) 8.66-8.71 (m, 1H), 8.57 (s, 1H), 8.49-8.54 (m, 1H), 7.87-7.94 (m, 1H), 7.66-7.72 (m, 1H), 4.73-4.82 (m, 2H).

Step B: Preparation of 4-amino-2-(2,2,2-trifluoroethyl)isoquinolin-1(2H)-one. 4-nitro-2-(2,2,2-trifluoroethyl)isoquinolin-1(2H)-one (5.00 mg, 0.0184 mmol) was dissolved in MeOH (0.5 mL) and aqueous saturated NH$_4$Cl (0.2 mL) was added followed by Zn dust (6.01 mg, 0.0919 mmol). The reaction was stirred at ambient temperature overnight, filtered, and extracted with several portions of DCM in a phase separator frit. The combined DCM extracts were concentrated to provide the title compound (4.00 mg, 0.0165 mmol, 89.9% yield). MS (apci) m/z=243.1 (M+H).

Step C: Preparation of 1-(1',4-dimethyl-1-phenyl-1H,1'H-[3,4'-bipyrazol]-5-yl)-3-(1-oxo-2-(2,2,2-trifluoroethyl)-1,2-dihydroisoquinolin-4-yl)urea. 4-Amino-2-(2,2,2-trifluoroethyl)isoquinolin-1(2H)-one (2.60 mg, 0.0107 mmol), phenyl (1',4-dimethyl-1-phenyl-1H,1'H-[3,4'-bipyrazol]-5-yl)carbamate (4.01 mg, 0.0107 mmol) and NEt$_3$ (4.49 μL, 0.0322 mmol) were combined in 0.2 mL of DMF and stirred at ambient temperature for 2 hours. The mixture was loaded onto a samplet and purified by reverse-phase column chromatography, eluting with 0-70% acetonitrile/water, to afford the title compound (2.63 mg, 0.00504 mmol, 47.0% yield). MS (apci) m/z=522.2 (M+H).

Example 39

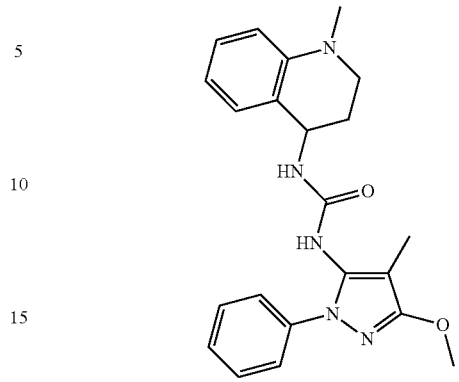

1-(3-methoxy-4-methyl-1-phenyl-1H-pyrazol-5-yl)-3-(1-methyl-1,2,3,4-tetrahydroquinolin-4-yl)urea Step A: Preparation of tert-butyl (1-methyl-1,2,3,4-tetrahydroquinolin-4-yl)carbamate: To a solution of tert-butyl (1,2,3,4-tetrahydroquinolin-4-yl)carbamate (250 mg, 1.01 mmol) and DIEA (526 μL, 3.02 mmol) in dry DMF (2.0 mL) was added methyl iodide (66.1 μL, 1.06 mmol). The mixture was stirred at ambient temperature for 7 hours. Additional methyl iodide (33 μL) was added and the mixture was stirred for an additional 16 hours. The mixture was diluted with H$_2$O (6 mL) and extracted with Et$_2$O (3×). The combined extracts were washed with H$_2$O (2×) and Brine, dried (MgSO$_4$) and filtered through a SiO$_2$ plug (Et$_2$O elution). The eluent was concentrated and the residual colorless syrup was purified on a SiO$_2$ column (CH$_2$Cl$_2$ elution) to provide the title compound as a colorless film (150 mg, 57% yield). $^1$H NMR (CDCl$_3$) δ 7.16 (dd, J=18.4, 8.7 Hz, 2H), 6.66 (t, J=7.4 Hz, 1H), 6.61 (d, J=8.3 Hz, 1H), 4.78 (br s, 1H), 4.74 (br s, 1H), 3.21 (t, J=5.7 Hz, 2H), 2.90 (s, 3H), 2.06, (m, 2H), 1.47 (s, 9H) ppm.

Step B: Preparation of 1-methyl-1,2,3,4-tetrahydroquinolin-4-amine dihydrochloride: To a solution of tert-butyl (1-methyl-1,2,3,4-tetrahydroquinolin-4-yl)carbamate (145 mg, 0.553 mmol) in EtOAc (4 mL) was added 4M HCl (2.07 mL, 8.29 mmol) in dioxane and the mixture was stirred at ambient temperature for 2.5 hours. The resulting white suspension was diluted with Et$_2$O (6 mL) and the solid collected via vacuum filtration. The solid was washed with Et$_2$O and dried under vacuum to afford the title compound as a white solid (100 mg, 77% yield). $^1$H NMR (CD$_3$OD) δ 7.47-7.38 (m, 2H), 7.18-7.05 (m, 2H), 4.62 (unresolved, 1H), 3.60-3.48 (m, 2H), 3.13 (s, 3H), 2.51-2.41 (m, 1H), 2.33-2.24 (m, 1H) ppm.

Step C: Preparation of 1-(3-methoxy-4-methyl-1-phenyl-1H-pyrazol-5-yl)-3-(1-methyl-1,2,3,4-tetrahydroquinolin-4-yl)urea: To a mixture of phenyl (3-methoxy-4-methyl-1-phenyl-1H-pyrazol-5-yl)carbamate (32.3 mg, 0.100 mmol) and 1-methyl-1,2,3,4-tetrahydroquinolin-4-amine dihydrochloride (28.2 mg, 0.120 mmol) in dry CH$_2$Cl$_2$ (0.4 mL) was added DIEA (69.7 μL, 0.400 mmol) and the resulting solution was stirred at ambient temperature for 5 hours. The reaction mixture was diluted with CH$_2$Cl$_2$ (3 mL) and washed sequentially with H$_2$O, 1M NaOH (2×) and H$_2$O. The organic phase was dried (Na$_2$SO$_4$) and passed through a short SiO$_2$ column eluting with CH$_2$Cl$_2$, then 50% EtOAc-hexanes. The 50% EtOAc-hexanes pool was concentrated and the residual white solid was dried under vacuum to provide the title compound (34 mg, 87% yield). $^1$H NMR (DMSO$_6$) δ 7.81 (s, 1H), 7.49 (d, J=8.3 Hz, 2H), 7.43 (t, J=7.3 Hz, 2H), 7.26 (t, J=7.3 Hz, 1H), 7.07 (t, J=7.4 Hz, 1H), 6.97 (d, J=8.2 Hz, 1H), 6.66 (d, J=8.2 Hz, 1H), 6.59 (app. dd, J=12.8, 7.4 Hz, 2H), 4.71 (dd, J=13.5, 5.6 Hz, 1H), 3.86 (s, 3H), 3.23-3.10 (m, 2H), 2.83 (s, 3H), 1.94-1.81 (m, 2H), 1.78 (s, 3H) ppm.

Example 40

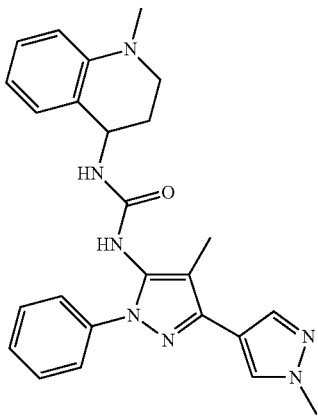 [SMILES: Cc1c(-c2cnn(C)c2)nn(-c2ccccc2)c1NC(=O)NC1CCN(C)c2ccccc21]

1-(1',4-dimethyl-1-phenyl-1H,1'H-[3,4'-bipyrazol]-5-yl)-3-(1-methyl-1,2,3,4-tetrahydroquinolin-4-yl)urea To a mixture of phenyl (1',4-dimethyl-1-phenyl-1H,1'H-[3,4'-bipyrazol]-5-yl)carbamate (Intermediate 13; 37.3 mg, 0.100 mmol) and 1-methyl-1,2,3,4-tetrahydroquinolin-4-amine dihydrochloride (28.2 mg, 0.120 mmol) in dry CH$_2$Cl$_2$ (0.4 mL) was added DIEA (69.7 μL, 0.400 mmol) and the resulting solution was stirred at ambient temperature for 5 hours. The reaction mixture was diluted with CH$_2$Cl$_2$ (3 mL) and washed sequentially with H$_2$O, 1M NaOH (2×) and H$_2$O. The organic phase was dried (Na$_2$SO$_4$) and passed through a short SiO$_2$ column eluting with CH$_2$Cl$_2$, 50% EtOAc-hexanes, then EtOAc. The EtOAc pool was concentrated and the residual white solid dried under vacuum to furnish the title compound (42 mg, 95% yield). MS (apci) m/z=442.2 (M+H).

Example 41

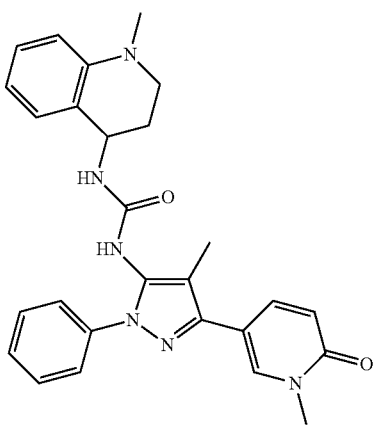 [SMILES: Cc1c(-c2ccc(=O)n(C)c2)nn(-c2ccccc2)c1NC(=O)NC1CCN(C)c2ccccc21]

1-(1-methyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea To a mixture of phenyl (4-methyl-3-(1-methyl-6-oxo-1,6-dihydropyridin-3-yl)-1-phenyl-1H-pyrazol-5-yl)carbamate (Intermediate 8; 20.0 mg, 0.050 mmol) and 1-methyl-1,2,3,4-tetrahydroquinolin-4-amine dihydrochloride (14.1 mg, 0.060 mmol) in dry CH$_2$Cl$_2$ (0.4 mL) was added DIEA (34.8 μL, 0.200 mmol) and the resulting solution was stirred at ambient temperature for 4.5 hours. The reaction mixture was diluted with CH$_2$Cl$_2$ (2 mL) and washed sequentially with H$_2$O, 1M NaOH (2×) and H$_2$O. The organic phase was dried (Na$_2$SO$_4$) and passed through a short SiO$_2$ column eluting with CH$_2$Cl$_2$, EtOAc then 5% MeOH/EtOAc. The 5% MeOH/EtOAc pool was concentrated and the residual solid washed with Et$_2$O and dried under vacuum to furnish the title compound as a white solid (17 mg, 73% yield). MS (apci) m/z=467.2 (M−H).

Example 42

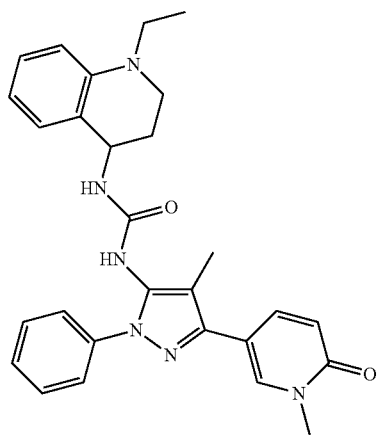 [SMILES: CCN1CCC(NC(=O)Nc2c(C)c(-c3ccc(=O)n(C)c3)nn2-c2ccccc2)c2ccccc21]

1-(1-ethyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea Step A: Preparation of tert-butyl (1-ethyl-1,2,3,4-tetrahydroquinolin-4-yl)carbamate: To a solution of tert-butyl (1,2,3,4-tetrahydroquinolin-4-yl)carbamate (250 mg, 1.01 mmol) and DIEA (526 μL, 3.02 mmol) in dry DMF (2.0 mL) was added ethyl iodide (121 μL, 1.50 mmol) and the mixture was stirred at ambient temperature for 5 hours. The mixture was heated at 50° C. for 16 hours and additional ethyl iodide (50.0 μL was added. The mixture was heated at 70° C. for 5 hours and was cooled to ambient temperature. The mixture was diluted with H$_2$O (12 mL) and extracted with Et$_2$O (3×). The combined extracts were washed with H$_2$O (2×) and Brine, dried (MgSO$_4$) and filtered through a SiO$_2$ plug (Et$_2$O elution). The eluent was concentrated and the residual colorless syrup was dried under vacuum to provide the title compound (264 mg, 95% yield). $^1$H NMR (CDCl$_3$) δ 7.17 (d, J=7.5 Hz, 1H), 7.12 (t, J=7.6 Hz, 1H), 6.61 (t, J=7.5 Hz, 2H), 4.73 (unresolved, 2H), 3.44-3.28 (m, 2H), 3.28-3.17 (m, 2H), 2.06-1.99, (m, 2H), 1.47 (s, 9H), 1.13 (t, J=7.1 Hz, 3H) ppm.

Step B: Preparation of 1-ethyl-1,2,3,4-tetrahydroquinolin-4-amine dihydrochloride: To a solution of tert-butyl (1-ethyl-1,2,3,4-tetrahydroquinolin-4-yl)carbamate (264 mg, 0.955 mmol) in EtOAc (3 mL) was added 4M HCl (3.58 mL, 14.3 mmol) in dioxane and the mixture was stirred at ambient temperature for 2 hours. The resulting white suspension was diluted with Et$_2$O (8 mL) and the solid collected via vacuum filtration. The solid was washed with Et$_2$O and dried under vacuum to afford the title compound as a white solid (222 mg, 93% yield). $^1$H NMR (CD$_3$OD) δ 7.68-7.59 (m, 1H), 7.57-7.50 (m, 1H), 7.47-7.36 (m, 2H), 4.78-4.72 (m, 1H), 3.80-3.60 (m, 4H), 2.67-2.56 (m, 1H), 2.41-2.30 (m, 1H), 1.40 (m, 3H) ppm.

Step C: Preparation of 1-(1-ethyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea: The title compound was prepared utilizing 1-ethyl-1,2,3,4-tetrahydroquinolin-4-amine dihydrochloride instead of 1-methyl-1,2,3,4-tetrahydroquinolin-4-amine dihydrochloride according to the procedure describe in Example 41. The compound was isolated as a white solid (25.0 mg, 83% yield). MS (apci) m/z=483.2 (M+H).

Example 43

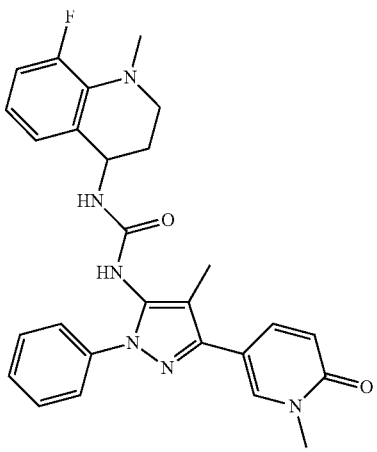 [SMILES: Cc1c(-c2ccc(=O)n(C)c2)nn(-c2ccccc2)c1NC(=O)NC1CCN(C)c2c(F)cccc21]

1-(8-fluoro-1-methyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea Step A: Preparation of 8-fluoro-2,3-dihydroquinolin-4(1H)-one oxime: To a mixture of 8-fluoro-2,3-dihydroquinolin-4(1H)-one (300 mg, 1.82 mmol) and hydroxylamine hydrochloride (379 mg, 5.45 mmol) in absolute EtOH (18 mL) was added pyridine (294 μL, 3.63 mmol) and the mixture was heated at reflux for 16 hours. The mixture was cooled to ambient temperature and concentrated. The residual oily solid was treated with H$_2$O and the mixture extracted with CH$_2$Cl$_2$ (3×). The combined organic extracts were washed with H$_2$O, dried over Na$_2$SO$_4$ and passed through a SiO$_2$ plug (eluting with CH$_2$Cl$_2$ and then 25% EtOAc-hexanes for elution). The eluent was concentrated to give a cloudy film that was washed with hexanes and dried under vacuum to provide the title compound as a white solid (245 mg, 75% yield). MS (apci) m/z=181.1 (M+H).

Step B: Preparation of 8-fluoro-1,2,3,4-tetrahydroquinolin-4-amine: A solution of 8-fluoro-2,3-dihydroquinolin-4 (1H)-one oxime (225 mg, 1.25 mmol) in MeOH (5 mL) was cooled to 0° C. and Zn dust (<10 micron, 408.2 mg, 6.24 mmol) was added in one portion. Saturated NH$_4$Cl (1.0 mL) was added over 2 minutes and the mixture was stirred for 5 minutes. The mixture was allowed to reach ambient temperature and was stirred for 6 hours. The mixture was filtered through packed Celite® (MeOH for rinse and elution) and concentrated to a colorless syrup. The syrup was treated with 1M K$_2$CO$_3$ (5 mL) and extracted with EtOAc (3×). The combined extracts were dried over MgSO$_4$, filtered through packed Celite® and concentrated to provide the title compound as a colorless syrup that was dried under vacuum (183 mg, 88% yield). $^1$H NMR (CDCl$_3$) δ 6.99 (d, J=7.4 Hz, 1H), 6.84 (dd, J=11.3, 8.0 Hz, 1H), 6.56 (app dt, J=8.0, 5.2 Hz, 1H), 4.14 (br s, 1H), 4.03 (t, J=4.8 Hz, 1H), 3.46-3.33 (m, 2H), 2.06-1.98 (m, 1H), 1.88-1.81 (m, 1H), 1.56 (br s, 2H) ppm.

Step C: Preparation of tert-butyl (8-fluoro-1,2,3,4-tetrahydroquinolin-4-yl)carbamate: A solution of 8-fluoro-1,2,3,4-tetrahydroquinolin-4-amine (180 mg, 1.08 mmol) in THF (3 mL) was cooled to 0° C. and Boc$_2$O (244 mg, 1.08 mmol) was added in one portion. The mixture was stirred for 15 minutes then at ambient temperature for 2 hours. The mixture was concentrated to a colorless syrup that was dried under vacuum for 16 hours. The syrup was dissolved in Et$_2$O and eluted through a SiO$_2$ plug eluting with Et$_2$O. The eluent was concentrated and the residual colorless film was dried under vacuum to provide the title compound as a white foam (289 mg, 100% yield). $^1$H NMR (CDCl$_3$) δ 6.98 (d, J=7.7 Hz, 1H), 6.86 (dd, J=11.0, 8.0 Hz, 1H), 6.56 (app dt, J=7.9, 5.3 Hz, 1H), 4.84 (unresolved, 1H), 4.74 (unresolved, 1H), 4.13 (br s, 1H), 3.43-3.36 (m, 1H), 3.34-2.26 (m, 1H), 2.05 (q, J=5.4 Hz, 2H), 1.47 (s, 9H) ppm.

Step D: Preparation of tert-butyl (8-fluoro-1-methyl-1,2,3,4-tetrahydroquinolin-4-yl)carbamate: To a solution of tert-butyl (8-fluoro-1,2,3,4-tetrahydroquinolin-4-yl)carbamate (288 mg, 1.08 mmol) and DIEA (565 μL, 3.24 mmol) in dry DMA (4 mL) was added methyl iodide (101 μL, 1.62 mmol) and the mixture stirred at ambient temperature for 5 hours. Additional methyl iodide (101 μL, 1.62 mmol) was added and the mixture heated at 50° C. for 6 hours. The reaction mixture was cooled to ambient temperature and was diluted with H$_2$O (25 mL). The mixture was extracted with Et$_2$O (3×) and the combined organic extracts were washed with H$_2$O (2×) and saturated NaCl. The organic portion was dried over MgSO$_4$/activated carbon and eluted through a SiO$_2$ plug (Et$_2$O elution). The eluent was concentrated to provide the title compound as a white solid after drying under vacuum (100 mg, 33% yield). $^1$H NMR (CDCl$_3$) δ 7.00 (d, J=7.7 Hz, 1H), 6.89 (dd, J=11.0, 8.0 Hz, 1H), 6.68 (app dt, J=7.9, 5.3 Hz, 1H), 4.84 (unresolved, 1H), 4.74 (br s, 2H), 3.18-3.08 (m, 2H), 2.98 (s, 3H), 2.06-1.95 (m, 2H), 1.47 (s, 9H) ppm.

Step E: Preparation of 8-fluoro-1-methyl-1,2,3,4-tetrahydroquinolin-4-amine dihydrochloride: To a solution of tert-butyl (8-fluoro-1-methyl-1,2,3,4-tetrahydroquinolin-4-yl) carbamate (45.0 mg, 0.161 mmol) in EtOAc (0.6 mL) was added 4M HCl (602 μL, 2.41 mmol) in dioxane and the mixture was stirred at ambient temperature for 3 hours. The resulting white suspension was diluted with Et$_2$O (5 mL) and the solid collected via vacuum filtration. The solid was washed with Et$_2$O and dried under vacuum to afford the title compound as an ivory white solid (39 mg, 96% yield). MS (apci) m/z=181.1 (M+H).

Step F: 1-(8-fluoro-1-methyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea: The title compound was prepared utilizing 8-fluoro-1-methyl-1,2,3,4-tetrahydroquinolin-4-amine dihydrochloride instead of 1-methyl-1,2,3,4-tetrahydroquinolin-4-amine dihydrochloride in the preparation outlined for Example 41. The compound was isolated as a white solid (18 mg, 59% yield). MS (apci) m/z=487.2 (M+H).

Example 44

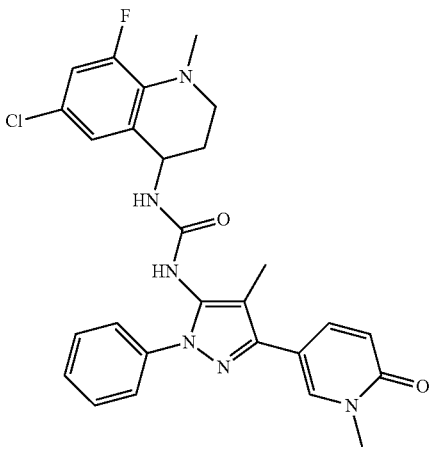 [SMILES: Cc1c(-c2ccc(=O)n(C)c2)nn(-c2ccccc2)c1NC(=O)NC1CCN(C)c2c(F)cc(Cl)cc21]

1-(6-chloro-8-fluoro-1-methyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea Step A: Preparation of tert-butyl (6-chloro-8-fluoro-1-methyl-1,2,3,4-tetrahydroquinolin-4-yl)carbamate: A solution of tert-butyl (8-fluoro-1-methyl-1,2,3,4-tetrahydroquinolin-4-yl)carbamate (45.0 mg, 0.160 mmol) in CH₃CN (1.6 mL) was cooled to 0° C. and N-chlorosuccinimide (23.6 mg, 0.177 mmol) was added in one portion. The mixture was stirred for 4 hours during which time the temperature rose to ambient after 1 hour. The mixture was treated with pyridin-1-ium 4-methylbenzenesulfonate (PPTS) (4.03 mg, 0.016 mmol) and was heated at 45° C. for 20 hours. The reaction mixture was added to half-saturated NaHCO₃ (4 mL) and mixed. The mixture was extracted with CH₂Cl₂ (3×) and the combined extracts washed with H₂O (2×) and dried over Na₂SO₄/activated carbon. The dried solution was filtered through a SiO₂ plug (CH₂Cl₂ elution) and concentrated. The residue was dried under vacuum to afford the title compound as a light yellow solid (30 mg, 59% yield). MS (apci) m/z=315.1 (M+H).

Step B: Preparation of 6-chloro-8-fluoro-1-methyl-1,2,3,4-tetrahydroquinolin-4-amine dihydrochloride: To a solution of tert-butyl (6-chloro-8-fluoro-1-methyl-1,2,3,4-tetrahydroquinolin-4-yl)carbamate (29.0 mg, 0.083 mmol) in EtOAc (1.0 mL) was added 4M HCl (1.04 µL, 4.15 mmol) in dioxane and the mixture was stirred at ambient temperature for 16 hours. The resulting white suspension was diluted with Et₂O (5 mL) and the solid collected via vacuum filtration. The solid was washed with Et₂O and dried under vacuum to afford the title compound as a white solid (18 mg, 75% yield). ¹H NMR (CD₃OD) δ 7.19-7.14 (m, 2H), 4.51 (m, 1H), 3.31 (s, 3H), 3.10-3.08 (m, 2H), 2.29-2.19 (m, 1H), 2.18-2.09 (m, 1H) ppm.

Step C: Preparation of 1-(6-chloro-8-fluoro-1-methyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea: Prepared according to the method of Example 41, using 6-chloro-8-fluoro-1-methyl-1,2,3,4-tetrahydroquinolin-4-amine dihydrochloride instead of 1-methyl-1,2,3,4-tetrahydroquinolin-4-amine dihydrochloride. The title compound was obtained as a white solid (16 mg, 56% yield). MS (apci) m/z=519.2 (M−H).

Example 45

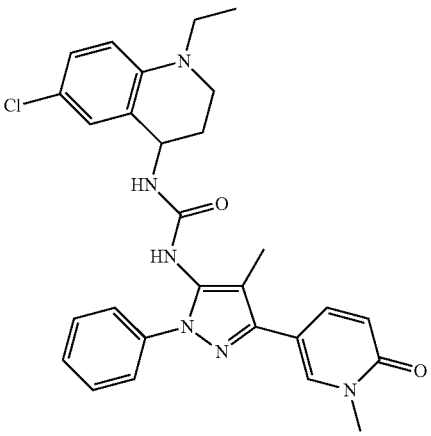 [SMILES: CCN1CCC(NC(=O)Nc2c(C)c(-c3ccc(=O)n(C)c3)nn2-c2ccccc2)c2cc(Cl)ccc21]

1-(6-chloro-1-ethyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea Step A: Preparation of tert-butyl (6-chloro-1-ethyl-1,2,3,4-tetrahydroquinolin-4-yl)carbamate: A solution of tert-butyl (1-ethyl-1,2,3,4-tetrahydroquinolin-4-yl)carbamate (165 mg, 0.597 mmol) in dry CH₃CN (3 mL) was cooled to 0° C. and N-chlorosuccinimide (85.4 mg, 0.627 mmol) was added in one portion. The mixture was stirred for 6 hours during which time the temperature rose to ambient after 1 hour. The reaction mixture was treated with saturated NaHCO₃ (4 mL) and H₂O (4 mL) and mixed. The mixture was extracted with Et₂O (3×) and the combined extracts were washed with H₂O (2×), saturated NaCl and dried over MgSO₄/activated carbon. The dried solution was filtered through a SiO₂ plug (Et₂O elution) and concentrated. The residue was purified on a SiO₂ column (25%, 50%, 100% CH₂Cl₂-hexanes step gradient) to provide the title compound as a white solid (70 mg, 38% yield). ¹H NMR (CDCl₃) δ 7.13 (s, 1H), 7.05 (d, J=8.8 Hz, 1H), 6.52 (d, J=8.8 Hz, 1H), 4.70 (unresolved, 2H), 3.42-3.24 (m, 2H), 3.23 (dd, J=5.4, 5.4 Hz, 2H), 2.01 (dd, J=10.6, 4.7 Hz, 2H), 1.48 (s, 9H), 1.12 (t, J=7.1 Hz, 3H) ppm.

Step B: Preparation of 6-chloro-1-ethyl-1,2,3,4-tetrahydroquinolin-4-amine dihydrochloride: To a solution of tert-butyl (6-chloro-1-ethyl-1,2,3,4-tetrahydroquinolin-4-yl)carbamate (69.0 mg, 0.220 mmol) in dry EtOAc (2.0 mL) was added 4M HCl (1.67 mL, 6.68 mmol) in dioxane and the mixture was stirred at ambient temperature for 4 hours. The mixture was treated with additional 4M HCl (1.67 mL, 6.68 mmol) in dioxane and MeOH (0.5 mL) and stirred for 1 hour. The mixture was concentrated to a clear glass that was treated with Et₂O and agitated until fine white suspension formed. The solid was allowed to settle, the solvent decanted and the residual solid washed with Et₂O (2×). The solid was dried under vacuum to furnish the title compound as a white solid (56 mg, 89% yield). MS (apci) m/z=194.1 (M-NH₂).

Step C: Preparation of 1-(6-chloro-1-ethyl-1,2,3,4-tetrahydroquinolin-4-yl)-3-(4-methyl-3-(1-methyl-6-oxo-1,6-dihydropyridin-3-yl)-1-phenyl-1H-pyrazol-5-yl)urea: The title compound was prepared utilizing 6-chloro-1-ethyl-1,2,3,4-tetrahydroquinolin-4-amine dihydrochloride instead of 1-methyl-1,2,3,4-tetrahydroquinolin-4-amine dihydrochloride in the preparation outlined for Example 41. The compound was isolated as a white solid (16 mg, 62% yield). MS (apci) m/z=515.2 (M-H).

Example 46

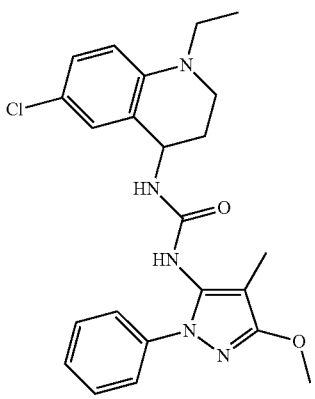 [SMILES: CCN1CCC(NC(=O)Nc2c(C)c(OC)nn2-c2ccccc2)c2cc(Cl)ccc21]

1-(6-chloro-1-ethyl-1,2,3,4-tetrahydroquinolin-4-yl)-3-(3-methoxy-4-methyl-1-phenyl-1H-pyrazol-5-yl) urea The title compound was prepared utilizing 6-chloro-1-ethyl-1,2,3,4-tetrahydroquinolin-4-amine dihydrochloride instead of 1-methyl-1,2,3,4-tetrahydroquinolin-4-amine dihydrochloride of in the preparation outlined for Example 39, Step C. The compound was isolated as a white solid (20 mg, 98% yield). MS (apci) m/z=440.1 (M+H).

Example 47

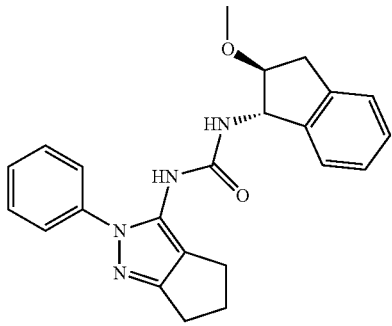 [SMILES: CO[C@H]1Cc2ccccc2[C@@H]1NC(=O)Nc1c2c(nn1-c1ccccc1)CCC2]

1-((1S,2S)-2-methoxy-2,3-dihydro-1H-inden-1-yl)-3-(2-phenyl-2,4,5,6-tetrahydrocyclopenta[c]pyrazol-3-yl)urea Step A: Preparation of tert-butyl ((1S,2S)-2-hydroxy-2,3-dihydro-1H-inden-1-yl)carbamate: To a turbid suspension of (1S,2S)-1-amino-2,3-dihydro-1H-inden-2-ol (140 mg, 0.938 mmol) in DCM (4.7 mL, 0.938 mmol) was added triethylamine (262 µL, 1.88 mmol), followed by Boc₂O (215 mg, 0.985 mmol) in one portion at ambient temperature. The reaction was stirred for 2 days, filtered (GF/F paper), rinsed with DCM and concentrated. The crude product was purified by silica gel chromatography (3:1 hexanes/EtOAc) to yield the product as white solid (200 mg, 86% yield). ¹H NMR (CDCl₃) δ 7.20-7.26 (m, 4 H), 5.05 (br s, 1 H), 4.88-4.92 (m, 1 H), 4.38-4.45 (m, 1 H), 4.29 (br s, 1 H), 3.25-3.31 (m, 1 H), 2.88-2.94 (m, 1 H), 1.50 (s, 9 H) ppm.

Step B: Preparation of tert-butyl ((1S,2S)-2-methoxy-2,3-dihydro-1H-inden-1-yl)carbamate: A mixture of tert-butyl (1S,2S)-2-hydroxy-2,3-dihydro-1H-inden-1-ylcarbamate (50 mg, 0.20 mmol), barium oxide (369 mg, 2.4 mmol), Ba(OH)₂ (206 mg, 1.2 mmol) and CH₃I (28 mg, 0.20 mmol) in DMF (1.34 mL) was stirred at ambient temperature overnight. The reaction mixture was poured into saturated NaHCO₃ (15 mL), and the aqueous mixture was extracted with DCM (3×20 mL). The combined organic extracts were washed with water (3×15 mL), dried (Na₂SO₄), filtered and concentrated. The crude product was purified by silica gel chromatography (20% EtOAc/hexanes) to yield the product as white waxy solid (17 mg, 32% yield). ¹H NMR (CDCl₃) δ 7.18-7.30 (m, 4 H), 5.08 (m, 1 H), 4.72 (m, 1 H), 3.93-3.98 (m, 1 H), 3.50 (s, 3 H), 3.24-3.30 (m, 1 H), 2.83-2.88 (m, 1 H), 1.49 (s, 9 H) ppm.

Step C: Preparation of 1-((1S,2S)-2-methoxy-2,3-dihydro-1H-inden-1-yl)-3-(2-phenyl-2,4,5,6-tetrahydrocyclopenta[c]pyrazol-3-yl)urea: A solution of tert-butyl (1S,2S)-2-methoxy-2,3-dihydro-1H-inden-1-ylcarbamate (15.9 mg, 0.0604 mmol) in hydrogen chloride (5-6 N in Isopropyl alcohol, 604 µL, 3.02 mmol) was stirred at ambient temperature for 1 hour. After removal of the solvent under vacuum, the white solid residue was taken up in DMA (302 µL), followed by addition of phenyl 2-phenyl-2,4,5,6-tetrahydrocyclopenta[c]pyrazol-3-ylcarbamate (19.3 mg, 0.0604 mmol) and DIEA (52.6 µL, 0.302 mmol), and the reaction was stirred at ambient temperature for 20 minutes. The reaction mixture was directly purified by reverse-phase chromatography (5 to 60% acetonitrile/water) to yield the product as white solid (6 mg, 26% yield). MS (apci) m/z=389.1 (M+H).

Example 48

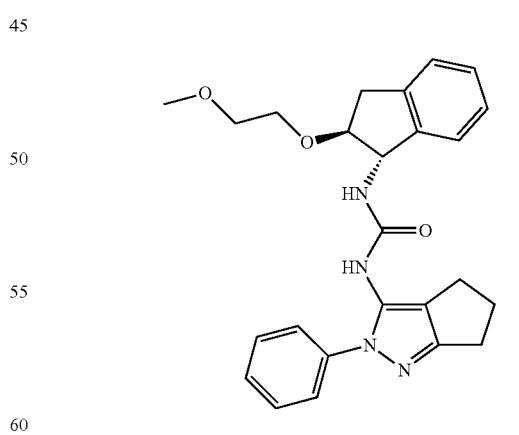

1-((1S,2S)-2-(2-methoxyethoxy)-2,3-dihydro-1H-inden-1-yl)-3-(2-phenyl-2,4,5,6-tetrahydrocyclopenta[c]pyrazol-3-yl)urea Step A: Preparation of tert-butyl ((1S,2S)-2-(2-methoxyethoxy)-2,3-dihydro-1H-inden-1-yl)carbamate: A mixture of tert-butyl (1S,2S)-2-hydroxy-2,3-dihydro-1H-inden-1-yl-carbamate (50 mg, 0.20 mmol), barium oxide (369 mg, 2.4 mmol), Ba(OH)$_2$ (206 mg, 1.2 mmol) and 1-bromo-2-methoxyethane (28 mg, 0.20 mmol) in DMF (1.3 mL) was stirred at ambient temperature overnight. The reaction mixture was filtered (GF/F paper), rinsed with acetonitrile, concentrated and directly purified by reverse-phase chromatography (5 to 60% acetonitrile/water) to yield the product as white solid (14 mg, 23% yield). $^1$H NMR (CDCl$_3$) δ 7.16-7.29 (m, 4 H), 5.08 (m, 1 H), 4.74-4.76 (m, 1 H), 4.08-4.12 (m, 1 H), 3.87-3.92 (m, 1 H), 3.73-3.79 (m, 1 H), 3.55-3.59 (m, 2 H), 3.38 (s, 3 H), 3.24-3.30 (m, 1 H), 2.90-2.95 (m, 1 H), 1.48 (s, 9 H) ppm.

Step B: Preparation of 1-((1S,2S)-2-(2-methoxyethoxy)-2,3-dihydro-1H-inden-1-yl)-3-(2-phenyl-2,4,5,6-tetrahydrocyclopenta[c]pyrazol-3-yl)urea: A solution of tert-butyl (1S,2S)-2-(2-methoxyethoxy)-2,3-dihydro-1H-inden-1-ylcarbamate (14 mg, 0.046 mmol) in hydrogen chloride (455 μL, 2.3 mmol) [5-6 N, IPA] was stirred at ambient temperature for 10 minutes, then concentrated under reduced pressure. The white solid residue was taken up in DMA (228 μL), followed by addition of phenyl 2-phenyl-2,4,5,6-tetrahydrocyclopenta[c]pyrazol-3-ylcarbamate (15 mg, 0.046 mmol) and DIEA (40 μL, 0.23 mmol). The reaction was stirred at ambient temperature for 1 hour, and directly purified by reverse-phase chromatography (5 to 60% acetonitrile/water) to yield the product as white solid (15 mg, 76% yield). MS (apci) m/z=433.2 (M+H).

Example 49

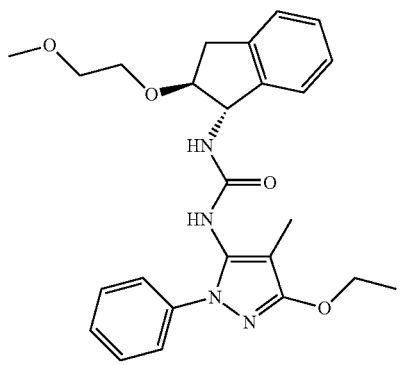 [SMILES: CCOc1nn(-c2ccccc2)c(NC(=O)N[C@H]2c3ccccc3C[C@@H]2OCCOC)c1C]

1-(3-ethoxy-4-methyl-1-phenyl-1H-pyrazol-5-yl)-3-((1S,2S)-2-(2-methoxyethoxy)-2,3-dihydro-1H-inden-1-yl)urea To a turbid solution of (1S,2S)-2-(2-methoxyethoxy)-2,3-dihydro-1H-inden-1-amine hydrochloride (30 mg, 0.12 mmol) and phenyl 3-ethoxy-4-methyl-1-phenyl-1H-pyrazol-5-ylcarbamate (39 mg, 0.12 mmol) in DMA (410 μL) was added DIEA (107 μL, 0.62 mmol) to obtain a clear solution, and the reaction was stirred at ambient temperature for 30 minutes. The reaction mixture was directly purified by reverse-phase chromatography (5 to 70% acetonitrile/water) to yield the product as white solid (27 mg, 49% yield). MS (apci) m/z=451.2 (M+H).

Example 50

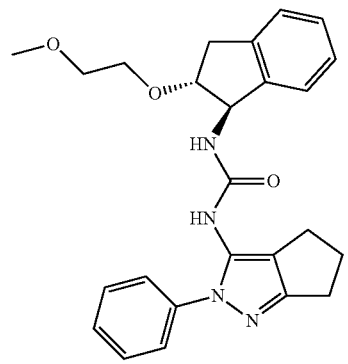 [SMILES: COCCO[C@@H]1Cc2ccccc2[C@H]1NC(=O)Nc1c2c(nn1-c1ccccc1)CCC2]

1-((1R,2R)-2-(2-methoxyethoxy)-2,3-dihydro-1H-inden-1-yl)-3-(2-phenyl-2,4,5,6-tetrahydrocyclopenta[c]pyrazol-3-yl)urea The title product was prepared as described for Example 48, using (1R,2R)-1-amino-2,3-dihydro-1H-inden-2-ol instead of (1S,2S)-1-amino-2,3-dihydro-1H-inden-2-ol in the initial step. MS (apci) m/z=433.2 (M+H).

Example 51

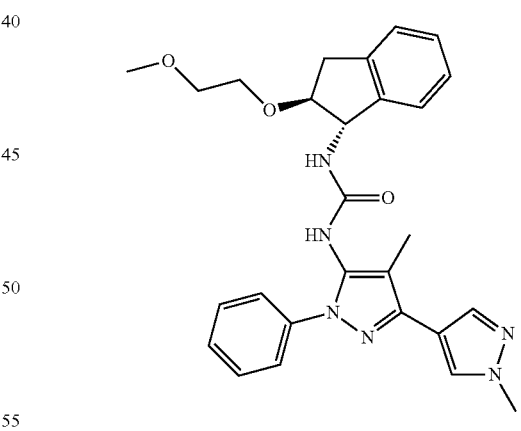

1-(1',4-dimethyl-1-phenyl-1H,1'H-[3,4'-bipyrazol]-5-yl)-3-((1S,2S)-2-(2-methoxyethoxy)-2,3-dihydro-1H-inden-1-yl)urea The title product was prepared as described for Example 48, using phenyl (1',4-dimethyl-1-phenyl-1H,1'H-[3,4'-bipyrazol]-5-yl)carbamate in the urea coupling step in place of phenyl 2-phenyl-2,4,5,6-tetrahydrocyclopenta[c]pyrazol-3-ylcarbamate. MS (apci) m/z=487.2 (M+H).

Example 52

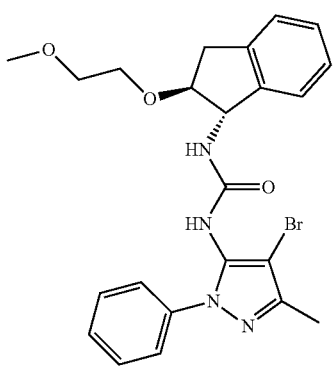 [SMILES: COCCO[C@H]1Cc2ccccc2[C@@H]1NC(=O)Nc1c(Br)c(C)nn1-c1ccccc1]

1-(4-bromo-3-methyl-1-phenyl-1H-pyrazol-5-yl)-3-((1S,2S)-2-(2-methoxyethoxy)-2,3-dihydro-1H-inden-1-yl)urea To a solution of phenyl 3-methyl-1-phenyl-1H-pyrazol-5-ylcarbamate (20 mg, 0.0682 mmol) in DCM (136 μL) was added NBS (12.7 mg, 0.0716 mmol) in one portion, followed by pyridin-1-ium 4-methylbenzenesulfonate (PPTS, 1.71 mg, 0.00682 mmol). After stirring at ambient temperature for 10 minutes, (1S,2S)-2-(2-methoxyethoxy)-2,3-dihydro-1H-inden-1-amine hydrochloride (17.4 mg, 0.0716 mmol) was introduced, followed by DIEA (59.4 μL, 0.341 mmol). The reaction was stirred for 1 hour and directly purified by reverse-phase chromatography (5 to 60% acetonitrile/water) to yield the product as white solid (17 mg, 50% yield). MS (apci) m/z=485.0 (M+H).

Example 53

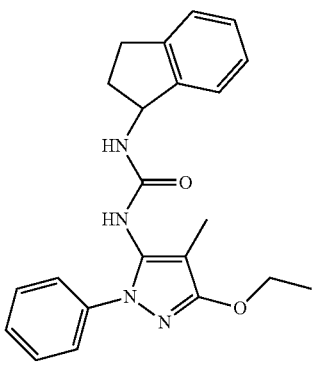 [SMILES: CCOc1nn(-c2ccccc2)c(NC(=O)NC2CCc3ccccc32)c1C]

1-(2,3-dihydro-1H-inden-1-yl)-3-(3-ethoxy-4-methyl-1-phenyl-1H-pyrazol-5-yl)urea The title product was as described for Example 49, using 2,3-dihydro-1H-inden-1-amine in place of (1S,2S)-2-(2-methoxyethoxy)-2,3-dihydro-1H-inden-1-amine hydrochloride. MS (apci) m/z=376.9 (M+H).

Example 54

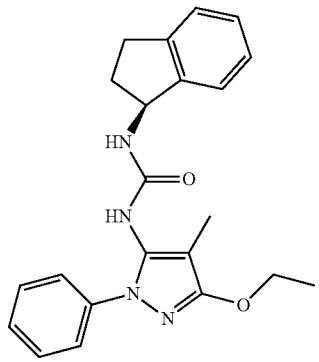 [SMILES: CCOc1nn(-c2ccccc2)c(NC(=O)N[C@H]2CCc3ccccc32)c1C]

(S)-1-(2,3-dihydro-1H-inden-1-yl)-3-(3-ethoxy-4-methyl-1-phenyl-1H-pyrazol-5-yl)urea The title product was prepared as described for Example 53, using (S)-2,3-dihydro-1H-inden-1-amine instead of 2,3-dihydro-1H-inden-1-amine. MS (apci) m/z=376.9 (M+H).

Example 55

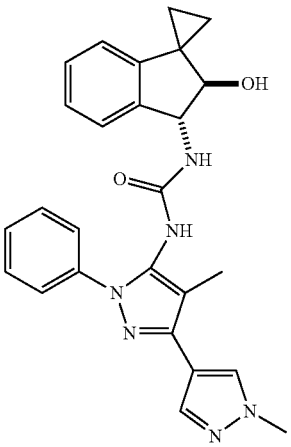

1-(1',4-dimethyl-1-phenyl-1H,1'H-[3,4'-bipyrazol]-5-yl)-3-(trans-2'-hydroxy-2',3'-dihydrospiro[cyclopropane-1,1'-inden]-3'-yl)urea Step A: spiro[cyclopropane-1,1'-indene]: To a suspension of N-benzyl-N,N-diethylethanaminium chloride (111 mg, 0.487 mmol) in NaOH (50 wt % aqueous, 18 mL) cooled to 0° C. was added dropwise a solution of 1H-indene (4.463 g, 38.42 mmol) and dibromoethane (6.6 mL, 76.84 mmol) in DMSO (7 mL). The reaction mixture was heated to 60° C. for 5 hours then cooled to ambient temperature. The reaction mixture was diluted with H$_2$O (30 mL) and extracted with Et$_2$O (3×30 mL). The combined organic phases were washed with H$_2$O (30 mL), then brine (3×30 mL), then dried (MgSO$_4$), filtered, and concentrated. The crude oil was purified by silica column chromatography eluting with hexanes to afford the title compound as a colorless oil (1.24 g, 23% yield). $^1$H NMR (CDCl$_3$) δ 7.42 (m, 1H), 7.24 (m, 1H), 7.26 (m, 1H), 6.98 (m, 1H), 6.88 (d, 1H), 6.23 (d, 1H), 1.70-1.65 (m, 2H), 1.63-1.59 (m, 2H).

Step B: 1a',6a'-dihydrospiro[cyclopropane-1,6'-indeno[1,2-b]oxirene]: To a solution of spiro[cyclopropane-1,1'-indene] (817 mg, 5.745 mmol) in MeOH (40 mL) cooled to 0° C. were added DCC (2.37 g, 11.49 mmol), KHCO$_3$ (1.15 g, 11.49 mmol), then H$_2$O$_2$ (30% aqueous, 8 mL). The reaction mixture was allowed to warm to ambient temperature over 3 hours, then was diluted with saturated aqueous NaHCO$_3$ (50 mL) and H$_2$O (50 mL), and extracted with DCM (3×100 mL). The combined organic extracts were dried (MgSO$_4$), filtered, and concentrated to give the title compound as a colorless oil/white solid mixture, which was used in the next step without further purification.

Step C: trans-3'-amino-2',3'-dihydrospiro[cyclopropane-1,1'-inden]-2'-ol: A mixture of 1a',6a'-dihydrospiro[cyclopropane-1,6'-indeno[1,2-b]oxirene] (909 mg, 5.75 mmol) and concentrated NH$_4$OH (22 mL) were heated to 60° C. for 1 hour. The reaction mixture was cooled, partially concentrated, then purified by reverse-phase column chromatography, eluting with 5-50% acetonitrile/water, to afford the title compound as a pale blue solid (493 mg, 49% yield). $^1$H NMR (CDCl$_3$) δ 7.32 (m, 1H), 7.22 (m, 2H), 6.75 (m, 1H), 4.18 (d, 1H), 3.98 (d, 1H), 1.99 (br s, 3H), 1.35 (m, 1H), 1.12 (m, 1H), 0.97 (m, 1H), 0.69 (m, 1H).

Step D: 1-(1',4-dimethyl-1-phenyl-1H,1'H-[3,4'-bipyrazol]-5-yl)-3-(trans-2'-hydroxy-2',3'-dihydrospiro[cyclopropane-1,1'-inden]-3'-yl)urea: To a solution of trans-3'-amino-2',3'-dihydrospiro[cyclopropane-1,1'-inden]-2'-ol (18.6 mg, 0.106 mmol) in i-PrOH (1 mL) was added phenyl (1',4-dimethyl-1-phenyl-1H,1'H-[3,4'-bipyrazol]-5-yl)carbamate (Intermediate 13, 41.6 mg, 0.111 mmol). The reaction mixture was heated to 75° C. for 1 hour, cooled to ambient temperature, then purified by reverse-phase column chromatography, eluting with 5-70% acetonitrile/water with 0.1% formic acid, to afford the title compound as a white solid (38.9 mg, 81% yield). MS (apci) m/z=455.2 (M+H).

Example 56

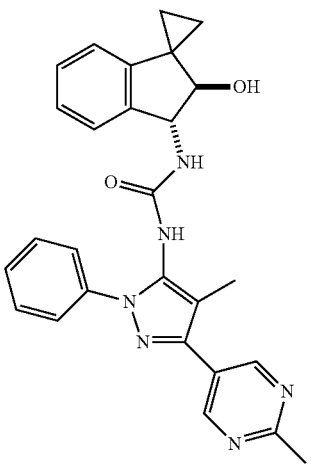

1-(trans-2'-hydroxy-2',3'-dihydrospiro[cyclopropane-1,1'-inden]-3'-yl)-3-(4-methyl-3-(2-methylpyrimidin-5-yl)-1-phenyl-1H-pyrazol-5-yl)urea To a suspension of 4-methyl-3-(2-methylpyrimidin-5-yl)-1-phenyl-1H-pyrazol-5-amine (Intermediate Y4, 22.7 mg, 0.086 mmol) in DCM (1 mL) were added triphosgene (12.7 mg, 0.043 mmol) then DIEA (0.045 mL, 0.257 mmol). The reaction mixture was stirred at ambient temperature for 2 hours, then a solution of trans-3'-amino-2',3'-dihydrospiro[cyclopropane-1,1'-inden]-2'-ol (Example 55, Step C, 15 mg, 0.086 mmol) and DIEA (0.045 mL, 0.257 mmol) in DCM (1 mL) was added. The reaction mixture was stirred at ambient temperature for 1 hour, concentrated, diluted with MeCN (1 mL) and stirred, and the resulting suspension was filtered and rinsed with Et$_2$O. The crude solid product was purified by silica column chromatography, eluting with 0-10% MeOH/DCM, to afford the title compound as a white solid (7.7 mg, 19% yield). MS (apci) m/z=467.2 (M+H).

Example 57

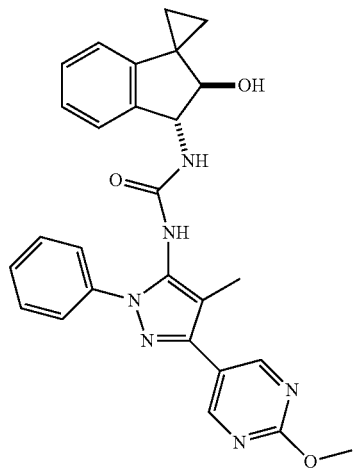

1-(trans-2'-hydroxy-2',3'-dihydrospiro[cyclopropane-1,1'-inden]-3'-yl)-3-(3-(2-methoxypyrimidin-5-yl)-4-methyl-1-phenyl-1H-pyrazol-5-yl)urea Prepared according to the procedure for Example 56, replacing 4-methyl-3-(2-methylpyrimidin-5-yl)-1-phenyl-1H-pyrazol-5-amine with 3-(2-methoxypyrimidin-5-yl)-4-methyl-1-phenyl-1H-pyrazol-5-amine (Intermediate Y5, 24.1 mg, 0.086 mmol). The crude product was purified by preparatory TLC (1 mm plate), eluted with 10% MeOH/DCM, to afford the title compound as a white solid (10.4 mg, 25% yield). MS (apci) m/z=483.2 (M+H).

Example 58

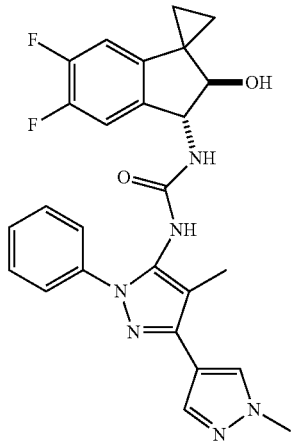

1-(trans-5',6'-difluoro-2'-hydroxy-2',3'-dihydrospiro [cyclopropane-1,1'-inden]-3'-yl)-3-(1',4-dimethyl-1-phenyl-1H,1'H-[3,4'-bipyrazol]-5-yl)urea Step A: 5,6-difluoro-2,3-dihydro-1H-inden-1-ol: To a solution of 5,6-difluoro-2,3-dihydro-1H-inden-1-one (2.0 g, 11.90 mmol) in MeOH (40 mL) cooled to 0° C. was added NaBH$_4$ (540 mg, 14.27 mmol) in portions over 5 minutes. The reaction mixture was stirred at 0° C. for 1 hour, then allowed to warm to ambient temperature and stirred for 19 hours. The reaction mixture was diluted with H$_2$O (50 mL) and extracted with DCM (3×50 mL). The combined organic extracts were washed with brine (50 mL), dried (MgSO$_4$), filtered, and concentrated to afford the title compound as a colorless oil (2438 mg, 120% yield), which was used in the next step without purification and assuming theoretical yield. $^1$H NMR (CDCl$_3$) δ 7.17 (dd, 1H), 7.00 (dd, 1H), 5.18 (t, 1H), 2.99 (m, 1H), 2.75 (m, 1H), 2.51 (m, 1H), 1.95 (m, 1H).

Step B: 5,6-difluoro-1H-indene: To a solution of 5,6-difluoro-2,3-dihydro-1H-inden-1-ol (2024 mg, 11.90 mmol) in toluene (40 mL) was added TsOH—H$_2$O (113 mg, 0.595 mmol). The reaction mixture heated to 110° C. for 1 hour, then cooled to ambient temperature. The reaction mixture was diluted with H$_2$O (50 mL) and extracted with DCM (3×50 mL). The combined organic extracts were dried (MgSO$_4$), filtered, and concentrated. The crude oil was purified by silica column chromatography eluting with hexanes to afford a colorless oil containing both the title compound and toluene (3.60 g, 200% yield). $^1$H NMR (CDCl$_3$) δ 7.25 (m, 2H, toluene), 7.13-7.18 (m, 6H, product 2H and toluene 4H), 7.14 (m, 2H, product), 6.78 (m, 1H, product), 6.59 (m, 1H, product), 3.36 (m, 2H, product), 2.36 (s, 6H, toluene).

Step C: 1-(trans-5',6'-difluoro-2'-hydroxy-2',3'-dihydrospiro[cyclopropane-1,1'-inden]-3'-yl)-3-(1',4-dimethyl-1-phenyl-1H,1'H-[3,4'-bipyrazol]-5-yl)urea: Prepared according to the procedure for Example 55, replacing 1H-indene in Step A with 5,6-difluoro-1H-indene, to afford the title compound as a white solid (13.9 mg, 86% yield). MS (apci) m/z=491.2 (M+H).

The compounds of Table 2 were prepared according to the methods of Examples 55 and 58, replacing Intermediate 13 with the appropriate Intermediate 3, 5, or 11.

TABLE 2

| Ex. # | Structure | name | MS (apci) m/z |
|---|---|---|---|
| 59 | 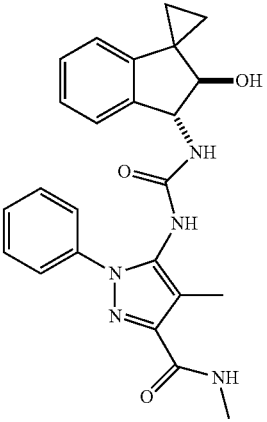 | 215-(3-(trans-2'-hydroxy-2',3'-dihydrospiro[cyclopropane-1,1'-inden]-3'-yl)ureido)-N,4-dimethyl-1-phenyl-1H-pyrazole-3-carboxamide | 432.2 (M + H) |
| 60 | 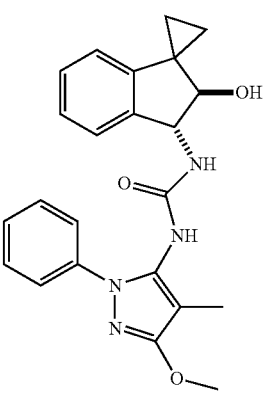 | 1-(trans-2'-hydroxy-2',3'-dihydrospiro[cyclopropane-1,1'-inden]-3-yl)-3-(3-methoxy-4-methyl-1-phenyl-1H-pyrazol-5-yl)urea | 405.2 (M + H) |

TABLE 2-continued

| Ex. # | Structure | name | MS (apci) m/z |
|---|---|---|---|
| 61 | 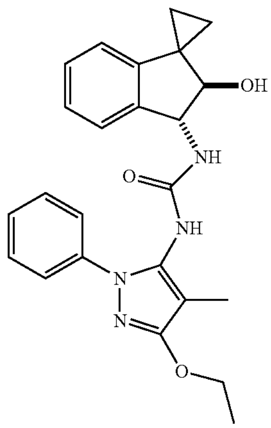 | 1-(3-ethoxy-4-methyl-1-phenyl-1H-pyrazol-5-yl)-3-(trans-2'-hydroxy-2',3'-dihydrospiro[cyclopropane-1,1'-inden]-3'-yl)urea | 419.2 (M + H) |
| 62 | 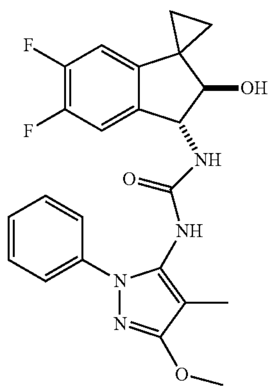 | 1-(trans-5',6'-difluoro-2'-hydroxy-2',3'-dihydrospiro[cyclopropane-1,1'-inden]-3'-yl)-3-(3-methoxy-4-methyl-1-phenyl-1H-pyrazol-5-yl)urea | 441.2 (M + H) |

Example 63

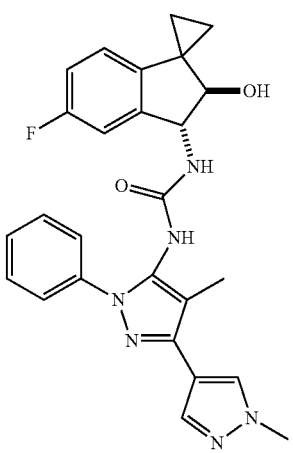

1-(1',4-dimethyl-1-phenyl-1H,1'H-[3,4'-bipyrazol]-5-yl)-3-(trans-5'-fluoro-2'-hydroxy-2',3'-dihydrospiro[cyclopropane-1,1'-inden]-3'-yl)urea Step A: 5-fluoro-1H-indene: Prepared according to the procedure for Example 58, Steps A-B, replacing 5,6-difluoro-2,3-dihydro-1H-inden-1-one with 6-fluoro-2,3-dihydro-1H-inden-1-one to afford the title compound as a colorless oil (0.78 g, 87% yield). $^1$H NMR (CDCl$_3$) δ 7.26 (dd, 1H), 7.07 (dd, 1H), 6.81-6.89 (m, 2H), 6.63 (m, 1H), 3.35 (m, 2H).

Step B: A 1:1 mixture of 5'-fluorospiro[cyclopropane-1,1'-indene] and 6'-fluorospiro[cyclopropane-1,1'-indene]: Prepared according to the procedure for Example 55, Step A, replacing 1H-indene with 5-fluoro-1H-indene to afford the title compound mixture as a colorless oil (183 mg, 20% yield). $^1$H NMR (CDCl$_3$) δ 7.30 (dd, 1H), 7.09 (m, 1H), 6.92 (m, 1H), 6.81-6.86 (m, 4H), 6.66 (dd, 1H), 6.29 (d, 1H), 6.19 (d, 1H), 1.65-1.70 (m, 4H), 1.54-1.58 (m, 4H).

Step C: A 1:1 mixture of 1-(1',4-dimethyl-1-phenyl-1H,1'H-[3,4'-bipyrazol]-5-yl)-3-(trans-5'-fluoro-2'-hydroxy-2',3'-dihydrospiro[cyclopropane-1,1'-inden]-3'-yl)urea and 1-(1',4-dimethyl-1-phenyl-1H,1'H-[3,4'-bipyrazol]-5-yl)-3-(trans-6'-fluoro-2'-hydroxy-2',3'-dihydrospiro[cyclopropane-1,1'-inden]-3'-yl)urea: Prepared according to the procedure for Example 55, Steps B-D, replacing spiro[cyclopropane-1,1'-indene] with a 1:1 mixture of 5'-fluorospiro[cyclopropane-1,1'-indene] and 6'-fluorospiro[cyclopropane-1,1'-indene] to afford the title compound mixture as a white solid (20.3 mg, 55% yield). MS (apci) m/z=473.2 (M+H).

Step D: 1-(1',4-dimethyl-1-phenyl-1H,1'H-[3,4'-bipyrazol]-5-yl)-3-(trans-5'-fluoro-2'-hydroxy-2',3'-dihydrospiro[cyclopropane-1,1'-inden]-3'-yl)urea: A 1:1 mixture of 1-(1',4-dimethyl-1-phenyl-1H,1'H-[3,4'-bipyrazol]-5-yl)-3-(trans-5'-fluoro-2'-hydroxy-2',3 dihydrospiro[cyclopropane-1,1'-inden]-3'-yl)urea and 1-(1',4-dimethyl-1-phenyl-1H, 1'H-[3,4'-bipyrazol]-5-yl)-3-(trans-6'-fluoro-2'-hydroxy-2',3'-dihydrospiro[cyclopropane-1,1'-inden]-3'-yl)urea (20.3 mg, 0.043 mmol) was purified by chiral HPLC on a Chiral Tech IA column (4.6 mm×250 mm, 5µ), eluted with 25% EtOH/hexanes, and the second of the two product peaks to elute was collected to afford the title compound as a white solid (4.5 mg, 22% yield). MS (apci) m/z=473.2 (M+H). $^1$H NMR (CD$_2$Cl$_2$) δ 7.80 (d, 1H), 7.45-7.53 (m, 5H), 7.38 (m, 1H), 6.88 (dt, 1H), 6.74 (d, 1H), 6.67 (dd, 1H), 4.96 (d, 1H), 3.99 (d, 1H), 3.91 (s, 3H), 2.14 (s, 3H), 1.31 (m, 1H), 1.00 (m, 1H), 0.85 (m, 1H), 0.59 (m, 1H).

Example 64

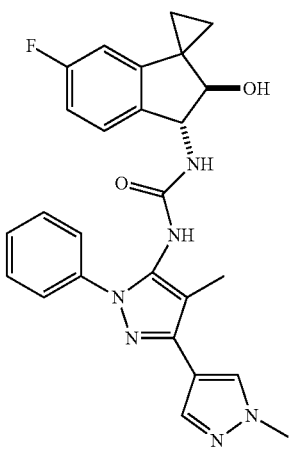

1-(1',4-dimethyl-1-phenyl-1H,1'H-[3,4'-bipyrazol]-5-yl)-3-(trans-6'-fluoro-2'-hydroxy-2',3'-dihydrospiro[cyclopropane-1,1'-inden]-3'-yl)urea Prepared according to the procedure for Example 63, but in Step D the first of the two product peaks to elute was collected to afford the title compound as a white solid (3.7 mg, 18% yield). MS (apci) m/z=473.2 (M+H). $^1$H NMR (CD$_2$Cl$_2$) δ 7.80 (d, 1H), 7.45-7.53 (m, 5H), 7.38 (m, 1H), 6.99 (m, 1H), 6.81 (dt, 1H), 6.41 (dd, 1H), 4.92 (d, 1H), 3.97 (d, 1H), 3.91 (s, 3H), 2.14 (s, 3H), 1.37 (m, 1H), 1.00 (m, 1H), 0.91 (m, 1H), 0.66 (m, 1H).

Example 65

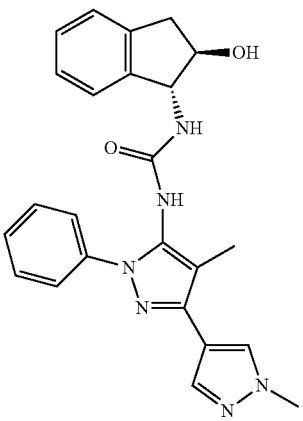 [SMILES: Cc1c(-c2cnn(C)c2)nn(-c2ccccc2)c1NC(=O)N[C@@H]1c2ccccc2C[C@H]1O]

1-(1',4-dimethyl-1-phenyl-1H,1'H-[3,4'-bipyrazol]-5-yl)-3-((1R,2R)-2-hydroxy-2,3-dihydro-1H-inden-1-yl)urea To a turbid solution of (1R,2R)-1-amino-2,3-dihydro-1H-inden-2-ol (50 mg, 0.335 mmol) in iPrOH (1.4 mL) was added phenyl (1',4-dimethyl-1-phenyl-1H,1'H-[3,4'-bipyrazol]-5-yl)carbamate (125 mg, 0.335 mmol) in one portion. The white suspension was stirred in a 40° C. sand bath for 2 hours, then heated to reflux. It was then slowly cooled to ambient temperature and filtered, rinsed with IPA, MeOH and ether (10 mL each), yielding the title product as fine white solid (90 mg, 63% yield). $^1$H NMR (400 MHz, d$^6$-DMSO) δ 8.06 (s, 1H), 7.94 (br s, 1H), 7.74 (s, 1H), 7.56-7.58 (m, 2H), 7.45-7.50 (m, 2H), 7.34-7.38 (m, 1 H), 7.12-7.17 (m, 3H), 6.91-6.93 (m, 1H), 6.78 (d, J=8.6 Hz, 1H), 5.25 (br d, J=5.5 Hz, 1H), 4.83 (br t, J=7.4 Hz, 1H), 4.13-4.18 (m, 1H), 3.88 (s, 3H), 3.03-3.08 (m, 1H), 2.61-2.67 (m, 1H), 2.05 (s, 3H). MS (apci) m/z=429.2 (M+H).

Example 66

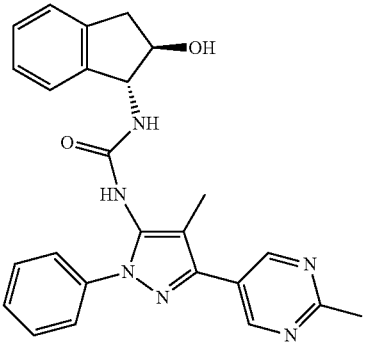 [SMILES: Cc1ncc(-c2nn(-c3ccccc3)c(NC(=O)N[C@@H]3c4ccccc4C[C@H]3O)c2C)cn1]

1-((1R,2R)-2-hydroxy-2,3-dihydro-1H-inden-1-yl)-3-(4-methyl-3-(2-methylpyrimidin-5-yl)-1-phenyl-1H-pyrazol-5-yl)urea To an orange suspension of 4-methyl-3-(2-methylpyrimidin-5-yl)-1-phenyl-1H-pyrazol-5-amine (Intermediate Y4, 53.4 mg, 0.20 mmol) in DriSolve DCM (1.0 mL) was added triphosgene (29.8 mg, 0.10 mmol), followed by DIEA (105 µL, 0.60 mmol). After 2 hours, (1R,2R)-1-amino-2,3-dihydro-1H-inden-2-ol (30 mg, 0.20 mmol) was added in one portion. After 30 minutes, the reaction mixture was vacuum-filtered, rinsed with DCM and ether (2 mL each), giving the product as white powder (54 mg, 58% yield). $^1$H NMR (400 MHz, d$^6$-DMSO) δ 9.01 (s, 2H), 8.40 (br s, 1H), 7.62-7.64 (m, 2H), 7.49-7.54 (m, 2H), 7.40-7.44 (m, 1 H), 7.11-7.19 (m, 3H), 6.87-6.91 (m, 2H), 5.26 (br d, J=5.5 Hz, 1H), 4.83 (br t, J=7.8 Hz, 1H), 4.12-4.19 (m, 1H), 3.03-3.09 (m, 1H), 2.66 (s, 3H), 2.61-2.66 (m, 1H), 2.15 (s, 3H). MS (apci) m/z=441.2 (M+H).

Example 67

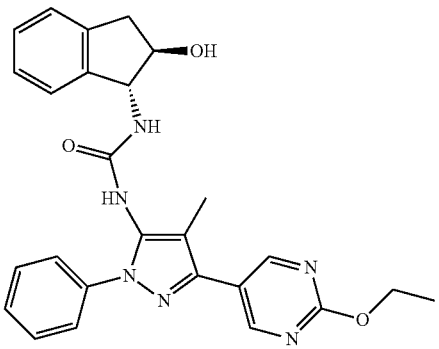 [SMILES: CCOc1ncc(-c2nn(-c3ccccc3)c(NC(=O)N[C@@H]3c4ccccc4C[C@H]3O)c2C)cn1]

1-(3-(2-ethoxypyrimidin-5-yl)-4-methyl-1-phenyl-1H-pyrazol-5-yl)-3-((1R,2R)-2-hydroxy-2,3-dihydro-1H-inden-1-yl)urea The title product was prepared as described for Example 66, using 3-(2-ethoxypyrimidin-5-yl)-4-methyl-1-phenyl-1H-pyrazol-5-amine (49.5 mg, 0.17 mmol) instead of 4-methyl-3-(2-methylpyrimidin-5-yl)-1-phenyl-1H-pyrazol-5-amine. The product was isolated as white solid (51 mg, 61% yield). $^1$H NMR (400 MHz, d$^6$-DMSO) δ 8.90 (s, 2H), 7.61-7.63 (m, 2H), 7.48-7.53 (m, 2H), 7.40-7.43 (m, 1 H), 7.25-7.31 (m, 1H), 7.14 (m, 3H), 6.84-6.91 (m, 2H), 5.26 (br d, J=5.5 Hz, 1H), 4.83 (br t, J=7.8 Hz, 1H), 4.39 (q, J=7.0 Hz, 2H), 4.11-4.19 (m, 1H), 3.03-3.08 (m, 1H), 2.61-2.67 (m, 1H), 2.12 (s, 3H), 1.35 (t, J=7.0 Hz, 3H). MS (apci) m/z=471.2 (M+H).

Example 68

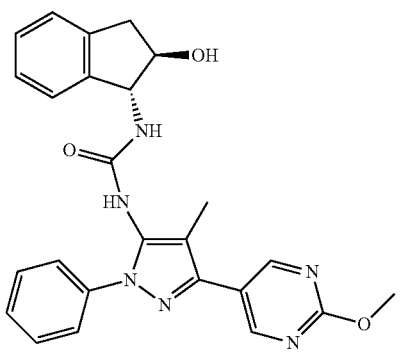 [SMILES: COc1ncc(-c2nn(-c3ccccc3)c(NC(=O)N[C@@H]3c4ccccc4C[C@H]3O)c2C)cn1]

1-((1R,2R)-2-hydroxy-2,3-dihydro-1H-inden-1-yl)-3-(3-(2-methoxypyrimidin-5-yl)-4-methyl-1-phenyl-1H-pyrazol-5-yl)urea The title product was prepared as described for Example 66, using 3-(2-methoxypyrimidin-5-yl)-4-methyl-1-phenyl-1H-pyrazol-5-amine (47 mg, 0.17 mmol) instead of 4-methyl-3-(2-methylpyrimidin-5-yl)-1-phenyl-1H-pyrazol-5-amine. The product was isolated as white solid (50 mg, 62% yield). $^1$H NMR (400 MHz, d$^6$-DMSO) δ 8.92 (s, 2H), 7.61-7.63 (m, 2H), 7.49-7.53 (m, 2H), 7.40-7.43 (m, 1 H), 7.24-7.30 (m, 1H), 7.11-7.17 (m, 3H), 6.85-6.92 (m, 2H), 5.26 (br d, J=5.5 Hz, 1H), 4.83 (br t, J=7.4 Hz, 1H), 4.12-4.18 (m, 1H), 3.96 (s, 3H), 3.03-3.09 (m, 1H), 2.61-2.67 (m, 1H), 2.12 (s, 3H). MS (apci) m/z=457.2 (M+H).

Example 69

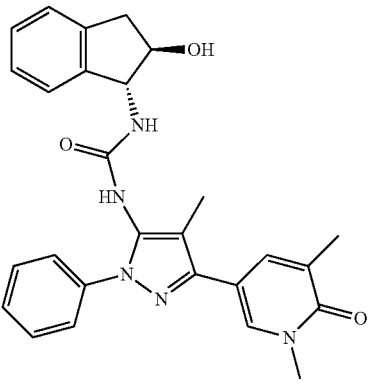 [SMILES: Cc1c(-c2cc(C)c(=O)n(C)c2)nn(-c2ccccc2)c1NC(=O)N[C@@H]1c2ccccc2C[C@H]1O]

1-(3-(1,5-dimethyl-6-oxo-1,6-dihydropyridin-3-yl)-4-methyl-1-phenyl-1H-pyrazol-5-yl)-3-((1R,2R)-2-hydroxy-2,3-dihydro-1H-inden-1-yl)urea The title product was prepared as described for Example 66, using 5-(5-amino-4-methyl-1-phenyl-1H-pyrazol-3-yl)-1,3-dimethylpyridin-2(1H)-one (49 mg, 0.17 mmol) instead of 4-methyl-3-(2-methylpyrimidin-5-yl)-1-phenyl-1H-pyrazol-5-amine. The product was isolated as white solid (45 mg, 54% yield). MS (apci) m/z=468.2 (M–H).

Example 70

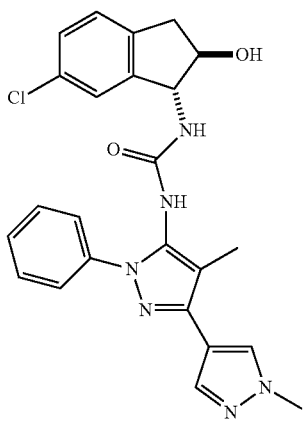

1-((1,2-trans)-6-chloro-2-hydroxy-2,3-dihydro-1H-inden-1-yl)-3-(1',4-dimethyl-1-phenyl-1H,1'H-[3,4'-bipyrazol]-5-yl)urea The title product was prepared as described for Example 65, using trans-1-amino-6-chloro-2,3-dihydro-1H-inden-2-ol (30 mg, 0.16 mmol) instead of (1R,2R)-1-amino-2,3-dihydro-1H-inden-2-ol. The product was isolated as crystalline white solid (65 mg, 84% yield). $^1$H NMR (400 MHz, d$^6$-DMSO) δ 8.03 (s, 1H), 7.99 (br s, 1H), 7.73 (s, 1H), 7.55-7.58 (m, 2H), 7.45-7.49 (m, 2H), 7.33-7.37 (m, 1 H), 7.15-7.22 (m, 2H), 6.93 (br, 1H), 6.90 (m, 1H), 5.33 (br d, J=5.9 Hz, 1H), 4.81 (br t, J=7.8 Hz, 1H), 4.14-4.21 (m, 1H), 3.87 (s, 3H), 3.00-3.06 (m, 1H), 2.57-2.63 (m, 1H), 2.04 (s, 3H). MS (apci) m/z=461.1 (M−H).

Example 71

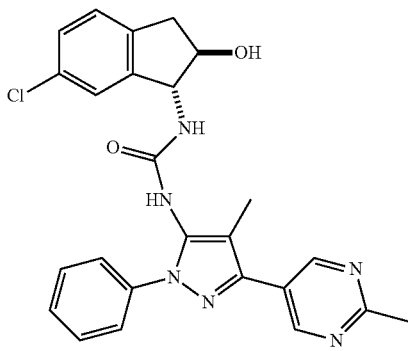

1-((1,2-trans)-6-chloro-2-hydroxy-2,3-dihydro-1H-inden-1-yl)-3-(4-methyl-3-(2-methylpyrimidin-5-yl)-1-phenyl-1H-pyrazol-5-yl)urea The title product was prepared as described for Example 66, using trans-1-amino-6-chloro-2,3-dihydro-1H-inden-2-ol (30 mg, 0.16 mmol) instead of (1R,2R)-1-amino-2,3-dihydro-1H-inden-2-ol. The product was isolated as crystalline white solid (12 mg, 44% yield). MS (apci) m/z=473.2 (M−H).

Example 72

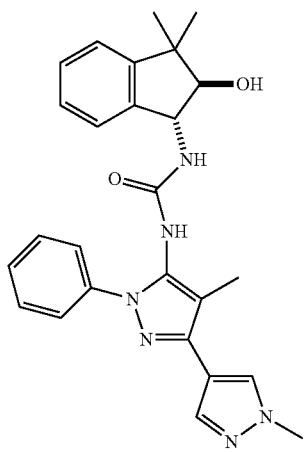

1-(1',4-dimethyl-1-phenyl-1H,1'H-[3,4'-bipyrazol]-5-yl)-3-(1,2-trans)-2-hydroxy-3,3-dimethyl-2,3-dihydro-1H-inden-1-yl)urea Step 1. Synthesis of 3,3-dimethyl-2,3-dihydro-1H-inden-1-ol. A light suspension of 3,3-dimethyl-2,3-dihydro-1H-inden-1-one (2.5 g, 16 mmol) in DriSolve MeOH (52 mL) was first cooled in an ice-water bath, followed by addition of NaBH$_4$ (0.71 g, 19 mmol) in small portions. The reaction was then warmed up to ambient temperature and stirred for 30 minutes. The reaction was poured onto ice water (50 mL) in a separatory funnel, rinsed over with water, giving a white suspension. The suspension was extracted with DCM (3×50 mL). The combined organic extracts were washed with water, brine (50 mL each), dried (Na$_2$SO$_4$), filtered and concentrated to yield the crude product as clear colorless oil (2.5 g, 99% yield), which was used for the next reaction without further purification. $^1$H NMR (400 MHz, CDCl$_3$) δ 7.37-7.40 (m, 1H), 7.17-7.31 (m, 3H), 5.23-5.28 (m, 1H), 2.35-2.40 (m, 1H), 1.79-1.85 (m, 2H), 1.39 (s, 3H), 1.22 (s, 3H).

Step 2. Synthesis of 1,1-dimethyl-1H-indene. A clear colorless solution of 3,3-dimethyl-2,3-dihydro-1H-inden-1-ol (1.83 g, 11.3 mmol) and 4-methylbenzenesulfonic acid hydrate (0.107 g, 0.564 mmol) [5 mol %] in toluene (37.6 mL) was stirred at 110° C. for 2 hours. The light yellowish reaction solution was cooled to ambient temperature, diluted with Et$_2$O (50 mL) and washed with saturated aqueous NaHCO$_3$ and brine (50 mL each). The organic layer was phase-separated and dried over Na$_2$SO$_4$, then concentrated in vacuo. The crude was taken up in hexanes and purified by silica chromatography (hexanes) to yield the product as clear colorless oil (0.85 g, 52% yield). $^1$H NMR (400 MHz, CDCl$_3$) δ 7.28-7.32 (m, 2H), 7.16-7.23 (m, 2H), 6.62 (d, J=6.3 Hz 1H), 6.36 (d, J=5.5 Hz, 1H), 1.31 (s, 6H).

Step 3. Synthesis of 6,6-dimethyl-6,6a-dihydro-1aH-indeno[1,2-b]oxirene. To a solution of 1,1-dimethyl-1H-indene (590 mg, 4.09 mmol) in DCM (20 mL) was added mCPBA (1210 mg, 4.91 mmol) in four portions at 20-minute intervals and stirred at ambient temperature for 5 hours. The reaction was treated with saturated aqueous NaHCO$_3$ (20 mL), stirred for an additional 30 minutes, and then diluted with water and DCM (20 mL each). The aqueous layer was separated and extracted with DCM (2×30 mL). The combined organic layers was dried (Na$_2$SO$_4$), filtered and concentrated. The crude product was purified by silica chromatography (DCM) to yield the product. $^1$H NMR (400 MHz, CDCl$_3$) δ 7.23-7.31 (m, 2H), 7.15-7.20 (m, 2H), 4.24 (d, J=2.7 Hz 1H), 3.71 (d, J=2.7 Hz, 1H), 1.41 (s, 3H), 1.23 (s, 3H).

Step 4. Synthesis of (2,3-trans)-3-amino-1,1-dimethyl-2,3-dihydro-1H-inden-2-ol. A mixture of 6,6-dimethyl-6,6a-dihydro-1aH-indeno[1,2-b]oxirene (0.35 g, 2.2 mmol) in concentrated NH$_4$OH (3.8 g, 109 mmol) was stirred at 60° C. for 6 hours. The reaction mixture was briefly subjected to mild vacuum, then filtered and rinsed with water. The solid was then rinsed with small amount of ether to yield first batch of product as fine solid (13 mg). To recover additional product, the aqueous layer and ether filtrate were concentrated and treated with reverse-phase chromatography (C18, 5 to 40% acetonitrile/water) to yield a second batch of product as solid (78 mg). $^1$H NMR (400 MHz, CDCl$_3$) δ 7.22-7.29 (m, 3H), 7.15-7.18 (m, 1H), 4.08 (d, J=8.2 Hz 1H), 3.65 (d, J=8.2 Hz, 1H), 2.79 (br, 3H), 1.36 (s, 3H), 1.11 (s, 3H).

Step 5. Synthesis of 1-(1',4-dimethyl-1-phenyl-1H,1'H-[3,4'-bipyrazol]-5-yl)-3-((1,2-trans)-2-hydroxy-3,3-dimethyl- 2,3-dihydro-1H-inden-1-yl)urea. To a clear solution of (2,3-trans)-3-amino-1,1-dimethyl-2,3-dihydro-1H-inden-2-ol (12 mg, 0.0677 mmol) in iPrOH (282 µL) was added phenyl (1',4-dimethyl-1-phenyl-1H,1'H-[3,4'-bipyrazol]-5-yl)carbamate (25.3 mg, 0.0677 mmol) in one portion. The resulting milky suspension was stirred at 40° C. for 4 hours and then brought to reflux. The reaction mixture was slowly cooled to ambient temperature and stirred for another 1 hour. The reaction mixture was vacuum-filtered, rinsed with iPrOH and ether (2 mL each), giving first batch product (14 mg). A second batch of product was obtained from reverse-phase purification of the filtrate (C18, 5 to 60% acetontrile/water). The two batch of product was combined to give a white solid (26 mg, 82% yield). $^1$H NMR (400 MHz, CDCl$_3$) δ 7.84 (s, 1H), 7.76 (s, 1H), 7.56-7.60 (m, 2H), 7.45-7.50 (m, 2H), 7.35-7.39 (m, 1 H), 7.25-7.29 (m, 1H), 7.16-7.20 (m, 3H), 6.94-6.96 (m, 1H), 5.55 (br, 1H), 5.04 (m, 1H), 3.94 (s, 3H), 3.66 (d, J=8.2 Hz, 1 H), 2.29 (s, 3H), 1.34 (s, 3H), 1.10 (s, 3H). MS (apci) m/z=457.2 (M+H).

Example 73

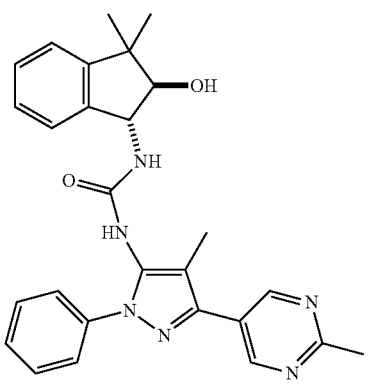

1-((1,2-trans)-2-hydroxy-3,3-dimethyl-2,3-dihydro-1H-inden-1-yl)-3-(4-methyl-3-(2-methylpyrimidin-5-yl)-1-phenyl-1H-pyrazol-5-yl)urea To a suspension of 4-methyl-3-(2-methylpyrimidin-5-yl)-1-phenyl-1H-pyrazol-5-amine (Intermediate Y4, 37 mg, 0.14 mmol) in DriSolve DCM (0.7 mL) was added triphosgene (21 mg, 0.07 mmol), followed by DIEA (74 µL, 0.4 mmol). After 1 hour, trans-3-amino-1,1-dimethyl-2,3-dihydro-1H-inden-2-ol (25 mg, 0.14105 mmol) was added in one portion. After 30 minutes, the reaction was concentrated and directly purified by reverse-phase chromatography (C18, 5 to 60% acetonitrile/water with 0.1 v/v % formic acid) to yield the product as white solid (20 mg, 29% yield). $^1$H NMR (400 MHz, CDCl$_3$) δ 8.97 (s, 2H), 7.57-7.59 (m, 2H), 7.43-7.47 (m, 2H), 7.34-7.38 (m, 1 H), 7.25-7.30 (m, 2H), 7.14-7.18 (m, 2H), 6.94-6.96 (m, 1H), 5.48 (br, 1H), 5.00 (br t, J=7.0 Hz, 1H), 3.72 (d, J=7.8 Hz, 1H), 2.76 (s, 3H), 2.21 (s, 3H), 1.33 (s, 3H), 1.20 (m, 3H), 1.08 (s, 3H). MS (apci) m/z=467.2 (M−H).

Example 74

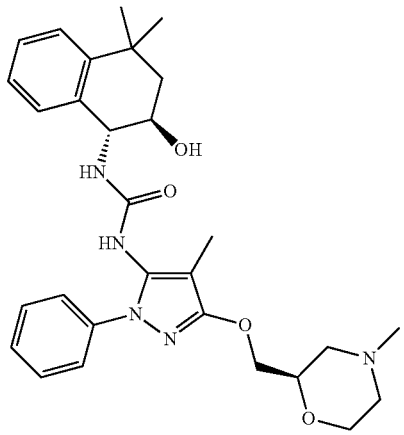 [SMILES: Cc1c(OC[C@H]2CN(C)CCO2)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(4-methyl-3-(((R)-4-methylmorpholin-2-yl)methoxy)-1-phenyl-1H-pyrazol-5-yl)urea To a solution of triphosgene (44.1 mg, 0.146 mmol) in dry CH$_2$Cl$_2$ (1.0 mL) was added a solution of (R)-4-methyl-3-((4-methylmorpholin-2-yl)methoxy)-1-phenyl-1H-pyrazol-5-amine (Intermediate Y2, 110 mg, 0.364 mmol) and DIEA (76.0 µL, 0.437 mmol) in dry CH$_2$Cl$_2$ (1.0 mL) dropwise over 45 minutes. The mixture was stirred for 15 minutes and (1R,2R)-1-amino-4,4-dimethyl-1,2,3,4-tetrahydronaphthalen-2-ol (Intermediate X2, 83.5 mg, 0.437 mmol) was added. The reaction mixture was stirred for 16 hours and was diluted with CH$_2$Cl$_2$ (4 mL). The mixture was washed with 1M NaOH (2×) and H$_2$O. The organic portion was dried over Na$_2$SO$_4$, filtered, concentrated and the residue purified on a SiO$_2$ column (EtOAc, 5%, 10% MeOH/EtOAc). The resulting white foam was dissolved in 50% CH$_2$Cl$_2$-hexanes and concentrated to provide the title compound as a white solid that was dried in vacuum (187 mg, 99%). MS(apci) m/z=520.3 (M+H).

Example 75

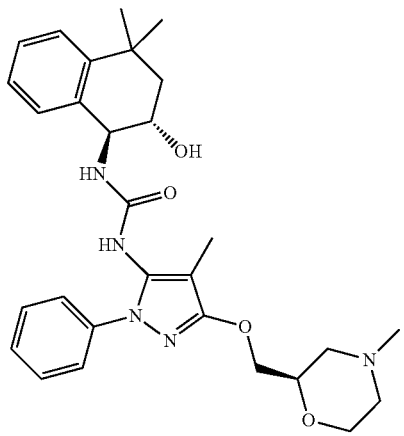 [SMILES: Cc1c(OC[C@H]2CN(C)CCO2)nn(-c2ccccc2)c1NC(=O)N[C@H]1c2ccccc2C(C)(C)C[C@@H]1O]

1-((1S,2S)-2-hydroxy-4,4-dimethyl-1,2,3,4-tetrahydronaphthalen-1-yl)-3-(4-methyl-3-(((R)-4-methylmorpholin-2-yl)methoxy)-1-phenyl-1H-pyrazol-5-yl)urea Using (1S,2S)-1-amino-4,4-dimethyl-1,2,3,4-tetrahydronaphthalen-2-ol (Intermediate X3) in the procedure for Example 74, the title compound was obtained as a white solid (94 mg, 55%). MS(apci) m/z=520.3 (M+H).

Example 76

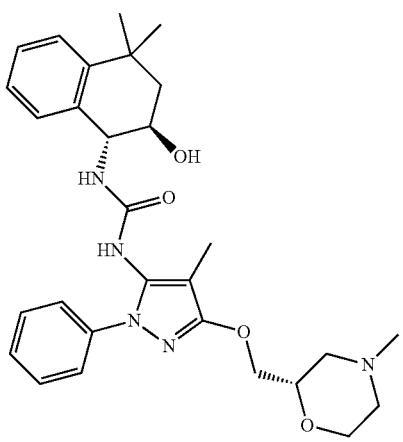 [SMILES: Cc1c(OC[C@@H]2CN(C)CCO2)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(4-methyl-3-(((S)-4-methylmorpholin-2-yl)methoxy)-1-phenyl-1H-pyrazol-5-yl)urea Using (S)-4-methyl-3-((4-methylmorpholin-2-yl)methoxy)-1-phenyl-1H-pyrazol-5-amine (Intermediate Y1) in the procedure for Example 74, the title compound was obtained as a white solid (54 mg, 35%). MS(apci) m/z=520.3 (M+H).

Example 77

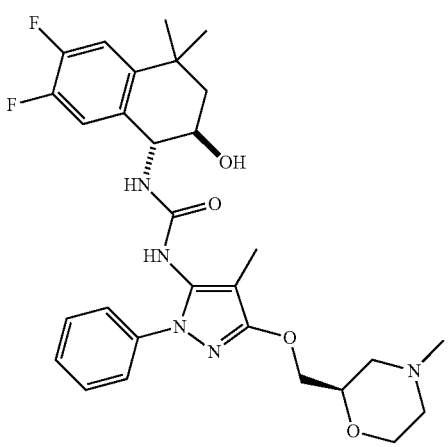

1-(trans-6,7-difluoro-2-hydroxy-4,4-dimethyl-1,2,3,4-tetrahydronaphthalen-1-yl)-3-(4-methyl-3-(((R)-4-methylmorpholin-2-yl)methoxy)-1-phenyl-1H-pyrazol-5-yl)urea Using trans-1-amino-6,7-difluoro-4,4-dimethyl-1,2,3,4-tetrahydronaphthalen-2-ol in the procedure described for Example 74, the title compound was obtained as a white solid (31 mg, 28%). MS(apci) m/z=556.3 (M+H).

Example 78

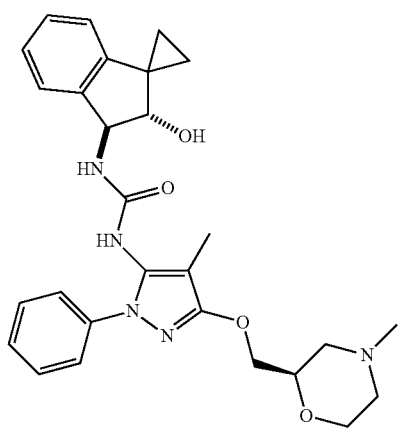

1-(trans-2'-hydroxy-2,3'-dihydrospiro[cyclopropane-1,1'-inden]-3'-yl)-3-(4-methyl-3-(((R)-4-methylmorpholin-2-yl)methoxy)-1-phenyl-1H-pyrazol-5-yl)urea To a solution of (R)-4-methyl-3-((4-methylmorpholin-2-yl)methoxy)-1-phenyl-1H-pyrazol-5-amine (Intermediate Y2, 51.8 mg, 0.171 mmol) in dry DMF (1.0 mL) was added carbonyldiimidazole (33.3 mg, 0.205 mmol) and the mixture was stirred at ambient temperature for 64 hours. The reaction mixture was treated with trans-3'-amino-2',3'-dihydrospiro[cyclopropane-1,1'-inden]-2'-ol (Example 55, Step C, 30.0 mg, 0.171 mmol) in dry DMF (0.5 mL) and stirred for 8 hours. The reaction mixture was added to H$_2$O (6 mL), treated with 2M NaOH to pH=11 and extracted with EtOAc (4×). The combined extracts were washed with saturated NaCl (2×), dried over MgSO$_4$/activated charcoal, filtered and concentrated. The residue was purified on a SiO$_2$ column (EtOAc, 5%, 10% (9:1 MeOH/NH$_4$OH)/EtOAc) to provide the title compound as a white solid (36 mg, 42%). MS(apci) m/z=504.2 (M+H).

Example 79

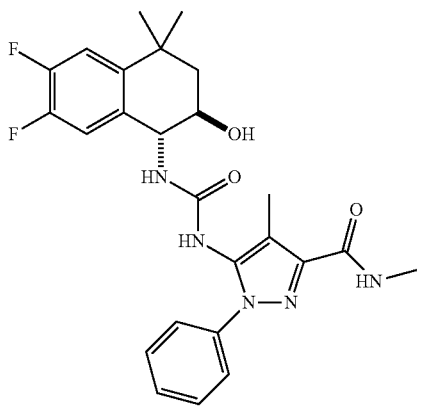

5-(3-((1,2-trans)-6,7-difluoro-2-hydroxy-4,4-dimethyl-1,2,3,4-tetrahydronaphthalen-1-yl)ureido)-N,4-dimethyl-1-phenyl-1H-pyrazole-3-carboxamide Step A: Preparation of 6,7-difluoro-4,4-dimethyl-3,4-dihydronaphthalen-1(2H)-one: A stainless steel bomb equipped with a Teflon insert and a stir bar was charged with 1,2-difluorobenzene (9.5 g, 83 mmol), 5,5-dimethyldihydrofuran-2(3H)-one (9.5 g, 83 mmol), and lastly aluminum trichloride (13 g, 100 mmol). The reaction mixture was heated to 100° C. overnight with stirring behind a safety shield. The reaction mixture was cooled to ambient temperature and the bomb was placed in an ice bath before opening. The reaction mixture was partitioned between water (100 mL) and EtOAc (150 mL). The phases were separated and the aqueous phase was extracted aqueous with EtOAc (2×50 mL). The combined organic phases were washed with saturated NaHCO$_3$ (100 mL), dried (MgSO$_4$), filtered, and concentrated. The crude material was purified by Redi-Sep 330 silica gel column, eluting with 10% EtOAc/hexanes. Yield: 4.4 g (24%).

Step B: Preparation of 6,7-difluoro-4,4-dimethyl-1,2,3,4-tetrahydronaphthalen-1-ol: A round bottomed flask was charged with 6,7-difluoro-4,4-dimethyl-3,4-dihydronaphthalen-1(2H)-one (4.4 g, 21 mmol) and MeOH (75 mL). Next added NaBH$_4$ (0.87 g, 23 mmol) in portions over a 15 minute period. The reaction mixture was stirred at ambient temperature for 3 hours and then concentrated under vacuum. The residue was partitioned between 2N NaOH (30 mL) and EtOAc (50 mL). The phases were separated and the aqueous phase was extracted with EtOAc (50 mL). The combined organic phases were washed with brine (30 mL), dried (MgSO4), filtered, and concentrated. Yield: 4.6 g (93%).

Step C: Preparation of 6,7-difluoro-1,1-dimethyl-1,2-dihydronaphthalene: A round bottomed flask was charged with 6,7-difluoro-4,4-dimethyl-1,2,3,4-tetrahydronaphthalen-1-ol (4.4 g, 21 mmol), 1,2-dichloroethane (50 mL) and 4-methylbenzenesulfonic acid hydrate (0.20 g, 1.0 mmol). The reaction mixture was heated to 60° C. for 1 hour. The reaction mixture was allowed to cool to ambient temperature. The crude reaction mixture was used directly into the next step without workup.

Step D: Preparation of 5,6-difluoro-3,3-dimethyl-1a,2,3,7b-tetrahydronaphtho[1,2-b]oxirene: The reaction mixture from Step C was cooled in an ice bath and saturated aqueous NaHCO$_3$ (50 mL) was added. 3-chlorobenzoperoxoic acid (5.6 g, 23 mmol) was added in portions over a 10 min period, and the reaction mixture was allowed to warm to ambient temperature and was stirred vigorously overnight. The reaction mixture was filtered through GF/F paper, rinsing with DCM. The phases were separated and the aqueous phase was extracted with DCM (50 mL). The combined organic phases were washed with 1N NaOH (50 mL). The resulting emulsion was filtered through GF/F paper which allowed the phases to separate. The organic phase was dried over Na2SO4, filtered, and concentrated in vacuo (rotary evaporator, water temperature was set to 30° C. to avoid loss of product). The crude material was placed under high vacuum for 10 minutes to provide 5.7 g of crude product, which was used the next step without purification.

Step E: Preparation of trans-1-amino-6,7-difluoro-4,4-dimethyl-1,2,3,4-tetrahydronaphthalen-2-ol: A stainless steel bomb equipped with a Teflon insert and a stir bar was charged with 5,6-difluoro-3,3-dimethyl-1a,2,3,7b-tetrahydronaphtho[1,2-b]oxirene (4.3 g, 20 mmol), using a few mL's of EtOH to transfer, followed by addition aqueous ammonium hydroxide (30 mL). The reaction mixture was heated to 90° C. in an oil bath overnight with stirring. The reaction mixture was cooled to ambient temperature and the bomb was placed in an ice bath before opening. The contents of the bomb were transferred to a round bottomed flask (using EtOH to rinse the bomb) and concentrated in vacuo. EtOH (3×30 mL) was used to azeotrope residual water and ammonium hydroxide. The residue was partitioned between 2N aqueous HCl (75 mL) and diethyl ether (75 mL). The phases were separated and the organic phase was extracted with 1N HCl (25 mL). The combined organic phases were extracted with diethyl ether (50 mL). The aqueous phase was chilled in an ice bath and basified with NaOH pellets (added 5-6 at a time with some sonication to dissolve, until pH was >12). The product precipitated out of the basic aqueous phase. The product was extracted with 2:1 diethyl ether/EtOAc (3×50 mL). The combined organic phases were dried (Na2SO4), filtered, and concentrated to give the desired product. Yield: 1.7 g (33%).

Step F: Preparation of 5-(3-((1,2-trans)-6,7-difluoro-2-hydroxy-4,4-dimethyl-1,2,3,4-tetrahydronaphthalen-1-yl)ureido)-N,4-dimethyl-1-phenyl-1H-pyrazole-3-carboxamide: A vial was charged with 5-amino-N,4-dimethyl-1-phenyl-1H-pyrazole-3-carboxamide (Intermediate 10; 25 mg, 0.11 mmol), DCM (0.5 mL) and N-ethyl-N-isopropylpropan-2-amine (58 µL, 0.33 mmol). Triphosgene (20 mg, 0.066 mmol) was added, and the reaction mixture was stirred for 15 minutes. trans-1-amino-6,7-difluoro-4,4-dimethyl-1,2,3,4-tetrahydronaphthalen-2-ol (25 mg, 0.11 mmol) was added, followed by N-ethyl-N-isopropylpropan-2-amine (58 µL, 0.33 mmol). The reaction mixture was stirred over the weekend for convenience. The reaction mixture was diluted with water and DCM. The phases were separated and the aqueous phase was extracted with DCM. The combined organic phases were dried (MgSO$_4$), filtered, and concentrated. The crude material was purified by preparative HPLC using reverse phase YMC ODS-AQ (250×20 mm) column. Fractions containing the product were pooled and concentrated, and then partitioned between EtOAc (10 mL) and saturated NaHCO$_3$ (10 mL). The aqueous phase was extracted with EtOAc (2×10 mL). The combined organic phases were dried (MgSO4), filtered, and concentrated. The product was further purified by preparative TLC (0.5 mm thickness, Rf=0.60) eluting with 10% MeOH/DCM. Yield: 9 mg (17%). MS m/z (APCI-neg) M−1=482.2.

Example 80

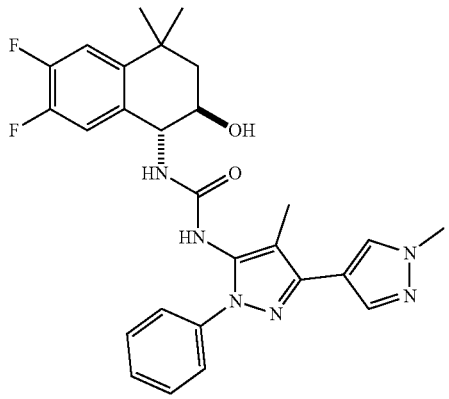 [SMILES: Cc1c(-c2cnn(C)c2)nn(-c2ccccc2)c1NC(=O)N[C@@H]1c2cc(F)c(F)cc2C(C)(C)C[C@H]1O]

1-((1,2-trans)-6,7-difluoro-2-hydroxy-4,4-dimethyl-1,2,3,4-tetrahydronaphthalen-1-yl)-3-(1',4-dimethyl-1-phenyl-1H,1'H-[3,4'-bipyrazol]-5-yl)urea The title compound was prepared from (1,2-trans)-1-amino-6,7-difluoro-4,4-dimethyl-1,2,3,4-tetrahydronaphthalen-2-ol (Example 79, Step E; 25 mg, 0.11 mmol) and 1',4-dimethyl-1-phenyl-1H,1H-[3,4'-bipyrazol]-5-amine (Intermediate 12, Step C; 28 mg, 0.11 mmol) according to the procedure described for Example 79, Step F. Yield: 9 mg (16%). MS m/z (APCI-pos) M+1=507.2.

Example 81

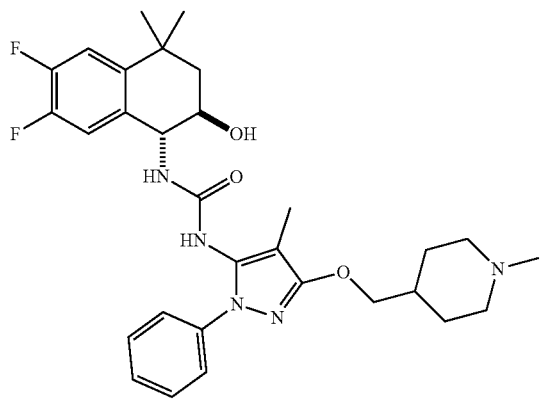 [SMILES: Cc1c(OCC2CCN(C)CC2)nn(-c2ccccc2)c1NC(=O)N[C@@H]1c2cc(F)c(F)cc2C(C)(C)C[C@H]1O]

1-((1,2-trans)-6,7-difluoro-2-hydroxy-4,4-dimethyl-1,2,3,4-tetrahydronaphthalen-1-yl)-3-(4-methyl-3-((1-methylpiperidin-4-yl)methoxy)-1-phenyl-1H-pyrazol-5-yl)urea The title compound was prepared from (1,2-trans)-1-amino-6,7-difluoro-4,4-dimethyl-1,2,3,4-tetrahydronaphthalen-2-ol (Example 79, Step E; 25 mg, 0.11 mmol) and 4-methyl-3-((1-methylpiperidin-4-yl)methoxy)-1-phenyl-1H-pyrazol-5-amine (Intermediate Y3; 33 mg, 0.11 mmol) according to the procedure described for Example 79, Step F. Yield: 10 mg (16%). MS m/z (APCI-pos) M+1=554.3.

Example 82

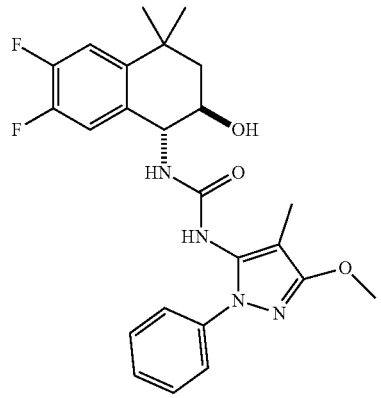 [SMILES: COc1nn(-c2ccccc2)c(NC(=O)N[C@@H]2c3cc(F)c(F)cc3C(C)(C)C[C@H]2O)c1C]

1-((1,2-trans)-6,7-difluoro-2-hydroxy-4,4-dimethyl-1,2,3,4-tetrahydronaphthalen-1-yl)-3-(3-methoxy-4-methyl-1-phenyl-1H-pyrazol-5-yl)urea The title compound was prepared from trans-1-amino-6,7-difluoro-4,4-dimethyl-1,2,3,4-tetrahydronaphthalen-2-ol (Example 79, Step E; 25 mg, 0.11 mmol) and 3-methoxy-4-methyl-1-phenyl-1H-pyrazol-5-amine (Intermediate 2; 22 mg, 0.11 mmol) according to the procedure described for Example 79, Step F. Yield: 6 mg (12%). MS m/z (APCI-neg) M−1=455.1.

Example 83

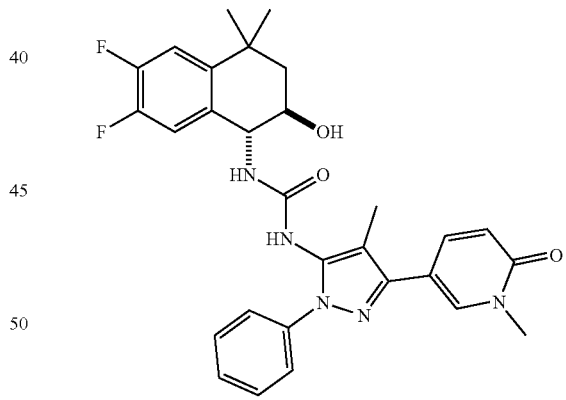

1-((1,2-trans)-6,7-difluoro-2-hydroxy-4,4-dimethyl-1,2,3,4-tetrahydronaphthalen-1-yl)-3-(4-methyl-3-(1-methyl-6-oxo-1,6-dihydropyridin-3-yl)-1-phenyl-1H-pyrazol-5-yl)urea The title compound was prepared from trans-1-amino-6,7-difluoro-4,4-dimethyl-1,2,3,4-tetrahydronaphthalen-2-ol (Example 79, Step E; 25 mg, 0.11 mmol) and 5-(5-amino-4-methyl-1-phenyl-1H-pyrazol-3-yl)-1-methylpyridin-2(1H)-one (Intermediate 7; 31 mg, 0.11 mmol) according to the procedure described for Example 79, Step F. Yield: 2 mg (3%). MS m/z (APCI-neg) M−1=532.2.

Example 84

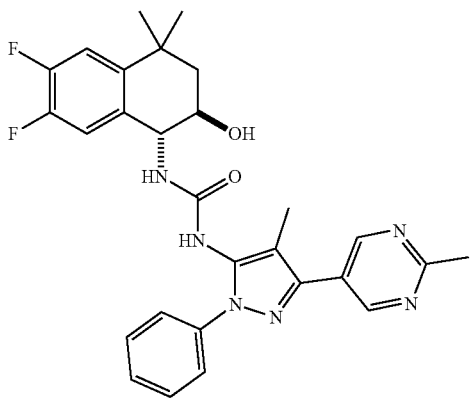 [SMILES: Cc1ncc(-c2nn(-c3ccccc3)c(NC(=O)N[C@@H]3c4cc(F)c(F)cc4C(C)(C)C[C@H]3O)c2C)cn1]

1-((1,2-trans)-6,7-difluoro-2-hydroxy-4,4-dimethyl-1,2,3,4-tetrahydronaphthalen-1-yl)-3-(4-methyl-3-(2-methylpyrimidin-5-yl)-1-phenyl-1H-pyrazol-5-yl)urea The title compound was prepared from trans-1-amino-6,7-difluoro-4,4-dimethyl-1,2,3,4-tetrahydronaphthalen-2-ol (Example 79, Step E; 25 mg, 0.11 mmol) and 4-methyl-3-(2-methylpyrimidin-5-yl)-1-phenyl-1H-pyrazol-5-amine (Intermediate Y4, 29 mg, 0.11 mmol) according to the procedure described for Example 79, Step F. Yield: 8 mg (14%). MS m/z (APCI-neg) M−1=517.2.

Example 85

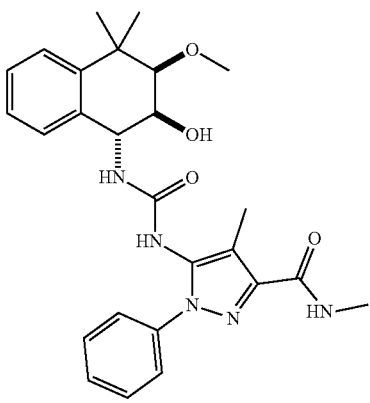 [SMILES: CNC(=O)c1nn(-c2ccccc2)c(NC(=O)N[C@@H]2c3ccccc3C(C)(C)[C@@H](OC)[C@H]2O)c1C]

5-(3-((r-1,t-2,t-3)-2-hydroxy-3-methoxy-4,4-dimethyl-1,2,3,4-tetrahydronaphthalen-1-yl)ureido)-N,4-dimethyl-1-phenyl-1H-pyrazole-3-carboxamide Step A: Preparation of 1-methylnaphthalen-2-ol: A round bottomed flask was charged with naphthalen-2-ol (100 g, 694 mmol) and anhydrous MeOH (250 mL). The solution was chilled in an ice bath and sodium methanolate (158 mL, 694 mmol; 25 wt % in MeOH) was added by addition funnel over 1 hour under a stream of $N_2$ with stirring. The ice bath was removed and the reaction mixture was stirred for 30 minutes at ambient temperature. The reaction mixture was concentrated mixture in vacuo, using toluene (3×150 mL) to azeotrope residual MeOH. The resulting solids were dried under high vacuum. The solids were suspended in anhydrous toluene (500 mL), and iodomethane (129 mL, 2076 mmol) was added while stirring. The mixture was heated to reflux (oil bath temp=70° C.) under $N_2$ overnight. Due to incomplete reaction, additional iodomethane (100 mL) was added, and the reaction mixture was heated at 70-75° C. for 2 days. The reaction mixture was cooled to ambient temperature and concentrated in vacuo. The residue was partitioned between 1N NaOH (600 mL) and diethyl ether (400 mL). The phases were separated and the organic phase was extracted with 1N NaOH (200 mL). The combined aqueous phases were extracted with diethyl ether (300 mL) The aqueous phases was then chilled in an ice bath, and carefully acidified with concentrated HCl (approximately 70 mL), and then extracted with diethyl ether (3×100 mL). The combined organic phases were dried (MgSO$_4$), filtered, and concentrated, then dried under high vacuum for one hour to provide 57.8 g of brown solids containing a 69:31 ratio of desired 1-methylnaphthalen-2-ol to starting material naphthalen-2-ol was obtained. The mixture was carried forward to the next step without separation.

Step B: Preparation of 1,1-dimethylnaphthalen-2(1H)-one: A round bottomed flask was charged with 1-methyl-naphthalen-2-ol from Step A (57.8 g, 365 mmol) and anhydrous MeOH (100 mL). The solution was chilled in an ice bath and sodium methanolate (83.1 mL, 365 mmol; 25 wt % in MeOH) was added dropwise under $N_2$ by addition funnel while stirring. The ice bath was removed and the reaction mixture was stirred for 30 minutes at ambient temperature, then concentrated in vacuo. Toluene (3×100 mL) was used to azeotrope residual MeOH. To the resulting solids was added iodomethane (203 mL, 3257 mmol), and the mixture was heated to reflux (oil bath temp=50° C.) for 4 hours with stirring. Due to incomplete reaction, added toluene (300 mL) and DMF (50 mL) and increased the heat to 60° C. 1H NMR analysis of the crude indicated the starting material had been consumed. The reaction was allowed to cool to ambient temperature, then concentrated in vacuo. The residue was partitioned between 1N NaOH (300 mL) and diethyl ether (300 mL). The phases were separated and the aqueous phase was extracted with diethyl ether (2×100 mL). The combined organic phases were washed with water (200 mL), brine (200 mL), dried (MgSO$_4$), filtered, and concentrated to a dark oil (75 g). The crude material was purified by Biotage Flash 75 L silica gel column, eluting with hexanes followed by 10% EtOAc/hexanes. Yield of 1,1-dimethylnaphthalen-2(1H)-one: 6.5 g (9%). The major by-product (which eluted from silica gel column with hexanes) was 2-methoxy-1-methylnaphthalene resulting from O-methylation.

Step C: Preparation of 1,1-dimethyl-1,2-dihydronaphthalen-2-ol: A round bottomed flask was charged with 1,1-dimethylnaphthalen-2(1H)-one (3.4 g, 20 mmol) and MeOH (50 mL). The solution was chilled in an ice bath and NaBH$_4$ (0.76 g, 20 mmol) was added in portions over 10 minutes. The reaction mixture was stirred for 10 minutes after addition was completion. The ice bath was removed and the reaction mixture was stirred for 30 minutes at ambient temperature. The reaction mixture was chilled in ice bath and carefully quenched with 2N NaOH (20 mL), and then partially concentrated mixture in vacuo. The residue was extracted with EtOAc (3×25 mL) The combined organic phases were washed with brine (30 mL), dried (MgSO$_4$), filtered, and concentrated. Yield: 3.2 g (87%).

Step D: Preparation of 2-methoxy-1,1-dimethyl-1,2-dihydronaphthalene: A round bottomed flask was charged with 1,1-dimethyl-1,2-dihydronaphthalen-2-ol (1.74 g, 10 mmol) and anhydrous DMF (30 mL). The solution was chilled in an ice bath and sodium hydride (0.480 g, 12.0 mmol; 60% in oil) was added in portions over 10 minutes under a stream of $N_2$. The reaction mixture was stirred for 30 minutes in ice bath, then added iodomethane (0.93 mL, 15 mmol). The ice bath was removed and the reaction mixture was warmed to ambient temperature and stirred for 30 minutes. The reaction mixture was carefully quenched with saturated aqueous NH₄Cl (20 mL), and the aqueous layer was extracted with EtOAc (2×30 mL). The combined organic phases were washed with water (2×20 mL), brine (20 mL), dried (MgSO₄), filtered, and concentrated to provide the desired product. Yield: 1.98 g (95%).

Step E: Preparation of (r-1a,c-2,c-7b)-2-methoxy-3,3-dimethyl-1a,2,3,7b-tetrahydronaphtho[1,2-b]oxirene: 2-methoxy-1,1-dimethyl-1,2-dihydronaphthalene (1.5 g, 8.0 mmol) and 1,2-dichloroethane (50 mL) were combined in a flask, and the flask was placed in an ice bath. Saturated aqueous NaHCO₃ (50 mL) was added, followed by addition of 3-chlorobenzoperoxoic acid (3.9 g, 16 mmol). The reaction mixture was allowed to warm to ambient temperature and was stirred overnight. The mixture was diluted with water (30 mL) and DCM (30 mL). The phases were separated and the aqueous phase was extracted with DCM (30 mL). The combined organic phases were washed with 2N NaOH (30 mL), dried (MgSO₄), filtered, and concentrated to provide the desired product. Yield: 1.8 g. Relative stereochemical assignments were based on NOE correlations between the gem-dimethyl hydrogen atoms and the saturated ring hydrogen atoms. The crude product carried into next step without purification.

Step F: Preparation of (r-1,t-2,t-3)-1-amino-3-methoxy-4,4-dimethyl-1,2,3,4-tetrahydronaphthalen-2-ol: Title compound prepared from (r-1a,c-2,c-7b)-2-methoxy-3,3-dimethyl-1a,2,3,7b-tetrahydronaphtho[1,2-b]oxirene (1.6 g, 7.83 mmol) according to the procedure described for Example 79, Step E. Yield: 538 mg (28%).

Step G: Preparation of 5-(3-((r-1,t-2,t-3)-2-hydroxy-3-methoxy-4,4-dimethyl-1,2,3,4-tetrahydronaphthalen-1-yl)ureido)-N,4-dimethyl-1-phenyl-1H-pyrazole-3-carboxamide: Title compound prepared from (r-1,t-2,t-3)-1-amino-3-methoxy-4,4-dimethyl-1,2,3,4-tetrahydronaphthalen-2-ol from Step F (20 mg, 0.090 mmol) and 5-amino-N,4-dimethyl-1-phenyl-1H-pyrazole-3-carboxamide (Intermediate 10; 21 mg, 0.090 mmol) according to the procedure described for Example 79, Step F. Yield: 12 mg (27%). MS m/z (APCI-neg) M−1=476.2.

Example 86

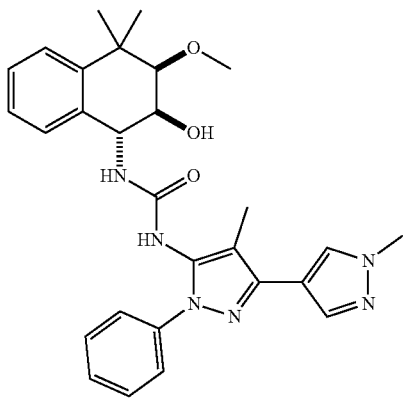 [SMILES: CO[C@H]1[C@@H](O)[C@H](NC(=O)Nc2c(C)c(-c3cnn(C)c3)nn2-c2ccccc2)c2ccccc2C1(C)C]

1-(1',4-dimethyl-1-phenyl-1H,1'H-[3,4'-bipyrazol]-5-yl)-3-((r-1,t-2,t-3)-2-hydroxy-3-methoxy-4,4-dimethyl-1,2,3,4-tetrahydronaphthalen-1-yl)urea The title compound was prepared from (r-1,t-2,t-3)-1-amino-3-methoxy-4,4-dimethyl-1,2,3,4-tetrahydronaphthalen-2-ol (Example 85, Step F; 20 mg, 0.090 mmol) and 1',4-dimethyl-1-phenyl-1H,1'H-[3,4'-bipyrazol]-5-amine (Intermediate 12, Step C; 23 mg, 0.090 mmol) according to the procedure described for Example 79, Step F. Yield: 10 mg (22%). MS m/z (APCI-pos) M+1=501.2.

Example 87

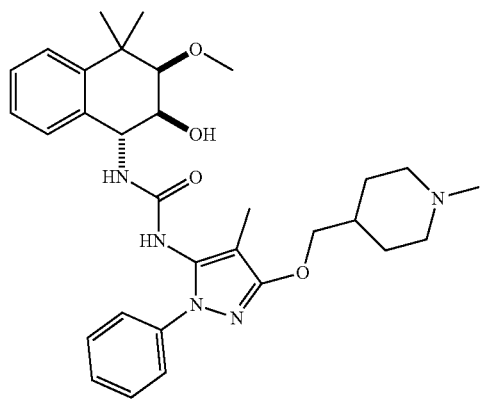 [SMILES: CO[C@H]1[C@@H](O)[C@H](NC(=O)Nc2c(C)c(OCC3CCN(C)CC3)nn2-c2ccccc2)c2ccccc2C1(C)C]

1-((r-1,t-2,t-3)-2-hydroxy-3-methoxy-4,4-dimethyl-1,2,3,4-tetrahydronaphthalen-1-yl)-3-(4-methyl-3-((1-methylpiperidin-4-yl)methoxy)-1-phenyl-1H-pyrazol-5-yl)urea The title compound was prepared from (r-1,t-2,t-3)-1-amino-3-methoxy-4,4-dimethyl-1,2,3,4-tetrahydronaphthalen-2-ol (Example 85, Step F; 20 mg, 0.090 mmol) and 4-methyl-3-((1-methylpiperidin-4-yl)methoxy)-1-phenyl-1H-pyrazol-5-amine (Intermediate Y3; 27 mg, 0.090 mmol) according to the procedure described for Example 79, Step F. Yield: 12 mg (24%). MS m/z (APCI-pos) M+1=548.3.

Example 88

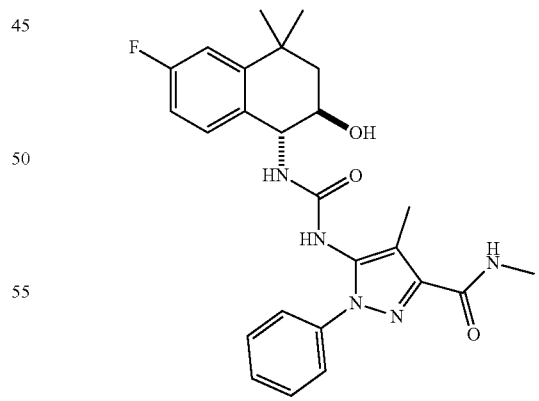

5-(3-((1,2-trans)-6-fluoro-2-hydroxy-4,4-dimethyl-1,2,3,4-tetrahydronaphthalen-1-yl)ureido)-N,4-dimethyl-1-phenyl-1H-pyrazole-3-carboxamide Step A: Preparation of 6-fluoro-4,4-dimethyl-3,4-dihydronaphthalen-1(2H)-one: 5,5-Dimethyldihydrofuran-2

(3H)-one (10.0 g, 87.6 mmol) and fluorobenzene (16.8 g, 175 mmol) were combined in a sealed tube and AlCl₃ (26.9 g, 202 mmol) added in small portions over 2 hours. The sealed tube was heated to 100° C. overnight with stirring. After cooling to ambient temperature, the reaction mixture was poured onto ice (75 mL) using more ice (50 mL) and EtOAc (100 mL) to help transfer. The phases were separated and the aqueous phase was extracted with EtOAc (2×25 mL). The combined organic phases were washed with saturated aqueous NaHCO₃ (50 mL). The resulting emulsion was filtered through GF/F paper, rinsing with EtOAc. The phases were separated and the organic phase was dried (MgSO4) filtered, and concentrated. The crude material was purified by Redi-Sep 330 silica gel column, eluting with a gradient of 5%-10% EtOAc/hexanes. ¹H NMR indicated a 70:30 ratio of two regioisomers: 6-fluoro-4,4-dimethyl-3,4-dihydronaphthalen-1(2H)-one and 7-fluoro-4,4-dimethyl-3,4-dihydronaphthalen-1(2H)-one, respectively. Yield of mixture: 2.7 g (11%). The mixture was used directly in the next step.

Step B: Preparation of 6-fluoro-4,4-dimethyl-1,2,3,4-tetrahydronaphthalen-1-ol: A round bottomed flask was charged with a 70:30 mixture of the two regioisomers from step A (6-fluoro-4,4-dimethyl-3,4-dihydronaphthalen-1 (2H)-one and 7-fluoro-4,4-dimethyl-3,4-dihydronaphthalen-1(2H)-one, respectively) (2.7 g, 14.0 mmol) and MeOH (30 mL). The solution was chilled in an ice bath. NaBH₄ (0.585 g, 15.5 mmol) was added in portions over a 15 minutes period, and the reaction mixture was stirred at ambient temperature for 2 hours. A majority of the solvent was removed in vacuo. The residue was partitioned between 2N NaOH (20 mL) and EtOAc (30 mL). The phases were separated and the aqueous phase was extracted with EtOAc (20 mL). The combined organic phases were washed with brine (20 mL), dried (MgSO₄), filtered, and concentrated. The two regioisomers were separated by RediSep 330 silica gel column eluting with a gradient of 20%-30% EtOAc/hexanes. Yield of 6-fluoro-4,4-dimethyl-1,2,3,4-tetrahydronaphthalen-1-ol: 1.48 g (49%). Yield of 7-fluoro-4,4-dimethyl-1,2,3,4-tetrahydronaphthalen-1-ol: 601 mg (13%).

Step C: Preparation of 7-fluoro-1,1-dimethyl-1,2-dihydronaphthalene: A round bottomed flask was charged with 6-fluoro-4,4-dimethyl-1,2,3,4-tetrahydronaphthalen-1-ol (1.48 g, 7.62 mmol), 1,2-dichloroethane (20 mL) and 4-methylbenzenesulfonic acid hydrate (0.0725 g, 0.381 mmol). The reaction mixture was heated to 60° C. for 1 hour. The reaction mixture was cooled to ambient temperature, and then used directly into next step without workup or purification.

Step D: Preparation of 5-fluoro-3,3-dimethyl-1a,2,3,7b-tetrahydronaphtho[1,2-b]oxirene: The reaction mixture containing 7-fluoro-1,1-dimethyl-1,2-dihydronaphthalene from Step C (1.34 g, 7.60 mmol) was stirred in an ice bath and saturated aqueous NaHCO₃ (20 mL) was added. 3-Chlorobenzoperoxoic acid (2.81 g, 11.4 mmol) was added and the reaction mixture was allowed to warm to ambient temperature, and stirring was continued overnight. The reaction mixture diluted with water (20 mL) and DCM (20 mL). The phases were separated and the aqueous phase was extracted with DCM (20 mL). The combined organic phases were washed with 2N NaOH (20 mL), dried (MgSO₄), filtered, and concentrated. The crude was used in the next step without purification. Yield: 1.49 g (71%).

Step E: Preparation of trans-1-amino-6-fluoro-4,4-dimethyl-1,2,3,4-tetrahydronaphthalen-2-ol: A stainless steel bomb equipped with a Teflon insert and a stir bar was charged with 5-fluoro-3,3-dimethyl-1a,2,3,7b-tetrahydronaphtho[1,2-b]oxirene (1.46 g, 7.60 mmol) using a few mL's of EtOH to transfer, and aqueous ammonium hydroxide (15 mL). The reaction mixture was heated to 90° C. in an oil bath overnight. The reaction mixture was cooled to ambient temperature and the bomb was placed in an ice bath before opening. The contents of the bomb were transferred to a round bottomed flask using EtOH, and then concentrated in vacuo. The crude mixture was partitioned between 1N aqueous HCl (15 mL) and diethyl ether (15 mL). The phases were separated and the organic phase was extracted with 1N HCl (5 mL) The combined aqueous phases were extracted with diethyl ether (20 mL) The aqueous phases were chilled in an ice bath and basified with NaOH pellets (added a few at a time with sonication to dissolve, until pH was >12). The product precipitated out of basic aqueous phase. The product was extracted with 20% EtOAc in diethyl ether (2×20 mL). The combined organic phases were dried (MgSO₄), filtered, and concentrated in vacuo to provide the crude desired product. Yield: 572 mg (32%). The crude carried was used directly in the next step without purification.

Step F: Preparation of 5-(3-((1,2-trans)-6-fluoro-2-hydroxy-4,4-dimethyl-1,2,3,4-tetrahydronaphthalen-1-yl) ureido)-N,4-dimethyl-1-phenyl-1H-pyrazole-3-carboxamide: The title compound was prepared from trans-1-amino-6-fluoro-4,4-dimethyl-1,2,3,4-tetrahydronaphthalen-2-ol (20 mg, 0.096 mmol) and 5-amino-N,4-dimethyl-1-phenyl-1H-pyrazole-3-carboxamide (Intermediate 10, 22 mg, 0.096 mmol) according to the procedure for Example 79, Step F. Yield: 12 mg (26%). MS m/z (APCI-neg) M−1=464.2.

Example 89

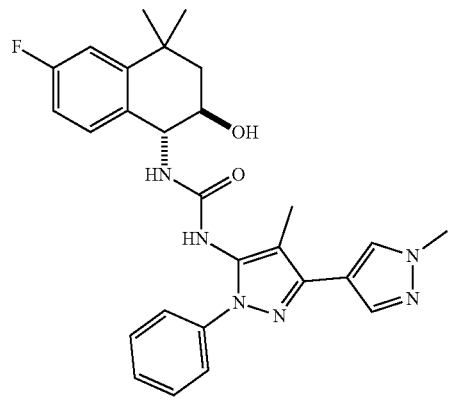 [SMILES: Cc1c(-c2cnn(C)c2)nn(-c2ccccc2)c1NC(=O)N[C@@H]1c2ccc(F)cc2C(C)(C)C[C@H]1O]

1-(1',4-dimethyl-1-phenyl-1H,1'H-[3,4'-bipyrazol]-5-yl)-3-((1,2-trans)-6-fluoro-2-hydroxy-4,4-dimethyl-1,2,3,4-tetrahydronaphthalen-1-yl)urea The title compound was prepared from trans-1-amino-6-fluoro-4,4-dimethyl-1,2,3,4-tetrahydronaphthalen-2-ol (Example 88, Step E; 20 mg, 0.096 mmol) and 1',4-dimethyl-1-phenyl-1H,1'H-[3,4'-bipyrazol]-5-amine (Intermediate 12, 24 mg, 0.096 mmol) according to the procedure for Example 79, Step F. Yield: 9 mg (19%). MS m/z (APCI-pos) M+1=489.2.

Example 90

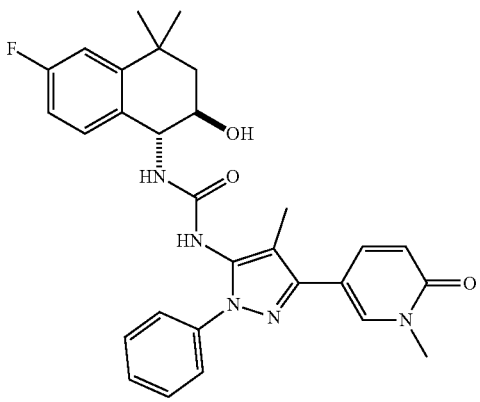 [SMILES: Cc1c(-c2ccc(=O)n(C)c2)nn(-c2ccccc2)c1NC(=O)N[C@@H]1c2ccc(F)cc2C(C)(C)C[C@H]1O]

1-(1,2-trans)-6-fluoro-2-hydroxy-4,4-dimethyl-1,2,3,4-tetrahydronaphthalen-1-yl)-3-(4-methyl-3-(1-methyl-6-oxo-1,6-dihydropyridin-3-yl)-1-phenyl-1H-pyrazol-5-yl)urea The title compound was prepared from trans-1-amino-6-fluoro-4,4-dimethyl-1,2,3,4-tetrahydronaphthalen-2-ol (Example 88, Step E; 20 mg, 0.096 mmol) and 5-(5-amino-4-methyl-1-phenyl-1H-pyrazol-3-yl)-1-methylpyridin-2(1H)-one (Intermediate 7, 27 mg, 0.096 mmol) according to the procedure for Example 79, Step F. Yield: 11 mg (22%). MS m/z (APCI-neg) M−1=514.2.

Example 91

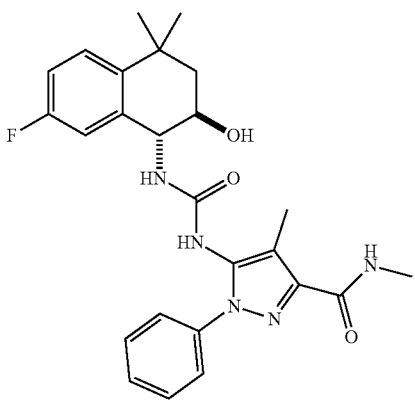 [SMILES: CNC(=O)c1nn(-c2ccccc2)c(NC(=O)N[C@@H]2c3cc(F)ccc3C(C)(C)C[C@H]2O)c1C]

5-(3-((1,2-trans)-7-fluoro-2-hydroxy-4,4-dimethyl-1,2,3,4-tetrahydronaphthalen-1-yl)ureido)-N,4-dimethyl-1-phenyl-1H-pyrazole-3-carboxamide Step A: Preparation of 6-fluoro-1,1-dimethyl-1,2-dihydronaphthalene: Prepared from 7-fluoro-4,4-dimethyl-1,2,3,4-tetrahydronaphthalen-1-ol (Example 88, Step B; 601 mg, 3.09 mmol) according to the procedure for Example 88, Step C. Crude reaction mixture was carried forward into next step without workup or purification.

Step B: Preparation of 6-fluoro-3,3-dimethyl-1a,2,3,7b-tetrahydronaphtho[1,2-b]oxirene: Prepared from the crude reaction mixture containing 6-fluoro-1,1-dimethyl-1,2-dihydronaphthalene from Step A according to the procedure for Example 88, Step D. Purified crude by Red-Sep 120 silica gel column eluting with a gradient of 5%-10% EtOAc/ hexanes. Yield: 110 mg (17%). Structural assignment was based on $^1$H NMR NOE correlations.

Step C: Preparation of trans-1-amino-7-fluoro-4,4-dimethyl-1,2,3,4-tetrahydronaphthalen-2-ol: Prepared from 6-fluoro-3,3-dimethyl-1a,2,3,7b-tetrahydronaphtho[1,2-b]oxirene (110 mg, 0.572 mmol) according to the procedure for Example 88, Step E. Yield: 93 mg (70%).

Step D: Preparation of 5-(3-((1,2-trans)-7-fluoro-2-hydroxy-4,4-dimethyl-1,2,3,4-tetrahydronaphthalen-1-yl) ureido)-N,4-dimethyl-1-phenyl-1H-pyrazole-3-carboxamide: Prepared from trans-1-amino-7-fluoro-4,4-dimethyl-1,2,3,4-tetrahydronaphthalen-2-ol (20 mg, 0.096 mmol) and 5-amino-N,4-dimethyl-1-phenyl-1H-pyrazole-3-carboxamide (Intermediate 10, 22 mg, 0.096 mmol) according to the procedure for Example 7, Step F. Yield: 9 mg (20%). MS m/z (APCI-neg) M−1=464.2.

Example 92

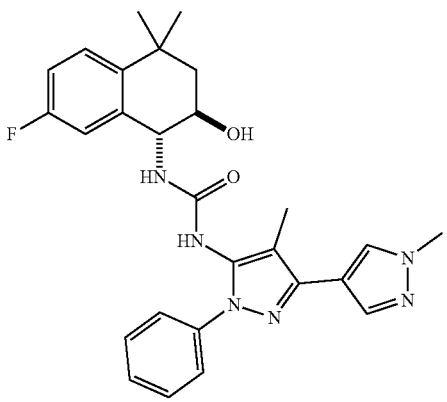 [SMILES: Cc1c(-c2cnn(C)c2)nn(-c2ccccc2)c1NC(=O)N[C@@H]1c2cc(F)ccc2C(C)(C)C[C@H]1O]

1-(1',4-dimethyl-1-phenyl-1H,1'H-[3,4'-bipyrazol]-5-yl)-3-((1,2-trans)-7-fluoro-2-hydroxy-4,4-dimethyl-1,2,3,4-tetrahydronaphthalen-1-yl)urea The title compound was prepared from trans-1-amino-7-fluoro-4,4-dimethyl-1,2,3,4-tetrahydronaphthalen-2-ol (Example 91, Step C; 20 mg, 0.096 mmol) and 1',4-dimethyl-1-phenyl-1H,1'H-[3,4'-bipyrazol]-5-amine (Intermediate 12, 24 mg, 0.096 mmol) according to the procedure for Example 79, Step F. Yield: 12 mg (24%). MS m/z (APCI-pos) M+1=489.2.

Example 93

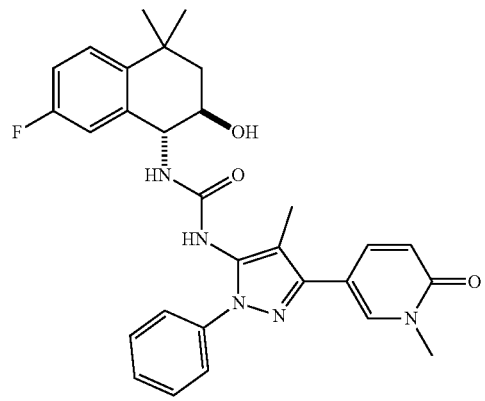 [SMILES: Cc1c(-c2ccc(=O)n(C)c2)nn(-c2ccccc2)c1NC(=O)N[C@@H]1c2cc(F)ccc2C(C)(C)C[C@H]1O]

1-((1,2-trans)-7-fluoro-2-hydroxy-4,4-dimethyl-1,2,3,4-tetrahydronaphthalen-1-yl)-3-(4-methyl-3-(1-methyl-6-oxo-1,6-dihydropyridin-3-yl)-1-phenyl-1H-pyrazol-5-yl)urea The title compound was prepared from trans-1-amino-7-fluoro-4,4-dimethyl-1,2,3,4-tetrahydronaphthalen-2-ol (Example 91, Step C; 20 mg, 0.096 mmol) and 5-(5-amino-4-methyl-1-phenyl-1H-pyrazol-3-yl)-1-methylpyridin-2(1H)-one (Intermediate 7, 27 mg, 0.096 mmol) according to the procedure for Example 79, Step F. Yield: 10 mg (19%). MS m/z (APCI-neg) M−1=514.2.

Example 94

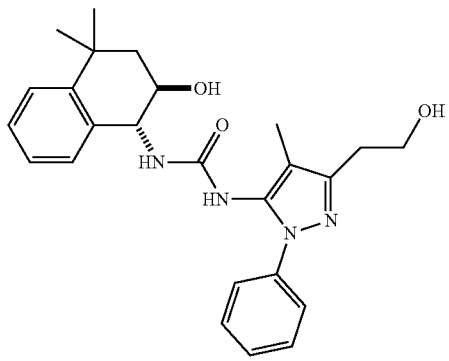 [SMILES: Cc1c(CCO)nn(-c2ccccc2)c1NC(=O)N[C@@H]1c2ccccc2C(C)(C)C[C@H]1O]

1-(trans-2-hydroxy-4,4-dimethyl-1,2,3,4-tetrahydronaphthalen-1-yl)-3-(3-(2-hydroxyethyl)-4-methyl-1-phenyl-1H-pyrazol-5-yl)urea Step A: Preparation of 1-(3-(2-((tert-butyldimethylsilyl)oxy)ethyl)-4-methyl-1-phenyl-1H-pyrazol-5-yl)-3-(trans-2-hydroxy-4,4-dimethyl-1,2,3,4-tetrahydronaphthalen-1-yl)urea: A mixture of phenyl (3-(2-((tert-butyldimethylsilyl)oxy)ethyl)-4-methyl-1-phenyl-1H-pyrazol-5-yl)carbamate (13.4 mg, 0.03 mmol), trans-1-amino-4,4-dimethyl-1,2,3,4-tetrahydronaphthalen-2-ol (Intermediate X1, 12.5 mg, 0.033 mmol) and triethylamine (15.0 mg, 0.15 mmol) were combined in 0.2 mL of DMF and stirred at ambient temperature for 1 hour. The mixture was loaded onto a samplet and purified by reverse-phase column chromatography, eluting with 0-70% acetonitrile/water, to afford the title compound (7.5 mg, 0.014 mmol, 46% yield). MS (apci) m/z=549.3 (M+H).

Step B: Preparation of 1-(trans-2-hydroxy-4,4-dimethyl-1,2,3,4-tetrahydronaphthalen-1-yl)-3-(3-(2-hydroxyethyl)-4-methyl-1-phenyl-1H-pyrazol-5-yl)urea: 1-(3-(2-((tert-butyldimethylsilyl)oxy)ethyl)-4-methyl-1-phenyl-1H-pyrazol-5-yl)-3-(trans-2-hydroxy-4,4-dimethyl-1,2,3,4-tetrahydronaphthalen-1-yl)urea (7.0 mg, 0.0128 mmol) and HCl (21.3 µL, 0.128 mmol) (in IPA) were combined in 1 mL of DCM and stirred at ambient temperature for 1 hour. The mixture was concentrated and purified by reverse-phase column chromatography, eluting with 0-60% acetonitrile/water, to afford the title compound (2.3 mg, 0.00529 mmol, 41.5% yield). MS (apci) m/z=435.2 (M+H).

Example 95

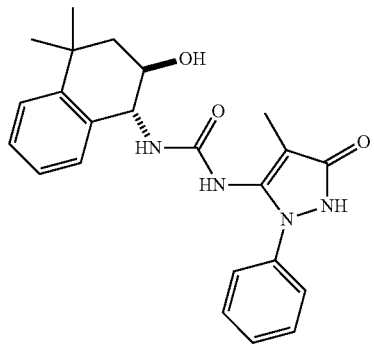

1-(trans-2-hydroxy-4,4-dimethyl-1,2,3,4-tetrahydronaphthalen-1-yl)-3-(4-methyl-5-oxo-2-phenyl-2,5-dihydro-1H-pyrazol-3-yl)urea CDI (565.6 mg, 3.488 mmol), 5-amino-4-methyl-1-phenyl-1H-pyrazol-3(2H)-one (Intermediate 2, Step A, 300 mg, 1.586 mmol) and NEt₃ (497.2 µL, 3.567 mmol) were combined in 3 mL of DMF and stirred at ambient temperature overnight. Additional CDI (200 mg) was added and the reaction stirred for 3 days. 1 mL of the resultant solution was added to a solution of trans-1-amino-4,4-dimethyl-1,2,3,4-tetrahydronaphthalen-2-ol (Intermediate X1, 50 mg, 0.26 mmol) and NEt₃ (109 µL, 0.78 mmol) in 0.2 mL of DMF. The mixture was and stirred at ambient temperature for 1 hour, loaded onto a samplet and purified by reverse-phase column chromatography, eluting with 0-70% acetonitrile/water, to afford the title compound (36 mg, 0.089 mmol, 34% yield). MS (apci) m/z=407.2 (M+H).

Example 96

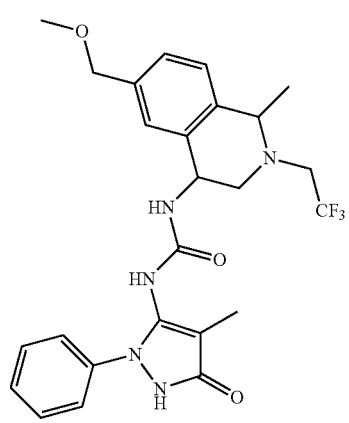 [SMILES: COCc1ccc2c(c1)C(NC(=O)Nc1c(C)c(=O)[nH]n1-c1ccccc1)CN(CC(F)(F)F)C2C]

1-(6-(methoxymethyl)-1-methyl-2-(2,2,2-trifluoroethyl)-1,2,3,4-tetrahydroisoquinolin-4-yl)-3-(4-methyl-5-oxo-2-phenyl-2,5-dihydro-1H-pyrazol-3-yl)urea CDI (565.6 mg, 3.488 mmol), 5-amino-4-methyl-1-phenyl-1H-pyrazol-3(2H)-one (Intermediate 2, Step A, 300 mg, 1.586 mmol) and NEt₃ (497 µL, 3.567 mmol) were combined in 3 mL of DMF and stirred at ambient temperature overnight. Additional CDI (200 mg) was added and the reaction stirred for 3 days. 0.1 mL of the resultant solution were added to a solution of 6-(methoxymethyl)-1-methyl-2-(2,2,2-trifluoroethyl)-1,2,3,4-tetrahydroisoquinolin-4-amine (10 mg, 0.035 mmol), and NEt$_3$ (11 µL, 0.078 mmol) in 0.1 mL of DMF. The mixture was and stirred at ambient temperature for 1 hour, loaded onto a samplet and purified by reverse-phase column chromatography, eluting with 0-50% acetonitrile/water, to afford the title compound (6.9 mg, 0.014 mmol, 40% yield). MS (apci) m/z=504.2 (M+H).

Example 97

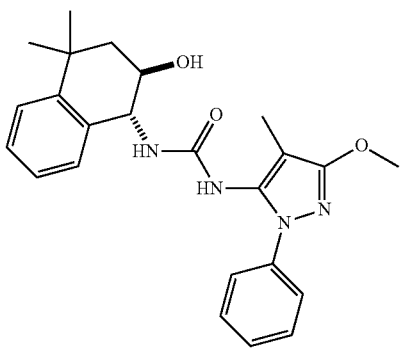

1-(trans-2-hydroxy-4,4-dimethyl-1,2,3,4-tetrahydronaphthalen-1-yl)-3-(3-methoxy-4-methyl-1-phenyl-1H-pyrazol-5-yl)urea 1-(trans-2-hydroxy-4,4-dimethyl-1,2,3,4-tetrahydronaphthalen-1-yl)-3-(4-methyl-5-oxo-2-phenyl-2,5-dihydro-1H-pyrazol-3-yl)urea (Example 95, 77 mg, 0.19 mmol) was dissolved in DCM (10 mL) and MeOH (10 mL) and a solution of TMS-Diazomethane in hexanes (142 µL, 0.28 mmol) was added dropwise. The reaction was stirred at ambient temperature for 1 hour, concentrated and purified by reverse-phase column chromatography, eluting with 0-70% acetonitrile/water, to afford the title product as white solid (40 mg, 0.095 mmol, 50% yield) (peak 2, MS (apci) m/z=421.1 (M+H)) and regioisomeric side-product 1-(1,4-dimethyl-5-oxo-2-phenyl-2,5-dihydro-1H-pyrazol-3-yl)-3-(trans-2-hydroxy-4,4-dimethyl-1,2,3,4-tetrahydronaphthalen-1-yl)urea (11 mg, 0.026 mmol, 14% yield) (peak 1, MS (apci) m/z=421.2 (M+H)).

Example 98

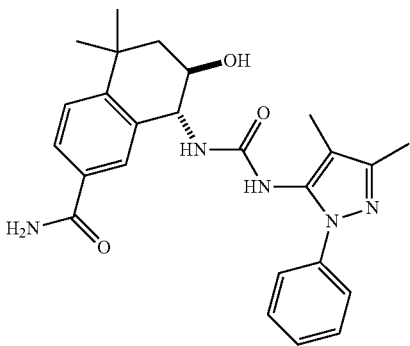

trans-8-(3-(3,4-dimethyl-1-phenyl-1H-pyrazol-5-yl)ureido)-7-hydroxy-5,5-dimethyl-5,6,7,8-tetrahydronaphthalene-2-carboxamide Step A: Preparation of methyl 3,3-dimethyl-1a,2,3,7b-tetrahydronaphtho[1,2-b]oxirene-6-carboxylate: 6-bromo-1,1-dimethyl-1,2-dihydronaphthalene (200 mg, 0.843 mmol) (prepared as described in Step B, Intermediate X4) was dissolved in THF (10 mL) and cooled to −78° C. A 1.7N solution of tert-BuLi in pentane (1.141 mL, 1.94 mmol) was added dropwise and the reaction was stirred at −78° C. for 20 minutes. Methyl chloroformate (130 µL, 1.69 mmol) was added and the reaction was allowed to warm to ambient temperature overnight, quenched with brine (10 mL) and extracted with EtOAc (2×25 mL) The combined organic extracts were filtered through phase separator paper and concentrated. The crude product was purified by silica gel column, eluting with 0-10% EtOAc/hexanes, to afford methyl 5,5-dimethyl-5,6-dihydronaphthalene-2-carboxylate (69 mg, 0.319 mmol, 37.8% yield) which was dissolved in DCM (5 mL) and NaHCO$_3$ (saturated aqueous, 5 ml) and stirred at 0° C. 3-chlorobenzoperoxoic acid (87 mg, 0.35 mmol) was added and the reaction was allowed to warm to ambient temperature overnight. The mixture was extracted with several portions of DCM, and the combined organic extracts were filtered through phase separator paper and concentrated to afford methyl 3,3-dimethyl-1a,2,3,7b-tetrahydronaphtho[1,2-b]oxirene-6-carboxylate (66 mg, 0.28 mmol, 89% yield). 1H NMR (CDCl3) 8.10-8.12 (m, 1H), 7.96-8.00 (m, 1H), 7.41-7.46 (m, 1H), 3.90-3.95 (m, 4H), 3.72-3.77 (m, 1H), 2.18-2.28 (s, 6H), 1.18-1.90 (m, 1H), 1.37 (s, 1H), 1.32 (s, 1H) ppm.

Step B: Preparation of "Solution A": CDI (144 mg, 0.534 mmol), 3,4-dimethyl-1-phenyl-1H-pyrazol-5-amine (100 mg, 0.534 mmol) and NEt$_3$ (250 µL, 1.79 mmol) were combined in 1.75 mL of DMF and stirred at ambient temperature over the weekend. The resultant solution was used in the procedure described below.

Step C: Preparation of trans-8-(3-(3,4-dimethyl-1-phenyl-1H-pyrazol-5-yl)ureido)-7-hydroxy-5,5-dimethyl-5,6,7,8-tetrahydronaphthalene-2-carboxamide: methyl 3,3-dimethyl-1a,2,3,7b-tetrahydronaphtho[1,2-b]oxirene-6-carboxylate (66 mg, 0.2841 mmol) and concentrated ammonium hydroxide (3.161 mL, 28.41 mmol) were combined in a sealed vessel and stirred in a 50° C. sand bath for 5 hour. The reaction was cooled, concentrated and dissolved in DMF (1 mL). 1052 µL, of "Solution A" were added followed by NEt$_3$ (196 µL, 1.40 mmol). The reaction was stirred at ambient temperature for 1 hour, loaded onto a samplet and purified by reverse-phase column chromatography, eluting with 0-70% acetonitrile/water, to afford the title product as white solid (4.1 mg, 0.00916 mmol, 3.26% yield) (peak 2, MS (apci) m/z=448.3 (M+H)), as well as a side-product trans-8-(3-(3,4-dimethyl-1-phenyl-1H-pyrazol-5-yl)ureido)-7-hydroxy-5,5-dimethyl-5,6,7,8-tetrahydronaphthalene-2-carboxylic acid (11.3 mg, 0.0252 mmol, 8.97% yield) (peak 1, (MS (apci) m/z=449.2 (M+H)).

Example 99

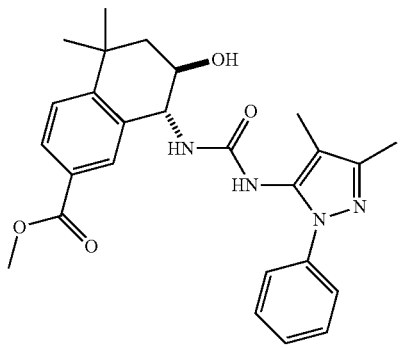

trans-methyl 8-(3-(3,4-dimethyl-1-phenyl-1H-pyrazol-5-yl)ureido)-7-hydroxy-5,5-dimethyl-5,6,7,8-tetrahydronaphthalene-2-carboxylate trans-8-(3-(3,4-dimethyl-1-phenyl-1H-pyrazol-5-yl)ureido)-7-hydroxy-5,5-dimethyl-5,6,7,8-tetrahydronaphtalene-2-carboxylic acid (Example 98 Side Product, 5.0 mg, 0.011 mmol) was dissolved in MeOH (0.5 mL) and DCM (0.5 mL) and a 2M solution of TMS-Diazomethane in hexanes (11.1 μL, 0.022 mmol) was added. The reaction was stirred for 1 hour, formic acid (1 drop) was added and the reaction was concentrated to afford trans-methyl 8-(3-(3,4-dimethyl-1-phenyl-1H-pyrazol-5-yl)ureido)-7-hydroxy-5,5-dimethyl-5,6,7,8-tetrahydronaphthalene-2-carboxylate (5.10 mg, 0.011 mmol, 98.9% yield). MS (apci) m/z=463.3 (M+H).

Example 100

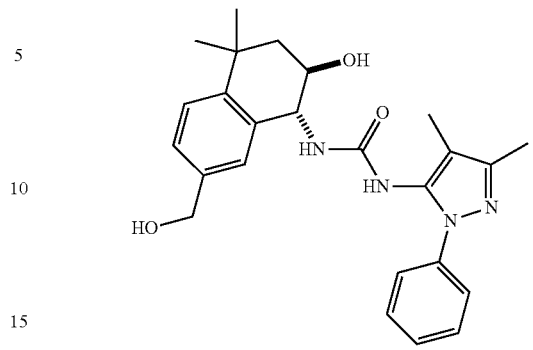

(1-(3,4-dimethyl-1-phenyl-1H-pyrazol-5-yl)-3-(trans-2-hydroxy-7-(hydroxymethyl)-4,4-dimethyl-1,2,3,4-tetrahydronaphthalen-1-yl)urea trans-methyl 8-(3-(3,4-dimethyl-1-phenyl-1H-pyrazol-5-yl)ureido)-7-hydroxy-5,5-dimethyl-5,6,7,8-tetrahydronaphthalene-2-carboxylate (10 mg, 0.0216 mmol) was dissolved in THF (1 mL) and cooled to 0° C. A 1M solution of LiAlH$_4$ in THF (21.6 μl, 0.0216 mmol) was added and the reaction was allowed to warm to ambient temperature overnight. Sodium sulfate decahydrate (69 mg, 0.22 mmol) was added and the reaction was stirred for 2 hours, filtered and concentrated. The crude product was purified by reverse-phase column chromatography, eluting with 0-60% acetonitrile/water, to afford 1-(3,4-dimethyl-1-phenyl-1H-pyrazol-5-yl)-3-(trans-2-hydroxy-7-(hydroxymethyl)-4,4-dimethyl-1,2,3,4-tetrahydronaphthalen-1-yl)urea (4.2 mg, 0.01 mmol, 44.7% yield). MS (apci) m/z=435.2 (M+H).

The compounds listed in Table 3 were prepared in a similar fashion as described in Example 1, replacing 1,2,3,4-tetrahydronaphthalen-1-amine and phenyl 1',4-dimethyl-1-phenyl-1H,1'H-3,4'-bipyrazol-5-ylcarbamate with the appropriate amine and phenylcarbamate starting materials, respectively.

TABLE 3

| Example # | Structure | Name | MS (apci) m/z |
|---|---|---|---|
| 101 | 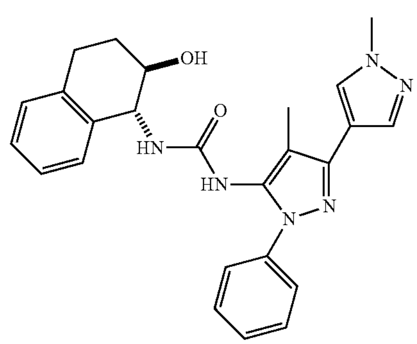 | 1-(1',4-dimethyl-1-phenyl-1H,1'H-[3,4'-bipyrazol]-5-yl)-3-(trans-2-hydroxy-1,2,3,4-tetrahydronaphthalen-1-yl)urea | 443.2 (M + H) |

TABLE 3-continued

| Example # | Structure | Name | MS (apci) m/z |
|---|---|---|---|
| 102 | 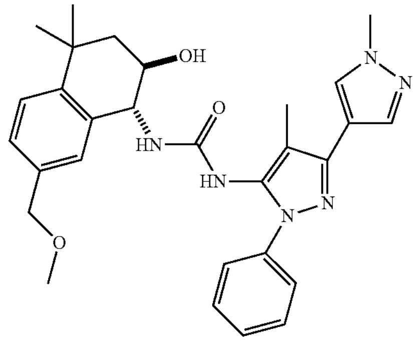 | 1-(1',4-dimethyl-1-phenyl-1H,1'H-[3,4'-bipyrazol]-5-yl)-3-(trans-2-hydroxy-7-(methoxymethyl)-4,4-dimethyl-1,2,3,4-tetrahydronaphthalen-1-yl)urea | 515.3 |
| 103 | 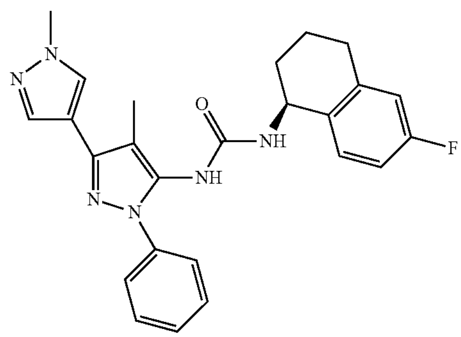 [SMILES: Cc1c(-c2cnn(C)c2)nn(-c2ccccc2)c1NC(=O)N[C@H]1CCCc2cc(F)ccc21] | (S)-1-(1',4-dimethyl-1-phenyl-1H,1'H-[3,4'-bipyrazol]-5-yl)-3-(6-fluoro-1,2,3,4-tetrahydronaphthalen-1-yl)urea | 445.2 (M + H) |
| 104 | 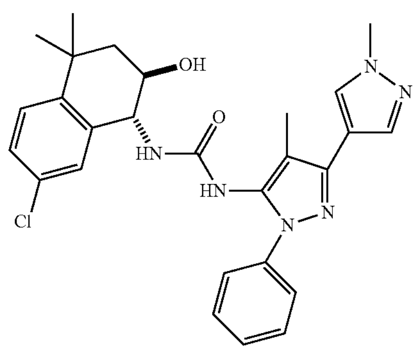 | 1-(trans-7-chloro-2-hydroxy-4,4-dimethyl-1,2,3,4-tetrahydronaphthalen-1-yl)-3-(1',4-dimethyl-1-phenyl-1H,1'H-[3,4'-bipyrazol]-5-yl)urea | 505.3 (M + H) |
| 105 | 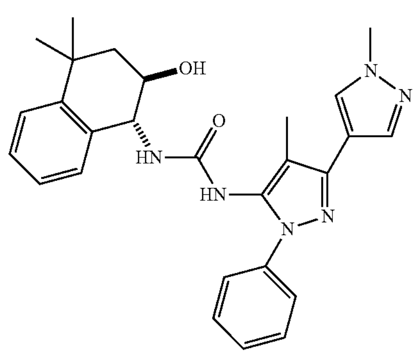 | 1-(1',4-dimethyl-1-phenyl-1H,1'H-[3,4'-bipyrazol]-5-yl)-3-(trans-2-hydroxy-4,4-dimethyl-1,2,3,4-tetrahydronaphthalen-1-yl)urea | 471.2 (M + H) |

TABLE 3-continued

| Example # | Structure | Name | MS (apci) m/z |
|---|---|---|---|
| 106 | 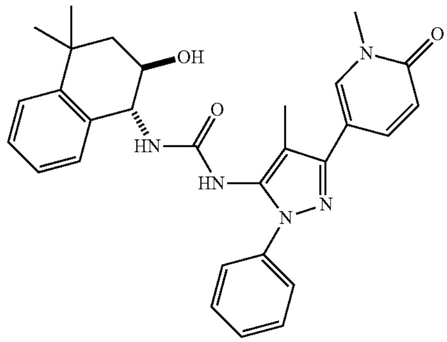 | 1-(trans-2-hydroxy-4,4-dimethyl-1,2,3,4-tetrahydronaphthalen-1-yl)-3-(4-methyl-3-(1-methyl-6-oxo-1,6-dihydropyridin-3-yl)-1-phenyl-1H-pyrazol-5-yl)urea | 496.2 (M − H) |
| 107 | 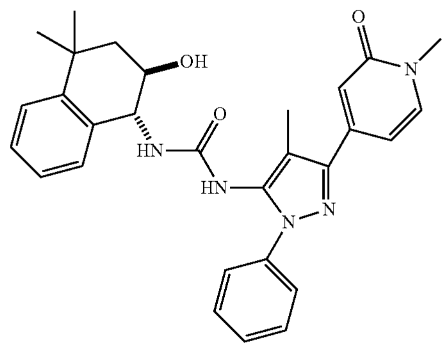 | 1-(trans-2-hydroxy-4,4-dimethyl-1,2,3,4-tetrahydronaphthalen-1-yl)-3-(4-methyl-3-(1-methyl-2-oxo-1,2-dihydropyridin-4-yl)-1-phenyl-1H-pyrazol-5-yl)urea | 496.2 (M − H) |
| 108 | 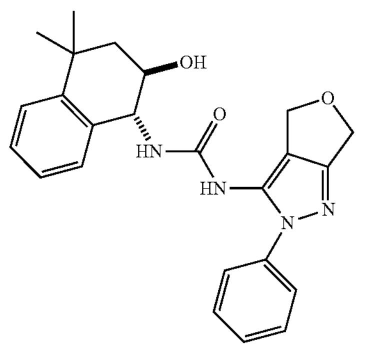 | 1-(trans-2-hydroxy-4,4-dimethyl-1,2,3,4-tetrahydronaphthalen-1-yl)-3-(2-phenyl-4,6-dihydro-2H-furo[3,4-c]pyrazol-3-yl)urea | 517.2 (M − H) |
| 109 | 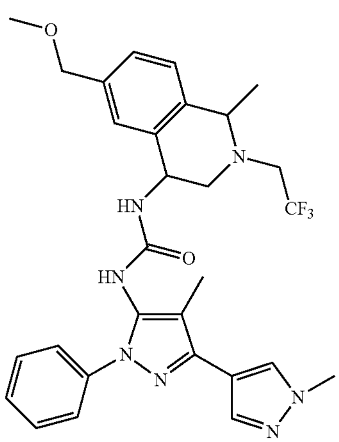 [SMILES: COCc1ccc2c(c1)C(NC(=O)Nc1c(C)c(-c3cnn(C)c3)nn1-c1ccccc1)CN(CC(F)(F)F)C2C] | 1-(1',4-dimethyl-1-phenyl-1H,1'H-[3,4'-bipyrazol]-5-yl)-3-(6-(methoxymethyl)-1-methyl-2-(2,2,2-trifluoroethyl)-1,2,3,4-tetrahydroisoquinolin-4-yl)urea | 568.3 (M + H) |

TABLE 3-continued
| Example # | Structure | Name | MS (apci) m/z |
|---|---|---|---|
| 110 | 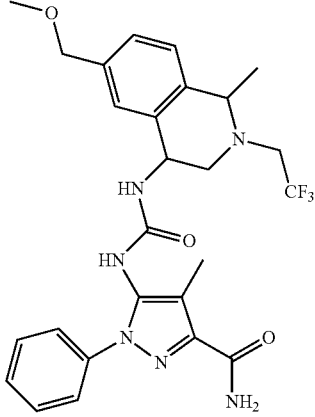 [SMILES: COCc1ccc2c(c1)C(NC(=O)Nc1c(C)c(C(N)=O)nn1-c1ccccc1)CN(CC(F)(F)F)C2C] | 5-(3-(6-(methoxymethyl)-1-methyl-2-(2,2,2-trifluoroethyl)-1,2,3,4-tetrahydroisoquinolin-4-yl)ureido)-4-methyl-1-phenyl-1H-pyrazole-3-carboxamide | 529.2 (M − H) |
| 111 | 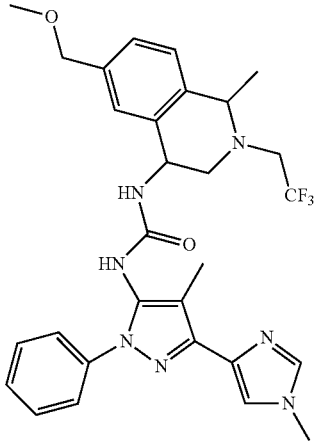 [SMILES: COCc1ccc2c(c1)C(NC(=O)Nc1c(C)c(-c3cn(C)cn3)nn1-c1ccccc1)CN(CC(F)(F)F)C2C] | 1-(6-(methoxymethyl)-1-methyl-2-(2,2,2-trifluoroethyl)-1,2,3,4-tetrahydroisoquinolin-4-yl)-3-(4-methyl-3-(1-methyl-1H-imidazol-4-yl)-1-phenyl-1H-pyrazol-5-yl)urea | 568.2 (M + H) |
| 112 | 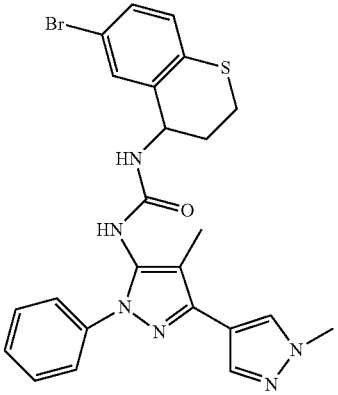 | 1-(6-bromothiochroman-4-yl)-3-(1',4-dimethyl-1-phenyl-1H,1'H-[3,4'-bipyrazol]-5-yl)urea | 523.0 525.0 (M + H) |

TABLE 3-continued

| Example # | Structure | Name | MS (apci) m/z |
|---|---|---|---|
| 113 | 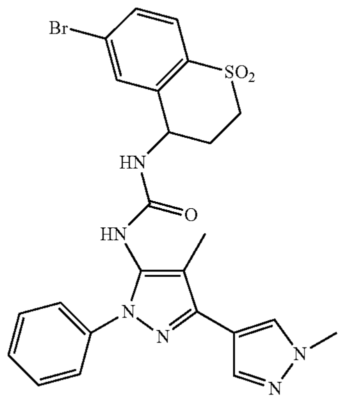 [SMILES: Cc1c(-c2cnn(C)c2)nn(-c2ccccc2)c1NC(=O)NC1CCS(=O)(=O)c2ccc(Br)cc21] | 1-(6-bromo-1,1-dioxidothiochroman-4-yl)-3-(1',4-dimethyl-1-phenyl-1H,1'H-[3,4'-bipyrazol]-5-yl)urea | 555.1 557.1 (M + H) |
| 114 | 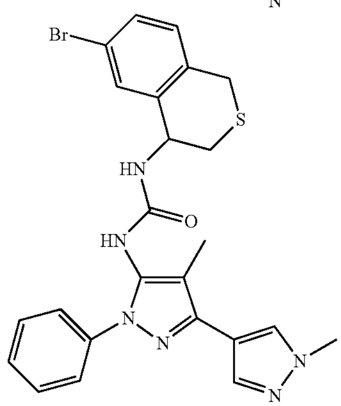 | 1-(6-bromoisothiochroman-4-yl)-3-(1',4-dimethyl-1-phenyl-1H,1'H-[3,4'-bipyrazol]-5-yl)urea | 521.1 523.1 (M − H) |
| 115 | 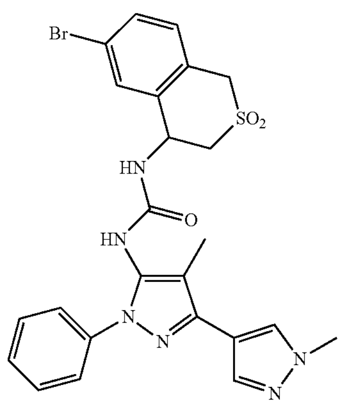 [SMILES: Cc1c(-c2cnn(C)c2)nn(-c2ccccc2)c1NC(=O)NC1CS(=O)(=O)Cc2ccc(Br)cc21] | 1-(6-bromo-2,2-dioxidoisothiochroman-4-yl)-3-(1',4-dimethyl-1-phenyl-1H,1'H-[3,4'-bipyrazol]-5-yl)urea | 553.0 555.0 (M − H) |
| 116 | 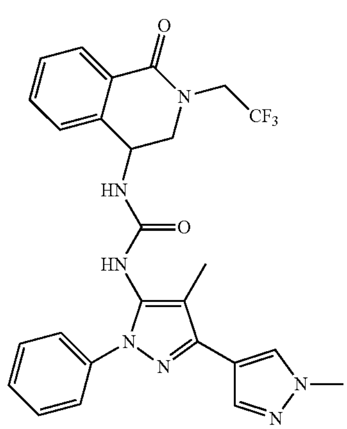 [SMILES: Cc1c(-c2cnn(C)c2)nn(-c2ccccc2)c1NC(=O)NC1CN(CC(F)(F)F)C(=O)c2ccccc21] | 1-(1',4-dimethyl-1-phenyl-1H,1'H-[3,4'-bipyrazol]-5-yl)-3-(1-oxo-2-(2,2,2-trifluoroethyl)-1,2,3,4-tetrahydroisoquinolin-4-yl)urea | 522.1 (M − H) |

Example 117

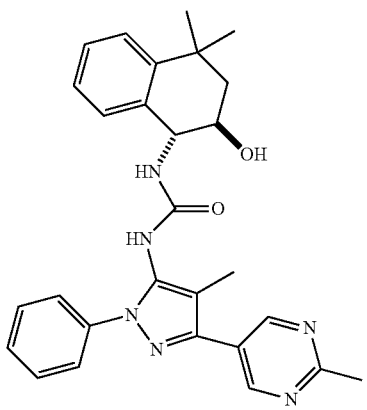

1-((1,2-trans)-2-hydroxy-4,4-dimethyl-1,2,3,4-tetrahydronaphthalen-1-yl)-3-(4-methyl-3-(2-methylpyrimidin-5-yl)-1-phenyl-1H-pyrazol-5-yl)urea A mixture of CDI (61.1 mg, 0.226 mmol) (estimated 60% potent based on previous experiments), 4-methyl-3-(2-methylpyrimidin-5-yl)-1-phenyl-1H-pyrazol-5-amine (Intermediate Y4, 60 mg, 0.226 mmol) and NEt₃ (99.3 µL, 0.712 mmol) were combined in DMF (0.9 mL) and stirred at ambient temperature for 48 hours. An aliquot of this solution containing 5-(5-isocyanato-4-methyl-1-phenyl-1H-pyrazol-3-yl)-2-methylpyrimidine (approx. 0.22 M, 108 µL, 0.024 mmol) was diluted with DMF (0.2 mL), followed by addition of trans-1-amino-4,4-dimethyl-1,2,3,4-tetrahydronaphthalen-2-ol (Intermediate X1, 5 mg, 0.026 mmol) and triethylamine (12 mg, 0.12 mmol). After stirring at ambient temperature for 1 hour, the mixture was directly purified by reverse phase chromatography (C18, 0-70% acetonitrile/water) to afford the title product as white solid (4.3 mg, 37% yield). MS (apci) m/z=483.3 (M+H).

The compounds listed in Table 4 were prepared in a similar fashion as described in Example 117, replacing 4-methyl-3-(2-methylpyrimidin-5-yl)-1-phenyl-1H-pyrazol-5-amine and trans-1-amino-4,4-dimethyl-1,2,3,4-tetrahydronaphthalen-2-ol with the appropriate aminopyrazole and amine starting materials, respectively.

TABLE 4

| Example # | Structure | Name | MS (apci) m/z |
|---|---|---|---|
| 118 | 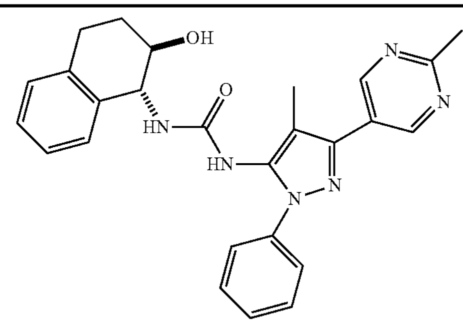 | 1-(trans-2-hydroxy-1,2,3,4-tetrhydronaphthalen-1-yl)-3-(4-methyl-3-(2-methylpyrimidin-5-yl)-1-phenyl-1H-pyrazol-5-yl)urea | 455.2 (M + H) |
| 119 | 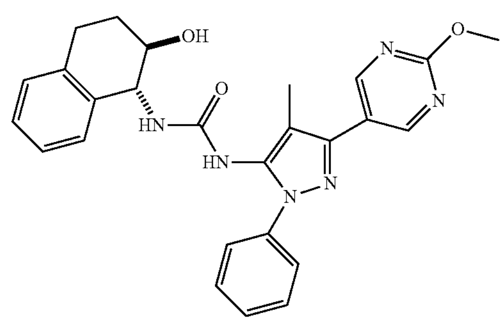 | 1-(trans-2-hydroxy-1,2,3,4-tetrahydronaphthalen-1-yl)-3-(3-(2-methoxypyrimidin-5-yl)-4-methyl-1-phenyl-1H-pyrazol-5-yl)urea | 471.2 (M + H) |
| 120 | 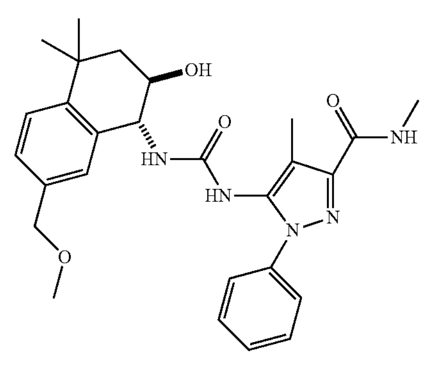 | 5-(3-(trans-2-hydroxy-7-(methoxymethyl)-4,4-dimethyl-1,2,3,4-tetrahydronaphthalen-1-yl)ureido)-N,4-dimethyl-1-phenyl-1H-pyrazole-3-carboxamide | 490.3 (M − H) |

TABLE 4-continued

| Example # | Structure | Name | MS (apci) m/z |
|---|---|---|---|
| 121 | 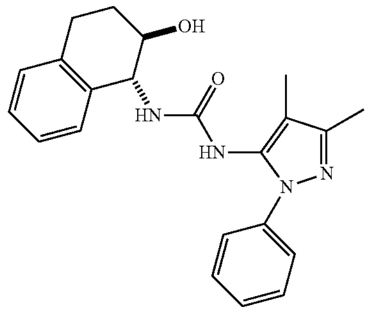 | 1-(3,4-dimethyl-1-phenyl-1H-pyrazol-5-yl)-3-(trans-2-hydroxy-1,2,3,4-tetrahydronaphthalen-1-yl)urea | 377.2 (M + H) |
| 122 | 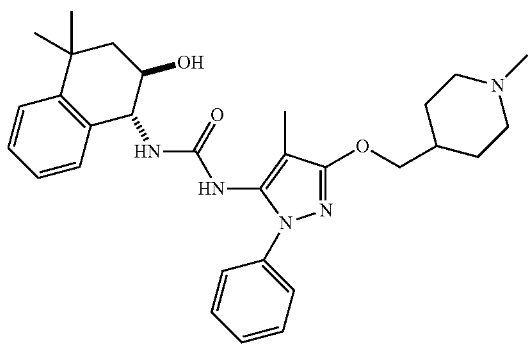 | 1-(trans-2-hydroxy-4,4-dimethyl-1,2,3,4-tetrahydronaphthalen-1-yl)-3-(4-methyl-3-((1-methylpiperidin-4-yl)methoxy)-1-phenyl-1H-pyrazol-5-yl)urea | 518.3 (M + H) |
| 123 | 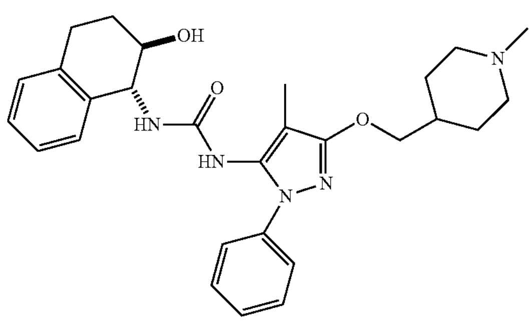 | 1-(trans-2-hydroxy-1,2,3,4-tetrahydronaphthalen-1-yl)-3-(4-methyl-3-((1-methylpiperidin-4-yl)methoxy)-1-phenyl-1H-pyrazol-5-yl)urea | 490.3 (M + H) |
| 124 | 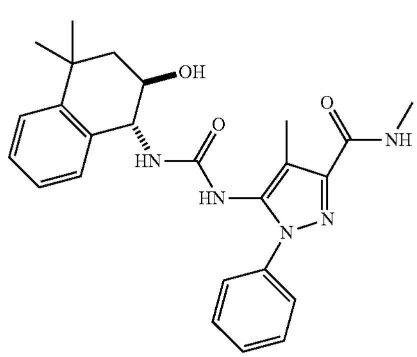 | 5-(3-(trans-2-hydroxy-4,4-dimethyl-1,2,3,4-tetrahydronaphthalen-1-yl)ureido)-N,4-dimethyl-1-phenyl-1H-pyrazole-3-carboxamide | 448.2 (M + H) |

TABLE 4-continued

| Example # | Structure | Name | MS (apci) m/z |
|---|---|---|---|
| 125 | 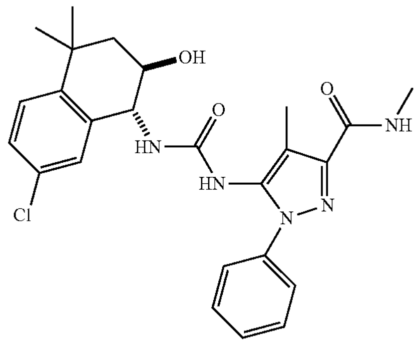 | 5-(3-(trans-7-chloro-2-hydroxy-4,4-dimethyl-1,2,3,4-tetrahydronaphthalen-1-yl)ureido)-N,4-dimethyl-1-phenyl-1H-pyrazole-3-carboxamide | 482.2 (M + H) |
| 126 | 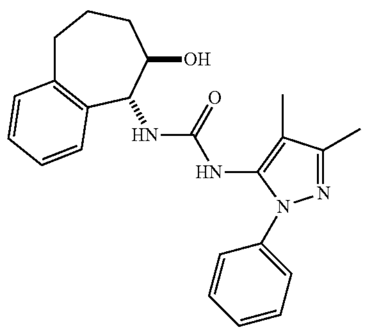 | 1-(3,4-dimethyl-1-phenyl-1H-pyrazol-5-yl)-3-(trans-6-hydroxy-6,7,8,9-tetrahydro-5H-benzo[7]annulen-5-yl)urea | 391.2 (M + H) |
| 127 | 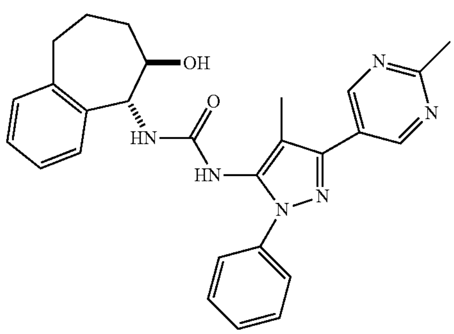 | 1-(trans-6-hydroxy-6,7,8,9-tetrahydro-5H-benzo[7]annulen-5-yl)-3-(4-methyl-3-(2-methylpyrimidin-5-yl)-1-phenyl-1H-pyrazol-5-yl)urea | 469.2 (M + H) |
| 128 | 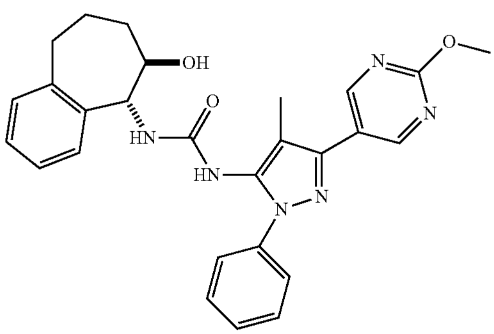 | 1-(trans-6-hydroxy-6,7,8,9-tetrahydro-5H-benzo[7]annulen-5-yl)-3-(3-(2-methoxypyrimidin-5-yl)-4-methyl-1-phenyl-1H-pyrazol-5-yl)urea | 485.2 (M + H) |

TABLE 4-continued

| Example # | Structure | Name | MS (apci) m/z |
|---|---|---|---|
| 129 | 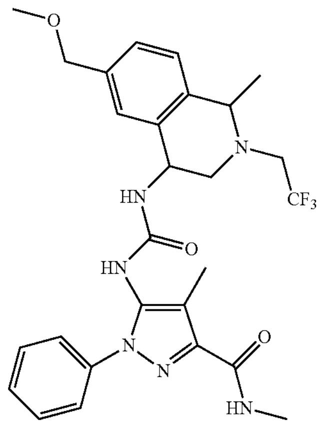 [SMILES: CNC(=O)c1nn(-c2ccccc2)c(NC(=O)NC2CN(CC(F)(F)F)C(C)c3ccc(COC)cc32)c1C] | 5-(3-(6-(methoxymethyl)-1-methyl-2-(2,2,2-trifluoroethyl)-1,2,3,4-tetrahydroisoquinolin-4-yl)ureido)-N,4-dimethyl-1-phenyl-1H-pyrazole-3-carboxamide | 543.2 (M − H) |
| 130 | 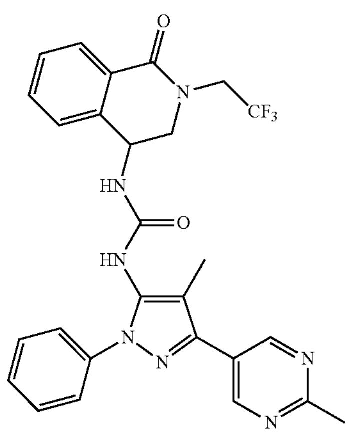 [SMILES: Cc1ncc(-c2nn(-c3ccccc3)c(NC(=O)NC3CN(CC(F)(F)F)C(=O)c4ccccc43)c2C)cn1] | 1-(4-methyl-3-(2-methylpyrimidin-5-yl)-1-phenyl-1H-pyrazol-5-yl)-3-(1-oxo-2-(2,2,2-trifluoroethyl)-1,2,3,4-tetrahydroisoquinolin-4-yl)urea | 534.2 (M − H) |
| 131 | 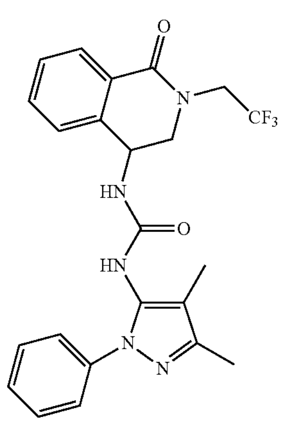 [SMILES: Cc1nn(-c2ccccc2)c(NC(=O)NC2CN(CC(F)(F)F)C(=O)c3ccccc32)c1C] | 1-(3,4-dimethyl-1-phenyl-1H-pyrazol-5-yl)-3-(1-oxo-2-(2,2,2-trifluoroethyl)-1,2,3,4-tetrahydroisoquinolin-4-yl)urea | 458.2 (M + H) |

Example 132

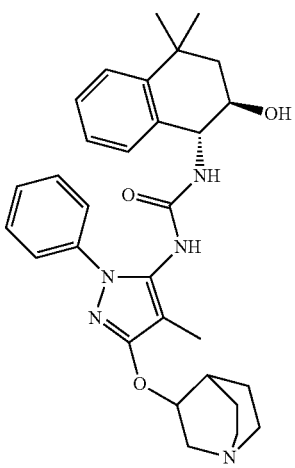 [SMILES: Cc1c(OC2CN3CCC2CC3)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(4-methyl-1-phenyl-3-(quinuclidin-3-yloxy)-1H-pyrazol-5-yl)urea To a solution of 4-methyl-1-phenyl-3-(quinuclidin-3-yloxy)-1H-pyrazol-5-amine (0.051 g, 0.17 mmol) in DriSolve DCM (1.7 mL) cooled in an ice-water bath was added triphosgene (0.0304 g, 0.10 mmol) followed by DIEA (0.089 mL, 0.51 mmol). It was stirred at 0° C. for 1 hour, then (1R,2R)-1-amino-4,4-dimethyl-1,2,3,4-tetrahydronaphthalen-2-ol (Intermediate X2, 0.033 g, 0.17 mmol) was added in one portion. The reaction mixture was allowed to warm to ambient temperature and was stirred for 1 hour. The reaction mixture was concentrated and directly purified by reverse phase chromatography (C18, 5 to 70% methanol/water) to yield the product as white solid (28.3 mg, 32% yield). MS (apci) m/z=516.3 (M+H).

Example 133

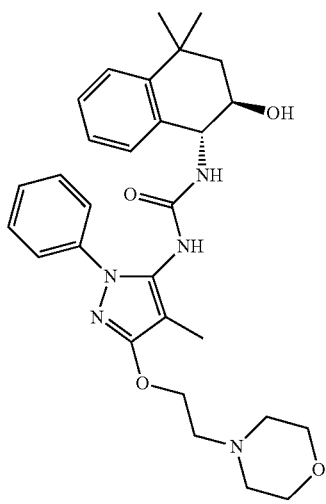 [SMILES: Cc1c(OCCN2CCOCC2)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(4-methyl-3-(2-morpholinoethoxy)-1-phenyl-1H-pyrazol-5-yl)urea The title product was prepared as described for Example 132, using 4-methyl-3-(2-morpholinoethoxy)-1-phenyl-1H-pyrazol-5-amine (Intermediate P141, 0.025 g, 0.0827 mmol) instead of 4-methyl-1-phenyl-3-(quinuclidin-3-yloxy)-1H-pyrazol-5-amine. The crude material was purified via reverse-phase chromatography (C18, 5 to 50% acetonitrile/water) to provide the title compound as white solid (24 mg, 55% yield). MS (apci) m/z=520.3 (M+H).

Example 134

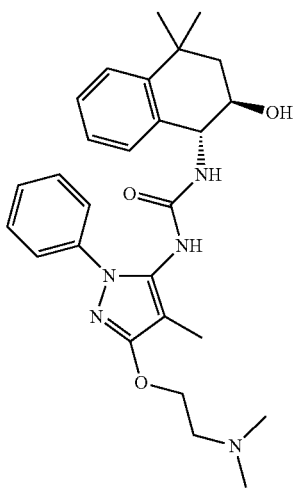 [SMILES: Cc1c(OCCN(C)C)nn(-c2ccccc2)c1NC(=O)N[C@@H]1c2ccccc2C(C)(C)C[C@H]1O]

1-(3-(2-(dimethylamino)ethoxy)-4-methyl-1-phenyl-1H-pyrazol-5-yl)-3-((1R,2R)-2-hydroxy-4,4-dimethyl-1,2,3,4-tetrahydronaphthalen-1-yl)urea The title product was prepared as described for Example 132, using 3-(2-(dimethylamino)ethoxy)-4-methyl-1-phenyl-1H-pyrazol-5-amine (Intermediate Y6, 0.030 g, 0.115 mmol) instead of 4-methyl-1-phenyl-3-(quinuclidin-3-yloxy)-1H-pyrazol-5-amine. The product was isolated via reverse-phase chromatography (C18, 5 to 50% acetonitrile/water) as white solid (10 mg, 18% yield). MS (apci) m/z=478.3 (M+H).

Example 135

1-((1R,2S)-2-hydroxy-1,2,3,4-tetrahydronaphthalen-1-yl)-3-(3-methoxy-4-methyl-1-phenyl-1H-pyrazol-5-yl)urea Step 1. Synthesis of tert-butyl ((1R,2S)-2-hydroxy-1,2,3,4-tetrahydronaphthalen-1-yl)carbamate. Tert-butyl carbamate (363 mg, 3.10 mmol) was dissolved in 1-propanol (4 mL) in a 20-mL scintillation vial equipped with a magnetic stir bar. To this solution was added a freshly prepared solution of sodium hydroxide (122 mg, 3.05 mmol) in water (7.5 mL) while stirring, followed by freshly prepared tert-butyl hypochlorite (331 mg, 3.05 mmol, 0.35 mL) A solution of the ligand (DHQD)2PHAL (38.9 mg, 0.0499 mmol) in 1-propanol (3.5 mL) was added to provide a clear colorless solution. The reaction vessel was immersed in a ambient-temperature water bath and stirred for a few minutes, and then 1,2-dihydronaphthalene (130 mg, 0.999 mmol) was added, followed by K2OsO4-2H2O (14.7 mg, 0.0399 mmol) in one portion. After 1 hour, the reaction mixture was diluted with EtOAc (7 mL) and the phases were separated. The aqueous phase was extracted with EtOAc (3×5 mL). The combined organic layers were washed with water and brine, dried (Na2SO4), filtered and concentrated. The crude material was purified first by silica chromatography (10% acetone in hexanes) and then by reverse-phase chromatography (C18, 5 to 65% MeOH/water) to yield the product as colorless glassy solid (50 mg, 19% yield).

Step 2. Synthesis of 1-((1R,2S)-2-hydroxy-1,2,3,4-tetrahydronaphthalen-1-yl)-3-(3-methoxy-4-methyl-1-phenyl-1H-pyrazol-5-yl)urea. Tert-butyl ((1R,2S)-2-hydroxy-1,2,3,4-tetrahydronaphthalen-1-yl)carbamate (25 mg, 0.095 mmol) was treated with 1:1 v/v TFA/DCM (1 mL) at ambient temperature for 1 hour, then concentrated. The residue was taken up in DCM (2 mL) and washed with 1N NaOH and brine (1 mL each), and the organic phase was separated and concentrated. The residue was taken up in IPA (0.4 mL), followed by addition of phenyl (3-methoxy-4-methyl-1-phenyl-1H-pyrazol-5-yl)carbamate (intermediate 3, 31 mg, 0.095 mmol) in one portion. The resulting milky suspension was warmed up briefly with a heat gun to obtain a clear solution and then heated at 50° C. for 3 hours, then at reflux for 1 hour. After cooling to ambient temperature, the reaction mixture was filtered, rinsed with ice-cold IPA first followed by ether (0.5 mL each), yielding the product as white solid (10 mg, 27% yield). MS (apci) m/z=393.2 (M+H).

Example 136

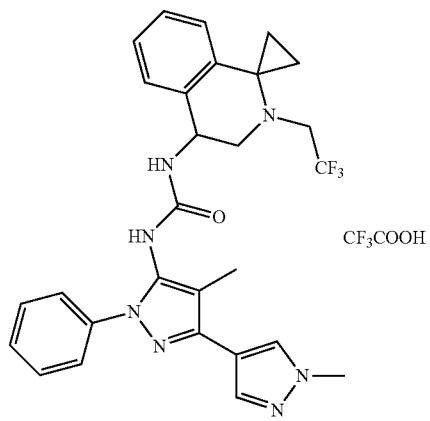 [SMILES: Cc1c(-c2cnn(C)c2)nn(-c2ccccc2)c1NC(=O)NC1CN(CC(F)(F)F)C2(CC2)c2ccccc21 ; "CF3COOH"]

1-(1',4-dimethyl-1-phenyl-1H,1'H-[3,4'-bipyrazol]-5-yl)-3-(2'-(2,2,2-trifluoroethyl)-3',4'-dihydro-2'H-spiro[cyclopropane-1,1'-isoquinolin]-4'-yl)urea trifluoroacetate Step A: Preparation of N-(2,2-dimethoxyethyl)-1-phenylcyclopropanamine: A solution of 1-phenylcyclopropanamine (3.14 g, 23.6 mmol) in anhydrous DCM (100 mL) was treated with 2,2-dimethoxyacetaldehyde (4.09 g, 60% in water, 23.6 mmol) followed by acetic acid (135 μL, 2.36 mmol) and MgSO4 (6.0 g). The mixture was stirred at ambient temperature for 16 hours then filtered, washed with a small amount of DCM and the filtrate treated with Na(OAc)3BH (5.5 g, 25.9 mmol). After stirring at ambient temperature for 16 hours, the mixture was treated with ice and 2N NaOH and then extracted with DCM (3×30 mL). The combined organic phases were washed with brine (20 mL), dried over Na2SO4, filtered and concentrated. The residue was purified by silica column chromatography eluting with 4:1 hexanes:EtOAc, to afford N-(2,2-dimethoxyethyl)-1-phenylcyclopropanamine (2.31 g, 44% yield) as a pale yellow oil. MS (EI) m/z=220.05 (M–H).

Step B: Preparation of N-(2,2-dimethoxyethyl)-1-phenyl-N-(2,2,2-trifluoroethyl)cyclopropanamine: To a solution of N-(2,2-dimethoxyethyl)-1-phenylcyclopropanamine (2.31 g, 10.44 mmol) in anhydrous DMF (10 mL) was added 2,2,2-trifluoroethyltriflate (3.76 mL, 26.1 mmol) followed by Et3N (6.36 mL, 36.5 mmol). The mixture was heated in a sealed vial at 45° C. for 16 hours, then treated with 2,2,2-trifluoroethyltriflate (5 mL) and stirred at 65° C. for 6 hours. The cooled mixture was partitioned between water (50 mL) and EtOAc (50 mL) and the aqueous layer extracted with EtOAc (2×30 mL). The combined organic phases were washed with water (4×20 mL) and brine (20 mL) then dried over Na2SO4, filtered and concentrated. The residue was purified by silica column chromatography eluting with 9:1 to 4:1 hexanes:EtOAc, to afford N-(2,2-dimethoxyethyl)-1-phenyl-N-(2,2,2-trifluoroethyl)cyclopropanamine (934 mg, 29% yield) as a pale yellow oil. MS (apci) m/z=303.2 (M+H).

Step C: Preparation of 2'-(2,2,2-trifluoroethyl)-3',4'-dihydro-2'H-spiro[cyclopropane-1,1'-isoquinolin]-4'-ol: N-(2,2-dimethoxyethyl)-1-phenyl-N-(2,2,2-trifluoroethyl)cyclopropanamine (934 mg, 3.08 mmol) was treated with perchloric acid (3.72 mL, 61.6 mmol) and stirred at ambient temperature for 3 hours. The mixture was treated with ice and 2N NaOH, stirred for 1 hour then extracted with DCM (3×20 mL). The combined organic phases were washed with brine (10 mL), dried over Na2SO4, filtered and concentrated. The residue was purified by silica column chromatography eluting with 9:1 hexanes:EtOAc, to afford 2'-(2,2,2-trifluoroethyl)-3',4'-dihydro-2'H-spiro[cyclopropane-1,1'-isoquinolin]-4'-ol (328 mg, 41% yield) as a cream, crystalline solid. MS (apci) m/z=258.1 (M+H).

Step D: Preparation of 4'-chloro-2'-(2,2,2-trifluoroethyl)-3',4'-dihydro-2'H-spiro[cyclopropane-1,1'-isoquinoline]: To a solution of 2'-(2,2,2-trifluoroethyl)-3',4'-dihydro-2'H-spiro[cyclopropane-1,1'-isoquinolin]-4'-ol (50 mg, 0.19 mmol) in anhydrous DCM (1 mL) at 0° C. was added mesyl chloride (17 μL, 0.21 mmol) followed by DIEA (68 μL, 0.39 mmol). The mixture was stirred at ambient temperature for 2 hours then partitioned between water (10 mL) and DCM (10 mL) The aqueous layer was extracted with DCM (2×5 mL) and the combined organic phases were washed with brine (10 mL), dried over Na2SO4, filtered and concentrated. The residue was dissolved in DCM (10 mL) and concentrated to afford 4'-chloro-2'-(2,2,2-trifluoroethyl)-3',4'-dihydro-2'H-spiro[cyclopropane-1,1'-isoquinoline] (50 mg, 93% yield) as a pale yellow oil. MS (EI) m/z=275.89 (M+H).

Step E: Preparation of 4'-azido-2'-(2,2,2-trifluoroethyl)-3',4'-dihydro-2'H-spiro[cyclopropane-1,1'-isoquinoline]: To a solution of 4'-chloro-2'-(2,2,2-trifluoroethyl)-3',4'-dihydro-2'H-spiro[cyclopropane-1,1'-isoquinoline] (50 mg, 0.18 mmol) in anhydrous DMF (1 mL) was added sodium azide (24 mg, 0.36 mmol). The mixture was stirred at 65° C. for 3 hours then cooled and partitioned between water (10 mL) and EtOAc (10 mL). The aqueous layer was extracted with EtOAc (2×5 mL) and the combined organic phases were washed with water (4×5 mL) and brine (5 mL) then dried over $Na_2SO_4$, filtered and concentrated. The residue was purified by column chromatography eluting with 9:1 hexanes:EtOAc, to afford 4'-azido-2'-(2,2,2-trifluoroethyl)-3',4'-dihydro-2'H-spiro[cyclopropane-1,1'-isoquinoline] (19 mg, 37% yield) as a colorless oil. MS (apci) m/z=255.1 (M[-N2]+H).

Step F: Preparation of 2'-(2,2,2-trifluoroethyl)-3',4'-dihydro-2'H-spiro[cyclopropane-1,1'-isoquinolin]-4'-amine: A solution of 4'-azido-2'-(2,2,2-trifluoroethyl)-3',4'-dihydro-2'H-spiro[cyclopropane-1,1'-isoquinoline] (19 mg, 0.067 mmol) in methanol (5 mL) was treated with 5% Pd/C (wet, Degussa type, 2 mg) and stirred under a hydrogen balloon atmosphere for 3 hours. The mixture was filtered through GF paper and the filtrate concentrated to afford 2'-(2,2,2-trifluoroethyl)-3',4'-dihydro-2'H-spiro[cyclopropane-1,1'-isoquinolin]-4'-amine (14 mg, 81% yield) as a colorless gum. MS (apci) m/z=257.1 (M+H).

Step G: Preparation of 1-(1',4-dimethyl-1-phenyl-1H,1'H-[3,4'-bipyrazol]-5-yl)-3-(2'-(2,2,2-trifluoroethyl)-3',4'-dihydro-2'H-spiro[cyclopropane-1,1'-isoquinolin]-4'-yl)urea 2,2,2-trifluoroacetate: To a solution of 2'-(2,2,2-trifluoroethyl)-3',4'-dihydro-2'H-spiro[cyclopropane-1,1'-isoquinolin]-4'-amine (14 mg, 0.055 mmol) in anhydrous DCM (1 mL) was added phenyl (1',4-dimethyl-1-phenyl-1H,1'H-[3,4'-bipyrazol]-5-yl)carbamate [Intermediate 13] (18 mg, 0.50 mmol) followed by DIEA (26 µL, 0.15 mmol). The mixture was stirred at ambient temperature for 16 hours then partitioned between water (10 mL) and DCM (10 mL). The aqueous layer was extracted with DCM (2×5 mL) and the combined organic phases were washed with brine (10 mL), dried over $Na_2SO_4$, filtered and concentrated. The residue was purified by silica column chromatography eluting with 2% MeOH/DCM, then by reverse-phase HPLC (5-95% ACN/water/0.1% TFA over 20 minutes) to afford the title compound TFA salt (3.7 mg, 11% yield) as a white solid. MS (apci) m/z=534.2 (M−H).

Example 137

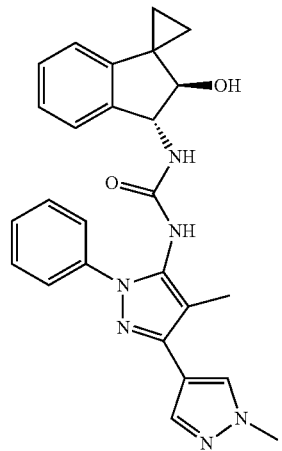 [SMILES: Cc1c(-c2cnn(C)c2)nn(-c2ccccc2)c1NC(=O)N[C@@H]1c2ccccc2C2(CC2)[C@H]1O]

1-(1',4-dimethyl-1-phenyl-1H,1'H-[3,4'-bipyrazol]-5-yl)-3-((2'R,3'R)-2'-hydroxy-2',3'-dihydrospiro[cyclopropane-1,1'-inden]-3'-yl)urea To (2'R,3'R)-3'-amino-2',3'-dihydrospiro[cyclopropane-1,1'-inden]-2'-ol (Intermediate X9, 10.6 mg, 0.0605 mmol) were added iPrOH (0.6 mL) then phenyl (1',4-dimethyl-1-phenyl-1H,1'H-[3,4'-bipyrazol]-5-yl)carbamate (Intermediate 13, 22.6 mg, 0.0605 mmol). The reaction mixture was heated to 70° C. for 15 minutes, then was allowed to cool slowly to ambient temperature. The suspension was filtered, rinsed with Et2O (4×1 mL), and the solid was collected to afford the product as a white solid (20.4 mg, 74% yield). MS (apci) m/z=455.2 (M+H).

Example 138

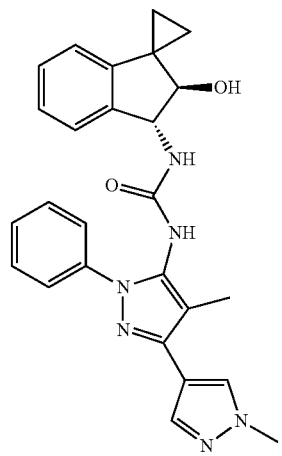 [SMILES: Cc1c(-c2cnn(C)c2)nn(-c2ccccc2)c1NC(=O)N[C@@H]1c2ccccc2C2(CC2)[C@H]1O]

1-(1',4-dimethyl-1-phenyl-1H,1'H-[3,4'-bipyrazol]-5-yl)-3-((2'S,3'S)-2'-hydroxy-2',3'-dihydrospiro[cyclopropane-1,1'-inden]-3'-yl)urea To (2'S,3'S)-3'-amino-2',3'-dihydrospiro[cyclopropane-1,1'-inden]-2'-ol (Intermediate X10, 18.4 mg, 0.105 mmol)

were added iPrOH (1 mL) then phenyl (1',4-dimethyl-1-phenyl-1H,1'H-[3,4'-bipyrazol]-5-yl)carbamate (Intermediate 13, 39.2 mg, 0.105 mmol). The reaction mixture was heated to 70° C. for 15 minutes and then allowed to cool slowly to ambient temperature. The suspension was filtered, rinsed with Et2O (4×1 mL), and the solid was collected to afford the product as a white solid (37.4 mg, 78% yield). MS (apci) m/z=455.2 (M+H).

Example 139

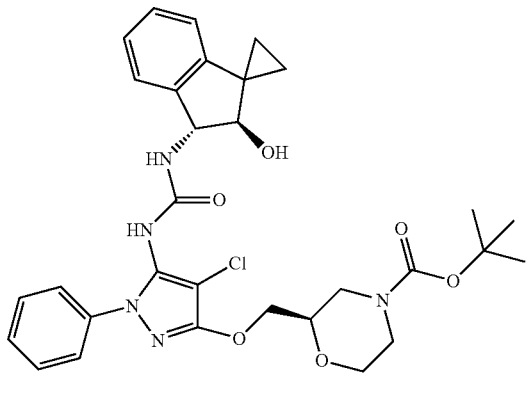 [SMILES: CC(C)(C)OC(=O)N1CCO[C@@H](COc2nn(-c3ccccc3)c(NC(=O)N[C@@H]3c4ccccc4C4(CC4)[C@H]3O)c2Cl)C1]

(R)-tert-butyl 2-(((4-chloro-5-(3-((2'R,3'R)-2'-hydroxy-2',3'-dihydrospiro[cyclopropane-1,1'-inden]-3'-yl)ureido)-1-phenyl-1H-pyrazol-3-yl)oxy)methyl)morpholine-4-carboxylate Step A: Preparation of (R)-tert-butyl 2-(((5-((phenoxycarbonyl)amino)-1-phenyl-1H-pyrazol-3-yl)oxy)methyl)morpholine-4-carboxylate: To a solution of (R)-tert-butyl 2-(((5-amino-1-phenyl-1H-pyrazol-3-yl)oxy)methyl)morpholine-4-carboxylate (Intermediate Y8, 200 mg, 0.534 mmol) in EtOAc (5 mL) was added aqueous NaOH (2M, 0.534 ml, 1.068 mmol) then phenyl chloroformate (100 μL, 0.8012 mmol). The reaction mixture was stirred at ambient temperature for 23 hours and then transferred to separatory funnel with EtOAc (25 mL). The phases were separated, and the organic phase was washed with H2O (25 mL), brine (25 mL), dried (MgSO4), filtered and concentrated to a thick syrup. Added hexanes (10 mL), sonicated, decanted hexanes, then dried under high vacuum to afford the product as a brown solid (242 mg, 92% yield). MS (apci) m/z=495.2 (M+H).

Step B: Preparation of (R)-tert-butyl 2-(((4-chloro-5-((phenoxycarbonyl)amino)-1-phenyl-1H-pyrazol-3-yl)oxy)methyl)morpholine-4-carboxylate: To a solution of (R)-tert-butyl 2-(((5-((phenoxycarbonyl)amino)-1-phenyl-1H-pyrazol-3-yl)oxy)methyl)morpholine-4-carboxylate (242 mg, 0.489 mmol) in DCM (5 mL) were added NCS (85 mg, 0.636 mmol) and PPTS (12.3 mg, 0.049 mmol). The reaction mixture was stirred at ambient temperature for 6 days, then was diluted with H2O (10 mL), extracted with DCM (3×10 mL), and the combined organic phases were dried (MgSO4), filtered, and concentrated. The crude oil was purified by silica column chromatography, eluting with 0-30% acetone/hexanes, to afford the product as an orange solid (153 mg, 66% yield). MS (apci) m/z=429.1 (M-Boc).

Step C: Preparation of (R)-tert-butyl 2-(((4-chloro-5-(3-((2'R,3'R)-2'-hydroxy-2',3'-dihydrospiro[cyclopropane-1,1'-inden]-3'-yl)ureido)-1-phenyl-1H-pyrazol-3-yl)oxy)methyl)morpholine-4-carboxylate: To a solution of (2'R,3'R)-3'-amino-2',3'-dihydrospiro[cyclopropane-1,1'-inden]-2'-ol (Intermediate X9, 24.2 mg, 0.138 mmol) in iPrOH (1.4 mL) was added (R)-tert-butyl 2-(((4-chloro-5-((phenoxycarbonyl)amino)-1-phenyl-1H-pyrazol-3-yl)oxy)methyl)morpholine-4-carboxylate (73 mg, 0.138 mmol). The reaction mixture was stirred at ambient temperature for 16 hours, then was diluted with DCM (2 mL) and purified by silica column chromatography, eluting with 0-10% MeOH/DCM, to afford the product as an off-white solid (64 mg, 76% yield). MS (apci) m/z=510.2 (M-Boc).

Example 140

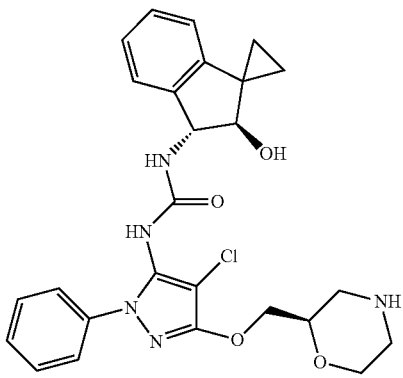 [SMILES: O=C(Nc1c(Cl)c(OC[C@H]2CNCCO2)nn1-c1ccccc1)N[C@@H]1c2ccccc2C2(CC2)[C@H]1O]

1-(4-chloro-3-((R)-morpholin-2-ylmethoxy)-1-phenyl-1H-pyrazol-5-yl)-3-((2'R,3'R)-2'-hydroxy-2',3'-dihydrospiro[cyclopropane-1,1'-inden]-3'-yl)urea To a suspension of (R)-tert-butyl 2-(((4-chloro-5-(3-((2'R,3'R)-2'-hydroxy-2',3'-dihydrospiro[cyclopropane-1,1'-inden]-3'-yl)ureido)-1-phenyl-1H-pyrazol-3-yl)oxy)methyl)morpholine-4-carboxylate (Example 139, 61 mg, 0.100 mmol) in iPrOH (0.2 mL) was added HCl (5-6M in iPrOH, 500 μL). The reaction mixture was stirred at ambient temperature for 19 hours, then was diluted with saturated aqueous NaHCO3 (10 mL) and extracted with DCM (15 mL). The aqueous phase was diluted with H2O (5 mL), then the aqueous phase was extracted with 10% MeOH/90% DCM (2×10 mL) The combined organic phases were dried (MgSO4), filtered, concentrated, and dried under high vacuum to give the product as a white solid (44.7 mg, 88% yield). MS (apci) m/z=510.2 (M+H).

Example 141

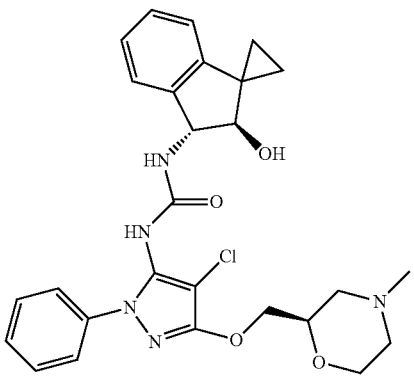 [SMILES: CN1CCO[C@@H](COc2nn(-c3ccccc3)c(NC(=O)N[C@@H]3c4ccccc4C4(CC4)[C@H]3O)c2Cl)C1]

285

1-(4-chloro-3-(((R)-4-methylmorpholin-2-yl)methoxy)-1-phenyl-1H-pyrazol-5-yl)-3-((2'R,3'R)-2'-hydroxy-2',3'-dihydrospiro[cyclopropane-1,1'-inden]-3'-yl)urea To a suspension of 1-(4-chloro-3-((R)-morpholin-2-ylmethoxy)-1-phenyl-1H-pyrazol-5-yl)-3-((2'R,3'R)-2'-hydroxy-2',3'-dihydrospiro[cyclopropane-1,1'-inden]-3'-yl)urea (Example 140, 25 mg, 0.049 mmol) in DCE (1 mL) were added paraformaldehyde (3.5 mg, 0.117 mmol) then sodium triacetoxyborohydride (15.6 mg, 0.074 mmol). The reaction mixture was stirred at ambient temperature for 16 hours, then at 50° C. for 1 hour. Additional sodium triacetoxyborohydride (8 mg, 0.038 mmol) was added and the reaction mixture was stirred at ambient temperature for 1 hour, then additional sodium triacetoxyborohydride (8 mg, 0.038 mmol) was added and the reaction mixture was stirred at ambient temperature for 18 hours. The reaction mixture was diluted with DCM (10 mL) and saturated aqueous NaHCO$_3$ (10 mL). The phases were separated and the aqueous phase was extracted with 10% MeOH/90% DCM (2×10 mL) The combined organic phases were dried (MgSO$_4$), filtered, and concentrated. The crude product was purified by silica column chromatography, eluting with 0-10% NH$_3$/MeOH in DCM, to afford the product as a white solid (14.3 mg, 56% yield). MS (apci) m/z=524.2 (M+H).

Example 142

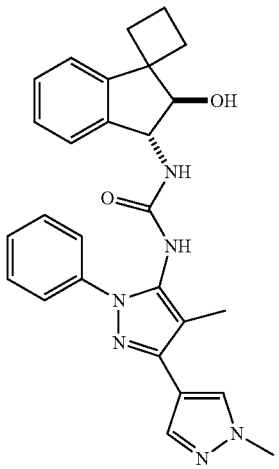 [SMILES: Cc1c(-c2cnn(C)c2)nn(-c2ccccc2)c1NC(=O)N[C@@H]1c2ccccc2C2(CCC2)[C@H]1O]

1-(1',4-dimethyl-1-phenyl-1H,1'H-[3,4'-bipyrazol]-5-yl)-3-(trans-2'-hydroxy-2',3'-dihydrospiro[cyclobutane-1,1'-inden]-3'-yl)urea Step A: Preparation of spiro[cyclobutane-1,1'-indene]: To a solution of 1H-indene (1.00 g, 8.609 mmol) and 1,3-dibromopropane (967 µL, 9.470 mmol) in DMSO (43 mL) was added KOtBu (2.125 g, 18.939 mmol) in 4 portions over 5 min. The reaction mixture was stirred at ambient temperature for 3 days, then was diluted with H$_2$O (50 mL) and extracted with Et$_2$O (3×50 mL). The combined organic phases were washed with H$_2$O (50 mL), then brine (3×50 mL), then dried (MgSO$_4$), filtered, and concentrated. The crude oil was purified by silica column chromatography, eluting with hexanes, to afford the product as a colorless oil (0.57 g, 42% yield).

286

Step B: Preparation of 1-(1',4-dimethyl-1-phenyl-1H,1'H-[3,4'-bipyrazol]-5-yl)-3-(trans-2'-hydroxy-2',3'-dihydrospiro[cyclobutane-1,1'-inden]-3'-yl)urea: Prepared according to the procedure of Example 55, Steps B-D, replacing spiro[cyclopropane-1,1'-indene] in Step B with spiro[cyclobutane-1,1'-indene]. The reaction mixture was purified by silica column chromatography, eluting with 0-60% acetone/hexanes, to afford the product as a white solid (5.2 mg, 42% yield). MS (apci) m/z=469.2 (M+H).

Example 143

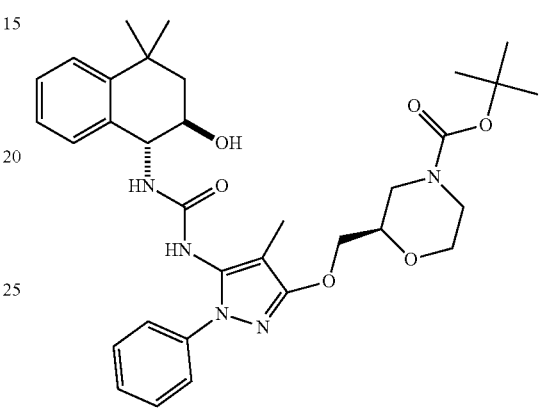

(R)-tert-butyl 2-(((5-(3-(trans-2-hydroxy-4,4-dimethyl-1,2,3,4-tetrahydronaphthalen-1-yl)ureido)-4-methyl-1-phenyl-1H-pyrazol-3-yl)oxy)methyl)morpholine-4-carboxylate Step A: Preparation of (R)-tert-butyl 2-(((4-methyl-5-((phenoxycarbonyl)amino)-1-phenyl-1H-pyrazol-3-yl)oxy)methyl)morpholine-4-carboxylate: To a solution of (R)-tert-butyl 2-(((5-amino-4-methyl-1-phenyl-1H-pyrazol-3-yl)oxy)methyl)morpholine-4-carboxylate (Intermediate Y7, 20 mg, 0.0515 mmol) in EtOAc (0.5 mL) were added aqueous NaOH (2M, 51 µL, 0.103 mmol) then phenyl chloroformate (10 µL, 0.077 mmol). The reaction mixture was stirred at ambient temperature for 4 days, then transferred to separatory funnel with EtOAc (10 mL) The phases were separated and the organic phase was washed with H$_2$O (10 mL), brine (10 mL), dried (MgSO$_4$), filtered, and concentrated to a thick syrup. Added hexanes (10 mL), sonicated, decanted hexanes, then dried under high vacuum to afford the product as an orange solid (20.5 mg, 78% yield). MS (apci) m/z=509.2 (M+H).

Step B: Preparation of (R)-tert-butyl 2-(((5-(3-(trans-2-hydroxy-4,4-dimethyl-1,2,3,4-tetrahydronaphthalen-1-yl)ureido)-4-methyl-1-phenyl-1H-pyrazol-3-yl)oxy)methyl)morpholine-4-carboxylate: To a solution of (R)-tert-butyl 2-(((4-methyl-5-((phenoxycarbonyl)amino)-1-phenyl-1H-pyrazol-3-yl)oxy)methyl)morpholine-4-carboxylate (20 mg, 0.033 mmol) in iPrOH (0.5 mL) was added trans-1-amino-4,4-dimethyl-1,2,3,4-tetrahydronaphthalen-2-ol (Intermediate X1, 7.5 mg, 0.039 mmol). The reaction mixture was stirred at ambient temperature for 18 hours, then directly purified by silica column chromatography, eluting with 0-10% MeOH/DCM, to afford the product as an off-white solid (13.7 mg, 53% yield). MS (apci) m/z=606.3 (M+H).

Example 144

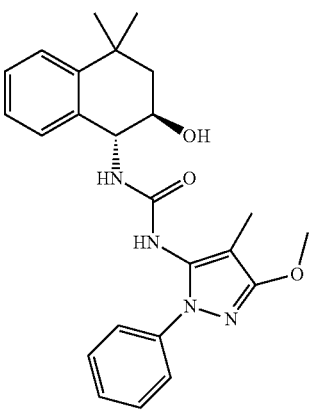 [SMILES: COc1nn(-c2ccccc2)c(NC(=O)N[C@@H]2c3ccccc3C(C)(C)C[C@H]2O)c1C]

1-((1R,2R)-2-hydroxy-4,4-dimethyl-1,2,3,4-tetrahydronaphthalen-1-yl)-3-(3-methoxy-4-methyl-1-phenyl-1H-pyrazol-5-yl)urea Step A: Preparation of phenyl (3-methoxy-4-methyl-1-phenyl-1H-pyrazol-5-yl)carbamate: To a solution of 3-methoxy-4-methyl-1-phenyl-1H-pyrazol-5-amine (Intermediate 2, 646 mg, 3.179 mmol) in EtOAc (32 mL) were added aqueous NaOH (2M, 3.18 mL, 6.357 mmol) then phenyl chloroformate (0.5981 ml, 4.768 mmol). The reaction mixture was stirred at ambient temperature for 17 hours and then transferred to separatory funnel with EtOAc (25 mL). The phases were separated and the organic phase was washed with $H_2O$ (25 mL), brine (25 mL), dried ($MgSO_4$), filtered, and concentrated to a thick syrup. Hexane (10 mL) was added, and the mixture was sonicated. The hexanes were decanted and then dried under high vacuum to afford the product as a pale yellow solid (908 mg, 88% yield). MS (apci) m/z=324.1 (M+H).

Step B: Preparation of 1-((1R,2R)-2-hydroxy-4,4-dimethyl-1,2,3,4-tetrahydronaphthalen-1-yl)-3-(3-methoxy-4-methyl-1-phenyl-1H-pyrazol-5-yl)urea: To (1R,2R)-1-amino-4,4-dimethyl-1,2,3,4-tetrahydronaphthalen-2-ol (Intermediate X2, 198 mg, 1.04 mmol) were added iPrOH (5 mL) and phenyl (3-methoxy-4-methyl-1-phenyl-1H-pyrazol-5-yl)carbamate (335 mg, 1.04 mmol). The reaction mixture was heated to 70° C. for 45 minutes, then cooled to ambient temperature. The suspension was filtered, rinsed with iPrOH (2×0.5 mL) then $Et_2O$ (5×1 mL). The solid was collected, then recrystallized in iPrOH (2 mL), to afford the product as a white solid (95 mg, 22% yield). MS (apci) m/z=421.2 (M+H).

The examples in Table 5 were prepared according to the procedure of Example 144, substituting the appropriate aminopyrazole intermediate in Step A.

TABLE 5

| Ex. # | Structure | Name | MS (apci) m/z |
|---|---|---|---|
| 145 | 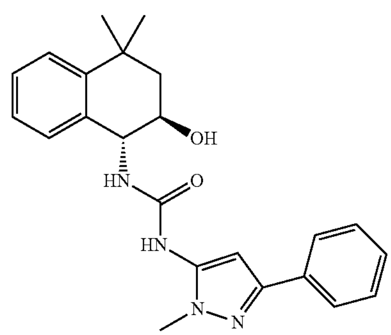 [SMILES: Cn1nc(-c2ccccc2)cc1NC(=O)N[C@@H]1c2ccccc2C(C)(C)C[C@H]1O] | 1-((1R,2R)-2-hydroxy-4,4-dimethyl-1,2,3,4-tetrahydronaphthalen-1-yl)-3-(1-methyl-3-phenyl-1H-pyrazol-5-yl)urea | 391.2 (M + H) |
| 146 | 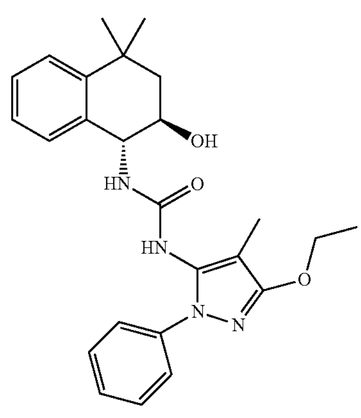 [SMILES: CCOc1nn(-c2ccccc2)c(NC(=O)N[C@@H]2c3ccccc3C(C)(C)C[C@H]2O)c1C] | 1-(3-ethoxy-4-methyl-1-phenyl-1H-pyrazol-5-yl)-3-((1R,2R)-2-hydroxy-4,4-dimethyl-1,2,3,4-tetrahydronaphthalen-1-yl)urea | 435.3 (M + H) |

TABLE 5-continued

| Ex. # | Structure | Name | MS (apci) m/z |
|---|---|---|---|
| 147 | 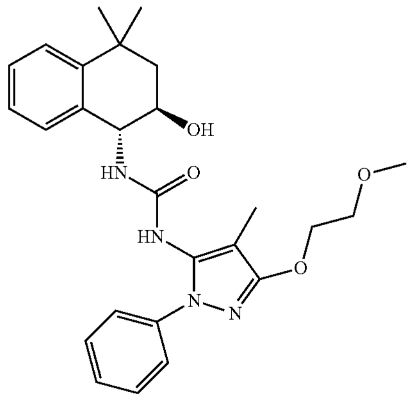 [SMILES: COCCOc1nn(-c2ccccc2)c(NC(=O)N[C@@H]2c3ccccc3C(C)(C)C[C@H]2O)c1C] | 1-((1R,2R)-2-hydroxy-4,4-dimethyl-1,2,3,4-tetrahydronaphthalen-1-yl)-3-(3-(2-methoxyethoxy)-4-methyl-1-phenyl-1H-pyrazol-5-yl)urea | 465.3 (M + H) |

Example 148

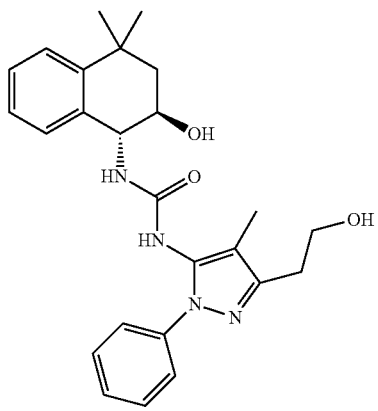 [SMILES: Cc1c(CCO)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(3-(2-hydroxyethyl)-4-methyl-1-phenyl-1H-pyrazol-5-yl)urea Step A: Preparation of 1-(3-(2-((tert-butyldimethylsilyl)oxy)ethyl)-4-methyl-1-phenyl-1H-pyrazol-5-yl)-3-((1R,2R)-2-hydroxy-4,4-dimethyl-1,2,3,4-tetrahydronaphthalen-1-yl)urea: Prepared according to the procedure of Example 144, replacing 3-methoxy-4-methyl-1-phenyl-1H-pyrazol-5-amine in Step A with 3-(2-(tert-butyldimethylsilyloxy)ethyl)-4-methyl-1-phenyl-1H-pyrazol-5-amine (Intermediate Y9). The reaction mixture was purified by silica column chromatography, eluting with 0-60% acetone/hexanes, to afford the product as a pale yellow solid (26.8 mg, 47% yield). MS (apci) m/z=549.3 (M+H).

Step B: Preparation of 1-((1R,2R)-2-hydroxy-4,4-dimethyl-1,2,3,4-tetrahydronaphthalen-1-yl)-3-(3-(2-hydroxyethyl)-4-methyl-1-phenyl-1H-pyrazol-5-yl)urea: To a solution of 1-(3-(2-((tert-butyldimethylsilyl)oxy)ethyl)-4-methyl-1-phenyl-1H-pyrazol-5-yl)-3-((1R,2R)-2-hydroxy-4,4-dimethyl-1,2,3,4-tetrahydronaphthalen-1-yl)urea (26.8 mg, 0.0488 mmol) in EtOH (0.5 mL) was added HCl (5-6M in iPrOH, 0.2 mL). The reaction mixture was stirred at ambient temperature for 2 hours. The reaction mixture was concentrated, then diluted with Et₂O (3×3 mL) and concentrated after each addition, and dried under high vacuum to afford the product as a pale yellow solid (24.1 mg, 113% yield). MS (apci) m/z=435.3 (M+H).

Example 149

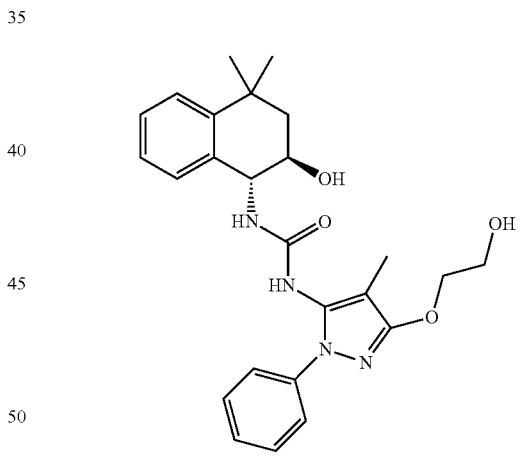

1-((1R,2R)-2-hydroxy-4,4-dimethyl-1,2,3,4-tetrahydronaphthalen-1-yl)-3-(3-(2-hydroxyethoxy)-4-methyl-1-phenyl-1H-pyrazol-5-yl)urea Prepared according to the procedure of Example 148, replacing 3-(2-(tert-butyldimethylsilyloxy)ethyl)-4-methyl-1-phenyl-1H-pyrazol-5-amine in Step A with 3-(2-((tert-butyldimethylsilyl)oxy)ethoxy)-4-methyl-1-phenyl-1H-pyrazol-5-amine (Intermediate P203), to afford the product as an off-white solid (33.7 mg, 106% yield). MS (apci) m/z=451.3 (M+H).

Example 150

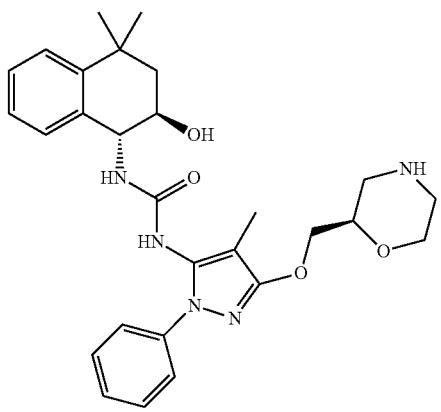 [SMILES: Cc1c(OC[C@H]2CNCCO2)nn(-c2ccccc2)c1NC(=O)N[C@@H]1c2ccccc2C(C)(C)C[C@H]1O]

1-((1R,2R)-2-hydroxy-4,4-dimethyl-1,2,3,4-tetrahydronaphthalen-1-yl)-3-(4-methyl-3-((R)-morpholin-2-ylmethoxy)-1-phenyl-1H-pyrazol-5-yl)urea Step A: Preparation of (R)-tert-butyl 2-(((5-(3-((1R,2R)-2-hydroxy-4,4-dimethyl-1,2,3,4-tetrahydronaphthalen-1-yl)ureido)-4-methyl-1-phenyl-1H-pyrazol-3-yl)oxy)methyl)morpholine-4-carboxylate: Prepared according to the procedure of Example 143, replacing trans-1-amino-4,4-dimethyl-1,2,3,4-tetrahydronaphthalen-2-ol in Step B with (1R,2R)-1-amino-4,4-dimethyl-1,2,3,4-tetrahydronaphthalen-2-ol (Intermediate X2), to afford the product as a pale yellow solid (134 mg, 75% yield). MS (apci) m/z=606.3 (M+H).

Step B: Preparation of 1-((1R,2R)-2-hydroxy-4,4-dimethyl-1,2,3,4-tetrahydronaphthalen-1-yl)-3-(4-methyl-3-((R)-morpholin-2-ylmethoxy)-1-phenyl-1H-pyrazol-5-yl)urea: To a solution of (R)-tert-butyl 2-(((5-(3-((1R,2R)-2-hydroxy-4,4-dimethyl-1,2,3,4-tetrahydronaphthalen-1-yl)ureido)-4-methyl-1-phenyl-1H-pyrazol-3-yl)oxy)methyl)morpholine-4-carboxylate (134 mg, 0.221 mmol) in iPrOH (3 mL) was added HCl (5-6M in iPrOH, 350 µL). The reaction mixture was stirred at ambient temperature for 17 hours, then additional HCl (5-6M in iPrOH, 1 mL) was added. The reaction mixture was stirred at ambient temperature for 24 hours, then diluted with saturated aqueous NaHCO₃ (25 mL) and extracted with DCM (3×25 mL). The combined organic phases were dried (MgSO₄), filtered, concentrated, and dried under high vacuum to give the product as a yellowish-tan solid (99 mg, 81% yield). MS (apci) m/z=506.3 (M+H).

Example 151

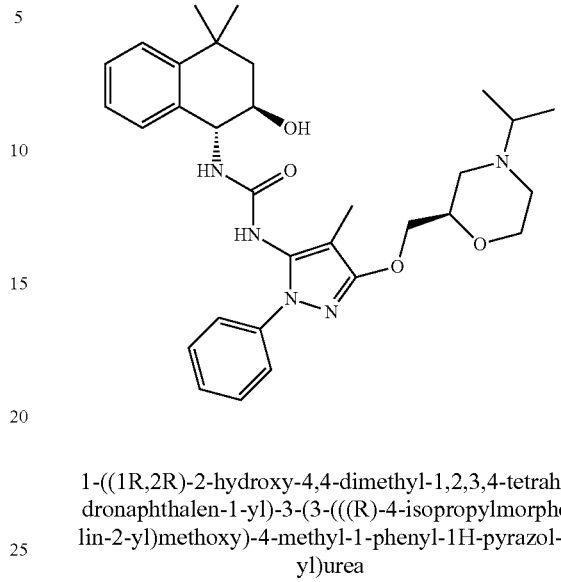

1-((1R,2R)-2-hydroxy-4,4-dimethyl-1,2,3,4-tetrahydronaphthalen-1-yl)-3-(3-(((R)-4-isopropylmorpholin-2-yl)methoxy)-4-methyl-1-phenyl-1H-pyrazol-5-yl)urea To a suspension of 1-((1R,2R)-2-hydroxy-4,4-dimethyl-1,2,3,4-tetrahydronaphthalen-1-yl)-3-(4-methyl-3-((R)-morpholin-2-ylmethoxy)-1-phenyl-1H-pyrazol-5-yl)urea (Example 150, 20 mg, 0.040 mmol) in DCE (0.5 mL) were added acetone (29 µL, 0.396 mmol) then NaBH(OAc)₃ (13 mg, 0.059 mmol). The reaction mixture was stirred at ambient temperature for 19 hours, then additional acetone (60 µL, 0.817 mmol) and NaBH(OAc)₃ (20 mg, 0.094 mmol). The reaction mixture was stirred at ambient temperature for 2 hours, then diluted with DCM (10 mL) and saturated aqueous NaHCO₃ (10 mL). The phases were separated and the aqueous phase was extracted with 10% MeOH/90% DCM (2×10 mL). The combined organic phases were dried (MgSO₄), filtered, and concentrated. The crude product was purified by silica column chromatography, eluting with 0-10% NH₃/MeOH in DCM, to afford the product as a white solid (16.3 mg, 75% yield). MS (apci) m/z=548.3 (M+H).

Example 152

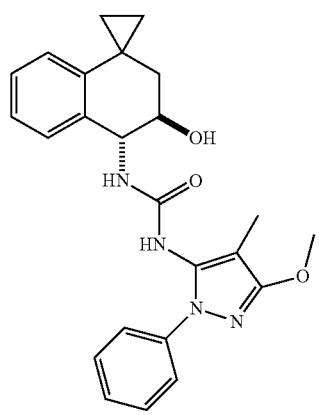 [SMILES: COc1nn(-c2ccccc2)c(NC(=O)N[C@@H]2c3ccccc3C3(CC3)C[C@H]2O)c1C]

1-(trans-3'-hydroxy-3',4'-dihydro-2'H-spiro[cyclopropane-1,1'-naphthalen]-4'-yl)-3-(3-methoxy-4-methyl-1-phenyl-1H-pyrazol-5-yl)urea Prepared according to the procedure of Example 144, replacing (1R,2R)-1-amino-4,4-dimethyl-1,2,3,4-tetrahydronaphthalen-2-ol in Step B with trans-4'-amino-3',4'-dihydro-2'H-spiro[cyclopropane-1,1'-naphthalen]-3'-ol (Intermediate X11). The reaction mixture was purified by silica column chromatography, eluting with 0-10% NH$_3$/MeOH in DCM, to afford the product as a white solid (5.0 mg, 40% yield). MS (apci) m/z=419.2 (M+H).

The following examples in Table 6 were prepared according to the procedure of Example 85, using the appropriate aminopyrazole intermediate.

TABLE 6

| Ex. # | Structure | Name | MS (apci) m/z |
|---|---|---|---|
| 153 | 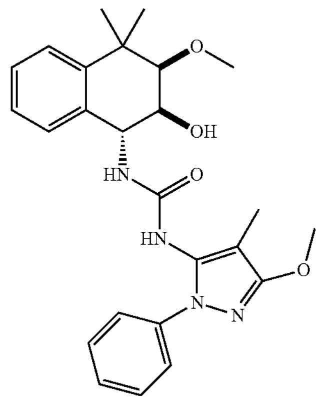 [SMILES: COc1nn(-c2ccccc2)c(NC(=O)N[C@@H]2c3ccccc3C(C)(C)[C@@H](OC)[C@H]2O)c1C] | 1-((r-1,t-2,t-3)-2-hydroxy-3-methoxy-4,4-dimethyl-1,2,3,4-tetrahydronaphthalen-1-yl)-3-(3-methoxy-4-methyl-1-phenyl-1H-pyrazol-5-yl)urea | 451.2 (M + H) |
| 154 | 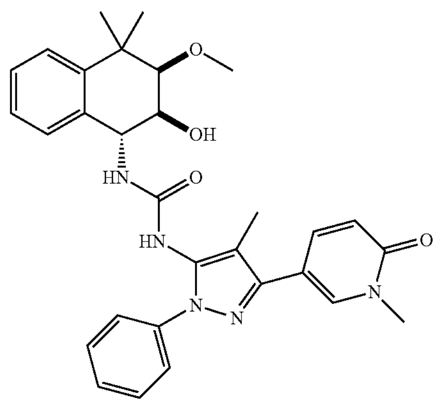 [SMILES: CO[C@H]1[C@@H](O)[C@H](NC(=O)Nc2c(C)c(-c3ccc(=O)n(C)c3)nn2-c2ccccc2)c2ccccc2C1(C)C] | 1-((r-1,t-2,t-3)-2-hydroxy-3-methoxy-4,4-dimethyl-1,2,3,4-tetrahydronaphthalen-1-yl)-3-(4-methyl-3-(1-methyl-6-oxo-1,6-dihydropyridin-3-yl)-1-phenyl-1H-pyrazol-5-yl)urea | 528.2 (M + H) |
| 155 | 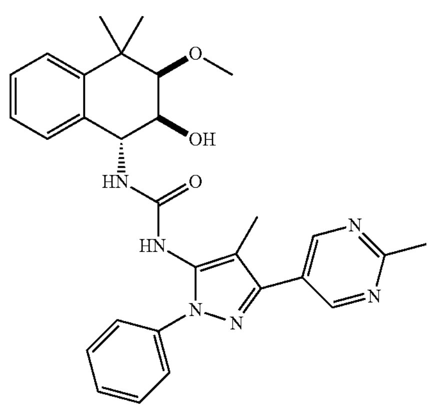 [SMILES: CO[C@H]1[C@@H](O)[C@H](NC(=O)Nc2c(C)c(-c3cnc(C)nc3)nn2-c2ccccc2)c2ccccc2C1(C)C] | 1-((r-1,t-2,t-3)-2-hydroxy-3-methoxy-4,4-dimethyl-1,2,3,4-tetrahydronaphthalen-1-yl)-3-(4-methyl-3-(2-methylpyrimidin-5-yl)-1-phenyl-1H-pyrazol-5-yl)urea | 513.2 (M + H) |

Example 156

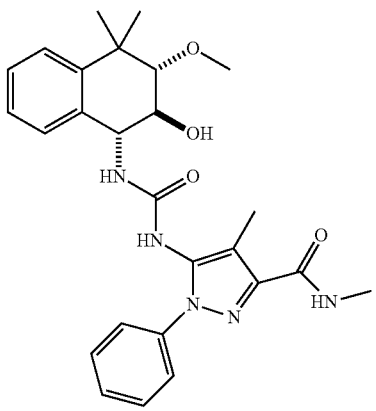 [SMILES: CNC(=O)c1nn(-c2ccccc2)c(NC(=O)N[C@@H]2c3ccccc3C(C)(C)[C@H](OC)[C@H]2O)c1C]

5-(3-((r-1,t-2,c-3)-2-hydroxy-3-methoxy-4,4-dimethyl-1,2,3,4-tetrahydronaphthalen-1-yl)ureido)-N,4-dimethyl-1-phenyl-1H-pyrazole-3-carboxamide Step A: Preparation of (r-1a,c-2,t-7b)-3,3-dimethyl-1a,2,3,7b-tetrahydronaphtho [1,2-b]oxiren-2-ol: Stirred 1,1-dimethyl-1,2-dihydronaphthalen-2-ol (Example 85, Step C, 1.2 g, 6.89 mmol) with 1,2-dichloroethane (15 mL) in an ice bath and added saturated aqueous NaHCO₃ (15 mL). 3-chlorobenzoperoxoic acid (2.55 g, 10.3 mmol) was added and the reaction mixture was allowed to warm to ambient temperature and stir overnight. The mixture was diluted with water (30 mL) and DCM (30 mL). The phased were separated and the aqueous phase was extracted with DCM (30 mL). The combined organic layers were washed with 2N NaOH (30 mL), dried (MgSO₄), filtered, and concentrated. The crude product was purified by silica gel column chromatography, eluting with 25% EtOAc/hexanes followed by 40% EtOAc/hexanes. Yield: 662 mg (51%).

Step B: Preparation of (r-1a,c-2,t-7b)-2-methoxy-3,3-dimethyl-1a,2,3,7b-tetrahydronaphtho[1,2-b]oxirene: A round bottomed flask was charged with (r-1a,c-2,t-7b)-3,3-dimethyl-1a,2,3,7b-tetrahydronaphtho[1,2-b]oxiren-2-ol (662 mg, 3.48 mmol) and anhydrous DMF (10 mL). The reaction mixture was chilled in an ice bath and sodium hydride (209 mg, 5.22 mmol; 60% in oil) was added in portions over 10 minutes under a stream of N₂. The reaction mixture was stirred for 30 minutes in ice bath, and then iodomethane (433 µL, 6.96 mmol) was added. The flask was removed from ice bath and the reaction mixture was warmed to ambient temperature and stirred for 30 minutes. The reaction mixture was carefully quenched with saturated aqueous NH₄Cl (10 mL), then diluted with H₂O (20 mL) and extracted with EtOAc (2×20 mL) The combined organic phases were washed with water (20 mL), brine (20 mL), dried (MgSO₄), filtered, and concentrated. The crude material was used in the next step without further purification (assuming theoretical yield. Yield: 777 g (109%).

Step C: Preparation of (r-1,t-2,c-3)-1-amino-3-methoxy-4,4-dimethyl-1,2,3,4-tetrahydronaphthalen-2-ol: The title compound was prepared from (r-1a,c-2,t-7b)-2-methoxy-3,3-dimethyl-1a,2,3,7b-tetrahydronaphtho[1,2-b]oxirene (711 mg, 3.48 mmol) according to the procedure described for Example 79, Step E. Yield: 315 mg (41%).

Step D: Preparation of 5-(3-((r-1,t-2,c-3)-2-hydroxy-3-methoxy-4,4-dimethyl-1,2,3,4-tetrahydronaphthalen-1-yl)ureido)-N,4-dimethyl-1-phenyl-1H-pyrazole-3-carboxamide: The title compound was prepared from (r-1,t-2,c-3)-1-amino-3-methoxy-4,4-dimethyl-1,2,3,4-tetrahydronaphthalen-2-ol (20 mg, 0.090 mmol) and 5-amino-N,4-dimethyl-1-phenyl-1H-pyrazole-3-carboxamide (Intermediate 10; 21 mg, 0.090 mmol) according to the procedure described for Example 79, Step F. Yield: 4 mg (9%). MS m/z (APCI-pos) M+1=478.2.

The compounds in Table 7 were prepared according to the procedure of Example 156, using the appropriate aminopyrazole intermediate.

TABLE 7

| Ex. # | Structure | Name | MS (apci) m/z |
|---|---|---|---|
| 157 | 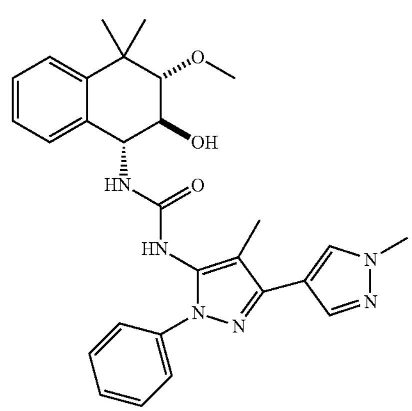 [SMILES: CO[C@@H]1[C@@H](O)[C@H](NC(=O)Nc2c(C)c(-c3cnn(C)c3)nn2-c2ccccc2)c2ccccc2C1(C)C] | 1-(1',4-dimethyl-1-phenyl-1H,1'H-[3,4'-bipyrazol]-5-yl)-3-((r-1,t-2,c-3)-2-hydroxy-3-methoxy-4,4-dimethyl-1,2,3,4-tetrahydronaphthalen-1-yl)urea | 501.2 (M + H) |

| Ex. # | Structure | Name | MS (apci) m/z |
|---|---|---|---|
| 158 | 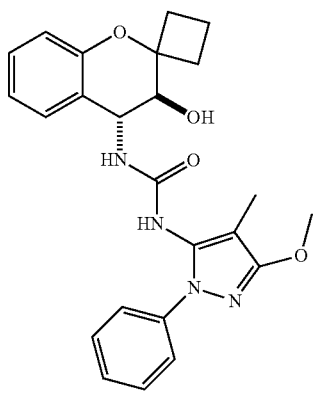 | 1-((r-1,t-2,c-3)-2-hydroxy-3-methoxy-4,4-dimethyl-1,2,3,4-tetrahydronaphthalen-1-yl)-3-(4-methyl-3-((1-methylpiperidin-4-yl)methoxy)-1-phenyl-1H-pyrazol-5-yl)urea | 548.3 (M + H) |

Example 159

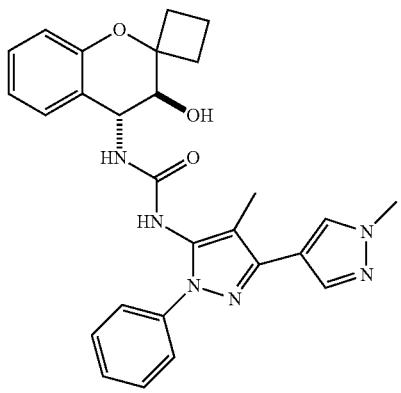 [SMILES: Cc1c(-c2cnn(C)c2)nn(-c2ccccc2)c1NC(=O)N[C@@H]1c2ccccc2OC2(CCC2)[C@H]1O]

1-(trans-3-hydroxyspiro[chroman-2,1'-cyclobutan]-4-yl)-3-(3-methoxy-4-methyl-1-phenyl-1H-pyrazol-5-yl)urea Prepared according to the procedure of Example 144, replacing (1R,2R)-1-amino-4,4-dimethyl-1,2,3,4-tetrahydronaphthalen-2-ol in Step B with trans-4-aminospiro[chroman-2,1'-cyclobutan]-3-ol (Intermediate X12, 10 mg, 0.049 mmol). The reaction mixture was purified by silica column chromatography, eluting with 0-50% acetone/hexanes, to afford the product as a white solid (17.2 mg, 81% yield). MS (apci) m/z=435.3 (M+H).

Example 160

1-(1',4-dimethyl-1-phenyl-1H,1'H-[3,4'-bipyrazol]-5-yl)-3-(trans-3-hydroxyspiro[chroman-2,1'-cyclobutan]-4-yl)urea Prepared according to the procedure of Example 159, replacing phenyl (3-methoxy-4-methyl-1-phenyl-1H-pyrazol-5-yl)carbamate with phenyl (1',4-dimethyl-1-phenyl-1H,1'H-[3,4'-bipyrazol]-5-yl)carbamate (Intermediate 13, 18.2 mg, 0.049 mmol). The reaction mixture was filtered and rinsed Et$_2$O (3×0.5 mL) to afford the product as a white solid (17.1 mg, 72% yield). MS (apci) m/z=485.2 (M+H).

What is claimed is:
1. A compound of the Formula I:

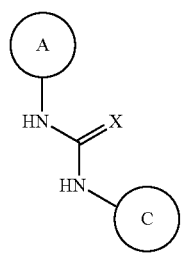

I or stereoisomers, tautomers, or pharmaceutically acceptable salts, or solvates thereof, wherein:
X is O;
Ring A is formula A-1

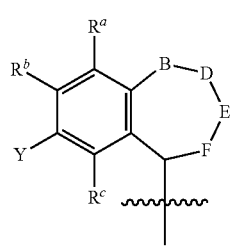

A-1

Y is H, halogen, (1-3C alkoxy)(1-6C)alkyl, (1-6C)alkyl [optionally substituted with 1-5 fluoros], cyano(1-6C)

alkyl, hydroxy(1-6C)alkyl, dihydroxy(2-6C)alkyl, aminocarbonyl(1-6C)alkyl, (1-6C)alkoxy [optionally substituted with 1-5 fluoros], CN, aminocarbonyl or (1-4C alkoxy)carbonyl;

$R^a$, $R^b$ and $R^c$ are independently selected from H, halogen, (1-3C)alkyl, (1-3C)alkoxy and CN;

B is $NR^1$, O, a bond, $CR^d R^e$, S or $SO_2$;
D is $NR^1$, O, a bond, $CR^f R^g$, S or $SO_2$;
E is $NR^1$, O, a bond, or $CR^h R^i$, S or $SO_2$;
F is $CR^j R^k$;

provided that the ring formed by B, D, E, and F together with the atoms to which they are attached contains at least five atoms and zero or one of B, D or E is $NR^1$ or O;

$R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom;

Ring C is formula C-1

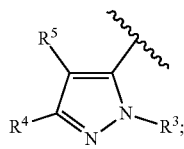

C-1

$R^3$ is (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more groups independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2$(O)$CH_2$—, (1-4C alkoxycarbonyl)(1-6C)alkoxy, hydroxycarbonyl(1-6C)alkoxy, aminocarbonyl(1-6C) alkoxy, $hetCyc^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, $hetCyc^2$C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy) aminocarbonyl, $hetCyc^3$, halogen, CN, trifluoromethylsulfonyl, N-(1-3C alkyl)oxadiazolonyl, $hetAr^5$ or $hetCyc^4$-O—;

$hetCyc^2$ is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl;

$hetCyc^3$ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, 1-6C)alkylsulfonyl, trifluoromethylsulfonyl and (1-4C alkoxy)carbonyl;

$hetAr^3$ is a 5-membered heteroaryl ring having 1-3 ring atoms independently selected from N, O and S and optionally substituted with (1-6C)alkyl;

$Ar^3$ is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl) amino, (1-3C trifluoroalkoxy), fluoro(1-6C alkyl) amino, difluoro(1-6C alkyl)amino, trifluoro(1-6C alkyl)amino, and (3-4C cycloalkyl)amino;

$hetAr^5$ is a group selected from the structures:

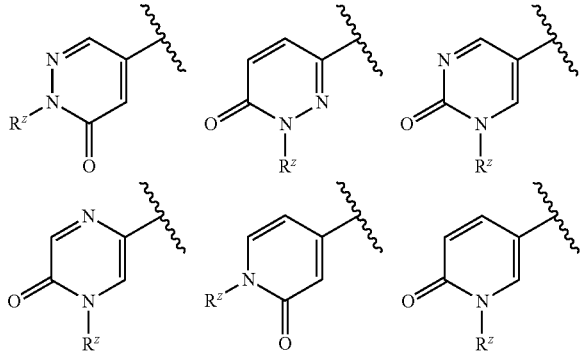

where $R^z$ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

hetCyc⁴ is a 7-8 membered bridged heterocycle having a ring nitrogen atom and optionally substituted with one or more groups independently selected from (1-6C)alkyl and halogen;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—; and R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂.

2. A compound according to claim 1, wherein zero to four of $R^d$, $R^e$, $R^f$, $R^g$, $R^h$, $R^i$, $R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is Oil if F is connected to a heteroatom.

3. A compound according to claim 2, wherein zero to two of $R^d$, $R^e$, $R^f$, $R^g$, $R^h$, $R^i$, $R^j$ and $R^k$ are independently OH, methyl, methoxy, CH₃OCH₂CH₂O—, or cyclopropyl, or one of a pair of $R^d$ and $R^e$, or $R^f$ and $R^g$, or $R^h$ and $R^i$, or $R^j$ and $R^k$, together with the carbon atom to which they are attached form a (3-6C)cycloalkyl, oxetanyl or azetidinyl ring, or one of a pair of $R^d$ and $R^e$, or $R^f$ and $R^g$, or $R^h$ and $R^i$, or $R^j$ and $R^k$ form an oxo group, and the remainder are hydrogen, wherein only one of $R^d$ and $R^e$ can be OH and neither is OH if B is connected to a heteroatom, and only one of $R^f$ and $R^g$ can be OH and neither is OH if D is connected to a heteroatom, and only one of $R^h$ and $R^i$ can be OH and neither is OH if E is connected to a heteroatom, and only one of $R^j$ and $R^k$ can be OH and neither is OH if F is connected to a heteroatom.

4. A compound according to claim 3, wherein B is a bond or $CR^dR^e$, D is a bond or $CR^fR^g$, E is a bond or $CR^hR^i$, and F is $CR^jR^k$, provided that the ring formed by B, D, E, and F together with the atoms to which they are attached contains at least five atoms.

5. A compound according to claim 3, wherein B is O, a bond or $CR^dR^e$, D is O, a bond or $CR^fR^g$, E is O, a bond or $CR^hR^i$, and F is $CR^jR^k$, provided that the ring formed by B, D, E, and F together with the atoms to which they are attached contains at least five atoms and contains one oxygen atom.

6. A compound according to claim 3, wherein B is NR¹, a bond or $CR^dR^e$, D is NR¹, a bond or $CR^fR^g$, E is NR¹, a bond or $CR^hR^i$, and F is $CR^jR^k$, provided that the ring formed by B, D, E, and F together with the atoms to which they are attached contains at least five atoms and contains one nitrogen atom.

7. A compound according to claim 3, wherein B is a NR¹ or O, D is a bond or $CR^fR^g$, E is a bond or $CR^hR^i$, and F is $CR^jR^k$, provided that the ring formed by B, D, E, and F together with the atoms to which they are attached contains at least five atoms.

8. A compound according to claim 3, wherein B is a bond or $CR^dR^e$, D is NR¹ or O, E is a bond or $CR^hR^i$, and F is $CR^jR^k$, provided that the ring formed by B, D, E, and F together with the atoms to which they are attached contains at least five atoms.

9. A compound according to claim 4, wherein Y is H, halogen or (1-3C alkoxy)(1-6C)alkyl.

10. A compound according to claim 9, wherein $R^a$, $R^b$ and $R^c$ are independently selected from halogen, (1-3C)alkyl, (1-3C)alkoxy and CN.

11. A compound according to claim 9, wherein:

R⁴ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl (1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy) aminocarbonyl, hetCyc³, halogen, CN, trifluoromethylsulfonyl, N-(1-3C alkyl)oxadiazolonyl, or hetAr⁵;

and

R[5] is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy).

12. A compound according to claim 11, wherein R[4] is selected from (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr[4] and hetAr[5].

13. A compound according to claim 11, wherein R[4] is selected from 1-6C)alkoxy, hetAr[4] and hetAr[5].

14. A compound according to claim 12, wherein R[4] is hetAr[4] or hetAr[5].

15. A compound according to claim 13, wherein R[5] is selected from halogen, CN, (1-6C)alkyl, (1-4C)alkoxy, hydroxy(1-4C)alkyl, (1-6C)alkylthio, or phenyl optionally substituted with one or more groups independently selected from halogen, (1-6C)alkyl and (1-6C)alkoxy.

16. A compound according to claim 15, wherein R[5] is selected from halogen and (1-6C)alkyl.

17. A compound according to claim 16, wherein R[5] is (1-6C)alkyl.

18. A compound according to claim 10, wherein:

R[4] and R[5] together with the atoms to which they are attached form a 5-6 membered saturated heterocyclic ring having a ring heteroatom selected from N, O or S, wherein said ring nitrogen atom is optionally substituted with (1-6C alkyl)C(=O)O—, or (1-6)acyl, and said sulfur ring atom is optionally oxidized to S(=O) or $SO_2$.

19. A compound according to claim 17, wherein R[3] is selected from Ar[2], hetAr[2] and (1-6C)alkyl.

20. A compound according to claim 19, wherein R[3] is selected from Ar[2] and (1-6C)alkyl.

21. A compound according to claim 20, wherein R[3] is Ar[2].

22. A compound according to claim 1, selected from

| Ex. # | Structure |
|---|---|
| 1 | 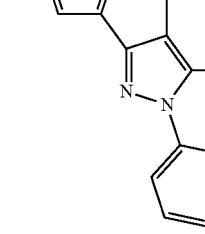 |
| 2 | 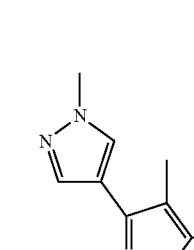 |
| 4 | 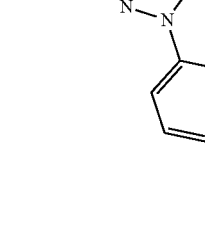 |
| 5 | 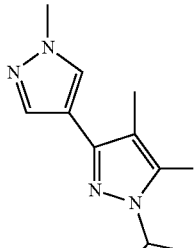 |
| 6 | 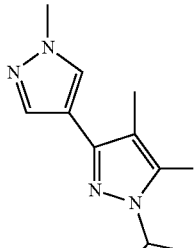 |

| Ex. # | Structure |
|---|---|
| 7 | 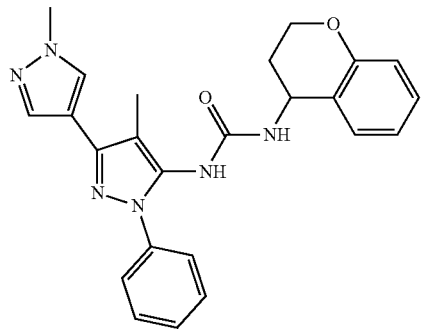 [SMILES: Cc1c(-c2cnn(C)c2)nn(-c2ccccc2)c1NC(=O)NC1CCOc2ccccc21] |
| 8 | 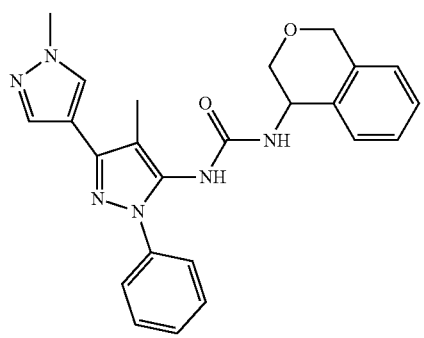 [SMILES: Cc1c(-c2cnn(C)c2)nn(-c2ccccc2)c1NC(=O)NC1COCc2ccccc21] |
| 9 | 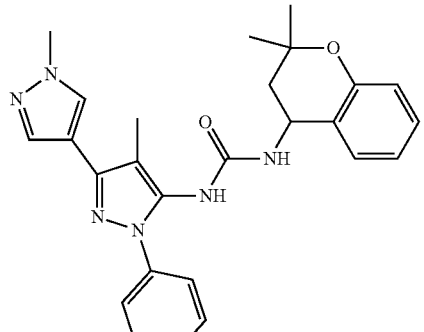 |
| 10 | 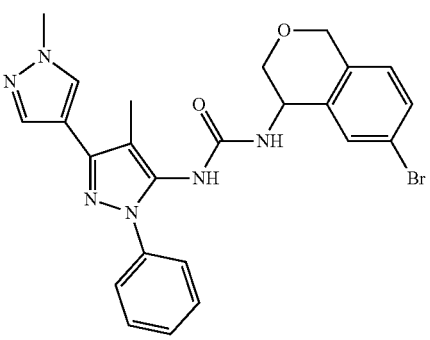 [SMILES: Cc1c(-c2cnn(C)c2)nn(-c2ccccc2)c1NC(=O)NC1COCc2ccc(Br)cc21] |
| Ex. # | Structure |
|---|---|
| 11 | 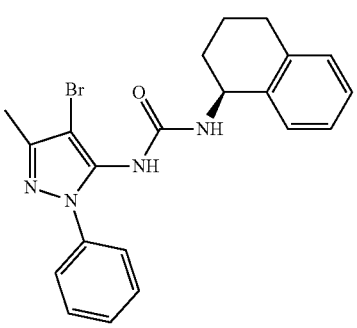 [SMILES: Cc1nn(-c2ccccc2)c(NC(=O)N[C@H]2CCCc3ccccc32)c1Br] |
| 12 | 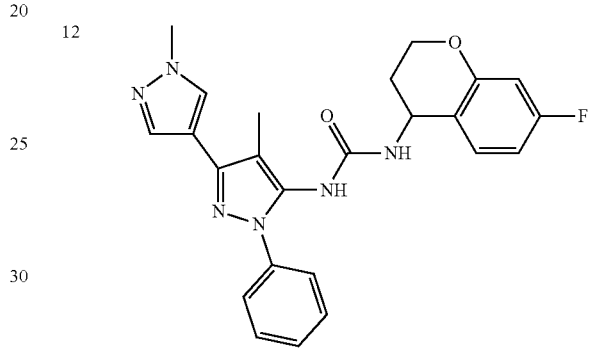 |
| 13 | 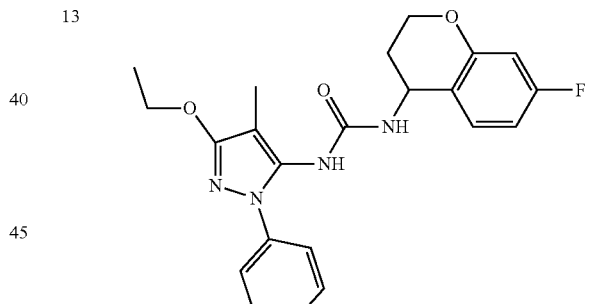 |
| 14 | 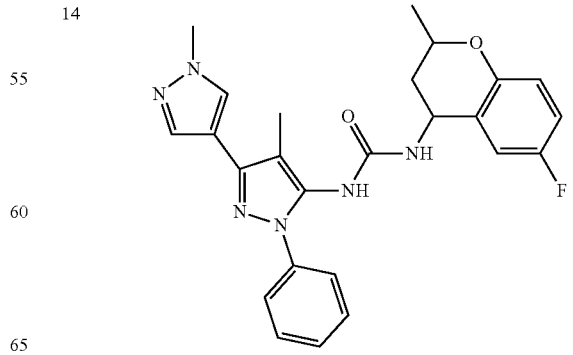 |

| Ex. # | Structure |
|---|---|
| 15 | 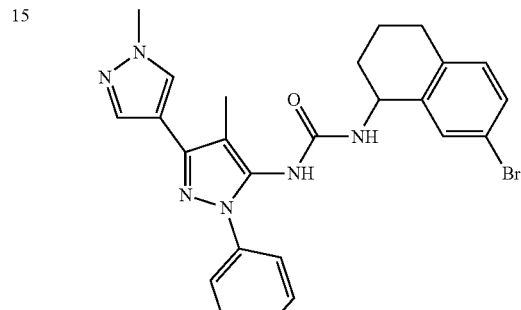 |
| 16 | 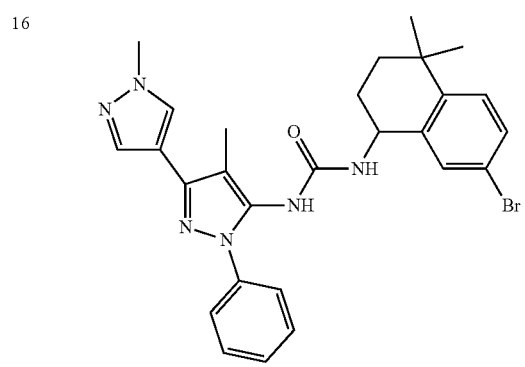 |
| 17 | 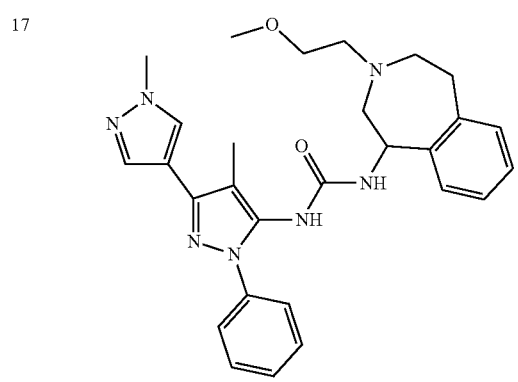 |
| 18 | 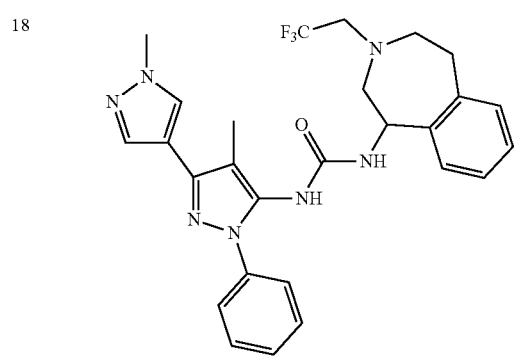 |
| Ex. # | Structure |
|---|---|
| 19 | 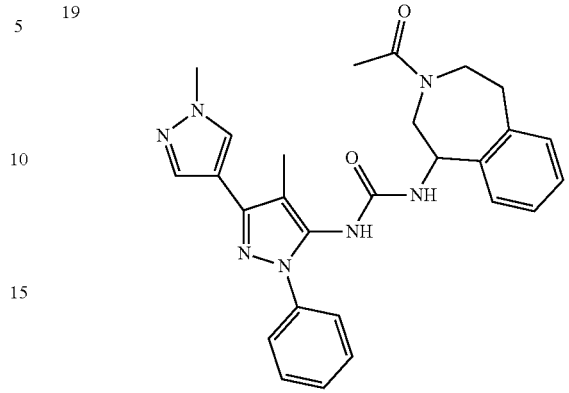 |
| 20 | 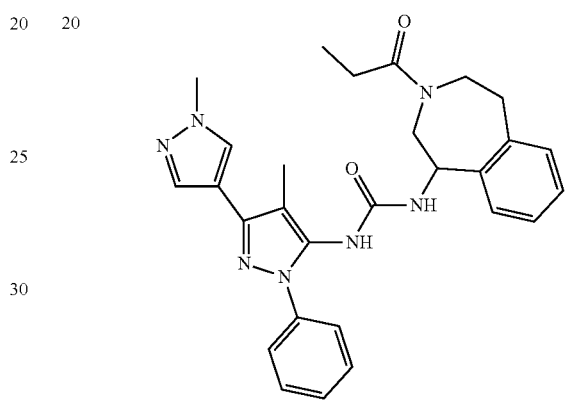 |
| 21 | 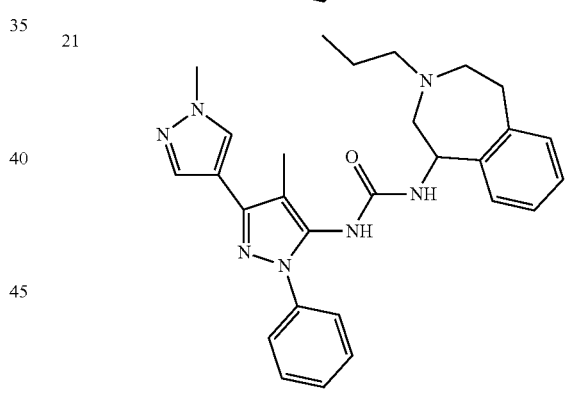 |
| 25 | 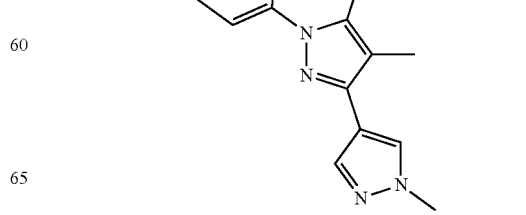 |

| Ex. # | Structure |
|---|---|
| 26 | 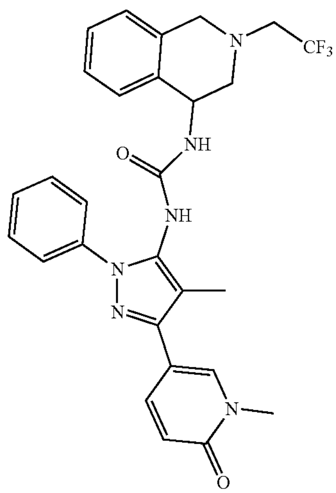 [SMILES: Cc1c(-c2ccc(=O)n(C)c2)nn(-c2ccccc2)c1NC(=O)NC1CN(CC(F)(F)F)Cc2ccccc21] |
| 27 | 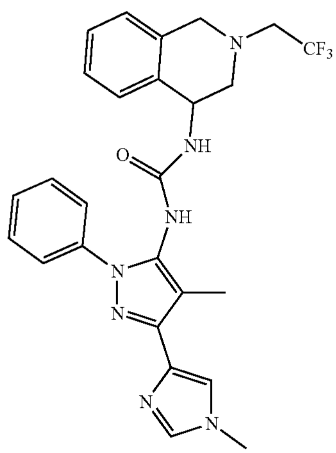 [SMILES: Cc1c(-c2cn(C)cn2)nn(-c2ccccc2)c1NC(=O)NC1CN(CC(F)(F)F)Cc2ccccc21] |
| 29 | 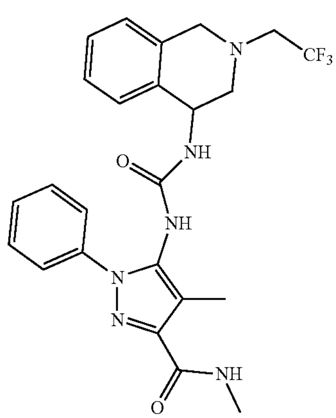 [SMILES: CNC(=O)c1nn(-c2ccccc2)c(NC(=O)NC2CN(CC(F)(F)F)Cc3ccccc32)c1C] |
| 30 | |
| 31 | |
| 32 | |

TABLE-continued
| Ex. # | Structure |
|---|---|
| 33 | 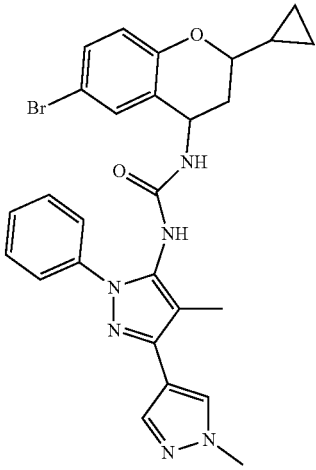 [SMILES: Cc1c(-c2cnn(C)c2)nn(-c2ccccc2)c1NC(=O)NC1CC(C2CC2)Oc2ccc(Br)cc21] |
| 34 | 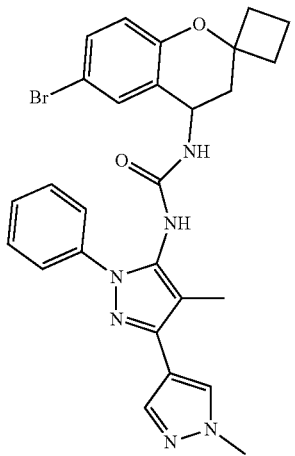 [SMILES: Cc1c(-c2cnn(C)c2)nn(-c2ccccc2)c1NC(=O)NC1CC2(CCC2)Oc2ccc(Br)cc21] |
| 35A | 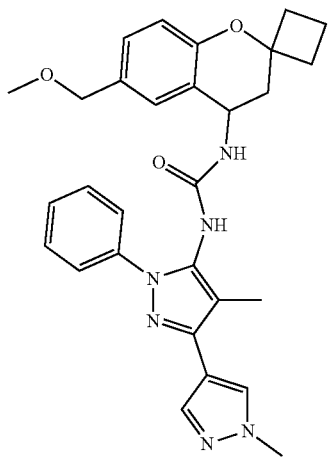 [SMILES: COCc1ccc2c(c1)C(NC(=O)Nc1c(C)c(-c3cnn(C)c3)nn1-c1ccccc1)CC1(CCC1)O2] |
TABLE-continued
| Ex. # | Structure |
|---|---|
| 35B | 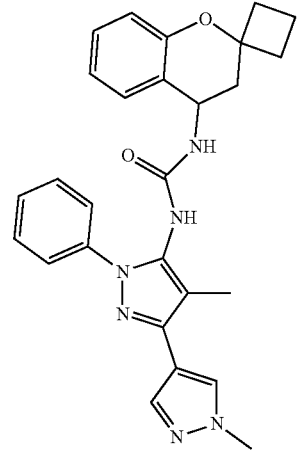 [SMILES: Cc1c(-c2cnn(C)c2)nn(-c2ccccc2)c1NC(=O)NC1CC2(CCC2)Oc2ccccc21] |
| 36 | 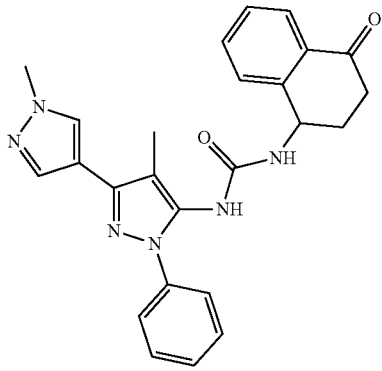 [SMILES: Cc1c(-c2cnn(C)c2)nn(-c2ccccc2)c1NC(=O)NC1CCC(=O)c2ccccc21] |
| 37 | 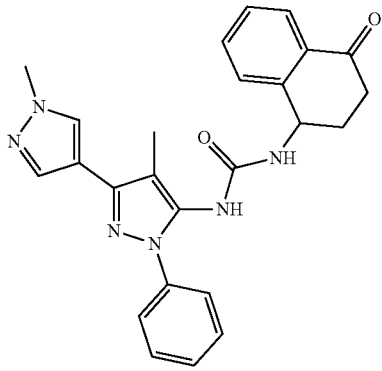 [SMILES: Cc1c(-c2cnn(C)c2)nn(-c2ccccc2)c1NC(=O)NC1CCC(=O)c2ccccc21] |
| 39 | 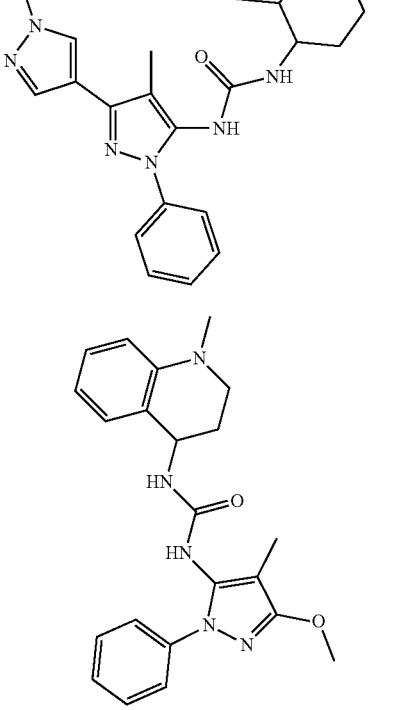 |

| Ex. # | Structure |
|---|---|
| 40 | 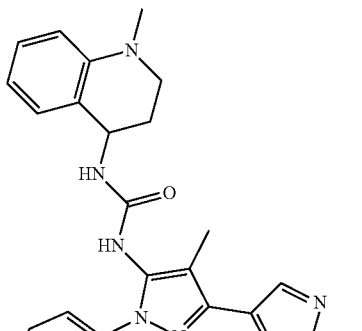 |
| 41 | 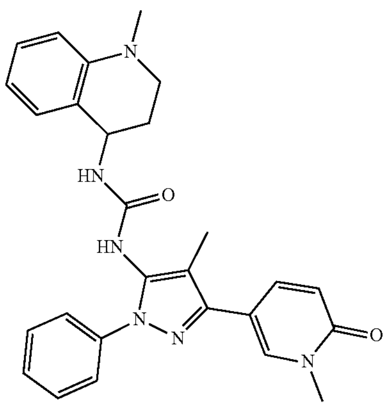 [SMILES: Cc1c(-c2ccc(=O)n(C)c2)nn(-c2ccccc2)c1NC(=O)NC1CCN(C)c2ccccc21] |
| 42 | 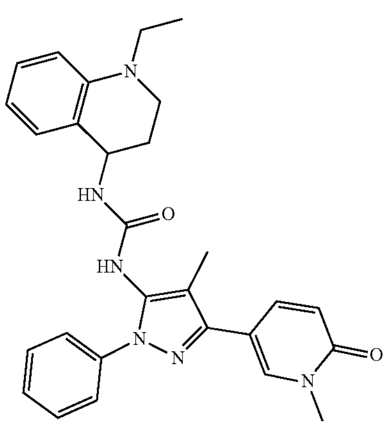 [SMILES: CCN1CCC(NC(=O)Nc2c(C)c(-c3ccc(=O)n(C)c3)nn2-c2ccccc2)c2ccccc21] |
| 43 | |
| 44 | |
| 45 | |

| Ex. # | Structure |
|---|---|
| 46 | 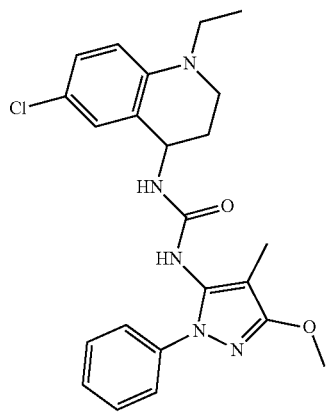 [SMILES: CCN1CCC(NC(=O)Nc2c(C)c(OC)nn2-c2ccccc2)c2cc(Cl)ccc21] |
| 49 | 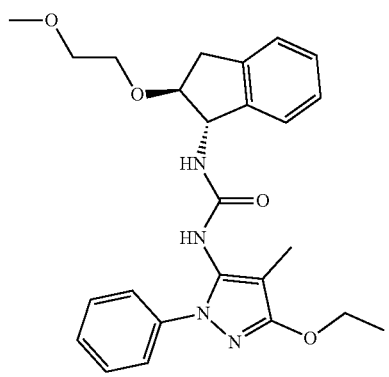 [SMILES: CCOc1nn(-c2ccccc2)c(NC(=O)N[C@H]2c3ccccc3C[C@@H]2OCCOC)c1C] |
| 51 | 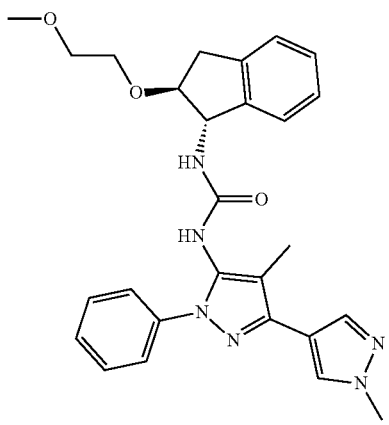 |
| 52 | 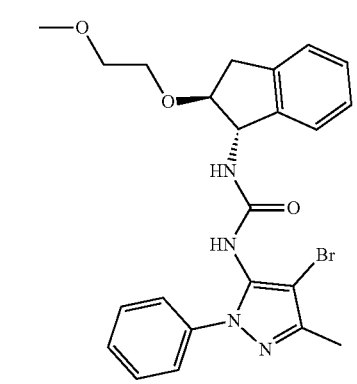 [SMILES: COCCO[C@H]1Cc2ccccc2[C@@H]1NC(=O)Nc1c(Br)c(C)nn1-c1ccccc1] |
| Ex. # | Structure |
|---|---|
| 53 | 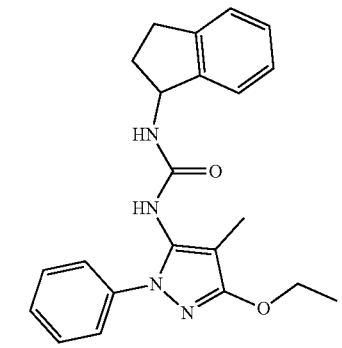 [SMILES: CCOc1nn(-c2ccccc2)c(NC(=O)NC2CCc3ccccc32)c1C] |
| 54 | 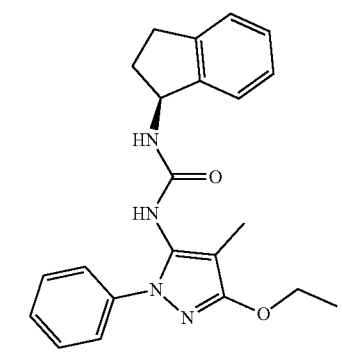 [SMILES: CCOc1nn(-c2ccccc2)c(NC(=O)N[C@H]2CCc3ccccc32)c1C] |
| 55 | 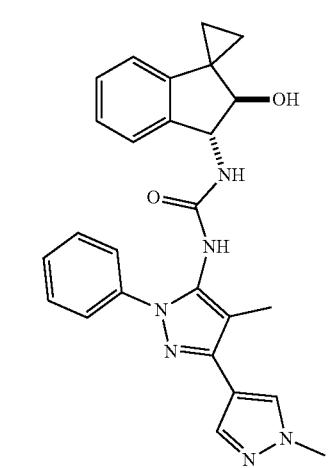 [SMILES: Cc1c(-c2cnn(C)c2)nn(-c2ccccc2)c1NC(=O)N[C@@H]1c2ccccc2C2(CC2)[C@H]1O] |

| Ex. # | Structure |
|---|---|
| 56 | 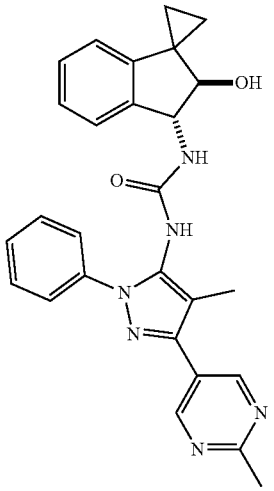 [SMILES: Cc1ncc(-c2nn(-c3ccccc3)c(NC(=O)N[C@@H]3c4ccccc4C4(CC4)[C@H]3O)c2C)cn1] |
| 57 | 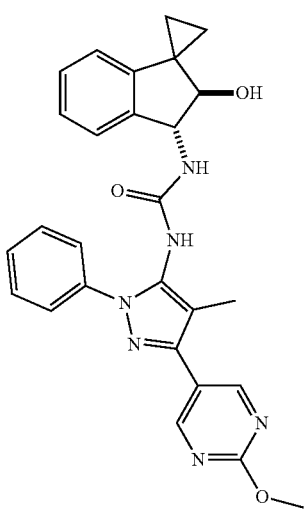 [SMILES: COc1ncc(-c2nn(-c3ccccc3)c(NC(=O)N[C@@H]3c4ccccc4C4(CC4)[C@H]3O)c2C)cn1] |
| 58 | 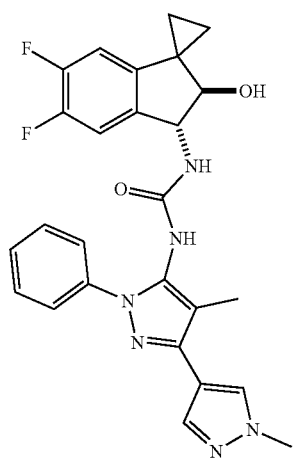 [SMILES: Cc1c(-c2cnn(C)c2)nn(-c2ccccc2)c1NC(=O)N[C@@H]1c2cc(F)c(F)cc2C2(CC2)[C@H]1O] |
| Ex. # | Structure |
|---|---|
| 59 | 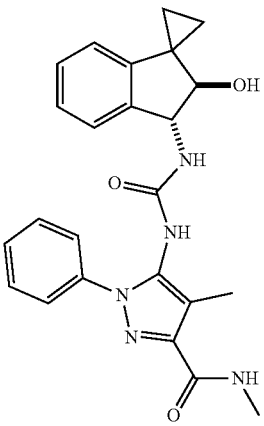 [SMILES: CNC(=O)c1nn(-c2ccccc2)c(NC(=O)N[C@@H]2c3ccccc3C3(CC3)[C@H]2O)c1C] |
| 60 | 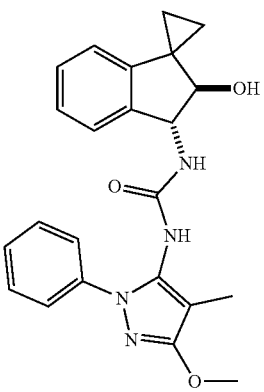 [SMILES: COc1nn(-c2ccccc2)c(NC(=O)N[C@@H]2c3ccccc3C3(CC3)[C@H]2O)c1C] |
| 61 | 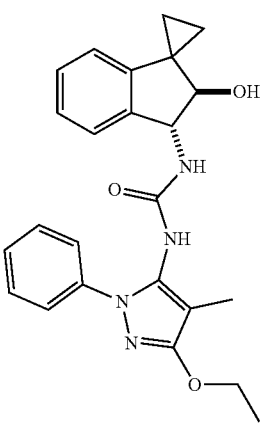 [SMILES: CCOc1nn(-c2ccccc2)c(NC(=O)N[C@@H]2c3ccccc3C3(CC3)[C@H]2O)c1C] |

| Ex. # | Structure |
|---|---|
| 62 | 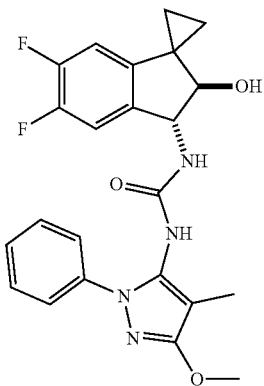 [SMILES: COc1nn(-c2ccccc2)c(NC(=O)N[C@@H]2c3cc(F)c(F)cc3C3(CC3)[C@H]2O)c1C] |
| 63 | 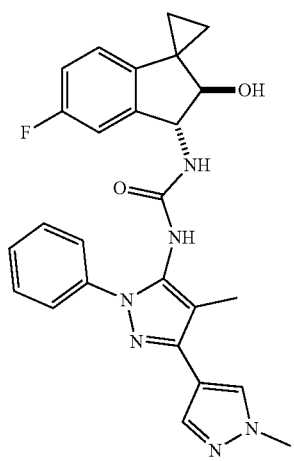 [SMILES: Cc1c(-c2cnn(C)c2)nn(-c2ccccc2)c1NC(=O)N[C@@H]1c2cc(F)ccc2C2(CC2)[C@H]1O] |
| 64 | 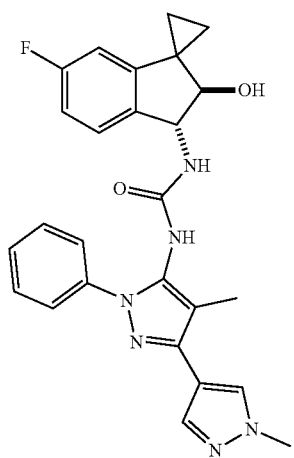 [SMILES: Cc1c(-c2cnn(C)c2)nn(-c2ccccc2)c1NC(=O)N[C@@H]1c2ccc(F)cc2C2(CC2)[C@H]1O] |─
| Ex. # | Structure |
|---|---|
| 65 | 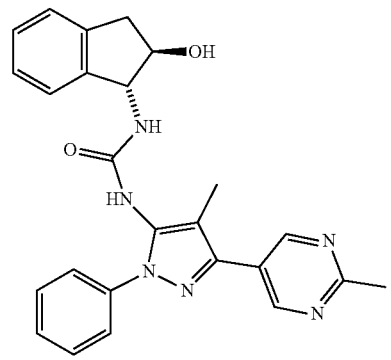 [SMILES: Cc1ncc(-c2nn(-c3ccccc3)c(NC(=O)N[C@@H]3c4ccccc4C[C@H]3O)c2C)cn1] |
| 66 | 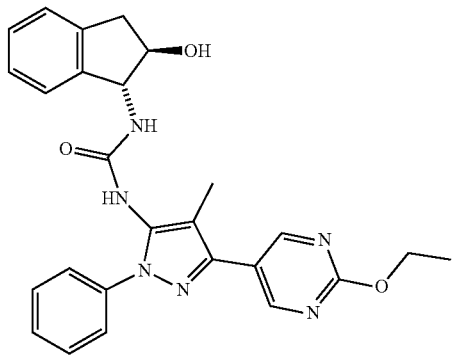 [SMILES: CCOc1ncc(-c2nn(-c3ccccc3)c(NC(=O)N[C@@H]3c4ccccc4C[C@H]3O)c2C)cn1] |
| 67 | 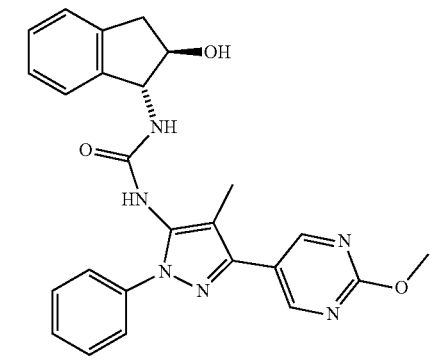 [SMILES: COc1ncc(-c2nn(-c3ccccc3)c(NC(=O)N[C@@H]3c4ccccc4C[C@H]3O)c2C)cn1] |
| 68 | 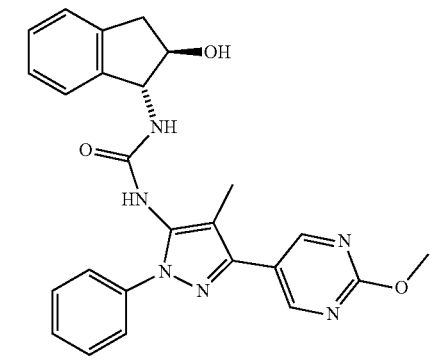 [SMILES: COc1ncc(-c2nn(-c3ccccc3)c(NC(=O)N[C@@H]3c4ccccc4C[C@H]3O)c2C)cn1] |

| Ex. # | Structure |
|---|---|
| 69 | 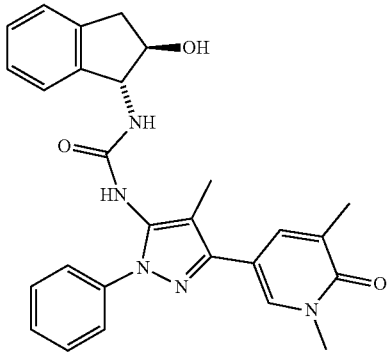 [SMILES: Cc1c(-c2cc(C)c(=O)n(C)c2)nn(-c2ccccc2)c1NC(=O)N[C@@H]1c2ccccc2C[C@H]1O] |
| 70 | 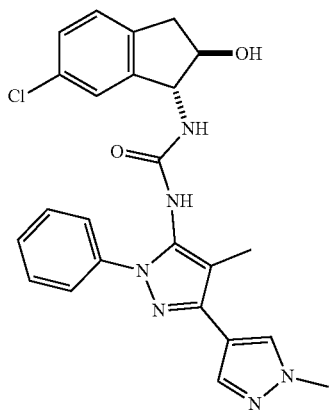 [SMILES: Cc1c(-c2cnn(C)c2)nn(-c2ccccc2)c1NC(=O)N[C@@H]1c2cc(Cl)ccc2C[C@H]1O] |
| 71 | 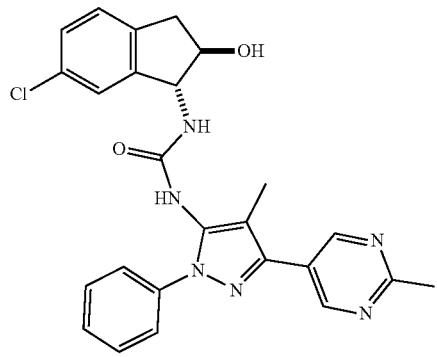 [SMILES: Cc1ncc(-c2nn(-c3ccccc3)c(NC(=O)N[C@@H]3c4cc(Cl)ccc4C[C@H]3O)c2C)cn1] |
| 72 | 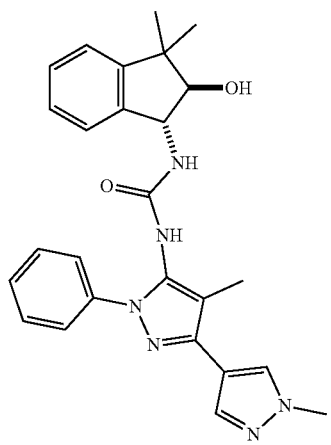 [SMILES: Cc1c(-c2cnn(C)c2)nn(-c2ccccc2)c1NC(=O)N[C@@H]1c2ccccc2C(C)(C)[C@H]1O] |
| Ex. # | Structure |
|---|---|
| 73 | 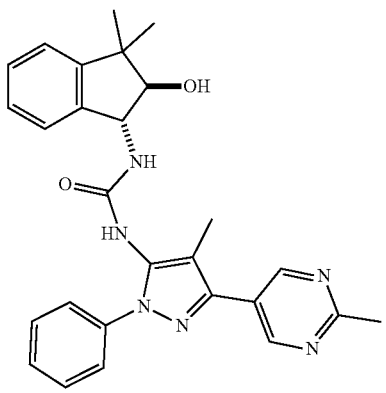 [SMILES: Cc1ncc(-c2nn(-c3ccccc3)c(NC(=O)N[C@@H]3c4ccccc4C(C)(C)[C@H]3O)c2C)cn1] |
| 74 | 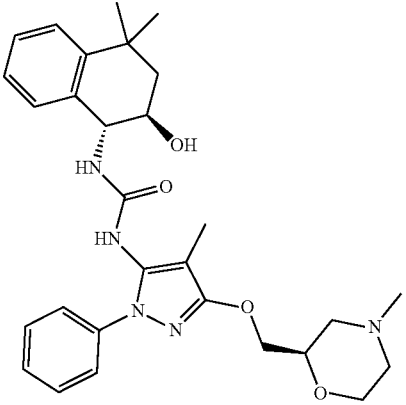 [SMILES: Cc1c(OC[C@H]2CN(C)CCO2)nn(-c2ccccc2)c1NC(=O)N[C@@H]1c2ccccc2C(C)(C)C[C@H]1O] |
| 75 | 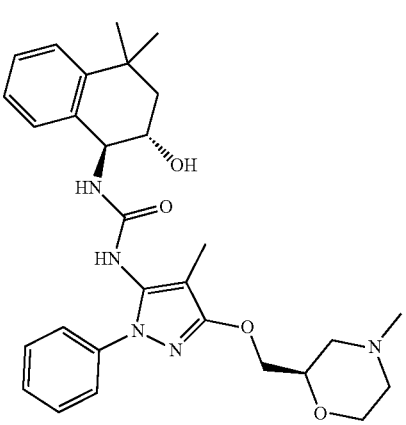 [SMILES: Cc1c(OC[C@H]2CN(C)CCO2)nn(-c2ccccc2)c1NC(=O)N[C@H]1c2ccccc2C(C)(C)C[C@@H]1O] |

| Ex. # | Structure |
|---|---|
| 76 | 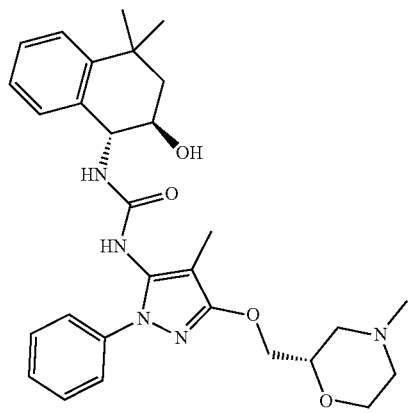 [SMILES: Cc1c(OC[C@@H]2CN(C)CCO2)nn(-c2ccccc2)c1NC(=O)N[C@@H]1c2ccccc2C(C)(C)C[C@H]1O] |
| 77 | 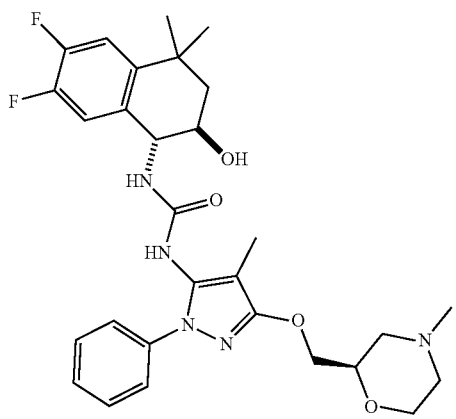 [SMILES: Cc1c(OC[C@H]2CN(C)CCO2)nn(-c2ccccc2)c1NC(=O)N[C@@H]1c2cc(F)c(F)cc2C(C)(C)C[C@H]1O] |
| 78 | 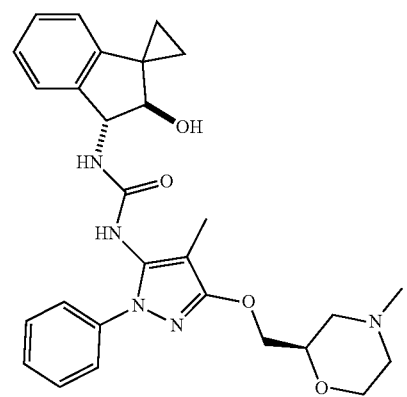 [SMILES: Cc1c(OC[C@H]2CN(C)CCO2)nn(-c2ccccc2)c1NC(=O)N[C@@H]1c2ccccc2C2(CC2)[C@H]1O] |
| Ex. # | Structure |
|---|---|
| 79 | 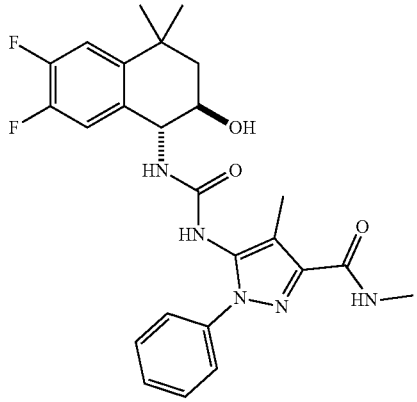 [SMILES: CNC(=O)c1nn(-c2ccccc2)c(NC(=O)N[C@@H]2c3cc(F)c(F)cc3C(C)(C)C[C@H]2O)c1C] |
| 80 | 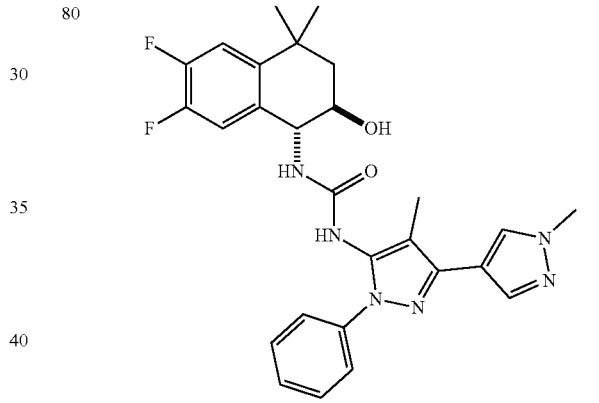 |
| 81 | 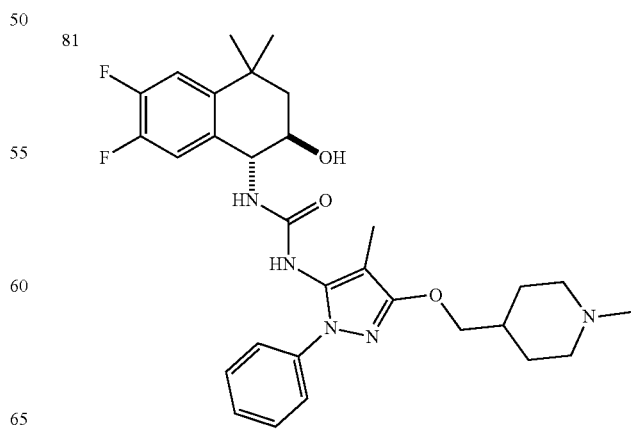 |

| Ex. # | Structure |
|---|---|
| 82 | (structure) |
| 83 | (structure) |
| 84 | (structure) |
| 85 | (structure) |
| 86 | (structure) |
| 87 | (structure) |

327
-continued
| Ex. # | Structure |
|---|---|
| 88 | 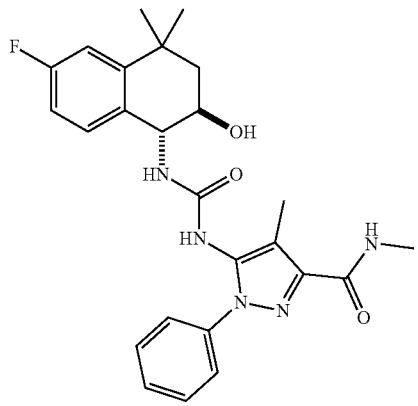 [SMILES: CNC(=O)c1nn(-c2ccccc2)c(NC(=O)N[C@@H]2c3ccc(F)cc3C(C)(C)C[C@H]2O)c1C] |
| 89 | 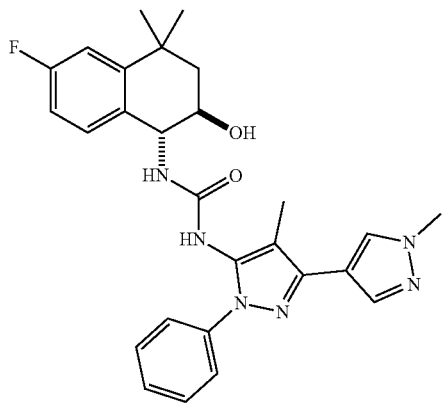 [SMILES: Cc1c(-c2cnn(C)c2)nn(-c2ccccc2)c1NC(=O)N[C@@H]1c2ccc(F)cc2C(C)(C)C[C@H]1O] |
| 90 | 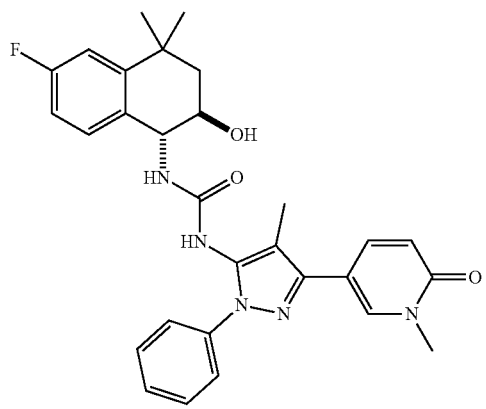 [SMILES: Cc1c(-c2ccc(=O)n(C)c2)nn(-c2ccccc2)c1NC(=O)N[C@@H]1c2ccc(F)cc2C(C)(C)C[C@H]1O] |
328
-continued
| Ex. # | Structure |
|---|---|
| 91 | 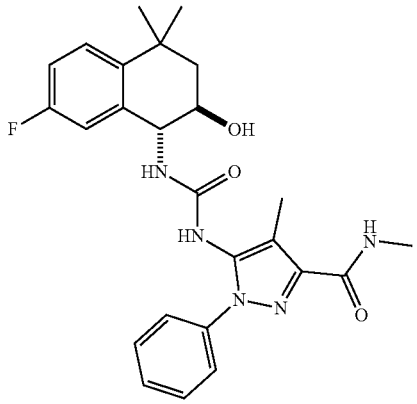 [SMILES: CNC(=O)c1nn(-c2ccccc2)c(NC(=O)N[C@@H]2c3cc(F)ccc3C(C)(C)C[C@H]2O)c1C] |
| 92 | 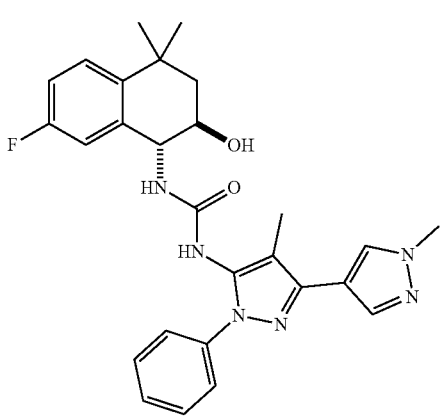 [SMILES: Cc1c(-c2cnn(C)c2)nn(-c2ccccc2)c1NC(=O)N[C@@H]1c2cc(F)ccc2C(C)(C)C[C@H]1O] |
| 93 | 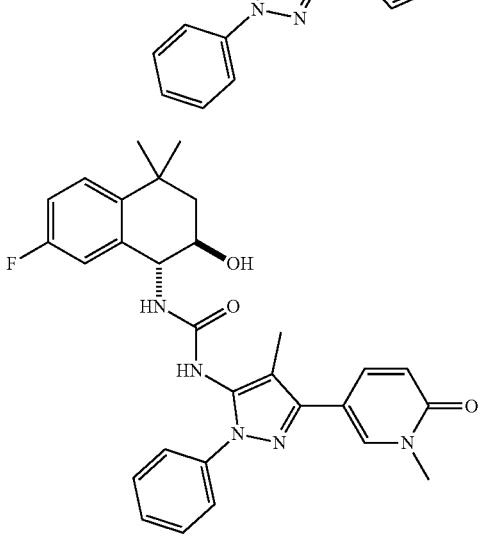 |
| 94 | 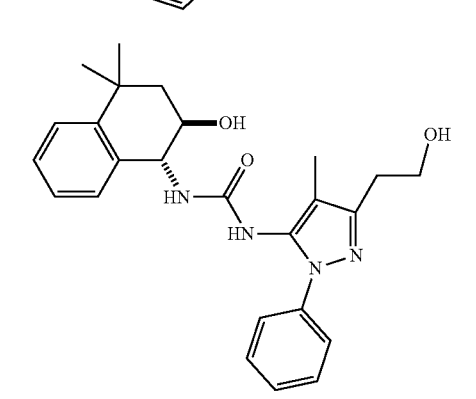 |

| Ex. # | Structure |
|---|---|
| 95 | 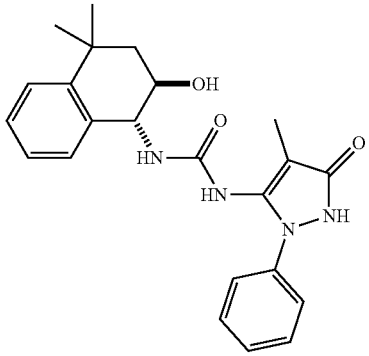 [SMILES: Cc1c(NC(=O)N[C@@H]2c3ccccc3C(C)(C)C[C@H]2O)n(-c2ccccc2)[nH]c1=O] |
| 96 | 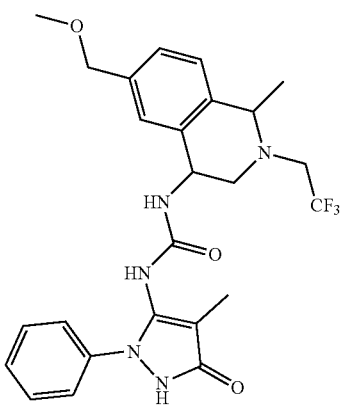 [SMILES: COCc1ccc2c(c1)C(NC(=O)Nc1c(C)c(=O)[nH]n1-c1ccccc1)CN(CC(F)(F)F)C2C] |
| 97 | 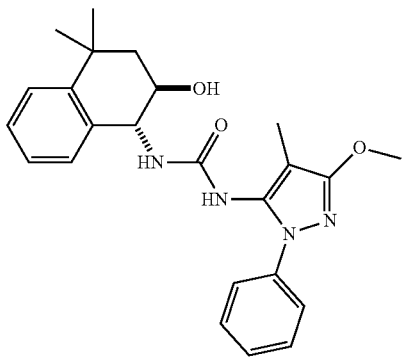 [SMILES: COc1nn(-c2ccccc2)c(NC(=O)N[C@@H]2c3ccccc3C(C)(C)C[C@H]2O)c1C] |
| 98 | 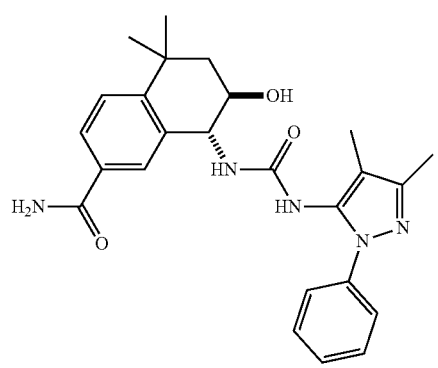 [SMILES: Cc1nn(-c2ccccc2)c(NC(=O)N[C@@H]2c3cc(C(N)=O)ccc3C(C)(C)C[C@H]2O)c1C] |
| 99 | 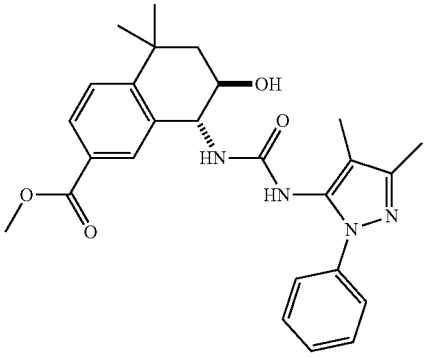 |
| 100 | 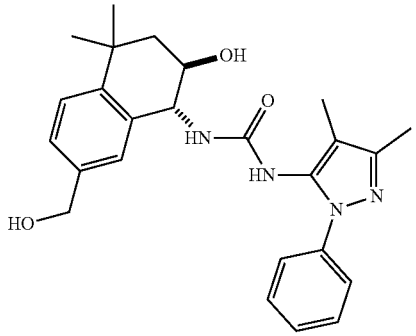 [SMILES: Cc1nn(-c2ccccc2)c(NC(=O)N[C@@H]2c3cc(CO)ccc3C(C)(C)C[C@H]2O)c1C] |
| 101 | 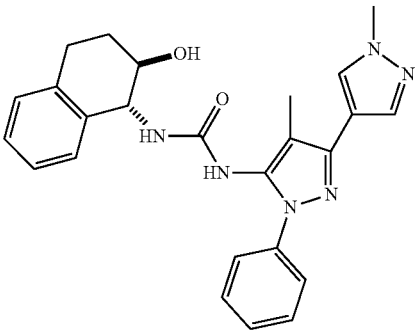 [SMILES: Cc1c(-c2cnn(C)c2)nn(-c2ccccc2)c1NC(=O)N[C@@H]1c2ccccc2CC[C@H]1O] |
| 102 | 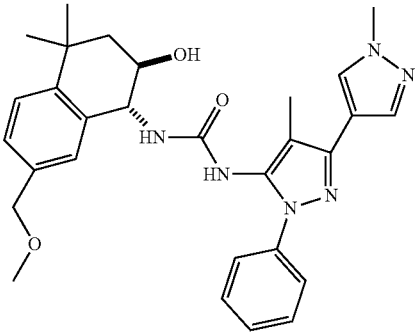 [SMILES: COCc1ccc2c(c1)[C@@H](NC(=O)Nc1c(C)c(-c3cnn(C)c3)nn1-c1ccccc1)[C@H](O)CC2(C)C] |

| Ex. # | Structure |
|---|---|
| 103 | 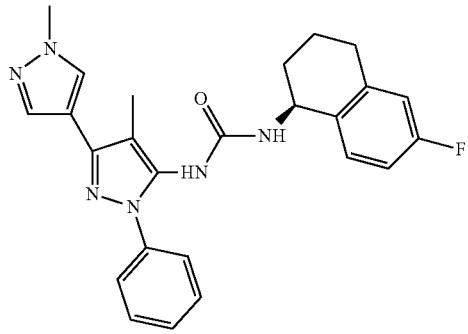 [SMILES: Cc1c(-c2cnn(C)c2)nn(-c2ccccc2)c1NC(=O)N[C@H]1CCCc2cc(F)ccc21] |
| 104 | 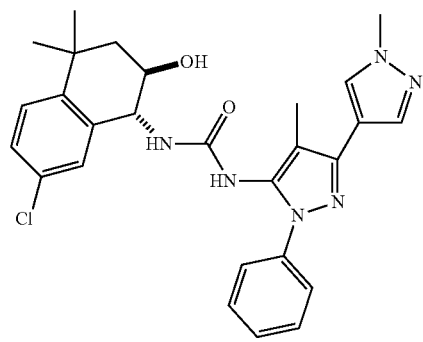 [SMILES: Cc1c(-c2cnn(C)c2)nn(-c2ccccc2)c1NC(=O)N[C@@H]1c2cc(Cl)ccc2C(C)(C)C[C@H]1O] |
| 105 | 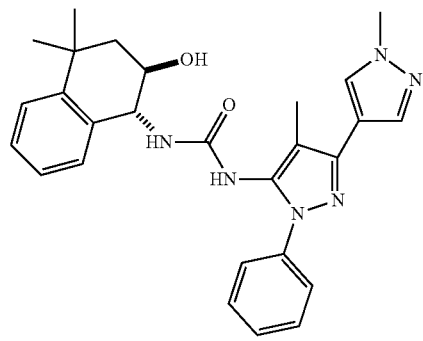 [SMILES: Cc1c(-c2cnn(C)c2)nn(-c2ccccc2)c1NC(=O)N[C@@H]1c2ccccc2C(C)(C)C[C@H]1O] |
| 106 | 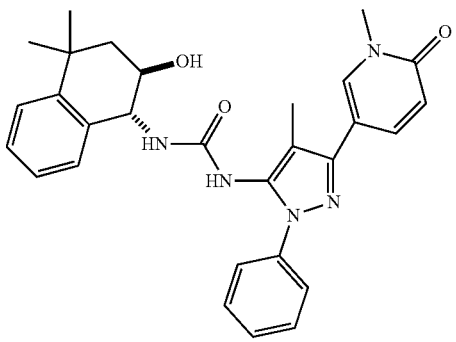 [SMILES: Cc1c(-c2ccc(=O)n(C)c2)nn(-c2ccccc2)c1NC(=O)N[C@@H]1c2ccccc2C(C)(C)C[C@H]1O] |
| Ex. # | Structure |
|---|---|
| 107 | 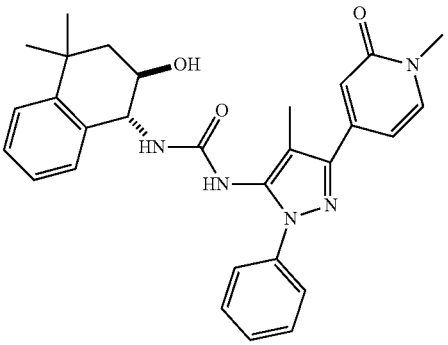 [SMILES: Cc1c(-c2ccn(C)c(=O)c2)nn(-c2ccccc2)c1NC(=O)N[C@@H]1c2ccccc2C(C)(C)C[C@H]1O] |
| 108 | 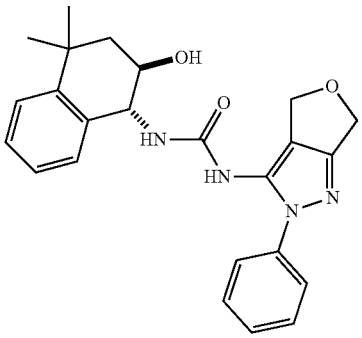 [SMILES: CC1(C)C[C@@H](O)[C@H](NC(=O)Nc2c3c(nn2-c2ccccc2)COC3)c2ccccc21] |
| 109 | 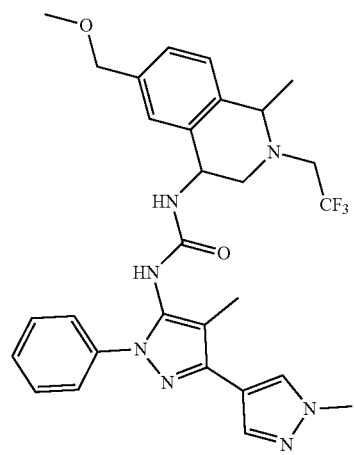 [SMILES: COCc1ccc2c(c1)C(NC(=O)Nc1c(C)c(-c3cnn(C)c3)nn1-c1ccccc1)CN(CC(F)(F)F)C2C] |
| 110 | 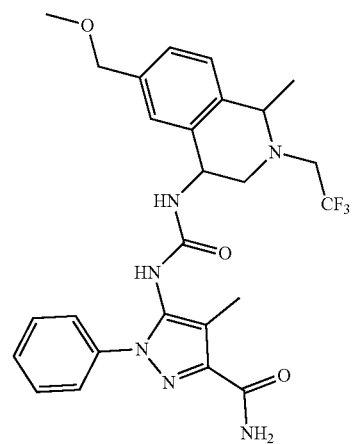 [SMILES: COCc1ccc2c(c1)C(NC(=O)Nc1c(C)c(C(N)=O)nn1-c1ccccc1)CN(CC(F)(F)F)C2C] |

| Ex. # | Structure |
|---|---|
| 111 | 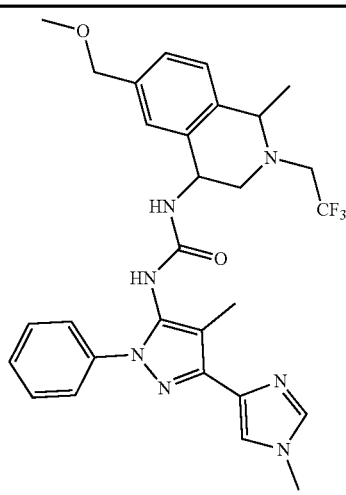 |
| 112 | 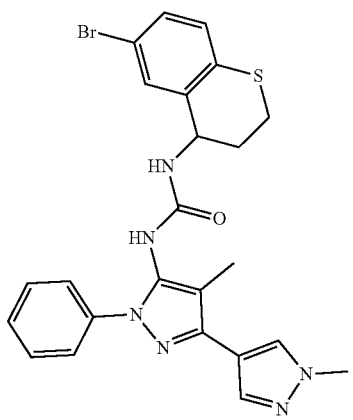 [SMILES: Cc1c(-c2cnn(C)c2)nn(-c2ccccc2)c1NC(=O)NC1CCSc2ccc(Br)cc21] |
| 113 | 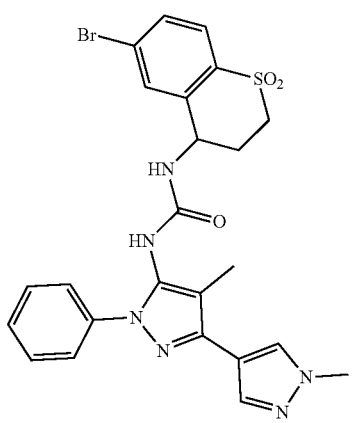 [SMILES: Cc1c(-c2cnn(C)c2)nn(-c2ccccc2)c1NC(=O)NC1CCS(=O)(=O)c2ccc(Br)cc21] |
| Ex. # | Structure |
|---|---|
| 114 | 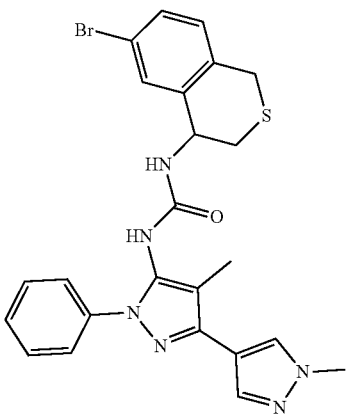 [SMILES: Cc1c(-c2cnn(C)c2)nn(-c2ccccc2)c1NC(=O)NC1CSCc2ccc(Br)cc21] |
| 115 | 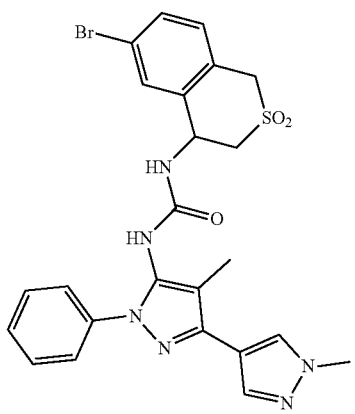 [SMILES: Cc1c(-c2cnn(C)c2)nn(-c2ccccc2)c1NC(=O)NC1CS(=O)(=O)Cc2ccc(Br)cc21] |
| 116 | 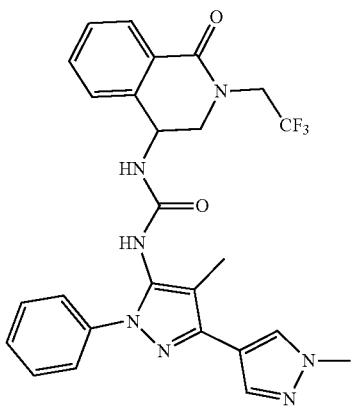 [SMILES: Cc1c(-c2cnn(C)c2)nn(-c2ccccc2)c1NC(=O)NC1CN(CC(F)(F)F)C(=O)c2ccccc21] |

| Ex. # | Structure |
|---|---|
| 117 | 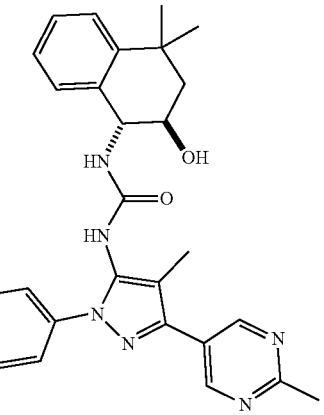 |
| 118 | 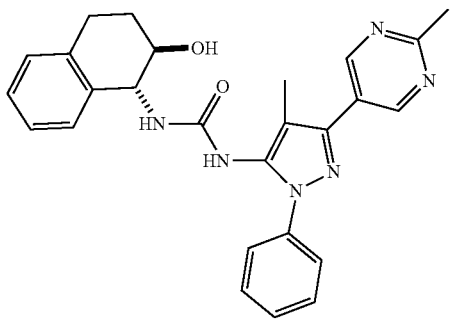 [SMILES: Cc1ncc(-c2nn(-c3ccccc3)c(NC(=O)N[C@@H]3c4ccccc4CC[C@H]3O)c2C)cn1] |
| 119 | 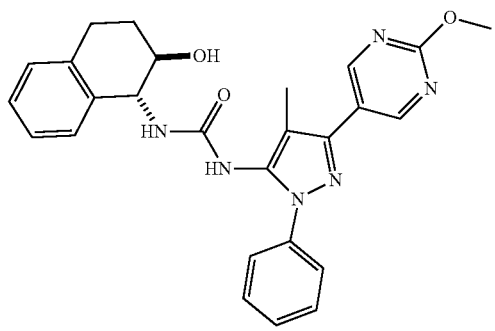 [SMILES: COc1ncc(-c2nn(-c3ccccc3)c(NC(=O)N[C@@H]3c4ccccc4CC[C@H]3O)c2C)cn1] |
| 120 | 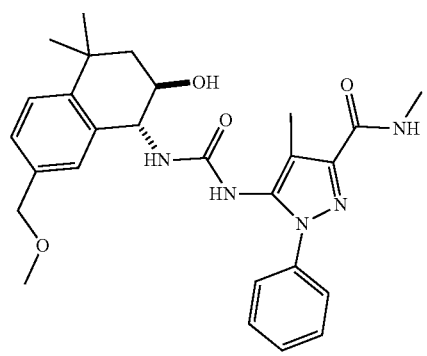 [SMILES: CNC(=O)c1nn(-c2ccccc2)c(NC(=O)N[C@@H]2c3cc(COC)ccc3C(C)(C)C[C@H]2O)c1C] |
| Ex. # | Structure |
|---|---|
| 121 | 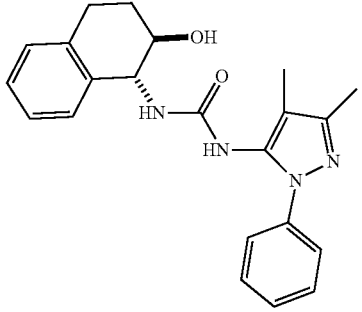 [SMILES: Cc1nn(-c2ccccc2)c(NC(=O)N[C@@H]2c3ccccc3CC[C@H]2O)c1C] |
| 122 | 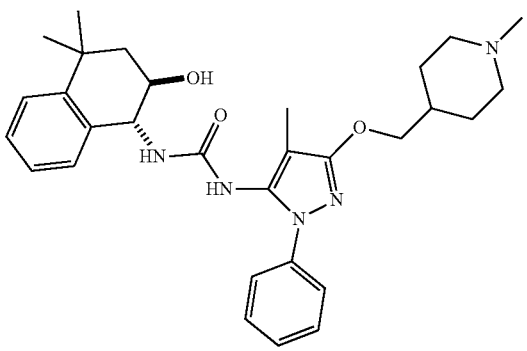 [SMILES: Cc1c(OCC2CCN(C)CC2)nn(-c2ccccc2)c1NC(=O)N[C@@H]1c2ccccc2C(C)(C)C[C@H]1O] |
| 123 | 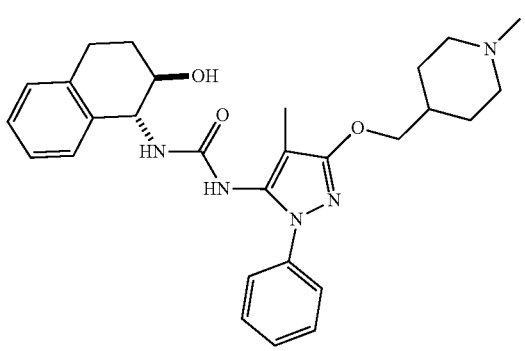 [SMILES: Cc1c(OCC2CCN(C)CC2)nn(-c2ccccc2)c1NC(=O)N[C@@H]1c2ccccc2CC[C@H]1O] |
| 124 | 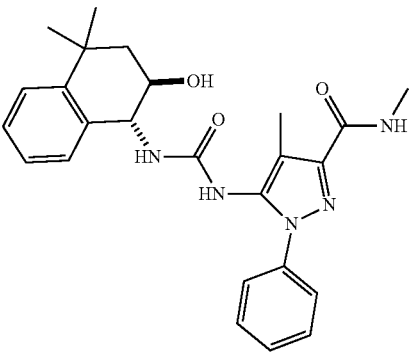 [SMILES: CNC(=O)c1nn(-c2ccccc2)c(NC(=O)N[C@@H]2c3ccccc3C(C)(C)C[C@H]2O)c1C] |

| Ex. # | Structure |
|---|---|
| 125 | 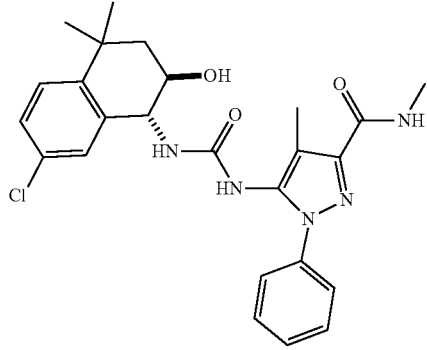 [SMILES: CNC(=O)c1nn(-c2ccccc2)c(NC(=O)N[C@@H]2c3cc(Cl)ccc3C(C)(C)C[C@H]2O)c1C] |
| 126 | 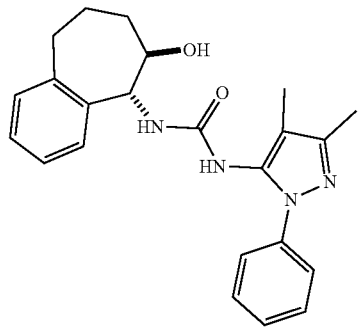 [SMILES: Cc1nn(-c2ccccc2)c(NC(=O)N[C@@H]2c3ccccc3CCC[C@H]2O)c1C] |
| 127 | 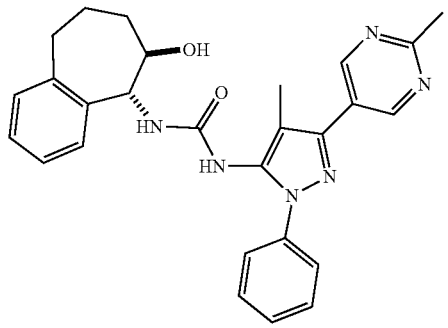 [SMILES: Cc1ncc(-c2nn(-c3ccccc3)c(NC(=O)N[C@@H]3c4ccccc4CCC[C@H]3O)c2C)cn1] |
| 128 | 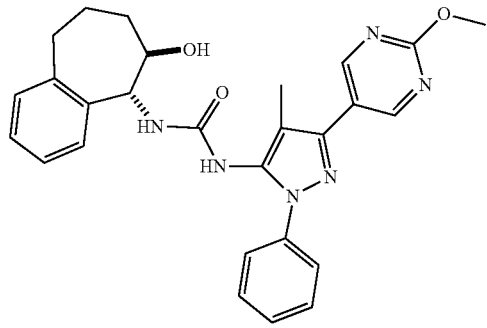 [SMILES: COc1ncc(-c2nn(-c3ccccc3)c(NC(=O)N[C@@H]3c4ccccc4CCC[C@H]3O)c2C)cn1] |
| Ex. # | Structure |
|---|---|
| 129 | 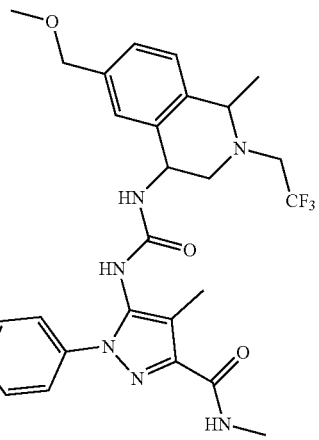 |
| 130 | 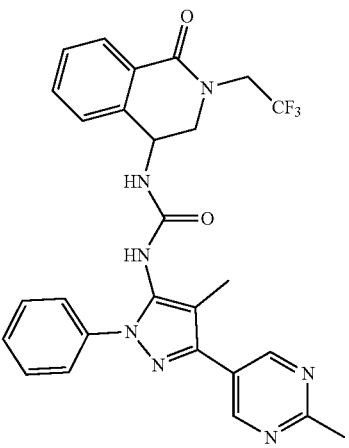 [SMILES: Cc1ncc(-c2nn(-c3ccccc3)c(NC(=O)NC3CN(CC(F)(F)F)C(=O)c4ccccc43)c2C)cn1] |
| 131 | 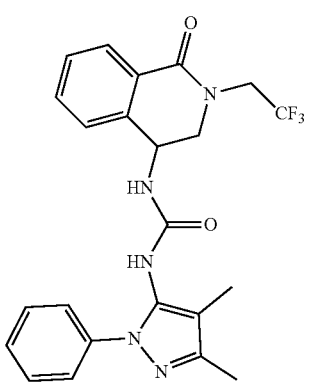 [SMILES: Cc1nn(-c2ccccc2)c(NC(=O)NC2CN(CC(F)(F)F)C(=O)c3ccccc32)c1C] |

| Ex. # | Structure |
|---|---|
| 132 | 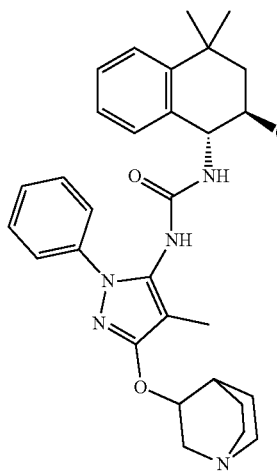 |
| 133 | 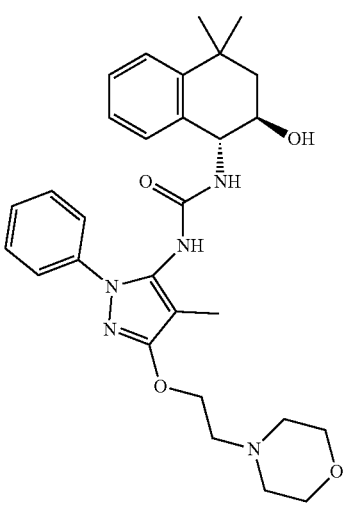 [SMILES: Cc1c(OCCN2CCOCC2)nn(-c2ccccc2)c1NC(=O)N[C@@H]1c2ccccc2C(C)(C)C[C@H]1O] |
| 134 | 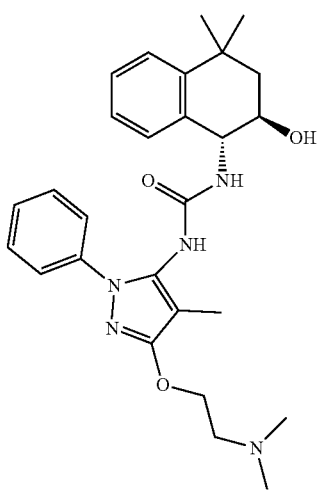 [SMILES: Cc1c(OCCN(C)C)nn(-c2ccccc2)c1NC(=O)N[C@@H]1c2ccccc2C(C)(C)C[C@H]1O] |
| Ex. # | Structure |
|---|---|
| 135 | 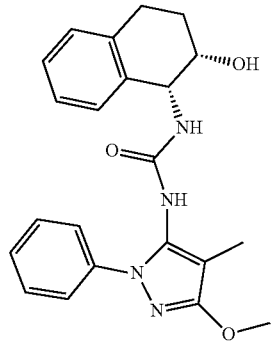 [SMILES: COc1nn(-c2ccccc2)c(NC(=O)N[C@@H]2c3ccccc3CC[C@@H]2O)c1C] |
| 136 | 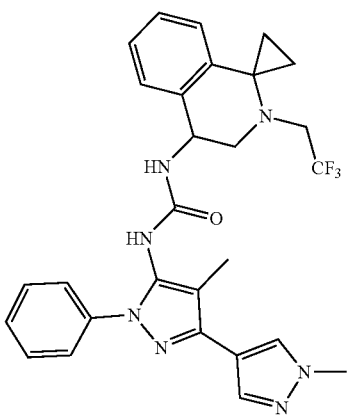 [SMILES: Cc1c(-c2cnn(C)c2)nn(-c2ccccc2)c1NC(=O)NC1CN(CC(F)(F)F)C2(CC2)c2ccccc21] |
| 137 | 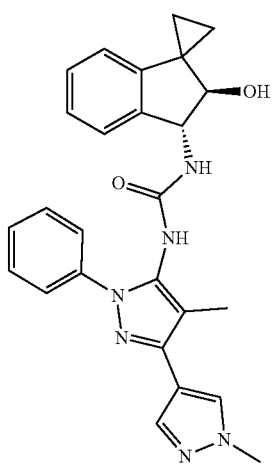 [SMILES: Cc1c(-c2cnn(C)c2)nn(-c2ccccc2)c1NC(=O)N[C@@H]1c2ccccc2C2(CC2)[C@H]1O] |

| Ex. # | Structure |
|---|---|
| 138 | 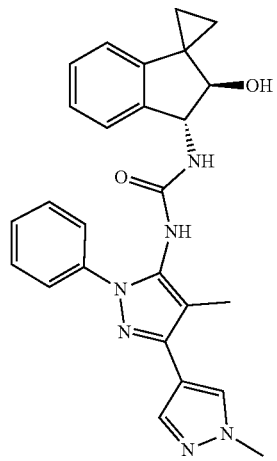 [SMILES: Cc1c(-c2cnn(C)c2)nn(-c2ccccc2)c1NC(=O)N[C@@H]1c2ccccc2C2(CC2)[C@H]1O] |
| 139 | 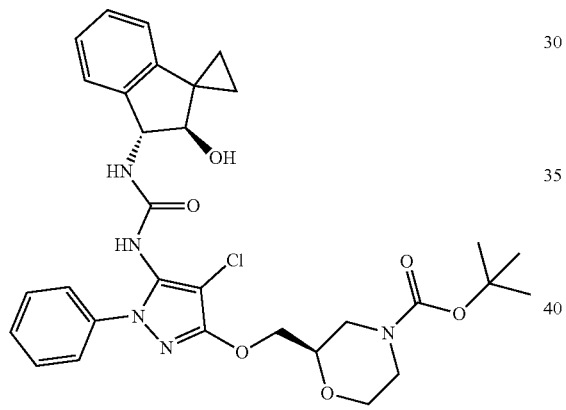 |
| 140 | 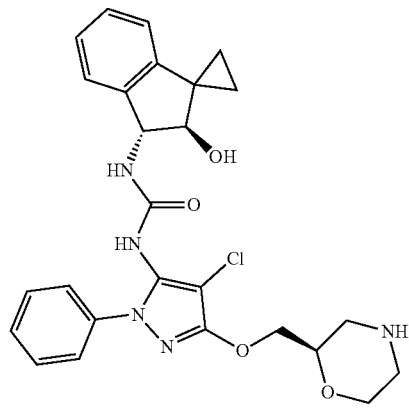 [SMILES: O=C(Nc1c(Cl)c(OC[C@H]2CNCCO2)nn1-c1ccccc1)N[C@@H]1c2ccccc2C2(CC2)[C@H]1O] |
| Ex. # | Structure |
|---|---|
| 141 | 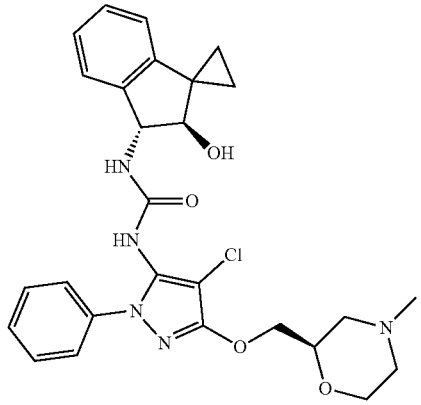 [SMILES: CN1CCO[C@@H](COc2nn(-c3ccccc3)c(NC(=O)N[C@@H]3c4ccccc4C4(CC4)[C@H]3O)c2Cl)C1] |
| 142 | 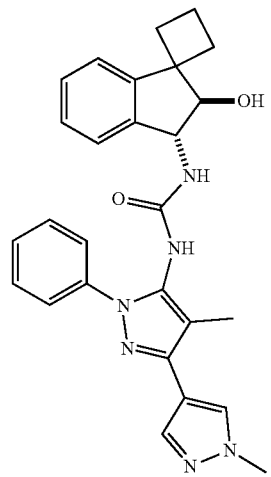 [SMILES: Cc1c(-c2cnn(C)c2)nn(-c2ccccc2)c1NC(=O)N[C@@H]1c2ccccc2C2(CCC2)[C@H]1O] |
| 143 | 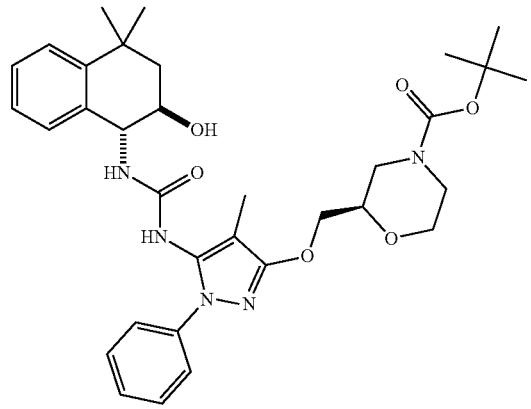 |

| Ex. # | Structure |
|---|---|
| 144 | 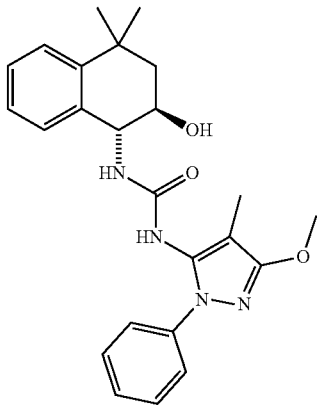 [SMILES: COc1nn(-c2ccccc2)c(NC(=O)N[C@@H]2c3ccccc3C(C)(C)C[C@H]2O)c1C] |
| 146 | 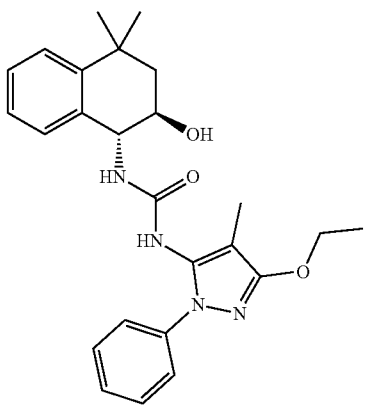 [SMILES: CCOc1nn(-c2ccccc2)c(NC(=O)N[C@@H]2c3ccccc3C(C)(C)C[C@H]2O)c1C] |
| 147 | 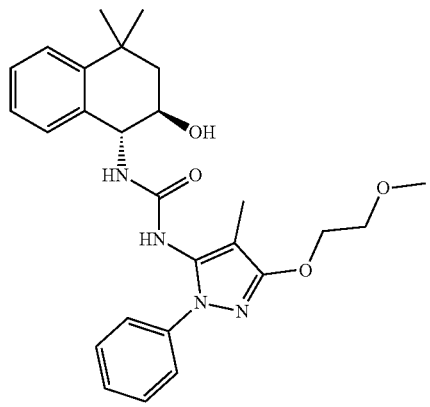 [SMILES: COCCOc1nn(-c2ccccc2)c(NC(=O)N[C@@H]2c3ccccc3C(C)(C)C[C@H]2O)c1C] |
| 148 | 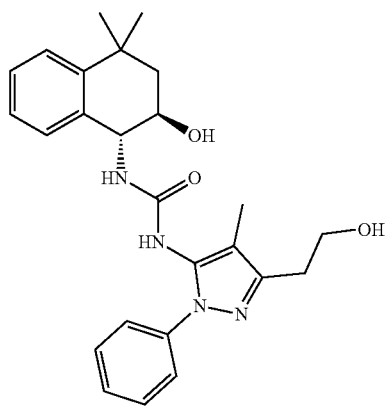 [SMILES: Cc1c(CCO)nn(-c2ccccc2)c1NC(=O)N[C@@H]1c2ccccc2C(C)(C)C[C@H]1O] |
| 149 | 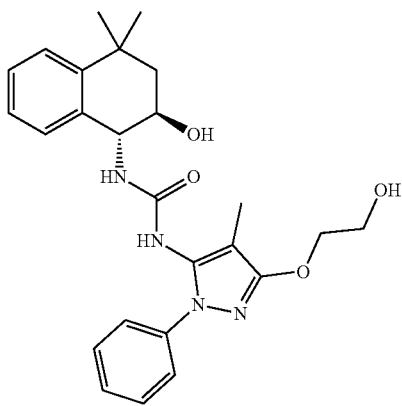 [SMILES: Cc1c(OCCO)nn(-c2ccccc2)c1NC(=O)N[C@@H]1c2ccccc2C(C)(C)C[C@H]1O] |
| 150 | 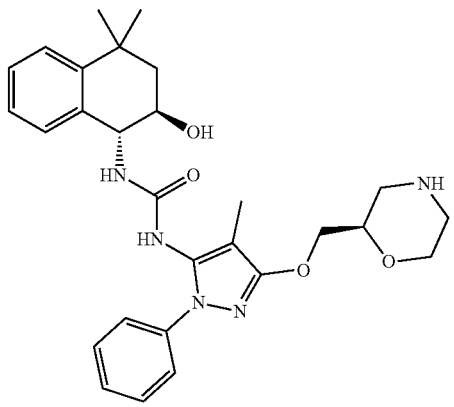 [SMILES: Cc1c(OC[C@H]2CNCCO2)nn(-c2ccccc2)c1NC(=O)N[C@@H]1c2ccccc2C(C)(C)C[C@H]1O] |

| Ex. # | Structure |
|---|---|
| 151 | 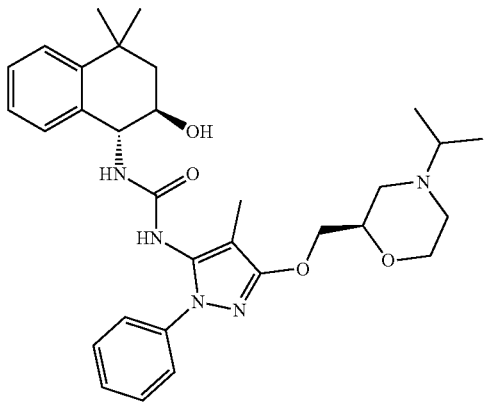 [SMILES: Cc1c(OC[C@H]2CN(C(C)C)CCO2)nn(-c2ccccc2)c1NC(=O)N[C@@H]1c2ccccc2C(C)(C)C[C@H]1O] |
| 152 | 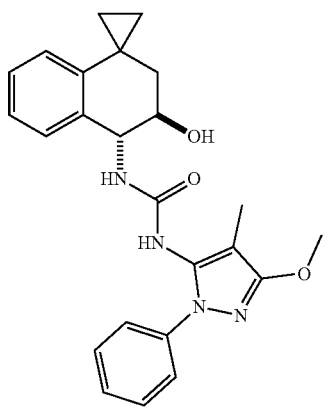 [SMILES: COc1nn(-c2ccccc2)c(NC(=O)N[C@@H]2c3ccccc3C3(CC3)C[C@H]2O)c1C] |
| 153 | 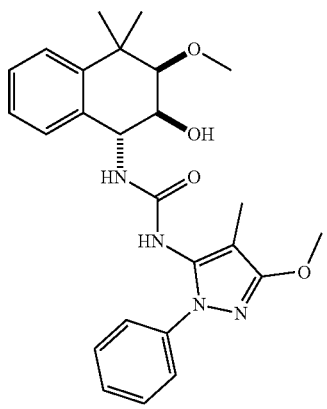 [SMILES: COc1nn(-c2ccccc2)c(NC(=O)N[C@@H]2c3ccccc3C(C)(C)[C@@H](OC)[C@H]2O)c1C] |
| Ex. # | Structure |
|---|---|
| 154 | 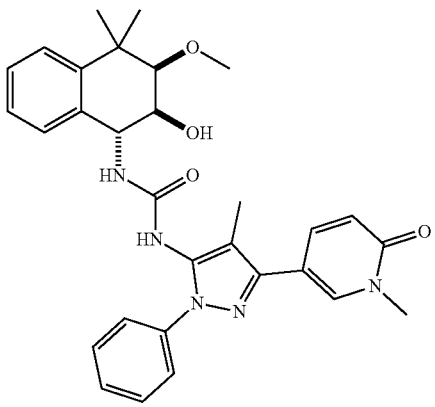 [SMILES: CO[C@H]1[C@@H](O)[C@H](NC(=O)Nc2c(C)c(-c3ccc(=O)n(C)c3)nn2-c2ccccc2)c2ccccc2C1(C)C] |
| 155 | 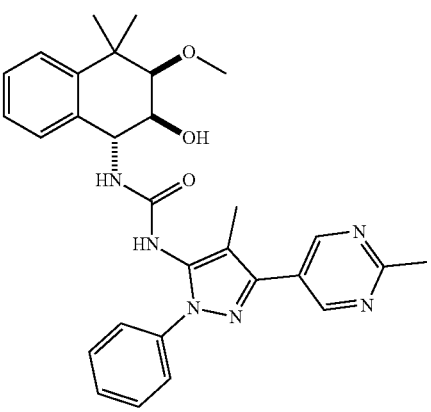 [SMILES: CO[C@H]1[C@@H](O)[C@H](NC(=O)Nc2c(C)c(-c3cnc(C)nc3)nn2-c2ccccc2)c2ccccc2C1(C)C] |
| 156 | 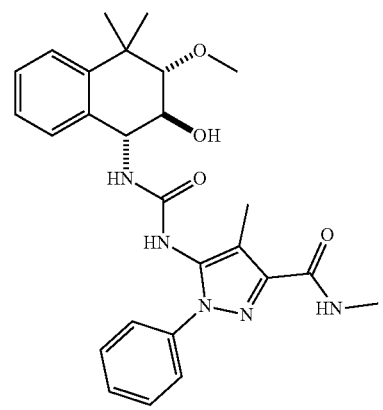 [SMILES: CNC(=O)c1nn(-c2ccccc2)c(NC(=O)N[C@@H]2c3ccccc3C(C)(C)[C@H](OC)[C@H]2O)c1C] |

| Ex. # | Structure |
|---|---|
| 157 | 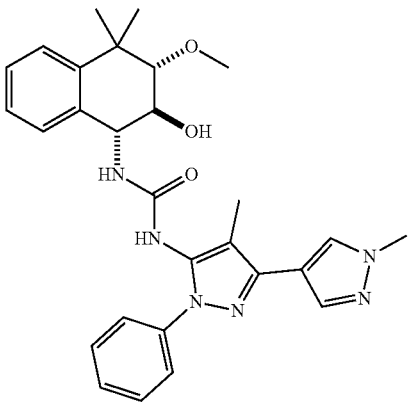 [SMILES: CO[C@@H]1[C@@H](O)[C@H](NC(=O)Nc2c(C)c(-c3cnn(C)c3)nn2-c2ccccc2)c2ccccc2C1(C)C] |
| 158 | 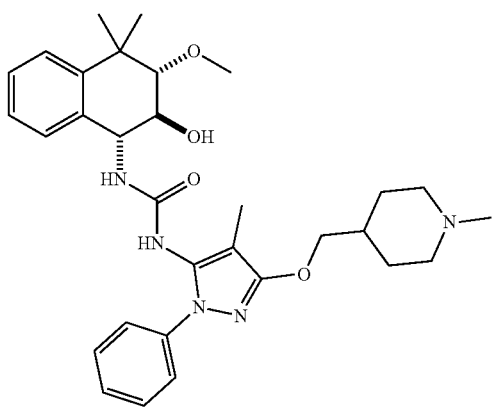 [SMILES: CO[C@@H]1[C@@H](O)[C@H](NC(=O)Nc2c(C)c(OCC3CCN(C)CC3)nn2-c2ccccc2)c2ccccc2C1(C)C] |
| 159 | 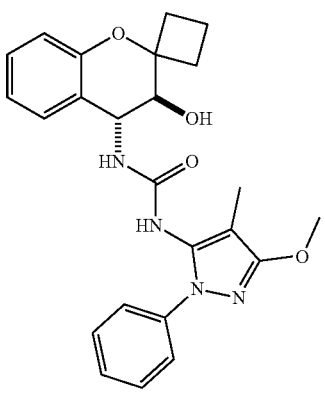 [SMILES: COc1nn(-c2ccccc2)c(NC(=O)N[C@@H]2c3ccccc3OC3(CCC3)[C@H]2O)c1C] |

| Ex. # | Structure |
|---|---|
| 160 | 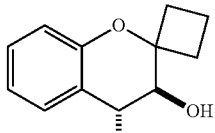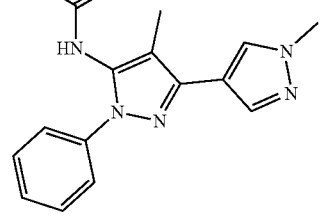 | or a pharmaceutically acceptable salt thereof.

23. A pharmaceutical composition, which comprises a compound of Formula I as defined in claim 1 or a pharmaceutically acceptable salt thereof, and a pharmaceutically acceptable diluent or carrier.

24. A method for treating a disease or disorder selected from pain, non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, meloanom, head and neck squamous cell carcinoma and gastric carcinoma in a mammal, which comprises administering to said mammal a therapeutically effective amount of a compound of Formula I as defined in claim 1, or a pharmaceutically acceptable salt thereof.

25. The method of claim 24, wherein the method is a method of treating pain.

26. The method of claim 24, wherein said cancer is a cancer having a dysregulation of TrkA.

27. A process for the preparation of a compound of claim 1, which comprises:

(a) coupling a corresponding compound having the formula II

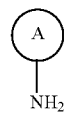

II with a corresponding compound having the formula III

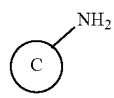

III in the presence carbonyldiimidazole or triphosgene and a base; or (c) coupling a corresponding compound having the formula II

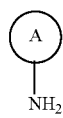

with a corresponding compound having the formula IV

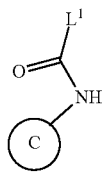

where $L^1$ is a leaving group, in the presence of a base; or
(d) coupling a corresponding compound having the formula V

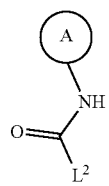

where $L^2$ is a leaving group, with a corresponding compound having the formula III

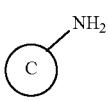

in the presence of a base; or
(e) activating a corresponding compound having the formula VI

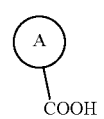

with diphenylphosphoryl azide followed by coupling the activated intermediate with a corresponding compound having the formula III

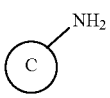

in the presence a base; or
(f) coupling a corresponding compound having the formula II

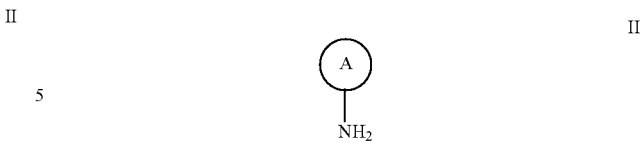

with a corresponding compound having the formula VII

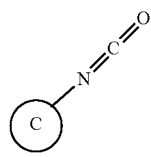

in the presence of a base; or
(g) coupling a corresponding compound having the formula VIII

with a corresponding compound having the formula III

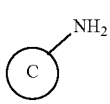

in the presence of a base; and optionally removing protecting groups and optionally preparing a pharmaceutically acceptable salt thereof.

28. A compound according to claim 12, where $R^4$ is selected from the group consisting of (1-6C)alkyl, trifluoro(1-6C)alkyl, cyano(1-6C)alkyl, (1-3C alkoxy)(1-6C)alkyl, (1-6C)alkoxy, monofluoro(1-6C)alkoxy, cyano(1-6C)alkoxy, hydroxy(1-6C)alkoxy, dihydroxy(2-6C)alkoxy, hetCyc²(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl, hetAr⁴, hetAr⁴—O—, Ar⁴, and hetAr⁵.

29. A compound according to claim 28, wherein $R^4$ is hetCyc²(1-6C)alkoxy.

30. A compound according to claim 29, wherein $R^5$ is (1-6C)alkyl.

31. A compound according to claim 30, wherein $R^3$ is Ar².

32. A compound according to claim 31, wherein Y is H.

33. A compound according to claim 22, selected from the group consisting of:

| Ex. # | Structure |
|---|---|
| 37 | 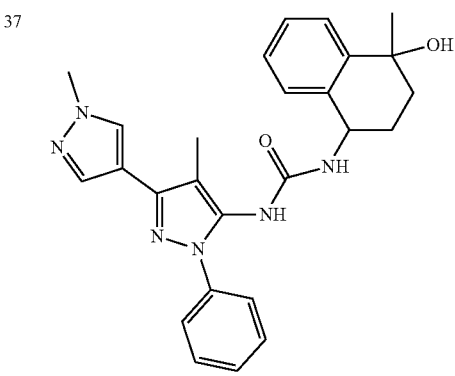 |
| 55 | 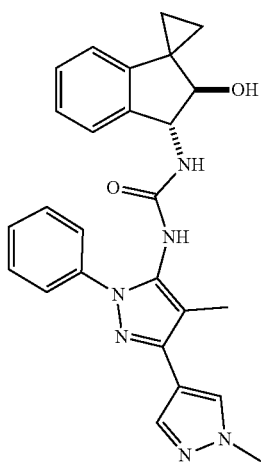 [SMILES: Cc1c(-c2cnn(C)c2)nn(-c2ccccc2)c1NC(=O)N[C@@H]1c2ccccc2C2(CC2)[C@H]1O] |
| 56 | 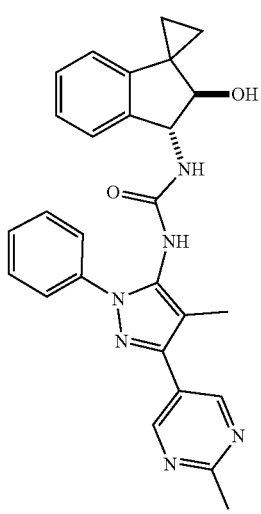 [SMILES: Cc1ncc(-c2nn(-c3ccccc3)c(NC(=O)N[C@@H]3c4ccccc4C4(CC4)[C@H]3O)c2C)cn1] |
-continued
| Ex. # | Structure |
|---|---|
| 57 | 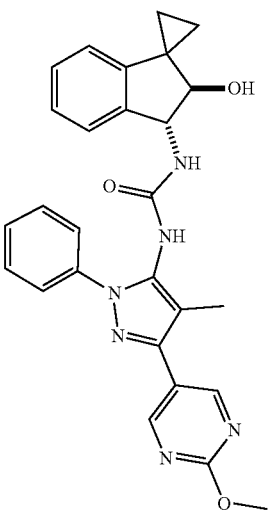 [SMILES: COc1ncc(-c2nn(-c3ccccc3)c(NC(=O)N[C@@H]3c4ccccc4C4(CC4)[C@H]3O)c2C)cn1] |
| 58 | 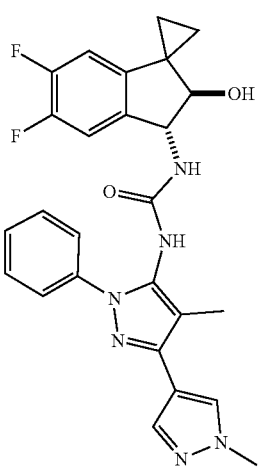 [SMILES: Cc1c(-c2cnn(C)c2)nn(-c2ccccc2)c1NC(=O)N[C@@H]1c2cc(F)c(F)cc2C2(CC2)[C@H]1O] |
| 59 | 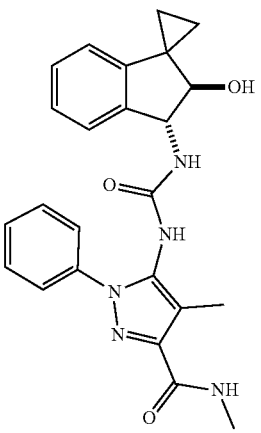 [SMILES: CNC(=O)c1nn(-c2ccccc2)c(NC(=O)N[C@@H]2c3ccccc3C3(CC3)[C@H]2O)c1C] |

-continued
| Ex. # | Structure |
|---|---|
| 60 | 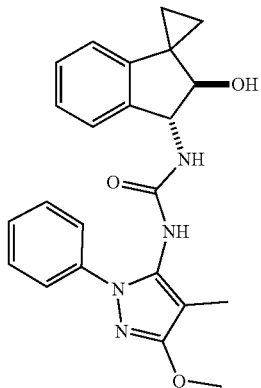 [SMILES: COc1nn(-c2ccccc2)c(NC(=O)N[C@@H]2c3ccccc3C3(CC3)[C@H]2O)c1C] |
| 61 | 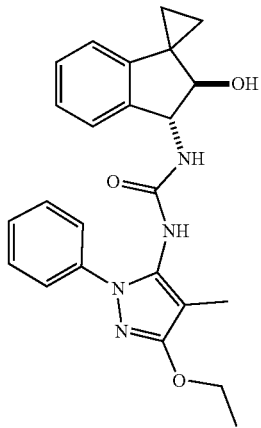 [SMILES: CCOc1nn(-c2ccccc2)c(NC(=O)N[C@@H]2c3ccccc3C3(CC3)[C@H]2O)c1C] |
| 62 | 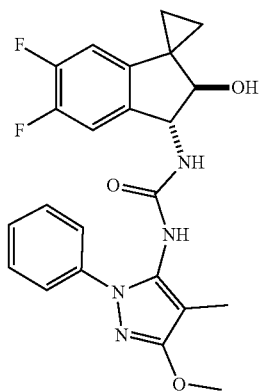 [SMILES: COc1nn(-c2ccccc2)c(NC(=O)N[C@@H]2c3cc(F)c(F)cc3C3(CC3)[C@H]2O)c1C] |
-continued
| Ex. # | Structure |
|---|---|
| 63 | 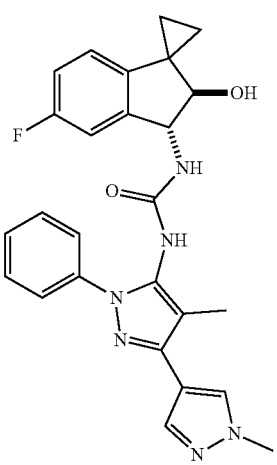 [SMILES: Cc1c(-c2cnn(C)c2)nn(-c2ccccc2)c1NC(=O)N[C@@H]1c2cc(F)ccc2C2(CC2)[C@H]1O] |
| 64 | 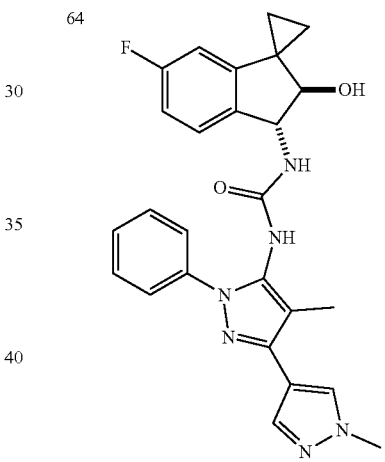 |
| 65 | 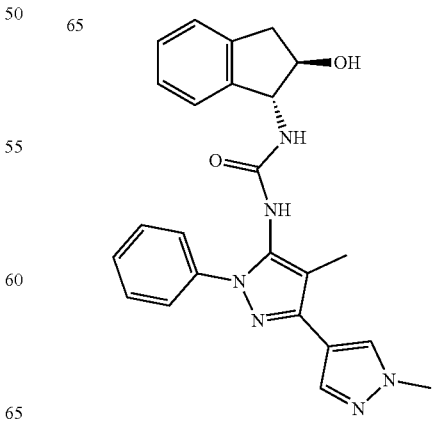 |

| Ex. # | Structure |
|---|---|
| 66 | 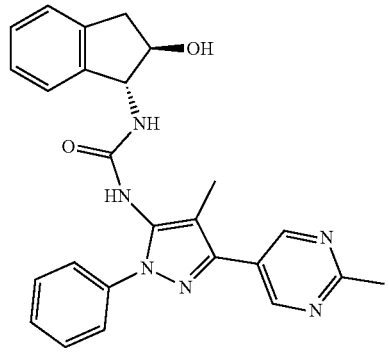 [SMILES: Cc1ncc(-c2nn(-c3ccccc3)c(NC(=O)N[C@@H]3c4ccccc4C[C@H]3O)c2C)cn1] |
| 67 | 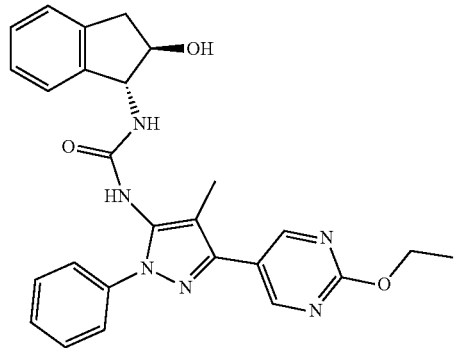 [SMILES: CCOc1ncc(-c2nn(-c3ccccc3)c(NC(=O)N[C@@H]3c4ccccc4C[C@H]3O)c2C)cn1] |
| 68 | 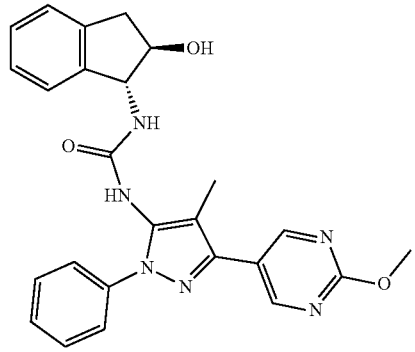 [SMILES: COc1ncc(-c2nn(-c3ccccc3)c(NC(=O)N[C@@H]3c4ccccc4C[C@H]3O)c2C)cn1] |
| 69 | 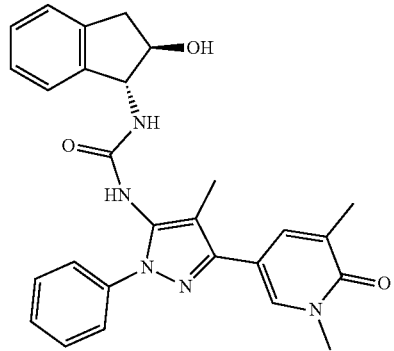 [SMILES: Cc1c(-c2cc(C)c(=O)n(C)c2)nn(-c2ccccc2)c1NC(=O)N[C@@H]1c2ccccc2C[C@H]1O] |
| Ex. # | Structure |
|---|---|
| 70 | 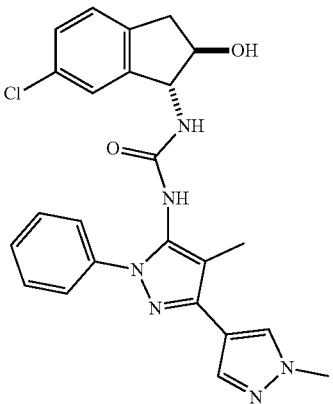 [SMILES: Cc1c(-c2cnn(C)c2)nn(-c2ccccc2)c1NC(=O)N[C@@H]1c2cc(Cl)ccc2C[C@H]1O] |
| 71 | 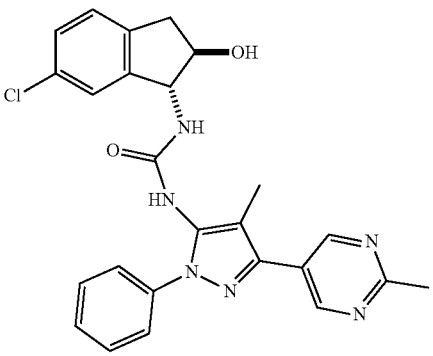 [SMILES: Cc1ncc(-c2nn(-c3ccccc3)c(NC(=O)N[C@@H]3c4cc(Cl)ccc4C[C@H]3O)c2C)cn1] |
| 72 | 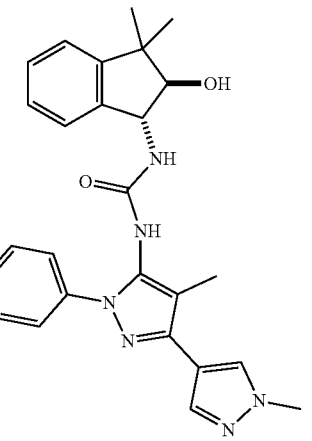 |
| 73 | 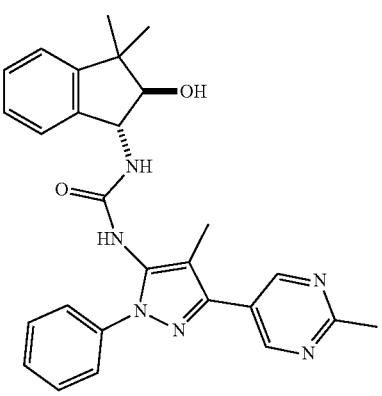 [SMILES: Cc1ncc(-c2nn(-c3ccccc3)c(NC(=O)N[C@@H]3c4ccccc4C(C)(C)[C@H]3O)c2C)cn1] |

| Ex. # | Structure |
|---|---|
| 74 | 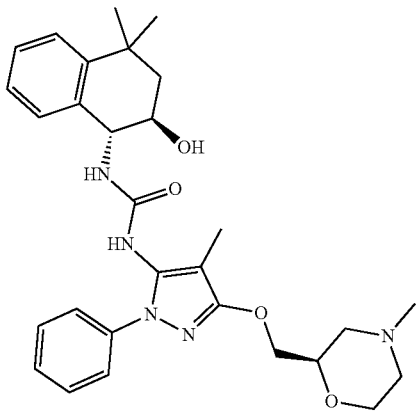 [SMILES: Cc1c(OC[C@H]2CN(C)CCO2)nn(-c2ccccc2)c1NC(=O)N[C@@H]1c2ccccc2C(C)(C)C[C@H]1O] |
| 75 | 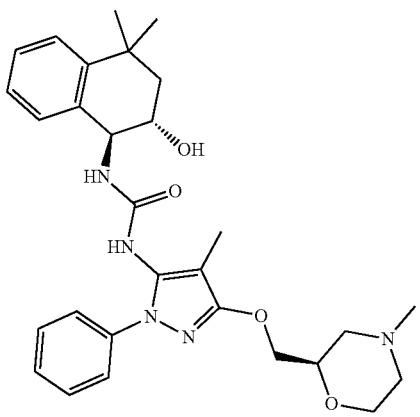 [SMILES: Cc1c(OC[C@H]2CN(C)CCO2)nn(-c2ccccc2)c1NC(=O)N[C@H]1c2ccccc2C(C)(C)C[C@@H]1O] |
| 76 | 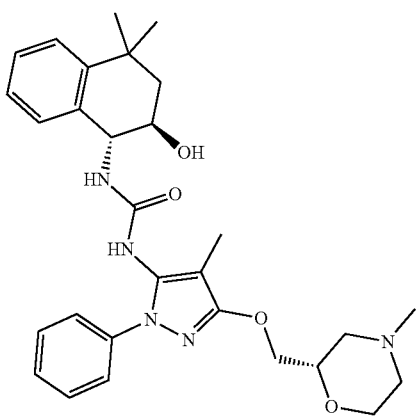 [SMILES: Cc1c(OC[C@@H]2CN(C)CCO2)nn(-c2ccccc2)c1NC(=O)N[C@@H]1c2ccccc2C(C)(C)C[C@H]1O] |
| Ex. # | Structure |
|---|---|
| 77 | 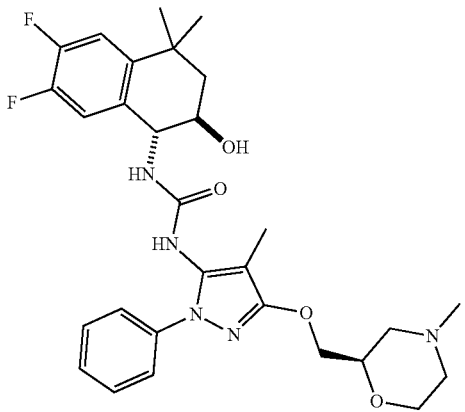 [SMILES: Cc1c(OC[C@H]2CN(C)CCO2)nn(-c2ccccc2)c1NC(=O)N[C@@H]1c2cc(F)c(F)cc2C(C)(C)C[C@H]1O] |
| 78 | 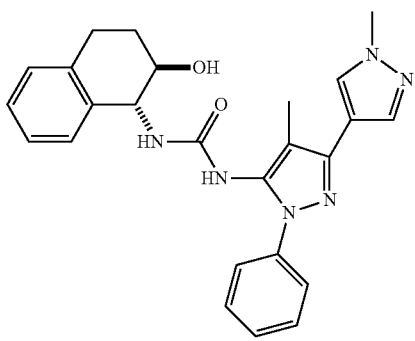 |
| 101 | 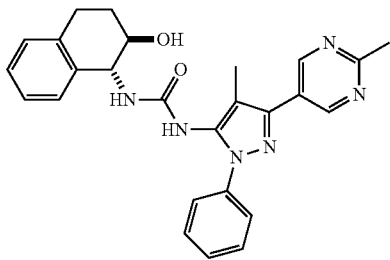 |
| 118 | 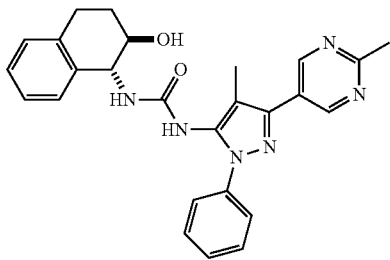 |

-continued
| Ex. # | Structure |
|---|---|
| 121 | 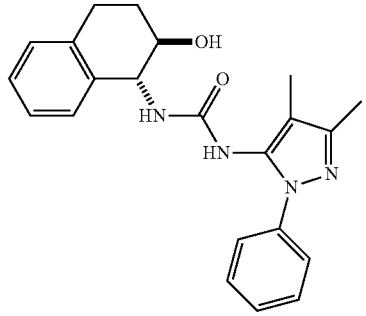 |
| 123 | 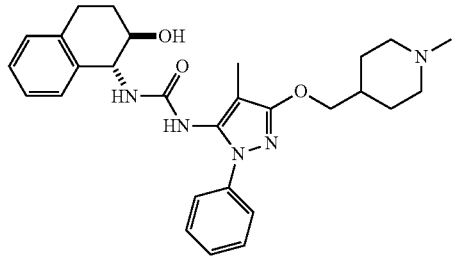 |
| 127 | 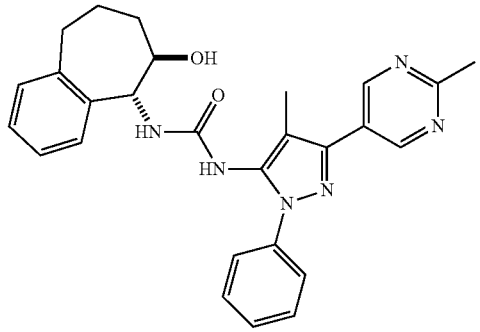 |
| 128 | 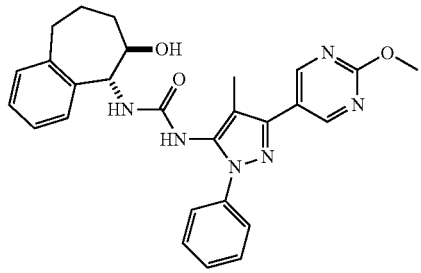 |
-continued
| Ex. # | Structure |
|---|---|
| 137 | 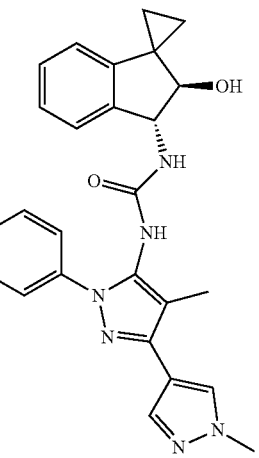 |
| 138 | 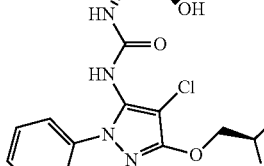 |
| 139 | 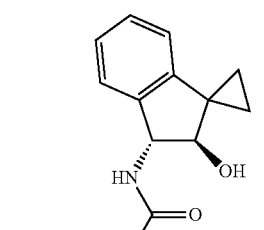 |
| 140 | 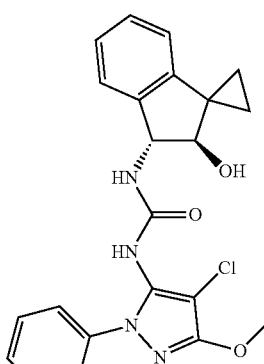 |

| Ex. # | Structure |
|---|---|
| 141 | 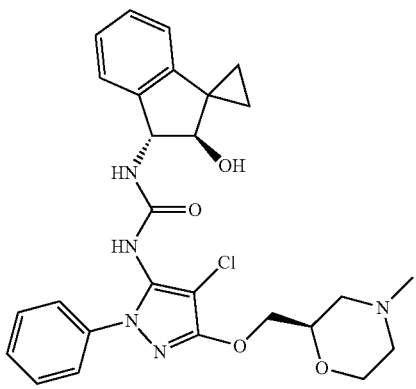 [SMILES: CN1CCO[C@@H](COc2nn(-c3ccccc3)c(NC(=O)N[C@@H]3c4ccccc4C4(CC4)[C@H]3O)c2Cl)C1] |
| 142 | 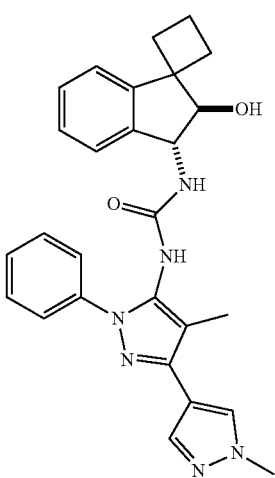 [SMILES: Cc1c(-c2cnn(C)c2)nn(-c2ccccc2)c1NC(=O)N[C@@H]1c2ccccc2C2(CCC2)[C@H]1O] |
| 154 | 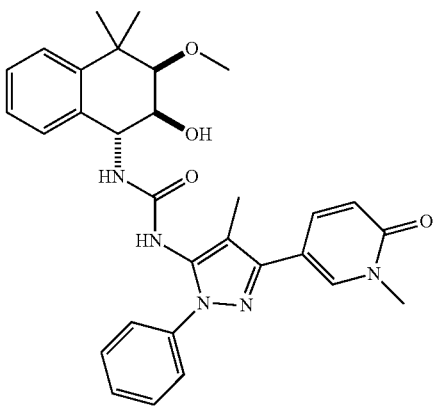 [SMILES: CO[C@H]1[C@@H](O)[C@H](NC(=O)Nc2c(C)c(-c3ccc(=O)n(C)c3)nn2-c2ccccc2)c2ccccc2C1(C)C] |
| Ex. # | Structure |
|---|---|
| 155 | 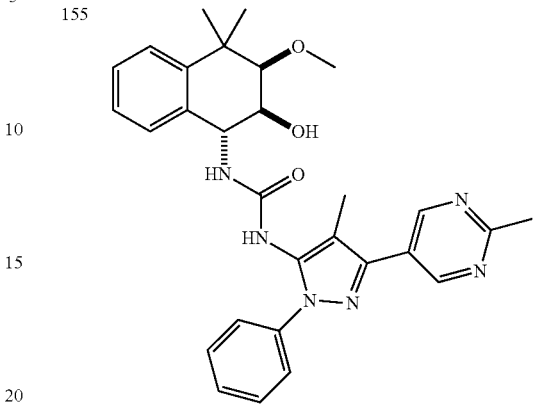 |
and pharmaceutically acceptable salts thereof.
34. A compound according to claim 22, selected from the group consisting of:
| Ex. | Structure |
|---|---|
| 74 | 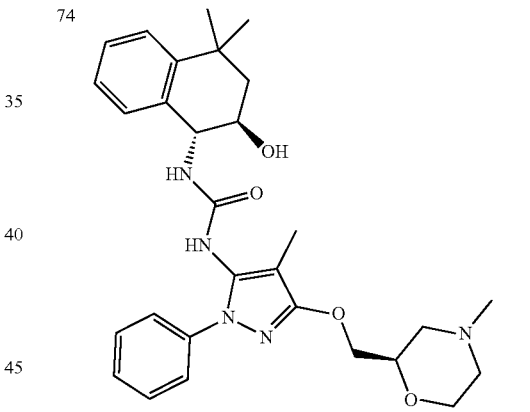 |
| 80 | 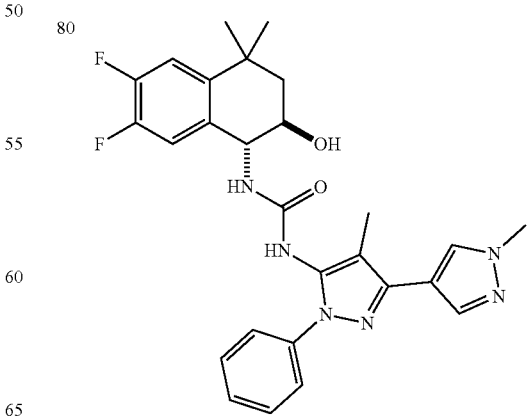 |

| Ex. | Structure |
|---|---|
| 82 | 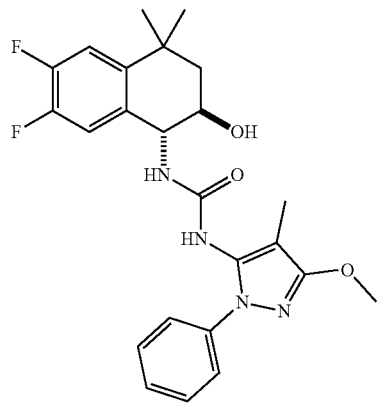 [SMILES: COc1nn(-c2ccccc2)c(NC(=O)N[C@@H]2c3cc(F)c(F)cc3C(C)(C)C[C@H]2O)c1C] |
| 84 | 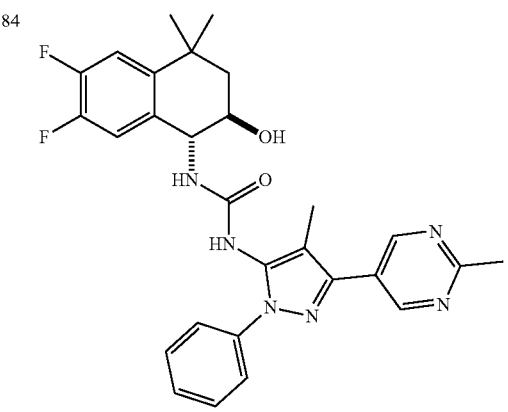 |
| 86 | 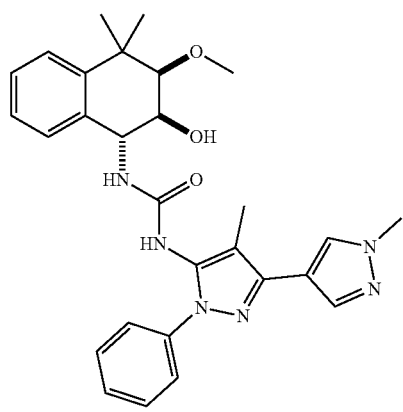 [SMILES: CO[C@H]1[C@@H](O)[C@H](NC(=O)Nc2c(C)c(-c3cnn(C)c3)nn2-c2ccccc2)c2ccccc2C1(C)C] |
| Ex. | Structure |
|---|---|
| 87 | 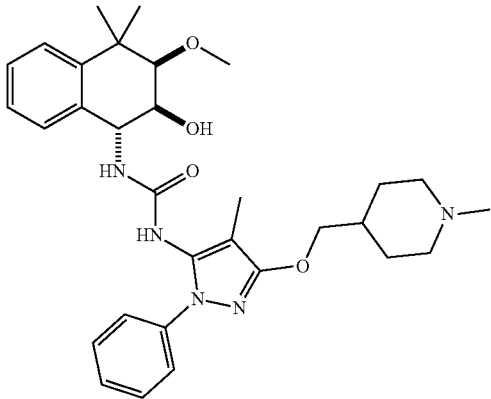 [SMILES: CO[C@H]1[C@@H](O)[C@H](NC(=O)Nc2c(C)c(OCC3CCN(C)CC3)nn2-c2ccccc2)c2ccccc2C1(C)C] |
| 117 | 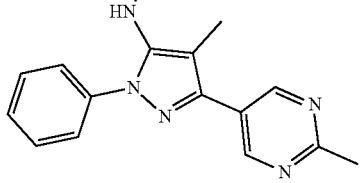 |
| 122 | 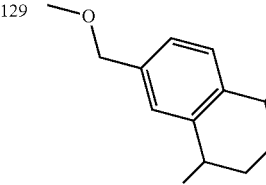 |
| 129 | 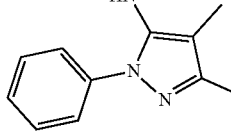 |

| Ex. | Structure |
|---|---|
| 144 | 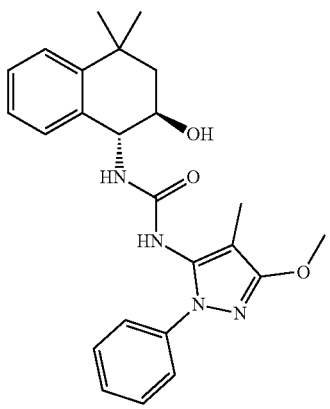 [SMILES: COc1nn(-c2ccccc2)c(NC(=O)N[C@@H]2c3ccccc3C(C)(C)C[C@H]2O)c1C] |
| 146 | 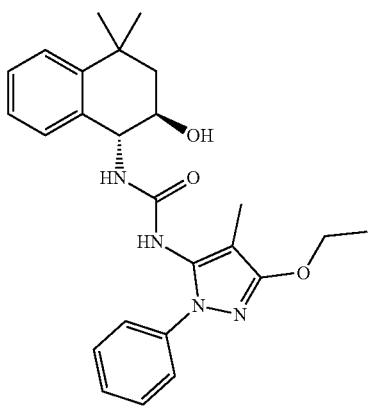 [SMILES: CCOc1nn(-c2ccccc2)c(NC(=O)N[C@@H]2c3ccccc3C(C)(C)C[C@H]2O)c1C] |
| 147 | 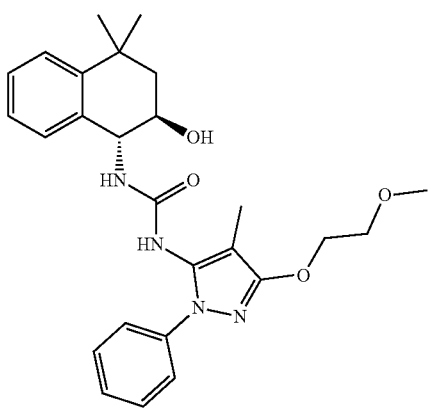 [SMILES: COCCOc1nn(-c2ccccc2)c(NC(=O)N[C@@H]2c3ccccc3C(C)(C)C[C@H]2O)c1C] |

| Ex. | Structure |
|---|---|
| 151 | 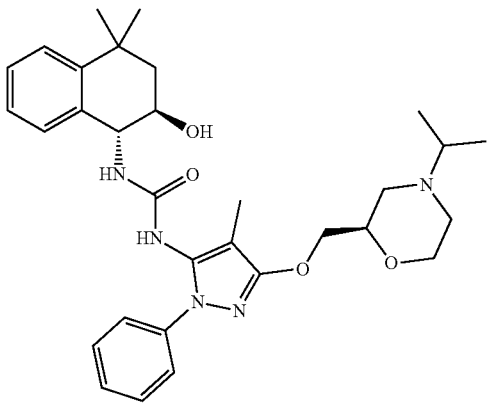 [SMILES: Cc1c(OC[C@H]2CN(C(C)C)CCO2)nn(-c2ccccc2)c1NC(=O)N[C@@H]1c2ccccc2C(C)(C)C[C@H]1O] |
| 153 | 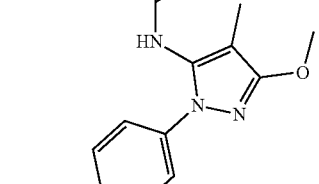 |
| 155 | 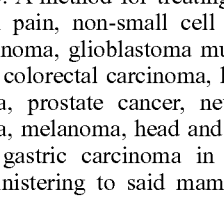 | and pharmaceutically acceptable salts thereof.

35. A pharmaceutical composition, which comprises a compound of Formula I as defined in claim 33 or a pharmaceutically acceptable salt thereof, and a pharmaceutically acceptable diluent or carrier.

36. A method for treating a disease or disorder selected from pain, non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma in a mammal, which comprises administering to said mammal a therapeutically effective amount of a compound of Formula I as defined in claim 33, or a pharmaceutically acceptable salt thereof.

37. The method of claim 36, wherein the method is a method of treating pain.

38. The method of claim 37, wherein the pain is chronic pain.

39. The method of claim 37, wherein the pain is acute pain.

40. The method of claim 37, wherein the pain is inflammatory pain, neuropathic pain, pain is associated with cancer, or pain is associated with bone fracture.

41. The method of claim 36, wherein said cancer is a cancer having a dysregulation of TrkA.

42. A pharmaceutical composition, which comprises a compound of Formula I as defined in claim 34 or a pharmaceutically acceptable salt thereof, and a pharmaceutically acceptable diluent or carrier.

43. A method for treating a disease or disorder selected from pain, non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma, in a mammal, which comprises administering to said mammal a therapeutically effective amount of a compound of Formula I as defined in claim 34, or a pharmaceutically acceptable salt thereof.

44. The method of claim 43, wherein the method is a method of treating pain.

45. The method of claim 44, wherein the pain is chronic pain.

46. The method of claim 44, wherein the pain is acute pain.

47. The method of claim 44, wherein the pain is inflammatory pain, neuropathic pain, pain is associated with cancer, or pain is associated with bone fracture.

48. The method of claim 43, wherein said cancer is a cancer having a dysregulation of TrkA.

* * * * *

UNITED STATES PATENT AND TRADEMARK OFFICE
CERTIFICATE OF CORRECTION

PATENT NO.         : 10,351,575 B2
APPLICATION NO.    : 14/442609
DATED              : July 16, 2019
INVENTOR(S)        : Shelley Allen et al.

Page 1 of 3

It is certified that error appears in the above-identified patent and that said Letters Patent is hereby corrected as shown below:

In the Claims

Column 300, Line 10, Claim 1, please delete "(1-6C) alkoxy," and insert -- (1-6C)alkoxy, --;

Column 300, Line 44, Claim 1, please delete "(3-6C cycloalkyl)CH2- (3-6C cycloalkyl)C(=O)," and insert -- (3-6C cycloalkyl)CH2-, (3-6C cycloalkyl)C(=O), --;

Column 302, Line 49, Claim 11, please delete "pentafluoro(2-6C)alkoxy cyano(1-6C)alkoxy," and insert -- pentafluoro(2-6C)alkoxy, cyano(1-6C)alkoxy, --;

Column 302, Line 55, Claim 11, please delete "(1-6C) alkoxy," and insert -- (1-6C)alkoxy, --;

Column 320, Lines 5-20, Claim 22, please delete the following compound:

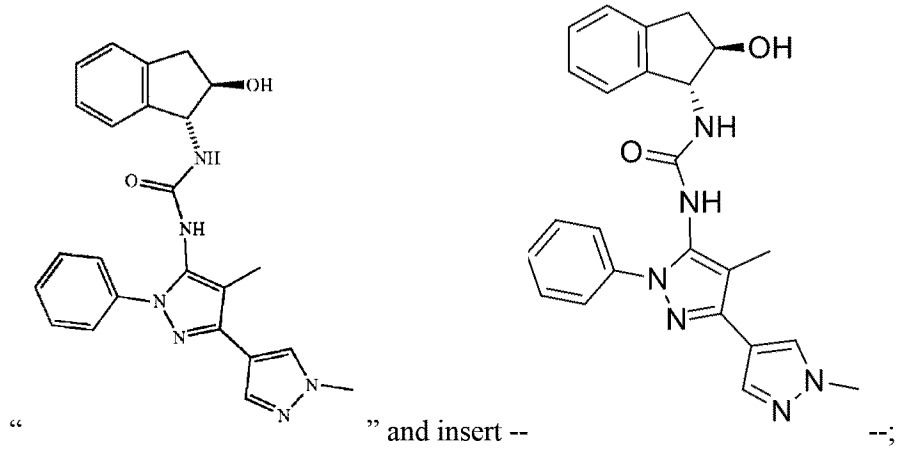

Signed and Sealed this
Twenty-fourth Day of September, 2019

Andrei Iancu
*Director of the United States Patent and Trademark Office*

CERTIFICATE OF CORRECTION (continued)
U.S. Pat. No. 10,351,575 B2

Column 320, Lines 21-35, Claim 22, please delete the following compound:

" 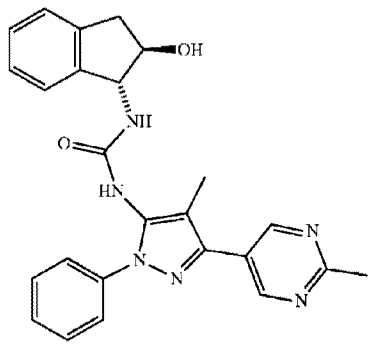 " and insert -- 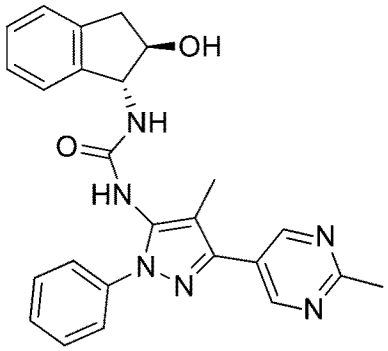 --;

Column 320, Lines 36-50, Claim 22, please delete the following compound:

" 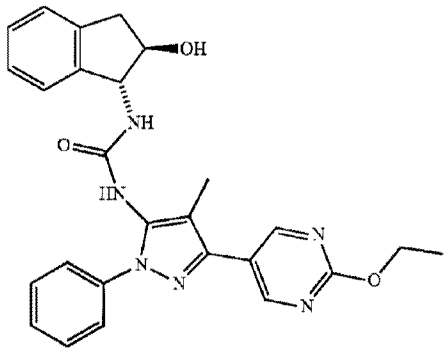 " and insert -- 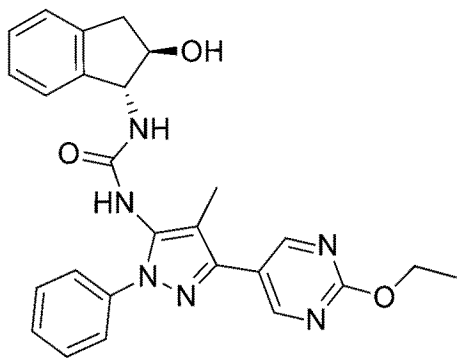 --;

Column 320, Lines 51-65, Claim 22, please delete the following compound:

" 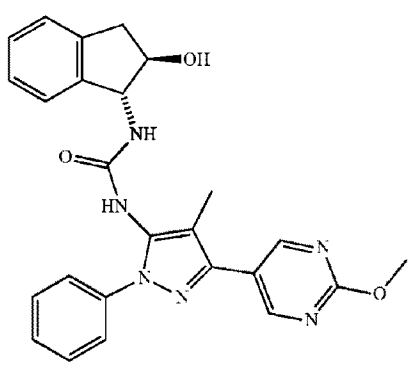 " and insert -- 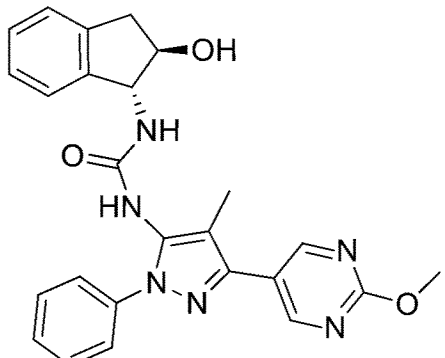 --;

CERTIFICATE OF CORRECTION (continued)
U.S. Pat. No. 10,351,575 B2

Page 3 of 3

Column 321, Lines 5-18, Claim 22, please delete the following compound:

" 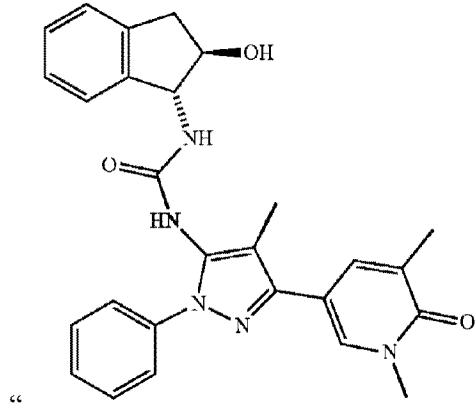 " and insert -- 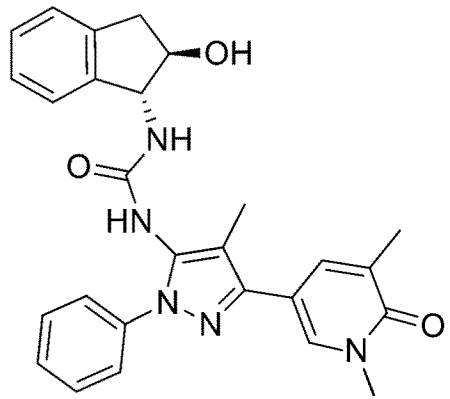 --;

Column 348, Line 31, Claim 22, please delete "meloanom," and insert -- melanoma, --;

Column 350, Line 51, Claim 22, please delete "(1-6C)alkyl, cyano(1-6C)alkyl," and insert -- (1-6C)alkyl, hydroxy(1-6C)alkyl, cyano(1-6C)alkyl, -- therefor.